(12) United States Patent
Boys et al.

(10) Patent No.: US 11,834,453 B2
(45) Date of Patent: Dec. 5, 2023

(54) SUBSTITUTED PYRIMIDO[5,4-D]PYRIMIDINES AS HER2 INHIBITORS

(71) Applicant: Array BioPharma Inc., Boulder, CO (US)

(72) Inventors: Mark Laurence Boys, Lyons, CO (US); Bryan Daniel Ellis, Boulder, CO (US); John Joseph Gaudino, Longmont, CO (US); Erik James Hicken, Longmont, CO (US); Ellen Ruth Laird, Longmont, CO (US); Nicholas Charles Lazzara, Denver, CO (US); Bradley Jon Newhouse, Broomfield, CO (US); Spencer Phillip Pajk, Boulder, CO (US)

(73) Assignee: Array BioPharma Inc., New York, NY (US)

(*) Notice: Subject to any disclaimer, the term of this patent is extended or adjusted under 35 U.S.C. 154(b) by 0 days.

(21) Appl. No.: 17/362,580

(22) Filed: Jun. 29, 2021

(65) Prior Publication Data

US 2023/0023851 A1 Jan. 26, 2023

Related U.S. Application Data

(60) Provisional application No. 63/208,901, filed on Jun. 9, 2021, provisional application No. 63/046,506, filed on Jun. 30, 2020.

(51) Int. Cl.
| | | |
|---|---|---|
| *A61K 31/519* | (2006.01) | |
| *C07D 487/04* | (2006.01) | |
| *A61K 45/06* | (2006.01) | |
| *C07D 519/00* | (2006.01) | |

(52) U.S. Cl.
CPC ............ *C07D 487/04* (2013.01); *A61K 45/06* (2013.01); *C07D 519/00* (2013.01)

(58) Field of Classification Search
CPC ............................ A61K 31/519; C07D 487/04

USPC ....................................... 514/262.1; 544/256
See application file for complete search history.

(56) References Cited

FOREIGN PATENT DOCUMENTS

| | | |
|---|---|---|
| EP | 3677583 | 7/2020 |
| WO | 2005/016346 | 2/2005 |
| WO | 2007059257 | 5/2007 |
| WO | 2020/057511 | 3/2020 |
| WO | 2021/127397 | 6/2021 |
| WO | 2021/156178 | 8/2021 |
| WO | 2021/156180 | 8/2021 |
| WO | 2021/213800 | 10/2021 |
| WO | 2022/006386 | 1/2022 |
| WO | 2022/221227 | 10/2022 |
| WO | 2022/266458 | 12/2022 |
| WO | 2022/269531 | 12/2022 |

*Primary Examiner* — Douglas M Willis
(74) *Attorney, Agent, or Firm* — Corey M. Williams

(57) ABSTRACT

This invention relates to compounds of Formula (I):

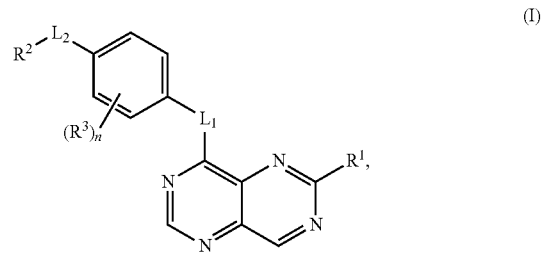

(I)

and enantiomers thereof, and to pharmaceutically acceptable salts of Formula (I) and said enantiomers, wherein $L_1$, $L_2$, $R^1$, $R^2$, $R^3$ and n are as defined herein. The invention further relates to pharmaceutical compositions comprising such compounds and salts, and to methods and uses of such compounds, salts and compositions for the treatment of abnormal cell growth, including cancer, in a subject in need thereof.

28 Claims, No Drawings
Specification includes a Sequence Listing.

SUBSTITUTED PYRIMIDO[5,4-D]PYRIMIDINES AS HER2 INHIBITORS

CROSS-REFERENCE TO RELATED APPLICATIONS

This application claims the benefit of priority to U.S. Provisional Application Ser. No. 63/046,506 filed Jun. 30, 2020, and to U.S. Provisional Application Ser. No. 63/208,901 filed Jun. 9, 2021, each of which is incorporated herein by reference in its entirety.

BACKGROUND OF THE INVENTION

Reference to Sequence Listing

This application was filed electronically via EFS-Web and includes an electronically submitted sequence listing in .txt format. The .txt file contains a sequence listing entitled "PC072637A_SEQ_LISTING_ST25.txt" created on Jun. 29, 2021 and having a size of 6 KB. The sequence listing contained in this .txt file is part of the specification and is herein incorporated by reference in its entirety.

Field of the Invention

The invention relates to pyrimido[5,4-d]pyrimidine compounds that act as HER2 inhibitors. The invention relates to compounds of Formula (I) and pharmaceutically acceptable salts thereof, to pharmaceutical compositions comprising such compounds and salts, and to the uses thereof. The invention also relates to the preparation of the compounds of the invention and intermediates in their preparation, compositions containing the compounds of the invention, and uses of compounds of the invention including treatment of abnormal cell growth, such as cancer, in a subject.

Description of the State of the Art

Human epidermal growth factor receptor 2 (ErbB2, also known as HER2) is a receptor tyrosine kinase that belongs to a family of four kinases (EGFR, ErbB2, ErbB3 and ErbB4). The role of HER2 amplification in oncology is well known, particularly breast, gastric, lung and colon cancers. HER2 amplified breast and lung cancers are also known to metastasize and develop brain metastases. HER2 inhibitors are known, such as tucatinib, lapatinib, neratinib, sapitinib, poziotinib, canertinib, TAK-285 and varlitinib, but not all those HER2 inhibitors are selective. Additionally, there are monoclonal antibodies used for HER2 positive cancers, such as trastuzumab and pertuzumab.

Activating mutations in the HER2 gene are becoming increasingly reported. One common type of HER2 mutation is an insertion mutation. A frequently occurring insertion mutation is the HER2 YVMA mutation in exon 20. HER2 mutation cancers are also known to metastasize and develop brain metastases. See Subramanian, Janakiraman, et al. "Emergence of ErbB2 Mutation as a Biomarker and an Actionable Target in Solid Cancers." *The Oncologist.* 24(12) (2019): pp. e1303-e1314; and Offin, Michael, et al. "Frequency and outcomes of Brain Metastases in Patients with HER2-Mutant Lung Cancers." *Cancer.* 125(24) (2019): pp. 4380-4387.

There remains a need to discover HER2 mutation inhibitors having novel activity profiles, such as selective HER2 mutation inhibitors, which may be useful for the treatment of HER2 mutation cancers or other proliferative diseases or conditions. Furthermore, brain penetrant HER2 mutation inhibitors may be useful in treating brain metastases from HER2 amplified or HER2 positive cancers, including brain metastases from HER2 mutation amplified or HER2 mutation positive cancers.

BRIEF SUMMARY OF THE INVENTION

The present invention provides, in part, compounds of Formula (I) and pharmaceutically acceptable salts thereof. Such compounds can inhibit the activity of HER2, including HER2 mutations, thereby effecting biological functions. In some embodiments, the invention provides compounds that are selective for HER2 mutations. In some embodiments, the invention provides compound with an affinity for inhibiting HER2 and HER2 mutations greater than their affinity for inhibiting EGFR. In some embodiments, the invention provides compounds that can inhibit the activity of brain metasteses from HER2 positive or HER2 amplified cancers. In a further embodiment, the invention provides compounds that can inhibit the activity of brain metasteses from HER2 mutation positive or HER2 mutation amplified cancers. Also provided are pharmaceutical compositions and medicaments, comprising the compounds or salts of the invention, alone or in combination with additional anti-cancer therapeutic agents.

The present invention also provides, in part, methods for preparing the compounds, pharmaceutically acceptable salts and compositions of the invention, and methods of using the foregoing.

In one aspect, the invention provides a compound of Formula (I):

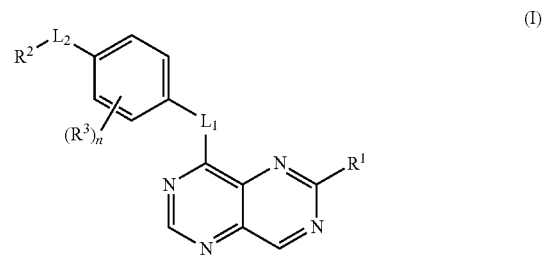

(I)

or a stereoisomer, tautomer or pharmaceutically acceptable salt thereof, wherein $L_1$, $L_2$, $R^1$, $R^2$, and $R^3$ and n are as defined herein.

In another aspect, the invention provides a pharmaceutical composition comprising a compound of Formula (I), (II), (III) or (IV), or a pharmaceutically acceptable salt thereof.

In another aspect, the invention provides a pharmaceutical composition comprising a compound of Formula (I), (II), (III) or (IV), or a pharmaceutically acceptable salt thereof, and a pharmaceutically acceptable carrier or excipient. In some embodiments, the pharmaceutical composition comprises two or more pharmaceutically acceptable carriers and/or excipients.

In another aspect, the invention provides a pharmaceutical composition for the treatment of a disease or condition for which an inhibitor of HER2 mutations is indicated, comprising a compound of Formula (I), (II), (III) or (IV), or a pharmaceutically acceptable salt thereof.

In another aspect, the invention provides a pharmaceutical composition for the treatment of a disease or condition for which a brain penetrant inhibitor of HER2 is indicated, comprising a compound of Formula (I), (II), (III) or (IV), or a pharmaceutically acceptable salt thereof. In a further aspect, the invention provides a pharmaceutical composition for the treatment of a disease or condition for which a brain penetrant inhibitor of HER2 mutations is indicated, comprising a compound of Formula (I), (II), (III) or (IV), or a pharmaceutically acceptable salt thereof.

In another aspect, the invention provides a pharmaceutical composition for use in the treatment of abnormal cell growth, in particular cancer, in a subject in need thereof, which pharmaceutical composition comprises a compound of Formula (I), (II), (III) or (IV), or a pharmaceutically acceptable salt thereof, and a pharmaceutically acceptable carrier or excipient.

The invention also provides therapeutic methods and uses comprising administering a compound of Formula (I), (II), (III) or (IV), or a pharmaceutically acceptable salt thereof, to a subject.

In another aspect, the invention provides a compound of Formula (I), (II), (III) or (IV), or a pharmaceutically acceptable salt thereof, for use in the treatment of a subject in need of such treatment. In some embodiments, the invention provides a compound of Formula (I), (II), (III) or (IV), or a pharmaceutically acceptable salt thereof, for use in the treatment of abnormal cell growth, in particular cancer, in a subject.

In a further aspect, the invention provides the use of a compound of Formula (I), (II), (III) or (IV), or a pharmaceutically acceptable salt thereof, for the treatment of abnormal cell growth, in particular cancer, in a subject.

In yet another aspect, the invention provides the use of a compound of Formula (I), (II), (III) or (IV), or a pharmaceutically acceptable salt thereof, for the manufacture of a medicament for the treatment of abnormal cell growth, such as cancer, in a subject.

In another aspect, the invention provides a compound of Formula (I), (II), (III) or (IV), or a pharmaceutically acceptable salt thereof, for use as a medicament, in particular a medicament for the treatment of abnormal cell growth, such as cancer.

In yet another aspect, the invention provides the use of a compound of Formula (I), (II), (III) or (IV), or a pharmaceutically acceptable salt thereof, as defined in any of the embodiments described herein, for the manufacture of a medicament for treating a disease or condition for which an inhibitor of HER2 mutations is indicated.

In yet another aspect, the invention provides the use of a compound of Formula (I), (II), (III) or (IV), or a pharmaceutically acceptable salt thereof, as defined in any of the embodiments described herein, for the manufacture of a medicament for treating a disease or condition for which a brain penetrant inhibitor of HER2 is indicated. In a further aspect, the invention provides the use of a compound of Formula (I), (II), (III) or (IV), or a pharmaceutically acceptable salt thereof, as defined in any of the embodiments described herein, for the manufacture of a medicament for treating a disease or condition for which a brain penetrant inhibitor of HER2 mutations is indicated.

In yet another aspect, the invention provides a compound of Formula (I), (II), (III) or (IV), or a pharmaceutically acceptable salt thereof, as defined in any of the embodiments described herein, for use in the treatment of a disease or condition for which an inhibitor of HER2 mutations is indicated.

In yet another aspect, the invention provides a compound of Formula (I), (II), (III) or (IV), or a pharmaceutically acceptable salt thereof, as defined in any of the embodiments described herein, for use in the treatment of a disease or condition for which a brain penetrant inhibitor of HER2 is indicated. In a further aspect, the invention provides a compound of Formula (I), (II), (III) or (IV), or a pharmaceutically acceptable salt thereof, as defined in any of the embodiments described herein, for use in the treatment of a disease or condition for which a brain penetrant inhibitor of HER2 mutations is indicated.

In another aspect, the invention provides a compound of Formula (I), (II), (III) or (IV), or a pharmaceutically acceptable salt thereof, as defined in any of the embodiments herein, for use in the treatment of cancer.

In another aspect, the invention provides a compound of Formula (I), (II), (III) or (IV), or a pharmaceutically acceptable salt thereof, as defined in any of the embodiments herein, for use as a medicament.

In another aspect, the invention provides a compound of Formula (I), (II), (III) or (IV), or a pharmaceutically acceptable salt thereof, as defined in any of the embodiments herein, for use in therapy.

In yet another aspect, the invention provides a compound of Formula (I), (II), (III) or (IV), or a pharmaceutically acceptable salt thereof, as defined in any of the embodiments herein, for use in the treatment of a disease or condition for which an inhibitor of HER2 mutations is indicated.

In yet another aspect, the invention provides a compound of Formula (I), (II), (III) or (IV), or a pharmaceutically acceptable salt thereof, as defined in any of the embodiments herein, for use in the treatment of a disease or condition for which a brain penetrant inhibitor of HER2 is indicated. In a further aspect, the invention provides a compound of Formula (I), (II), (III) or (IV), or a pharmaceutically acceptable salt thereof, as defined in any of the embodiments herein, for use in the treatment of a disease or condition for which a brain penetrant inhibitor of HER2 mutations is indicated.

In one aspect, the invention provides a method for treating abnormal cell growth, in particular cancer, in a subject in need thereof, comprising administering to the subject a therapeutically effective amount of a compound of Formula (I), (II), (III) or (IV), or a pharmaceutically acceptable salt thereof. Compounds of Formula (I), (II), (III) or (IV), may be administered as single agents or may be administered in combination with other anti-cancer therapeutic agents, in particular with standard of care agents appropriate for the particular cancer.

In another aspect, the invention provides a method for treating abnormal cell growth, in particular cancer, comprising administering a therapeutically effective amount of a compound of Formula (I), (II), (III) or (IV), or a pharmaceutically acceptable salt thereof.

In another aspect, the invention provides a method for treating or ameliorating abnormal cell growth, in particular cancer, in a patient in need thereof comprising administering to the patient a compound of Formula (I), (II), (III) or (IV), or a pharmaceutically acceptable salt thereof.

In another aspect, the invention provides a method for treating a disorder mediated by HER2 mutations in a subject, comprising administering to the subject a compound of Formula (I), (II), (III) or (IV), or a pharmaceutically acceptable salt thereof, in an amount that is effective for treating said disorder, in particular cancer.

In another aspect, the invention provides a method for treating a disorder mediated by brain metasteses from HER2 amplified or HER2 positive cancer in a subject, comprising administering to the subject a compound of Formula (I), (II), (III) or (IV), or a pharmaceutically acceptable salt thereof, in an amount that is effective for treating said disorder.

In another aspect, the invention provides a method for treating a disease or disorder modulated by HER2 mutations, comprising administering to a mammal in need of such treatment an effective amount of a compound of Formula (I), (II), (III) or (IV), or a pharmaceutically acceptable salt thereof.

In another aspect, the invention provides a method for treating a disease or disorder modulated by brain metasteses from HER2 amplified or HER2 positive cancer, comprising administering to a mammal in need of such treatment an effective amount of a compound of Formula (I), (II), (III) or (IV), or a pharmaceutically acceptable salt thereof.

In a further aspect, the invention provides a method for treating abnormal cell growth, in particular cancer, in a subject in need thereof, comprising administering to the subject an amount of a compound of Formula (I), (II), (III) or (IV), or a pharmaceutically acceptable salt thereof, in combination with an amount of an additional anti-cancer therapeutic agent, which amounts are together effective in treating said abnormal cell growth.

In another aspect, the invention provides a method of inhibiting HER2 mutation activity in a cell comprising treating the cell with a compound of Formula (I), (II), (III) or (IV), or a pharmaceutically acceptable salt thereof.

In another aspect, the invention provides a method of inhibiting HER2 mutation activity in a patient in need thereof comprising administering to the patient a compound of Formula (I), (II), (III) or (IV), or a pharmaceutically acceptable salt thereof.

In another aspect, the invention provides a method of inhibiting brain metastasis activity from HER2 amplified or HER2 positive cancer in a patient in need thereof comprising administering to the patient a compound of Formula (I), (II), (III) or (IV), or a pharmaceutically acceptable salt thereof.

Each of the embodiments of the compounds of the present invention described below can be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein unless explicitly indicated to the contrary.

Besides being useful for human treatment, compounds of Formula (I) (II), (III) or (IV) are also useful for veterinary treatment of companion animals, exotic animals and farm animals.

DETAILED DESCRIPTION OF THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. In the event that one or more of the incorporated literature and similar materials differs from or contradicts this application, including but not limited to defined terms, term usage, described techniques, or the like, this application controls.

Definitions

As used herein, the singular form "a", "an", and "the" include plural references unless indicated otherwise. For example, "a" substituent includes one or more substituents.

The invention described herein may be practiced in the absence of any element(s) not specifically disclosed herein. Thus, for example, in each instance herein any of the terms "comprising", "consisting essentially of", and "consisting of" may be replaced with either of the other two terms.

"Alkyl", as used herein, means a saturated, monovalent aliphatic hydrocarbon radical including straight chain and branched chain groups having the specified number of carbon atoms. Alkyl substituents typically contain 1 to 12 carbon atoms ("$C_1$-$C_{12}$ alkyl"), frequently 1 to 8 carbon atoms ("$C_1$-$C_8$ alkyl"), or more frequently 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl") or 1 to 2 carbon atoms ("$C_1$-$C_2$ alkyl"). Examples of alkyl groups include methyl, ethyl, n-propyl, isopropyl, n-butyl, sec-butyl, isobutyl, tert-butyl, n-pentyl, isopentyl, neopentyl, n-hexyl, n-heptyl, n-octyl and the like. Preferred $C_1$-$C_4$ alkyl groups include methyl, ethyl, n-propyl, isopropyl, n-butyl, sec-butyl, isobutyl, and tert-butyl. Preferred $C_1$-$C_6$ alkyl groups include methyl, ethyl, n-propyl, isopropyl, n-butyl, sec-butyl, isobutyl, tert-butyl, n-pentyl, isopentyl, neopentyl, and n-hexyl.

Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or f-butyl ("f-Bu") and the like. The abbreviations are sometimes used in conjunction with elemental abbreviations and chemical structures, for example, methanol ("MeOH") or ethanol ("EtOH").

Alkyl groups described herein as optionally substituted may be substituted by one or more substituent groups, as further defined by the claims herein. Such optional substituent groups are selected independently unless otherwise indicated. The total number of substituent groups may equal the total number of hydrogen atoms on the alkyl moiety, to the extent such substitution makes chemical sense.

In some instances, substituted alkyl groups are specifically named by reference to the substituent group. For example, "haloalkyl" refers to an alkyl group having the specified number of carbon atoms that is substituted by one or more halo substituents, and typically contains 1-6 carbon atoms, 1-5 carbon atoms, 1-4 carbon atoms or 1-2 carbon atoms and 1, 2 or 3 halo atoms (i.e., "$C_1$-$C_5$ haloalkyl", "$C_1$-$C_4$ haloalkyl" or "$C_1$-$C_2$ haloalkyl"). Non-limiting examples include fluoromethyl, difluoromethyl, trifluoromethyl and 2,2,2-trifluoroethyl.

More specifically, fluorinated alkyl groups may be specifically referred to as "fluoroalkyl" groups, (e.g., $C_1$-$C_6$, $C_1$-$C_5$, $C_1$-$C_4$ or $C_1$-$C_2$ fluoroalkyl groups), which are typically substituted by 1, 2 or 3 fluoro atoms. For example, a $C_1$-$C_4$ fluoroalkyl includes trifluoromethyl (—$CF_3$), difluoromethyl (—$CF_2H$), fluoromethyl (—$CFH_2$), difluoroethyl (—$CH_2CF_2H$), and the like. Such groups may be further substituted by optional substituent groups as further described herein. Similarly, alkyl groups substituted by —OH, $C_1$-$C_4$ alkoxy or $NR^xR^y$ could be referred to as "hydroxyalkyl", "alkoxyalkyl" or "aminoalkyl", in each case having the indicated number of carbon atoms.

In some embodiments of the present invention, alkyl and fluoroalkyl groups are optionally substituted by one or more optional substituents.

"Alkoxy", as used herein, means a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes methoxy, ethoxy, isopropoxy, tert-butyloxy, (i.e., —$OCH_3$, —$OCH_2CH_3$, —$OCH(CH_3)_2$, —$OC(CH_3)_3$), and the like. Alkoxy groups may be optionally substituted by one or more halo atoms, and in particular one or more fluoro atoms, up to the total number of hydrogen atoms present on the alkyl portion. Such groups may be referred to as "haloalkoxy" (or, where fluorinated, more specifically as "fluoroalkoxy") groups having the specified number of carbon atoms and substituted by one or more halo substituents. Typically, such groups contain from 1-6 carbon atoms, preferably 1-4 carbon atoms, and sometimes 1-2 carbon atoms, and 1, 2 or 3 halo atoms (i.e., "$C_1$-$C_6$ haloalkoxy", "$C_1$-$C_4$ haloalkoxy" or "$C_1$-$C_2$ haloalkoxy"). More specifically, fluorinated alkyl groups may be specifically referred to as "fluoroalkoxy" groups, e.g., $C_1$-$C_6$, $C_1$-$C_4$ or $C_1$-$C_2$ fluoroalkoxy groups, which are typically substituted by 1, 2 or 3 fluoro atoms. Thus, a $C_1$-$C_4$ fluoroalkoxy includes, but is not limited to, trifluoromethyloxy (—$OCF_3$), difluoromethyloxy (—$OCF_2H$), fluoromethyloxy (—$OCFH_2$), difluoroethyloxy (—$OCH_2CF_2H$), and the like.

"Alkoxyalkyl", as used herein, means an alkoxy group attached through an alkyl group. Non-limiting examples include methoxymethyl, 2-ethoxyethyl, 2-methoxyethyl, and methoxymethyl.

When a substituent is defined as a combination of two groups (e.g., alkoxyalkyl) the moiety concerned is always attached through the second of the two groups named (in this case alkyl). Thus, for example, ethoxymethyl corresponds to $CH_2CH_3$—O—$CH_2$—.

"Cycloalkyl" as used herein, means a non-aromatic, saturated carbocyclic ring system of the formula —$C_nH_{(2n-1)}$, containing at least three carbon atoms, which may be a monocyclic, spirocyclic, bridged or fused bicyclic, or polycyclic ring system that is connected to the base molecule through a carbon atom of the cycloalkyl ring. Typically, the cycloalkyl groups of the invention contain 3 to 8 carbon atoms ("$C_3$-$C_8$cycloalkyl"), preferably 3 to 7 carbon atoms ("$C_3$-$C_7$ cycloalkyl") or 3 to 6 carbon atoms ("$C_3$-$C_6$ cycloalkyl"). Representative examples of cycloalkyl rings include, e.g., cyclopropane, cyclobutane, cyclopentane, cyclohexane, cycloheptane, and the like. Cycloalkyl groups may be optionally substituted, unsubstituted or substituted by the groups described herein.

"Heterocyclyl" or "heterocyclic", as used herein, may be used interchangeably to mean a non-aromatic, saturated ring system containing the specified number of ring atoms, containing at least one heteroatom selected from N, O, S, SO and $SO_2$ as a ring member, and where the heterocyclic ring is connected to the base molecule via a ring atom. Where specifically indicated, such heterocyclic rings may be partially unsaturated. Heterocyclic rings include rings that are spirocyclic, bridged, or fused to one or more other heterocyclic or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocyclic portion of the ring system. Preferably, heterocyclic rings contain 1 to 3 heteroatoms selected from N, O, and $S(O)_2$ as ring members, and more preferably 1 to 2 ring heteroatoms, provided that such heterocyclic rings do not contain two contiguous oxygen atoms.

Heterocyclyl groups are unsubstituted or substituted by suitable substituent groups as described herein. Such substituents may be present on the heterocyclic ring attached to the base molecule, or on a spirocyclic, bridged or fused ring attached thereto. In addition, ring N or C atoms are optionally substituted by suitable groups.

Heterocycles typically include 3-10 membered heterocyclyl groups, and more preferably 4-10 or 4-6 membered heterocyclyl groups, in accordance with the definition herein.

Examples of saturated heterocycles include, but are not limited to, oxirane (oxiranyl), thiirane (thiaranyl), aziridine (aziridinyl), oxetane (oxetanyl), thietane (thietanyl), azetidine (azetidinyl), tetrahydrofuran (tetrahydrofuranyl), tetrahydrothiophene (tetrahydrothiophenyl), pyrrolidine (pyrrolidinyl), tetrahydropyran (tetrahydropyranyl), tetrahydrothiopyran (tetrahydrothiopyranyl), piperidine (piperidinyl), 1,4-dioxane (1,4-dioxanyl), 1,4-oxathiarane (1,4-oxathiaranyl), morpholine (morpholinyl), 1,4-dithiane (1,4-dithianyl), piperazine (piperazinyl), thiomorpholine (thiomorpholinyl), oxepane (oxepanyl), thiepane (thiepanyl), azepane (azepanyl), 1,4-dioxepane (1,4-dioxepanyl), 1,4-oxathiepane (1,4-oxathiepanyl), 1,4-oxaazepane (1,4-oxaazepanyl), 1,4-thieazepane (1,4-thieazapanyl), 1,4-diazepane (1,4-diazepanyl), and 1,4-dithiepane (1,4-dithiepanyl).

It is understood that no more than two N, O or S atoms are ordinarily connected sequentially, except where an oxo group is attached to S to form a sulfonyl group, or in the case of certain heteroaryl rings, such as triazole, tetrazole, oxadiazole, thiadiazole, triazine and the like.

"Aryl", as used herein, means an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl or heteroaryl ring or fused to a saturated or partially unsaturated carbocyclic or heterocyclic ring, provided the point of attachment to the base molecule on such fused ring systems is an atom of the aromatic portion of the ring system. Examples, without limitation, of aryl groups include phenyl, biphenyl, naphthyl, anthracenyl, phenanthrenyl, indanyl, indenyl, and tetrahydronaphthyl. The aryl group is unsubstituted or substituted as further described herein.

"Heteroaryl", as used herein, means a monocyclic or fused bicyclic or polycyclic ring systems having the well-known characteristics of aromaticity that contain the specified number of ring atoms as defined above under "aryl" which include at least one heteroatom selected from N, O and S as a ring member in an aromatic ring. The inclusion of a heteroatom permits aromaticity in 5-membered rings as well as 6-membered rings. Typically, heteroaryl groups contain 5 to 12 ring atoms ("5-12 membered heteroaryl"), and more preferably 5 to 10 ring atoms ("5-10 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Heteroaryl groups may also be fused to another aryl or heteroaryl ring or fused to a saturated or partially unsaturated carbocyclic or heterocyclic ring, provided the point of attachment to the base molecule on such fused ring systems is an atom of the heteroaromatic portion of the ring system. Examples of unsubstituted heteroaryl groups include, but are not limited to, monocyclic heteroaryl groups such as pyrrole (pyrrolyl), furan (furanyl), thiophene (thiophenyl), pyrazole (pyrazolyl), imidazole (imidazolyl), isoxazole (isoxazolyl), oxazole (oxazolyl), isothiazole (isothiazolyl), thiazole (thiazolyl), 1,2,3-triazole (1,2,3-triazolyl), 1,3,4-triazole (1,3,4-triazolyl), 1-oxa-2,3-diazole (1-oxa-2,3-diazolyl), 1-oxa-2,4-diazole (1-oxa-2,4-diazolyl), 1-oxa-2,5-diazole (1-oxa-2,5-diazolyl), 1-oxa-3,4-diazole (1-oxa-3,4-diazolyl), 1-thia-2,3-diazole (1-thia-2,3-diazolyl), 1-thia-2,4-diazole (1-thia-2,4-diazolyl), 1-thia-2,5-diazole (1-thia-2,5-diazolyl), 1-thia-3,4-diazole (1-thia-3,4-diazolyl), tetrazole (tetrazolyl), pyridine (pyridinyl), pyridazine (pyridazinyl), pyrimidine (pyrimidinyl) and pyrazine (pyrazinyl), and fused heteroaryl groups such as benzofuran (benzofuranyl), benzothiophene (benzothiophenyl), indole (indolyl), benzimidazole (benzimidazolyl), indazole (indazolyl), benzotriazole (benzotriazolyl), pyrrolo[2,3-b]pyridine (pyrrolo[2,3-b]pyridinyl), pyrrolo[2,3-c]pyridine (pyrrolo[2,3-c]pyridinyl), pyrrolo[3,2-c]pyridine (pyrrolo[3,2-c]pyridinyl), pyrrolo[3,2-b]pyridine (pyrrolo[3,2-b]pyridinyl), imidazo[4,5-b]pyridine (imidazo[4,5-b]pyridinyl), imidazo[4,5-c]pyridine (imidazo[4,5-c]pyridinyl), pyrazolo[4,3-d]pyridine (pyrazolo[4,3-d]pyridinyl), pyrazolo[4,3-c]pyridine (pyrazolo[4,3-c]pyridinyl), pyrazolo[3,4-c]pyridine (pyrazolo[3,4-c]pyridinyl), pyrazolo[3,4-b]pyridine (pyrazolo[3,4-b]pyridinyl), isoindole (isoindolyl), indazole (indazolyl), purine (purinyl), indolizine (indolizinyl), imidazo[1,2-a]pyridine (imidazo[1,2-a]pyridinyl, imidazo[1,5-a]pyridine (imidazo[1,5-a]pyridinyl, pyrazolo[1,5-a]pyridine (pyrazolo[1,5-a]pyridinyl), pyrrolo[1,2-b]pyridazine (pyrrolo[1,2-b]pyridazinyl), imidazo[1,2-c]pyrimidine (imidazo[1,2-b]pyridazinyl), quinoline (quinolinyl), isoquinoline (isoquinolinyl), cinnoline (cinnolinyl), quinazoline (quinazolinyl), quinoxaline (quinoxalinyl), phthalazine (phthalazinyl), 1,5-naphthyridine (1,5-napthyridinyl), 1,6-naphthyridine (1,6-napthyridinyl), 1,7-naphthyridine (1,7-napthyridinyl), 1,8-naphthyridine (1,8-napthyridinyl), 2,6-naphthyridine (2,6-napthyridinyl), 2,7-naphthyridine (2,7-napthyridinyl), pyrido[3,2-d]pyrimidine (pyrido[3,2-d]pyrimidinyl), pyrido[4,3-d]pyrimidine (pyrido[4,3-d]pyrimidinyl), pyrido[3,4-d]pyrimidine (pyrido[3,4-d]pyrimidinyl), pyrido[2,3-d]pyrimidine (pyrido[2,3-d]pyrimidinyl), pyrido[2,3-b]pyrazine (pyrido[2,3-b]pyrazinyl), pyrido[3,4-b]pyrazine (pyrido[3,4-b]pyrazinyl), pyrimido[5,4-d]pyrimidine (pyrimido[5,4-d]pyrimindinyl), pyrazino[2,3-b]pyrazine (pyrazino[2,3-b]pyrazinyl), and pyrimido[4,5-d]pyrimidine (pyrimido[4,5-d]pyrimidinyl). The heteroaryl group is unsubstituted or substituted as further described herein.

Aryl and heteroaryl moieties described herein as optionally substituted may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings.

"Benzyl", as used herein, means a phenylmethyl group.
"Carboxy", as used herein, means a —CO$_2$H group.
"Cyano", as used herein, means a —C≡N group.
"Formyl", as used herein, means a —C(O)H group.
"Hydroxy", as used herein, means an OH group.
"Halogen" or "halo", as used herein, means fluoro, chloro, bromo and iodo (F, Cl, Br, I). Preferably, halo refers to fluoro or chloro (F or Cl).
"Oxo", as used herein, refers to a double bonded oxygen (=O).
"Alkylthio", as used herein, means an alkyl group attached through a sulfur molecule (—S(alkyl)). For example, $C_1$-$C_3$ alkylthio means a —S($C_1$-$C_3$ alkyl) group, and methylthio means a —S(CH$_3$) group.
"Unsubstituted amino", as used herein, means a group —NH$_2$. Where the amino is described as substituted or optionally substituted, the term includes groups of the form —NR$^x$R$^y$, where each of R$^x$ and R$^y$ is defined as further described herein. For example, "alkylamino" refers to a group —NR$^x$R$^y$, wherein one of R$^x$ and R$^y$ is an alkyl moiety and the other is H, and "dialkylamino" refers to —NR$^x$R$^y$ wherein both of R$^x$ and R$^y$ are alkyl moieties, where the alkyl moieties having the specified number of carbon atoms (e.g., —NH($C_1$-$C_4$ alkyl) or —N($C_1$-$C_4$ alkyl)$_2$). It will be understood that NR$^x$R$^y$ is being used generically in this paragraph to refer to amino substituents (e.g., NR$^{10}$R$^{11}$ as part of an optional substituent group R$^5$ or NR$^{14}$R$^{15}$ as part of an optional substituent group R$^{13}$) as defined by the claims.

"Optional" or "optionally" means that the subsequently described event or circumstance may but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups are the same or different. Throughout the disclosure, it will be understood that the number and nature of optional substituent groups will be limited to the extent that such substitutions make chemical sense.

Frequently, a group described herein as optionally substituted by "one or more" substituent groups is optionally substituted by 1 to 4, preferably optionally substituted by 1 to 3, and more preferably optionally substituted by 1 to 2 such substituents. The recitation herein that a group is "optionally substituted by one or more" of a list of optional substituents may be replaced by "optionally substituted by 1 to 4", "optionally substituted by 1 to 3", "optionally substituted by 1 to 2", "optionally substituted by one, two, three or four", "optionally substituted by one, two or three" or "optionally substituted by one or two" of such optional substituent groups.

If substituents are described as being "independently selected" from a group, each substituent is selected independent of the other. Each substituent therefore may be identical to or different from the other substituent(s).

"Pharmaceutically acceptable", as used herein, means that the substance or composition is compatible chemically and/or toxicologically, with the other ingredients comprising a formulation, and/or the mammal being treated therewith.

"HER2 mutations", as used herein, means one or more mutations in the HER2 receptor tyrosine-protein kinase. In certain embodiments, the HER2 mutation is the YVMA (SEQ ID NO: 2) insertion at exon 20 of HER2 ("HER2-YVMA").

"Selective", as used herein to describe a functionally-defined receptor ligand or enzyme inhibitor, means selective for the defined receptor or enzyme subtype as compared with other receptor or enzyme subtypes in the same family. For instance, a selective HER2 mutation inhibitor is a compound that inhibits the HER2-YVMA (SEQ ID NO: 2) insert enzyme subtype more potently than EGFR enzyme subtype. Such selectivity is, in one embodiment, at least 2-fold (as measured using conventional binding assays), or, in another embodiment, at least 10-fold, or, in a further embodiment, at least 100-fold.

Additional abbreviations used throughout the application include: approximately ("~"), acetyl ("Ac"), acetonitrile ("AON"), acetoxy ("AcO" or "OAc"), aqueous ("aq"), benzyl ("Bn"), methylene chloride/dichloromethane/CFhCh ("DCM"), diethylamine ("DEA"), diisopropylethyl amine ("DIPEA"), N,N-dimethylacetamide ("DMA"), 4-dimethylaminopyridine ("DMAP"), N,N-dimethyl formamide ("DMF"), dimethylsulfoxide ("DMSO"), ethyl acetate ("EtOAc"), hours ("h"), 1-[bis(dimethylamino)methylene]-1H-1,2,3-triazolo[4,5-b]pyridinium 3-oxid hexafluorophosphate ("HATU"), acetic acid ("HOAc" or "AcOH"), isopropyl alcohol ("IPA"), minutes ("min"), mass spectrometry ("MS"), methyl tert-butyl ether ("MTBE"), phenyl ("Ph"), retention fraction ("Rf"), retention time ("rt"), saturated ("sat."), supercritical fluid chromatography ("SFC"), propylphosphonic anhydride ("T3P"), trifluoroacetic acid ("TFA"), tetrahydrofuran ("THF"), thin layer chromatography ("TLC").

A bond drawn into a ring system (as opposed to connected at a distinct vertex) indicates that the bond may be attached to any of the suitable ring atoms. A wavy line ($\mathcal{X}$) across a bond indicates the point of attachment.

HER2 Mutation Inhibitor Compounds

In one aspect, the invention provides a compound of Formula (I):

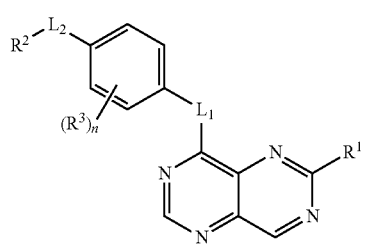

(I)

or a pharmaceutically acceptable salt thereof, wherein:
$L_1$ is selected from NH and O;
$L_2$ is selected from O and S;
$R^1$ is selected from the group consisting of $C_{1-3}$ alkylthio; methylsulfonyl; $OR^c$; $C_{1-6}$ alkoxy optionally substituted with 1 to 3 groups selected from the group consisting of halogen, hydroxy, methoxy, and a 4 to 6 membered heterocyclyl containing 1 to 3 heteroatoms selected from the group consisting of N, O and S, wherein the heterocyclyl is optionally substituted with 1 to 3 groups selected from halogen and methyl; $NR^aR^b$; a 4-10 membered heterocyclyl containing 1-3 heteroatoms selected from the group consisting of N, O, S, SO and $SO_2$, wherein the heterocyclyl is optionally substituted with 1 to 5 groups selected from the group consisting of halogen, hydroxy, oxo, acetyl, acetoxy, cyano, methylsulfonyl, $C_{1-5}$ alkyl optionally substituted with 1 to 5 groups selected from the group consisting of halogen, hydroxy, cyano, methyl, methylsulfonyl, methoxy, difluoromethoxy, and oxo, $C_{1-4}$ alkoxy optionally substituted with 1 or 2 groups selected from halogen, methoxy, and methylsulfonyl, $C_{1-4}$ haloalkyl, and a 4-6 membered heterocyclyl containing 1-3 heteroatoms selected from N, O and S; a 5-6 membered heteroaryl containing 1 to 3 heteroatoms selected from N, O and S, wherein the heteroaryl is optionally substituted with one $C_{1-3}$ alkyl group; (4,4-dimethyl-4,5-dihydrooxazol-2-yl)amino; (4-oxido-1,4$\lambda^6$-oxathian-4-ylidene)amino; 4-methyl-4-oxido-1,4-azaphosphinan-1-yl; and 4,4-dimethyl-1,4-azasilinan-1-yl;

$R^2$ is a 9-10 membered bicyclic heteroaryl containing one to three heteroatoms selected from N, O and S, wherein the bicyclic heteroaryl may be optionally substituted with one or two groups selected from halogen, $C_1$-$C_3$ alkyl and cyclopropyl;

each $R^3$ is selected from halogen and methyl;

$R^a$ and $R^b$ are independently selected from the group consisting of hydrogen; $C_{1-6}$ alkyl optionally substituted with 1 to 6 groups selected from hydroxy, methoxy, trifluoromethoxy, halogen, cyano, methoxy (methyl)amino, a 4-6 membered heterocyclyl containing 1 to 3 heteroatoms selected from N, O and S, wherein the heterocyclyl is optionally substituted with a hydroxy group, and $C_{3-6}$ cycloalkyl optionally substituted with a hydroxy group; $C_{1-6}$ alkoxy optionally substituted with 1 to 3 groups selected from hydroxy and halogen; $C_{3-6}$ cycloalkyl optionally substituted with 1 or 2 groups selected from hydroxy, methoxy and $C_{1-3}$ alkyl optionally substituted with a hydroxy group; a 4-6 membered heterocyclyl containing 1 to 3 heteroatoms selected from N, O and S, wherein the heterocyclyl is optionally substituted with 1 to 3 groups selected from halogen, $C_{1-3}$ alkyl, and $C_{1-3}$ alkoxy; a 5-6 membered heteroaryl containing 1 to 3 heteroatoms selected from N, O and S, wherein the heteroaryl is optionally substituted by 1 to 3 $C_{1-3}$ alkyl groups; and benzyl;

$R^c$ is a 4 to 6 membered heterocyclyl containing 1 to 3 heteroatoms selected from the group consisting of N, O and S, wherein the heterocyclyl is optionally substituted with 1 or 2 groups selected from halogen, and $C_{1-3}$ alkyl optionally substituted with one to three halogens;

n is 0, 1 or 2.

In another embodiment, the invention provides a compound of Formula (II):

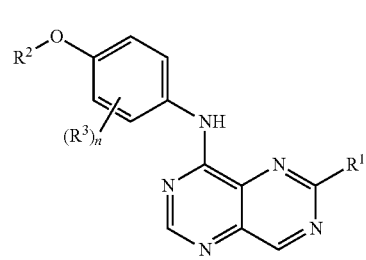

(II)

or a pharmaceutically acceptable salt thereof, wherein $R^1$, $R^2$, $R^3$ and n are as defined in any of the embodiments described herein.

In another embodiment, the invention provides a compound of Formula (III):

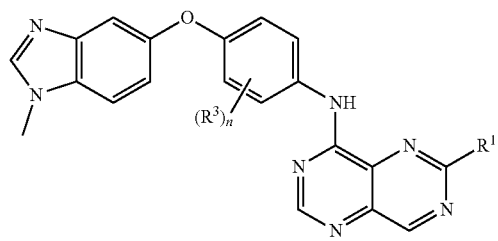

(III)

or a pharmaceutically acceptable salt thereof, wherein $R^1$, $R^2$, $R^3$ and n are as defined in any of the embodiments described herein.

In another embodiment, the invention provides a compound of Formula (IV):

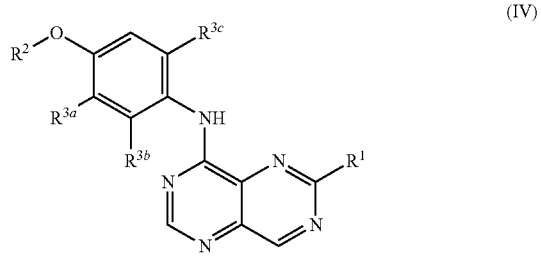

(IV)

or a pharmaceutically acceptable salt thereof, wherein $R^1$ and $R^2$ are as defined in any of the embodiments described herein, $R^{3a}$ is halogen or methyl, $R^{3b}$ is hydrogen or halogen, and $R^{3c}$ is hydrogen or halogen, wherein at least one of $R^{3b}$ and $R^{3c}$ is hydrogen. In another embodiment of Formula (IV), $R^{3a}$ is fluoro, chloro or methyl, $R^{3b}$ is hydrogen, fluoro or chloro, and $R^{3c}$ is hydrogen, fluoro or chloro, wherein at least one of $R^{3b}$ and $R^{3c}$ is hydrogen. In another embodiment of Formula (IV):

$R^{3a}$ is methyl, $R^{3b}$ is hydrogen, and $R^{3c}$ is hydrogen;
$R^{3a}$ is methyl, $R^{3b}$ is fluoro or chloro, and $R^{3c}$ is hydrogen;
$R^{3a}$ is methyl, $R^{3b}$ is hydrogen, and $R^{3c}$ is fluoro or chloro;
$R^{3a}$ is fluoro, $R^{3b}$ is hydrogen, and $R^{3c}$ is hydrogen;
$R^{3a}$ is chloro, $R^{3b}$ is hydrogen, and $R^{3c}$ is hydrogen; or
$R^{3a}$ is chloro, $R^{3b}$ is fluoro, and $R^{3c}$ is hydrogen.

In another embodiment of Formula (IV), $R^{3a}$ is methyl, $R^{3b}$ is hydrogen, and $R^{3c}$ is hydrogen. In another embodiment of Formula (IV), $R^{3a}$ is methyl, $R^{3b}$ is fluoro, and $R^{3c}$ is hydrogen. In another embodiment of Formula (IV), $R^{3a}$ is methyl, $R^{3b}$ is hydrogen, and $R^{3c}$ is fluoro. In another embodiment of Formula (IV), $R^{3a}$ is fluoro, $R^{3b}$ is hydrogen, and $R^{3c}$ is hydrogen. In another embodiment of Formula (IV), $R^{3a}$ is chloro, $R^{3b}$ is hydrogen, and $R^{3c}$ is hydrogen. In another embodiment of Formula (IV), $R^{3a}$ is chloro, $R^{3b}$ is fluoro, and $R^{3c}$ is hydrogen.

In another embodiment, the invention provides compounds of Formula (I), or pharmaceutically acceptable salts thereof, wherein:
$L_1$ is selected from NH and O;
$L_2$ is selected from O and S;
$R^1$ is selected from the group consisting of hydrogen, halogen, $C_{1-3}$ alkylthio, methylsulfonyl, $NR^aR^b$, $C_{1-3}$ alkoxy, and a 4-7 membered heterocyclyl containing 1 to 3 heteroatoms independently selected from N, O, and S, wherein the heterocyclyl is optionally substituted with 1 or 2 groups selected from halogen, $C_1$-$C_4$ alkyl, $C_1$-$C_4$ alkoxy, and $C_1$-$C_4$ haloalkyl;
$R^2$ is a 9-10 membered bicyclic heteroaryl containing one to three heteroatoms selected from N, O and S, wherein the bicyclic heteroaryl may be optionally substituted with one or two groups selected from halogen and $C_1$-$C_3$ alkyl;
each $R^3$ is selected from halogen and methyl;
$R^a$ and $R^b$ are independently selected from hydrogen and $C_1$-$C_3$ alkyl; and
n is 0, 1 or 2.

In another embodiment, the invention provides compounds of Formula (I), or pharmaceutically acceptable salts thereof, wherein:
$L_1$ is NH;
$L_2$ is O;
$R^1$ is selected from the group consisting of $C_{1-3}$ alkylthio, methylsulfonyl, $NR^aR^b$, $C_{1-3}$ alkoxy, and a 4-7 membered heterocyclyl containing 1 or 2 heteroatoms independently selected from N and O;
$R^2$ is selected from 1H-benzo[d]imidazole-5-yl, benzo[c]isoxazole-6-yl, and benzo[c]isothiazol-6-yl, wherein each may be optionally substituted with a methyl group;
$R^3$ is methyl;
each $R^a$ and $R^b$ are independently selected from hydrogen and methyl; and
n is 1.

In another embodiment, the invention provides compounds of Formula (I), or pharmaceutically acceptable salts thereof, wherein:
$L_1$ is NH;
$L_2$ is O;
$R^1$ is selected from the group consisting of methylthio; methylsulfonyl; $OR^c$; $C_{1-4}$ alkoxy optionally substituted with 1 or 2 groups selected from the group consisting of halogen, hydroxy, methoxy, and a 4 membered heterocyclyl containing 1 N heteroatom, wherein the heterocyclyl is optionally substituted with 1 or 2 groups selected from halogen and methyl; $NR^aR^b$; a 4-10 membered heterocyclyl containing 1-3 heteroatoms selected from the group consisting of N, O and $SO_2$, wherein the heterocyclyl is optionally substituted with 1 to 3 groups selected from the group consisting of fluoro, hydroxy, oxo, acetyl, acetoxy, cyano, methylsulfonyl, $C_{1-3}$ alkyl optionally substituted with 1 to 3 groups selected from the group consisting of halogen, hydroxy, cyano, methyl, methylsulfonyl, methoxy, and difluoromethoxy, $C_{1-2}$ alkoxy optionally substituted with 1 or 2 groups selected from fluoro, methoxy, and methylsulfonyl, and oxetanyl; a 5-6 membered heteroaryl containing 1 or 2 heteroatoms selected from N, O and S, wherein the heteroaryl is optionally substituted with methyl; (4,4-dimethyl-4,5-dihydrooxazol-2-yl)amino; (4-oxido-1,4$\lambda^6$-oxathian-4-ylidene)amino; 4-methyl-4-oxido-1,4-azaphosphinan-1-yl; and 4,4-dimethyl-1,4-azasilinan-1-yl;
$R^2$ is selected from 1H-benzo[d]imidazole-5-yl, benzo[c]isoxazole-6-yl, benzo[c]isothiazol-6-yl, benzo[d]thiazol-5-yl, 2H-indazol-6yl, and [1,2,4]triazolo[1,5-a]pyridine-7-yl, wherein each may be optionally substituted with one or two groups selected from halogen, methyl, ethyl and cyclopropyl;

each $R^3$ is selected from halogen and methyl;

$R^a$ and $R^b$ are independently selected from the group consisting of hydrogen; $C_{1-5}$ alkyl optionally substituted with 1 to 4 groups selected from hydroxy, halogen, cyano, methoxy(methyl)amino, a 4-6 membered heterocyclyl containing 1 or 2 O heteroatoms optionally substituted with a hydroxy group, and $C_{3-4}$ cycloalkyl optionally substituted with a hydroxy group; $C_{1-4}$ alkoxy optionally substituted with 1 to 3 groups selected from hydroxy and fluoro; $C_{3-5}$ cycloalkyl optionally substituted with 1 or 2 groups selected from halogen, hydroxy, methoxy and $C_{1-3}$ alkyl optionally substituted with a hydroxy group; a 4-6 membered heterocyclyl containing 1 or 2 heteroatoms selected from N and O, wherein the heterocyclyl is optionally substituted with 1 to 2 groups selected from fluoro, methyl and methoxy; a 5 membered heteroaryl containing 2 N heteroatoms substituted by 1 methyl group; and benzyl;

$R^c$ is a 5 to 6 membered heterocyclyl containing 1 N heteroatom, wherein the heterocyclyl is optionally substituted with 1 or 2 groups selected from fluoro and methyl; and n is 1 or 2.

In another embodiment, the invention provides a compound of Formula (I), (II), (III) or (IV), wherein $L_1$ is NH. In another embodiment, the invention provides a compound of Formula (I), wherein $L_1$ is O.

In another embodiment, the invention provides a compound of Formula (I), (II), (III) or (IV), wherein $L_2$ is O. In another embodiment, $L_2$ is S.

In another embodiment, the invention provides a compound of Formula (I), wherein $L_1$ is selected from NH and O and $L_2$ is O. In another embodiment, the invention provides a compound of Formula (I), wherein $L_1$ is NH and $L_2$ is O. In another embodiment, the invention provides a compound of Formula (I), wherein $L_1$ is O and $L_2$ is O.

In another embodiment, the invention provides a compound of Formula (I), wherein $L_1$ is NH and $L_2$ is O; $L_1$ is NH and $L_2$ is S; or $L_1$ is O and $L_2$ is O.

In another embodiment, the invention provides a compound of Formula (I), (II), (III), or (IV), wherein the $R^1$ is selected from the group consisting of $C_{1-3}$ alkylthio; methylsulfonyl; $OR^c$; $C_{1-6}$ alkoxy optionally substituted with 1 to 3 groups selected from the group consisting of halogen, hydroxy, methoxy, and a 4 to 6 membered heterocyclyl containing 1 to 3 heteroatoms selected from the group consisting of N, O and S, wherein the heterocyclyl is optionally substituted with 1 to 3 groups selected from halogen and methyl; $NR^aR^b$; a 4-10 membered heterocyclyl containing 1-3 heteroatoms selected from the group consisting of N, O, S, SO and $SO_2$, wherein the heterocyclyl is optionally substituted with 1 to 5 groups selected from the group consisting of halogen, hydroxy, oxo, acetyl, acetoxy, cyano, methylsulfonyl, $C_{1-5}$ alkyl optionally substituted with 1 to 5 groups selected from the group consisting of halogen, hydroxy, cyano, methyl, methylsulfonyl, methoxy, difluoromethoxy, and oxo, $C_{1-4}$ alkoxy optionally substituted with 1 or 2 groups selected from halogen, methoxy, and methylsulfonyl, $C_{1-4}$ haloalkyl, and a 4-6 membered heterocyclyl containing 1-3 heteroatoms selected from N, O and S; a 5-6 membered heteroaryl containing 1 to 3 heteroatoms selected from N, O and S, wherein the heteroaryl is optionally substituted with one $C_{1-3}$ alkyl group; (4,4-dimethyl-4,5-dihydrooxazol-2-yl)amino; (4-oxido-1,4$\lambda^6$-oxathian-4-ylidene)amino; 4-methyl-4-oxido-1,4-azaphosphinan-1-yl; and 4,4-dimethyl-1,4-azasilinan-1-yl.

In another embodiment, the invention provides a compound of Formula (I), (II), (III), or (IV), wherein $R^1$ is selected from the group consisting of methylthio; methylsulfonyl; $OR^c$; $C_{1-4}$ alkoxy optionally substituted with 1 or 2 groups selected from the group consisting of halogen, hydroxy, methoxy, and a 4 membered heterocyclyl containing 1 N heteroatom, wherein the heterocyclyl is optionally substituted with 1 or 2 groups selected from halogen and methyl; $NR^aR^b$; a 4-10 membered heterocyclyl containing 1-3 heteroatoms selected from the group consisting of N, O and $SO_2$, wherein the heterocyclyl is optionally substituted with 1 to 3 groups selected from the group consisting of fluoro, hydroxy, oxo, acetyl, acetoxy, cyano, methylsulfonyl, $C_{1-3}$ alkyl optionally substituted with 1 to 3 groups selected from the group consisting of halogen, hydroxy, cyano, methyl, methylsulfonyl, methoxy, and difluoromethoxy, $C_{1-2}$ alkoxy optionally substituted with 1 or 2 groups selected from fluoro, methoxy, and methylsulfonyl, and oxetanyl; a 5-6 membered heteroaryl containing 1 or 2 heteroatoms selected from N, O and S, wherein the heteroaryl is optionally substituted with methyl; (4,4-dimethyl-4,5-dihydrooxazol-2-yl)amino; (4-oxido-1,4$\lambda^6$-oxathian-4-ylidene)amino; 4-methyl-4-oxido-1,4-azaphosphinan-1-yl; and 4,4-dimethyl-1,4-azasilinan-1-yl.

In another embodiment, the invention provides a compound of Formula (I), (II), (III), or (IV), wherein $R^1$ is selected from the group consisting of methylthio, methylsulfonyl, (4-fluoropyrrolidin-3-yl)oxy, (4-fluoro-1-methylpyrrolidin-3-yl)oxy, (3-fluoropiperidin-4-yl)oxy, (3-fluoro-1-methylpiperidin-4-yl)oxy, (4-fluoropiperidin-3-yl)oxy, (4-fluoro-1-methylpiperidin-3-yl)oxy, (5-fluoropiperidin-3-yl)oxy, (4,4-difluoropyrrolidin-3-yl)oxy, (5-fluoro-1-methylpiperidin-3-yl)oxy, methoxy, ethoxy, 2-methoxyethoxy, 2,2-difluoroethoxy, propoxy, (3-fluoroazetidin-3-yl)methoxy, (3-fluoro-1-methylazetidin-3-yl)methoxy, 2-hydroxy-2-methylpropoxy, amino, dimethylamine, methylamine, cyclobutylamino, (tetrahydrofuran-3-yl)amino, bicyclo[1.1.1]pentan-1-ylamino, (2-hydroxy-2-methylpropyl)(methyl)amino, (cyclopropylmethyl)amino, methoxy(methyl)amino, (3,3-difluorocyclobutyl)amino, cyclopropyl(methyl)amino, (2,2-difluorocyclobutyl)amino, (2,2-difluoroethyl)(methyl)amino, (1-methoxypropan-2-yl)amino, (1-(trifluoromethoxy)propan-2-yl)amino, (3-fluoropiperidin-4-yl)amino, (3-fluoro-1-methylpiperidin-4-yl)amino, (4-fluoropyrrolidin-3-yl)(methyl)amino, (4-fluoro-1-methylpyrrolidin-3-yl)(methyl)amino, (2-hydroxy-3-methoxypropyl)(methyl)amino, (3-hydroxy-3-methylbutyl)(methyl)amino, ((1,5-dimethyl-1H-pyrazol-4-yl)methyl)amino, methyl(1-methyl-1H-pyrazol-4-yl)amino, (3-hydroxy-3-methylcyclobutyl)(methyl)amino, methyl(tetrahydrofuran-3-yl)amino, methyl(oxetan-3-yl)amino, methyl(tetrahydro-2H-pyran-4-yl)amino, ((1-hydroxycyclobutyl)methyl)(methyl)amino, (3-hydroxy-3-methylcyclobutyl)(methyl)amino, ((1-hydroxycyclopropyl)methyl)(methyl)amino, (2-hydroxycyclopentyl)(methyl)amino, (3-hydroxycyclobutyl)(methyl)amino, methyl(3,3,3-trifluoro-2-hydroxypropyl)amino, (2-hydroxypropyl)(methyl)amino, (2-cyano-2-methylpropyl)(methyl)amino, (2,2-difluoroethyl)amino, (2-hydroxyethyl)(methyl)amino, (2-hydroxy-2-methylpropoxy)amino, (2-(methoxy(methyl)amino)ethyl)amino, (1-methoxypyrrolidin-3-yl)amino, oxetan-3-ylamino, (3-methoxycyclobutyl)amino, isopropylamino, (1-methylcyclopropyl)amino, ethylamino, cyclopropylamino, cyclopentylamino, (4-fluoropyrrolidin-3-yl)amino, (4-fluoro-1-methylpyrrolidin-3-yl)amino, (4,4- difluoropyrrolidin-3-yl)amino, ((3-hydroxyoxetan-3-yl)methyl)amino, benzyl(methyl)amino, bis(2,2-difluoroethyl)amino, methyl(tetrahydro-2H-pyran-3-yl)amino, methyl(oxetan-2-ylmethyl)amino, ((1,4-dioxan-2-yl)methyl)(methyl)amino, (3-hydroxy-2,2-dimethylpropyl)(methyl)amino, methyl(oxetan-3-ylmethyl)amino, (3-(2-hydroxypropan-2-yl)cyclobutyl)(methyl)amino, ethyl(2-hydroxy-2-methylpropyl)amino, morpholino, 2-oxa-7-azaspiro[4.4]nonan-7-yl, octahydro-2H-4,7-epoxyisoindol-2-yl, 6-oxa-2-azaspiro[3.4]octan-2-yl, 3-acetyl-3,6-diazabicyclo[3.1.1]heptan-6-yl, 4-acetylpiperazin-1-yl, 2,6-dimethylmorpholino, 2-oxa-6-azaspiro[3.3]heptan-6-yl, 6-oxa-1-azaspiro[3.3]heptan-1-yl, 2-oxa-5-azabicyclo[4.1.0]heptan-5-yl, 3-methyl-2-oxoimidazolidin-1-yl, 5-methyl-1,1-dioxido-1,2,5-thiadiazolidin-2-yl, 6-methyl-3,6-diazabicyclo[3.1.1]heptan-3-yl, 2-oxopyrrolidin-1-yl, 4-methoxypiperazin-1-yl, azetidin-1-yl, 3-(difluoromethyl)azetidin-1-yl, 3,3-difluoroazetidin-1-yl, 3-azabicyclo[3.1.1]heptan-3-yl, 3-(difluoromethoxy)piperidin-1-yl, 3-methoxyazetidin-1-yl, 2-oxa-6-azaspiro[3.5]nonan-6-yl, 3-methyl-2-oxopyrrolidin-1-yl, 2-oxa-5-azabicyclo[2.2.2]octan-5-yl, 2-(difluoromethyl)pyrrolidin-1-yl, 4-oxa-7-azaspiro[2.5]octan-7-yl, 3-oxa-8-azabicyclo[3.2.1]octan-8-yl, 3-oxotetrahydro-1H-pyrrolo[1,2-c]imidazol-2(3H)-yl, 6-oxa-3-azabicyclo[3.2.1]octan-3-yl, 2-methylmorpholino, 2-oxa-5-azabicyclo[2.2.1]heptan-5-yl, 3-methyl-1,1-dioxidoisothiazolidin-2-yl, (2,2,2-trifluoroethyl)piperazin-1-yl, 6-acetyl-3,6-diazabicyclo[3.1.1]heptan-3-yl, 3-acetoxy-4-fluoropyrrolidin-1-yl, 3-fluoro-4-hydroxypyrrolidin-1-yl, 1,1-dioxidohexahydro-5H-thieno[2,3-c]pyrrol-5-yl, 6-oxa-1-azaspiro[3.4]octan-1-yl, 3-hydroxy-3-methylpyrrolidin-1-yl, 2-hydroxy-7-azabicyclo[2.2.1]heptan-7-yl, 3-(difluoromethyl)-3-hydroxypyrrolidin-1-yl, 3-hydroxy-4-methoxypyrrolidin-1-yl, 3-(2-hydroxypropan-2-yl)pyrrolidin-1-yl, hexahydro-1H-furo[3,4-b]pyrrol-1-yl, 7-oxa-1-azaspiro[4.4]nonan-1-yl, 3-(2-hydroxypropan-2-yl)azetidin-1-yl, 3-(methylsulfonyl)pyrrolidin-1-yl, 4-hydroxy-4-methylpiperidin-1-yl, 3-(trifluoromethyl)piperazin-1-yl, 3-(cyanomethyl)pyrrolidin-1-yl, 6-oxa-3-azabicyclo[3.1.1]heptan-3-yl, 3,4-dimethylpiperazin-1-yl, 1,1-dioxidoisothiazolidin-2-yl, 4-methyl-1,1-dioxidoisothiazolidin-2-yl, 4-methylpiperazin-1-yl, 3-methylmorpholino, 3-hydroxy-3-methylpiperidin-1-yl, hexahydropyrazino[2,1-c][1,4]oxazin-8(1H)-yl, 3-cyanopyrrolidin-1-yl, isoxazolidin-2-yl, 6-hydroxy-6-methyl-2-azaspiro[3.3]heptan-2-yl, 5-hydroxy-2-azabicyclo[2.2.1]heptan-2-yl, 1-hydroxy-3-azabicyclo[3.1.0]hexan-3-yl, 3-(difluoromethyl)-3-hydroxyazetidin-1-yl, 4-fluoro-3-hydroxypiperidin-1-yl, 3-hydroxy-4-methylpyrrolidin-1-yl, 4-(difluoromethyl)-4-hydroxypiperidin-1-yl, 3-hydroxypyrrolidin-1-yl, 3,3-difluoro-4-hydroxypyrrolidin-1-yl, 2-(difluoromethyl)morpholino, 5-oxa-6-azaspiro[2.4]heptan-6-yl, 4-hydroxy-4-methylisoxazolidin-2-yl, 3-oxopiperazin-1-yl, 6-(difluoromethyl)-6-hydroxy-2-azaspiro[3.3]heptan-2-yl, 7-hydroxy-5-azaspiro[2.4]heptan-5-yl, 6-hydroxy-2-azaspiro[3.3]heptan-2-yl, pyrrolidin-1-yl, 4-(methylsulfonyl)piperidin-1-yl, 1-methyl-3-azabicyclo[3.1.0]hexan-3-yl, 3-methoxypiperidin-1-yl, 2-(trifluoromethyl)pyrrolidin-1-yl, 2-oxa-5-azabicyclo[3.4]octan-5-yl, 3-((methylsulfonyl)methyl)azetidin-1-yl, 6,6-difluoro-3-azabicyclo[3.1.0]hexan-3-yl, 4,4-difluoropiperidin-1-yl, 6-methoxy-2-azaspiro[3.3]heptan-2-yl, 2-(trifluoromethyl)azetidin-1-yl, 3-(2-methoxyethoxy)azetidin-1-yl, piperidin-1-yl, 3-(difluoromethoxy)azetidin-1-yl, 3-((difluoromethoxy)methyl)azetidin-1-yl, 3-hydroxy-3-methylazetidin-1-yl, 3-(difluoromethyl)pyrrolidin-1-yl, 3-oxa-6-azabicyclo[3.1.1]heptan-6-yl, 8-oxa-3-azabicyclo[3.2.1]octan-3-yl, 5,5-dioxido-5-thia-6-azaspiro[2.4]heptan-6-yl, 5-methyl-1,1-dioxidoisothiazolidin-2-yl, 2,2-dimethylmorpholino, 3-methylpiperazin-1-yl, 1-oxa-6-azaspiro[3.3]heptan-6-yl, 3-methoxy-3-methylazetidin-1-yl, 3,3-difluoropyrrolidin-1-yl, 1,1-difluoro-5-azaspiro[2.3]hexan-5-yl, 2-(2-hydroxypropan-2-yl)azetidin-1-yl, 2-(methoxymethyl)azetidin-1-yl, 6-hydroxy-3-azabicyclo[3.1.1]heptan-3-yl, 4-hydroxy-3,3-dimethylpiperidin-1-yl, 4-hydroxy-3,3-dimethylpyrrolidin-1-yl, 8-hydroxy-3-azabicyclo[3.2.1]octan-3-yl, 1-oxa-7-azaspiro[3.5]nonan-7-yl, 4-oxohexahydropyrazino[2,1-c][1,4]oxazin-8(1H)-yl, 3-oxa-6-azabicyclo[3.2.0]heptan-6-yl, 3-(difluoromethoxy)pyrrolidin-1-yl, 2,6-dioxa-9-azaspiro[4.5]decan-9-yl), 1-oxa-6-azaspiro[3.4]octan-6-yl, 1-oxa-6-azaspiro[3.5]nonan-6-yl, 2-(difluoromethyl)azetidin-1-yl, 3-oxo-2-azaspiro[4.4]nonan-2-yl, 6-cyano-3-azabicyclo[3.1.0]hexan-3-yl, 3-methoxypyrrolidin-1-yl, 2-(2-hydroxypropan-2-yl)pyrrolidin-1-yl, 4-methoxypiperidin-1-yl, 2-oxa-6-azaspiro[3.4]octan-6-yl, 6-methyl-5-oxo-2,6-diazaspiro[3.4]octan-2-yl, hexahydrofuro[3,4-b]pyridin-1(2H)-yl, 1,1-dioxido-1,2-thiazinan-2-yl, 4,4-difluoro-3-hydroxypiperidin-1-yl, hexahydro-5H-furo[2,3-c]pyrrol-5-yl, 5-hydroxy-2-azaspiro[3.3]heptan-2-yl, tetrahydro-1H-furo[3,4-c]pyrrol-5(3H)-yl, 4-hydroxy-3,3-dimethylpyrrolidin-1-yl, 3-cyano-3-methylpyrrolidin-1-yl, 4-(2,2-difluoroethyl)piperazin-1-yl, 4-ethoxypiperazin-1-yl, 4-(oxetan-3-yl)piperazin-1-yl, 6-hydroxy-6-(trifluoromethyl)-2-azaspiro[3.3]heptan-2-yl, 5-methylthiazol-2-yl, 2-methylthiazol-5-yl, pyridin-4-yl, oxazol-5-yl, 2-methyloxazol-5-yl, oxazol-2-yl, isothiazol-4-yl, 5-methyloxazol-2-yl, pyridin-3-yl, thiazol-4-yl, pyridin-2-yl, 2-methylthiazol-4-yl, (4,4-dimethyl-4,5-dihydrooxazol-2-yl)amino, (4-oxido-1,4$\lambda^6$-oxathian-4-ylidene)amino, 4-methyl-4-oxido-1,4-azaphosphinan-1-yl, and 4,4-dimethyl-1,4-azasilinan-1-yl.

In another embodiment, the invention provides a compound of Formula (I), (II), (III), or (IV), wherein $R^1$ is $C_{1-3}$ alkylthio. In certain embodiments, $R^1$ is methylthio.

In another embodiment, the invention provides a compound of Formula (I), (II), (III), or (IV), wherein $R^1$ is methylsulfonyl.

In another embodiment, the invention provides a compound of Formula (I), (II), (III), or (IV), wherein $R^1$ is $OR^c$. In another embodiment, the invention provides a compound of Formula (I), (II), (III), or (IV), wherein $R^c$ is a 4 to 6 membered heterocyclyl containing 1 to 3 heteroatoms selected from the group consisting of N, O and S, wherein the heterocyclyl is optionally substituted with 1 or 2 groups selected from halogen and $C_{1-3}$ alkyl optionally substituted with one to three halogens. In certain embodiments, $R^c$ is a 5 to 6 membered heterocyclyl containing 1 N heteroatom, wherein the heterocyclyl is optionally substituted with 1 or 2 groups selected from fluoro and methyl. In another embodiment, the invention provides a compound of Formula (I), (II), (III), or (IV), wherein $R^1$ is (4-fluoropyrrolidin-3-yl)oxy, (4-fluoro-1-methylpyrrolidin-3-yl)oxy, (3-fluoropiperidin-4-yl)oxy, (3-fluoro-1-methylpiperidin-4-yl)oxy, (4-fluoropiperidin-3-yl)oxy, (4-fluoro-1-methylpiperidin-3-yl)oxy, (5-fluoropiperidin-3-yl)oxy, (4,4-difluoropyrrolidin-3-yl)oxy, and (5-fluoro-1-methylpiperidin-3-yl)oxy.

In another embodiment, the invention provides a compound of Formula (I), (II), (III), or (IV), wherein $R^1$ is $C_{1-6}$ alkoxy optionally substituted with 1 to 3 groups selected from the group consisting of halogen, hydroxy, methoxy, and a 4 to 6 membered heterocyclyl containing 1 to 3 heteroatoms selected from the group consisting of N, O and S, wherein the heterocyclyl is optionally substituted with 1 to 3 groups selected from halogen and methyl. In another embodiment, the invention provides a compound of Formula (I), (II), (III), or (IV), wherein $R^1$ is $C_{1-4}$ alkoxy optionally substituted with 1 or 2 groups selected from the group consisting of halogen, hydroxy, methoxy, and a 4 membered heterocyclyl containing 1 N heteroatom, wherein the heterocyclyl is optionally substituted with 1 or 2 groups selected from halogen and methyl. In another embodiment, the invention provides a compound of Formula (I), (II), (III), or (IV), wherein $R^1$ is methoxy, ethoxy, 2-methoxyethoxy, 2,2-difluoroethoxy, propoxy, (3-fluoroazetidin-3-yl)methoxy, (3-fluoro-1-methylazetidin-3-yl)methoxy, and 2-hydroxy-2-methylpropoxy.

In a preferred embodiment, the invention provides a compound of Formula (I), (II), (III), or (IV), wherein $R^1$ is $NR^aR^b$. In another embodiment, the invention provides a compound of Formula (I), (II), (III), or (IV), wherein $R^a$ and $R^b$ are independently selected from the group consisting of hydrogen; $C_{1-6}$ alkyl optionally substituted with 1 to 6 groups selected from hydroxy, methoxy, trifluoromethoxy, halogen, cyano, methoxy(methyl)amino, a 4-6 membered heterocyclyl containing 1 to 3 heteroatoms selected from N, O and S, wherein the heterocyclyl is optionally substituted with a hydroxy group, and $C_{3-6}$ cycloalkyl optionally substituted with a hydroxy group; $C_{1-6}$ alkoxy optionally substituted with 1 to 3 groups selected from hydroxy and halogen; $C_{3-6}$ cycloalkyl optionally substituted with 1 or 2 groups selected from halogen, hydroxy, methoxy and $C_{1-3}$ alkyl optionally substituted with a hydroxy group; a 4-6 membered heterocyclyl containing 1 to 3 heteroatoms selected from N, O and S, wherein the heterocyclyl is optionally substituted with 1 to 3 groups selected from halogen, $C_{1-3}$ alkyl, and $C_{1-3}$ alkoxy; a 5-6 membered heteroaryl containing 1 to 3 heteroatoms selected from N, O and S, wherein the heteroaryl is optionally substituted by 1 to 3 $C_{1-3}$ alkyl groups; and benzyl. In another embodiment, the invention provides a compound of Formula (I), (II), (III), or (IV), wherein $R^a$ and $R^b$ are independently selected from the group consisting of hydrogen; $C_{1-5}$ alkyl optionally substituted with 1 to 4 groups selected from hydroxy, halogen, cyano, methoxy(methyl)amino, a 4-6 membered heterocyclyl containing 1 or 2 O heteroatoms optionally substituted with a hydroxy group, and $C_{3-4}$ cycloalkyl optionally substituted with a hydroxy group; $C_{1-4}$ alkoxy optionally substituted with 1 to 3 groups selected from hydroxy and fluoro; $C_{3-5}$ cycloalkyl optionally substituted with 1 or 2 groups selected from halogen, hydroxy, methoxy and $C_{1-3}$ alkyl optionally substituted with a hydroxy group; a 4-6 membered heterocyclyl containing 1 or 2 heteroatoms selected from N and O, wherein the heterocyclyl is optionally substituted with 1 to 2 groups selected from fluoro, methyl and methoxy; a 5 membered heteroaryl containing 2 N heteroatoms substituted by 1 methyl group; and benzyl.

In another embodiment, the invention provides a compound of Formula (I), (II), (III), or (IV), wherein $R^a$ is selected from the group consisting of hydrogen; $C_{1-6}$ alkyl optionally substituted with 1 to 6 groups selected from hydroxy, methoxy, trifluoromethoxy, halogen, cyano, methoxy(methyl)amino, a 4-6 membered heterocyclyl containing 1 to 3 heteroatoms selected from N, O and S, wherein the heterocyclyl is optionally substituted with a hydroxy group, and $C_{3-6}$ cycloalkyl optionally substituted with a hydroxy group; $C_{1-6}$ alkoxy optionally substituted with 1 to 3 groups selected from hydroxy and halogen; $C_{3-6}$ cycloalkyl optionally substituted with 1 or 2 groups selected from halogen, hydroxy, methoxy and $C_{1-3}$ alkyl optionally substituted with a hydroxy group; a 4-6 membered heterocyclyl containing 1 to 3 heteroatoms selected from N, O and S, wherein the heterocyclyl is optionally substituted with 1 to 3 groups selected from halogen, $C_{1-3}$ alkyl, and $C_{1-3}$ alkoxy; a 5-6 membered heteroaryl containing 1 to 3 heteroatoms selected from N, O and S, wherein the heteroaryl is optionally substituted by 1 to 3 $C_{1-3}$ alkyl groups; and benzyl. In another embodiment, the invention provides a compound of Formula (I), (II), (III), or (IV), wherein $R^a$ is selected from the group consisting of hydrogen; $C_{1-5}$ alkyl optionally substituted with 1 to 4 groups selected from hydroxy, halogen, cyano, methoxy(methyl)amino, a 4-6 membered heterocyclyl containing 1 or 2 O heteroatoms optionally substituted with a hydroxy group, and $C_{3-4}$ cycloalkyl optionally substituted with a hydroxy group; $C_{1-4}$ alkoxy optionally substituted with 1 to 3 groups selected from hydroxy and fluoro; $C_{3-5}$ cycloalkyl optionally substituted with 1 or 2 groups selected from halogen, hydroxy, methoxy and $C_{1-3}$ alkyl optionally substituted with a hydroxy group; a 4-6 membered heterocyclyl containing 1 or 2 heteroatoms selected from N and O, wherein the heterocyclyl is optionally substituted with 1 to 2 groups selected from fluoro, methyl and methoxy; a 5 membered heteroaryl containing 2 N heteroatoms substituted by 1 methyl group; and benzyl.

In another embodiment, the invention provides a compound of Formula (I), (II), (III), or (IV), wherein $R^a$ is selected from the group consisting of hydrogen, methyl, cyclobutyl, tetrahydrofuran-3-yl, bicyclo[1.1.1]pentan-1-yl, 2-hydroxy-2-methylpropyl, cyclopropylmethyl, methoxy, 3,3-difluorocyclobutyl, cyclopropyl, 2,2-difluorocyclobutyl, 2,2-difluoroethyl, 1-(trifluoromethoxy)propan-2-yl, 3-fluoropiperidin-4-yl, 3-fluoro-1-methylpiperidin-4-yl, 4-fluoropyrrolidin-3-yl, 4-fluoro-1-methylpyrrolidin-3-yl, 2-hydroxy-3-methoxypropyl, 3-hydroxy-3-methylbutyl, 1,5-dimethyl-1H-pyrazol-4-yl, 1-methyl-1H-pyrazol-4-yl, 3-hydroxy-3-methylcyclobutyl, tetrahydrofuran-3-yl, oxetan-3-yl, tetrahydro-2H-pyran-4-yl, (1-hydroxycyclobutyl)methyl, 3-hydroxy-3-methylcyclobutyl, (l-hydroxycyclopropyl)methyl, 2-hydroxycyclopentyl, 3-hydroxycyclobutyl, 3,3,3-trifluoro-2-hydroxypropyl, 2-hydroxypropyl, 2-cyano-2-methylpropyl, 2,2-difluoroethyl, 2-hydroxyethyl, 2-hydroxy-2-methylpropoxy, 2-(methoxy(methyl)amino)ethyl, 1-methoxypyrrolidin-3-yl, oxetan-3-yl, 3-methoxycyclobutyl, isopropylamino, 1-methylcyclopropyl, ethyl, cyclopropyl, cyclopentyl, 4-fluoropyrrolidin-3-yl, 4-fluoro-1-methylpyrrolidin-3-yl, 4,4-difluoropyrrolidin-3-yl, (3-hydroxyoxetan-3-yl)methyl, benzyl, 2,2-difluoroethyl, tetrahydro-2H-pyran-3-yl, oxetan-2-ylmethyl, (1,4-dioxan-2-yl)methyl, 3-hydroxy-2,2-dimethylpropyl, oxetan-3-ylmethyl, 3-(2-hydroxypropan-2-yl)cyclobutyl, and 2-hydroxy-2-methylpropyl.

In another embodiment, the invention provides a compound of Formula (I), (II), (III), or (IV), wherein $R^b$ is selected from the group consisting of hydrogen and $C_{1-3}$ alkyl optionally substituted with halogen. In another embodiment, the invention provides a compound of Formula (I), (II), (III), or (IV), wherein $R^b$ is selected from the group consisting of hydrogen and $C_{1-3}$ alkyl optionally substituted with 1 to 3 halogen groups. In another embodiment, the invention provides a compound of Formula (I), (II), (III), or (IV), wherein $R^b$ is selected from the group consisting of hydrogen and $C_{1-3}$ alkyl optionally substituted with 1 or 2 halogen groups. In another embodiment, the invention provides a compound of Formula (I), (II), (III), or (IV), wherein $R^b$ is selected from the group consisting of hydrogen and $C_{1-2}$ alkyl optionally substituted with 1 or 2 halogen groups. In another embodiment, the invention provides a compound of Formula (I), (II), (III), or (IV), wherein $R^b$ is selected from the group consisting of hydrogen and $C_{1-2}$ alkyl.

In another embodiment, the invention provides a compound of Formula (I), (II), (III), or (IV), wherein $R^b$ is selected from the group consisting of hydrogen, methyl, ethyl, and 2,2-difluoroethyl. In another embodiment, the invention provides a compound of Formula (I), (II), (III), or (IV), wherein $R^b$ is selected from the group consisting of hydrogen, methyl, and ethyl. In another embodiment, the invention provides a compound of Formula (I), (II), (III), or (IV), wherein $R^b$ is selected from the group consisting of hydrogen and methyl.

In another embodiment, the invention provides a compound of Formula (I), (II), (III), or (IV), wherein $R^1$ is selected from the group consisting of amino, dimethylamine, methylamine, cyclobutylamino, (tetrahydrofuran-3-yl) amino, bicyclo[1.1.1]pentan-1-ylamino, (2-hydroxy-2-methylpropyl)(methyl)amino, (cyclopropylmethyl)amino, methoxy(methyl)amino, (3,3-difluorocyclobutyl)amino, cyclopropyl(methyl)amino, (2,2-difluorocyclobutyl)amino, (2,2-difluoroethyl)(methyl)amino, (1-methoxypropan-2-yl) amino, (1-(trifluoromethoxy)propan-2-yl)amino, (3-fluoropiperidin-4-yl)amino, (3-fluoro-1-methylpiperidin-4-yl) amino, (4-fluoropyrrolidin-3-yl)(methyl)amino, (4-fluoro-1-methylpyrrolidin-3-yl)(methyl)amino, (2-hydroxy-3-methoxypropyl)(methyl)amino, (3-hydroxy-3-methylbutyl) (methyl)amino, ((1,5-dimethyl-1H-pyrazol-4-yl)methyl) amino, methyl(1-methyl-1H-pyrazol-4-yl)amino, (3-hydroxy-3-methylcyclobutyl)(methyl)amino, methyl(tetrahydrofuran-3-yl)amino, methyl(oxetan-3-yl)amino, methyl(tetrahydro-2H-pyran-4-yl)amino, ((1-hydroxycyclobutyl)methyl)(methyl)amino, (3-hydroxy-3-methylcyclobutyl)(methyl)amino, ((1-hydroxycyclopropyl)methyl) (methyl)amino, (2-hydroxycyclopentyl)(methyl)amino, (3-hydroxycyclobutyl)(methyl)amino, methyl(3,3,3-trifluoro-2-hydroxypropyl)amino, (2-hydroxypropyl)(methyl) amino, (2-cyano-2-methylpropyl)(methyl)amino, (2,2-difluoroethyl)amino, (2-hydroxyethyl)(methyl)amino, (2-hydroxy-2-methylpropoxy)amino, (2-(methoxy(methyl) amino)ethyl)amino, (1-methoxypyrrolidin-3-yl)amino, oxetan-3-ylamino, (3-methoxycyclobutyl)amino, isopropylamino, (l-methylcyclopropyl)amino, ethylamino, cyclopropylamino, cyclopentylamino, (4-fluoropyrrolidin-3-yl) amino, (4-fluoro-1-methylpyrrolidin-3-yl)amino, (4,4-difluoropyrrolidin-3-yl)amino, ((3-hydroxyoxetan-3-yl) methyl)amino, benzyl(methyl)amino, bis(2,2-difluoroethyl) amino, methyl(tetrahydro-2H-pyran-3-yl)amino, methyl (oxetan-2-ylmethyl)amino, ((1,4-dioxan-2-yl)methyl) (methyl)amino, (3-hydroxy-2,2-dimethylpropyl)(methyl) amino, methyl(oxetan-3-ylmethyl)amino, (3-(2-hydroxypropan-2-yl)cyclobutyl)(methyl)amino, and ethyl (2-hydroxy-2-methylpropyl)amino.

In another embodiment, the invention provides a compound of Formula (I), (II), (III), or (IV), wherein $R^a$ is selected from the group consisting of $C_{1-6}$ alkyl optionally substituted with 1 to 6 groups selected from hydroxy, methoxy, trifluoromethoxy, halogen, cyano, methoxy(methyl)amino, a 4-6 membered heterocyclyl containing 1 to 3 heteroatoms selected from N, O and S, wherein the heterocyclyl is optionally substituted with a hydroxy group, and $C_{3-6}$ cycloalkyl optionally substituted with a hydroxy group; and $R^b$ is selected from hydrogen and methyl. In another embodiment, the invention provides a compound of Formula (I), (II), (III), or (IV), wherein $R^a$ is selected from the group consisting of $C_{1-6}$ alkyl optionally substituted with 1 to 3 groups selected from hydroxy, methoxy, trifluoromethoxy, halogen, cyano, methoxy(methyl)amino, a 4-6 membered heterocyclyl containing 1 to 3 heteroatoms selected from N, O and S, wherein the heterocyclyl is optionally substituted with a hydroxy group, and $C_{3-6}$ cycloalkyl optionally substituted with a hydroxy group; and $R^b$ is selected from hydrogen and methyl. In another embodiment, the invention provides a compound of Formula (I), (II), (III), or (IV), wherein $R^a$ is selected from the group consisting of $C_{1-6}$ alkyl optionally substituted with 1 to 3 groups selected from hydroxy, methoxy, trifluoromethoxy, halogen, and cyano; and $R^b$ is selected from hydrogen and methyl. In another embodiment, the invention provides a compound of Formula (I), (II), (III), or (IV), wherein $R^a$ is selected from the group consisting of $C_{1-4}$ alkyl optionally substituted with 1 to 3 groups selected from hydroxy, methoxy, trifluoromethoxy, halogen, and cyano; and $R^b$ is selected from hydrogen and methyl. In a preferred embodiment, the invention provides a compound of Formula (I), (II), (III), or (IV), wherein $R^a$ is selected from the group consisting of $C_{1-4}$ alkyl optionally substituted with 1 group selected from hydroxy, methoxy, trifluoromethoxy, halogen, and cyano; and $R^b$ is selected from hydrogen and methyl. In a preferred embodiment, the invention provides a compound of Formula (I), (II), (III), or (IV), wherein $R^a$ is selected from the group consisting of $C_{1-4}$ alkyl optionally substituted with 1 hydroxy group.

In another embodiment, the invention provides a compound of Formula (I), (II), (III), or (IV), wherein $R^1$ is a 4-10 membered heterocyclyl containing 1-3 heteroatoms selected from the group consisting of N, O, S, SO and $SO_2$, wherein the heterocyclyl is optionally substituted with 1 to 5 groups selected from the group consisting of:
  halogen;
  hydroxy;
  oxo;
  acetyl;
  acetoxy;
  cyano;
  methylsulfonyl;
  $C_{1-5}$ alkyl optionally substituted with 1 to 5 groups selected from the group consisting of halogen, hydroxy, cyano, methyl, methylsulfonyl, methoxy, difluoromethoxy, and oxo;
  $C_{1-4}$ alkoxy optionally substituted with 1 or 2 groups selected from halogen, methoxy, and methylsulfonyl;
  $C_{1-4}$ haloalkyl;
  a 4-6 membered heterocyclyl containing 1-3 heteroatoms selected from N, O and S.

In another embodiment, the invention provides a compound of Formula (I), (II), (III), or (IV), wherein $R^1$ is a 4-10 membered heterocyclyl containing 1-3 heteroatoms selected from the group consisting of N, O and $SO_2$, wherein the heterocyclyl is optionally substituted with 1 to 3 groups selected from the group consisting of fluoro, hydroxy, oxo, acetyl, acetoxy, cyano, methylsulfonyl, $C_{1-3}$ alkyl optionally substituted with 1 to 3 groups selected from the group consisting of halogen, hydroxy, cyano, methyl, methylsulfonyl, methoxy, and difluoromethoxy, $C_{1-2}$ alkoxy optionally substituted with 1 or 2 groups selected from fluoro, methoxy, and methylsulfonyl, and oxetanyl.

In another embodiment, the invention provides a compound of Formula (I), (II), (III), or (IV), wherein $R^1$ is selected from the group consisting of morpholino, 2-oxa-7-azaspiro[4.4]nonan-7-yl, octahydro-2H-4,7-epoxyisoindol-2-yl, 6-oxa-2-azaspiro[3.4]octan-2-yl, 3-acetyl-3,6-diazabicyclo[3.1.1]heptan-6-yl, 4-acetylpiperazin-1-yl, 2,6-dimethylmorpholino, 2-oxa-6-azaspiro[3.3]heptan-6-yl, 6-oxa-1-azaspiro[3.3]heptan-1-yl, 2-oxa-5-azabicyclo [4.1.0]heptan-5-yl, 3-methyl-2-oxoimidazolidin-1-yl, 5-methyl-1,1-dioxido-1,2,5-thiadiazolidin-2-yl, 6-methyl-3, 6-diazabicyclo[3.1.1]heptan-3-yl, 2-oxopyrrolidin-1-yl, 4-methoxypiperazin-1-yl, azetidin-1-yl, 3-(difluoromethyl) azetidin-1-yl, 3,3-difluoroazetidin-1-yl, 3-azabicyclo[3.1.1] heptan-3-yl, 3-(difluoromethoxy)piperidin-1-yl, 3-methoxyazetidin-1-yl, 2-oxa-6-azaspiro[3.5]nonan-6-yl, 3-methyl-2-oxopyrrolidin-1-yl, 2-oxa-5-azabicyclo[2.2.2] octan-5-yl, 2-(difluoromethyl)pyrrolidin-1-yl, 4-oxa-7-azaspiro[2.5]octan-7-yl, 3-oxa-8-azabicyclo[3.2.1]octan-8-yl, 3-oxotetrahydro-1H-pyrrolo[1,2-c]imidazol-2(3H)-yl, 6-oxa-3-azabicyclo[3.2.1]octan-3-yl, 2-methylmorpholino, 2-oxa-5-azabicyclo[2.2.1]heptan-5-yl, 3-methyl-1,1-dioxidoisothiazolidin-2-yl, (2,2,2-trifluoroethyl)piperazin-1-yl, 6-acetyl-3,6-diazabicyclo[3.1.1]heptan-3-yl, 3-acetoxy-4-fluoropyrrolidin-1-yl, 3-fluoro-4-hydroxypyrrolidin-1-yl, 1,1-dioxidohexahydro-5H-thieno[2,3-c]pyrrol-5-yl, 6-oxa-1-azaspiro[3.4]octan-1-yl, 3-hydroxy-3-methylpyrrolidin-1-yl, 2-hydroxy-7-azabicyclo[2.2.1]heptan-7-yl, 3-(difluoromethyl)-3-hydroxypyrrolidin-1-yl, 3-hydroxy-4-methoxypyrrolidin-1-yl, 3-(2-hydroxypropan-2-yl) pyrrolidin-1-yl, hexahydro-1H-furo[3,4-b]pyrrol-1-yl, 7-oxa-1-azaspiro[4.4]nonan-1-yl, 3-(2-hydroxypropan-2-yl) azetidin-1-yl, 3-(methylsulfonyl)pyrrolidin-1-yl, 4-hydroxy-4-methylpiperidin-1-yl, 3-(trifluoromethyl)piperazin-1-yl, 3-(cyanomethyl)pyrrolidin-1-yl, 6-oxa-3-azabicyclo[3.1.1] heptan-3-yl, 3,4-dimethylpiperazin-1-yl, 1,1-dioxidoisothiazolidin-2-yl, 4-methyl-1,1-dioxidoisothiazolidin-2-yl, 4-methylpiperazin-1-yl, 3-methylmorpholino, 3-hydroxy-3-methylpiperidin-1-yl, hexahydropyrazino[2,1-c][1,4] oxazin-8(1H)-yl, 3-cyanopyrrolidin-1-yl, isoxazolidin-2-yl, 6-hydroxy-6-methyl-2-azaspiro[3.3]heptan-2-yl, 5-hydroxy-2-azabicyclo[2.2.1]heptan-2-yl, 1-hydroxy-3-azabicyclo[3.1.0]hexan-3-yl, 3-(difluoromethyl)-3-hydroxyazetidin-1-yl, 4-fluoro-3-hydroxypiperidin-1-yl, 3-hydroxy-4-methylpyrrolidin-1-yl, 4-(difluoromethyl)-4-hydroxypiperidin-1-yl, 3-hydroxypyrrolidin-1-yl, 3,3-difluoro-4-hydroxypyrrolidin-1-yl, 2-(difluoromethyl) morpholino, 5-oxa-6-azaspiro[2.4]heptan-6-yl, 4-hydroxy-4-methylisoxazolidin-2-yl, 3-oxopiperazin-1-yl, 6-(difluoromethyl)-6-hydroxy-2-azaspiro[3.3]heptan-2-yl, 7-hydroxy-5-azaspiro[2.4]heptan-5-yl, 6-hydroxy-2-azaspiro[3.3]heptan-2-yl, pyrrolidin-1-yl, 4-(methylsulfonyl)piperidin-1-yl, 1-methyl-3-azabicyclo[3.1.0]hexan-3-yl, 3-methoxypiperidin-1-yl, 2-(trifluoromethyl)pyrrolidin-1-yl, 2-oxa-5-azaspiro[3.4]octan-5-yl, 3-((methylsulfonyl) methyl)azetidin-1-yl, 6,6-difluoro-3-azabicyclo[3.1.0] hexan-3-yl, 4,4-difluoropiperidin-1-yl, 6-methoxy-2-azaspiro[3.3]heptan-2-yl, 2-(trifluoromethyl)azetidin-1-yl, 3-(2-methoxyethoxy)azetidin-1-yl, piperidin-1-yl, 3-(difluoromethoxy)azetidin-1-yl, 3-((difluoromethoxy)methyl)azetidin-1-yl, 3-hydroxy-3-methylazetidin-1-yl, 3-(difluoromethyl)pyrrolidin-1-yl, 3-oxa-6-azabicyclo[3.1.1]heptan-6-yl, 8-oxa-3-azabicyclo[3.2.1]octan-3-yl, 5,5-dioxido-5-thia-6-azaspiro[2.4]heptan-6-yl, 5-methyl-1,1-dioxidoisothiazolidin-2-yl, 2,2-dimethylmorpholino, 3-methylpiperazin-1-yl, 1-oxa-6-azaspiro[3.3]heptan-6-yl, 3-methoxy-3-methylazetidin-1-yl, 3,3-difluoropyrrolidin-1-yl, 1,1-difluoro-5-azaspiro[2.3]hexan-5-yl, 2-(2-hydroxypropan-2-yl)azetidin-1-yl, 2-(methoxymethyl)azetidin-1-yl, 6-hydroxy-3-azabicyclo[3.1.1]heptan-3-yl, 4-hydroxy-3,3-dimethylpiperidin-1-yl, 4-hydroxy-3,3-dimethylpyrrolidin-1-yl, 8-hydroxy-3-azabicyclo[3.2.1]octan-3-yl, 1-oxa-7-azaspiro[3.5]nonan-7-yl, 4-oxohexahydropyrazino[2,1-c][1,4]oxazin-8(1H)-yl, 3-oxa-6-azabicyclo[3.2.0]heptan-6-yl, 3-(difluoromethoxy)pyrrolidin-1-yl, 2,6-dioxa-9-azaspiro[4.5]decan-9-yl, 1-oxa-6-azaspiro[3.4]octan-6-yl, 1-oxa-6-azaspiro[3.5]nonan-6-yl, 2-(difluoromethyl)azetidin-1-yl, 3-oxo-2-azaspiro[4.4]nonan-2-yl, 6-cyano-3-azabicyclo[3.1.0]hexan-3-yl, 3-methoxypyrrolidin-1-yl, 2-(2-hydroxypropan-2-yl)pyrrolidin-1-yl, 4-methoxypiperidin-1-yl, 2-oxa-6-azaspiro[3.4]octan-6-yl, 6-methyl-5-oxo-2,6-diazaspiro[3.4]octan-2-yl, hexahydrofuro[3,4-b]pyridin-1 (2H)-yl, 1,1-dioxido-1,2-thiazinan-2-yl, 4,4-difluoro-3-hydroxypiperidin-1-yl, hexahydro-5H-furo[2,3-c]pyrrol-5-yl, 5-hydroxy-2-azaspiro[3.3]heptan-2-yl, tetrahydro-1H-furo[3,4-c]pyrrol-5(3H)-yl, 4-hydroxy-3,3-dimethylpyrrolidin-1-yl, 3-cyano-3-methylpyrrolidin-1-yl, 4-(2,2-difluoroethyl) piperazin-1-yl, 4-ethoxypiperazin-1-yl, 4-(oxetan-3-yl) piperazin-1-yl, and 6-hydroxy-6-(trifluoromethyl)-2-azaspiro[3.3]heptan-2-yl.

In another embodiment, the invention provides a compound of Formula (I), (II), (III), or (IV), wherein $R^1$ is a 5-6 membered heteroaryl containing 1 to 3 heteroatoms selected from N, O and S, wherein the heteroaryl is optionally substituted with one $C_{1-3}$ alkyl group. In another embodiment, the invention provides a compound of Formula (I), (II), (III), or (IV), wherein $R^1$ is a 5-6 membered heteroaryl containing 1 or 2 heteroatoms selected from N, O and S, wherein the heteroaryl is optionally substituted with methyl. In another embodiment, the invention provides a compound of Formula (I), (II), (III), or (IV), wherein $R^1$ is selected from the group consisting of 5-methylthiazol-2-yl, 2-methylthiazol-5-yl, pyridin-4-yl, oxazol-5-yl, 2-methyloxazol-5-yl, oxazol-2-yl, isothiazol-4-yl, 5-methyloxazol-2-yl, pyridin-3-yl, thiazol-4-yl, pyridin-2-yl, and 2-methylthiazol-4-yl.

In another embodiment, the invention provides a compound of Formula (I), (II), (III), or (IV), wherein $R^1$ is (4,4-dimethyl-4,5-dihydrooxazol-2-yl)amino.

In another embodiment, the invention provides a compound of Formula (I), (II), (III), or (IV), wherein $R^1$ is (4-oxido-1,4$\lambda^6$-oxathian-4-ylidene)amino.

In another embodiment, the invention provides a compound of Formula (I), (II), (III), or (IV), wherein $R^1$ is 4-methyl-4-oxido-1,4-azaphosphinan-1-yl.

In another embodiment, the invention provides a compound of Formula (I), (II), (III), or (IV), wherein $R^1$ is 4,4-dimethyl-1,4-azasilinan-1-yl.

In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 to 3 heteroatoms independently selected from N, O, and S, wherein the heterocyclyl is optionally substituted with 1 or 2 groups selected from halogen, $C_1$-$C_4$ alkyl, $C_1$-$C_4$ alkoxy, and $C_1$-$C_4$ haloalkyl. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 to 3 heteroatoms independently selected from N, O, and S, wherein the heterocyclyl is optionally substituted with 1 or 2 groups selected from halogen, $C_1$-$C_4$ alkyl, $C_1$-$C_4$ alkoxy, and $C_1$-$C_4$ haloalkyl. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 to 3 heteroatoms independently selected from N, O, and S. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 to 3 heteroatoms independently selected from N, O, and S. In another embodiment, the invention provides a compound of Formula (I), (II), (III), or (IV), wherein $R^1$ is selected from the group consisting of hydrogen, halogen, $C_{1-3}$ alkylthio, methylsulfonyl, $NR^aR^b$, $C_{1-3}$ alkoxy, and a 4-7 membered heterocyclyl containing 1 or 2 heteroatoms independently selected from N and O, and wherein the heterocyclyl is optionally substituted with 1 or 2 groups selected from fluoro, methyl, methoxy, and $C_1$ fluoroalkyl. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 or 2 heteroatoms independently selected from N and O, and wherein the heterocyclyl is optionally substituted with 1 or 2 groups selected from fluoro, methyl, methoxy, and $C_1$ fluoroalkyl. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 or 2 heteroatoms independently selected from N and O. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and a 4-7 membered heterocyclyl containing 1 or 2 heteroatoms independently selected from N and O. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and 6 membered heterocyclyl containing 2 heteroatoms selected from N and O. In another embodiment, the invention provides a compound of Formula (I), (II), (III), or (IV), wherein $R^1$ is selected from the group consisting of $C_{1-3}$ alkylthio, methylsulfonyl, $NR^aR^b$, $C_{1-3}$ alkoxy, and 6 membered heterocyclyl containing 2 heteroatoms selected from N and O. In another embodiment, $R^1$ is selected from the group consisting of methylthio, methylsulfonyl, dimethylamine, methylamine, methoxy, and 6-morpholino.

In another embodiment, $R^a$ and $R^b$ are independently selected from hydrogen and $C_1$-$C_3$ alkyl. In another embodiment, the invention provides a compound of Formula (I), (II), (III), or (IV), wherein $R^a$ and $R^b$ are independently selected from hydrogen and methyl.

In another embodiment, the invention provides a compound of Formula (I), (II), or (IV), wherein $R^2$ is a 9-10 membered bicyclic heteroaryl containing one to three heteroatoms selected from N, O and S, wherein the bicyclic heteroaryl may be optionally substituted with one or two groups selected from halogen and $C_1$-$C_3$ alkyl. In another embodiment, the invention provides a compound of Formula (I), (II), or (IV), wherein $R^2$ is a 9 membered bicyclic heteroaryl containing two or three heteroatoms selected from N, O and S, wherein the bicyclic heteroaryl may be optionally substituted with one or two groups selected from halogen and $C_1$-$C_3$ alkyl. In another embodiment, the invention provides a compound of Formula (I), (II), or (IV), wherein $R^2$ is a 9 membered bicyclic heteroaryl containing two heteroatoms selected from N, O and S, wherein the bicyclic heteroaryl may be optionally substituted with a $C_1$-$C_3$ alkyl group. In another embodiment, the invention provides a compound of Formula (I), (II), or (IV), wherein $R^2$ is a 9 membered bicyclic heteroaryl containing two heteroatoms selected from N, O and S, wherein the bicyclic heteroaryl may be optionally substituted with a methyl group. In another embodiment, the invention provides a compound of Formula (I), (II), or (IV), wherein $R^2$ is selected from benzoimidazole, indazole, benzoisothiazole, triazolopyridine, benzoisoxazole, benzothiazole, imidazopyridine, and benzothiadiazole, wherein each may be optionally substituted with one or two groups selected from halogen and $C_1$-$C_3$ alkyl. In another embodiment, the invention provides a compound of Formula (I), (II), or (IV), wherein $R^2$ is selected from benzoimidazole, indazole, benzoisothiazole, triazolopyridine, benzoisoxazole, benzothiazole, imidazopyridine, and benzothiadiazole, wherein each may be optionally substituted with one or two groups selected from fluoro and methyl. In another embodiment, the invention provides a compound of Formula (I), (II), or (IV), wherein $R^2$ is selected from benzoimidazole, benzoisoxazole, and benzoisothiazole, wherein each may be optionally substituted with one or two groups selected from halogen and $C_1$-$C_3$ alkyl. In another embodiment, the invention provides a compound of Formula (I), (II), or (IV), wherein $R^2$ is selected from benzoimidazole, benzoisoxazole, and benzoisothiazole, wherein each may be optionally substituted with a methyl group. In another embodiment, the invention provides a compound of Formula (I), (II), or (IV), wherein $R^2$ is selected from 1H-benzo[d]imidazole-5-yl, 2H-indazol-6yl, benzo[c]isothiazol-6-yl, [1,2,4]triazolo[1,5-a]pyridine-7-yl, benzo[c]isoxazole-6-yl, benzo[d]thiazol-5-yl, imidazo[1,2-a]pyridine-7-yl, benzo[c]isoxazole-5-yl, and benzo[c][1,2,5]thiadiazol-5-yl, wherein each may be optionally substituted with one or two groups selected from halogen and $C_1$-$C_3$ alkyl. In another embodiment, the invention provides a compound of Formula (I), (II), or (IV), wherein $R^2$ is selected from 1H-benzo[d]imidazole-5-yl, 2H-indazol-6yl, benzo[c]isothiazol-6-yl, [1,2,4]triazolo[1,5-a]pyridine-7-yl, benzo[c]isoxazole-6-yl, benzo[d]thiazol-5-yl, imidazo[1,2-a]pyridine-7-yl, benzo[c]isoxazole-5-yl, and benzo[c][1,2,5]thiadiazol-5-yl, wherein each may be optionally substituted with one or two groups selected from fluoro and methyl. In another embodiment, the invention provides a compound of Formula (I), (II), or (IV), wherein $R^2$ is selected from 1H-benzo[d]imidazole-5-yl, benzo[c]isoxazole-6-yl, and benzo[c]isothiazol-6-yl, wherein each may be optionally substituted with one or two groups selected from halogen and $C_1$-$C_3$ alkyl. In another embodiment, the invention provides a compound of Formula (I), (II), or (IV), wherein $R^2$ is selected from 1H-benzo[d]imidazole-5-yl, benzo[c]isoxazole-6-yl, and benzo[c]isothiazol-6-yl, wherein each may be optionally substituted with a methyl group.

In another embodiment, the invention provides a compound of Formula (I), (II), or (IV), wherein $R^2$ is a 9-10 membered bicyclic heteroaryl containing one to three heteroatoms selected from N, O and S, wherein the bicyclic heteroaryl may be optionally substituted with one or two groups selected from the group consisting of halogen, $C_1$-$C_3$ alkyl and cyclopropyl. In another embodiment, the invention provides a compound of Formula (I), (II), or (IV), wherein $R^2$ is a 9 membered bicyclic heteroaryl containing two or three heteroatoms selected from N, O and S, wherein the bicyclic heteroaryl may be optionally substituted with one or two groups selected from the group consisting of halogen, $C_1$-$C_3$ alkyl and cyclopropyl. In another embodiment, the invention provides a compound of Formula (I), (II), or (IV), wherein $R^2$ is a 9 membered bicyclic heteroaryl containing two or three heteroatoms selected from N, O and S, wherein the bicyclic heteroaryl may be optionally substituted with one or two groups selected from the group consisting of methyl, ethyl, cyclopropyl and fluoro. In another embodiment, the invention provides a compound of Formula (I), (II), or (IV), wherein $R^2$ is selected from benzoimidazole, indazole, benzoisothiazole, triazolopyridine, benzoisoxazole, and benzothiazole, wherein each may be optionally substituted with one or two groups selected from methyl, ethyl, cyclopropyl and fluoro. In another embodiment, the invention provides a compound of Formula (I), (II), or (IV), wherein $R^2$ is selected from 1H-benzo[d]imidazole-5-yl, benzo[c]isoxazole-6-yl, benzo[c]isothiazol-6-yl, benzo[d]thiazol-5-yl, 2H-indazol-6yl, and [1,2,4]triazolo[1,5-a]pyridine-7-yl, wherein each may be optionally substituted with one or two groups selected from halogen, $C_1$-$C_3$ alkyl and cyclopropyl. In another embodiment, the invention provides a compound of Formula (I), (II), or (IV), wherein $R^2$ is selected from 1H-benzo[d]imidazole-5-yl, benzo[c]isoxazole-6-yl, benzo[c]isothiazol-6-yl, benzo[d]thiazol-5-yl, 2H-indazol-6yl, and [1,2,4]triazolo[1,5-a]pyridine-7-yl, wherein each may be optionally substituted with one or two groups selected from halogen, methyl, ethyl and cyclopropyl.

In another embodiment, the invention provides a compound of Formula (I), (II), or (IV), wherein $R^2$ is selected from 1H-benzo[d]imidazole-5-yl, benzo[c]isoxazole-6-yl, benzo[c]isothiazol-6-yl, benzo[d]thiazol-5-yl, and 2H-indazol-6yl, wherein each may be optionally substituted with one or two groups selected from halogen, $C_1$-$C_3$ alkyl and cyclopropyl. In another embodiment, the invention provides a compound of Formula (I), (II), or (IV), wherein $R^2$ is selected from 1H-benzo[d]imidazole-5-yl, benzo[c]isoxazole-6-yl, benzo[c]isothiazol-6-yl, benzo[d]thiazol-5-yl, and 2H-indazol-6yl, wherein each may be optionally substituted with one or two groups selected from halogen, methyl, ethyl and cyclopropyl.

In another embodiment, the invention provides a compound of Formula (I), (II), or (IV), wherein $R^2$ is selected from the group consisting of:

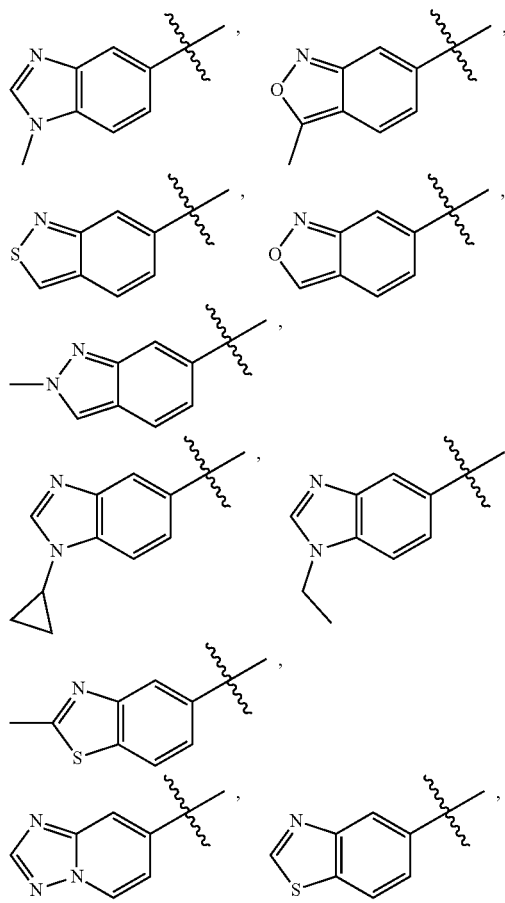

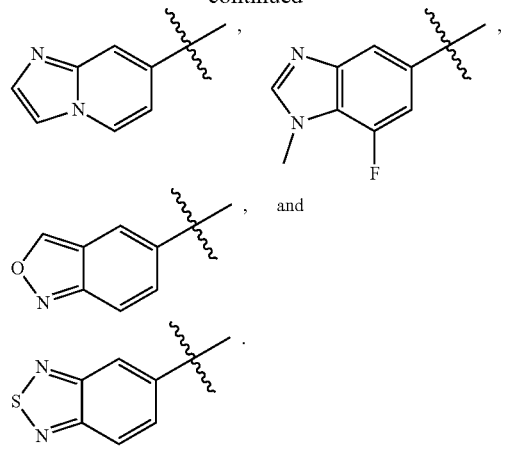

In another embodiment, the invention provides a compound of Formula (I), (II), or (IV), wherein $R^2$ is selected from the group consisting of:

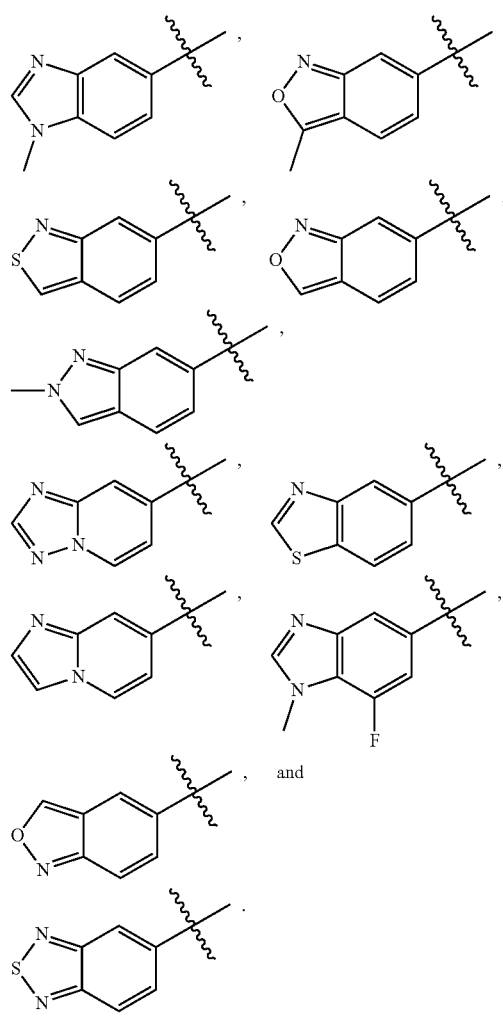

In another embodiment, the invention provides a compound of Formula (I), (II), or (IV), wherein $R^2$ is selected from the group consisting of:

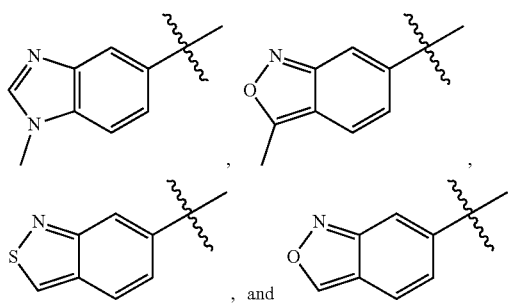

In another embodiment, the invention provides a compound of Formula (I), (II), or (IV), wherein R² is selected from the group consisting of:

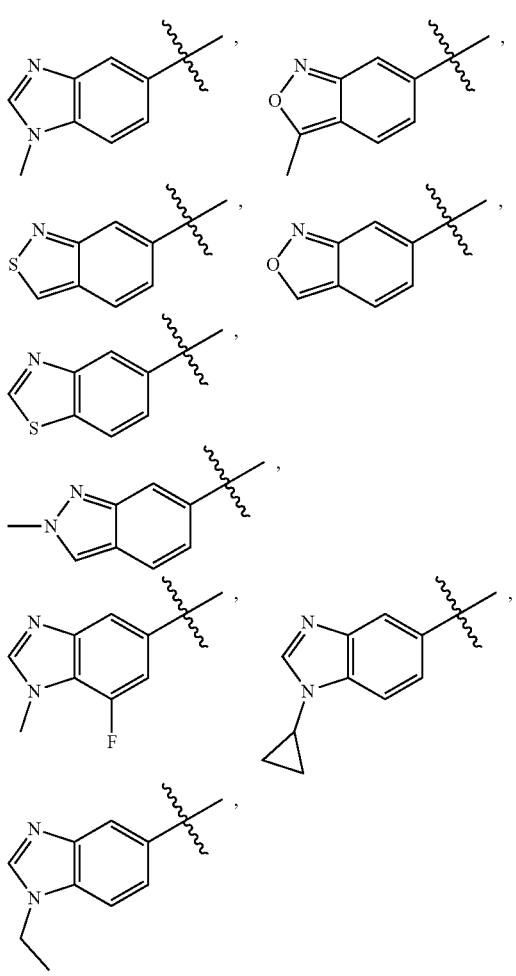

In another embodiment, the invention provides a compound of Formula (I), (II), or (IV), wherein R² is selected from the group consisting of:

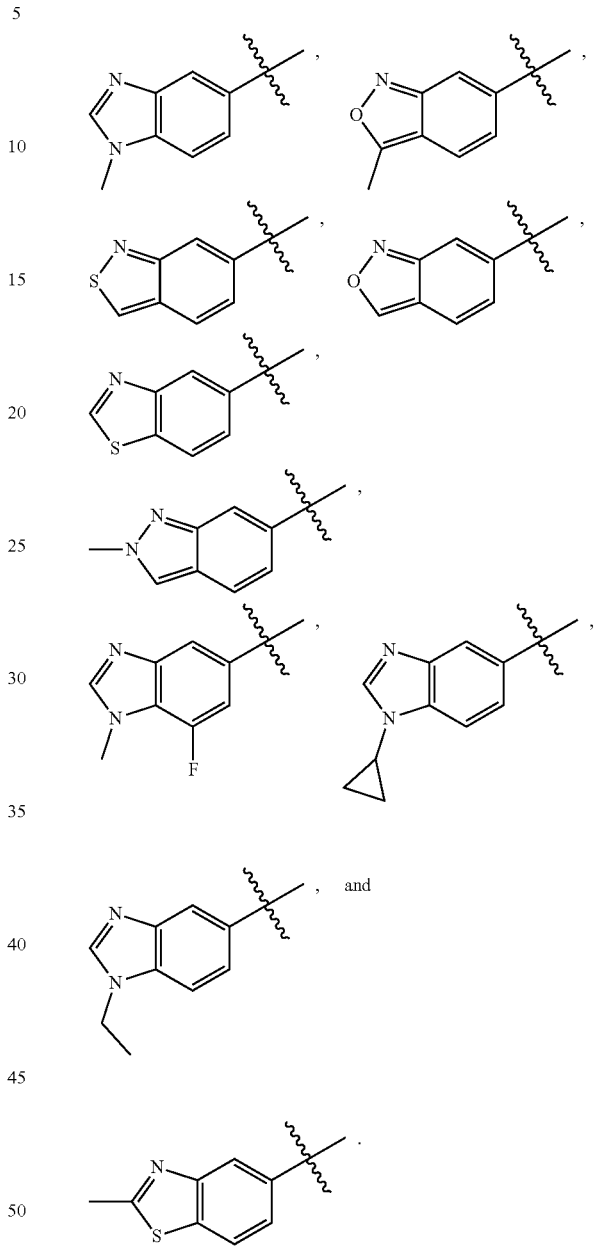

In a preferred embodiment, the invention provides a compound of Formula (I), (II), or (IV), wherein R² is:

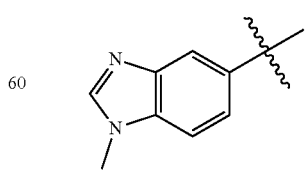

In another embodiment, the invention provides a compound of Formula (I), (II), (III), or (IV), wherein R² is

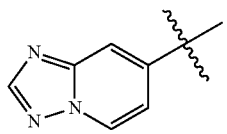

In another embodiment, the invention provides a compound of Formula (I), (II), or (III), wherein each $R^3$ is independently selected from halogen and methyl. In another embodiment, the invention provides a compound of Formula (I), (II), or (III), wherein each $R^3$ is independently selected from the group consisting of fluoro, chloro, and methyl. In another embodiment, the invention provides a compound of Formula (I), (II), or (III), wherein each $R^3$ is methyl. In another embodiment, the invention provides a compound of Formula (I), (II), or (III), wherein $R^3$ is methyl.

In another embodiment, the invention provides a compound of Formula (I), (II), or (III), wherein n is 0, 1 or 2. In a preferred embodiment, the invention provides a compound of Formula (I), (II), or (III), wherein n is 1.

In a preferred embodiment, the invention provides a compound of Formula (I), (II), or (III), wherein n is 1 or 2.

In another embodiment, the invention provides a compound of Formula (I), (II), or (III), wherein $L_1$ is NH, $L_2$ is O, and each $R^3$ is methyl. In another embodiment, the invention provides a compound of Formula (I), (II), or (III), wherein $L_1$ is NH, $L_2$ is O, and $R^3$ is methyl. In another embodiment, the invention provides a compound of Formula (I), (II), or (III), wherein $L_1$ is NH, $L_2$ is O, $R^3$ is methyl and n is 1.

In another embodiment, the invention provides a compound of Formula (I), (II), or (III), wherein $L_1$ is NH, $L_2$ is O, and each $R^3$ is selected from halogen and methyl. In a preferred embodiment, the invention provides a compound of Formula (I), (II), or (III), wherein $L_1$ is NH, $L_2$ is O, and each $R^3$ is selected from fluoro, chloro and methyl. In a preferred embodiment, the invention provides a compound of Formula (I), (II), or (III), wherein $L_1$ is NH, $L_2$ is O, each $R^3$ is selected from halogen and methyl, and n is 1 or 2. In a preferred embodiment, the invention provides a compound of Formula (I), (II), or (III), wherein $L_1$ is NH, $L_2$ is O, each $R^3$ is selected from fluoro, chloro and methyl, and n is 1 or 2.

In another embodiment, a compound, or pharmaceutically acceptable salt thereof, of Examples 1 to 492 is provided. In another embodiment, a compound, or pharmaceutically acceptable salt thereof, of Examples 1 to 12 is provided.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, acid addition salts and base addition salts of the compounds of one of the formulae provided herein.

"Pharmaceutically acceptable salt", as used herein, means those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

The compounds described herein also include other salts of such compounds that are not necessarily pharmaceutically acceptable salts, and which may be useful as intermediates for preparing and/or purifying compounds described herein and/or for separating enantiomers of compounds described herein. For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and 1,1'-methylene-bis-(2-hydroxy-3-naphthoate) (i.e., pamoate) salts.

Examples of salts include, but are not limited to, acetate, acrylate, adipate, aspartate, benzenesulfonate, benzoate (such as chlorobenzoate, methylbenzoate, dinitrobenzoate, hydroxybenzoate, and methoxybenzoate), besylate, bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edisylate, estolate, esylate, ethylsuccinate, formate, fumarate, gluceptate, gluconate, glucoronate, glutamate, glycollate, glycollylarsanilate, heptanoate, hexafluorophosphate, hexyne-1,6-dioate, hexylresorcinate, hibenzate, hydrabamine, hydrobromide, hydrochloride, hydroiodide, γ-hydroxy butyrate, iodide, isobutyrate, isethionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-1,5-disulfonic acid, naphthalene-2-sulfonate, naphthylate, 2-napsylate, nicotinate, nitrate, oleate, orotate, oxalate, pamoate (embonate), palmitate, pamoate, pantothenate, phenylacetates, phenylbutyrate, phenylpropionate, phthalate, phosphate/diphosphate, polygalacturonate, propanesulfonate, propionate, propiolate, pyroglutamate, pyrophosphate, pyrosulfate, saccharate, salicylate, stearate, subacetate, suberate, succinate, sulfate, sulfonate, sulfite, tannate, tartrate, teoclate, tosylate, triethiodide, trifluoroacetate, valerate and xinofoate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds that are acidic in nature may be capable of forming base salts with various pharmacologically acceptable cations. Examples of such salts include the alkali metal or alkaline-earth metal salts, and particularly, the sodium and potassium salts. These salts are all prepared by conventional techniques. The chemical bases that are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts, such as N-methylglucamine-(meglumine), and the lower alkanolammonium and other base salts of pharmaceutically acceptable organic amines.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Stahl, P. Heinrich and Camilli G. Wermuth, Eds. *Handbook of Pharmaceutical Salts: Properties. Selection, and Use*. New York: Wiley-VCH, 2011. Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of Formula (I), (II), (III) or (IV) in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

It will also be understood by those of skill in the art that some of the embodiments include compounds that may exist in various salt forms or free base form, while other compounds may not form salts. For instance, lapatinib may exist in its free base form, as lapatinib ditosylate or as another salt. For convenience, certain embodiments of the present invention list compounds by their name (e.g., compounds of Formula (I), (II), (III) or (IV) or lapatinib) with the nomenclatures "or salts thereof" or "or pharmaceutically acceptable salts thereof." In such instances, those of skill in the art will recognize that some of those compounds within the list may exist in various salt forms or as a free base (e.g., compounds of Formula (I), (II), (III) or (IV) or lapatinib), while other compounds may not exist in salt forms (e.g., trastuzumab), even though the language appears to apply to all the compounds within the list.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. "Solvate", as used herein, means a molecular complex comprising the compound of Formula (I), (II), (III) or (IV) and one or more pharmaceutically acceptable solvent molecules, for example, ethanol. "Hydrate", as used herein, means a solvate where the solvent is water. Pharmaceutically acceptable solvates in accordance with the invention include hydrates and solvates wherein the solvent of crystallization may be isotopically substituted, e.g., $D_2O$, $d_6$-acetone (($CD_3)_2CO$), $d_6$-DMSO (($CD_3)_2SO$).

A currently accepted classification system for organic hydrates is one that defines isolated site, channel, or metal-ion coordinated hydrates, see Brittain, Harry G., Ed. *Polymorphism in Pharmaceutical Solids*. New York: Informa Healthcare USA, Inc., 2016. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionized, partially ionized, or non-ionized. For a review of such complexes, see Haleblian, J K. "Characterization of habits and crystalline modification of solids and their pharmaceutical applications." *J Pharm Sci.* 64(8) (1975): pp. 1269-1288, the disclosure of which is incorporated herein by reference in its entirety.

The invention also relates to prodrugs of the compounds of the formulae provided herein. Thus, certain derivatives of compounds of Formula (I), (II), (III) or (IV) that may have little or no pharmacological activity themselves can, when administered to a patient, be converted into the compounds of the invention having the desired activity, for example, by hydrolytic cleavage. Such derivatives are referred to as "prodrugs." Further information on the use of prodrugs may be found in Higuchi, T., and V. Stella, Eds. *Pro-drugs as Novel Delivery Systems.* ACS Symposium Series Vol. 14, Washington DC: American Chemical Society, 1975 and Roche, Edward P. *Bioreversible Carriers in Drug Design: Theory and Application.* New York: Pergamon Press, 1987, the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in Bundgaard, Hans, ed. *Design of Prodrugs.* New York: Elsevier, 1985, the disclosure of which is incorporated herein by reference in its entirety.

Thus, a prodrug in accordance with the invention is (a) an ester or amide derivative of a carboxylic acid in a compound of Formula (I), (II), (III) or (IV); (b) an ester, carbonate, carbamate, phosphate or ether derivative of a hydroxyl group in a compound of Formula (I), (II), (III) or (IV); (c) an amide, imine, carbamate or amine derivative of an amino group in a compound form Formula (I), (II), (III) or (IV); (d) a thioester, thiocarbonate, thiocarbamate or sulfide derivatives of a thiol group in a compound of Formula (I), (II), (III) or (IV); or (e) an oxime or imine derivative of a carbonyl group in a compound of Formula (I), (II), (III) or (IV).

Some non-limiting examples of prodrugs in accordance with the invention include:
(i) where the compound of the invention contains a carboxylic acid functionality (—COOH), an ester thereof, for example, replacement of the hydrogen with $C_1$-$C_8$ alkyl;
(ii) where the compound contains an alcohol functionality (—OH), an ether thereof, for example, replacement of the hydrogen with $C_1$-$C_6$ alkanoyloxymethyl, or with a phosphate ether group; and
(iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references. Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms as part of substituent groups or optional substituents attached to these groups. At such asymmetric centers, a solid line is used to indicate that all possible stereoisomers at that carbon atom are included, while a solid or dotted wedge indicates that only the isomer shown is meant to be included at such stereocenter, unless otherwise indicated. Compounds of the formulae herein can include substituent groups containing as and trans geometric isomers, rotational isomers, atropisomers, conformational isomers, and tautomers, including compounds exhibiting more than one type of isomerism.

Also included are acid addition salts or base addition salts, wherein the counterion is optically active, for example, d-lactate or i-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided. It must be emphasised that while, for conciseness, the compounds of Formula (I), (II), (III) or (IV) have been drawn herein in a single tautomeric form, all possible tautomeric forms are included within the scope of the invention.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Compounds of Formula (I), (II), (III) or (IV) containing one or more asymmetric carbon atoms can exist as two or more stereoisomers. Where a compound of the invention contains an alkenyl group, geometric cis/trans (or Z/E) isomers are possible. Cis/trans isomers may be separated by conventional techniques well known to those skilled in the art, for example, chromatography and fractional crystallization. It follows that a single compound may exhibit more than one type of isomerism.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography ("HPLC") or superfluid critical chromatography ("SFC").

Alternatively, the racemate (or a racemic precursor) may be reacted with a suitable optically active compound, for example, an alcohol, or, in the case where the compound contains an acidic or basic moiety, an acid or base, such as tartaric acid or 1-phenylethylamine. The resulting diastereomeric mixture may be separated by chromatography and/or fractional crystallization and one or both diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, Eliel, E. and Wilen, S. *Stereochemistry of Organic Compounds*. New York: John Wiley & Sons, Inc., 1994, and Lochmuller, C. H., et al. "Chromatographic resolution of enantiomers: Selective review." *J. Chromatogr.* 113(3) (1975): pp. 283-302, the disclosures of which are incorporated herein by reference in its entirety.

The enantiomeric purity of compounds described herein may be described in terms of enantiomeric excess ("ee"), which indicates the degree to which a sample contains one enantiomer in greater amounts than the other. A racemic mixture has an ee of 0%, while a single completely pure enantiomer has an ee of 100%. Similarly, diastereomeric purity may be described in terms of diastereomeric excess ("de"). "Enantiomerically pure" or "substantially enantiomerically pure", as used herein, means a compound that comprises one enantiomer of the compound and is substantially free of the opposite enantiomer of the compound. A typical enantiomerically pure compound comprises greater than about 95% by weight of one enantiomer of the compound and less than about 5% by weight of the opposite enantiomer of the compound, preferably greater than about 97% by weight of one enantiomer of the compound and less than about 3% by weight of the opposite enantiomer of the compound, more preferably greater than about 98% by weight of one enantiomer of the compound and less than about 2% by weight of the opposite enantiomer of the compound, and even more preferably greater than about 99% by weight of one enantiomer of the compound and less than about 1% by weight of the opposite enantiomer of the compound.

The present invention also includes isotopically-labeled compounds, which are identical to those recited in one of the formulae provided, but for the fact that one or more atoms are replaced by an atom having an atomic mass or mass number different from the atomic mass or mass number usually found in nature. Isotopically-labeled compounds can generally be prepared by conventional techniques known to those skilled in the art or by processes analogous to those described herein, using an appropriate isotopically-labeled reagent in place of the non-labeled reagent otherwise employed. Examples of isotopes that may be incorporated into compounds of the invention include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl. Certain isotopically-labeled compounds of the invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds may generally be prepared by carrying out the procedures disclosed in the Schemes and/or in the Examples below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds of the invention may exist in a continuum of solid states ranging from fully amorphous to fully crystalline. "Amorphous", as used herein, means a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs, which is characterised by a change of state, typically second order (glass transition). "Crystalline", as used herein, means a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order (melting point).

The compounds of Formula (I), (II), (III) or (IV) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as thermotropic, and that resulting from the addition of a second component, such as water or another solvent, is described as lyotropic. Compounds that have the potential to form lyotropic mesophases are described as amphiphilic and consist of molecules that possess an ionic (such as —COO$^-$Na$^+$, —COO$^-$K$^+$, or —SO$_3$$^-$Na$^+$) or non-ionic (such as —N—N$^+$(CH$_3$)$_3$) polar head group, see Hartshorne, N. H. and A. Stuart. *Crystals and the Polarizing Microscope*. London: Edward Arnold Publishers Ltd., 1970.

The compounds of Formula (I), (II), (III) or (IV) may exhibit polymorphism and/or one or more kinds of isomerism (e.g., optical, geometric or tautomeric isomerism). The compounds of Formula (I), (II), (III) or (IV) may also be isotopically labelled. Such variation is implicit to the compounds of Formula (I), (II), (III) or (IV) defined as they are by reference to their structural features and therefore within the scope of the invention.

Synthesis of Compounds

Compounds described herein may be synthesized by synthetic routes that include processes analogous to those well-known in the chemical arts, particularly in light of the description contained herein. The starting materials are generally available from commercial sources, such as MilliporeSigma (St. Louis, MO), Alfa Aesar (Ward Hill, MA), TCI (Portland, OR) or the like, or are readily prepared using methods well known to those skilled in the art (e.g., prepared by methods generally described in Louis F. Fieser and Mary Fieser, *Reagents for Organic Synthesis*, v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

In preparing compounds of Formula (I), (II), (III) or (IV), protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Formulations and Administration

A typical formulation or composition is prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005, the disclosures of which are herein incorporated by reference.

"Pharmaceutical composition", as used herein, means a mixture of one or more of the compounds of Formula (I), (II), (III) or (IV), or a pharmaceutically acceptable salt, solvate, hydrate or prodrug thereof as an active ingredient, and at least one pharmaceutically acceptable carrier or excipient. In another embodiment, the pharmaceutical composition comprises two or more pharmaceutically acceptable carriers and/or excipients. In another embodiment, the pharmaceutical composition further comprises at least one additional anti-cancer therapeutic agent. In another embodiment, the combination provides an additive, greater than additive, or synergistic anti-cancer effect.

In one aspect, the invention provides a pharmaceutical composition comprising a compound of Formula (I), (II), (III) or (IV), or a pharmaceutically acceptable salt thereof. In a further aspect, the invention provides a pharmaceutical composition comprising a compound of Formula (I), (II), (III) or (IV), or a pharmaceutically acceptable salt thereof, and a pharmaceutically acceptable carrier or excipient. In another embodiment, the pharmaceutical composition comprises two or more pharmaceutically acceptable carriers and/or excipients.

In another aspect, the invention provides a pharmaceutical composition for the treatment of a disease or condition for which an inhibitor of HER2 mutations is indicated, comprising a compound of Formula (I), (II), (III) or (IV), or a pharmaceutically acceptable salt thereof.

In another aspect, the invention provides a pharmaceutical composition for the treatment of a disease or condition for which a brain penetrant inhibitor of HER2 is indicated, comprising a compound of Formula (I), (II), (III) or (IV), or a pharmaceutically acceptable salt thereof. In a further aspect, the invention provides a pharmaceutical composition for the treatment of a disease or condition for which a brain penetrant inhibitor of HER2 mutations is indicated, comprising a compound of Formula (I), (II), (III) or (IV), or a pharmaceutically acceptable salt thereof.

In another aspect, the invention provides a pharmaceutical composition comprising a compound of Formula (I), (II), (III) or (IV), or a pharmaceutically acceptable salt thereof, for use in the treatment of abnormal cell growth.

In yet another aspect, the invention provides a pharmaceutical composition for use in the treatment of abnormal cell growth in a subject in need thereof, which pharmaceutical composition comprises a compound of Formula (I), (II), (III) or (IV), or a pharmaceutically acceptable salt thereof. In a further aspect, the invention provides a pharmaceutical composition for use in the treatment of abnormal cell growth in a subject in need thereof, which pharmaceutical composition comprises a compound of Formula (I), (II), (III) or (IV), or a pharmaceutically acceptable salt thereof, and a pharmaceutically acceptable carrier or excipient.

"Additive", as used herein, means that the result of the combination of two compounds, components or targeted agents is no greater than the sum of each compound, component or targeted agent individually.

"Synergy" or "synergistic", as used herein, mean that the result of the combination of two compounds, components or targeted agents is greater than the sum of each compound, component or targeted agent individually. This improvement in the disease, condition or disorder being treated is a "synergistic" effect. A "synergistic amount" is an amount of the combination of the two compounds, components or targeted agents that results in a synergistic effect.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

"Pharmaceutically acceptable carrier", as used herein, means a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors, such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients, such as flavorings, binders, excipients and the like. Thus, for oral administration, tablets containing various excipients, such as citric acid, may be employed together with various disintegrants, such as starch, alginic acid and certain complex silicates, and with binding agents, such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents, such as water, ethanol, propylene glycol, glycerin, or combinations thereof.

Administration of the compounds of Formula (I), (II), (III) or (IV) may be affected by any method that enables delivery of the compounds to the site of action. These methods include oral routes, intraduodenal routes, parenteral injection (including intravenous, subcutaneous, intramuscular, intravascular or infusion), topical, and rectal administration.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of Formula (I), (II), (III) or (IV) and methods for their preparation will be readily apparent to those skilled in the art. Such compositions and methods for their preparation can be found, for example, in Gennaro, supra.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms, such as those described in Liang, Alfred C. and Li-Ian H. Chen. "Fast-dissolving intraoral drug delivery systems." *Expert Opinion in Therapeutic Patents*. Vol. 11, No. 6 (2001): pp. 981-986, the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants, such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated, uncoated, or encapsulated. The formulation of tablets is discussed in detail in Ansel, supra.

Solid formulations for oral administration may be formulated to be immediate and/or modified release. Modified release formulations include delayed, sustained, pulsed, controlled, targeted and programmed release.

Suitable modified release formulations are described in U.S. Pat. No. 6,106,864. Details of other suitable release technologies, such as high energy dispersions and osmotic and coated particles can be found in Verma, Rajan K., and Sanjay Garg. "Current Status of Drug Delivery Technologies and Future Directions." *Pharmaceutical Technology On-Line.* 25(2) (2001): pp. 1-14. The use of chewing gum to achieve controlled release is described in WO 00/35298. The disclosures of these references are incorporated herein by reference in their entireties.

The compounds of Formula (I), (II), (III) or (IV) may also be administered directly into the blood stream, into muscle, or into an internal organ. Suitable means for parenteral administration includes intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions, which may contain excipients such as salts, carbohydrates and buffering agents (preferably a pH of 3 to 9), but, for some applications, they may be more suitably formulated as a sterile, non-aqueous solution or as a dried form to be used in conjunction with a suitable vehicle, such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula (I), (II), (III) or (IV) used in the preparation of parenteral solutions may be increased using appropriate formulation techniques, such as the incorporation of solubility-enhancing agents.

Formulations for parenteral administration may be formulated to be immediate and/or modified release. Modified release formulations include delayed, sustained, pulsed, controlled, targeted and programmed release. Thus, compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, Finnin, Barrie C. and Timothy M. Morgan. "Transdermal penetration enhancers: Applications, limitations, and potential." *J Pharm Sci.* 88(10) (1999): pp. 955-958, the disclosure of which is herein incorporated by reference in its entirety. Other means of topical administration include delivery by electroporation, iontophoresis, phonophoresis, sonophoresis and micro needle or needle-free (e.g., Powderject™, Bioject™, etc.) injection.

Formulations for topical administration may be formulated to be immediate and/or modified release. Modified release formulations include delayed, sustained, pulsed, controlled, targeted and programmed release.

The compounds of Formula (I), (II), (III) or (IV) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of a compound of Formula (I), (II), (III) or (IV), comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of Formula (I), (II), (III) or (IV), a suitable powder base, such as lactose or starch, and a performance modifier, such as l-leucine, mannitol, or magnesium stearate. The lactose may be anhydrous or in the form of lactose monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of Formula (I), (II), (III) or (IV) per actuation, and the actuation volume may vary from 1 μL to 100 μL. A typical formulation includes a compound of Formula (I), (II), (III) or (IV), propylene glycol, sterile water, ethanol and sodium chloride. Alternative solvents that may be used instead of propylene glycol include glycerol and polyethylene glycol.

Suitable flavors, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, poly(D,L-lactic-coglycolic acid) (PLGA). Modified release formulations include delayed, sustained, pulsed, controlled, targeted and programmed release.

In the case of dry powder inhalers and aerosols, the dosage unit is determined by means of a valve, which delivers a metered amount. Units in accordance with the invention are typically arranged to administer a metered dose or "puff" containing a desired mount of the compound of Formula (I), (II), (III) or (IV). The overall daily dose may be administered in a single dose or, more usually, as divided doses throughout the day.

Compounds of Formula (I), (II), (III) or (IV) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed, sustained, pulsed, controlled, targeted and programmed release.

Compounds of Formula (I), (II), (III) or (IV) may also be administered directly to the eye or ear, typically in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer, such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed, sustained, pulsed, controlled, targeted, or programmed release.

Compounds of Formula (I), (II), (III) or (IV) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. "Dosage unit form", as used herein, means physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of Formula (I), (II), (III) or (IV) administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Therapeutic Methods and Uses

The invention further provides therapeutic methods and uses comprising administering the compounds of Formula (I), (II), (III) or (IV), or pharmaceutically acceptable salts thereof, alone or in combination with other therapeutic agents or palliative agents.

In one aspect, the invention provides a method for treating abnormal cell growth in a subject in need thereof, comprising administering to the subject a therapeutically effective amount of a compound of Formula (I), (II), (III) or (IV), or a pharmaceutically acceptable salt thereof.

In another aspect, the invention provides a method for treating abnormal cell growth comprising administering a therapeutically effective amount of a compound of Formula (I), (II), (III) or (IV), or a pharmaceutically acceptable salt thereof, to a patient in need thereof.

In another aspect, the invention provides a method for treating or ameliorating the severity of abnormal cell growth in a patient in need thereof comprising administering to the patient a compound of Formula (I), (II), (III) or (IV), or a pharmaceutically acceptable salt thereof. In a further embodiment, the invention provides a method for treating the severity of abnormal cell growth in a patient in need thereof comprising administering to the patient a compound of Formula (I), (II), (III) or (IV), or a pharmaceutically acceptable salt thereof. In another further embodiment, the invention provides a method for ameliorating the severity of abnormal cell growth in a patient in need thereof comprising administering to the patient a compound of Formula (I), (II), (III) or (IV), or a pharmaceutically acceptable salt thereof.

In a preferred aspect, the invention provides a method for treating a disorder mediated by HER2 mutations in a subject, comprising administering to the subject a compound of Formula (I), (II), (III) or (IV), or a pharmaceutically acceptable salt thereof, in an amount that is effective for treating said disorder, in particular cancer.

In a preferred aspect, the invention provides a method for treating a disorder mediated by brain metasteses from HER2 amplified or HER2 positive cancer in a subject, comprising administering to the subject a compound of Formula (I), (II), (III) or (IV), or a pharmaceutically acceptable salt thereof, in an amount that is effective for treating said disorder, in particular cancer. In a further preferred aspect, the invention provides a method for treating a disorder mediated by brain metasteses from HER2 mutation amplified or HER2 mutation positive cancer in a subject, comprising administering to the subject a compound of Formula (I), (II), (III) or (IV), or a pharmaceutically acceptable salt thereof, in an amount that is effective for treating said disorder, in particular cancer. In a preferred embodiment, the method for treating is of a disorder mediated by brain metasteses from HER2 amplified cancer. In a preferred embodiment, the method for treating is of a disorder mediated by brain metasteses from HER2 positive cancer. In a preferred embodiment, the method for treating is of a disorder mediated by brain metasteses from HER2 mutation amplified cancer. In a preferred embodiment, the method for treating is of a disorder mediated by brain metasteses from HER2 mutation positive cancer.

In some methods of the present invention, the methods are for treating brain metasteses. These brain metasteses occur when cancer cells spread from their original site to the brain. In a preferred embodiment of the present invention, the brain metasteses come from HER2 positive or HER2 amplified cancer. In another preferred embodiment of the present invention, the brain metasteses come from HER2 mutations positive or HER2 mutations amplified cancer.

In another preferred aspect, the invention provides a method for treating a disease or disorder modulated by HER2 mutations, comprising administering to a mammal in need of such treatment an amount of a compound of Formula (I), (II), (III) or (IV), or a pharmaceutically acceptable salt thereof. In another preferred aspect, the invention provides a method for treating a disease or disorder modulated by HER2 mutations, comprising administering to a mammal in need of such treatment an effective amount of a compound of Formula (I), (II), (III) or (IV), or a pharmaceutically acceptable salt thereof.

In another preferred aspect, the invention provides a method for treating a disease or disorder modulated by brain metasteses from HER2 amplified or HER2 positive cancer, comprising administering to a mammal in need of such treatment an amount of a compound of Formula (I), (II), (III) or (IV), or a pharmaceutically acceptable salt thereof. In a further preferred aspect, the invention provides a method for treating a disease or disorder modulated by brain metasteses from HER2 mutation amplified or HER2 mutation positive cancer, comprising administering to a mammal in need of such treatment an amount of a compound of Formula (I), (II), (III) or (IV), or a pharmaceutically acceptable salt thereof. In another preferred aspect, the invention provides a method for treating a disease or disorder modulated by brain metasteses from HER2 amplified or HER2 positive cancer, comprising administering to a mammal in need of such treatment an effective amount of a compound of Formula (I), (II), (III) or (IV), or a pharmaceutically acceptable salt thereof. In a further preferred aspect, the invention provides a method for treating a disease or disorder modulated by brain metasteses from HER2 mutation amplified or HER2 mutation positive cancer, comprising administering to a mammal in need of such treatment an effective amount of a compound of Formula (I), (II), (III) or (IV), or a pharmaceutically acceptable salt thereof. In another preferred embodiment, the method for treating is a disease or disorder modulated by HER2 amplified cancer. In another preferred embodiment, the method for treating is a disease or disorder modulated by HER2 positive cancer. In another preferred embodiment, the method for treating is a disease or disorder modulated by HER2 mutation amplified cancer. In another preferred embodiment, the method for treating is a disease or disorder modulated by HER2 mutation positive cancer.

In another aspect, the invention provides a method of inhibiting cancer cell proliferation in a subject, comprising administering to the subject a compound of Formula (I), (II), (III) or (IV), or a pharmaceutically acceptable salt thereof, in an amount effective to inhibit cell proliferation.

In another aspect, the invention provides a method of inhibiting cancer cell invasiveness in a subject, comprising administering to the subject a compound of Formula (I), (II), (III) or (IV), or a pharmaceutically acceptable salt thereof, in an amount effective to inhibit cell invasiveness.

In another aspect, the invention provides a method of inducing apoptosis in cancer cells in a subject, comprising administering to the subject a compound of Formula (I), (II), (III) or (IV), or a pharmaceutically acceptable salt thereof, in an amount effective to induce apoptosis.

In another aspect, the invention provides a method of inhibiting cancer cell metastasis in a subject, comprising administering to the subject a compound of Formula (I), (II), (III) or (IV), or a pharmaceutically acceptable salt thereof, in an amount effective to inhibit cell metastasis.

In another aspect, the invention provides a method of inhibiting angiogenesis in a subject, comprising administering to the subject a compound of Formula (I), (II), (III) or (IV), or a pharmaceutically acceptable salt thereof, in an amount effective to inhibit angiogenesis.

In one aspect, the invention provides a compound of Formula (I), (II), (III) or (IV), or a pharmaceutically acceptable salt thereof, for use in treatment. In a further aspect, the invention provides a compound of Formula (I), (II), (III) or (IV), or a pharmaceutically acceptable salt thereof, for use in the treatment of abnormal cell growth. In another aspect, the invention provides a compound of Formula (I), (II), (III) or (IV), or a pharmaceutically acceptable salt thereof, for use in the treatment of abnormal cell growth in a subject.

In another aspect, the invention provides a compound of Formula (I), (II), (III) or (IV), or a pharmaceutically acceptable salt thereof, for use in the treatment of a subject in need of such treatment. In another embodiment, the treatment is for abnormal cell growth.

In another aspect, the invention provides a compound of Formula (I), (II), (III) or (IV), or a pharmaceutically acceptable salt thereof, for use as a medicament. In a further aspect, the invention provides a compound of Formula (I), (II), (III) or (IV), or a pharmaceutically acceptable salt thereof, for use as a medicament for the treatment of abnormal cell growth. In another aspect, the invention provides a compound of Formula (I), (II), (III) or (IV), or a pharmaceutically acceptable salt thereof, for use as a medicament for the treatment of abnormal cell growth in a subject.

In another aspect, the invention provides a compound of Formula (I), (II), (III) or (IV), or a pharmaceutically acceptable salt thereof, for use in therapy. In a further aspect, the invention provides a compound of Formula (I), (II), (III) or (IV), or a pharmaceutically acceptable salt thereof, for use in therapy for the treatment of abnormal cell growth. In another aspect, the invention provides a compound of Formula (I), (II), (III) or (IV), or a pharmaceutically acceptable salt thereof, for use in therapy for the treatment of abnormal cell growth in a subject.

In one aspect, the invention provides a compound of Formula (I), (II), (III) or (IV), or a pharmaceutically acceptable salt thereof, for use in the treatment of a disease or condition for which an inhibitor of HER2 mutations is indicated. In another aspect, the invention provides a compound of Formula (I), (II), (III) or (IV), or a pharmaceutically acceptable salt thereof, for use in the treatment of a subject with a disease or condition for which an inhibitor of HER2 mutations is indicated.

In one preferred aspect, the invention provides a compound of Formula (I), (II), (III) or (IV), or a pharmaceutically acceptable salt thereof, for use in the treatment of a disease or condition for which a brain penetrant inhibitor of HER2 is indicated. In a further preferred aspect, the invention provides a compound of Formula (I), (II), (III) or (IV), or a pharmaceutically acceptable salt thereof, for use in the treatment of a disease or condition for which a brain penetrant inhibitor of HER2 mutations is indicated. In another preferred aspect, the invention provides a compound of Formula (I), (II), (III) or (IV), or a pharmaceutically acceptable salt thereof, for use in the treatment of a subject with a disease or condition for which a brain penetrant inhibitor of HER2 is indicated. In a further preferred aspect, the invention provides a compound of Formula (I), (II), (III) or (IV), or a pharmaceutically acceptable salt thereof, for use in the treatment of a subject with a disease or condition for which a brain penetrant inhibitor of HER2 mutations is indicated.

In another aspect, the invention provides the use of a compound of Formula (I), (II), (III) or (IV), or a pharmaceutically acceptable salt thereof, for the treatment of a subject in need of such treatment. In a further aspect, the invention provides the use of a compound of Formula (I), (II), (III) or (IV), or a pharmaceutically acceptable salt thereof, for the treatment of a subject with abnormal cell growth.

In yet another aspect, the invention provides the use of a compound of Formula (I), (II), (III) or (IV), or a pharmaceutically acceptable salt thereof, in the manufacture of a medicament for treatment. In a further aspect, the invention provides the use of a compound of Formula (I), (II), (III) or (IV), or a pharmaceutically acceptable salt thereof, in the manufacture of a medicament for treatment of a subject. In another aspect, the invention provides the use of a compound of Formula (I), (II), (III) or (IV), or a pharmaceutically acceptable salt thereof, in the manufacture of a medicament for the treatment of abnormal cell growth in a subject.

In another preferred aspect, the invention provides the use of a compound of Formula (I), (II), (III) or (IV), or a pharmaceutically acceptable salt thereof, in the manufacture of a medicament for treating a disease or condition for which an inhibitor of HER2 mutations is indicated. In another preferred aspect, the invention provides the use of a compound of Formula (I), (II), (III) or (IV), or a pharmaceutically acceptable salt thereof, in the manufacture of a medicament for treating a disease or condition in a subject for which an inhibitor of HER2 mutations is indicated.

In another preferred aspect, the invention provides the use of a compound of Formula (I), (II), (III) or (IV), or a pharmaceutically acceptable salt thereof, in the manufacture of a medicament for treating a disease or condition for which a brain penetrant inhibitor of HER2 is indicated. In a further preferred aspect, the invention provides the use of a compound of Formula (I), (II), (III) or (IV), or a pharmaceutically acceptable salt thereof, in the manufacture of a medicament for treating a disease or condition for which a brain penetrant inhibitor of HER2 mutations is indicated. In another preferred aspect, the invention provides the use of a compound of Formula (I), (II), (III) or (IV), or a pharmaceutically acceptable salt thereof, in the manufacture of a medicament for treating a disease or condition in a subject for which a brain penetrant inhibitor of HER2 is indicated. In a further preferred aspect, the invention provides the use of a compound of Formula (I), (II), (III) or (IV), or a pharmaceutically acceptable salt thereof, in the manufacture of a medicament for treating a disease or condition in a subject for which a brain penetrant inhibitor of HER2 mutations is indicated.

"Abnormal cell growth", as used herein, unless otherwise indicated, means cell growth that is independent of normal regulatory mechanisms (e.g., loss of contact inhibition). Abnormal cell growth may be benign (not cancerous) or malignant (cancerous).

Abnormal cell growth includes the abnormal growth of: (1) tumor cells (tumors) that show increased expression of HER2 mutation; (2) tumors that proliferate by aberrant HER2 mutation activation; (3) tumors characterized by amplification or overexpression of HER2 mutation; and (4) tumors that are resistant to HER2 therapy or HER2 inhibition.

In frequent preferred embodiments of the methods provided herein, the abnormal cell growth is cancer. "Cancer", as used herein, means the physiological condition in mammals that is typically characterized by abnormal or unregulated cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In another embodiment, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

"Ameliorating", as used herein, means a lessening or improvement of one or more symptoms upon treatment with a compound described herein, as compared to not administering the compound. Ameliorating also includes shortening or reduction in duration of a symptom.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered that will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukemias (cancers of the blood) generally do not form solid tumors.

"Tumor burden" or "tumor load", as used herein, means the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using callipers, or while in the body using imaging techniques, e.g., ultrasound, bone scan, computed tomography (CT), or magnetic resonance imaging (MRI) scans.

"Tumor size", as used herein, means the total size of the tumor which can be measured as the length and width of a tumor. Tumor size may be determined by a variety of methods known in the art, such as, e.g., by measuring the dimensions of tumor(s) upon removal from the subject, e.g., using callipers, or while in the body using imaging techniques, e.g., bone scan, ultrasound, CR or MRI scans.

"Mammal", as used herein, means a warm-blooded animal that has or is at risk of developing a disease described herein and includes, but is not limited to, guinea pigs, dogs, cats, rats, mice, hamsters, and primates, including humans.

"Subject", as used herein, means a human or animal subject. In another embodiment, the subject is a mammal. In a preferred embodiment, the subject is a human.

"Treat" or "treating", as used herein, means to administer a compound of Formula (I), (II), (III) or (IV) to a subject having the condition to be treated to achieve at least one positive therapeutic effect. For example, treating cancer means to administer a compound of Formula (I), (II), (III) or (IV) to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, or inhibiting the progress of the disorder or condition to which such term applies, or one or more symptoms of such disorder or condition. The term "treatment", as used herein, unless otherwise indicated, means the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in a number of ways (see, for example, Weber, Wolfgang A. "Assessing Tumor Response to Therapy." *J. Nucl. Med.* 50 Suppl. 1 (2009): 1S-10S).

In another embodiment, the treatment achieved by a compound of Formula (I), (II), (III) or (IV) is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In another embodiment, response to a combination of the invention is any of PR, CR, PFS, DFS, OR or OS that is assessed using Response Evaluation Criteria in Solid Tumors (RECIST) 1.1 response criteria.

The treatment regimen for a compound of Formula (I), (II), (III) or (IV) that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrat-testy and the Wilcon on-test.

The terms "treatment regimen", "dosing protocol" and "dosing regimen" are used interchangeably to refer to the dose and timing of administration of each compound of Formula (I), (II), (III) or (IV), alone or in combination with another therapeutic agent.

In a preferred embodiment of the compounds, compositions, methods and uses described herein, the compounds of Formula (I), (II), (III) or (IV) are selective for inhibiting HER2 mutations over EGFR inhibition. In a preferred embodiment, the compounds of the invention are selective for HER2-YVMA (SEQ ID NO: 2) over EGFR.

In frequent embodiments of the methods provided herein, the abnormal cell growth is cancer. In another embodiment, the cancer is selected from breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HOC), pancreatic cancer, stomach (i.e., gastric) cancer or thyroid cancer. In further embodiments of the methods provided herein, the cancer is breast cancer, ovarian cancer, bladder cancer, uterine cancer, prostate cancer, lung cancer, esophageal cancer, liver cancer, pancreatic cancer or stomach cancer.

In a preferred embodiment, the cancer is selected from breast cancer, lung cancer, colon cancer, ovarian cancer and gastric cancer. In a preferred embodiment, the cancer is selected from breast cancer, lung cancer, and colon cancer. In a preferred embodiment, the cancer is breast cancer. In a preferred embodiment, the cancer is lung cancer. In a preferred embodiment, the cancer is colon cancer. In a preferred embodiment, the cancer is ovarian cancer. In a preferred embodiment, the cancer is gastric cancer.

In another embodiment, the cancer is breast cancer, including, e.g., ER-positive/HR-positive, HER2-negative breast cancer; ER-positive/HR-positive, HER2-positive breast cancer; triple negative breast cancer (TNBC); or inflammatory breast cancer. In a preferred embodiment, the breast cancer is endocrine resistant breast cancer, trastuzumab resistant breast cancer, or breast cancer demonstrating primary or acquired resistance to HER2 inhibition. In another embodiment, the breast cancer is advanced or metastatic breast cancer. In a preferred embodiment of each of the foregoing, the breast cancer is characterized by amplification or overexpression of HER2 mutations or HER2-YVMA (SEQ ID NO: 2).

In another embodiment of the methods provided herein, the cancer is breast cancer, ovarian cancer, bladder cancer, uterine cancer, prostate cancer, lung cancer (including SCLC or NSCLC), esophageal cancer, liver cancer, pancreatic cancer or stomach cancer.

In a preferred embodiment, the cancer is HER2 positive. In another preferred embodiment, the cancer is HER2 mutations positive.

In a preferred embodiment, the cancer is HER2 amplified. In another preferred embodiment, the cancer is HER2 mutations amplified.

In a preferred embodiment of the methods provided herein, the abnormal cell growth is cancer characterized by amplification or overexpression of HER2 mutations. In another preferred embodiment of the methods provided herein, the subject is identified as having a cancer characterized by amplification or overexpression of HER2 mutations.

In a preferred embodiment of the methods provided herein, the abnormal cell growth is cancer characterized by metastasis in the brain. In another preferred embodiment of the methods provided herein, the subject is identified as having a cancer characterized by metastasis in the brain.

In a preferred embodiment of the methods provided herein, the abnormal cell growth is cancer characterized by metastasis in the brain having amplification or overexpression of HER2 mutations. In another preferred embodiment of the methods provided herein, the subject is identified as having a cancer characterized by metastasis in the brain having amplification or overexpression of HER2 mutations.

In another embodiment, the cancer is selected from the group consisting of breast cancer, lung cancer, colon cancer, ovarian cancer and gastric cancer. In a preferred such embodiment, the cancer is breast cancer, lung cancer, colon cancer, ovarian cancer or gastric cancer characterized by amplification or overexpression of HER2 mutations. In another preferred such embodiments, the cancer is (a) breast cancer or ovarian cancer; (b) characterized by amplification or overexpression of HER2 mutations; or (c) both (a) and (b).

In a preferred embodiment, the cancer is metastasis in the brain caused by other cancers characterized by amplification or overexpression of HER2. In a further preferred embodiment, the cancer is metastasis in the brain caused by other cancers characterized by amplification or overexpression of HER2 mutations.

In a preferred embodiment, the cancer is metastasis in the brain characterized by amplification or overexpression of HER2 caused by other cancers characterized by amplification or overexpression of HER2. In a further preferred embodiment, the cancer is metastasis in the brain characterized by amplification or overexpression of HER2 mutations caused by other cancers characterized by amplification or overexpression of HER2 mutations.

In another embodiment, the compound of Formula (I), (II), (III) or (IV), or a pharmaceutically acceptable salt thereof, is administered as first line therapy. In another embodiment, the compound of Formula (I), (II), (III) or (IV), or a pharmaceutically acceptable salt thereof, is administered as second (or later) line therapy. In another embodiment, the compound of Formula (I), (II), (III) or (IV), or a pharmaceutically acceptable salt thereof, is administered as second (or later) line therapy following treatment with trastuzumab. In another embodiment, the compound of Formula (I), (II), (III) or (IV), or a pharmaceutically acceptable salt thereof, is administered as second (or later) line therapy following treatment with trastuzumab, pertuzumab and either paclitaxel or docetaxel. In another embodiment, the compound of Formula (I), (II), (III) or (IV), or a pharmaceutically acceptable salt thereof, is administered as second (or later) line therapy following treatment with monoclonal antibodies (such as trastuzumab, pertuzumab or margetuximab), antibody-drug conjugates (such as ado-trastuzumab emtansine ("t-dm1"), sacituzumab or govitecan-hziy), HER2 inhibitors (such as neratinib, lapatinib ortucatinib), CDK4/6 inhibitors (such as palbociclib, ribociclib orabemaciclib), mTOR inhibitors (such as everolimus), PI3K inhibitors (such as alpelisib) or PARP inhibitors (such as olaparib ortalazoparib). In another embodiment, the compound of Formula (I), (II), (III) or (IV), or a pharmaceutically acceptable salt thereof, is administered as second (or later) line therapy following treatment with monoclonal antibodies, such as trastuzumab, pertuzumab or margetuximab. In another embodiment, the compound of Formula (I), (II), (III) or (IV), or a pharmaceutically acceptable salt thereof, is administered as second (or later) line therapy following treatment with antibody-drug conjugates, such as t-dm1, sacituzumab or govitecan-hziy. In another embodiment, the compound of Formula (I), (II), (III) or (IV), or a pharmaceutically acceptable salt thereof, is administered as second (or later) line therapy following treatment with HER2 inhibitors, such as neratinib, lapatinib ortucatinib. In another embodiment, the compound of Formula (I), (II), (III) or (IV), or a pharmaceutically acceptable salt thereof, is administered as second (or later) line therapy following treatment with CDK 4/6 inhibitors, such as palbociclib, ribociclib or abemaciclib. In another embodiment, the compound of Formula (I), (II), (III) or (IV), or a pharmaceutically acceptable salt thereof, is administered as second (or later) line therapy following treatment with mTOR inhibitors, such as everolimus. In another embodiment, the compound of Formula (I), (II), (III) or (IV), or a pharmaceutically acceptable salt thereof, is administered as second (or later) line therapy following treatment with PI3K inhibitors, such as alpelisib. In another embodiment, the compound of Formula (I), (II), (III) or (IV), or a pharmaceutically acceptable salt thereof, is administered as second (or later) line therapy following treatment with PARP inhibitors, such as olaparib ortalazoparib.

Combination Therapy

Compounds of Formula (I), (II), (III) or (IV), or a pharmaceutically acceptable salt thereof, may be administered as single agents or may be administered in combination with other anti-cancer therapeutic agents, in particular standard of care agents appropriate for the particular cancer. In another embodiment, the methods and uses comprise a compound of Formula (I), (II), (III) or (IV), or a pharmaceutically acceptable salt thereof, co-administered with at least one other anti-cancer therapeutic agent. In a further embodiment, the methods and uses comprise a compound of Formula (I), (II), (III) or (IV), or a pharmaceutically acceptable salt thereof, co-administered with at least one other anti-cancer therapeutic agent to treat or ameliorate abnormal cell growth. In another further embodiment, the methods and uses comprise a compound of Formula (I), (II), (III) or (IV), or a pharmaceutically acceptable salt thereof, co-administered with at least one other anti-cancer therapeutic agent to treat abnormal cell growth.

"Combination therapy" or "co-administration", as used herein, means the administration of a compound of Formula (I), (II), (III) or (IV), or a pharmaceutically acceptable salt thereof, together with at least one additional pharmaceutical or therapeutic agent (e.g., an anti-cancer agent), wherein said compound of Formula (I), (II), (III) or (IV) and said additional pharmaceutical or medicinal agent are part of the same or separate dosage forms and are administered via the same or different routes of administration and on the same or different administration schedules".

As noted above, the compounds of the invention may be used in combination with one or more additional anti-cancer agents. The efficacy of the compounds of Formula (I), (II), (III) or (IV), or a pharmaceutically acceptable salt thereof, in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

In one aspect, the invention provides a method for the treatment of abnormal cell growth in a subject in need thereof, comprising administering to the subject an amount of a compound of Formula (I), (II), (III) or (IV), or a pharmaceutically acceptable salt thereof, in combination with an amount of an additional therapeutic agent (e.g., an anti-cancer therapeutic agent), which amounts are together effective in treating said abnormal cell growth.

When a combination therapy is used, the one or more additional anti-cancer agents may be administered sequentially or simultaneously with the compound of Formula (I), (II), (III) or (IV), or a pharmaceutically acceptable salt thereof. In one embodiment, the additional anti-cancer agent is administered to a mammal (e.g., a human) prior to administration of the compound of Formula (I), (II), (III) or (IV), or a pharmaceutically acceptable salt thereof. In another embodiment, the additional anti-cancer agent is administered to the mammal after administration of the compound of Formula (I), (II), (III) or (IV), or a pharmaceutically acceptable salt thereof. In another embodiment, the additional anti-cancer agent is administered to the mammal (e.g., a human) simultaneously with the administration of the compound of Formula (I), (II), (III) or (IV), or a pharmaceutically acceptable salt thereof.

The invention also relates to a pharmaceutical composition for the treatment of abnormal cell growth in a mammal, including a human, which comprises an amount of a compound of Formula (I), (II), (III) or (IV), including hydrates, solvates and polymorphs or pharmaceutically acceptable salts thereof, in combination with one or more (preferably one to three) additional anti-cancer therapeutic agents.

"Additional anti-cancer therapeutic agent", as used herein, means any one or more therapeutic agent, other than a compound of Formula (I), (II), (III) or (IV), or a pharmaceutically acceptable salt thereof, that is or can be used in the treatment of cancer. In another embodiment, such additional anti-cancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like. In another embodiment, the additional anti-cancer therapeutic agent is a standard of care agent. In another embodiment, the additional anti-cancer therapeutic agent is discussed below in this Combination Therapy section, such as monoclonal antibodies, antibody-drug conjugates, HER2 inhibitors, CDK 4/6 inhibitors, mTOR inhibitors, PI3K inhibitors, PARP inhibitors, chemotherapy, anti-PD-1 monoclonal antibody, aromatase inhibitors, endocrine therapy, chemotherapeutic agents, and anti-HER2 agents.

In another embodiment, a compound of Formula (I), (II), (III) or (IV), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib ortucatinib), CDK 4/6 inhibitors (such as palbociclib, ribociclib or abemaciclib), mTOR inhibitors (such as everolimus), PI3K inhibitors (such as alpelisib), PARP inhibitors (such as olaparib or talazoparib), and pharmaceutically acceptable salts thereof, or combinations thereof. In another embodiment, a compound of Formula (I), (II), (III) or (IV), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib or tucatinib), CDK 4/6 inhibitors (such as palbociclib, ribociclib or abemaciclib), mTOR inhibitors (such as everolimus), PI3K inhibitors (such as alpelisib) or PARP inhibitors (such as olaparib or talazoparib), and pharmaceutically acceptable salts thereof. In another embodiment, a compound of Formula (I), (II), (III) or (IV), or a pharmaceutically acceptable salt thereof, may be administered with monoclonal antibodies (such as trastuzumab, pertuzumab or margetuximab), antibody-drug conjugates (such as t-dm1, sacituzumab or govitecan-hziy), HER2 inhibitors (such as neratinib, lapatinib or tucatinib), CDK 4/6 inhibitors (such as palbociclib, ribociclib or abemaciclib), mTOR inhibitors (such as everolimus), PI3K inhibitors (such as alpelisib), PARP inhibitors (such as olaparib or talazoparib), and pharmaceutically acceptable salts thereof, or combinations thereof.

In another embodiment, a compound of Formula (I), (II), (III) or (IV), or a pharmaceutically acceptable salt thereof, may be administered in combination with a standard of care agent.

In another embodiment, a compound of Formula (I), (II), (III) or (IV), or a pharmaceutically acceptable salt thereof, may be administered with trastuzumab. In another embodiment, a compound of Formula (I), (II), (III) or (IV), or a pharmaceutically acceptable salt thereof, may be administered with trastuzumab, doxorubicin, cyclophosphamide and either paclitaxel or docetaxel.

In another embodiment, a compound of Formula (I), (II), (III) or (IV), or a pharmaceutically acceptable salt thereof, may be administered with trastuzumab, docetaxel and carboplatin. In another embodiment, a compound of Formula (I), (II), (III) or (IV), or a pharmaceutically acceptable salt thereof, may be administered with trastuzumab and paclitaxel. In another embodiment, a compound of Formula (I), (II), (III) or (IV), or a pharmaceutically acceptable salt thereof, may be administered with trastuzumab, cisplatin and either capecitabine or 5-fluorouracil.

In another embodiment, a compound of Formula (I), (II), (III) or (IV), or a pharmaceutically acceptable salt thereof, may be administered with pertuzumab. In another embodiment, a compound of Formula (I), (II), (III) or (IV), or a pharmaceutically acceptable salt thereof, may be administered with pertuzumab and trastuzumab. In another embodiment, a compound of Formula (I), (II), (III) or (IV), or a pharmaceutically acceptable salt thereof, may be administered with pertuzumab, trastuzumab and docetaxel. In another embodiment, a compound of Formula (I), (II), (III) or (IV), or a pharmaceutically acceptable salt thereof, may be administered with pertuzumab, trastuzumab and chemotherapy.

In another embodiment, a compound of Formula (I), (II), (III) or (IV), or a pharmaceutically acceptable salt thereof, may be administered with margetuximab. In another embodiment, a compound of Formula (I), (II), (III) or (IV), or a pharmaceutically acceptable salt thereof, may be administered with margetuximab and chemotherapy. In another embodiment, a compound of Formula (I), (II), (III) or (IV), or a pharmaceutically acceptable salt thereof, may be administered with margetuximab and an anti-PD-1 monoclonal antibody. In another embodiment, a compound of Formula (I), (II), (III) or (IV), or a pharmaceutically acceptable salt thereof, may be administered with margetuximab and an anti-PD-1 monoclonal antibody selected from the group consisting of cemiplimab, nivolumab, pembrolizumab, avelumab, durvalumab and atezolizumab.

In another embodiment, a compound of Formula (I), (II), (III) or (IV), or a pharmaceutically acceptable salt thereof, may be administered with t-dm1.

In another embodiment, a compound of Formula (I), (II), (III) or (IV), or a pharmaceutically acceptable salt thereof, may be administered with sacituzumab govitecan-hziy.

In another embodiment, a compound of Formula (I), (II), (III) or (IV), or a pharmaceutically acceptable salt thereof, may be administered with neratinib, or a pharmaceutically acceptable salt thereof. In another embodiment, a compound of Formula (I), (II), (III) or (IV), or a pharmaceutically acceptable salt thereof, may be administered with neratinib and capecitabine, or a pharmaceutically acceptable salt thereof.

In another embodiment, a compound of Formula (I), (II), (III) or (IV), or a pharmaceutically acceptable salt thereof, may be administered with lapatinib, or a pharmaceutically acceptable salt thereof. In another embodiment, a compound of Formula (I), (II), (III) or (IV), or a pharmaceutically acceptable salt thereof, may be administered with lapatinib and capecitabine, or a pharmaceutically acceptable salt thereof. In another embodiment, a compound of Formula (I), (II), (III) or (IV), or a pharmaceutically acceptable salt thereof, may be administered with lapatinib and letrozole, or a pharmaceutically acceptable salt thereof.

In another embodiment, a compound of Formula (I), (II), (III) or (IV), or a pharmaceutically acceptable salt thereof, may be administered with tucatinib, or a pharmaceutically acceptable salt thereof. In another embodiment, a compound of Formula (I), (II), (III) or (IV), or a pharmaceutically acceptable salt thereof, may be administered with tucatinib, trastuzumab and capecitabine, or a pharmaceutically acceptable salt thereof.

In another embodiment, a compound of Formula (I), (II), (III) or (IV), or a pharmaceutically acceptable salt thereof, may be administered with palbociclib, or a pharmaceutically acceptable salt thereof. In another embodiment, a compound of Formula (I), (II), (III) or (IV), or a pharmaceutically acceptable salt thereof, may be administered with palbociclib and fulvestrant, or a pharmaceutically acceptable salt thereof. In another embodiment, a compound of Formula (I), (II), (III) or (IV), or a pharmaceutically acceptable salt thereof, may be administered with palbociclib and an aromatase inhibitor, or a pharmaceutically acceptable salt thereof. In a further embodiment, a compound of Formula (I), (II), (III) or (IV), or a pharmaceutically acceptable salt thereof, may be administered with palbociclib and an aromatase inhibitor selected from the group consisting of aminoglutethimide, testolactone, anastrozole, letrozole, exemestane, vorozole, formetsane, fadrozole, 1,4,6-androstatrien-3,17-dione ("ATD") and 4-androstene-3,6,17-trione ("6-OXO"), or a pharmaceutically acceptable salt thereof.

In another embodiment, a compound of Formula (I), (II), (III) or (IV), or a pharmaceutically acceptable salt thereof, may be administered with ribociclib, or a pharmaceutically acceptable salt thereof. In another embodiment, a compound of Formula (I), (II), (III) or (IV), or a pharmaceutically acceptable salt thereof, may be administered with ribociclib and fulvestrant, or a pharmaceutically acceptable salt thereof. In another embodiment, a compound of Formula (I), (II), (III) or (IV), or a pharmaceutically acceptable salt thereof, may be administered with ribociclib and an aromatase inhibitor, or a pharmaceutically acceptable salt thereof. In a further embodiment, a compound of Formula (I), (II), (III) or (IV), or a pharmaceutically acceptable salt thereof, may be administered with ribociclib and an aromatase inhibitor selected from the group consisting of aminoglutethimide, testolactone, anastrozole, letrozole, exemestane, vorozole, formetsane, fadrozole, ATD and 6-OXO, or a pharmaceutically acceptable salt thereof.

In another embodiment, a compound of Formula (I), (II), (III) or (IV), or a pharmaceutically acceptable salt thereof, may be administered with abemaciclib, or a pharmaceutically acceptable salt thereof. In another embodiment, a compound of Formula (I), (II), (III) or (IV), or a pharmaceutically acceptable salt thereof, may be administered with abemaciclib and fulvestrant, or a pharmaceutically acceptable salt thereof. In another embodiment, a compound of Formula (I), (II), (III) or (IV), or a pharmaceutically acceptable salt thereof, may be administered with abemaciclib and an aromatase inhibitor, or a pharmaceutically acceptable salt thereof. In a further embodiment, a compound of Formula (I), (II), (III) or (IV), or a pharmaceutically acceptable salt thereof, may be administered with abemaciclib and an aromatase inhibitor selected from the group consisting of aminoglutethimide, testolactone, anastrozole, letrozole, exemestane, vorozole, formetsane, fadrozole, ATD and 6-OXO, or a pharmaceutically acceptable salt thereof.

In another embodiment, a compound of Formula (I), (II), (III) or (IV), or a pharmaceutically acceptable salt thereof, may be administered with everolimus. In another embodiment, a compound of Formula (I), (II), (III) or (IV), or a pharmaceutically acceptable salt thereof, may be administered with everolimus and exemestane. In another embodiment, a compound of Formula (I), (II), (III) or (IV), or a pharmaceutically acceptable salt thereof, may be administered with everolimus and sunitinib or sorafenib, or a pharmaceutically acceptable salt thereof. In a further embodiment, a compound of Formula (I), (II), (III) or (IV), or a pharmaceutically acceptable salt thereof, may be administered with everolimus and sunitinib, or a pharmaceutically acceptable salt thereof. In a further embodiment, a compound of Formula (I), (II), (III) or (IV), or a pharmaceutically acceptable salt thereof, may be administered with everolimus and sorafenib, or a pharmaceutically acceptable salt thereof.

In another embodiment, a compound of Formula (I), (II), (III) or (IV), or a pharmaceutically acceptable salt thereof, may be administered with alpelisib, or a pharmaceutically acceptable salt thereof. In another embodiment, a compound of Formula (I), (II), (III) or (IV), or a pharmaceutically acceptable salt thereof, may be administered with alpelisib and fulvestrant, or a pharmaceutically acceptable salt thereof.

In another embodiment, a compound of Formula (I), (II), (III) or (IV), or a pharmaceutically acceptable salt thereof, may be administered with olaparib. In another embodiment, a compound of Formula (I), (II), (III) or (IV), or a pharmaceutically acceptable salt thereof, may be administered with olaparib and bevacizumab.

In another embodiment, a compound of Formula (I), (II), (III) or (IV), or a pharmaceutically acceptable salt thereof, may be administered with talazoparib, or a pharmaceutically acceptable salt thereof.

In another embodiment, a compound of Formula (I), (II), (III) or (IV), or a pharmaceutically acceptable salt thereof, may be administered with rucaparib, or a pharmaceutically acceptable salt thereof.

In another embodiment, a compound of Formula (I), (II), (III) or (IV), or a pharmaceutically acceptable salt thereof, may be administered with paclitaxel or docetaxel. In a further embodiment, a compound of Formula (I), (II), (III) or (IV), or a pharmaceutically acceptable salt thereof, may be administered with paclitaxel. In a further embodiment, a compound of Formula (I), (II), (III) or (IV), or a pharmaceutically acceptable salt thereof, may be administered with docetaxel.

In another embodiment, a compound of Formula (I), (II), (III) or (IV), or a pharmaceutically acceptable salt thereof, may be administered with docetaxel and carboplatin.

In another embodiment, a compound of Formula (I), (II), (III) or (IV), or a pharmaceutically acceptable salt thereof, may be administered with carboplatin.

In another embodiment, a compound of Formula (I), (II), (III) or (IV), or a pharmaceutically acceptable salt thereof, may be administered with cisplatin and either capecitabine or 5-fluorouracil. In a further embodiment, a compound of Formula (I), (II), (III) or (IV), or a pharmaceutically acceptable salt thereof, may be administered with cisplatin and capecitabine. In a further embodiment, a compound of Formula (I), (II), (III) or (IV), or a pharmaceutically acceptable salt thereof, may be administered with cisplatin and 5-fluorouracil.

In another embodiment, a compound of Formula (I), (II), (III) or (IV), or a pharmaceutically acceptable salt thereof, may be administered with cisplatin.

In another embodiment, a compound of Formula (I), (II), (III) or (IV), or a pharmaceutically acceptable salt thereof, may be administered with 5-fluorouracil.

In another embodiment, a compound of Formula (I), (II), (III) or (IV), or a pharmaceutically acceptable salt thereof, may be administered with capecitabine.

In another embodiment, a compound of Formula (I), (II), (III) or (IV), or a pharmaceutically acceptable salt thereof, may be administered with letrozole.

In another embodiment, a compound of Formula (I), (II), (III) or (IV), or a pharmaceutically acceptable salt thereof, may be administered with trastuzumab and capecitabine.

In another embodiment, a compound of Formula (I), (II), (III) or (IV), or a pharmaceutically acceptable salt thereof, may be administered with chemotherapy. In another embodiment, chemotherapy is selected from the group consisting of cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin. In another embodiment, chemotherapy is selected from the group consisting of cyclophosphamide, methotrexate, 5-fluorouracil, vinorelbine, and doxorubicin.

In another embodiment, a compound of Formula (I), (II), (III) or (IV), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, chemotherapy (such as cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin), anti-PD-1 monoclonal antibody (such as cemiplimab, nivolumab, pembrolizumab, avelumab, durvalumab and atezolizumab), aromatase inhibitor (such as aminoglutethimide, testolactone, anastrozole, letrozole, exemestane, vorozole, formetsane, fadrozole, ATD and 6-OXO), fulvestrant, sunitinib, sorafenib, bevacizumab, and pharmaceutically acceptable salts thereof, or combinations thereof. In a further embodiment, a compound of Formula (I), (II), (III) or (IV), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, or combinations thereof. In another embodiment, a compound of Formula (I), (II), (III) or (IV), or a pharmaceutically acceptable salt thereof, may be administered with trastuzumab, pertuzumab, margetuximab, t-dm1, sacituzumab govitecan-hziy, neratinib, lapatinib, tucatinib, palbociclib, ribociclib, abemaciclib, everolimus, alpelisib, olaparib, talazoparib, cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib and bevacizumab, and pharmaceutically acceptable salts thereof.

In another embodiment, a compound of Formula (I), (II), (III) or (IV), or a pharmaceutically acceptable salt thereof, may be administered with chemotherapy (such as cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid and oxaliplatin), anti-PD-1 monoclonal antibody (such as cemiplimab, nivolumab, pembrolizumab, avelumab, durvalumab and atezolizumab), aromatase inhibitor (such as aminoglutethimide, testolactone, anastrozole, letrozole, exemestane, vorozole, formetsane, fadrozole, ATD and 6-OXO), fulvestrant, sunitinib, sorafenib, bevacizumab, and pharmaceutically acceptable salts thereof, or combinations thereof. In a further embodiment, a compound of Formula (I), (II), (III) or (IV), or a pharmaceutically acceptable salt thereof, may be administered with cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib, bevacizumab, and pharmaceutically acceptable salts thereof, or combinations thereof. In another embodiment, a compound of Formula (I), (II), (III) or (IV), or a pharmaceutically acceptable salt thereof, may be administered with cyclophosphamide, methotrexate, 5-fluorouracil, vinorelbine, doxorubicin, paclitaxel, docetaxel, bleomycin, vinblastine, dacarbazine, mustine, vincristine, procarbazine, prednisolone, etoposide, cisplatin, carboplatin, epirubicin, capecitabine, folinic acid, oxaliplatin, cemiplimab, nivolumab, pembrolizumab, avelumab, durvalumab, atezolizumab, aminoglutethimide, testolactone, anastrozole, letrozole, exemestane, vorozole, formetsane, fadrozole, ATD, 6-OXO, fulvestrant, sunitinib, sorafenib and bevacizumab, and pharmaceutically acceptable salts thereof.

In another embodiment, a compound of Formula (I), (II), (III) or (IV), or a pharmaceutically acceptable salt thereof, may be administered in combination with endocrine therapy, e.g., agents such as letrozole, fulvestrant, tamoxifen, exemestane, or anastrozole. In another embodiment, a compound of Formula (I), (II), (III) or (IV), or a pharmaceutically acceptable salt thereof, may be administered in combination with a chemotherapeutic agent, e.g., docetaxel, paclitaxel, cisplatin, carboplatin, capecitabine, gemcitabine or vinorelbine. In another embodiment, a compound of Formula (I), (II), (III) or (IV), or a pharmaceutically acceptable salt thereof, may be administered in combination with an anti-HER2 agent, e.g., trastuzumab and/or pertuzumab.

In another embodiment, the additional anti-cancer therapeutic agent is an anti-angiogenesis agent, including for example VEGF inhibitors, VEGFR inhibitors, TIE-2 inhibitors, PDGFR inhibitors, angiopoietin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment, the additional anti-cancer therapeutic agent is a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB2, pan-ErbB inhibitors, IGF1R inhibitors, MEK inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway, and multi-targeted kinase inhibitors. Additional examples of signal transduction inhibitors that may be used in conjunction with a compound of Formula (I), (II), (III) or (IV) and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitors include gefitinib (Iressa™), cetuximab (Erbitux™), erlotinib (Tarceva™), trastuzumab (Herceptin™), sunitinib (Sutent™), imatinib (Gleevec™), tucatinib (Tukysa™), crizotinib (Pfizer), lorlatinib (Pfizer), dacomitinib (Pfizer), bosutinib (Pfizer), gedatolisib (Pfizer), canertinib (CI 1033), pertuzumab (Omnitarg™), lapatinib (Tykerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), selumetinib (AstraZeneca), everolimus (Certican™), zotarolimus (Endeavor™), temsirolimus (Torisel™), AP 23573 (ARIAD), VX 680 (Vertex), XL 647 (Exelixis), sorafenib (Nexavar™), LE-AON (Georgetown University), GI-4000 (GlobeImmune), binimetinib, and encorafenib. Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), palbociclib (Pfizer), and AG 024322 (Pfizer).

In another embodiment, the additional anti-cancer therapeutic agent is a classical antineoplastic agent. Classical antineoplastic agents include, but are not limited to, hormonal modulators, such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olaparib, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of Formula (I), (II), (III) or (IV), or a pharmaceutically acceptable salt thereof, optionally with one or more other agents include, but are not limited to, glucocorticoids, such as dexamethasone, prednisone, prednisolone, methylprednisolone, hydrocortisone, and progestins, such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, and CHF 4227 (Chiesi)), trilostane, Selective Estrogen-Receptor Downregulators (SERD's; such as fulvestrant), exemestane (Aromasin), anastrozole (Arimidex), atamestane, fadrozole, letrozole (Femara), formestane, gonadotropin-releasing hormone (GnRH; also commonly referred to as luteinizing hormone-releasing hormone [LHRH]) agonists, such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, antiandrogen agents, such as enzalutamide, abiraterone acetate, bicalutamide (Casodex), and combinations thereof. Other examples of classical antineoplastic agents used in combination with a compound of Formula (I), (II), (III) or (IV), or a pharmaceutically acceptable salt thereof, include, but are not limited to, suberolanilide hydroxamic acid (SAHA, Merck Inc./Aton Pharmaceuticals), depsipeptide (FR901228 or FK228), G2M-777, MS-275, pivaloyloxymethyl butyrate and PXD-101, Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds, such as cisplatin, Paraplatin (carboplatin), eptaplatin, lobaplatin, nedaplatin, Eloxatin (oxaliplatin, Sanofi), satraplatin, streptozocin, and combinations thereof.

In still another embodiment, the additional anti-cancer therapeutic agent is a dihydrofolate reductase inhibitors, such as methotrexate and NeuTrexin (trimetresate glucuronate), purine antagonists, such as 6-mercaptopurine riboside, mercaptopurine, 6-thioguanine, cladribine, clofarabine (Clolar), fludarabine, nelarabine, and raltitrexed, pyrimidine antagonists, such as 5-fluorouracil (5-FU), Alimta (premetrexed disodium, LY231514, MTA), capecitabine (Xeloda™), cytosine arabinoside, Gemzar™ (gemcitabine), Tegafur (LIFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine, and other antimetabolites, such as eflornithine, hydroxyurea, leucovorin, nolatrexed (Thymitaq), triapine, trimetrexate, raltitrexed, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere™), Ortataxel, paclitaxel (including Taxoprexin a DHA/paclitaxel conjugate), cisplatin, carboplatin, nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™), bexarotene (Targretin™), tesmilifene, Theratope™ (Biomira), Tretinoin (Vesanoid™), tirapazamine (Trizaone™), motexafin gadolinium (Xcytrin™), Cotara™ (mAb), NBI-3001 (Protox Therapeutics), polyglutamate-paclitaxel (Xyotax™) and combinations thereof. Further examples of classical antineoplastic agents include, but are not limited to, Advexin (ING 201), TNFerade (GeneVec), RB94 (Baylor College of Medicine), Genasense (Oblimersen, Genta), Combretastatin A4P (CA4P), Oxi-4503, AVE-8062, ZD-6126, TZT-1027, atorvastatin, pravastatin, lovastatin, simvastatin, fluvastatin, cerivastatin, rosuvastatin, niacin, amlodipine besylate and atorvastatin calcium, torcetrapib, and combinations thereof.

In another embodiment, the additional anti-cancer therapeutic agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In further embodiments, the additional anti-cancer therapeutic agent is an immunomodulatory agent, such as an inhibitor of CTLA-4, PD-1 or PD-L1 (e.g., pembrolizumab, nivolumab or avelumab), LAG-3, TIM-3, DIGIT, 4-1BB, OX40, GITR, CD40, or a CAR-T-cell therapy.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound of Formula (I), (II), (III) or (IV), may conveniently be combined in the form of a kit suitable for coadministration of the compositions. Thus, the kit of the invention includes two or more separate pharmaceutical compositions, at least one of which contains a compound of Formula (I), (II), (III) or (IV), and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In order that this invention may be better understood, the following examples are set forth. These examples are for purposes of illustration only and are not to be construed as limiting the scope of the invention in any manner. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as MilliporeSigma, Alfa Aesar, TCI, etc., and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; CD3OD: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Every Example or pharmaceutically acceptable salt thereof may be claimed individually or grouped together in any combination with any number of each and every embodiment described herein.

Intermediate Example A

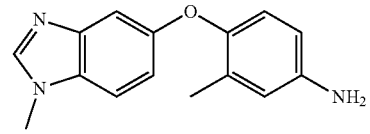 [SMILES: Cc1cc(N)ccc1Oc1ccc2c(c1)ncn2C]

3-methyl-4-((1-methyl-1H-benzo[d]imidazol-5-yl)oxy)aniline

Step A: A solution of 1-fluoro-2-methyl-4-nitrobenzene (1.05 g, 6.75 mmol) and 1-methyl-1H-benzo[d]imidazol-5-ol (1.0 g, 6.75 mmol) in DMF (22 mL) was treated with $Cs_2CO_3$ (4.40 g, 13.5 mmol). The mixture was warmed to 50° C. and stirred for 2 hours. The mixture was cooled to ambient temperature and diluted with EtOAc. The mixture was then washed with brine (2×), dried over $Na_2SO_4$, filtered and concentrated to provide 1-methyl-5-(2-methyl-4-nitrophenoxy)-1H-benzo[d]imidazole (1.9 g, quant.). m/z (APCI-pos) M$^+$1=284.1.

Step B: A solution of 1-methyl-5-(2-methyl-4-nitrophenoxy)-1H-benzo[d]imidazole (2.2 g, 7.8 mmol) in MeOH (78 mL) was treated with palladium hydroxide on carbon (2.0 g, 10 wt %). The mixture was then put through a vacuum/purge cycle three times with hydrogen gas, held under balloon pressure, and stirred for 5.5 hours. The reaction mixture was purged with argon and filtered. The filter cake was washed with MeOH. The filtrate was then concentrated to give 3-methyl-4-((1-methyl-1H-benzo[d]imidazol-5-yl)oxy)aniline (1.5 g, 76%) as a solid that was used directly. m/z (APCI-pos) M$^+$1=254.1.

Intermediate Example B

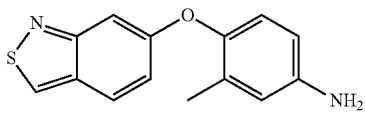

4-(benzo[c]isothiazol-6-yloxy)-3-methylaniline

Step A: Thionyl chloride (28.6 mL, 394.3 mmol) was added to a solution of methanesulfonamide (25 g, 263 mmol) in benzene (45.0 mL), and the mixture was refluxed at 90° C. for 16 hours. Benzene was then removed under reduced pressure. The residue was distilled at 99-100° C. at 0.3 mm Hg pressure to afford N-(oxo-$\lambda^4$-sulfanylidene)methanesulfonamide (28 g, 75% yield) as a liquid. m/z $(M^+)$=141.0 (GC-MS).

Step B: N-(Oxo-$\lambda^4$-sulfanylidene)methanesulfonamide (20.6 g, 146 mmol, in 20 mL of benzene) to a solution of 5-methoxy-2-methylaniline (5 g, 36.4 mmol) in benzene (20 mL), which was followed by the addition of pyridine (5.9 mL, 72.9 mmol, in 10 mL benzene). The mixture was refluxed at 90° C. for 48 hours. Benzene was then removed by evaporation under reduced pressure, and the residue was diluted with ice water and DCM. The organic layer was separated, washed with brine, dried over anhydrous $Na_2SO_4$, filtered, and concentrated under reduced pressure to provide the crude material, which was purified by silica gel column chromatography (10-12% EtOAc/hexane) to afford 6-methoxybenzo[c]isothiazole (1.2 gm, 20% yield) as an oil. $^1$H NMR (400 MHz, $(CD_3)_2SO$) δ 9.05 (s, 1H), 7.60 (d, J=9.2 Hz, 1H), 7.07 (s, 1H), 6.94 (dd, J=9.2, 1.2 Hz, 2H); m/z $(M^+)$=165.1.

Step C: $BBr_3$ (2.85 mL, 30.12 mmol) was added to a stirred solution of 6-methoxybenzo[c]isothiazole (1 g, 6.02 mmol) in DCM (8 mL) at 0° C., and the mixture was stirred at 0° C. for 2 hours. The volatilities were evaporated under reduced pressure, and the reaction mixture was diluted with ice water and DCM. The organic layer was separated, washed with saturated $NaHCO_3$ solution, dried over anhydrous $Na_2SO_4$, filtered, and concentrated under reduced pressure to provide the crude product. The crude product was mixed with another batch (batch size 200 mg), and the combined material was purified by silica gel column chromatography (40-45% EtOAc/hexane) to afford benzo[c]isothiazol-6-ol (850 mg, 78% yield) as a solid. $^1$H NMR (400 MHz, $(CD_3)_2SO$) δ 10.37 (s, 1H), 9.56 (s, 1H), 7.72 (d, J=9.2 Hz, 1H), 6.92-6.91 (m, 2H); m/z $(M^+)$=151.0.

Step D: A solution of benzo[c]isothiazol-6-ol (0.05 g, 0.33 mmol) and 1-fluoro-2-methyl-4-nitrobenzene (0.062 g, 0.4 mmol) in DMF (3.3 mL) was treated with $Cs_2CO_3$ (0.22 g, 0.66 mmol). The mixture was warmed to 100° C. and stirred for 17 hours. The mixture was cooled to ambient temperature and diluted with EtOAc and $H_2O$. The aqueous layer was extracted with EtOAc (2×). The organics were washed with brine (3×), dried over $Na_2SO_4$, and concentrated to give 6-(2-methyl-4-nitrophenoxy)benzo[c]isothiazole (0.095, quant.). m/z (APCI-pos) $M^+$1=287.

Step E: A solution of 6-(2-methyl-4-nitrophenoxy)benzo[c]isothiazole (0.33 g, 5.1 mmol) in THF (5.1 mL) was treated with aqueous saturated ammonium chloride (5.1 mL) and cooled to 0° C. Zinc dust (0.22 g, 3.3 mmol) was added to the mixture. The mixture was warmed to ambient temperature. After 48 hours, the mixture was diluted with $H_2O$ and EtOAc, and filtered. The filter cake was washed with EtOAc. The aqueous layer was extracted with EtOAc (3×), the organics were washed with brine, dried over $Na_2SO_4$, and concentrated. The product was purified via normal phase chromatography (0 to 40% EtOAc/hexanes). Fractions containing the desired product were pooled and concentrated to provide 4-(benzo[c]isothiazol-6-yloxy)-3-methylaniline (0.053 g, 20%). m/z (APCI-pos) $M^+$1=257.1.

Intermediate Example C

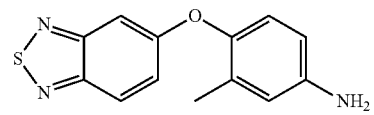 [SMILES: Cc1cc(N)ccc1Oc1ccc2nsnc2c1]

4-(benzo[c][1,2,5]thiadiazol-5-yloxy)-3-methylaniline

Step A: A solution of benzo[c][1,2,5]thiadiazol-5-ol (0.25 g, 1.64 mmol) and 1-fluoro-2-methyl-4-nitrobenzene (0.305 g, 1.97 mmol) in DMA (8.2 mL) was treated with $Cs_2CO_3$ (1.07 g, 3.29 mmol). The mixture was heated to 50° C. and stirred for 6 hours. The mixture was diluted with brine, extracted with EtOAc (2×), dried over $Na_2SO_4$ and concentrated. The product was purified via normal phase chromatography (5 to 75% EtOAc/hexanes). Fractions containing the desired product were pooled and concentrated to provide 5-(2-methyl-4-nitrophenoxy)benzo[c][1,2,5]thiadiazole (0.326 g, 69.1%) as a solid.

Step B: A solution of 5-(2-methyl-4-nitrophenoxy)benzo[c][1,2,5]thiadiazole (0.326 g, 1.13 mmol) in THF (10 mL) and aqueous saturated ammonium chloride (10 mL) was treated with zinc dust (0.742 g, 11.3 mmol). The mixture stirred at ambient temperature for 1.5 hours. The mixture was diluted with $H_2O$ and EtOAc and filtered. The filtrated was extracted with EtOAc (2×), combined organics were dried over $Na_2SO_4$ and concentrated to give 4-(benzo[c][1,2,5]thiadiazol-5-yloxy)-3-methylaniline (0.291 g, 99.7%) as a solid. m/z (APCI-pos) $M^+$1=257.1.

Intermediate Example D

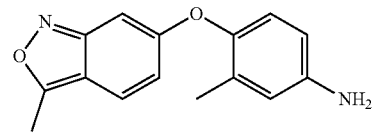 [SMILES: Cc1cc(N)ccc1Oc1ccc2c(C)onc2c1]

3-methyl-4-((3-methylbenzo[c]isoxazol-6-yl)oxy)aniline

Step A: A solution of tert-butyl (4-hydroxy-3-methylphenyl)carbamate (0.175 g, 0.784 g) and 1-(4-fluoro-2-nitrophenyl)ethan-1-one (0.144 g, 0.784 mmol) in DMF (7.8 mL was treated with $Cs_2CO_3$ (0.511 g, 1.57 mmol). The mixture was heated to 50° C. and stirred for 17 hours. The mixture was diluted with $H_2O$ and DCM. The aqueous layer was extracted with DCM (3×), the combined organics were washed with brine, dried over Na$_2$SO$_4$, and concentrated to give tert-butyl (4-(4-acetyl-3-nitrophenoxy)-3-methylphenyl)carbamate (0.300 g, 99.1%) as a solid that was used in subsequent step without purification. m/z (APCI-pos) M$^-$Boc=287.1.

Step B: A solution of tert-butyl (4-(4-acetyl-3-nitrophenoxy)-3-methylphenyl)carbamate (0.0814 g, 0.211 mmol) in 1:1 EtOAc/MeOH (2 mL) was treated with dichloro-I2-stannane dihydrate (0.143 g, 0.632 mmol). The mixture was stirred at ambient temperature for 19 hours. The mixture was diluted with aqueous saturated NaHCO$_3$. The aqueous layer was extracted with EtOAc (3×). The combined organics were washed with brine, dried over Na$_2$SO$_4$, and concentrated to give tert-butyl (3-methyl-4-((3-methylbenzo[c]isoxazole-6-yl)oxy)phenyl)carbamate (0.0792 g, quant.) as a solid. m/z (APCI-pos) M+1=355.2.

Step C: Trifluoroacetic acid (1.19 mL, 15.5 mmol) was added to a solution of tert-butyl (3-methyl-4-((3-methylbenzo[c]isoxazol-6-yl)oxy)phenyl)carbamate (0.11 g, 0.31 mmol) in DCM (3.1 mL). The reaction mixture was stirred at ambient temperature for 90 minutes. The reaction mixture was diluted with aqueous 10% potassium carbonate and stirred for 10 minutes. The aqueous layer was extracted with DCM (3×). The combined organics were washed with brine, dried over Na$_2$SO$_4$, and concentrated to give 3-methyl-4-((3-methylbenzo[c]isoxazol-6-yl)oxy)aniline (0.020, 25.3%). m/z (APCI-pos) M$^+$1=255.1.

Intermediate Example E

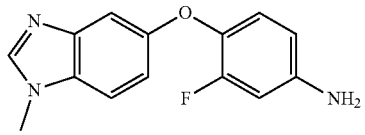 [SMILES: Cn1cnc2cc(Oc3ccc(N)cc3F)ccc21]

3-fluoro-4-((1-methyl-1H-benzo[d]imidazol-5-yl)oxy)aniline

Step A: A solution of 1-methyl-1H-benzo[d]imidazol-5-ol (8.4 mL, 1.7 mmol) and potassium hydroxide (0.19 g, 3.4 mmol) was stirred in DMSO (10 mL) at ambient temperature as 1,2-difluoro-4-nitrobenzene (0.21 mL, 1.9 mmol) was added. After 21 hours, the reaction mixture was diluted with water and DCM. The aqueous and organic phases were separated. The aqueous phase was extracted with DCM twice. The combined organic phases were washed with brine, dried via Na$_2$SO$_4$, and concentrated. This crude material was purified via prepacked column (40 g) using a gradient of 100% EtOAc to 90:10 EtOAc:MeOH as the eluent. Product containing fractions were combined and concentrated to give 5-(2-fluoro-4-nitrophenoxy)-1-methyl-1H-benzo[d]imidazole (0.47 g, 96%).

Step B: Zinc (0.046 g, 0.70 mmol) was added to a solution of 5-(2-fluoro-4-nitrophenoxy)-1-methyl-1H-benzo[d]imidazole (0.02 g, 0.070 mmol) in THF (1 mL), followed by saturated NH$_4$Cl (aq.) (1 mL). The next day, the reaction mixture was filtered, and the filter cake was washed with ACN. The organic and aqueous phases were separated. The organic phase was washed brine, dried via Na$_2$SO$_4$ and concentrated to give 3-fluoro-4-((1-methyl-1H-benzo[d]imidazol-5-yl)oxy)aniline (0.01 g, 56%). m/z (APCI-pos) M$^+$1=258.1.

Intermediate Example F

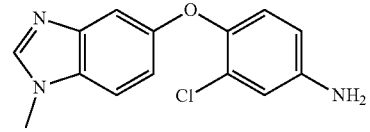 [SMILES: Cn1cnc2cc(Oc3ccc(N)cc3Cl)ccc21]

3-chloro-4-((1-methyl-1H-benzo[d]imidazol-5-yl)oxy)aniline

Step A: Cesium carbonate (3.71 g, 11.4 mmol) was added to a solution of 1-methyl-1H-benzo[d]imidazol-5-ol (0.84 g, 5.7 mmol) in DMF (25 mL), followed by 2-chloro-1-fluoro-4-nitrobenzene (1.00 g, 5.70 mmol) at room temperature. Following this, the reaction mixture was heated to 80° C. After 24 hours, the reaction mixture was cooled to ambient temperature and was diluted with water and EtOAc. The aqueous and organic phases were separated. The aqueous phase was extracted with EtOAc twice. The combined organic phases were washed with brine (3×), dried via Na$_2$SO$_4$, and concentrated to give 5-(2-chloro-4-nitrophenoxy)-1-methyl-1H-benzo[d]imidazole (0.9 g, 52%).

Step B: Zinc (3.4 g, 53 mmol) was added to a stirring mixture at 0° C. of 5-(2-chloro-4-nitrophenoxy)-1-methyl-1H-benzo[d]imidazole (1.6 g, 5.3 mmol), THF (26 mL), and saturated aqueous ammonium chloride (26 mL). The mixture was warmed to ambient temperature and stirred for 90 minutes before being filtered. The insoluble product and solid zinc were then stirred overnight in 4M HCl (75 mL) to afford 3-chloro-4-((1-methyl-1H-benzo[d]imidazol-5-yl)oxy)aniline (1.3 g, 90%). m/z (APCI-pos) M$^+$1=274.1.

Intermediate Example G

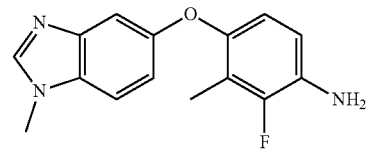 [SMILES: Cc1c(Oc2ccc3c(c2)ncn3C)ccc(N)c1F]

2-fluoro-3-methyl-4-((1-methyl-1H-benzo[d]imidazol-5-yl)oxy)aniline

Step A: Cs$_2$CO$_3$ (1.9 g, 11 mmol) was added to a solution of 1-methyl-1H-benzo[d]imidazol-5-ol (1.5 g, 10.1 mmol) in DMF (34 mL), followed by 1,3-difluoro-2-methyl-4-nitrobenzene (1.9 g, 11 mmol). The reaction mixture was heated to 50° C. After 18 hours, the reaction mixture was cooled to ambient temperature and was concentrated. The remaining solids were taken up in EtOAc and washed with water. The aqueous phase was extracted with EtOAc (2×), and the combined organic layers were washed with brine, dried via Na$_2$SO$_4$, and concentrated. This crude material was purified via reverse phase chromatography (240 g, C18) using a gradient of 5 to 95% ACN/water over 12 column volumes (0.1% TFA buffer). Product containing fractions were combined and treated with 10% K$_2$CO$_3$ (aq). After 10 minutes, the aqueous solution was extracted with 25%

IPA/DCM (3×), dried via Na₂SO₄, and concentrated to give 5-(3-fluoro-2-methyl-4-nitrophenoxy)-1-methyl-1H-benzo[d]imidazole (0.695 g, 23%).

Step B: A solution of 5-(3-fluoro-2-methyl-4-nitrophenoxy)-1-methyl-1H-benzo[d]imidazole (0.38 g, 1.3 mmol) in THF (12 mL) was added zinc (0.82 g, 12.6 mmol) followed by saturated NH₄Cl (12 mL). After 2 hours, the reaction mixture was filtered through GF/F paper.

The filter cake was washed with EtOAc, and the aqueous and organic phases were separated. The aqueous phase was extracted with EtOAc (2×). The combined organic phases were washed with brine, dried via Na₂SO₄, and concentrated to give 2-fluoro-3-methyl-4-((1-methyl-1H-benzo[d]imidazol-5-yl)oxy)aniline (0.17 g, 50%). m/z (APCI-pos) M+1=272.15.

Intermediate Example H

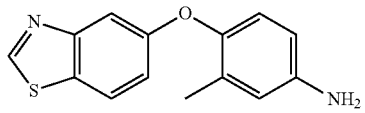

4-(benzo[d]thiazol-5-yloxy)-3-methylaniline

Step A: Cs₂CO₃ (1.6 g, 4.8 mmol) was added to a solution of benzo[d]thiazol-5-ol (0.29 g, 1.9 mmol) in DMF, followed by 2-fluoro-5-nitrotoluene (0.25 g, 1.6 mmol). After 4.5 hours, the reaction mixture was diluted with H₂O and DCM. The organic and aqueous phases were separated. The aqueous phase was extracted with DCM (3×). The combined organic phases were washed with water (3×), brine, dried via Na₂SO₄, and concentrated. The crude material was purified via a prepacked column (40 g) using a gradient of 10:90 EtOAc:Hexanes to 1:1 EtOAc:Hexanes as the eluent. Product containing fractions were combined and concentrated to afford 5-(2-methyl-4-nitrophenoxy)benzo[d]thiazole (0.40 g, 87%).

Step B: A solution of 5-(2-methyl-4-nitrophenoxy)benzo[d]thiazole (1.9 g, 6.6 mmol) in THF (30 mL) was cooled to 0° C., and then added to zinc (4.3 g, 66 mmol). Saturated NH₄Cl (30 mL) was added to the reaction mixture. After 5 minutes, the reaction mixture was warmed to ambient temperature. After 16 hours, the reaction mixture was filtered through GF/F paper. The filter cake was washed with EtOAc and deionized water. The aqueous and organic phases were separated. The aqueous phase was extracted with EtOAc. The combined organic layers were washed with brine, dried via Na₂SO₄, and concentrated to afford 4-(benzo[d]thiazol-5-yloxy)-3-methylaniline (1.6 g, 94%). m/z (APCI-pos) M+1=257.1.

Intermediate Example I

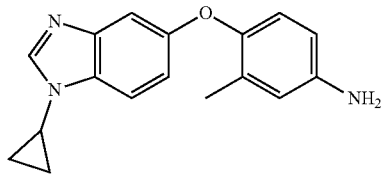 [SMILES: Cc1cc(N)ccc1Oc1ccc2c(c1)ncn2C1CC1]

4-((1-cyclopropyl-1H-benzo[d]imidazol-5-yl)oxy)-3-methylaniline

Step A: 4,4,4',4',5,5,5',5'-Octamethyl-2,2'-bi(1,3,2-dioxaborolane) (1.1 g, 4.3 mmol) was added to a solution of 5-bromo-1-cyclopropyl-1H-benzo[d]imidazole (0.78 g, 3.3 mmol) in DMF (33 mL), followed by dichloro[1,1'-bis(diphenylphosphino)ferrocene]palladium dichloromethane adduct (0.27 g, 0.33 mmol), and finally potassium acetate (0.97 g, 9.9 mmol). Argon was bubbled through the reaction mixture for 10 minutes while stirring. The reaction mixture was heated to 100° C. After 48 hours, the reaction mixture was cooled to ambient temperatures and was partitioned between water and EtOAc. The aqueous and organic phases were separated. The aqueous phase was extracted with EtOAc (2×). The combined organic phases were dried via Na₂SO₄ and concentrated to give 1-cyclopropyl-5-(4,4,5,5-tetramethyl-1,3,2-dioxaborolan-2-yl)-1H-benzo[d]imidazole (0.7 g, 75%).

Step B: 2M NaOH (2.64 mL, aqueous solution) was added to a solution of 1-cyclopropyl-5-(4,4,5,5-tetramethyl-1,3,2-dioxaborolan-2-yl)-1H-benzo[d]imidazole (0.30 g, 1.1 mmol) in THF (10 mL). The solution was cooled to 0° C. Hydrogen peroxide (0.73 mL, 8.5 mmol; 35% weight) was added to the reaction mixture. The reaction mixture was stirred at 0° C. for 5 minutes before being warmed to ambient temperatures. After 10 minutes, the reaction mixture was taken up in EtOAc. The aqueous and organic phases were separated. The aqueous phase was extracted with EtOAc (2×). The combined organic phases were washed with saturated Na₂S₂O₃, dried via Na₂SO₄, and concentrated to afford 1-cyclopropyl-1H-benzo[d]imidazol-5-ol (0.19 g, quantitative yield).

Step C: Cs₂CO₃ (0.71 g, 2.2 mmol) was added to a solution of 1-cyclopropyl-1H-benzo[d]imidazol-5-ol (10.9 mL, 1.1 mmol) in DMF (10 mL), followed by 1-fluoro-2-methyl-4-nitrobenzene (0.17 g, 1.1 mmol). After these additions, the reaction mixture was heated to 80° C. After 1.5 hours, the reaction mixture was concentrated. This crude material was taken up in EtOAc, washed with water, followed by brine, dried via Na₂SO₄, and concentrated to afford 1-cyclopropyl-5-(2-methyl-4-nitrophenoxy)-1H-benzo[d]imidazole (0.24 g, 71%).

Step D: A solution 1-cyclopropyl-5-(2-methyl-4-nitrophenoxy)-1H-benzo[d]imidazole (0.24 g, 0.77 mmol) in THF (8 mL) was cooled to 0° C., zinc powder (0.50 g, 7.7 mmol) was then added, followed by saturated NH₄Cl (8 mL). After 10 minutes at 0° C., the reaction mixture was warmed to ambient temperatures. After 18 hours, the reaction mixture was filtered through GF/F paper. The aqueous and organic phases were separated. The organic phase was washed with brine, dried Na₂SO₄, and concentrated to afford 4-((1-cyclopropyl-1H-benzo[d]imidazol-5-yl)oxy)-3-methylaniline (0.061 g, 28%). m/z (APCI-pos) M+1=280.1.

Intermediate Example J

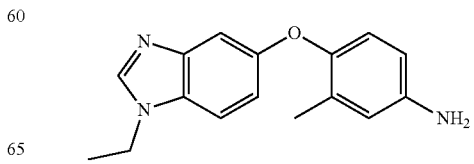

4-((1-ethyl-1H-benzo[d]imidazol-5-yl)oxy)-3-methylaniline

Step A: A solution of 5-bromo-1-ethyl-1H-benzo[d]imidazole (0.78 g, 3.3 mmol) in DMF (33 mL) was added 4,4,4',4',5,5,5',5'-octamethyl-2,2'-bi(1,3,2-dioxaborolane) (1.1 g, 4.3 mmol) followed by Dichloro[1,1'-bis(diphenylphosphino)ferrocene]palladium dichloromethane adduct (0.27 g, 0.33 mmol), and finally potassium acetate (0.97 g, 9.9 mmol). Argon was bubbled through the reaction mixture for 10 min while stirring. After, the reaction mixture was heated to 100° C. After 48 h, the reaction mixture was cooled to ambient temperature and was partitioned between water and EtOAc. The aqueous and organic phases were separated, the aqueous phase was extracted with EtOAc (2×), the combined organic phases were dried via Na2SO4, and concentrated to afford 1-ethyl-5-(4,4,5,5-tetramethyl-1,3,2-dioxaborolan-2-yl)-1H-benzo[d]imidazole (0.7 g, 75%)

Step B: Sodium hydroxide (1.7 mL, 3.3 mmol) as a 2M solution (aq.) was added to a solution of 1-ethyl-5-(4,4,5,5-tetramethyl-1,3,2-dioxaborolan-2-yl)-1H-benzo[d]imidazole (0.18 g, 0.66 mmol) in THF (7 mL). The reaction mixture was cooled to 0° C., then hydrogen peroxide (0.46 mL, 5.3 mmol; 35% weight) was added. The reaction mixture was stirred at 0° C. for 5 minutes before being allowed to warm to room temperature. After 10 minutes, LCMS showed the consumption of starting materials and the presence of the desired product. The reaction mixture was taken up in EtOAc. The aqueous and organic layers were separated. The aqueous layer was extracted with EtOAc (2×). The combined organic layers were washed with saturated $Na_2S_2O_3$, dried via $Na_2SO_4$, and concentrated to give 1-ethyl-1H-benzo[d]imidazol-5-ol (137 mg) as an oil. This material was used as in in the following step.

Step C: $Cs_2CO_3$ (0.550 g, 2 equiv) was added to a solution of 1-ethyl-1H-benzo[d]imidazol-5-ol (0.14 g, 0.85 mmol) in DMF (8 mL), followed by 1-fluoro-2-methyl-4-nitrobenzene (0.13 g, 0.85 mmol). The reaction mixture was heated to 80° C. After 1.5 hours, the reaction mixture was concentrated. The resulting crude solid was taken up in EtOAc, washed with water, followed by brine, dried via $Na_2SO_4$, and concentrated to afford 1-ethyl-5-(2-methyl-4-nitrophenoxy)-1H-benzo[d]imidazole (0.21 g, 85%).

Step D: A solution of 1-ethyl-5-(2-methyl-4-nitrophenoxy)-1H-benzo[d]imidazole (0.21 g, 0.72 mmol) in THF (7 mL) was cooled to 0° C. Once cooled, zinc powder (0.47 g, 7.2 mmol) was added to the reaction mixture, followed by saturated $NH_4Cl$ (7 mL). After 10 minutes, the reaction mixture was warmed to ambient temperature. After 18 hours, the reaction mixture was filtered through GF/F paper. The aqueous and organic phases were separated. The organic phases was washed with brine, dried with $Na_2SO_4$, and concentrated to afford 4-((1-ethyl-1H-benzo[d]imidazol-5-yl)oxy)-3-methylaniline (0.068 g, 35%). m/z (APCI-pos) $M^+1=268.2$.

Intermediate Example K

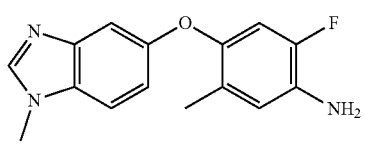 [SMILES: Cc1cc(N)c(F)cc1Oc1ccc2c(c1)ncn2C]

2-fluoro-5-methyl-4-((1-methyl-1H-benzo[d]imidazol-5-yl)oxy)aniline

Step A: $Cs_2CO_3$ (4.4 g, 13 mmol) was added to a solution of 1,5-difluoro-2-methyl-4-nitrobenzene (1.4 g, 8.1 mmol) in DMF (45 mL), followed by 1-methyl-1H-benzo[d]imidazol-5-ol (1 g, 6.7 mmol). The reaction mixture was heated to 80° C. After 2 hours, the reaction mixture was concentrated. This crude solid was taken up in EtOAc, washed with water, followed by brine, dried via $Na_2SO_4$, and concentrated to afford a mixture of 5-(5-fluoro-2-methyl-4-nitrophenoxy)-1-methyl-1H-benzo[d]imidazole and 5-(5-fluoro-4-methyl-2-nitrophenoxy)-1-methyl-1H-benzo[d]imidazole (2.1 g, 100%).

Step B: A solution of 5-(5-fluoro-2-methyl-4-nitrophenoxy)-1-methyl-1H-benzo[d]imidazole (2.1 g, 7.0 mmol) in ACN:THF (1:1, 30 mL) was cooled to 0° C. Zinc powder (4.6 g, 70 mmol) was added to the mixture, followed by saturated $NH_4Cl$ (30 mL). After 10 minutes at 0° C., the reaction mixture was warmed to ambient temperature. After 1.25 hours, the reaction mixture was filtered through GF/F paper. The aqueous and organic phases were separated. The aqueous phase was extracted with EtOAc, dried via $Na_2SO_4$, and concentrated to give a mixture of 2-fluoro-5-methyl-4-((1-methyl-1H-benzo[d]imidazol-5-yl)oxy)aniline and 4-fluoro-5-methyl-2-((1-methyl-1H-benzo[d]imidazol-5-yl)oxy)aniline (1.9 g) as a solid. m/z (APCI-pos) $M^+1=272.1$. This material was used as a mixture in subsequent reactions, and the resulting regioisomers separated at that stage.

Intermediate Example L

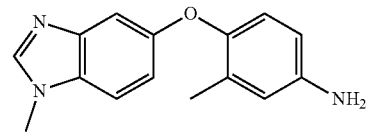 [SMILES: Cc1cc(N)ccc1Oc1ccc2c(c1)ncn2C]

3-methyl-4-((1-methyl-1H-benzo[d]imidazol-5-yl)oxy)aniline

Step A: $K_2CO_3$ (13.98 g, 101.35 mmol) was added to a stirred solution of 1-methyl-1H-benzo[d]imidazol-5-ol (5 g, 33.8 mmol) in DMSO (35 mL), and the mixture was stirred at ambient temperature for 5 minutes. 1-Fluoro-2-methyl-4-nitrobenzene (5.24 g, 33.78 mmol) was added to the solution, and the reaction was stirred at 80° C. for 4 hours. The reaction mixture was cooled to ambient temperature, diluted with EtOAc and washed with cold water followed by brine. The organic layer was dried over anhydrous $Na_2SO_4$, filtered, and concentrated under reduced pressure. The crude solid was purified by silica gel column chromatography (0-2% MeOH/DCM) to get 1-methyl-5-(2-methyl-4-nitrophenoxy)-1H-benzo[d]imidazole (7.6 g, 84%) as a solid. m/z (esi) $M^+1=284.0$.

Step B: 20% $Pd(OH)_2$ on carbon (1.4 g) was added to a stirred solution of 1-methyl-5-(2-methyl-4-nitrophenoxy)-1H-benzo[d]imidazole (7 g, 24.74 mmol) in THF:MeOH (1:6) (105 mL) at ambient temperature. The reaction mixture was purged with argon for 10 minutes and then stirred for 16 hours under $H_2$ atmosphere. Then it was filtered through a Celite® bed and washed with 10% MeOH/DCM (100 mL×3). The filtrate was concentrated, and the residue washed with diethyl ether (40 mL×2) to get 3-methyl-4-((1-methyl-1H-benzo[d]imidazole-5-yl)oxy)aniline (6.2 g, 98%) as a solid. m/z (esi) M+1=253.9; $^1$H NMR (400 MHz, (CD$_3$)$_2$SO) δ 8.10 (s, 1H), 7.46 (d, J=8.5 Hz, 1H), 6.92-6.84 (m, 2H), 6.66 (d, J=8.4 Hz, 1H), 6.50 (d, J=2.7 Hz, 1H), 6.42 (dd, J=2.8, 8.5 Hz, 1H), 4.91 (s, 2H), 3.80 (s, 3H), 2.00 (s, 3H).

Intermediate Example M

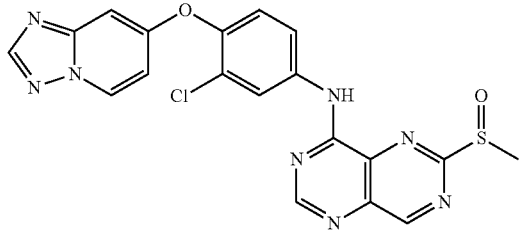 [SMILES: CS(=O)c1ncc2ncnc(Nc3ccc(Oc4ccn5ncnc5c4)c(Cl)c3)c2n1]

N-(4-([1,2,4]triazolo[1,5-a]pyridin-7-yloxy)-3-chlorophenyl)-6-(methylsulfinyl)pyrimido[5,4-d]pyrimidin-4-amine Step A: In a 100 mL recovery flask equipped with a stir bar, 2-chloro-1-fluoro-4-nitrobenzene (1.20 g, 6.84 mmol), [1,2,4]triazolo[1,5-a]pyridin-7-ol (924 mg, 6.8 mmol), cesium carbonate (3.34 g, 10.3 mmol) and DMF (23 mL) were stirred at 80° C. for 16 hours. Water (80 mL) was added to the reaction flask, and the resultant solid was collected via vacuum filtration, washed with water, and dried to furnish 7-(2-chloro-4-nitrophenoxy)-[1,2,4]triazolo[1,5-a]pyridine (2.1 g, 100%). m/z (esi) M+1=291.1.

Step B: Zinc dust (4.5 g, 69 mmol), saturated aqueous ammonium chloride (34 mL), THF (34 mL), and 7-(2-chloro-4-nitrophenoxy)-[1,2,4]triazolo[1,5-a]pyridine (2.0 g, 6.9 mmol) were charged to a 250 mL round bottom flask equipped with a stir bar. The mixture was stirred overnight at 25° C. The mixture was diluted with water and ethyl acetate and filtered through GF/F paper. The aqueous layer was extracted with ethyl acetate (2×). The combined organics were dried over Na$_2$SO$_4$ and concentrated in vacuo to furnish 4-([1,2,4]triazolo[1,5-a]pyridin-7-yloxy)-3-chloroaniline (1.3 g, 72%). m/z (esi) M+1=261.1.

Step C: 4-([1,2,4]Triazolo[1,5-a]pyridin-7-yloxy)-3-chloroaniline (0.80 g, 3.1 mmol) and propan-2-ol (31 mL) were combined in a 50 mL round bottom flask equipped with an egg shaped stir bar. The mixture was heated to 50° C. 8-Chloro-2-(methylthio)pyrimido[5,4-d]pyrimidine (0.65 g, 3.1 mmol) was added to the mixture. The temperature was maintained at 50° C. for 30 minutes. The mixture was dry loaded onto silica gel and purified by column chromatography (Redisep 40 g, 0 to 2% MeOH in DCM with 2% NH$_4$OH) to furnish N-(4-([1,2,4]triazolo[1,5-a]pyridin-7-yloxy)-3-chlorophenyl)-6-(methylthio)pyrimido[5,4-d]pyrimidin-4-amine (0.89 g, 67%). m/z (esi) M+1=437.1.

Step D: m-CPBA (605 mg, 70% Wt, 30% water, 2.46 mmol) was added to a stirred mixture of N-(4-([1,2,4]triazolo[1,5-a]pyridin-7-yloxy)-3-chlorophenyl)-6-(methylthio)pyrimido[5,4-d]pyrimidin-4-amine (0.894 g, 2.05 mmol) and dichloromethane (34 mL) at 0° C. The mixture was stirred at 0° C. for 1 hour and then diluted with DCM and saturated aqueous sodium thiosulfate. Organics were washed twice with saturated aqueous sodium bicarbonate and then dried over Na$_2$SO$_4$ and concentrated in vacuo to furnish N-(4-([1,2,4]triazolo[1,5-a]pyridin-7-yloxy)-3-chlorophenyl)-6-(methylsulfinyl)pyrimido[5,4-d]pyrimidin-4-amine (0.87 g, 94%). m/z (APCI-pos) M+1=453.1.

Intermediate Example N

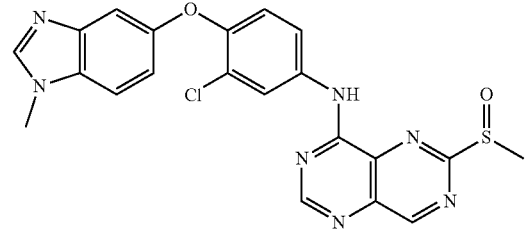 [SMILES: Cn1cnc2cc(Oc3ccc(Nc4ncnc5cnc(S(C)=O)nc45)cc3Cl)ccc21]

N-(3-chloro-4-((1-methyl-1H-benzo[d]imidazol-5-yl)oxy)phenyl)-6-(methylsulfinyl)pyrimido[5,4-d]pyrimidin-4-amine Step A: 8-Chloro-2-(methylthio)pyrimido[5,4-d]pyrimidine (0.5 g, 2 mmol) was added to a stirred solution of 3-chloro-4-((1-methyl-1H-benzo[d]imidazol-5-yl)oxy)aniline (0.6 g, 2 mmol) in DMSO (20 mL) at 100° C. under sealed tube. After 24 hours, the reaction mixture was cooled to ambient temperature, diluted with water, and extracted with CHCl$_3$ (3×). The combined organic layers were washed with brine (5×), dried via Na$_2$SO$_4$, and concentrated. This crude material was purified via reverse phase chromatography using a gradient of 5 to 95% ACN/water over 8 column volumes (0.1% TFA buffer). Product containing fractions were combined and treated with 10% K$_2$CO$_3$ (aqueous). After 10 minutes, the aqueous solution was extracted with CHCl$_3$ (3×), dried via Na$_2$SO$_4$, and concentrated to afford N-(3-chloro-4-((1-methyl-1H-benzo[d]imidazol-5-yl)oxy)phenyl)-6-(methylthio)pyrimido[5,4-d]pyrimidin-4-amine (0.353 g, 40%) as a solid.

Step B: Potassium peroxymonosulfate (0.9 g, 1 mmol) was added to a solution of N-(3-chloro-4-((1-methyl-1H-benzo[d]imidazol-5-yl)oxy)phenyl)-6-(methylthio)pyrimido[5,4-d]pyrimidin-4-amine (0.353 g, 2 mmol) in ACN/water (2:1, 20 mL). The mixture was stirred at ambient temperature for 60 minutes, upon which water was added. The aqueous solution was extracted with CHCl$_3$ (3×). The combined organic layers were dried over Na$_2$SO$_4$ and concentrated. Purification by normal phase chromatography (0-8% MeOH in DCM) provided N-(3-chloro-4-((1-methyl-1H-benzo[d]imidazol-5-yl)oxy)phenyl)-6-(methylsulfinyl)pyrimido[5,4-d]pyrimidin-4-amine (0.59 g, 1.3 mmol, 60%). m/z (APCI-pos) M+1=466.1.

Intermediate Example O

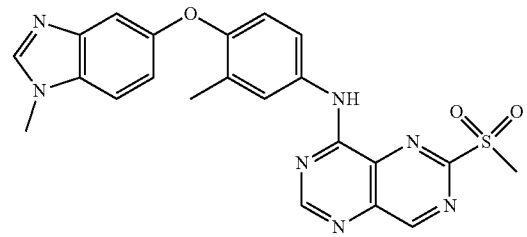 [SMILES: Cc1cc(Nc2ncnc3cnc(S(C)(=O)=O)nc23)ccc1Oc1ccc2c(c1)ncn2C]

N-(3-methyl-4-((1-methyl-1H-benzo[d]imidazol-5-yl)oxy)phenyl)-6-(methylsulfonyl)pyrimido[5,4-d]pyrimidin-4-amine Step A: 8-Chloro-2-(methylthio)pyrimido[5,4-d]pyrimidine (5.04 g, 23.7 mmol) was added to a stirred solution of 3-methyl-4-((1-methyl-1H-benzo[d]imidazol-5-yl)oxy)aniline (6 g, 23.7 mmol) in IPA (50 mL), and the mixture was stirred at 80° C. for 2 hours. The reaction mixture was then concentrated. The residue was dissolved in 5% MeOH/DCM and washed with saturated NaHCO$_3$ aqueous solution, followed by brine and then dried over Na$_2$SO$_4$, filtered and concentrated. The crude product was purified by silica gel column chromatography (2-4% MeOH/DCM) to afford N-(3-methyl-4-((1-methyl-1H-benzo[d]imidazol-5-yl)oxy)phenyl)-6-(methylthio)pyrimido[5,4-d]pyrimidin-4-amine (10 g, 98% yield) as a solid. m/z (esi) M$^+$1=430.0.

Step B: m-CPBA (100%) (5.01 g, 29.1 mmol) was added to a stirred solution of N-(3-methyl-4-((1-methyl-1H-benzo[d]imidazol-5-yl)oxy)phenyl)-6-(methylthio)pyrimido[5,4-d]pyrimidin-4-amine (5 g, 11.7 mmol) in DCM (120 mL) at 0° C., and it was stirred at room temperature for 3 hours. The reaction was then diluted with DCM and washed with saturated NaHCO$_3$ aqueous solution, and then a brine solution. The organic phase was dried over Na$_2$SO$_4$, filtered and concentrated under reduced pressure. The crude residue was purified by silica gel column chromatography (0-2% MeOH/DCM) to get N-(3-methyl-4-((1-methyl-1H-benzo[d]imidazol-5-yl)oxy)phenyl)-6-(methylsulfonyl)pyrimido[5,4-d]pyrimidin-4-amine (4 g, 74% yield) as a solid. m/z (esi) M$^+$1=461.8; $^1$H NMR (400 MHz, (CD$_3$)$_2$SO) δ 10.47 (s, 1H), 9.65 (s, 1H), 8.83 (s, 1H), 8.18 (s, 1H), 7.81 (d, J=2.6 Hz, 1H), 7.69 (dd, J=2.6, 8.7 Hz, 1H), 7.59 (d, J=8.7 Hz, 1H), 7.14 (d, J=2.3 Hz, 1H), 7.02 (dd, J=2.3, 8.7 Hz, 1H), 6.89 (d, J=8.7 Hz, 1H), 3.84 (s, 3H), 3.69 (s, 3H), 2.29 (s, 3H).

Example 1

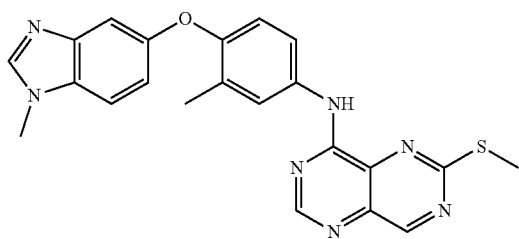 [SMILES: CSc1ncc2ncnc(Nc3ccc(Oc4ccc5c(c4)ncn5C)c(C)c3)c2n1]

N-(3-methyl-4-((1-methyl-1H-benzo[d]imidazol-5-yl)oxy)phenyl)-6-(methylthio)pyrimido[5,4-d]pyrimidin-4-amine 8-Chloro-2-(methylthio)pyrimido[5,4-d]pyrimidine (0.139 g, 0.651 mmol) was added to a solution of 3-methyl-4-((1-methyl-1H-benzo[d]imidazol-5-yl)oxy)aniline (0.150 g, 0.592 mmol) in IPA (5.92 mL). The mixture was heated to 50° C. and stirred for 17 hours. The reaction mixture was concentrated, and this product was purified via normal phase chromatography (0 to 20% MeOH:EtOAc). Fractions containing the desired product were pooled and concentrated to provide N-(3-methyl-4-((1-methyl-1H-benzo[d]imidazol-5-yloxy)phenyl)-6-(methylthio)pyrimido[5,4-d]pyrimidin-4-amine (0.208 g, 81.8%) as a solid. $^1$H NMR (400 MHz, CDCl$_3$) δ 9.20 (s, 1H), 8.73 (s, 1H), 8.70 (br s, 1H), 7.86 (s, 1H), 7.74 (d, J=2.6, 1H), 7.64 (dd, J=2.6 Hz, 9.1 Hz, 1H), 7.35 (s, 1H), 7.33 (d, J=2.2 Hz, 1H) 7.07 (dd, J=2.3 Hz, 8.8 Hz, 1H), 3.85 (s, 3H), 2.72 (s, 3H), 2.36 (s, 3H); m/z (APCI-pos) M$^+$1=430.1.

Example 2

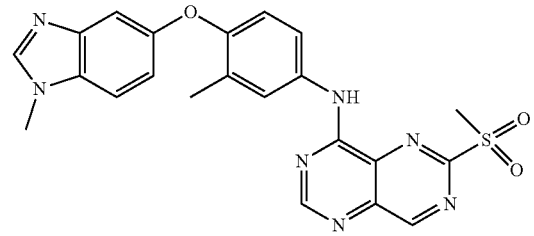 [SMILES: Cc1cc(Nc2ncnc3cnc(S(C)(=O)=O)nc23)ccc1Oc1ccc2c(c1)ncn2C]

N-(3-methyl-4-((1-methyl-1H-benzo[d]imidazol-5-yl)oxy)phenyl)-6-(methylsulfonyl)pyrimido[5,4-d]pyrimidin-4-amine A solution of N-(3-methyl-4-((1-methyl-1H-benzo[d]imidazol-5-yloxy)phenyl)-6-(methylthio)pyrimido[5,4-d]pyrimidin-4-amine (0.208 g, 0.48 mmol) in CH$_2$Cl$_2$ was treated with 3-chlorobenzoperoxoic acid (0.478 g, 1.94 mmol). After 60 hours, the reaction mixture was concentrated. This product was purified via normal phase chromatography (5 to 20% MeOH:EtOAc). Fractions containing the desired product were pooled and concentrated to provide N-(3-methyl-4-((1-methyl-1H-benzo[d]imidazol-5-yl)oxy)phenyl)-6-(methylsulfonyl)pyrimido[5,4-d]pyrimidin-4-amine (0.102 g, 45.6%) as a solid. $^1$H NMR (400 MHz, CDCl$_3$) δ 9.54 (s, 1H), 8.99 (s, 2H), 8.96 (s, 1H), 7.86 (d, J=2.9, 1H), 7.83 (dd, J=2.1, 8.6, 1H), 7.54 (m, 2H), 7.34 (dd, J=2.3 Hz, 9.1 Hz, 1H), 7.04 (d, J=8.5 Hz, 1H) 7.00 (s, 1H), 4.05 (s, 3H), 3.49 (s, 3H), 2.30 (s, 3H); m/z (APCI-pos) M$^+$1=462.1.

Example 3

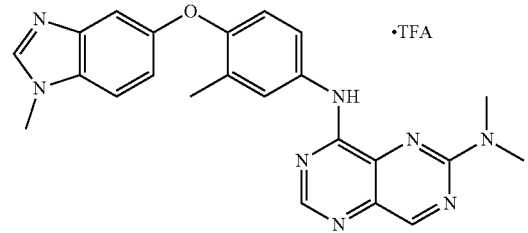 [SMILES: Cc1cc(Nc2ncnc3cnc(N(C)C)nc23)ccc1Oc1ccc2c(c1)ncn2C]

N2,N2-dimethyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate A solution of N-(3-methyl-4-((1-methyl-1H-benzo[d]imidazol-5-yl)oxy)phenyl)-6-(methylsulfonyl)pyrimido[5,4-d]pyrimidin-4-amine (0.017 g, 0.036 mmol) in THF (2 mL) was treated with dimethylamine (0.121 g, 0.134 mmol). Then, the mixture was heated to 65° C. and stirred for 22 hours. The mixture was concentrated, and the crude product was purified via reverse phase chromatography (5 to 95% ACN/H$_2$O with 0.1% TFA buffer). Fractions containing the desired product were pooled and lyophilized to give N2,N2-dimethyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate (0.012 g, 79.4%). $^1$H NMR (400 MHz, CDCl$_3$) δ 9.32 (s, 1H), 9.05 (s, 1H), 9.03 (br s, 1H), 8.63 (s, 1H), 7.77 (m, 2H), 7.56 (d, J=9.1 Hz, 1H), 7.35 (dd, J=2.3 Hz, 9.1 Hz, 1H), 7.21 (d, J=2.1 Hz, 1H), 7.04 (d, J=8.6 Hz, 1H), 4.07 (s, 3H), 3.38 (s, 6H), 2.29 (s, 3H); m/z (APCI-pos) M$^+$1=427.2.

Example 4

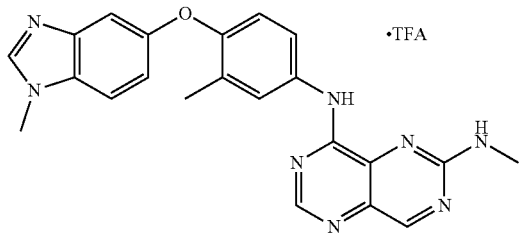 [SMILES: CNc1ncc2ncnc(Nc3ccc(Oc4ccc5c(c4)ncn5C)c(C)c3)c2n1]

N2-methyl-N8-(3-methyl-4-((1-methyl-1H-benzo[d]imidazol-5-yl)oxy)phenyl)pyrimido[5,4-d]pyrimidine-2,8-diamine N2-Methyl-N8-(3-methyl-4-((1-methyl-1H-benzo[d]imidazol-5-yl)oxy)phenyl)pyrimido[5,4-d]pyrimidine-2,8-diamine (6.7 mg, 60% yield) was prepared according to the general procedure of Example 3, substituting methylamine for dimethylamine. $^1$H NMR (400 MHz, (CD$_3$)$_2$SO) δ 9.63 (s, 1H), 9.30 (s, 1H), 9.01 (s, 1H), 8.46 (s, 1H), 7.93 (m, 4H), 7.56 (d, J=9.1 Hz, 1H), 7.31 (dd, J=2.2 Hz, 9.1 Hz, 1H), 7.17 (d, J=2.2 Hz, 1H), 7.07 (d, J=8.6 Hz, 1H), 4.04 (s, 3H), 3.05 (s, 3H), 2.22 (s, 3H).

Example 5

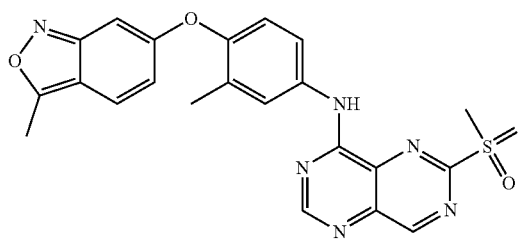

N-(3-methyl-4-((3-methylbenzo[c]isoxazol-6-yl)oxy)phenyl)-6-(methylsulfonyl)pyrimido[5,4-d]pyrimidin-4-amine N-(3-Methyl-4-((3-methylbenzo[c]isoxazol-6-yl)oxy)phenyl)-6-(methylsulfonyl)pyrimido[5,4-d]pyrimidin-4-amine (11.8 mg, 35% yield) was prepared according to the general procedure of Examples 1 and 2, substituting 3-methyl-4-((3-methylbenzo[c]isoxazol-6-yl)oxy)aniline for 3-methyl-4-((1-methyl-1H-benzo[d]imidazol-5-yl)oxy)aniline in Example 1. $^1$H NMR (400 MHz, CDCl$_3$) δ 9.53 (s, 1H), 8.99 (s, 1H), 8.96 (s, 1H), 7.83 (m, 2H), 7.45 (d, J=9.4 Hz, 1H), 7.15 (d, J=8.5 Hz, 1H), 6.85 (dd, J=2.0, 9.3, 1H), 6.49 (d, J=1.7 Hz, 1H), 3.49 (s, 3H), 2.76 (s, 3H), 2.30 (s, 3H); m/z (APCI-pos) M$^+$1=463.1.

Example 6

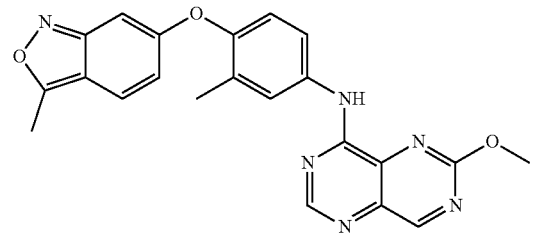

6-methoxy-N-(3-methyl-4-((3-methylbenzo[c]isoxazol-6-yl)oxy)phenyl)pyrimido[5,4-d]pyrimidin-4-amine A solution of N-(3-methyl-4-((3-methylbenzo[c]isoxazol-6-yl)oxy)phenyl)-6-(methylsulfonyl)pyrimido[5,4-d]pyrimidin-4-amine (0.01 g, 0.022 mmol) in MeOH (2 mL) was treated with a solution of sodium methoxide in MeOH (0.0039 g, 0.0216 mmol). The reaction mixture was heated to 40° C. and stirred for 2 hours 30 minutes. The reaction mixture was concentrated, and the product was purified via reverse phase chromatography (5 to 95% ACN/H$_2$O with 0.1% TFA buffer). Fractions containing the desired product were pooled and lyophilized to give 6-methoxy-N-(3-methyl-4-((3-methylbenzo[c]isoxazol-6-yl)oxy)phenyl)pyrimido[5,4-d]pyrimidin-4-amine (0.009 g, 34.6%). $^1$H NMR (400 MHz, CDCl$_3$) δ 9.52 (s, 1H), 9.00 (br s, 1H), 8.82 (s, 1H), 7.84 (d, 2.4 Hz, 1H), 7.79 (dd, J=2.6 Hz, 8.8 Hz, 1H), 7.46 (d, J=9.3 Hz, 1H), 7.15 (d, J=8.5 Hz, 1H), 6.86 (dd, J=1.9 Hz, 9.4 Hz, 1H), 6.49 (d, J=1.6 Hz, 1H), 4.24 (s, 3H), 2.76 (s, 3H), 2.30 (s, 3H); m/z (APCI-pos) M$^+$1=415.1.

Example 7

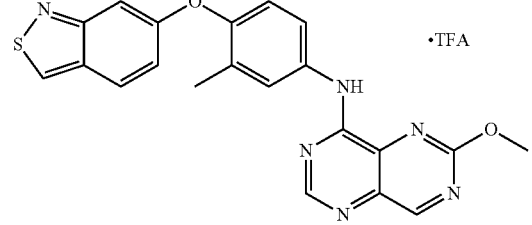

N-(4-(benzo[c]isothiazol-6-yloxy)-3-methylphenyl)-6-methoxypyrimido[5,4-d]pyrimidin-4-amine 2,2,2-trifluoroacetate Step A: N-(4-(Benzo[c]isothiazol-6-yloxy)-3-methylphenyl)-6-(methylsulfonyl)pyrimido[5,4-d]pyrimidin-4-amine (0.005 g, 13%) was prepared according to the general procedure of Example 1 and 2, substituting 4-(benzo[c]isothiazol-6-yloxy)-3-methylaniline for 3-methyl-4-((1-methyl-1H-benzo[d]imidazol-5-yl)oxy)aniline.

Step B: N-(4-(Benzo[c]isothiazol-6-yloxy)-3-methylphenyl)-6-methoxypyrimido[5,4-d]pyrimidin-4-amine 2,2,2-trifluoroacetate (0.003 g, 71%) was prepared according to the general procedure of Example 6, substituting N-(4-(benzo[c]isothiazol-6-yloxy)-3-methylphenyl)-6-(methylsulfonyl)pyrimido[5,4-d]pyrimidin-4-amine for N-(3-methyl-4-((3-methylbenzo[c]isoxazol-6-yl)oxy)phenyl)-6-(methylsulfonyl)pyrimido[5,4-d]pyrimidin-4-amine. $^1$H NMR (400 MHz, CDCl$_3$) δ 9.54 (s, 1H), 9.14 (s, 1H), 9.05 (br s, 1H), 8.81 (s, 1H), 7.93 (d, J=8.8 Hz, 1H), 7.81 (s, 1H), 7.74 (d, J=8.8 Hz, 1H), 7.61 (d, J=1.9 Hz, 1H), 7.06 (d, J=9.0 Hz, 1H), 4.25 (s, 3H), 2.36 (s, 3H); m/z (APCI-pos) M$^+$1=417.2.

Example 8

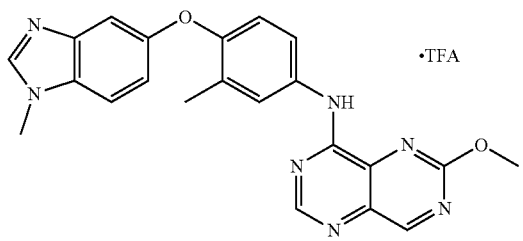 [SMILES: COc1ncc2ncnc(Nc3ccc(Oc4ccc5c(c4)ncn5C)c(C)c3)c2n1]

6-methoxy-N-(3-methyl-4-((1-methyl-1H-benzo[d]imidazol-5-yl)oxy)phenyl)pyrimido[5,4-d]pyrimidin-4-amine 2,2,2-trifluoroacetate 6-Methoxy-N-(3-methyl-4-((1-methyl-1H-benzo[d]imidazol-5-yl)oxy)phenyl)pyrimido[5,4-d]pyrimidin-4-amine 2,2,2-trifluoroacetate (0.005 g, 28%) was prepared according to general procedure of Example 6, substituting N-(3-methyl-4-((1-methyl-1H-benzo[d]imidazol-5-yl)oxy)phenyl)-6-(methylsulfonyl)pyrimido[5,4-d]pyrimidin-4-amine for N-(3-methyl-4-((3-methylbenzo[c]isoxazol-6-yl)oxy)phenyl)-6-(methylsulfonyl)pyrimido[5,4-d]pyrimidin-4-amine. $^1$H NMR (400 MHz, CDCl$_3$) δ 9.40 (s, 1H), 9.13 (s, 1H), 8.82 (br s, 1H), 8.78 (s, 1H), 7.84 (d, 2.3 Hz, 1H), 7.79 (dd, J=2.7 Hz, 8.5 Hz, 1H), 7.56 (d, J=9.0 Hz, 1H), 7.36 (dd, J=2.2 Hz, 8.8 Hz, 1H) 7.21 (d, J=2.2 Hz, 1H), 7.05 (d, J=8.7 Hz, 1H), 4.23 (s, 3H), 4.07 (s, 3H), 2.28 (s, 3H); m/z (APCI-pos) M$^+$1=414.1.

Example 9

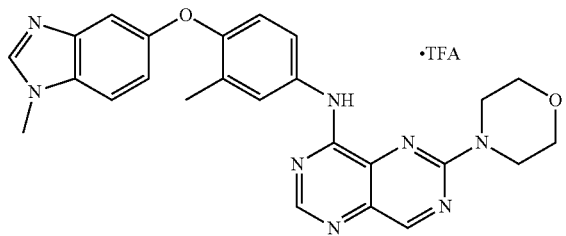 [SMILES: Cc1cc(Nc2ncnc3cnc(N4CCOCC4)nc23)ccc1Oc1ccc2c(c1)ncn2C]

N-(3-methyl-4-((1-methyl-1H-benzo[d]imidazol-5-yl)oxy)phenyl)-6-morpholinopyrimido[5,4-d]pyrimidin-4-amine 2,2,2-trifluoroacetate A solution of N-(3-methyl-4-((1-methyl-1H-benzo[d]imidazol-5-yl)oxy)phenyl)-6-(methylsulfonyl)pyrimido[5,4-d]pyrimidin-4-amine (0.022 g, 0.048 mmol) in dioxane (2 mL) was treated with morpholine (0.125 g, 1.43 mmol). The mixture was heated to 80° C. and stirred for 4 hours. The reaction mixture was concentrated, and the product was purified via reverse phase chromatography (5 to 95% ACN/H$_2$O with 0.1% TFA buffer). Fractions containing the desired product were pooled and lyophilized to give N-(3-methyl-4-((1-methyl-1H-benzo[d]imidazol-5-yl)oxy)phenyl)-6-morpholinopyrimido[5,4-d]pyrimidin-4-amine 2,2,2-trifluoroacetate (0.003 g, 14.3%). $^1$H NMR (400 MHz, (CD$_3$)$_2$SO) δ 9.70 (s, 1H), 9.12 (s, 1H), 8.45 (s, 1H), 7.90 (s, 1H), 7.86 (s, 2H), 7.26 (d, J=8.5 Hz, 1H), 7.15 (d, J=2.1 Hz, 1H), 7.04 (d, J=8.7 Hz, 1H), 4.01 (s, 6H), 3.74 (s, 3H), 2.22 (s, 3H); m/z (APCI-pos) M$^+$1=469.2.

Example 10

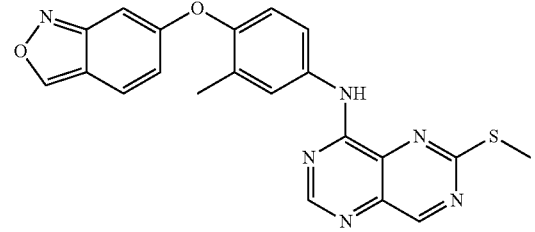 [SMILES: CSc1ncc2ncnc(Nc3ccc(Oc4ccc5conc5c4)c(C)c3)c2n1]

N-(4-(benzo[c]isoxazol-6-yloxy)-3-methylphenyl)-6-(methylthio)pyrimido[5,4-d]pyrimidin-4-amine Step A: A mixture of tert-butyl (4-hydroxy-3-methylphenyl)carbamate (0.51 g, 2.3 mmol), 4-fluoro-2-nitrobenzaldehyde (0.39 g, 2.3 mmol), DMF (23 mL) and cesium carbonate (1.5 g, 4.6 mmol) was heated to 60° C. for 2 hours and then allowed to cool to ambient temperature. The mixture was diluted with water/brine and extracted with EtOAc. The organics were washed with brine, dried over sodium sulfate and concentrated under reduced pressure. Flash chromatography (hexane:EtOAc, 5-15%) afforded tert-butyl (4-(4-formyl-3-nitrophenoxy)-3-methylphenyl)carbamate (0.31 g, 36%). m/z (APCI-pos) M$^-$Boc=273.1.

Step B: A mixture of tert-butyl (4-(4-formyl-3-nitrophenoxy)-3-methylphenyl)carbamate (0.31 g, 0.82 mmol), SnCl$_2$2H$_2$O (0.55 g, 2.5 mmol), and methanol/EtOAc 1:1 (8 mL) was stirred at room temperature for 20 hours. The mixture was then diluted with 10% aqueous potassium carbonate and extracted with EtOAc. The organics were dried over sodium sulfate, filtered and concentrated under reduced pressure. Flash chromatography (5% EtOAc/Hexanes to 50% EtOAc/hexanes) afforded tert-butyl (4-(benzo[c]isoxazol-6-yloxy)-3-methylphenyl)carbamate (0.19 g, 67%). m/z (APCI-pos) M$^+$1=341.1.

Step C: A mixture of tert-butyl (4-(benzo[c]isoxazol-6-yloxy)-3-methylphenyl)carbamate (0.19 g, 0.55 mmol), DCM (5 mL) and 20 equivalents of TFA was stirred at room temperature for 30 minutes. The mixture was then diluted with EtOAc and washed with 10% aqueous potassium carbonate. The organics were dried over sodium sulfate and concentrated under reduced pressure to give 4-(benzo[c]isoxazol-6-yloxy)-3-methylaniline (0.12 g, 94%). m/z (APCI-pos) M$^+$1=241.1.

Step D: A solution of 4-(benzo[c]isoxazol-6-yloxy)-3-methylaniline (0.05 g, 0.208 mmol) in dioxane (2 mL) was treated with 8-chloro-2-(methylthio)pyrimido[5,4-d]pyrimidine (0.049 g, 0.229 mmol), followed by addition of N-ethyl-N-isopropylpropan-2-amine (0.027 g, 0.208 mmol). The mixture was heated to 100° C. and stirred for 22 hours. The mixture was diluted with H₂O and DCM, and the aqueous layer was extracted with DCM (2×). The combined organics were concentrated to give N-(4-(benzo[c]isoxazol-6-yloxy)-3-methylphenyl)-6-(methylthio)pyrimido[5,4-d]pyrimidin-4-amine (0.094 g, quant.) as a solid. ¹H NMR (400 MHz, CDCl₃) δ 9.23 (s, 1H), 9.01 (s, 1H), 8.78 (br s, 1H), 8.77 (s, 1H), 7.82 (m, 2H), 7.57 (dd, J=0.6 Hz, 9.3 Hz, 1H), 7.15 (d, J=8.5 Hz, 1H), 6.95 (dd, J=2.1 Hz, 9.3 Hz, 1H) 6.56 (p, J=1.0 Hz, 1H), 2.74 (s, 3H), 2.29 (s, 3H); m/z (APCI-pos) M⁺1=417.1.

Example 11

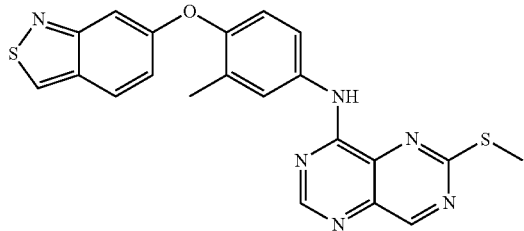 [SMILES: CSc1ncc2ncnc(Nc3ccc(Oc4ccc5csnc5c4)c(C)c3)c2n1]

N-(4-(benzo[c]isothiazol-6-yloxy)-3-methylphenyl)-6-(methylthio)pyrimido[5,4-d]pyrimidin-4-amine 2,2,2-trifluoroacetate N-(4-(Benzo[c]isothiazol-6-yloxy)-3-methylphenyl)-6-(methylthio)pyrimido[5,4-d]pyrimidin-4-amine 2,2,2-trifluoroacetate (34 mg, 41%) was prepared according to the general procedure described in Example 1, substituting 4-(benzo[c]isothiazol-6-yloxy)-3-methylaniline for 3-methyl-4-((1-methyl-1H-benzo[d]imidazol-5-yl)oxy)aniline. ¹H NMR (400 MHz, CDCl₃) δ 9.42 (s, 1H), 9.13 (s, 1H), 9.06 (br s, 1H), 8.81 (s, 1H), 7.92 (d, J=8.8, 1H), 7.80 (d, J=2.5 Hz, 1H), 7.74 (dd, J=2.6 Hz, 8.4 Hz, 1H), 7.61 (d, J=2.3 Hz, 1H) 7.06 (d, J=8.7 Hz, 1H), 2.73 (s, 3H), 2.36 (s, 3H); m/z (APCI-pos) M⁺1=433.1.

Example 12

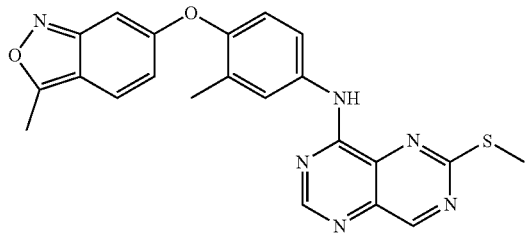 [SMILES: CSc1ncc2ncnc(Nc3ccc(Oc4ccc5c(C)onc5c4)c(C)c3)c2n1]

N-(3-methyl-4-((3-methylbenzo[c]isoxazol-6-yl)oxy)phenyl)-6-(methylthio)pyrimido[5,4-d]pyrimidin-4-amine N-(3-Methyl-4-((3-methylbenzo[c]isoxazol-6-yl)oxy)phenyl)-6-(methylthio)pyrimido[5,4-d]pyrimidin-4-amine (34 mg, 54%) was prepared according to the general method described in Example 1, substituting 3-methyl-4-((3-methylbenzo[c]isoxazol-6-yl)oxy)aniline for 3-methyl-4-((1-methyl-1H-benzo[d]imidazol-5-yl)oxy)aniline. ¹H NMR (400 MHz, CDCl₃) δ 9.22 (s, 1H), 8.77 (s, 2H), 7.81 (m, 2H), 7.43 (d, J=9.3 Hz, 1H), 7.13 (d, J=8.6, 1H), 6.85 (dd, J=1.7 Hz, 9.1, 1H), 6.47 (d, J=1.3 Hz, 1H), 2.75 (s, 3H), 2.73 (s, 3H), 2.28 (s, 1H); m/z (APCI-pos) M⁺1=431.1.

Example 13

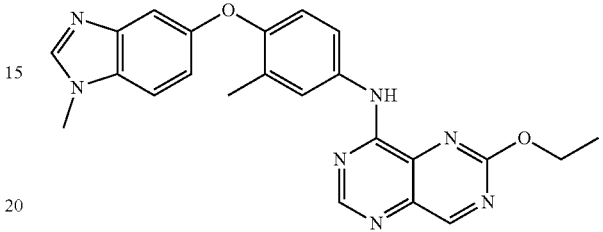

6-ethoxy-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine 2,2,2-trifluoroacetate (0.010 g, 0.017 mmol) and 20% NaOEt/EtOH solution (1 mL) was warmed to 70° C. for 16 hours and then concentrated under reduced pressure. Reverse phase purification and neutralization of the product fractions afforded 6-ethoxy-N-(3-methyl-4-((1-methyl-1H-benzo[d]imidazol-5-yl)oxy)phenyl)pyrimido[5,4-d]pyrimidin-4-amine (4.3 mg, 58%) as a solid. m/z (APCI-pos) M⁺1=472.2; ¹H NMR (400 MHz, CDCl₃) δ 8.67 (s, 1H), 8.57 (s, 1H), 8.03 (d, J=9.0 Hz, 1H), 7.85 (s, 1H), 7.73 (s, 1H), 7.67-7.60 (m, 1H), 7.33 (d, J=7.7 Hz, 2H), 7.20 (d, J=9.0 Hz, 1H), 7.06 (d, J=8.8 Hz, 1H), 6.94 (d, J=8.7 Hz, 1H), 4.55 (q, J=7.1 Hz, 2H), 3.85 (s, 2H), 2.35 (s, 3H), 0.86 (br m, 3H).

Example 14

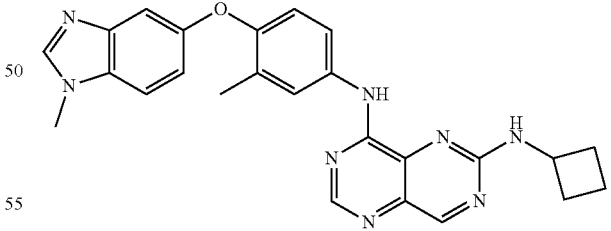

N2-cyclobutyl-N8-(3-methyl-4-((1-methyl-1H-benzo[d]imidazol-5-yl)oxy)phenyl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol), cyclobutanamine (0.019 g, 0.27 mmol), and DIEA (0.021 g, 0.16 mmol) in DMA (1 mL) was warmed to 80° C. for 1.5 hours, then allowed to cool to room temperature. The mixture was diluted with EtOAc, washed with water/brine, dried over sodium sulfate and concentrated under reduced pressure. Reverse phase purification of the crude and neutralization of the product fractions afforded N2-cyclobutyl-N8-(3-methyl-4-((1-methyl-1H-benzo[d]imidazol-5-yl)oxy)phenyl)pyrimido[5,4-d]pyrimidine-2,8-diamine (16.1 mg, 59%). m/z (APCI-pos) M$^+$1=453.2; $^1$H NMR (400 MHz, DMSO) δ 9.34 (s, 1H), 8.98 (s, 1H), 8.37 (s, 1H), 8.17 (s, 1H), 7.85 (s, 1H), 7.76 (d, J=8.8 Hz, 1H), 7.56 (d, J=8.7 Hz, 1H), 7.09 (d, J=2.3 Hz, 1H), 6.99 (dd, J=8.7, 2.3 Hz, 1H), 6.90 (d, J=8.7 Hz, 1H), 4.83 (s, 1H), 3.84 (s, 3H), 2.39-2.34 (m, 2H), 2.26 (s, 3H), 2.07-1.98 (m, 2H), 1.76-1.66 (m, 2H).

Example 15

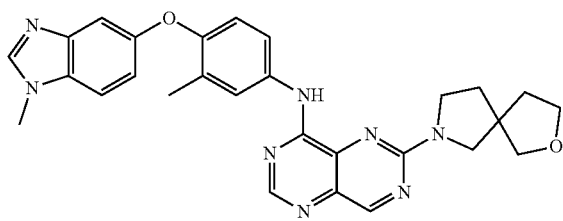 [SMILES: Cc1cc(Nc2ncnc3cnc(N4CCC5(CCOC5)C4)nc23)ccc1Oc1ccc2c(c1)ncn2C]

N-(3-methyl-4-((1-methyl-1H-benzo[d]imidazol-5-yl)oxy)phenyl)-6-(2-oxa-7-azaspiro[4.4]nonan-7-yl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), 2-oxa-7-azaspiro[4.4]nonane (0.14 g, 1.1 mmol) in dioxane (1 mL) was warmed to 65° C. for 2 hours, then concentrated under reduced pressure. Reverse phase purification of the crude and neutralization of the product fractions afforded N-(3-methyl-4-((1-methyl-1H-benzo[d]imidazol-5-yl)oxy)phenyl)-6-(2-oxa-7-azaspiro[4.4]nonan-7-yl)pyrimido[5,4-d]pyrimidin-4-amine (51.5 mg, 94%). m/z (APCI-pos) M$^+$1=509.2; $^1$H NMR (400 MHz, DMSO) δ 9.37 (br s, 1H), 9.05 (s, 1H), 8.37 (s, 1H), 8.15 (s, 1H), 7.83 (s, 1H), 7.78 (d, J=9.0 Hz, 1H), 7.54 (d, J=8.7 Hz, 1H), 7.07 (d, J=2.3 Hz, 1H), 6.97 (dd, J=8.7, 2.3 Hz, 1H), 6.87 (d, J=8.7 Hz, 1H), 3.88-3.56 (m, 11H), 2.23 (s, 3H), 2.03 (qd, J=8.2, 7.0, 3.7 Hz, 2H), 2.01-1.92 (m, 1H), 1.91 (d, J=6.9 Hz, 1H).

Example 16

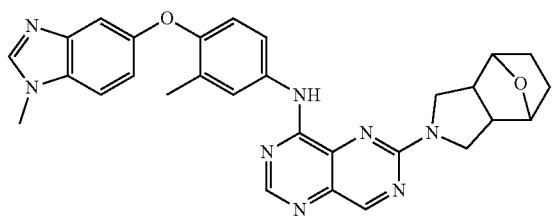 [SMILES: Cc1cc(Nc2ncnc3cnc(N4CC5C6CCC(O6)C5C4)nc23)ccc1Oc1ccc2c(c1)ncn2C]

N-(3-methyl-4-((1-methyl-1H-benzo[d]imidazol-5-yl)oxy)phenyl)-6-(octahydro-2H-4,7-epoxyisoindol-2-yl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol) and octahydro-1H-4,7-epoxyisoindole (0.075 g, 0.54 mmol) in DMA (1 mL) was warmed to 60° C. for 16 hours, then allowed to cool to room temperature. The mixture was diluted with EtOAc, washed with water, brine, dried over sodium sulfate and concentrated under reduced pressure. Reverse phase purification of the crude and neutralization of the product fractions afforded N-(3-methyl-4-((1-methyl-1H-benzo[d]imidazol-5-yl)oxy)phenyl)-6-(octahydro-2H-4,7-epoxyisoindol-2-yl)pyrimido[5,4-d]pyrimidin-4-amine (39.5 mg, 70%). m/z (APCI-pos) M$^+$1=522.2; $^1$H NMR (400 MHz, DMSO) δ 9.36 (s, 1H), 9.04 (s, 1H), 8.39 (s, 1H), 8.16 (s, 1H), 7.88 (d, J=2.8 Hz, 1H), 7.82 (dd, J=8.7, 2.8 Hz, 1H), 7.56 (dd, J=9.0, 3.0 Hz, 1H), 7.09 (t, J=2.8 Hz, 1H), 6.99 (dd, J=8.7, 2.4 Hz, 1H), 6.89 (dd, J=8.7, 2.8 Hz, 1H), 4.42 (m, 2H), 4.07-3.92 (m, 2H), 3.84 (s, 3H), 3.59-3.44 (m, 2H), 2.71-2.62 (m, 2H), 2.25 (s, 3H), 1.60-1.43 (m, 4H).

Example 17

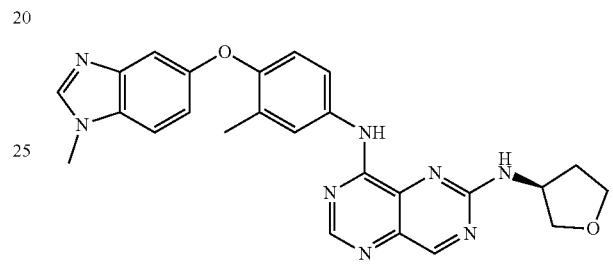

(S)—N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), (S)-tetrahydrofuran-3-amine hydrochloride (0.067 g, 0.54 mmol), DIEA (0.098 g, 0.76 mmol) in dioxane (1 mL) was warmed to 70° C. for 16 hours, then concentrated under reduced pressure. Reverse phase purification of the crude and neutralization of the product fractions afforded (S)—N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine (7.3 mg, 14%). m/z (APCI-pos) M$^+$1=469.1; $^1$H NMR (400 MHz, DMSO) δ 9.37 (s, 1H), 9.01 (s, 1H), 8.40 (s, 1H), 8.17 (s, 1H), 8.13 (s, 1H), 7.83 (s, 1H), 7.76 (dd, J=8.7, 2.7 Hz, 1H), 7.56 (d, J=8.7 Hz, 1H), 7.09 (d, J=2.3 Hz, 1H), 6.99 (dd, J=8.7, 2.3 Hz, 1H), 6.90 (d, J=8.7 Hz, 1H), 4.85 (s, 1H), 4.06 (s, 1H), 3.89 (q, J=7.5 Hz, 1H), 3.84 (s, 3H), 3.78 (td, J=8.1, 5.8 Hz, 1H), 3.59 (dd, J=8.8, 4.6 Hz, 1H), 2.26 (s, 3H), 2.01-1.87 (m, 1H).

Example 18

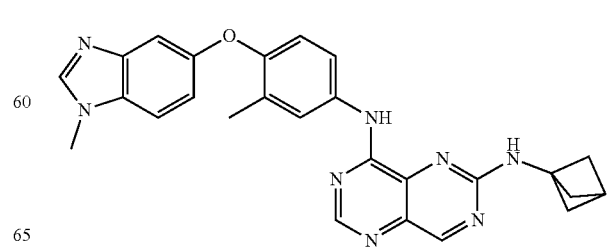

N2-(bicyclo[1.1.1]pentan-1-yl)-N8-(3-methyl-4-((1-methyl-1H-benzo[d]imidazol-5-yl)oxy)phenyl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), bicyclo[1.1.1]pentan-1-amine hydrochloride (0.065 g, 0.54 mmol), DIEA (0.098 g, 0.76 mmol) in DMA (1 mL) was warmed to 80° C. for 16 hours, then allowed to cool to room temperature. The mixture was then diluted with EtOAc, washed several times with water/brine, dried over sodium sulfate and concentrated under reduced pressure. Reverse phase purification of the crude and neutralization of the product fractions afforded N2-(bicyclo[1.1.1]pentan-1-yl)-N8-(3-methyl-4-((1-methyl-1H-benzo[d]imidazol-5-yl)oxy)phenyl)pyrimido[5,4-d]pyrimidine-2,8-diamine (21.9 mg, 58%). m/z (APCI-pos) M$^+$1=465.2; $^1$H NMR (400 MHz, DMSO) δ 9.04 (s, 1H), 8.87 (s, 1H), 8.57 (s, 1H), 8.44 (s, 1H), 8.17 (s, 1H), 7.81 (d, J=2.7 Hz, 1H), 7.69 (dd, J=8.7, 2.7 Hz, 1H), 7.56 (d, J=8.7 Hz, 1H), 7.09 (d, J=2.3 Hz, 1H), 6.99 (dd, J=8.7, 2.4 Hz, 1H), 6.92 (d, J=8.7 Hz, 1H), 3.84 (s, 3H), 2.53 (s, 1H), 2.26 (s, 3H), 2.22 (s, 6H).

Example 19

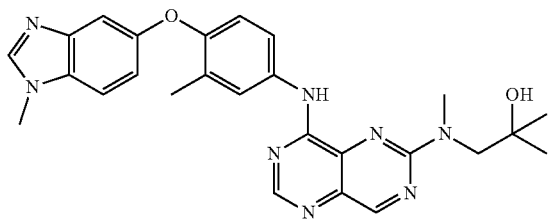 [SMILES: Cc1cc(Nc2ncnc3cnc(N(C)CC(C)(C)O)nc23)ccc1Oc1ccc2c(c1)ncn2C]

2-methyl-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol N-(3-Methyl-4-((1-methyl-1H-benzo[d]imidazol-5-yl)oxy)phenyl)-6-(methylsulfonyl)pyrimido[5,4-d]pyrimidin-4-amine (5.0 g, 11 mmol) was added to a solution of 2-methyl-1-(methylamino)propan-2-ol (3.9 g, 38 mmol) in DMSO (54 mL), and the mixture was heated to 75° C. where it stirred for 2 hours open to the air. The mixture was then cooled to ambient temperature. The mixture was poured into a stirring solution of 1:1 water:saturated aqueous NaHCO$_3$ (250 mL), and the mixture was stirred for 15 minutes. The resulting solid was isolated by vacuum filtration. The solid was then isolated, dissolved in IPA/CH$_2$Cl$_2$, dried over Na$_2$SO$_4$, filtered and concentrated. The crude product was then purified via column chromatography (4-7% MeOH/CHCl$_3$) to afford the desired product as a solid foam. The product was then dissolved in CH$_2$Cl$_2$ and EtOAc and concentrated again. The solid obtained was again treated with EtOAc and concentrated again to provide a nice free flowing solid 2-methyl-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol (3.5 g, 65%). m/z (APCI-pos) M$^+$1=485.2; $^1$H NMR (400 MHz, CDCl$_3$) δ 9.02 (s, 1H), 8.55 (s, 2H), 7.85 (s, 1H), 7.74 (d, J=2.7 Hz, 1H), 7.63 (dd, J=8.8, 2.7 Hz, 1H), 7.36-7.29 (m, 2H), 7.06 (dd, J=8.6, 2.3 Hz, 1H), 6.93 (d, J=8.7 Hz, 1H), 3.85 (s, 3H), 3.82 (s, 2H), 3.41 (s, 3H), 2.35 (s, 3H), 1.33 (s, 6H).

Example 20

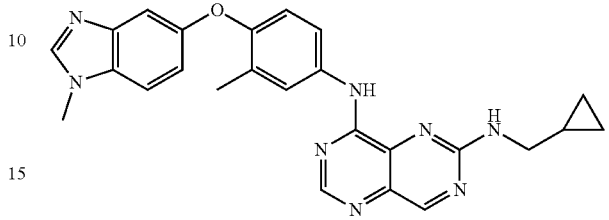

N2-(cyclopropylmethyl)-N8-(3-methyl-4-((1-methyl-1H-benzo[d]imidazol-5-yl)oxy)phenyl)pyrimido[5,4-d]pyrimidine-2,8-diamine A pressure tube equipped with a stir bar was charged with N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol), DMA (0.5 mL), and cyclobutylmethanamine (0.046 g, 0.54 mmol). The tube was sealed, and the mixture was warmed to 80° C. overnight, then allowed to cool to room temperature. The mixture was then diluted with EtOAc, washed with water/brine, dried over sodium sulfate and concentrated under reduced pressure. Reverse phase purification of the crude and neutralization of the product fractions afforded N2-(cyclopropylmethyl)-N8-(3-methyl-4-((1-methyl-1H-benzo[d]imidazol-5-yl)oxy)phenyl)pyrimido[5,4-d]pyrimidine-2,8-diamine (14.7 mg, 60%). m/z (APCI-pos) M$^+$1=453.2; $^1$H NMR (400 MHz, DMSO) δ 9.36 (s, 1H), 8.98 (s, 1H), 8.38 (s, 1H), 8.17 (s, 1H), 7.92 (s, 1H), 7.85 (s, 1H), 7.76 (dd, J=8.8, 2.7 Hz, 1H), 7.56 (d, J=8.7 Hz, 1H), 7.09 (d, J=2.3 Hz, 1H), 6.99 (dd, J=8.7, 2.3 Hz, 1H), 6.89 (d, J=8.7 Hz, 1H), 3.84 (s, 3H), 3.44 (s, 2H), 2.25 (s, 3H), 0.51-0.40 (m, 2H), 0.34-0.28 (m, 2H).

Example 21

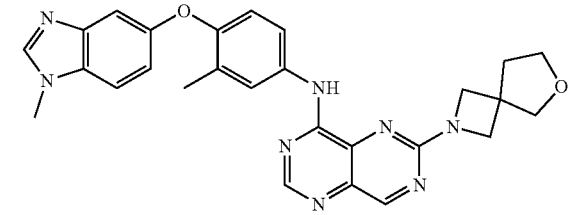 [SMILES: Cc1cc(Nc2ncnc3cnc(N4CC5(CCOC5)C4)nc23)ccc1Oc1ccc2c(c1)ncn2C]

N-(3-methyl-4-((1-methyl-1H-benzo[d]imidazol-5-yl)oxy)phenyl)-6-(6-oxa-2-azaspiro[3.4]octan-2-yl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), 6-oxa-2-azaspiro[3.4]octane (0.12 g, 1.1 mmol) in dioxane (1 mL) was warmed to 65° C. for 16 hours, then concentrated under reduced pressure. Reverse phase purification of the crude and neutralization of the product fractions afforded N-(3-methyl-4-((1-methyl-1H-benzo[d]imidazol-5-yl)oxy)phenyl)-6-(6-oxa-2-azaspiro[3.4]octan-2-yl)pyrimido[5,4-d]pyrimidin-4-amine (14.7 mg, 79%). m/z (APCI-pos) M$^+$1=495.2; $^1$H NMR (400 MHz, DMSO) δ 9.37 (s, 1H), 9.07 (s, 1H), 8.41 (s, 1H), 8.15 (s, 1H), 7.85 (d, J=2.6 Hz, 1H), 7.77 (dd, J=8.8, 2.7 Hz, 1H), 7.54 (d, J=8.7 Hz, 1H), 7.07 (d, J=2.3 Hz, 1H), 6.97 (dd, J=8.7, 2.3 Hz, 1H), 6.86 (d, J=8.7 Hz, 1H), 4.20 (s, 4H), 3.83 (d, J=13.0 Hz, 5H), 3.75 (t, J=7.0 Hz, 2H), 2.23 (s, 3H), 2.19 (t, J=7.0 Hz, 2H).

Example 22

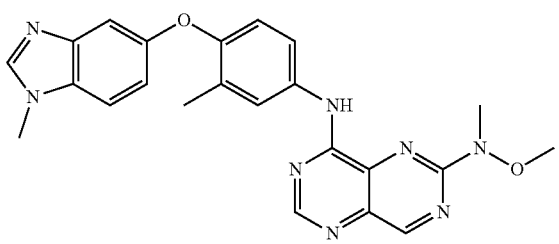 [SMILES: CON(C)c1ncc2ncnc(Nc3ccc(Oc4ccc5c(c4)ncn5C)c(C)c3)c2n1]

6-(methoxy(methyl)amino)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), N,O-dimethylhydroxylamine hydrochloride (0.053 g, 0.54 mmol), and DIEA (0.084 g, 0.65 mmol) in DMA (1 mL) was warmed to 100° C. for 3 days. The mixture was then diluted with water, extracted with EtOAc, extracts washed with brine, dried over sodium sulfate and concentrated under reduced pressure. Reverse phase purification of the crude and neutralization of the product fractions afforded 6-(methoxy(methyl)amino)-N-(3-methyl-4-((1-methyl-1H-benzo[d]imidazol-5-yl)oxy)phenyl)pyrimido[5,4-d]pyrimidin-4-amine (3.0 mg, 6.3%). m/z (APCI-pos) M$^+$1=443.2.

Example 23

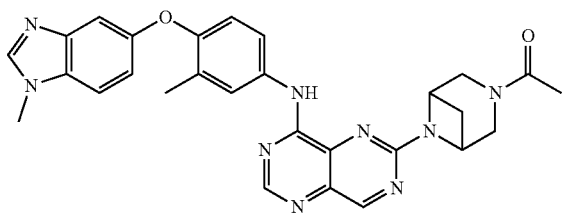 [SMILES: CC(=O)N1CC2CC(C1)N2c1ncc2ncnc(Nc3ccc(Oc4ccc5c(c4)ncn5C)c(C)c3)c2n1]

1-(6-(8-((3-methyl-4-((1-methyl-1H-benzo[d]imidazol-5-yl)oxy)phenyl)amino)pyrimido[5,4-d]pyrimidin-2-yl)-3,6-diazabicyclo[3.1.1]heptan-3-yl)ethan-1-one A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), diazabicyclo[3.1.1]heptan-3-yl)ethan-1-one hydrochloride (0.096 g, 0.54 mmol), DIEA (0.098 g, 0.76 mmol) in DMA (1 mL) was warmed to 100° C. for 3 hours, then allowed to cool to room temperature. The mixture was diluted with EtOAc, washed with brine/water, dried over sodium sulfate and concentrated under reduced pressure. Reverse phase purification of the crude and neutralization of the product fractions afforded 1-(6-(8-((3-methyl-4-((1-methyl-1H-benzo[d]imidazol-5-yl)oxy)phenyl)amino)pyrimido[5,4-d]pyrimidin-2-yl)-3,6-diazabicyclo[3.1.1]heptan-3-yl)ethan-1-one (34.3 mg, 61%). m/z (APCI-pos) M$^+$1=522.2; $^1$H NMR (400 MHz, DMSO) δ 9.58 (s, 1H), 9.13 (s, 1H), 8.46 (s, 1H), 8.18 (s, 1H), 7.82 (s, 1H), 7.76 (d, J=8.4 Hz, 1H), 7.57 (d, J=8.7 Hz, 1H), 7.10 (t, J=2.5 Hz, 1H), 6.99 (dt, J=8.9, 2.3 Hz, 1H), 6.93-6.86 (m, 1H), 4.64 (s, 2H), 3.84 (d, J=2.0 Hz, 3H), 3.66 (d, J=11.0 Hz, 1H), 3.48 (d, J=13.4 Hz, 1H), 3.30 (s, 1H), 2.78 (d, J=7.4 Hz, 1H), 2.49 (s, 1H), 2.26 (d, J=2.9 Hz, 3H), 1.86 (s, 3H), 1.67-1.61 (m, 1H).

Example 24

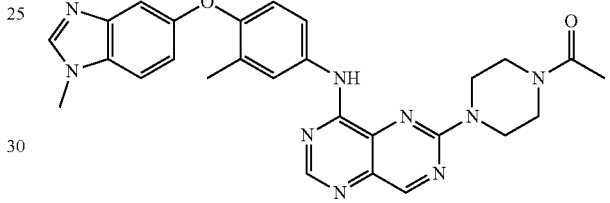

1-(4-(8-((3-methyl-4-((1-methyl-1H-benzo[d]imidazol-5-yl)oxy)phenyl)amino)pyrimido[5,4-d]pyrimidin-2-yl)piperazin-1-yl)ethan-1-one A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), 1-(piperazin-1-yl)ethan-1-one (0.069 g, 0.54 mmol) in DMA (1 mL) was warmed to 60° C. for 16 hours, then allowed to cool to room temperature. The mixture was diluted with EtOAc, washed with water/brine, dried over sodium sulfate and concentrated under reduced pressure. Reverse phase purification of the crude and neutralization of the product fractions afforded 1-(4-(8-((3-methyl-4-((1-methyl-1H-benzo[d]imidazol-5-yl)oxy)phenyl)amino)pyrimido[5,4-d]pyrimidin-2-yl)piperazin-1-yl)ethan-1-one (40.5 mg, 73%). m/z (APCI-pos) M$^+$1=510.3; $^1$H NMR (400 MHz, DMSO) δ 9.62 (s, 1H), 9.10 (s, 1H), 8.41 (s, 1H), 8.16 (s, OH), 7.87-7.81 (m, 1H), 7.78 (dd, J=8.7, 2.9 Hz, 1H), 7.56 (dd, J=8.9, 2.9 Hz, 1H), 7.09 (t, J=2.9 Hz, 1H), 6.99 (dt, J=9.6, 2.9 Hz, 1H), 6.89 (dd, J=8.9, 2.9 Hz, 1H), 4.14-3.88 (m, 3H), 3.83 (s, 2H), 3.64-3.55 (m, 4H), 3.31 (s, 4H), 3.30 (d, J=2.1 Hz, 1H), 2.48 (d, J=2.6 Hz, 1H), 2.26 (s, 2H), 2.08 (s, 3H).

Example 25

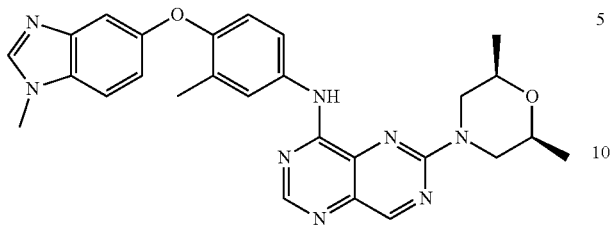

6-((2S,6R)-2,6-dimethylmorpholino)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.045 mmol) in DMA (0.50 mL) was treated with cis-2,6-dimethylmorpholine (0.026 g, 0.22 mmol) and heated to 60° C. for 4 hours. The mixture was diluted with EtOAc and washed with water (3×). The organic phase was dried over anhydrous sodium sulfate, filtered, and concentrated in vacuo. Purification by normal phase chromatography (0-6% MeOH in CHCl$_3$) provided 6-((2S,6R)-2,6-dimethylmorpholino)-N-(3-methyl-4-((1-methyl-1H-benzo[d]imidazol-5-yl)oxy)phenyl)pyrimido[5,4-d]pyrimidin-4-amine (0.022 g, 96% yield). m/z (APCI-pos) M$^+$1=497.3; $^1$H NMR (400 MHz, CDCl$_3$) δ 9.04 (s, 1H), 8.54 (s, 1H), 8.46 (br s, 1H), 7.85 (s, 1H), 7.73 (d, J=2.5 Hz, 1H), 7.63 (dd, J=8.5, 2.5 Hz, 1H), 7.33 (d, J=8.6 Hz, 1H), 7.31 (d, J=2.3 Hz, 1H), 7.06 (dd, J=8.7, 2.3 Hz, 1H), 6.93 (d, J=8.6 Hz, 1H), 4.70 (d, J=12.7 Hz, 2H), 3.85 (s, 3H), 3.76-3.68 (m, 2H), 2.76 (dd, J=13.2, 10.9, 2H), 2.35 (s, 3H), 1.33 (d, J=6.2 Hz, 6H).

Example 26

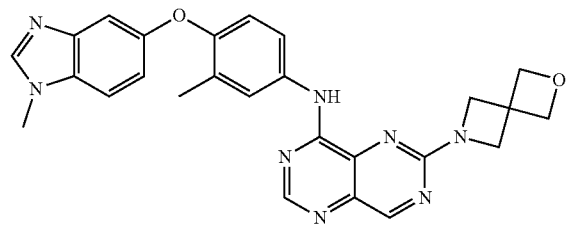 [SMILES: Cc1cc(Nc2ncnc3cnc(N4CC5(COC5)C4)nc23)ccc1Oc1ccc2c(c1)ncn2C]

N-(3-methyl-4-((1-methyl-1H-benzo[d]imidazol-5-yl)oxy)phenyl)-6-(2-oxa-6-azaspiro[3.3]heptan-6-yl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.015 g, 0.034 mmol) in DMA (0.65 mL) was treated with 2-oxa-6-azaspiro[3.3]heptane (0.017 g, 0.17 mmol) and heated to 60° C. for 2 hours. The mixture was diluted with EtOAc and washed with water (3×). The organic phase was dried over anhydrous sodium sulfate, filtered, and concentrated in vacuo. Purification by normal phase chromatography (2-7% MeOH in CHCl$_3$) provided N-(3-methyl-4-((1-methyl-1H-benzo[d]imidazol-5-yl)oxy)phenyl)-6-(2-oxa-6-azaspiro[3.3]heptan-6-yl)pyrimido[5,4-d]pyrimidin-4-amine (0.016 g, 95% yield). m/z (APCI-pos) M$^+$1=481.2; $^1$H NMR (400 MHz, CDCl$_3$) δ 9.05 (s, 1H), 8.55 (s, 1H), 8.54 (br s, 1H), 7.85 (s, 1H), 7.74 (d, J=2.4 Hz, 1H), 7.64 (dd, J=9.0, 2.9 Hz, 1H), 7.33 (d, J=8.9 Hz, 1H), 7.31 (d, J=2.4 Hz, 1H), 7.07 (dd, J=8.4, 2.4 Hz, 1H), 6.93 (d, J=8.8 Hz, 1H), 4.92 (s, 4H), 4.45 (s, 4H), 3.85 (s, 3H), 2.35 (s, 3H).

Example 27

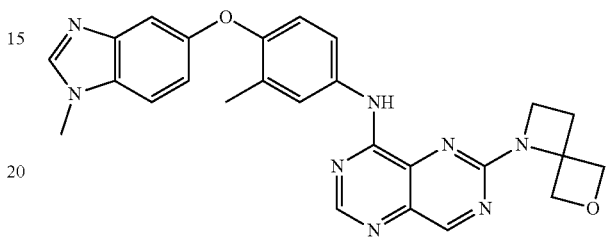

N-(3-methyl-4-((1-methyl-1H-benzo[d]imidazol-5-yl)oxy)phenyl)-6-(6-oxa-1-azaspiro[3.3]heptan-1-yl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) in DMA (1.10 mL) was treated with 6-oxa-1-azaspiro[3.3]heptane oxalate (2:1) (0.047 g, 0.17 mmol) and heated to 60° C. for 2 hours. The mixture was diluted with EtOAc and washed with water (3×). The organic phase was dried over anhydrous sodium sulfate, filtered, and concentrated in vacuo. Purification by normal phase chromatography (1-7% MeOH in CHCl$_3$) provided N-(3-methyl-4-((1-methyl-1H-benzo[d]imidazol-5-yl)oxy)phenyl)-6-(6-oxa-1-azaspiro[3.3]heptan-1-yl)pyrimido[5,4-d]pyrimidin-4-amine (0.019 g, 73% yield). m/z (APCI-pos) M$^+$1=481.2; $^1$H NMR (400 MHz, CDCl$_3$) δ 9.12 (br s, 1H), 8.58 (s, 1H), 7.84 (s, 1H), 7.77 (d, J=2.1 Hz, 1H), 7.67 (d, J=8.3 Hz, 1H), 7.34-7.28 (m, 2H), 7.04 (dd, J=8.6, 2.3 Hz, 1H), 6.93 (d, J=8.7 Hz, 1H), 5.62 (d, J=6.7 Hz, 2H), 4.81 (d, J=5.2 Hz, 2H), 4.12 (t, J=7.3 Hz, 2H), 3.84 (s, 3H), 2.69 (t, J=7.3 Hz, 2H), 2.33 (s, 3H).

Example 28

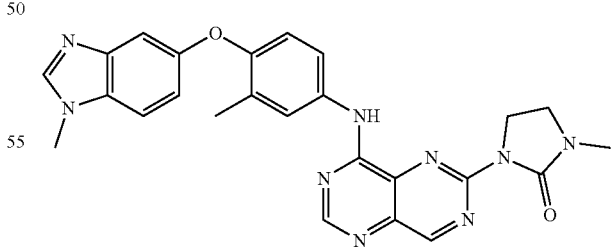

1-methyl-3-(8-((3-methyl-4-((1-methyl-1H-benzo[d]imidazol-5-yl)oxy)phenyl)amino)pyrimido[5,4-d]pyrimidin-2-yl)imidazolidin-2-one A solution of N-(3-methyl-4-((1-methyl-1H-benzo[d]imidazol-5-yl)oxy)phenyl)-6-(methylsulfonyl)pyrimido[5,4-d]

pyrimidin-4-amine (0.010 g, 0.022 mmol) in DMA (0.45 mL) was treated with 1-methyl-2-imidazolidinone (0.022 g, 0.22 mmol) and sodium tert-butoxide (0.011 g, 0.11 mmol) and heated to 125° C. for 1 hour. The mixture was diluted with EtOAc and washed with ammonium chloride (saturated, aq., 1×), water (1×), and brine (2×). The organic phase was dried over anhydrous sodium sulfate, filtered, and concentrated in vacuo. Purification by normal phase chromatography (0-10% MeOH in CHCl$_3$) provided 1-methyl-3-(8-((3-methyl-4-((1-methyl-1H-benzo[d]imidazol-5-yl)oxy)phenyl)amino)pyrimido[5,4-d]pyrimidin-2-yl)imidazolidin-2-one (0.008 g, 71% yield). m/z (APCI-pos) M$^+$1=482.2; $^1$H NMR (400 MHz, CDCl$_3$) δ 9.28 (s, 1H), 8.90 (br s, 1H), 8.67 (s, 1H), 7.85 (s, 1H), 7.74 (d, J=2.1 Hz, 1H), 7.69 (dd, J=8.6, 2.8 Hz, 1H), 7.33 (dd, J=5.4, 3.1 Hz, 2H), 7.05 (dd, J=8.9, 2.2 Hz, 1H), 6.90 (d, J=8.7 Hz, 1H), 4.20 (t, J=7.90 Hz, 2H), 3.84 (s, 3H), 3.57 (t, J=7.9 Hz, 2H), 2.99 (s, 3H), 2.34 (s, 3H).

Example 29

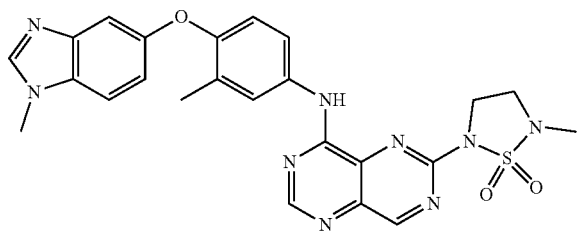 [SMILES: Cc1cc(Nc2ncnc3cnc(N4CCN(C)S4(=O)=O)nc23)ccc1Oc1ccc2c(c1)ncn2C]

2-methyl-5-(8-((3-methyl-4-((1-methyl-1H-benzo[d]imidazol-5-yl)oxy)phenyl)amino)pyrimido[5,4-d]pyrimidin-2-yl)-1,2,5-thiadiazolidine 1,1-dioxide A solution of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.044 mmol) in DMA (0.90 mL) was treated with 2-methyl-[1,2,5]thiadiazolidine-1,1-dioxide (0.031 g, 0.22 mmol) and sodium tert-butoxide (0.022 g, 0.22 mmol) and heated to 125° C. for 2 hours. The mixture was diluted with EtOAc and washed with ammonium chloride (saturated, aq., 1×), water (1×), and brine (2×). The organic phase was dried over anhydrous sodium sulfate, filtered, and concentrated in vacuo. Purification by normal phase chromatography (1-8% MeOH in CHCl$_3$) provided 2-methyl-5-(8-((3-methyl-4-((1-methyl-1H-benzo[d]imidazol-5-yl)oxy)phenyl)amino)pyrimido[5,4-d]pyrimidin-2-yl)-1,2,5-thiadiazolidine 1,1-dioxide (0.012 g, 47% yield). m/z (APCI-pos) M$^+$1=518.2; $^1$H NMR (400 MHz, CDCl$_3$) δ 9.30 (s, 1H), 8.71 (s, 1H), 8.64 (br s, 1H), 7.86 (s, 1H), 7.72 (d, J=2.7 Hz, 1H), 7.66 (dd, J=8.9, 2.8 Hz, 1H), 7.34 (dd, J=5.0, 2.8 Hz, 2H), 7.05 (dd, J=8.7, 2.1 Hz, 1H), 6.91 (d, J=8.6 Hz, 1H), 4.26 (t, J=6.4 Hz, 2H), 3.85 (s, 3H), 3.55 (t, J=6.4 Hz, 2H), 2.94 (s, 3H), 2.36 (s, 3H).

Example 30

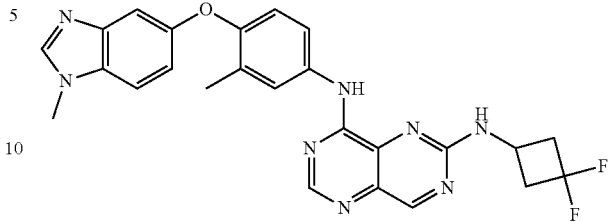

N2-(3,3-difluorocyclobutyl)-N8-(3-methyl-4-((1-methyl-1H-benzo[d]imidazol-5-yl)oxy)phenyl)pyrimido[5,4-d]pyrimidine-2,8-diamine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) in DMA (1.1 mL) was treated with 3,3-difluorocyclobutanamine hydrochloride (0.023 g, 0.16 mmol) and N,N-diisopropylethylamine (0.035 g, 0.27 mmol) and heated to 60° C. for 24 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by normal phase chromatography (1-7% MeOH in CHCl$_3$) provided N2-(3,3-difluorocyclobutyl)-N8-(3-methyl-4-((1-methyl-1H-benzo[d]imidazol-5-yl)oxy)phenyl)pyrimido[5,4-d]pyrimidine-2,8-diamine (0.022 g, 80% yield). m/z (APCI-pos) M$^+$1=489.2; $^1$H NMR (400 MHz, CDCl$_3$) δ 9.05 (s. 1H), 8.59 (s, 1H), 8.54 (br s, 1H), 7.85 (s, 1H), 7.75 (d, J=2.5 Hz, 1H), 7.65 (dd, J=8.8, 2.6 Hz, 1H), 7.33 (d, J=8.8 Hz, 1H), 7.31 (d, J=2.3 Hz, 1H), 7.06 (dd, J=8.7, 2.3 Hz, 1H), 6.93 (d, J=8.8 Hz, 1H), 5.74 (d, J=5.1 Hz, 1H), 4.41 (quint, 7.0 Hz, 1H), 3.85 (s, 3H), 3.19-3.09 (m, 2H), 2.87 (br s, 2H), 2.35 (s, 3H).

Example 31

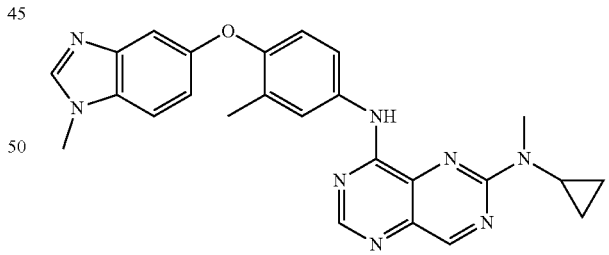

N2-cyclopropyl-N2-methyl-N8-(3-methyl-4-((1-methyl-1H-benzo[d]imidazol-5-yl)oxy)phenyl)pyrimido[5,4-d]pyrimidine-2,8-diamine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.044 mmol) in DMA (0.90 mL) was treated with N-methylcyclopropanamine (0.010 g, 0.14 mmol) and N,N-diisopropylethylamine (0.035 g, 0.27 mmol) and heated to 60° C. for 20 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by reverse phase chromatography (10-95% water in MeCN with 0.1% TFA buffer) provided N2-cyclopropyl-N2-methyl-N8-(3-methyl-4-((1-methyl-1H-benzo[d]imidazol-5-yl)oxy)phenyl)pyrimido[5,4-d]pyrimidine-2,8-diamine (0.020 g, 40% yield). m/z (APCI-pos) M+1=453.2; $^1$H NMR (400 MHz, CDCl$_3$) δ 9.12 (s, 1H), 8.69 (br s, 1H), 8.56 (s, 1H), 7.85 (s, 1H), 7.75 (d, J=2.6 Hz, 1H), 7.65 (dd, J=8.6, 2.6 Hz, 1H), 7.34-7.30 (m, 2H), 7.05 (dd, J=8.6, 2.3 Hz, 1H), 6.94 (d, J=8.7 Hz, 1H), 3.85 (s, 3H), 3.31 (s, 3H), 2.92 (quint, J=3.8 Hz, 1H), 2.35 (s, 3H), 1.03-0.97 (m, 2H), 0.80-0.75 (m, 2H).

Example 32

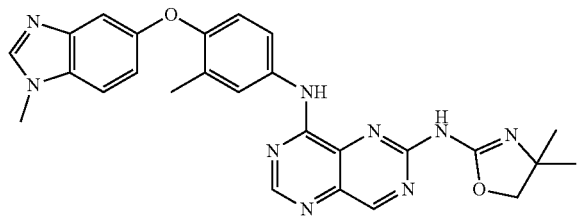 [SMILES: Cc1cc(Nc2ncnc3cnc(NC4=NC(C)(C)CO4)nc23)ccc1Oc1ccc2c(c1)ncn2C]

N2-(4,4-dimethyl-4,5-dihydrooxazol-2-yl)-N8-(3-methyl-4-((1-methyl-1H-benzo[d]imidazol-5-yl)oxy)phenyl)pyrimido[5,4-d]pyrimidine-2,8-diamine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.015 g, 0.034 mmol) in DMA (0.67 mL) was treated with 4,4-dimethyl-4,5-dihydrooxazol-2-amine (0.020 g, 0.17 mmol) and heated to 60° C. for 4 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by normal phase chromatography (1-7% MeOH in CHCl$_3$) provided N2-(4,4-dimethyl-4,5-dihydrooxazol-2-yl)-N8-(3-methyl-4-((1-methyl-1H-benzo[d]imidazol-5-yl)oxy)phenyl)pyrimido[5,4-d]pyrimidine-2,8-diamine (0.016 g, 93% yield). m/z (APCI-pos) M+1=496.2; $^1$H NMR (400 MHz, CDCl$_3$) δ 9.19 (s, 1H), 9.04 (br s, 1H), 8.65 (s, 1H), 7.85 (s, 1H), 7.83 (d, J=2.6 Hz, 1H), 7.65 (dd, J=8.7, 2.8 Hz, 1H), 7.35-7.31 (m, 2H), 7.05 (dd, J=8.7, 2.3 Hz, 1H), 6.90 (d, J=8.7 Hz, 1H), 4.24 (s, 2H), 3.85 (s, 3H), 2.35 (s, 3H), 1.54 (s, 6H).

Example 33

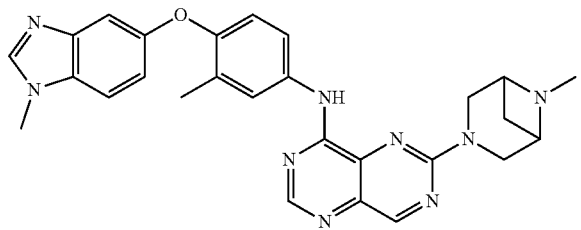 [SMILES: Cc1cc(Nc2ncnc3cnc(N4CC5CC(C4)N5C)nc23)ccc1Oc1ccc2c(c1)ncn2C]

N-(3-methyl-4-((1-methyl-1H-benzo[d]imidazol-5-yl)oxy)phenyl)-6-(6-methyl-3,6-diazabicyclo[3.1.1]heptan-3-yl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) in 1,4-dioxane (1.1 mL) was treated with 3-methyl-3,6-diazabicyclo[3.1.1]heptane, bis(trifluoroacetic acid) (0.046 g, 0.14 mmol) and N,N-diisopropylethylamine (0.042 g, 0.32 mmol) and heated to 100° C. for 4 hours. The mixture was concentrated in vacuo and purified using reverse phase column chromatography (5-95% water in MeCN with 0.1% TFA buffer), which provided N-(3-methyl-4-((1-methyl-1H-benzo[d]imidazol-5-yl)oxy)phenyl)-6-(6-methyl-3,6-diazabicyclo[3.1.1]heptan-3-yl)pyrimido[5,4-d]pyrimidin-4-amine (0.007 g, 24% yield). m/z (APCI-pos) M+1=494.3; $^1$H NMR (400 MHz, CDCl$_3$) δ 9.06 (s, 1H), 8.56 (s, 1H), 8.52 (br s, 1H), 7.85 (s, 1H), 7.72 (d, J=2.5 Hz, 1H), 7.63 (dd, J=8.7, 2.7 Hz, 1H), 7.35-7.30 (m, 2H), 7.06 (dd, J=8.7, 2.4 Hz, 1H), 6.93 (d, J=8.7 Hz, 1H), 4.59 (d, J=6.0 Hz, 1H), 3.85 (s, 3H), 3.19 (br s, 2H), 2.96 (d, J=10.5 Hz, 2H), 2.67 (q, J=7.0 Hz, 1H), 2.35 (s, 3H), 2.27 (s, 3H), 2.07 (d, J=7.8 Hz, 1H).

Example 34

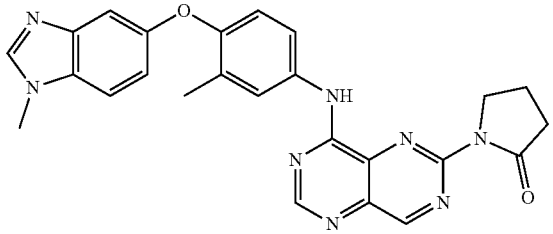 [SMILES: Cc1cc(Nc2ncnc3cnc(N4CCCC4=O)nc23)ccc1Oc1ccc2c(c1)ncn2C]

1-(8-((3-methyl-4-((1-methyl-1H-benzo[d]imidazol-5-yl)oxy)phenyl)amino)pyrimido[5,4-d]pyrimidin-2-yl)pyrrolidin-2-one A solution of N-(3-methyl-4-((1-methyl-1H-benzo[d]imidazol-5-yl)oxy)phenyl)-6-(methylsulfonyl)pyrimido[5,4-d]pyrimidin-4-amine (0.015 g, 0.032 mmol) in THF (0.62 mL) was treated with sodium hydride, 60% dispersion in mineral oil (0.004 g, 0.11 mmol) and 2-pyrrolidinone (0.008 g, 0.09 mmol) and heated to 60° C. for 1 hour. The mixture was diluted with DCM and washed with ammonium chloride (saturated, aq., 1×), water (1×), and brine (1×). The organic phase was dried over anhydrous sodium sulfate, filtered, and concentrated in vacuo. Purification by regular phase column chromatography (5-40% MeOH/CHCl$_3$) provided 1-(8-((3-methyl-4-((1-methyl-1H-benzo[d]imidazol-5-yl)oxy)phenyl)amino)pyrimido[5,4-d]pyrimidin-2-yl)pyrrolidin-2-one (0.006 g, 40% yield). m/z (APCI-pos) M+1=467.2; $^1$H NMR (400 MHz, CDCl$_3$) δ 9.36 (s, 1H), 8.86 (br s, 1H), 8.73 (s, 1H), 7.86 (s, 1H), 7.74 (d, J=2.3 Hz, 1H), 7.69 (dd, J=8.7, 2.6 Hz, 1H), 7.36-7.31 (m, 2H), 7.06 (dd, J=8.8, 2.1, 1H), 6.91 (d, J=8.6 Hz, 1H), 4.24 (t, J=7.0 Hz, 2H), 3.85 (s, 3H), 2.77 (t, J=8.0 Hz, 2H), 2.35 (s, 3H), 2.24 (quint, J=7.5 Hz, 2H).

Example 35

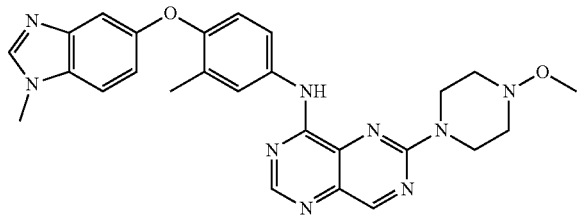 [SMILES: CON1CCN(c2ncc3ncnc(Nc4ccc(Oc5ccc6c(c5)ncn6C)c(C)c4)c3n2)CC1]

6-(4-methoxypiperazin-1-yl)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) in DMA (1.10 mL) was treated with 1-methoxypiperazine (0.016 g, 0.14 mmol) heated to 60° C. for 2 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by normal phase chromatography (1-7% MeOH in CHCl$_3$) provided 6-(4-methoxypiperazin-1-yl)-N-(3-methyl-4-((1-methyl-1H-benzo[d]imidazol-5-yl)oxy)phenyl)pyrimido[5,4-d]pyrimidin-4-amine (0.028 g, 98% yield). m/z (APCI-pos) M$^+$1=498.3; $^1$H NMR (400 MHz, CDCl$_3$) δ 9.04 (s, 1H), 8.54 (s, 1H), 8.48 (br s, 1H), 7.85 (s, 1H), 7.74 (d, J=2.6 Hz, 1H), 7.64 (dd, J=8.7, 2.7 Hz, 1H), 7.35-7.30 (m, 2H), 7.06 (dd, J=8.7, 2.2 Hz, 1H), 6.93 (d, J=8.6 Hz, 1H), 4.74 (d, J=11.5 Hz, 2H), 3.85 (s, 3H), 3.62 (s, 3H), 3.39 (br s, 4H), 2.67 (br s, 2H), 2.35 (s, 3H).

Example 36

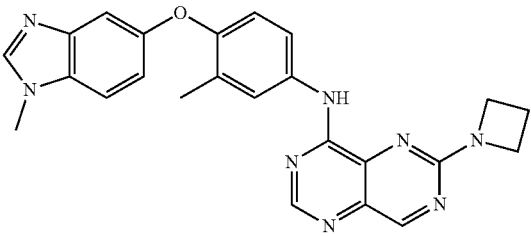 [SMILES: Cc1cc(Nc2ncnc3cnc(N4CCC4)nc23)ccc1Oc1ccc2c(c1)ncn2C]

6-(azetidin-1-yl)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.044 mmol) in DMA (0.90 mL) was treated with azetidine (0.013 g, 0.22 mmol) and heated to 60° C. for 8 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by regular phase chromatography (1-8% MeOH/CHCl$_3$) provided 6-(azetidin-1-yl)-N-(3-methyl-4-((1-methyl-1H-benzo[d]imidazol-5-yl)oxy)phenyl)pyrimido[5,4-d]pyrimidin-4-amine (0.012 g, 56% yield). m/z (APCI-pos) M$^+$1=439.2; $^1$H NMR (400 MHz, CDCl$_3$) δ 9.04 (s, 1H), 8.56 (br s, 1H), 8.53 (s, 1H), 7.85 (s, 1H), 7.74 (d, J=2.6 Hz, 1H), 7.65 (dd, J=8.7, 2.7 Hz, 1H), 7.35-7.30 (m, 2H), 7.06 (dd, J=8.7, 2.4 Hz, 1H), 6.93 (d, J=8.7 Hz, 1H), 4.31 (t, J=7.5 Hz, 4H), 3.85 (s, 3H), 2.48 (quint, J=7.6 Hz, 2H), 2.34 (s, 3H).

Example 37

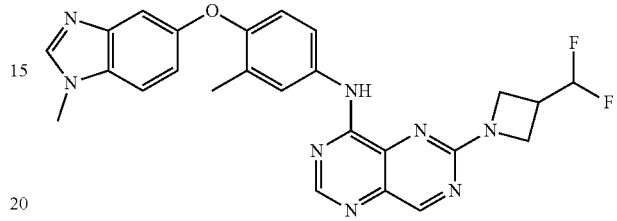

6-(3-(difluoromethyl)azetidin-1-yl)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.044 mmol) in DMA (0.90 mL) was treated with 3-(difluoromethyl)azetidine HCl (0.014 g, 0.14 mmol) and N,N-diisopropylethylamine (0.029 g, 0.22 mmol) heated to 60° C. for 8 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by regular phase chromatography (1-8% MeOH/CHCl$_3$) provided 6-(azetidin-1-yl)-N-(3-methyl-4-((1-methyl-1H-benzo[d]imidazol-5-yl)oxy)phenyl)pyrimido[5,4-d]pyrimidin-4-amine (0.012 g, 56% yield). m/z (APCI-pos) M$^+$1=489.2; $^1$H NMR (400 MHz, CDCl$_3$) δ 9.07 (s, 1H), 8.57 (s, 1H), 8.54 (br s, 1H), 7.85 (s, 1H), 7.74 (d, J=2.6 Hz, 1H), 7.64 (dd, J=8.6, 2.6 Hz, 1H), 7.35-7.30 (m, 2H), 7.06 (dd, J=8.7, 2.4 Hz, 1H), 6.93 (d, J=8.7 Hz, 1H), 6.10 (td, J=56.1, 4.3 Hz, 1H), 4.40 (t, J=9.2 Hz, 2H), 4.32-4.26 (m, 2H), 3.85 (s, 3H), 3.24 (m, 1H), 2.35 (s, 3H).

Example 38

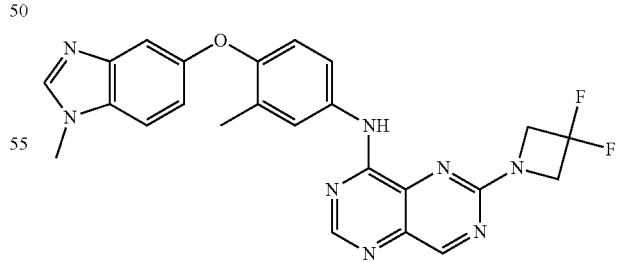

6-(3,3-difluoroazetidin-1-yl)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]

pyrimidin-4-amine (0.020 g, 0.044 mmol) in DMA (0.90 mL) was treated with 3,3-difluoroazetidine hydrochloride (0.017 g, 0.14 mmol) and N,N-diisopropylethylamine (0.029 g, 0.22 mmol) heated to 60° C. for 2 hours. The mixture was diluted with EtOAc and washed with sodium bicarbonate (saturated, aq., 1×), water (1×), and brine (2×). The organic phase was dried over anhydrous sodium sulfate, filtered, and concentrated in vacuo. Purification by regular phase chromatography (2-7% MeOH/CHCl$_3$) provided 6-(3,3-difluoroazetidin-1-yl)-N-(3-methyl-4-((1-methyl-1H-benzo[d]imidazol-5-yl)oxy)phenyl)pyrimido[5,4-d]pyrimidin-4-amine (0.021 g, 90% yield). m/z (APCI-pos) M$^+$1=475.2; $^1$H NMR (400 MHz, CDCl$_3$) δ 9.11 (s, 1H), 8.61 (s, 1H), 8.51 (br s, 1H), 7.85 (s, 1H), 7.74 (d, J=2.6 Hz, 1H), 7.64 (dd, J=8.6, 2.6 Hz, 1H), 7.35-7.30 (m, 2H), 7.06 (dd, J=8.7, 2.4 Hz, 1H), 6.93 (d, J=8.7 Hz, 1H), 4.63 (t, J=12.0 Hz, 4H), 3.85 (s, 3H), 2.35 (s, 3H).

Example 39

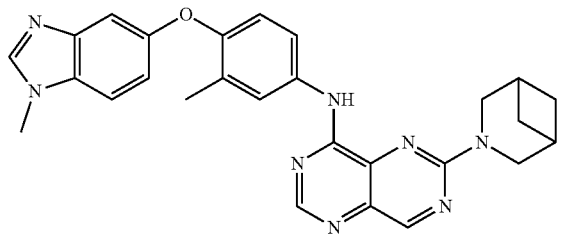 [SMILES: Cc1cc(Nc2ncnc3cnc(N4CC5CC(C5)C4)nc23)ccc1Oc1ccc2c(c1)ncn2C]

6-(3-azabicyclo[3.1.1]heptan-3-yl)-N-(3-methyl-4-((1-methyl-1H-benzo[d]imidazol-5-yl)oxy)phenyl)pyrimido[5,4-d]pyrimidin-4-amine Step A: 6-Chloropyrimido[5,4-d]pyrimidin-4-ol (0.6 g, 3.3 mmol), phosphoryl trichloride (32.9 mL, 3.29 mmol), pentachloro-l5-phosphane (3.4 g, 16 mmol), and N-ethyl-N-isopropylpropan-2-amine (1.14 mL, 6.6 mmol) were charged to a 125 mL round bottom flask equipped with a stir bar and fitted with a cold water condenser. The mixture was heated to 130° C. with stirring overnight. Volatiles were removed in vacuo, and the crude material was constituted in ethyl acetate (450 mL) and washed with saturated aqueous sodium bicarbonate (225 mL). Organics were dried over Na$_2$SO$_4$, concentrated in vacuo, and purified by column chromatography (Redisep 40 g, 0 to 40% ethyl acetate/hexanes) to furnish 2,8-dichloropyrimido[5,4-d]pyrimidine (0.33 g, 50% yield) as a solid.

Step B: 2,8-Dichloropyrimido[5,4-d]pyrimidine (0.33 g, 1.63 mmol) and 3-methyl-4-((1-methyl-1H-benzo[d]imidazol-5-yl)oxy)aniline (0.45 g, 1.8 mmol) were charged to a 50 mL round bottom flask. Propan-2-ol (16.3 mL, 1.63 mmol) was added, and the mixture was stirred for 10 minutes at room temperature. The mixture was dry loaded onto silica gel and then purified by column chromatography (Redisep 40 g, 0 to 4% MeOH/DCM with 2% NH$_4$OH) to furnish 6-chloro-N-(3-methyl-4-((1-methyl-1H-benzo[d]imidazol-5-yl)oxy)phenyl)pyrimido[5,4-d]pyrimidin-4-amine (0.560 g, 82%) as a powder. m/z (APCI-pos) M$^+$1=418.1.

Step C: N-Ethyl-N-isopropylpropan-2-amine (0.0313 mL, 0.179 mmol), 3-azabicyclo[3.1.1]heptane hydrochloride (0.0144 g, 0.108 mmol), 6-chloro-N-(3-methyl-4-((1-methyl-1H-benzo[d]imidazol-5-yl)oxy)phenyl)pyrimido[5,4-d]pyrimidin-4-amine (0.0150 g, 0.0359 mmol), and DMA (0.179 mL, 0.0359 mmol) were charged to a dram vial equipped with a stir bar. The mixture was heated to 75° C. for 1 hour. The mixture was diluted with ethyl acetate and washed with brine (5×). Organics were dried over Na$_2$SO$_4$, concentrated in vacuo, and purified by column chromatography (Redisep 4 g, 0 to 8% MeOH/DCM with 2% NH$_4$OH) to furnish 6-(3-azabicyclo[3.1.1]heptan-3-yl)-N-(3-methyl-4-((1-methyl-1H-benzo[d]imidazol-5-yl)oxy)phenyl)pyrimido[5,4-d]pyrimidin-4-amine (7.0 mg, 41% yield) as a solid. m/z (APCI-pos) M$^+$1=479.3; $^1$H NMR (400 MHz, CDCl$_3$) δ 9.11 (s, 1H), 8.64 (s, 1H), 8.54 (s, 1H), 7.84 (s, 1H), 7.75 (d, J=2.6 Hz, 1H), 7.66 (dd, J=8.7, 2.8 Hz, 1H), 7.33 (d, J=6.4 Hz, 1H), 7.31 (s, 1H), 7.05 (dd, J=8.7, 2.3 Hz, 1H), 6.93 (d, J=8.7 Hz, 1H), 3.95 (d, J=15.2 Hz, 3H), 3.84 (s, 3H), 2.68 (q, J=6.4 Hz, 2H), 2.34 (s, 3H), 2.33-2.24 (m, 1H), 1.73 (s, 2H), 1.55-1.47 (m, 2H).

Example 40

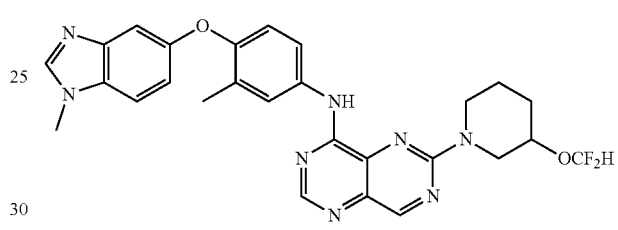

6-(3-(difluoromethoxy)piperidin-1-yl)-N-(3-methyl-4-((1-methyl-1H-benzo[d]imidazol-5-yl)oxy)phenyl)pyrimido[5,4-d]pyrimidin-4-amine N-Ethyl-N-isopropylpropan-2-amine (0.0125 mL, 0.0718 mmol), racemic 3-(difluoromethoxy)piperidine (0.0271 g, 0.179 mmol), 6-chloro-N-(3-methyl-4-((1-methyl-1H-benzo[d]imidazol-5-yl)oxy)phenyl)pyrimido[5,4-d]pyrimidin-4-amine (0.0150 g, 0.0359 mmol), and DMA (0.179 mL, 0.0359 mmol) were charged to a dram vial equipped with a stir bar. The temperature was elevated to 75° C. for 1 hour with stirring. The mixture was diluted with ethyl acetate and washed with brine (5×). Organics were dried over Na$_2$SO$_4$, concentrated in vacuo, and purified by column chromatography (Redisep 4 g, 0 to 8% MeOH/DCM with 2% NH$_4$OH). The material was further purified by reverse-phase preparatory HPLC (5-95% ACN/water with 0.1% TFA over 20 minutes). Product containing fractions were diluted with 2M aqueous K$_2$CO$_3$ and ethyl acetate. The organic layer was washed with ethyl acetate (3×), and the organics were combined, dried over Na$_2$SO$_4$, and concentrated in vacuo to furnish racemic 6-(3-(difluoromethoxy)piperidin-1-yl)-N-(3-methyl-4-((1-methyl-1H-benzo[d]imidazol-5-yl)oxy)phenyl)pyrimido[5,4-d]pyrimidin-4-amine (8.0 mg, 42% yield) as a solid. m/z (APCI-pos) M$^+$1=533.2; $^1$H NMR (400 MHz, CDCl$_3$) δ 9.05 (d, J=0.6 Hz, 1H), 8.56 (s, 1H), 8.54 (s, 1H), 8.04 (s, 1H), 7.77 (d, J=2.6 Hz, 1H), 7.65 (dd, J=8.7, 2.7 Hz, 1H), 7.35 (d, J=8.8 Hz, 1H), 7.29 (d, J=2.3 Hz, 1H), 7.09 (dd, J=8.8, 2.3 Hz, 1H), 6.94 (d, J=8.7 Hz, 1H), 6.41 (t, J=74.5 Hz, 1H), 4.48-4.35 (m, 2H), 4.21 (d, J=12.5 Hz, 1H), 3.87 (s, 3H), 3.77 (dd, J=12.8, 7.3 Hz, 1H), 3.74-3.63 (m, 1H), 2.32 (s, 3H), 1.99-1.79 (m, 1H), 1.66 (td, J=9.1, 4.5 Hz, 1H), 1.27-1.23 (m, 1H), 0.90-0.80 (m, 1H).

Example 41

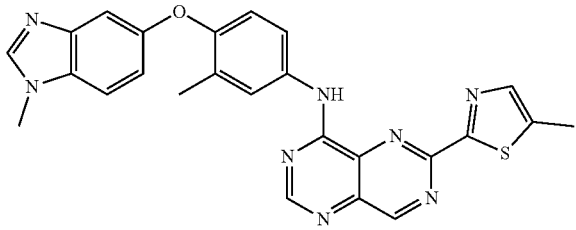 [SMILES: Cc1cnc(-c2ncc3ncnc(Nc4ccc(Oc5ccc6c(c5)ncn6C)c(C)c4)c3n2)s1]

N-(3-methyl-4-((1-methyl-1H-benzo[d]imidazol-5-yl)oxy)phenyl)-6-(5-methylthiazol-2-yl)pyrimido[5,4-d]pyrimidin-4-amine 6-Chloro-N-(3-methyl-4-((1-methyl-1H-benzo[d]imidazol-5-yl)oxy)phenyl)pyrido[3,2-d]pyrimidin-4-amine (0.020 g, 0.048 mmol), 5-methyl-2-(tributylstannyl)thiazole (0.037 g, 0.096 mmol), copper (I) iodide (0.0023 g, 0.012 mmol), palladium tetrakis (0.014 g, 0.012 mmol), and toluene (0.48 mL, 0.048 mmol) were charged to a 10 mL glass microwave vessel equipped with a stir bar. The mixture was sparged with argon, sealed, and heated to 110° C. overnight. The material was dry loaded onto silica gel and purified by column chromatography (Redisep 12 g, 0 to 8% MeOH/DCM with 2% NH$_4$OH). The material was purified again by column chromatography (Redisep 4 g, 0 to 8% MeOH/DCM with 2% NH$_4$OH) to furnish N-(3-methyl-4-((1-methyl-1H-benzo[d]imidazol-5-yl)oxy)phenyl)-6-(5-methylthiazol-2-yl)pyrimido[5,4-d]pyrimidin-4-amine (9.0 mg, 39% yield). m/z (APCI-pos) M$^+$1=481.1; $^1$H NMR (400 MHz, CDCl$_3$) δ 9.47 (s, 1H), 9.39 (s, 1H), 8.78 (s, 1H), 7.85 (s, 1H), 7.80 (d, J=2.7 Hz, 1H), 7.74 (d, J=1.3 Hz, 1H), 7.69 (dd, J=8.7, 2.7 Hz, 1H), 7.37-7.30 (m, 2H), 7.06 (dd, J=8.8, 2.2 Hz, 1H), 6.88 (d, J=8.7 Hz, 1H), 3.84 (s, 3H), 2.60 (s, 3H), 2.34 (s, 3H).

Example 42

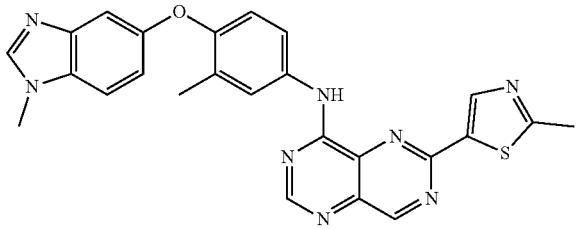 [SMILES: Cc1ncc(-c2ncc3ncnc(Nc4ccc(Oc5ccc6c(c5)ncn6C)c(C)c4)c3n2)s1]

N-(3-methyl-4-((1-methyl-1H-benzo[d]imidazol-5-yl)oxy)phenyl)-6-(2-methylthiazol-5-yl)pyrimido[5,4-d]pyrimidin-4-amine 6-Chloro-N-(3-methyl-4-((1-methyl-1H-benzo[d]imidazol-5-yl)oxy)phenyl)pyrimido[5,4-d]pyrimidin-4-amine (0.010 g, 0.024 mmol), 2-methyl-5-(4,4,5,5-tetramethyl-1,3,2-dioxaborolan-2-yl)thiazole (0.011 g, 0.048 mmol), 2M aqueous K$_2$CO$_3$ (0.036 mL, 0.072 mmol), palladium tetrakis (0.0055 g, 0.0048 mmol), and dioxane (0.24 mL, 0.024 mmol) were charged to a 10 mL glass microwave vessel equipped with a stir bar. The mixture was sparged with argon, sealed, and heated to 100° C. overnight. The mixture was cooled to room temperature and diluted with water and ethyl acetate. The aqueous layer was extracted with ethyl acetate (3×). The organics were combined, dried over Na$_2$SO$_4$, concentrated in vacuo, and purified by column chromatography (Redisep 12 g, 0 to 8% MeOH/DCM with 2% NH$_4$OH) to furnish N-(3-methyl-4-((1-methyl-1H-benzo[d]imidazol-5-yl)oxy)phenyl)-6-(2-methylthiazol-5-yl)pyrimido[5,4-d]pyrimidin-4-amine (10.0 mg, 8.7% yield) as a solid. m/z (APCI-pos) M$^+$1=481.2; $^1$H NMR (400 MHz, CDCl$_3$) δ 9.37 (s, 1H), 8.82 (s, 1H), 8.78 (s, 1H), 8.60 (s, 1H), 8.22 (s, 1H), 7.80 (d, J=2.7 Hz, 1H), 7.72 (dd, J=8.7, 2.7 Hz, 1H), 7.40 (d, J=8.8 Hz, 1H), 7.33 (d, J=2.3 Hz, 1H), 7.15 (dd, J=8.8, 2.2 Hz, 1H), 6.97 (d, J=8.7 Hz, 1H), 3.93 (s, 3H), 2.82 (s, 3H), 2.36 (s, 3H).

Example 43

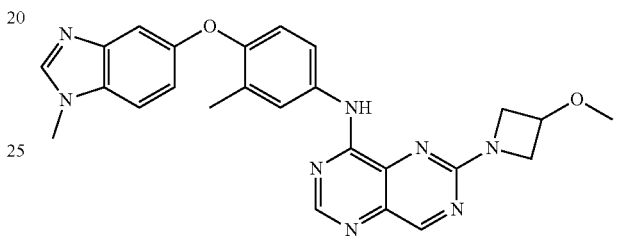

6-(3-methoxyazetidin-1-yl)-N-(3-methyl-4-((1-methyl-1H-benzo[d]imidazol-5-yl)oxy)phenyl)pyrimido[5,4-d]pyrimidin-4-amine N-Ethyl-N-isopropylpropan-2-amine (0.0094 mL, 0.054 mmol), 3-methoxyazetidine (0.0047 g, 0.054 mmol), 6-chloro-N-(3-methyl-4-((1-methyl-1H-benzo[d]imidazol-5-yl)oxy)phenyl)pyrimido[5,4-d]pyrimidin-4-amine (0.0150 g, 0.0359 mmol), and dioxane (0.179 mL, 0.0359 mmol) were charged to a dram vial equipped with a stir bar. The mixture was heated to 60° C. for 3 hours, and then the temperature was elevated to 75° C. overnight with stirring. The mixture was dry loaded onto silica gel and purified by column chromatography (Redisep 4 g, 0 to 6% MeOH/DCM with 2% NH$_4$OH) to furnish 6-(3-methoxyazetidin-1-yl)-N-(3-methyl-4-((1-methyl-1H-benzo[d]imidazol-5-yl)oxy)phenyl)pyrimido[5,4-d]pyrimidin-4-amine (1.5 mg, 8.9% yield) as a solid. m/z (APCI-pos) M$^+$1=469.2; $^1$H NMR (400 MHz, CDCl$_3$) δ 9.05 (s, 1H), 8.55 (s, 1H), 8.54 (s, 1H), 7.85 (s, 1H), 7.74 (d, J=2.7 Hz, 1H), 7.65 (dd, J=8.7, 2.8 Hz, 1H), 7.36-7.29 (m, 2H), 7.06 (dd, J=8.6, 2.4 Hz, 1H), 6.93 (d, J=8.7 Hz, 1H), 4.50-4.36 (m, 3H), 4.21-4.13 (m, 2H), 3.85 (s, 3H), 3.40 (s, 3H), 2.35 (s, 3H).

Example 44

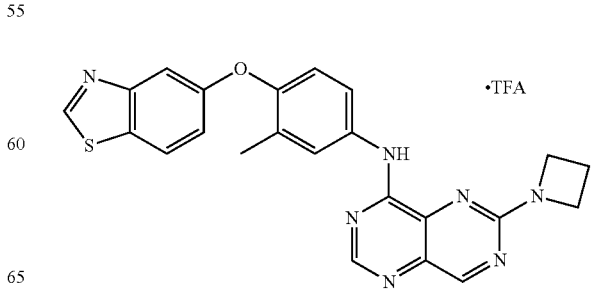

6-(azetidin-1-yl)-N-(4-(benzo[d]thiazol-5-yloxy)-3-methylphenyl)pyrimido[5,4-d]pyrimidin-4-amine 2,2,2-trifluoroacetate N-(4-(Benzo[d]thiazol-5-yloxy)-3-methylphenyl)-6-(methylsulfonyl)pyrimido[5,4-d]pyrimidin-4-amine (0.020 g, 0.043 mmol), THF (0.43 mL, 0.043 mmol), and azetidine (0.0580 mL, 0.86 mmol) were charged to a 10 mL glass microwave vessel equipped with a stir bar. Volatiles were removed in vacuo, and the crude material was purified by reverse-phase preparatory HPLC (5-95% ACN/water with 0.1% TFA). Product containing fractions were frozen and lyophilized overnight to furnish 6-(azetidin-1-yl)-N-(4-(benzo[d]thiazol-5-yloxy)-3-methylphenyl)pyrimido[5,4-d]pyrimidin-4-amine 2,2,2-trifluoroacetate (2.5 mg, 11% yield). m/z (APCI-pos) M$^+$1=442.2; $^1$H NMR (400 MHz, CD$_3$OD) δ 9.25 (s, 1H), 8.99 (s, 1H), 8.53 (s, 1H), 8.05 (d, J=8.8 Hz, 1H), 7.83 (d, J=2.6 Hz, 1H), 7.75 (dd, J=8.8, 2.6 Hz, 1H), 7.47 (d, J=2.3 Hz, 1H), 7.25 (dd, J=8.8, 2.4 Hz, 1H), 7.06 (d, J=8.7 Hz, 1H), 4.36 (t, J=7.6 Hz, 4H), 2.50 (p, J=7.7 Hz, 2H), 2.31 (s, 3H).

Example 45

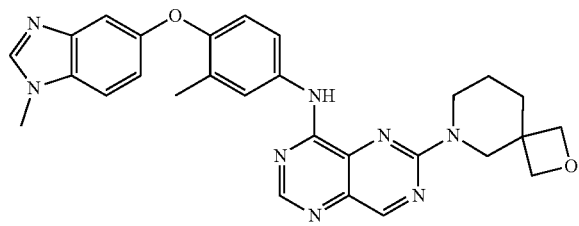 [SMILES: Cc1cc(Nc2ncnc3cnc(N4CCCC5(COC5)C4)nc23)ccc1Oc1ccc2c(c1)ncn2C]

N-(3-methyl-4-((1-methyl-1H-benzo[d]imidazol-5-yl)oxy)phenyl)-6-(2-oxa-6-azaspiro[3.5]nonan-6-yl)pyrimido[5,4-d]pyrimidin-4-amine N-Ethyl-N-isopropylpropan-2-amine (0.0125 mL, 0.0718 mmol), 2-oxa-6-azaspiro[3.5]nonane (0.0228 g, 0.179 mmol), 6-chloro-N-(3-methyl-4-((1-methyl-1H-benzo[d]imidazol-5-yl)oxy)phenyl)pyrimido[5,4-d]pyrimidin-4-amine (0.0150 g, 0.0359 mmol), and DMA (0.179 mL, 0.0359 mmol) were charged to a dram vial equipped with a stir bar. The temperature was elevated to 75° C. for 2 hours with stirring. The mixture was diluted with ethyl acetate and washed with brine (5×). Organics were dried over Na$_2$SO$_4$, concentrated in vacuo, and purified by reverse-phase preparatory HPLC (5-95% ACN/water with 0.1% TFA over 20 minutes). Product containing fractions were diluted with 2M aqueous K$_2$CO$_3$ and ethyl acetate. The organic layer was washed with ethyl acetate (3×). The organics were combined, dried over Na$_2$SO$_4$, and concentrated in vacuo to furnish N-(3-methyl-4-((1-methyl-1H-benzo[d]imidazol-5-yl)oxy)phenyl)-6-(2-oxa-6-azaspiro[3.5]nonan-6-yl)pyrimido[5,4-d]pyrimidin-4-amine (4.4 mg, 24% yield) as a solid. m/z (APCI-pos) M$^+$1=509.3; $^1$H NMR (400 MHz, CD$_3$OD) δ 8.96 (s, 1H), 8.33 (s, 1H), 8.09 (s, 1H), 7.79 (d, J=2.7 Hz, 1H), 7.70 (dd, J=8.7, 2.7 Hz, 1H), 7.53 (d, J=8.8 Hz, 1H), 7.12 (d, J=2.3 Hz, 1H), 7.07 (dd, J=8.8, 2.3 Hz, 1H), 6.89 (d, J=8.7 Hz, 1H), 4.51-4.41 (m, 4H), 4.29 (s, 2H), 3.95 (t, J=5.6 Hz, 2H), 3.89 (s, 3H), 2.30 (s, 3H), 1.98 (d, J=6.0 Hz, 2H), 1.68-1.63 (m, 2H).

Example 46

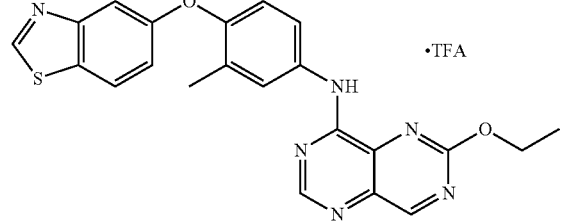

N-(4-(benzo[d]thiazol-5-yloxy)-3-methylphenyl)-6-ethoxypyrimido[5,4-d]pyrimidin-4-amine 2,2,2-trifluoroacetate N-(4-(Benzo[d]thiazol-5-yloxy)-3-methylphenyl)-6-(methylsulfonyl)pyrimido[5,4-d]pyrimidin-4-amine (0.010 g, 0.0215 mmol), sodium ethanolate (0.0209 g, 0.0646 mmol), and ethanol (0.215 mL, 0.0215 mmol) were charged to a dram vial equipped with a stir bar. The mixture was heated to 40° C. for 3 hours and then dry loaded onto silica gel and purified by column chromatography (Redisep 12 g, 0 to 10% MeOH/DCM with 2% NH$_4$OH). Material was further purified by reverse-phase preparatory HPLC (ACN/water 5-95% with 0.1% TFA over 15 minutes). Product containing fractions were frozen and lyophilized to furnish N-(4-(benzo[d]thiazol-5-yloxy)-3-methylphenyl)-6-ethoxypyrimido[5,4-d]pyrimidin-4-amine 2,2,2-trifluoroacetate (1.7 mg, 15% yield) as a solid. m/z (APCI-pos) M$^+$1=431.1; $^1$H NMR (400 MHz, MeOD) δ 9.15 (s, 1H), 9.14 (s, 1H), 8.54 (s, 1H), 7.95 (d, J=8.8 Hz, 1H), 7.77 (d, J=2.7 Hz, 1H), 7.69 (dd, J=8.6, 2.7 Hz, 1H), 7.37 (d, J=2.4 Hz, 1H), 7.15 (dd, J=8.8, 2.4 Hz, 1H), 6.97 (d, J=8.7 Hz, 1H), 4.60 (q, J=7.1 Hz, 2H), 2.21 (s, 3H), 1.42 (t, J=7.1 Hz, 3H).

Example 47

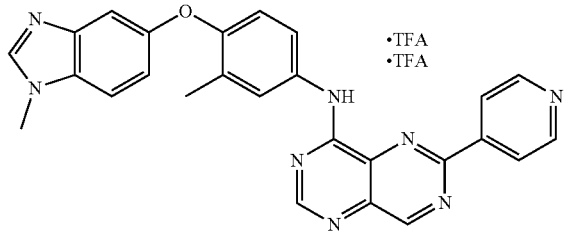 [SMILES: Cc1cc(Nc2ncnc3cnc(-c4ccncc4)nc23)ccc1Oc1ccc2c(c1)ncn2C]

N-(3-methyl-4-((1-methyl-1H-benzo[d]imidazol-5-yl)oxy)phenyl)-6-(pyridin-4-yl)pyrimido[5,4-d]pyrimidin-4-amine bis(2,2,2-trifluoroacetate)

6-Chloro-N-(3-methyl-4-((1-methyl-1H-benzo[d]imidazol-5-yl)oxy)phenyl)pyrimido[5,4-d]pyrimidin-4-amine (0.010 g, 0.024 mmol), 4-(4,4,5,5-tetramethyl-1,3,2-dioxaborolan-2-yl)pyridine (0.0098 g, 0.048 mmol), 2M aqueous K$_2$CO$_3$ (0.036 mL, 0.072 mmol), palladium tetrakis (0.0055 g, 0.0048 mmol), and dioxane (0.24 mL, 0.024 mmol) were charged to a 10 mL glass microwave vessel equipped with a stir bar. The mixture was sparged with argon, sealed, and heated to 100° C. for 60 hours. The mixture was dry loaded onto silica gel and purified by column chromatography (Redisep 12 g, 0 to 10% MeOH/DCM with 2% NH$_4$OH). The material was further purified by reverse-phase preparatory HPLC (5-95% ACN/water with 0.1% TFA over 20 minutes). Product containing fractions were lyophilized overnight to furnish N-(3-methyl-4-((1-methyl-1H-benzo[d]imidazol-5-yl)oxy)phenyl)-6-(pyridin-4-yl)pyrimido[5,4-d]pyrimidin-4-amine bis(2,2,2-trifluoroacetate) (2.0 mg, 12% yield) as a solid. m/z (APCI-pos) M$^+$1=461.2; $^1$H NMR (400 MHz, (CD$_3$)$_2$SO) δ 10.58 (s, 1H), 9.63 (s, 1H), 9.31 (s, 1H), 8.96-8.89 (m, 2H), 8.84-8.77 (m, 2H), 7.99-7.93 (m, 2H), 7.91 (dd, J=8.7, 2.7 Hz, 1H), 7.34 (dd, J=9.0, 2.3 Hz, 1H), 7.21 (d, J=2.3 Hz, 1H), 7.11 (d, J=8.7 Hz, 1H), 4.04 (s, 3H), 2.26 (s, 3H).

Example 48

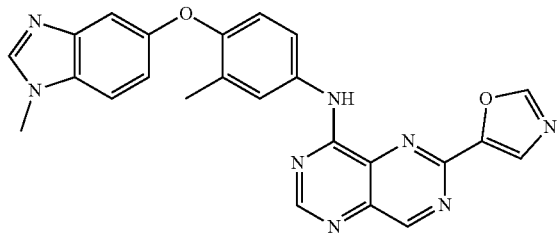 [SMILES: Cc1cc(Nc2ncnc3cnc(-c4cnco4)nc23)ccc1Oc1ccc2c(c1)ncn2C]

N-(3-methyl-4-((1-methyl-1H-benzo[d]imidazol-5-yl)oxy)phenyl)-6-(oxazol-5-yl)pyrimido[5,4-d]pyrimidin-4-amine 6-Chloro-N-(3-methyl-4-((1-methyl-1H-benzo[d]imidazol-5-yl)oxy)phenyl)pyrimido[5,4-d]pyrimidin-4-amine (0.015 g, 0.036 mmol), 5-(4,4,5,5-tetramethyl-1,3,2-dioxaborolan-2-yl)oxazole (0.014 g, 0.072 mmol), 2M aqueous K$_2$CO$_3$ (0.054 mL, 0.110 mmol), palladium tetrakis (0.0083 g, 0.0072 mmol), and toluene (0.36 mL, 0.036 mmol) were charged to a 10 mL glass microwave vessel equipped with a stir bar. The mixture was sparged with argon, sealed, and heated to 100° C. overnight. The mixture was cooled to room temperature and diluted with water and ethyl acetate. The aqueous layer was extracted with ethyl acetate (3×). The organics were combined, dried over Na$_2$SO$_4$, concentrated in vacuo, and purified by column chromatography (Redisep 12 g, 0 to 8% MeOH/DCM with 2% NH$_4$OH) to furnish N-(3-methyl-4-((1-methyl-1H-benzo[d]imidazol-5-yl)oxy)phenyl)-6-(oxazol-5-yl)pyrimido[5,4-d]pyrimidin-4-amine (6.0 mg, 37% yield) as a solid. m/z (APCI-pos) M$^+$1=451.2; $^1$H NMR (400 MHz, CDCl$_3$) δ 9.43 (s, 1H), 8.94 (s, 1H), 8.81 (s, 1H), 8.14 (s, 1H), 8.08 (s, 1H), 7.90 (s, 1H), 7.80 (d, J=2.7 Hz, 1H), 7.69 (dd, J=8.7, 2.7 Hz, 1H), 7.39-7.29 (m, 2H), 7.09 (dd, J=8.7, 2.3 Hz, 1H), 6.94 (d, J=8.7 Hz, 1H), 3.87 (s, 3H), 2.38 (s, 3H).

Example 49

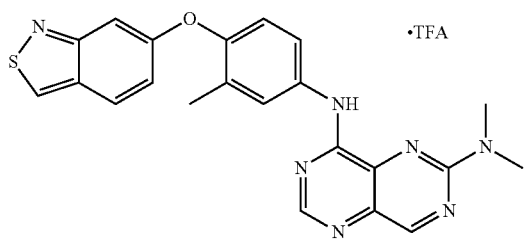 [SMILES: Cc1cc(Nc2ncnc3cnc(N(C)C)nc23)ccc1Oc1ccc2csnc2c1]

N8-(4-(benzo[c]isothiazol-6-yloxy)-3-methylphenyl)-N2,N2-dimethylpyrimido[5,4-d]pyrimidine-2,8-diamine 2,2,2-trifluoroacetate Step A: 8-Chloro-2-(methylthio)pyrimido[5,4-d]pyrimidine (0.25 g, 1.18 mmol) and cesium hydroxide hydrate (0.395 g, 2.35 mmol) were charged to a 25 mL round bottom flask equipped with a stir bar. Water (0.106 mL, 5.88 mmol) was dripped into the mixture with stirring. After 5 minutes, the mixture was dry loaded onto silica gel and purified by column chromatography (Redisep 24 g, 0 to 8% MeOH/DCM with 2% NH$_4$OH) to furnish 6-(methylthio)pyrimido[5,4-d]pyrimidin-4-ol (116 mg, 51% yield) as a solid. m/z (APCI-pos) M$^+$1=195.1.

Step B: 6-(Methylthio)pyrimido[5,4-d]pyrimidin-4-ol (0.116 g, 0.597 mmol) was diluted with dichloromethane (2.99 mL, 0.597 mmol) in a 10 mL round bottom flask equipped with a stir bar. 3-Chlorobenzoperoxoic acid (77% weight, 3-chlorobenzoic acid and water remaining mass; 0.327 g, 1.34 mmol) was added, and the mixture was stirred for 3 hours at room temperature. The mixture was filtered, and the filtrate was washed with ethyl acetate to furnish a mixture of 6-(methylsulfonyl)pyrimido[5,4-d]pyrimidin-4-ol (27 mg, 20% yield) and 6-(methylsulfinyl)pyrimido[5,4-d]pyrimidin-4-ol (68 mg, 54% yield) as a solid. The crude was carried on.

Step C: 6-(Methylsulfonyl)pyrimido[5,4-d]pyrimidin-4-ol (0.040 g, 0.177 mmol), dimethylamine (0.884 mL, 1.77 mmol), acetonitrile (0.442 mL, 0.177 mmol), and THF (0.442 mL, 0.177 mmol) were charged to a 10 mL glass microwave vessel equipped with a stir bar. The vessel was sealed and heated to 70° C. for 2 hours. Volatiles were removed in vacuo, and the mixture was dry loaded and purified by column chromatography (Redisep 12 g, 0 to 10% MeOH/DCM with 2% NH$_4$OH) to furnish 6-(dimethylamino)pyrimido[5,4-d]pyrimidin-4-ol (0.0225 g, 67% yield). m/z (APCI-pos) M$^+$1=192.2.

Step D: 6-(Dimethylamino)pyrimido[5,4-d]pyrimidin-4-ol (0.024 g, 0.13 mmol) was diluted with phosphoryl trichloride (1.3 mL, 0.13 mmol) in a 10 mL round bottom flask. The flask was fitted with a cold water condenser and heated to 100° C. for 3.5 hours with stirring. Volatiles were removed in vacuo, and the mixture was constituted in ethyl acetate and washed with 10% aqueous NaHCO$_3$ (2×). Organics were dried over Na$_2$SO$_4$ and concentrated in vacuo to furnish 8-chloro-N,N-dimethylpyrimido[5,4-d]pyrimidin-2-amine (30 mg, quantitative yield). m/z (APCI-pos) M$^+$1=210.1.

Step E: 8-Chloro-N,N-dimethylpyrimido[5,4-d]pyrimidin-2-amine (0.0093 g, 0.044 mmol), 4-(benzo[c]isothiazol-6-yloxy)-3-methylaniline (0.011 g, 0.044 mmol), and propan-2-ol (0.44 mL, 0.044 mmol) were charged to a dram vial equipped with a stir bar. The mixture was heated to 70° C. for 2 hours with stirring and then concentrated in vacuo and purified by reverse-phase preparatory HPLC (5-95% ACN/water with 0.1% TFA). Product containing fractions were frozen and lyophilized overnight to furnish N8-(4-(benzo[c]isothiazol-6-yloxy)-3-methylphenyl)-N2,N2-dimethylpyrimido[5,4-d]pyrimidine-2,8-diamine 2,2,2-trifluoroacetate (4.0 mg, 17% yield) as a powder. m/z (APCI-pos) M$^+$1=430.1; $^1$H NMR (400 MHz, (CD$_3$)$_2$SO) δ 10.02 (s, 1H), 9.74 (d, J=1.0 Hz, 1H), 9.11 (s, 1H), 8.53 (s, 1H), 7.96 (d, J=9.2 Hz, 1H), 7.89 (d, J=7.9 Hz, 2H), 7.24-7.16 (m, 2H), 6.77-6.72 (m, 1H), 3.35 (s, 6H), 2.22 (s, 3H).

Example 50

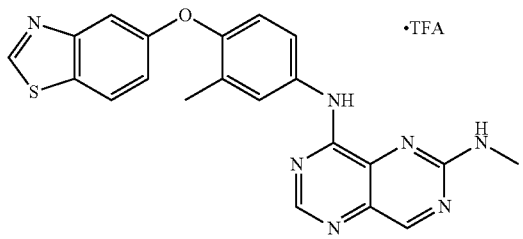 [SMILES: CNc1ncc2ncnc(Nc3ccc(Oc4ccc5scnc5c4)c(C)c3)c2n1]

N8-(4-(benzo[d]thiazol-5-yloxy)-3-methylphenyl)-N2-methylpyrimido[5,4-d]pyrimidine-2,8-diamine 2,2,2-trifluoroacetate Methanamine (0.323 mL, 0.646 mmol), N-(4-(benzo[d]thiazol-5-yloxy)-3-methylphenyl)-6-(methylsulfonyl)pyrimido[5,4-d]pyrimidin-4-amine (0.010 g, 0.0215 mmol), and THF (0.215 mL, 0.0215 mmol) were charged to a 10 mL glass microwave vessel equipped with a stir bar. The mixture was sparged with argon, sealed, and heated to 100° C. overnight. The mixture was dry loaded onto silica gel and then purified by column chromatography (Redisep 4 g, 0 to 100% ethyl acetate/hexanes). Material was further purified by reverse-phase preparatory LCMS (5-95% ACN/water with 0.1% TFA). Product containing fractions were frozen and lyophilized overnight to furnish N8-(4-(benzo[d]thiazol-5-yloxy)-3-methylphenyl)-N2-methylpyrimido[5,4-d]pyrimidine-2,8-diamine 2,2,2-trifluoroacetate (1.5 mg, 13% yield). m/z (APCI-pos) M$^+$1=416.1; $^1$H NMR (400 MHz, MeOD) δ 9.16 (s, 1H), 8.88 (s, 1H), 8.45 (s, 1H), 7.96 (d, J=8.8 Hz, 1H), 7.75 (d, J=2.8 Hz, 1H), 7.66 (dd, J=8.7, 2.8 Hz, 1H), 7.38 (d, J=2.4 Hz, 1H), 7.16 (dd, J=8.8, 2.4 Hz, 1H), 6.98 (d, J=8.7 Hz, 1H), 3.05 (s, 3H), 2.23 (s, 3H).

Example 51

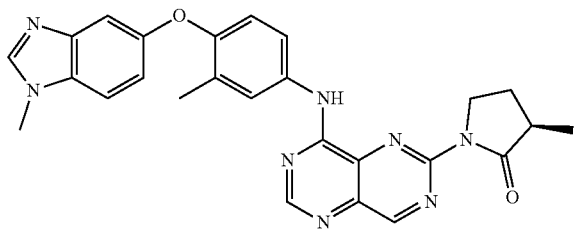 [SMILES: Cc1cc(Nc2ncnc3cnc(N4CC[C@@H](C)C4=O)nc23)ccc1Oc1ccc2c(c1)ncn2C]

(R)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-2-one XantPhos (0.0062 g, 0.011 mmol), 6-chloro-N-(3-methyl-4-((1-methyl-1H-benzo[d]imidazol-5-yl)oxy)phenyl)pyrimido[5,4-d]pyrimidin-4-amine (0.030 g, 0.072 mmol), Pd$_2$(dba)$_3$ (0.0099 g, 0.011 mmol), (R)-3-methylpyrrolidin-2-one (0.021 g, 0.22 mmol), cesium carbonate (0.070 g, 0.22 mmol) and dioxane (0.72 mL, 0.072 mmol) were charged to a 10 mL glass microwave vessel equipped with a stir bar. The vessel was sparged with argon and then sealed and heated to 75° C. overnight. The mixture was dry loaded onto silica gel and purified by column chromatography (Redisep 4 g, 0 to 8% MeOH/DCM with 2% NH$_4$OH), impurities were seen by NMR. The material was further purified by reverse-phase preparatory HPLC (5-95% ACN/water with 0.1% TFA over 20 minutes). The product containing fraction was diluted with ethyl acetate and 2M K$_2$CO$_3$. The aqueous layer was extracted with ethyl acetate (3×). The organics were combined, dried over Na$_2$SO$_4$, and concentrated in vacuo to furnish (R)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-2-one (3.0 mg, 8.7% yield) as a solid. m/z (APCI-pos) M$^+$1=481.2; $^1$H NMR (400 MHz, CDCl$_3$) δ 9.34 (s, 1H), 8.89 (s, 1H), 8.72 (s, 1H), 7.85 (s, 1H), 7.74 (d, J=2.6 Hz, 1H), 7.69 (dd, J=8.7, 2.8 Hz, 1H), 7.36-7.30 (m, 2H), 7.05 (dd, J=8.8, 2.2 Hz, 1H), 6.91 (d, J=8.6 Hz, 1H), 4.27 (ddd, J=11.2, 8.6, 2.8 Hz, 1H), 4.04 (ddd, J=10.9, 9.1, 7.1 Hz, 1H), 3.85 (s, 3H), 2.87-2.78 (m, 1H), 2.43 (s, 1H), 2.35 (s, 3H), 2.00 (s, 3H), 1.89-1.80 (m, 1H), 1.38 (d, J=7.1 Hz, 3H).

Example 52

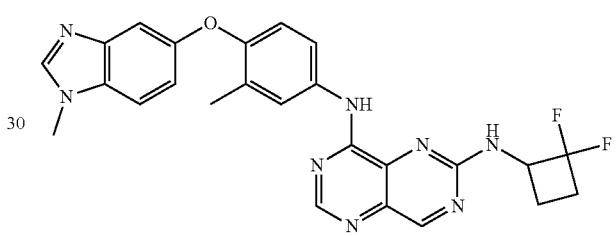

N2-(2,2-difluorocyclobutyl)-N8-(3-methyl-4-((1-methyl-1H-benzo[d]imidazol-5-yl)oxy)phenyl)pyrimido[5,4-d]pyrimidine-2,8-diamine N-Ethyl-N-isopropylpropan-2-amine (0.0208 mL, 0.120 mmol), 2,2-difluorocyclobutan-1-amine hydrochloride (0.0103 g, 0.0718 mmol), 6-chloro-N-(3-methyl-4-((1-methyl-1H-benzo[d]imidazol-5-yl)oxy)phenyl)pyrimido[5,4-d]pyrimidin-4-amine (0.010 g, 0.0239 mmol), and DMA (0.120 mL, 0.0239 mmol) were charged to a dram vial and stirred at 65° C. overnight. The mixture was diluted with ethyl acetate and washed with brine (5×). Organics were dried, concentrated, and purified by column chromatography (Redisep 4 g, 0 to 8% MeOH/DCM with 2% NH$_4$OH). The material was further purified by reverse-phase preparatory HPLC (5-95% ACN/water with 0.1% TFA over 15 minutes). Product containing fractions were pooled and diluted with ethyl acetate and 2M K$_2$CO$_3$. The aqueous layer was extracted with EtOAc (3×). The organics were combined, dried over Na$_2$SO$_4$, and concentrated in vacuo to furnish N2-(2,2-difluorocyclobutyl)-N8-(3-methyl-4-((1-methyl-1H-benzo[d]imidazol-5-yl)oxy)phenyl)pyrimido[5,4-d]pyrimidine-2,8-diamine (4.0 g, 0.00819 mmol, 34% yield) as a solid. m/z (APCI-pos) M$^+$1=489.2; $^1$H NMR (400 MHz, CDCl$_3$) δ 9.12 (s, 1H), 8.59 (s, 1H), 7.94 (s, 1H), 7.77-7.71 (m, 1H), 7.64 (dd, J=8.7, 2.8 Hz, 1H), 7.34 (d, J=8.7 Hz, 1H), 7.31 (d, J=2.2 Hz, 1H), 7.08 (dd, J=8.8, 2.2 Hz, 1H), 6.93 (d, J=8.7 Hz, 1H), 3.96-3.84 (m, 4H), 2.34 (s, 3H), 1.29-0.73 (m, 4H).

Example 53

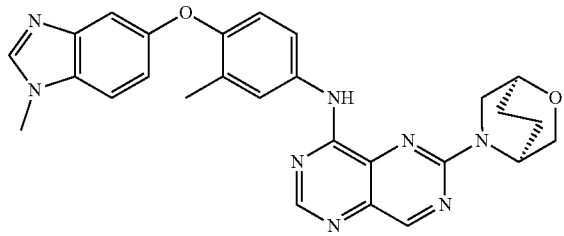 [SMILES: Cc1cc(Nc2ncnc3cnc(N4C[C@@H]5CC[C@H]4CO5)nc23)ccc1Oc1ccc2c(c1)ncn2C]

6-((1S,4S)-2-oxa-5-azabicyclo[2.2.2]octan-5-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and (1S,4S)-2-oxa-5-azabicyclo[2.2.2]octane hydrochloride (0.029 g, 0.195 mmol) was suspended in DMSO (0.500 mL). Then N,N-diisopropylethylamine (0.068 mL, 0.390 mmol) was added, and the mixture was heated to 80° C. for 2 hours. Upon cooling to ambient temperature, the solution was diluted with H$_2$O (2 mL). The resulting solid was isolated by vacuum filtration and then dissolved in CH$_2$Cl$_2$. The filtrate was then dried over anhydrous sodium sulfate, filtered, and concentrated. The crude product was purified via column chromatography (1-4% MeOH/CH$_2$Cl$_2$) to afford 6-((1S,4S)-2-oxa-5-azabicyclo[2.2.2]octan-5-yl)-N-(3-methyl-4-((1-methyl-1H-benzo[d]imidazol-5-yl)oxy)phenyl)pyrimido[5,4-d]pyrimidin-4-amine (0.027 g, 81%) as a solid. m/z (APCI-pos) M$^+$1=495.2; $^1$H NMR (400 MHz, CDCl$_3$) δ 9.12-9.00 (m, 1H), 8.57-8.44 (obs m, 1H), 8.54 (s, 1H), 7.85 (s, 1H), 7.74 (d, J=2.7 Hz, 1H), 7.65 (dd, J=8.7, 2.7 Hz, 1H), 7.37-7.29 (m, 2H), 7.06 (dd, J=8.7, 2.3 Hz, 1H), 6.93 (d, J=8.7 Hz, 1H), 4.99-4.83 (m, 1H), 4.30-4.06 (m, 4H), 3.85 (s, 3H), 3.81 (m, 1H), 2.35 (s, 3H), 2.33-2.24 (m, 1H), 2.19-2.00 (m, 2H), 1.88-1.76 (m, 1H).

Example 54

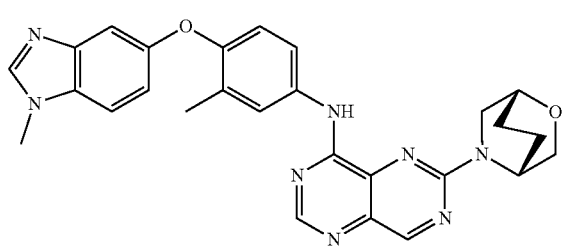 [SMILES: Cc1cc(Nc2ncnc3cnc(N4C[C@H]5CC[C@@H]4CO5)nc23)ccc1Oc1ccc2c(c1)ncn2C]

6-((1R,4R)-2-oxa-5-azabicyclo[2.2.2]octan-5-yl)-N-(3-methyl-4-((1-methyl-1H-benzo[d]imidazol-5-yl)oxy)phenyl)pyrimido[5,4-d]pyrimidin-4-amine 6-((1R,4R)-2-Oxa-5-azabicyclo[2.2.2]octan-5-yl)-N-(3-methyl-4-((1-methyl-1H-benzo[d]imidazol-5-yl)oxy)phenyl)pyrimido[5,4-d]pyrimidin-4-amine (0.164 g, 72%) was prepared in a manner similar to Example 53 replacing and (1S,4S)-2-oxa-5-azabicyclo[2.2.2]octane hydrochloride with (1R,4R)-2-oxa-5-azabicyclo[2.2.2]octane hydrochloride. m/z (APCI-pos) M$^+$1=495.2; $^1$H NMR (400 MHz, CDCl$_3$) δ 9.12-9.00 (m, 1H), 8.57-8.44 (obs m, 1H), 8.54 (s, 1H), 7.85 (s, 1H), 7.74 (d, J=2.7 Hz, 1H), 7.65 (dd, J=8.7, 2.7 Hz, 1H), 7.37-7.29 (m, 2H), 7.06 (dd, J=8.7, 2.3 Hz, 1H), 6.93 (d, J=8.7 Hz, 1H), 4.99-4.83 (m, 1H), 4.30-4.06 (m, 4H), 3.85 (s, 3H), 3.81 (m, 1H), 2.35 (s, 3H), 2.33-2.24 (m, 1H), 2.19-2.00 (m, 2H), 1.88-1.76 (m, 1H).

Example 55

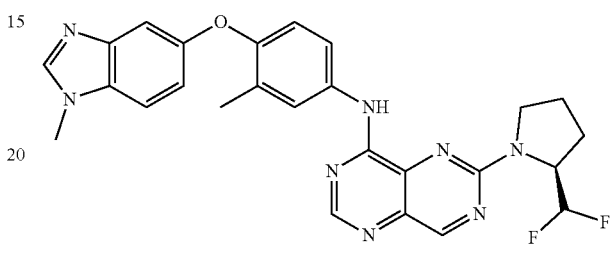

(S)-6-(2-(difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) and (2S)-2-(difluoromethyl)pyrrolidine hydrochloride (0.034 g, 0.217 mmol) was suspended in DMSO (1.0 mL). Then triethylamine (0.060 mL, 0.433 mmol) was added, and the mixture was heated to 80° C. for 8 hours. Upon cooling to ambient temperature, the solution was diluted with H$_2$O (2 mL). The resulting solid was isolated by vacuum filtration and then dissolved in CH$_2$Cl$_2$. The filtrate was dried over anhydrous sodium sulfate, filtered, and concentrated. The crude product was purified via column chromatography (1-4% MeOH/CH$_2$Cl$_2$) to afford (S)-6-(2-(difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine (0.009 g, 30%) as a solid. m/z (APCI-pos) M$^+$1=503.2; $^1$H NMR (400 MHz, CDCl$_3$) δ 9.08 (s, 1H), 8.57 (s, 1H), 8.57-8.52 (m, 1H), 7.85 (s, 1H), 7.73 (s, 1H), 7.63 (dd, J=8.7, 2.7 Hz, 1H), 7.36-7.29 (m, 2H), 7.05 (dd, J=8.8, 2.3 Hz, 1H), 6.93 (d, J=8.7 Hz, 1H), 6.32 (t, J=56.7 Hz, 1H), 4.58 (d, J=25.8 Hz, 1H), 3.87-3.82 (obs m, 1H), 3.85 (s, 3H), 3.80-3.73 (m, 1H), 2.46-2.38 (m, 1H), 2.35 (s, 3H), 2.29-2.04 (m, 3H).

Example 56

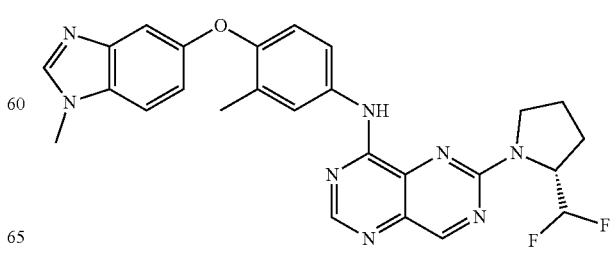

(R)-6-(2-(difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine (R)-6-(2-(Difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine (0.006 g, 21%) was prepared in a manner similar to Example 55 replacing (2S)-2-(difluoromethyl)pyrrolidine hydrochloride with (2R)-2-(difluoromethyl)pyrrolidine hydrochloride. m/z (APCI-pos) M+1=503.2; $^1$H NMR (400 MHz, CDCl$_3$) δ 9.08 (s, 1H), 8.57 (s, 1H), 8.57-8.52 (m, 1H), 7.85 (s, 1H), 7.73 (s, 1H), 7.63 (dd, J=8.7, 2.7 Hz, 1H), 7.36-7.29 (m, 2H), 7.05 (dd, J=8.8, 2.3 Hz, 1H), 6.93 (d, J=8.7 Hz, 1H), 6.32 (t, J=56.7 Hz, 1H), 4.58 (d, J=25.8 Hz, 1H), 3.87-3.82 (obs m, 1H), 3.85 (s, 3H), 3.80-3.73 (m, 1H), 2.46-2.38 (m, 1H), 2.35 (s, 3H), 2.29-2.04 (m, 3H).

Example 57

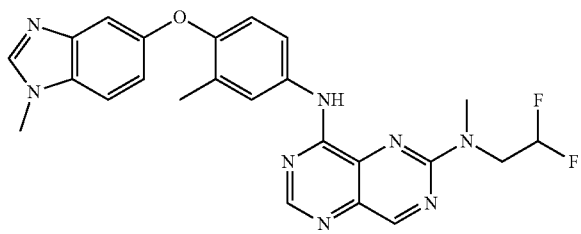

N2-(2,2-difluoroethyl)-N2-methyl-N8-(3-methyl-4-((1-methyl-1H-benzo[d]imidazol-5-yl)oxy)phenyl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and (2,2-difluoroethyl)-methyl-amine hydrochloride (0.034 g, 0.260 mmol) was suspended in DMSO (0.650 mL). Then N,N-diisopropylethylamine (0.090 mL, 0.520 mmol) was added, and the mixture was heated to 80° C. for 24 hours. Upon cooling to ambient temperature, the solution was diluted with H$_2$O (2 mL), and the resulting solid was isolated by vacuum filtration. The solid was then dissolved in CH$_2$Cl$_2$, and the filtrate was dried over anhydrous sodium sulfate, filtered, and concentrated. The crude product was then purified via column chromatography (1-4% MeOH/CH$_2$Cl$_2$) to afford N2-(2,2-difluoroethyl)-N2-methyl-N8-(3-methyl-4-((1-methyl-1H-benzo[d]imidazol-5-yl)oxy)phenyl)pyrimido[5,4-d]pyrimidine-2,8-diamine (0.007 g, 21%) as a solid. m/z (APCI-pos) M+1=477.2; $^1$H NMR (400 MHz, CDCl$_3$) δ 9.08 (s, 1H), 8.58 (s, 1H), 8.52 (s, 1H), 7.85 (s, 1H), 7.73 (d, J=2.7 Hz, 1H), 7.64 (dd, J=8.7, 2.7 Hz, 1H), 7.37-7.29 (m, 2H), 7.06 (dd, J=8.7, 2.3 Hz, 1H), 6.93 (d, J=8.7 Hz, 1H), 6.07 (t, J=56.2 Hz, 1H), 4.12 (td, J=13.8, 4.4 Hz, 2H), 3.85 (s, 3H), 3.42 (s, 3H), 2.35 (s, 3H).

Example 58

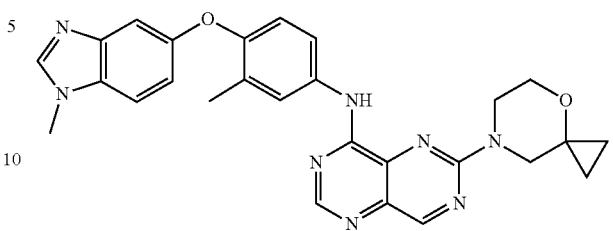

N-(3-methyl-4-((1-methyl-1H-benzo[d]imidazol-5-yl)oxy)phenyl)-6-(4-oxa-7-azaspiro[2.5]octan-7-yl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) and 4-oxa-7-azaspiro[2.5]octane hydrochloride (0.032 g, 0.217 mmol) was suspended in DMSO (0.542 mL). Triethylamine (0.060 mL, 0.433 mmol) was added, and the mixture was heated to 80° C. for 2 hours. Upon cooling to ambient temperature, the solution was diluted with H$_2$O (2 mL). The resulting solid was isolated by vacuum filtration and then dissolved in CH$_2$Cl$_2$. The filtrate was then dried over anhydrous sodium sulfate, filtered, and concentrated. The crude product was then purified via column chromatography (1-4% MeOH/CH$_2$Cl$_2$) to afford N-(3-methyl-4-((1-methyl-1H-benzo[d]imidazol-5-yl)oxy)phenyl)-6-(4-oxa-7-azaspiro[2.5]octan-7-yl)pyrimido[5,4-d]pyrimidin-4-amine (0.022 g, 79%) as a solid. m/z (APCI-pos) M+1=495.2; $^1$H NMR (400 MHz, CDCl$_3$) δ 9.04 (s, 1H), 8.54 (s, 1H), 8.44 (s, 1H), 7.85 (s, 1H), 7.74-7.69 (m, 1H), 7.63 (dd, J=8.6, 2.7 Hz, 1H), 7.35-7.30 (m, 2H), 7.06 (dd, J=8.7, 2.3 Hz, 1H), 6.93 (d, J=8.7 Hz, 1H), 4.09-4.01 (m, 2H), 3.97-3.90 (m, 4H), 3.85 (s, 3H), 2.35 (s, 3H), 0.93-0.84 (m, 2H), 0.74-0.66 (m, 2H).

Example 59

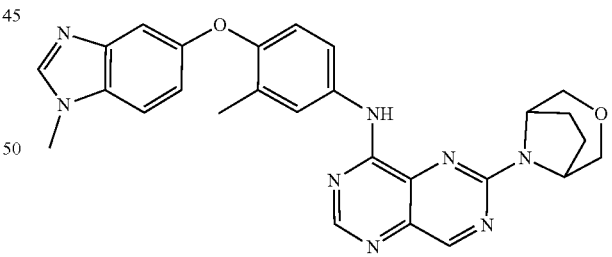

6-(3-oxa-8-azabicyclo[3.2.1]octan-8-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol) and (1R,5S)-3-oxa-8-azabicyclo[3.2.1]octane (0.031 g, 0.27 mmol) in DMA (0.54 mL) was heated to 60° C. for 5 hours.

Upon cooling to ambient temperature, the solution was diluted with 1:1 H$_2$O and NaHCO$_3$ (saturated, aqueous, 2 mL). The resulting solid was isolated by vacuum filtration and then dissolved in CH$_2$Cl$_2$. The filtrate was then dried over anhydrous sodium sulfate, filtered, and concentrated. The crude product was then purified via Prep LC RP chromatography (20 to 80% ACN/H$_2$O with 0.1% TFA buffer) to afford 6-(3-oxa-8-azabicyclo[3.2.1]octan-8-yl)-N-(3-methyl-4-((1-methyl-1H-benzo[d]imidazol-5-yl)oxy)phenyl)pyrimido[5,4-d]pyrimidin-4-amine (0.010 g, 34%) as a solid. m/z (APCI-pos) M$^+$1=495.2; $^1$H NMR (400 MHz, CDCl$_3$) δ 9.05 (s, 1H), 8.54 (s, 1H), 8.47 (s, 1H), 7.85 (s, 1H), 7.73 (d, J=2.7 Hz, 1H), 7.64 (dd, J=8.7, 2.7 Hz, 1H), 7.36-7.29 (m, 2H), 7.06 (dd, J=8.7, 2.2 Hz, 1H), 6.93 (d, J=8.7 Hz, 1H), 4.85 (s, 2H), 3.87-3.82 (obs m, 2H), 3.85 (s, 3H), 3.74 (d, J=10.9, 2H), 2.34 (s, 3H), 2.21-2.15 (m, 2H), 2.15-2.03 (m, 2H).

Example 60

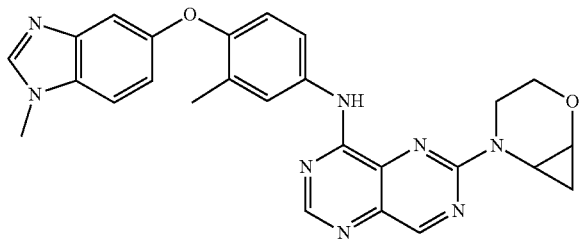 [SMILES: Cc1cc(Nc2ncnc3cnc(N4CCOC5CC54)nc23)ccc1Oc1ccc2c(c1)ncn2C]

6-(2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.400 g, 0.867 mmol) and 2-oxa-5-azabicyclo[4.1.0]heptane hydrochloride (0.470 g, 3.47 mmol) in DMSO (5.78 mL) was treated with N,N-diisopropylethylamine (1.21 mL, 6.93 mmol). The slurry was heated to 80° C. and stirred for 16 hours. Upon cooling to ambient temperature, the solution was poured into H$_2$O (40 mL). The resulting solid was isolated by vacuum filtration and then dissolved in CH$_2$Cl$_2$. The filtrate was dried over anhydrous sodium sulfate, filtered, and concentrated. The crude product was purified via column chromatography (1-5% MeOH/CH$_2$Cl$_2$) to afford 6-(2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine (0.230 g, 53%) as a solid. m/z (APCI-pos) M$^+$1=481.2; $^1$H NMR (400 MHz, CDCl$_3$) δ 9.16 (s, 1H), 8.60 (br s, 1H), 8.58 (s, 1H), 7.85 (s, 1H), 7.73 (d, J=2.7 Hz, 1H), 7.64 (dd, J=8.7, 2.7 Hz, 1H), 7.35-7.29 (m, 2H), 7.06 (dd, J=8.7, 2.3 Hz, 1H), 6.93 (d, J=8.7 Hz, 1H), 4.00-3.88 (m, 3H), 3.85 (s, 3H), 3.75-3.61 (m, 2H), 3.17 (m, 1H), 2.35 (s, 3H), 1.13 (q, J=6.9 Hz, 1H), 0.73 (dt, J=7.8, 4.3 Hz, 1H).

The mixture of enantiomers (0.205 g) was separated by SFC chiral separation (OJ-H (2×25 cm), 25% methanol, 0.2% DCM (0.1% DEA)/CO$_2$, 100 bar, 65 mL/min, 220 nm, inj vol.: 0.5 mL, 2 mg/mL, methanol:DCM) to afford Example 60a: 6-((1S,6R)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine (0.095 g) and Example 60b: 6-((1S,6R)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine (0.100 g).

Example 61

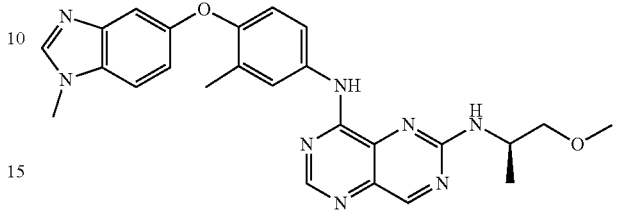

(R)—N2-(1-methoxypropan-2-yl)-N8-(3-methyl-4-((1-methyl-1H-benzo[d]imidazol-5-yl)oxy)phenyl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol), (R)-(−)-1-methoxy-2-propylamine (0.024 g, 0.27 mmol) and DMA (1.1 mL) was heated to 60° C. and stirred for 2 hours. Upon cooling to ambient temperature, the solution was diluted with 1:1 H$_2$O and NaHCO$_3$ (saturated, aqueous, 10 mL). The mixture was extracted with CH$_2$Cl$_2$ (3×10 mL), and the combined extracts were washed with brine. The organic phase was dried over anhydrous sodium sulfate, filtered, and concentrated to an oil. The crude product was then purified via column chromatography (1-6% MeOH/CHCl$_3$) to afford (R)—N2-(1-methoxypropan-2-yl)-N8-(3-methyl-1H-benzo[d]imidazol-5-yl)oxy)phenyl)pyrimido[5,4-d]pyrimidine-2,8-diamine as a solid (0.018 g, 68%). m/z (APCI-pos) M$^+$1=471.3; $^1$H NMR (400 MHz, CDCl$_3$) δ 9.01 (s, 1H), 8.54 (s, 2H), 7.85 (s, 1H), 7.74 (d, J=2.7 Hz, 1H), 7.63 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 5.67 (d, J=8.2 Hz, 1H), 4.41-4.35 (m, 1H), 3.85 (s, 3H), 3.54 (d, J=4.6 Hz, 2H), 3.43 (s, 3H), 2.35 (s, 3H), 1.37 (d, J=6.7 Hz, 3H).

Example 62

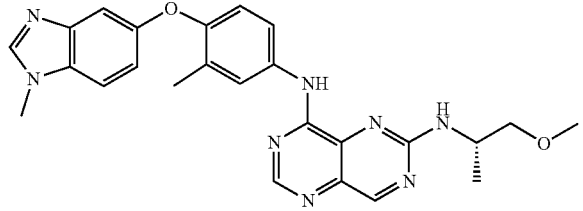 [SMILES: COC[C@H](C)Nc1ncc2ncnc(Nc3ccc(Oc4ccc5c(c4)ncn5C)c(C)c3)c2n1]

(S)—N2-(1-methoxypropan-2-yl)-N8-(3-methyl-4-((1-methyl-1H-benzo[d]imidazol-5-yl)oxy)phenyl)pyrimido[5,4-d]pyrimidine-2,8-diamine (S)—N2-(1-Methoxypropan-2-yl)-N8-(3-methyl-4-((1-methyl-1H-benzo[d]imidazol-5-yl)oxy)phenyl)pyrimido[5,4-d]pyrimidine-2,8-diamine (0.017 g, 65%) was prepared in a manner similar to Example 61 replacing (R)-(−)-1- methoxy-2-propylamine with (S)-(−)-1-methoxy-2-propylamine. m/z (APCI-pos) M+1=471.2; ¹H NMR (400 MHz, CDCl₃) δ 9.01 (s, 1H), 8.54 (s, 2H), 7.85 (s, 1H), 7.74 (d, J=2.7 Hz, 1H), 7.63 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 5.67 (d, J=8.2 Hz, 1H), 4.41-4.35 (m, 1H), 3.85 (s, 3H), 3.54 (d, J=4.6 Hz, 2H), 3.43 (s, 3H), 2.35 (s, 3H), 1.37 (d, J=6.7 Hz, 3H).

Example 63

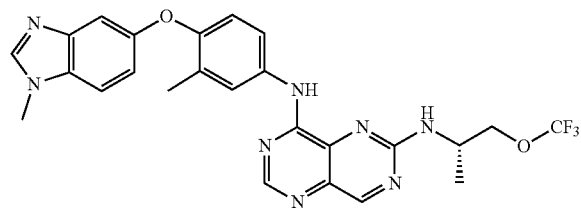 [SMILES: Cc1cc(Nc2ncnc3cnc(N[C@@H](C)COC(F)(F)F)nc23)ccc1Oc1ccc2c(c1)ncn2C]

(S)—N8-(3-methyl-4-((1-methyl-1H-benzo[d]imidazol-5-yl)oxy)phenyl)-N2-(1-(trifluoromethoxy)propan-2-yl)pyrimido[5,4-d]pyrimidine-2,8-diamine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), (S)-1-(trifluoromethoxy)propan-2-amine hydrochloride (0.058 g, 0.33 mmol) and DMA (1.1 mL) was treated with triethylamine (0.076 mL, 0.54 mmol), and the vial was capped and heated to 60° C. for 4 hours. At this point additional (S)-1-(trifluoromethoxy)propan-2-amine hydrochloride (0.058 g, 0.33 mmol) and triethylamine (0.076 mL, 0.54 mmol) were added, and the vial was heated for another 4 hours. Upon cooling to ambient temperature, the solution was diluted with 1:1 H₂O and NaHCO₃ (saturated, aqueous, 10 mL). The resulting solid was isolated by vacuum filtration. The solid was washed with water, dissolved in CH₂Cl₂, and then dried over Na₂SO₄, filtered and concentrated. The crude product was then purified via column chromatography (12 G Isco RediSep Gold, particle size: 20 to 40 microns, 30 mL/min, 1-6% MeOH/CHCl₃) to afford impure product as a solid (20 mg). The impure product was further purified via RP LC (5 to 80% ACN/H₂O with 0.5% TFA buffer). The fractions containing product were concentrated and then treated with saturated aqueous NaHCO₃. The mixture was extracted with CHCl₃ (3×). The combined organic layers were dried over Na₂SO₄, filtered and concentrated to afford (S)—N8-(3-methyl-4-((1-methyl-1H-benzo[d]imidazol-5-yl)oxy)phenyl)-N2-(1-(trifluoromethoxy)propan-2-yl)pyrimido[5,4-d]pyrimidine-2,8-diamine (0.007 g, 12%) as a solid (freebase). m/z (APCI-pos) M+1=525.2; ¹H NMR (400 MHz, CDCl₃) δ 9.04 (s, 1H), 8.58 (s, 1H), 8.50 (s, 1H), 7.85 (s, 1H), 7.74 (d, J=2.7 Hz, 1H), 7.62 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 5.48 (d, J=7.9 Hz, 1H), 4.50 (m, 1H), 4.22 (m, 1H), 4.05 (dd, J=9.8, 5.6 Hz, 1H), 3.85 (s, 3H), 2.35 (s, 3H), 1.46 (d, J=6.7 Hz, 3H).

Example 64

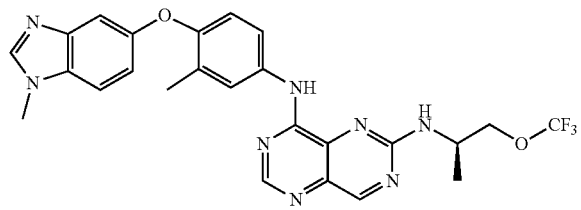 [SMILES: Cc1cc(Nc2ncnc3cnc(N[C@H](C)COC(F)(F)F)nc23)ccc1Oc1ccc2c(c1)ncn2C]

(R)—N8-(3-methyl-4-((1-methyl-1H-benzo[d]imidazol-5-yl)oxy)phenyl)-N2-(1-(trifluoromethoxy)propan-2-yl)pyrimido[5,4-d]pyrimidine-2,8-diamine (R)—N8-(3-methyl-4-((1-methyl-1H-benzo[d]imidazol-5-yl)oxy)phenyl)-N2-(1-(trifluoromethoxy)propan-2-yl)pyrimido[5,4-d]pyrimidine-2,8-diamine (0.003 g, 10%) was prepared in a manner similar to Example 63 replacing (S)-1-(trifluoromethoxy)propan-2-amine hydrochloride with (R)-1-(trifluoromethoxy)propan-2-amine hydrochloride. ¹H NMR (400 MHz, CDCl₃) δ 9.04 (s, 1H), 8.58 (s, 1H), 8.50 (s, 1H), 7.85 (s, 1H), 7.74 (d, J=2.7 Hz, 1H), 7.62 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 5.48 (d, J=7.9 Hz, 1H), 4.50 (m, 1H), 4.22 (m, 1H), 4.05 (dd, J=9.8, 5.6 Hz, 1H), 3.85 (s, 3H), 2.35 (s, 3H), 1.46 (d, J=6.7 Hz, 3H). m/z (APCI-pos) M+1=525.2.

Example 65

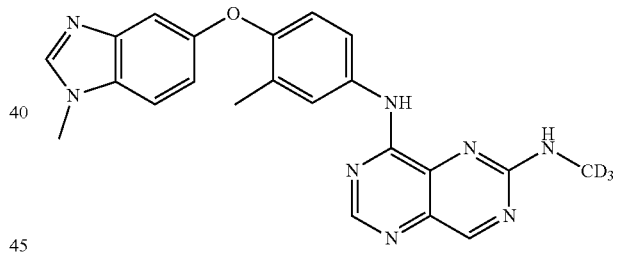

N2-(methyl-d3)-N8-(3-methyl-4-((1-methyl-1H-benzo[d]imidazol-5-yl)oxy)phenyl)pyrimido[5,4-d]pyrimidine-2,8-diamine A vial was cooled to −78° C. in a dry ice bath (open to the air), and methylamine-d3 (0.11 g, 3.3 mmol) was condensed into the vial from a lecture bottle. Then DMA (0.65 mL) was added, followed by N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol). The vial was then capped, and the mixture was warmed to 60° C. where it stirred for 1 hour. Upon cooling to ambient temperature, the solution was diluted with 1:1 H₂O and NaHCO₃ (saturated, aqueous, 2 mL). The resulting solid was isolated by vacuum filtration and then dissolved in IPA/CH₂Cl₂. The solution was then dried over anhydrous sodium sulfate, filtered, and concentrated. The crude product was then purified via column chromatography (1-5% MeOH/CHCl₃) to afford N2-(methyl-d3)-N8-(3-methyl-4-((1-methyl-1H-benzo[d]imidazol-5-yl)oxy)phenyl)pyrimido[5,4-d]pyrimidine-2,8-diamine (0.027 g, 99%) as a solid. m/z (APCI-pos) M+1=416.2; $^1$H NMR (400 MHz, CDCl$_3$) δ 9.01 (s, 1H), 8.61 (s, 1H), 8.56 (s, 1H), 7.85 (s, 1H), 7.76 (d, J=2.7 Hz, 1H), 7.65 (dd, J=8.7, 2.7 Hz, 1H), 7.37-7.30 (m, 2H), 7.06 (dd, J=8.7, 2.3 Hz, 1H), 6.93 (d, J=8.7 Hz, 1H), 5.48 (s, 1H), 3.85 (s, 3H), 2.35 (s, 3H).

Example 66

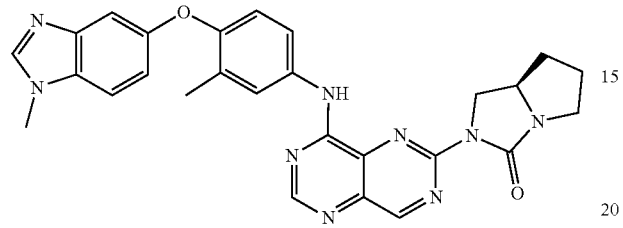

(R)-2-(8-((3-methyl-4-((1-methyl-1H-benzo[d]imidazol-5-yl)oxy)phenyl)amino)pyrimido[5,4-d]pyrimidin-2-yl)hexahydro-3H-pyrrolo[1,2-c]imidazol-3-one Step A: A mixture of 1-[(2R)-2-pyrrolidinyl]methanamine (0.200 g, 2.00 mmol) and N,N'-carbonyldiimidazole (0.324 g, 2.00 mmol) in CH$_2$Cl$_2$ (9.98 mL) was stirred at ambient temperature for 16 hours. The mixture was then concentrated and purified via column chromatography (2-10% MeOH/CH$_2$Cl$_2$) to afford (R)-hexahydro-3H-pyrrolo[1,2-c]imidazol-3-one (0.076 g, 30%) as a solid. m/z (APCI-pos) M+1=127.1

Step B: A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.020 g, 0.043 mmol), (R)-hexahydro-3H-pyrrolo[1,2-c]imidazol-3-one (0.022 g, 0.17 mmol) and DMA (0.870 mL) was treated with sodium tert-butoxide (0.017 g, 0.17 mmol). The mixture was heated to 80° C. where it stirred for 2 hours. Upon cooling to ambient temperature, the mixture was diluted with 1:1 H$_2$O and NaHCO$_3$ (saturated, aqueous, 10 mL). The mixture was extracted with CH$_2$Cl$_2$ (2×10 mL), and the combined extracts were washed with brine. The organic phase was dried over anhydrous sodium sulfate, filtered, and concentrated to an oil. The crude product was then purified via column chromatography (1-5% MeOH/CH$_2$Cl$_2$) to afford (R)-2-(8-((3-methyl-4-((1-methyl-1H-benzo[d]imidazol-5-yl)oxy)phenyl)amino)pyrimido[5,4-d]pyrimidin-2-yl)hexahydro-3H-pyrrolo[1,2-c]imidazol-3-one (0.006 g, 25%) as a solid. m/z (APCI-pos) M+1=508.2; $^1$H NMR (400 MHz, CDCl$_3$) δ 9.30 (s, 1H), 8.87 (s, 1H), 8.69 (s, 1H), 7.85 (s, 1H), 7.75 (d, J=2.7 Hz, 1H), 7.71 (dd, J=8.7, 2.7 Hz, 1H), 7.33 (dd, J=5.5, 3.0 Hz, 2H), 7.05 (dd, J=8.9, 2.1 Hz, 1H), 6.90 (d, J=8.6 Hz, 1H), 4.33 (dd, J=11.0, 8.6 Hz, 1H), 4.15 (dd, J=11.1, 3.8 Hz, 1H), 3.97-3.87 (m, 2H), 3.87-3.80 (m, 1H), 3.85 (s, 3H), 3.32-3.23 (m, 2H), 2.34 (s, 3H), 2.27-2.07 (m, 2H), 2.07-1.89 (m, 1H), 1.59-1.44 (m, 1H).

Example 67

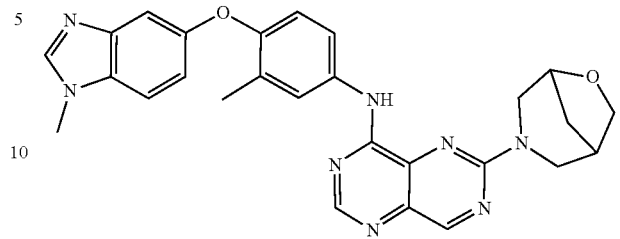

6-(6-oxa-3-azabicyclo[3.2.1]octan-3-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol), 6-oxa-3-azabicyclo[3.2.1]octane hydrochloride (0.032 g, 0.22 mmol) and DMSO (0.54 mL) was treated with triethylamine (0.060 mL, 0.43 mmol). The mixture was then heated to 80° C. for 2 hours. Upon cooling to ambient temperature, the solution was diluted with 1:1 H$_2$O and NaHCO$_3$ (saturated, aqueous, 2 mL). The resulting solid was isolated by vacuum filtration and then dissolved in CH$_2$Cl$_2$. The organic filtrate was then dried over anhydrous sodium sulfate, filtered, and concentrated. The crude product was then purified via column chromatography (1-4% MeOH/CH$_2$Cl$_2$) to afford 6-(6-oxa-3-azabicyclo[3.2.1]octan-3-yl)-N-(3-methyl-4-((1-methyl-1H-benzo[d]imidazol-5-yl)oxy)phenyl)pyrimido[5,4-d]pyrimidin-4-amine (0.020 g, 72%) as a solid. m/z (APCI-pos) M+1=495.3; $^1$H NMR (400 MHz, CDCl$_3$) δ 9.06 (s, 1H), 8.54 (s, 2H), 7.85 (s, 1H), 7.74 (d, J=2.7 Hz, 1H), 7.65 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 4.62-4.46 (m, 3H), 3.98-3.88 (m, 2H), 3.85 (s, 3H), 3.39-3.34 (m, 1H), 3.20-3.09 (m, 1H), 2.72 (s, 1H), 2.35 (s, 3H), 2.15-2.08 (m, 1H), 1.94 (d, J=11.3 Hz, 1H).

Example 68

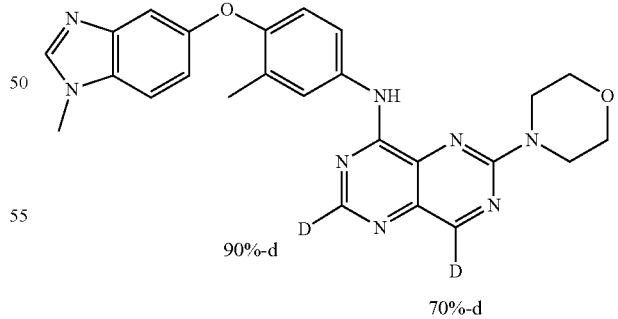

N-(3-methyl-4-((1-methyl-1H-benzo[d]imidazol-5-yl)oxy)phenyl)-6-morpholinopyrimido[5,4-d]pyrimidin-2,8-d2-4-amine Step A: 5-Amino-2-(methylthio)-4-pyrimidinecarboxylic acid (1.07 g, 5.78 mmol), which was suspended in neat formamide-d3 (3.85 mL), was added to a heavy walled pressure vial. The vial was capped, and the mixture was heated to 150° C. in a heating block. The mixture was stirred for 2 hours and then at 170° C. for 2 hours. The mixture was cooled to ambient temperature and poured into water (10 mL). The mixture was sonicated. The mixture was then chilled to 0° C. in an ice bath where it sat for 15 minutes. The resulting solid was then isolated by vacuum filtration, washed with H$_2$O and then dried in vacuo overnight to afford 6-(methylthio)pyrimido[5,4-d]pyrimidin-4(3H)-one-2,8-d2 (0.640 g, 56%) as a solid. m/z (APCI-pos) M$^+$1=197.0.

Step B: 6-(Methylthio)pyrimido[5,4-d]pyrimidin-4(3H)-one-2,8-d2 (0.300 g, 1.54 mmol), which was suspended in thionyl chloride (5.58 mL, 76.84 mmol) along with DMF (0.012 mL) was added to a 10 mL round bottom flask. The flask was fitted with a reflux condenser, and the mixture was then heated to 75° C. in an oil bath where the mixture stirred for 3 hours. The system was then cooled to ambient temperature, and the mixture was concentrated in vacuo. CH$_2$Cl$_2$ was added, and the mixture was carefully washed with cold saturated aqueous NaHCO$_3$. The aqueous phase was back extracted with CHCl$_3$. The combined organic layers were dried over Na$_2$SO$_4$, filtered and concentrated to afford crude 8-chloro-2-(methylthio)pyrimido[5,4-d]pyrimidine-4,6-d2 (0.140 g, 42%) as a solid that was used directly in the subsequent step.

Step C: 3-Methyl-4-((1-methyl-1H-benzo[d]imidazol-5-yl)oxy)aniline (0.165 g, 0.652 mmol) was added to a solution of 8-chloro-2-(methylthio)pyrimido[5,4-d]pyrimidine-4,6-d2 (0.140 g, 0.652 mmol) in IPA (6.52 mL). The mixture was heated to 50° C. After 1 hour, the reaction mixture was cooled to ambient temperature, diluted with a saturated aqueous NaHCO$_3$ solution, and then extracted with CHCl$_3$ (3×10 mL). The combined organic layers were then dried over anhydrous sodium sulfate, filtered, and concentrated. The crude product was then purified via column chromatography (1-4% MeOH/CHCl$_3$) to afford N-(3-methyl-4-((1-methyl-1H-benzo[d]imidazol-5-yl)oxy)phenyl)-6-(methylthio)pyrimido[5,4-d]pyrimidin-2,8-d2-4-amine (0.215 g, 76%) as a solid. m/z (APCI-pos) M$^+$1=432.2.

Step D: A solution of potassium peroxymonosulfate (0.12 g, 0.19 mmol) in water (0.64 mL) was added to a slurry of N-(3-methyl-4-((1-methyl-1H-benzo[d]imidazol-5-yl)oxy)phenyl)-6-(methylthio)pyrimido[5,4-d]pyrimidin-2,8-d2-4-amine (0.055 g, 0.13 mmol) in acetonitrile (1.3 mL). The mixture was stirred at ambient temperature for 1 hour. The mixture was then diluted with water and extracted with 20% IPA/CHCl$_3$ (3×). The combined organic extracts were washed with a saturated aqueous Na$_2$S$_2$O$_3$ solution and then dried over Na$_2$SO$_4$, filtered and concentrated to afford N-(3-methyl-4-((1-methyl-1H-benzo[d]imidazol-5-yl)oxy)phenyl)-6-(methylsulfinyl)pyrimido[5,4-d]pyrimidin-2,8-d2-4-amine (0.050 g, 88%) as a solid foam that was used directly in the subsequent reaction. The crude product was obtained as a 3:1 of sulfoxide:sulfone. Sulfoxide=m/z (APCI-pos) M$^+$1=448.2.

Step E: A mixture of N-(3-methyl-4-((1-methyl-1H-benzo[d]imidazol-5-yl)oxy)phenyl)-6-(methylsulfinyl)pyrimido[5,4-d]pyrimidin-2,8-d2-4-amine (0.050 g, 0.112 mmol), DMA (0.560 mL) and morpholine (0.098 mL, 1.12 mmol) was heated to 60° C. for 1.5 hours. Upon cooling to ambient temperature, the solution was diluted with 1:1 H$_2$O and NaHCO$_3$ (saturated, aqueous, 2 mL). The mixture was extracted with CHCl$_3$ (3×10 mL), and the combined extracts were washed with brine. The combined organic extracts were dried over anhydrous sodium sulfate, filtered, and concentrated. The crude product was then purified via column chromatography (1-5% MeOH/CHCl$_3$) to afford N-(3-methyl-4-((1-methyl-1H-benzo[d]imidazol-5-yl)oxy)phenyl)-6-morpholinopyrimido[5,4-d]pyrimidin-2,8-d2-4-amine (0.034 g, 62%) as a solid. NMR studies indicate 70% deuterium incorporation at C-8 and 90% deuterium incorporation at C-2. m/z (APCI-pos) M$^+$1=471.2; $^1$H NMR (400 MHz, CDCl$_3$) δ 8.48 (s, 1H), 7.85 (s, 1H), 7.73 (d, J=2.7 Hz, 1H), 7.64 (dd, J=8.6, 2.7 Hz, 1H), 7.35-7.28 (m, 2H), 7.06 (dd, J=8.7, 2.3 Hz, 1H), 6.92 (d, J=8.7 Hz, 1H), 3.97 (t, J=4.8 Hz, 4H), 3.85 (m, 7H), 2.34 (s, 3H).

Example 69

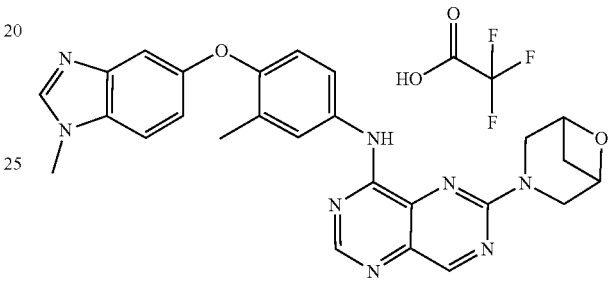

6-(6-oxa-3-azabicyclo[3.1.1]heptan-3-yl)-N-(3-methyl-4-((1-methyl-1H-benzo[d]imidazol-5-yl)oxy)phenyl)pyrimido[5,4-d]pyrimidin-4-amine 2,2,2-trifluoroacetate N-Ethyl-N-isopropylpropan-2-amine (0.170 mL, 0.975 mmol) was added to a solution of N-(3-methyl-4-((1-methyl-1H-benzo[d]imidazol-5-yl)oxy)phenyl)-6-(methylsulfonyl)pyrimido[5,4-d]pyrimidin-4-amine (0.03 g, 0.0650 mmol) in DMF (1 mL), followed by 6-oxa-3-azabicyclo[3.1.1]heptane hydrochloride (0.0881 g, 0.650 mmol). After these additions, the reaction mixture was heated to 80° C. After 1 hour 15 minutes, the reaction mixture was concentrated. This crude material was purified via a Gilson reverse phase preparatory HPLC using a gradient of 5 to 95% ACN/water over 20 minutes (0.1% TFA buffer). Product containing fractions were combined and lyophilized overnight to provide 6-(6-oxa-3-azabicyclo[3.1.1]heptan-3-yl)-N-(3-methyl-4-((1-methyl-1H-benzo[d]imidazol-5-yl)oxy)phenyl)pyrimido[5,4-d]pyrimidin-4-amine 2,2,2 trifluoroacetate (0.015 g, 48%). m/z (APCI-pos) M$^+$1=481.2; $^1$H NMR (400 MHz, CDCl$_3$) δ 9.35 (s, 1H), 8.97 (s, 1H), 8.65 (s, 1H), 7.78 (m, 2H), 7.54 (d, J=9.0 Hz, 1H), 7.35 (dd, J=2.3 Hz, 9.0 Hz, 1H) 7.20 (d, J=2.2 Hz, 1H), 7.04 (d, J=8.6 Hz, 1H), 4.84 (s, 2H), 4.04 (m, 7H), 3.38 (m 1H), 2.28 (s, 3H), 2.01 (d, 1H).

Example 70

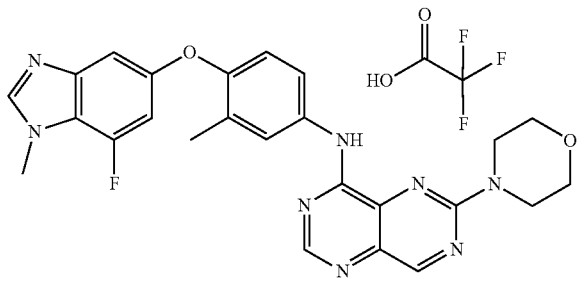

N-(4-((7-fluoro-1-methyl-1H-benzo[d]imidazol-5-yl)oxy)-3-methylphenyl)-6-morpholinopyrimido[5,4-d]pyrimidin-4-amine 2,2,2-trifluoroacetate Step A: A solution of 4-((7-fluoro-1-methyl-1H-benzo[d]imidazol-5-yl)oxy)-3-methylaniline (0.150 g, 0.553 mmol) in DMF (5 mL) was added to 8-chloro-2-(methylthio)pyrimido[5,4-d]pyrimidine (0.129 g, 0.608 mmol). Following this, the reaction vessel was sealed and heated to 50° C. After 18 hours, the reaction mixture was concentrated. The resulting residue was purified via reverse phase flash chromatography (60 g prepacked, C18) using a gradient of 5 to 95% ACN/water over 8 column volumes (0.1% TFA in each solvent). Product containing fractions were combined and treated with 10% $K_2CO_3$. After 10 minutes of stirring, the aqueous mixture was extracted with 25% IPA/CHCl$_3$ (3×), dried via $Na_2SO_4$, and concentrated to give N-(4-((7-fluoro-1-methyl-1H-benzo[d]imidazol-5-yl)oxy)-3-methylphenyl)-6-(methylthio)pyrimido[5,4-d]pyrimidin-4-amine (0.196 g, 79%). m/z (APCI-pos) $M^+1=448.2$.

Step B: A solution of N-(4-((7-fluoro-1-methyl-1H-benzo[d]imidazol-5-yl)oxy)-3-methylphenyl)-6-(methylthio)pyrimido[5,4-d]pyrimidin-4-amine (0.051 g, 0.11 mmol) in DCM (2 mL) was added 3-chlorobenzoperoxoic acid (0.056 g, 0.23 mmol). After 1 hour, the reaction mixture was concentrated. This crude material was taken up in EtOAc, washed with saturated $NaHCO_3$, followed by saturated $Na_2S_2O_3$, brine, dried with $Na_2SO_4$, and concentrated to give N-(4-((7-fluoro-1-methyl-1H-benzo[d]imidazol-5-yl)oxy)-3-methylphenyl)-6-(methylsulfonyl)pyrimido[5,4-d]pyrimidin-4-amine (0.038 g, 70%). m/z (APCI-pos) $M^+1=480.1$.

Step C: A solution of N-(4-((7-fluoro-1-methyl-1H-benzo[d]imidazol-5-yl)oxy)-3-methylphenyl)-6-(methylsulfonyl)pyrimido[5,4-d]pyrimidin-4-amine (0.038 g, 0.079 mmol) in DMF (1 mL) was added morpholine (0.070 mL, 0.79 mmol). The reaction mixture was heated to 80° C. After 1 hour 15 minutes, the reaction mixture was concentrated. This crude material was purified via a Gilson reverse phase preparatory HPLC using a gradient of 5 to 95% ACN/water over 20 minutes (0.1% TFA buffer). Product containing fractions were combined and lyophilized overnight to give N-(4-((7-fluoro-1-methyl-1H-benzo[d]imidazol-5-yl)oxy)-3-methylphenyl)-6-morpholinopyrimido[5,4-d]pyrimidin-4-amine 2,2,2-trifluoroacetate (0.0087 g, 23%). m/z (APCI-pos) $M^+1=487.2$; $^1H$ NMR (400 MHz, CDCl$_3$) δ 9.29 (s, 1H), 8.88 (br s, 1H), 8.66 (s, 1H), 8.63 (s, 1H), 7.78 (m, 2H), 7.04 (d, J=8.5 Hz, 1H), 6.98 (m, 2H), 4.15 (s, 3H), 4.01 (t, J=4.0, 5.7 Hz, 4H), 3.86 (t, J=4.05, 5.67, 4H), 2.28 (s, 3H).

Example 71

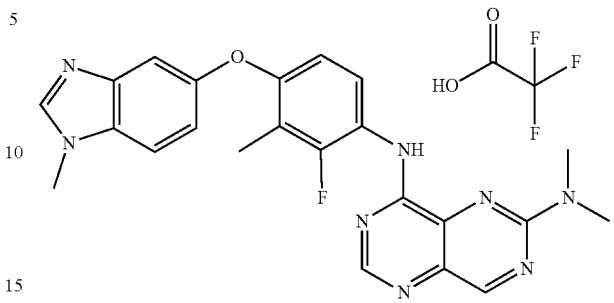

N8-(2-fluoro-3-methyl-4-((1-methyl-1H-benzo[d]imidazol-5-yl)oxy)phenyl)-N2,N2-dimethylpyrimido[5,4-d]pyrimidine-2,8-diamine 2,2,2-trifluoroacetate Step A: A solution of 2-fluoro-3-methyl-4-((1-methyl-1H-benzo[d]imidazol-5-yl)oxy)aniline (0.237 g, 0.874 mmol) in DMF (8 mL) was added to 8-chloro-2-(methylthio)pyrimido[5,4-d]pyrimidine (0.204 g, 0.961 mmol). The reaction mixture was heated to 50° C. After 16 hours, the reaction mixture was concentrated, and the resulting solid was purified via reverse phase chromatography (60 g, C18) using a gradient of 5 to 95% ACN/water over 10 column volumes (0.1% TFA buffer in each solvent). Product containing fractions were combined and treated with saturated $NaHCO_3$. After 10 minutes of stirring, the aqueous solution was extracted with 25% IPA/CHCl$_3$ (3×), dried via $Na_2SO_4$, and concentrated to afford N-(2-fluoro-3-methyl-4-((1-methyl-1H-benzo[d]imidazol-5-yl)oxy)phenyl)-6-(methylthio)pyrimido[5,4-d]pyrimidin-4-amine (0.244 g, 64%). m/z (APCI-pos) $M^+1=448.2$.

Step B: A solution of N-(2-fluoro-3-methyl-4-((1-methyl-1H-benzo[d]imidazol-5-yl)oxy)phenyl)-6-(methylthio)pyrimido[5,4-d]pyrimidin-4-amine (0.250 g, 0.559 mmol) in DCM (6 mL) was added to 3-chlorobenzoperoxoic acid (0.275 g, 1.12 mmol). After 1 hour, the reaction mixture was concentrated, and the resulting solid was taken up in EtOAc and saturated $NaHCO_3$. The aqueous and organic layers were separated. The aqueous layer was extracted with EtOAc (2×). The combined organic layers were washed with saturated $Na_2S_2O_3$, followed by brine, dried via $Na_2SO_4$, and concentrated to give N-(2-fluoro-3-methyl-4-((1-methyl-1H-benzo[d]imidazol-5-yl)oxy)phenyl)-6-(methylsulfonyl)pyrimido[5,4-d]pyrimidin-4-amine (0.082 g, 30%). m/z (APCI-pos) $M^+1=480.2$.

Step C: A solution of N-(2-fluoro-3-methyl-4-((1-methyl-1H-benzo[d]imidazol-5-yl)oxy)phenyl)-6-(methylsulfonyl)pyrimido[5,4-d]pyrimidin-4-amine (0.009 g, 0.019 mmol) in THF (1 mL) was added to dimethylamine (0.28 mL, 0.56 mmol) as a 2M solution in THF. Following this addition, the reaction vessel was sealed and heated to 60° C. After 1 hour 15 minutes, the reaction mixture was cooled to ambient temperature and was concentrated. This crude material was purified via a Gilson reverse phase preparatory HPLC using a gradient of 5 to 95% ACN/water over 20 minutes with 0.1% TFA buffer. Product containing fractions were lyophilized overnight to afford N8-(2-fluoro-3-methyl-4-((1-methyl-1H-benzo[d]imidazol-5-yl)oxy)phenyl)-N2,N2-dimethylpyrimido[5,4-d]pyrimidine-2,8-diamine 2,2,2-trifluoroacetate (0.004 g, 43%). m/z (APCI-pos)

M+1=445.2; ¹H NMR (400 MHz, CDCl₃) δ 9.26 (s, 1H), 8.93 (s, 1H), 8.61 (m, 2H), 7.54 (m, 1H), 7.31 (m, 2H), 6.85 (dd, J=1.7, 9.1 Hz, 1H), 4.05 (s, 3H), 3.38 (s, 6H), 2.23 (d, J=2.2, 3H).

Example 72

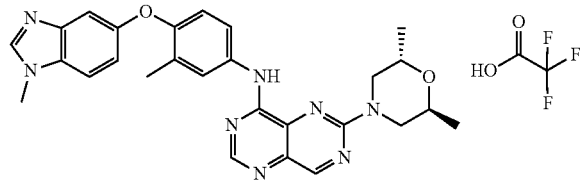 [SMILES: Cc1cc(Nc2ncnc3cnc(N4C[C@H](C)O[C@@H](C)C4)nc23)ccc1Oc1ccc2c(c1)ncn2C ; O=C(O)C(F)(F)F]

6-((2S,6S)-2,6-dimethylmorpholino)-N-(3-methyl-4-((1-methyl-1H-benzo[d]imidazol-5-yl)oxy)phenyl)pyrimido[5,4-d]pyrimidin-4-amine A solution of N-(3-methyl-4-((1-methyl-1H-benzo[d]imidazol-5-yl)oxy)phenyl)-6-(methylsulfonyl)pyrimido[5,4-d]pyrimidin-4-amine (0.650 mL, 0.0650 mmol) in DMF (1 mL) was added to (2S,6S)-2,6-dimethylmorpholine (0.0749 g, 0.650 mmol). The reaction mixture was heated to 80° C. After 45 hours, the reaction mixture was concentrated. The resulting material was purified via a Gilson reverse phase preparatory HPLC using a gradient of 5 to 95% ACN/water over 20 minutes (0.1% TFA). Product containing fractions were combined and lyophilized overnight to afford 6-((2S,6S)-2,6-dimethylmorpholino)-N-(3-methyl-4-((1-methyl-1H-benzo[d]imidazol-5-yl)oxy)phenyl)pyrimido[5,4-d]pyrimidin-4-amine 2,2,2-trifluoroacetate (0.020 g, 62%). m/z (APCI-pos) M+1=497.2; ¹H NMR (400 MHz, CDCl₃) δ 9.29 (s, 1H), 9.00 (s, 1H), 8.62 (s, 1H), 7.76 (m, 2H), 7.56 (d, J=9.0 Hz, 1H), 7.36 (dd, J=2.3, 9.0 Hz, 1H) 7.19 (d, J=2.3 Hz, 1H), 7.05 (d, J=8.6 Hz, 1H), 4.19 (m, 2H), 4.06 (m, 5H), 3.72 (m, 2H), 2.28 (s, 3H), 1.29 (d, J=6.4 Hz, 6H).

Example 73

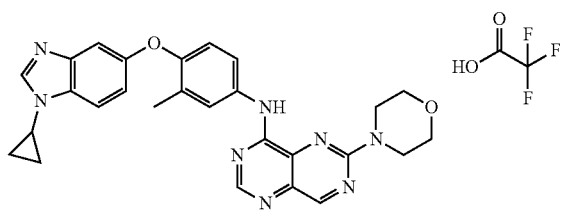 [SMILES: Cc1cc(Nc2ncnc3cnc(N4CCOCC4)nc23)ccc1Oc1ccc2c(c1)ncn2C1CC1 ; O=C(O)C(F)(F)F]

N-(4-((1-cyclopropyl-1H-benzo[d]imidazol-5-yl)oxy)-3-methylphenyl)-6-morpholinopyrimido[5,4-d]pyrimidin-4-amine 2,2,2-trifluoroacetate Step A: A solution of 4-((1-cyclopropyl-1H-benzo[d]imidazol-5-yl)oxy)-3-methylaniline (0.0605 g, 0.217 mmol) in DMF (3 mL) was added to 8-chloro-2-(methylthio)pyrimido[5,4-d]pyrimidine (0.0461 g, 0.217 mmol). The reaction mixture was heated to 80° C. After 1 hour 30 minutes, the crude oil was concentrated. The crude material was purified via reverse phase chromatography (60 g, prepacked) using a gradient of 20 to 95% ACN/water (0.1% TFA buffer) over 9 column volumes. Product containing fractions were combined and treated with saturated NaHCO₃. After 10 minutes of stirring, the solution was extracted with 25% IPA/DCM (2x), dried via Na₂SO₄, and concentrated to afford N-(4-((1-cyclopropyl-1H-benzo[d]imidazol-5-yl)oxy)-3-methylphenyl)-6-(methylthio)pyrimido[5,4-d]pyrimidin-4-amine (0.085 g, 86%). m/z (APCI-pos) M+1=456.2.

Step B: A solution of N-(4-((1-cyclopropyl-1H-benzo[d]imidazol-5-yl)oxy)-3-methylphenyl)-6-(methylthio)pyrimido[5,4-d]pyrimidin-4-amine (0.085 g, 0.187 mmol) in DCM (2 mL) was added to 3-chlorobenzoperoxoic acid (0.0920 g, 0.373 mmol). After 45 minutes, the reaction mixture was concentrated. This material was taken up in EtOAc, washed with saturated NaHCO₃, followed by saturated Na₂S₂O₃, then brine, dried via Na₂SO₄, and concentrated to afford N-(4-((1-cyclopropyl-1H-benzo[d]imidazol-5-yl)oxy)-3-methylphenyl)-6-(methylsulfonyl)pyrimido[5,4-d]pyrimidin-4-amine (0.0515 g, 57%). m/z (APCI-pos) M+1=488.1.

Step C: A solution of N-(4-((1-cyclopropyl-1H-benzo[d]imidazol-5-yl)oxy)-3-methylphenyl)-6-(methylsulfonyl)pyrimido[5,4-d]pyrimidin-4-amine (0.02 g, 0.0410 mmol) in DMF (1 mL) was added to morpholine (0.0361 mL, 0.410 mmol). The reaction vessel was heated to 80° C. After 17 hours, the reaction mixture was concentrated. The resulting crude material was purified via a Gilson reverse phase preparatory HPLC using a gradient of 5 to 95% ACN/water over 20 minutes (0.1% TFA buffer). Product containing fractions were lyophilized overnight to give N-(4-((1-cyclopropyl-1H-benzo[d]imidazol-5-yl)oxy)-3-methylphenyl)-6-morpholinopyrimido[5,4-d]pyrimidin-4-amine 2,2,2-trifluoroacetate (0.0116 g, 57%). m/z (APCI-pos) M+1=495.2; ¹H NMR (400 MHz, CDCl₃) δ 9.32 (s, 1H), 8.94 (s, 1H), 8.64 (s, 1H), 7.75 (m, 3H), 7.36 (dd, J=2.3, 9.0 Hz, 1H), 7.17 (d, J=2.3 Hz, 1H) 7.03 (d, J=8.6 Hz, 1H), 4.01 (t, J=4.8 Hz, 4H), 3.86 (t, J=4.8 Hz, 4H), 3.61 (m, 1H) 2.28 (s, 3H), 1.29 (m, 4H).

Example 74

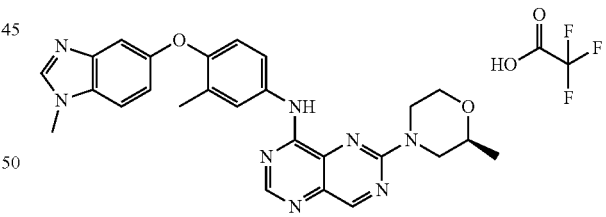

(S)—N-(3-methyl-4-((1-methyl-1H-benzo[d]imidazol-5-yl)oxy)phenyl)-6-(2-methylmorpholino)pyrimido[5,4-d]pyrimidin-4-amine 2,2,2-trifluoroacetate Step A: A 100-mL round bottom flask containing N-(3-methyl-4-((1-methyl-1H-benzo[d]imidazol-5-yl)oxy)phenyl)-6-(methylthio)pyrimido[5,4-d]pyrimidin-4-amine (1.42 g, 3.31 mmol) and DCM (33.1 mL, 3.31 mmol) was stirred vigorously, producing a slurry. 3-Chloroperoxybenzoic acid (1.79 g, 7.27 mmol) was added in several aliquots over about 5 minutes. Stirring was continued for 4 hours, upon which the solution was diluted with 5% MeOH/EtOAc (200 mL) and washed with NaHCO₃ (saturated aqueous, 4×40 mL) and sodium thiosulfate (saturated aqueous, 30 mL). The organic phase was dried over anhydrous sodium sulfate, filtered, and concentrated in vacuo to give N-(3-methyl-4-((1-methyl-1H-benzo[d]imidazol-5-yl)oxy)phenyl)-6-(methylsulfinyl)pyrimido[5,4-d]pyrimidin-4-amine (m/z (APCI-pos) M⁺1=483.2) and N-(3-methyl-4-((1-methyl-1H-benzo[d]imidazol-5-yl)oxy)phenyl)-6-(methylsulfonyl)pyrimido[5,4-d]pyrimidin-4-amine (m/z (APCI-pos) M⁺1=462.1) as a 1:1 mixture (800 mg, 53%).

Step B: A solution of N-(3-methyl-4-((1-methyl-1H-benzo[d]imidazol-5-yl)oxy)phenyl)-6-(methylsulfinyl)pyrimido[5,4-d]pyrimidin-4-amine (0.031 g, 0.0696 mmol) and N-(3-methyl-4-((1-methyl-1H-benzo[d]imidazol-5-yl)oxy)phenyl)-6-(methylsulfonyl)pyrimido[5,4-d]pyrimidin-4-amine (0.0321 g, 0.0696 mmol) in DMF (1 mL) was added to (S)-2-methylmorpholine (0.141 g, 1.39 mmol). The reaction mixture was heated to 80° C. After 45 hours, the reaction mixture was concentrated. The resulting material was purified via a Gilson reverse phase preparatory HPLC using a gradient of 5 to 95% ACN/water over 45 minutes (0.1% TFA). Product containing fractions were combined and lyophilized overnight to afford (S)—N-(3-methyl-4-((1-methyl-1H-benzo[d]imidazol-5-yl)oxy)phenyl)-6-(2-methylmorpholino)pyrimido[5,4-d]pyrimidin-4-amine 2,2,2-trifluoroacetate (0.0237 g, 71%). m/z (APCI-pos) M⁺1=483.2; ¹H NMR (400 MHz, CDCl₃) δ 9.29 (s, 1H), 9.03 (s, 1H), 8.62 (s, 1H), 7.76 (m, 2H), 7.56 (d, J=9.0 Hz, 1H), 7.36 (dd, J=2.4, 9.0 Hz, 1H), 7.21 (d, J=2.3 Hz, 1H) 7.04 (d, J=8.6 Hz, 1H), 4.70 (t, J=12.7 Hz, 2H), 4.06 (m, 4H), 3.71 (m, 2H), 3.25 (td, J=3.6, 12.6 Hz, 1H), 2.90 (dd, J=10.5, 13.3 Hz, 1H) 2.28 (s, 3H) 1.33 (d, J=6.2 Hz, 3H).

Example 75

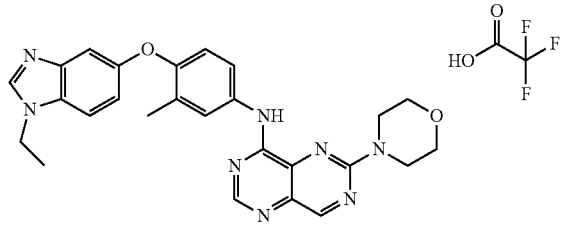 [SMILES: CCn1cnc2cc(Oc3ccc(Nc4ncnc5cnc(N6CCOCC6)nc45)cc3C)ccc21 ; O=C(O)C(F)(F)F]

N-(4-((1-ethyl-1H-benzo[d]imidazol-5-yl)oxy)-3-methylphenyl)-6-morpholinopyrimido[5,4-d]pyrimidin-4-amine 2,2,2-trifluoroacetate Step A: A solution of 4-((1-ethyl-1H-benzo[d]imidazol-5-yl)oxy)-3-methylaniline (0.068 g, 0.25 mmol) in DMF (3 mL) was added to 8-chloro-2-(methylthio)pyrimido[5,4-d]pyrimidine (0.054 g, 0.25 mmol). The reaction mixture was heated to 80° C. After 2 hours, the reaction mixture was concentrated. The resulting crude oil was purified via reverse phase chromatography (60 g, prepacked) using a gradient of 20 to 95% ACN/water (0.1% TFA buffer) over 9 column volumes. Product containing fractions were combined and treated with saturated NaHCO₃. After 10 minutes of stirring, the aqueous solution was extracted with 25% IPA/DCM (2×) dried via Na₂SO₄, and concentrated to afford N-(4-((1-ethyl-1H-benzo[d]imidazol-5-yl)oxy)-3-methylphenyl)-6-(methylthio)pyrimido[5,4-d]pyrimidin-4-amine (0.093 g, 82%). m/z (APCI-pos) M⁺1=444.2.

Step B: A solution of N-(4-((1-ethyl-1H-benzo[d]imidazol-5-yl)oxy)-3-methylphenyl)-6-(methylthio)pyrimido[5,4-d]pyrimidin-4-amine (0.093 g, 0.21 mmol) in DCM (2 mL) was added to 3-chlorobenzoperoxoic acid (0.10 g, 0.42 mmol). After 45 minutes, the reaction mixture was concentrated. This material was taken up in EtOAc, washed with saturated NaHCO₃, followed by saturated Na₂S₂O₃, then brine, dried via Na₂SO₄, and concentrated to afford N-(4-((1-ethyl-1H-benzo[d]imidazol-5-yl)oxy)-3-methylphenyl)-6-(methylsulfonyl)pyrimido[5,4-d]pyrimidin-4-amine (0.036 g, 36%). m/z (APCI-pos) M⁺1=476.2.

Step C: A solution of N-(4-((1-ethyl-1H-benzo[d]imidazol-5-yl)oxy)-3-methylphenyl)-6-(methylsulfonyl)pyrimido[5,4-d]pyrimidin-4-amine (0.012 g, 0.0252 mmol) in DMF (0.5 mL) was added to morpholine (0.0222 mL, 0.252 mmol). The reaction mixture was heated to 80° C. After 17 hours, the reaction mixture was concentrated. The resulting crude material was purified via a Gilson reverse phase preparatory HPLC using a gradient of 5 to 95% ACN/water over 20 minutes (0.1% TFA buffer). Product containing fractions were lyophilized overnight to afford N-(4-((1-ethyl-1H-benzo[d]imidazol-5-yl)oxy)-3-methylphenyl)-6-morpholinopyrimido[5,4-d]pyrimidin-4-amine 2,2,2-trifluoroacetate (0.0101 g, 83%). m/z (APCI-pos) M⁺1=483.3; ¹H NMR (400 MHz, CDCl₃) δ 9.30 (s, 1H), 9.03 (s, 1H), 8.64 (s, 1H), 7.77 (m, 2H), 7.57 (d, J=9.0 Hz, 1H), 7.35 (dd, J=2.3, 9.1 Hz, 1H), 7.19 (d, J=2.3 Hz, 1H) 7.05 (d, J=8.6 Hz, 1H), 4.41 (q, J=7.3 Hz, 2H), 4.01 (t, J=4.8 Hz, 4H), 3.86 (t, J=4.8 Hz, 4H), 2.28 (s, 3H), 1.70 (t, 3H).

Example 76

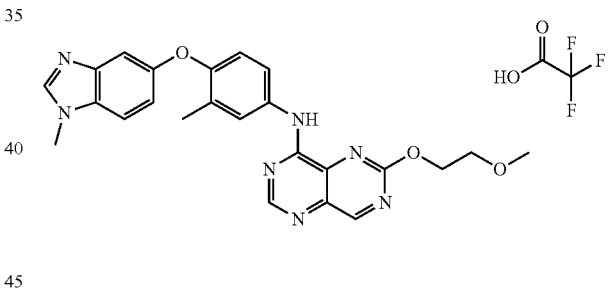

6-(2-methoxyethoxy)-N-(3-methyl-4-((1-methyl-1H-benzo[d]imidazol-5-yl)oxy)phenyl)pyrimido[5,4-d]pyrimidin-4-amine 2,2,2-trifluoroacetate A solution of N-(3-methyl-4-((1-methyl-1H-benzo[d]imidazol-5-yl)oxy)phenyl)-6-(methylsulfonyl)pyrimido[5,4-d]pyrimidin-4-amine (0.05 g, 0.108 mmol) and 2-methoxyethan-1-ol (0.0854 mL, 1.08 mmol) in DMA (2 mL) was added to sodium hydride (0.0650 g, 1.63 mmol) at ambient temperature and allowed to stir for 15 minutes. The reaction mixture was heated to 80° C. After 3 hours 30 minutes, the reaction mixture was cooled to ambient temperatures and was diluted with water and EtOAc. The organic and aqueous phases were separated. The aqueous layer was extracted with EtOAc (2×). The combined organic phases were washed with brine (5×), dried via Na₂SO₄, and concentrated. This crude material was purified via a Gilson reverse phase preparatory HPLC using a gradient of 5 to 95% ACN/water over 20 minutes (0.1% TFA buffer). Product containing fractions were lyophilized overnight. This material was combined and purified once more via a Gilson reverse phase preparatory HPLC using a gradient of 5 to 50% ACN/water over 45 minutes (0.1% TFA buffer). Product containing fractions were lyophilized overnight to afford 6-(2-methoxyethoxy)-N-(3-methyl-4-((1-methyl-1H-benzo[d]imidazol-5-yl)oxy)phenyl)pyrimido[5,4-d]pyrimidin-4-amine 2,2,2-trifluoroacetate (0.0012 g, 2.4%). m/z (APCI-pos) M$^+$1=458.2; $^1$H NMR (400 MHz, CDCl$_3$) δ 9.48 (s, 1H), 9.17 (s, 1H), 8.98 (s, 1H), 8.79 (s, 1H), 7.84 (d, J=2.7 Hz, 1H), 7.78 (dd, J=2.7, 8.7 Hz, 1H), 7.58 (d, J=9.1 Hz, 1H), 7.37 (dd, J=2.3, 9.1 Hz, 1H), 7.05 (d, J=8.7 Hz, 1H), 4.74 (m, 2H) 4.09 (s, 3H), 3.88 (m, 2H), 3.49 (s, 3H), 2.28 (s, 3H).

Example 77

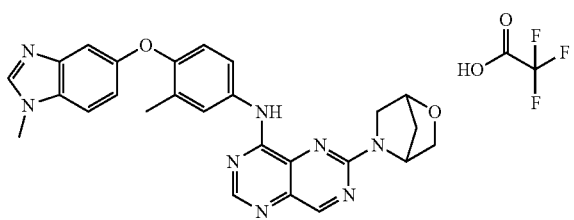 [SMILES: Cc1cc(Nc2ncnc3cnc(N4CC5CC4CO5)nc23)ccc1Oc1ccc2c(c1)ncn2C ; O=C(O)C(F)(F)F]

6-(2-oxa-5-azabicyclo[2.2.1]heptan-5-yl)-N-(3-methyl-4-((1-methyl-1H-benzo[d]imidazol-5-yl)oxy)phenyl)pyrimido[5,4-d]pyrimidin-4-amine 2,2,2-trifluoroacetate A solution of N-(3-methyl-4-((1-methyl-1H-benzo[d]imidazol-5-yl)oxy)phenyl)-6-(methylsulfonyl)pyrimido[5,4-d]pyrimidin-4-amine (0.02 g, 0.043 mmol) in DMF (1 mL) was added to 2-oxa-5-azabicyclo[2.2.1]heptane (0.043 g, 0.43 mmol). The reaction vessel was heated to 80° C. After 46 hours, the reaction mixture was concentrated. The crude product was purified via a Gilson reverse phase preparatory HPLC using a gradient of 5 to 95% ACN/water over 20 minutes (0.1% TFA buffer). Product containing fractions were lyophilized overnight to afford 6-(2-oxa-5-azabicyclo[2.2.1]heptan-5-yl)-N-(3-methyl-4-((1-methyl-1H-benzo[d]imidazol-5-yl)oxy)phenyl)pyrimido[5,4-d]pyrimidin-4-amine 2,2,2-trifluoroacetate (0.02 g, 95%). m/z (APCI-pos) M$^+$1=481.2; $^1$H NMR (400 MHz, CDCl$_3$) δ 9.32 (s, 1H), 9.00 (s, 1H), 8.63 (s, 1H), 7.76 (m, 2H), 7.56 (d, J=9.0 Hz, 1H), 7.04 (d, J=8.7 Hz, 1H), 4.82 (s, 1H), 4.07 (s, 3H), 3.93 (m, 2H), 3.71 (m, 2H), 2.28 (s, 3H), 2.08 (m, 2H).

Example 78

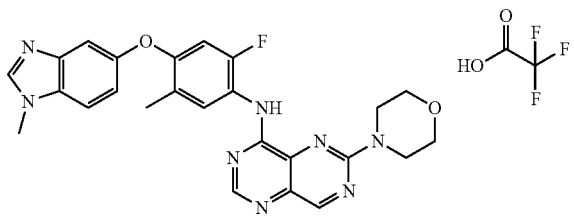 [SMILES: Cc1cc(Nc2ncnc3cnc(N4CCOCC4)nc23)c(F)cc1Oc1ccc2c(c1)ncn2C ; O=C(O)C(F)(F)F]

N-(2-fluoro-5-methyl-4-((1-methyl-1H-benzo[d]imidazol-5-yl)oxy)phenyl)-6-morpholinopyrimido[5,4-d]pyrimidin-4-amine 2,2,2-trifluoroacetate Step A: A solution of 1,5-difluoro-2-methyl-4-nitrobenzene (1.4 g, 8.1 mmol) in DMF (45 mL) was added Cs$_2$CO$_3$ (4.4 g, 13 mmol), followed by 1-methyl-1H-benzo[d]imidazol-5-ol (1 g, 6.7 mmol). The reaction mixture was heated to 80° C. After 2 hours, the reaction mixture was concentrated. This crude solid was taken up in EtOAc, washed with water, followed by brine, dried via Na$_2$SO$_4$, and concentrated to afford 5-(5-fluoro-2-methyl-4-nitrophenoxy)-1-methyl-1H-benzo[d]imidazole (2.1 g, 103%). m/z (APCI-pos) M$^+$1=302.1.

Step B: A solution of 5-(5-fluoro-2-methyl-4-nitrophenoxy)-1-methyl-1H-benzo[d]imidazole (2.1 g, 7.0 mmol) in ACN:THF (1:1, 30 mL) was cooled to 0° C., and zinc (4.6 g, 70 mmol) was added, followed by saturated NH$_4$Cl (30 mL). After 10 minutes at 0° C., the reaction mixture was warmed to ambient temperature. After 1 hour 15 minutes, the reaction mixture was filtered through GF/F paper. The aqueous and organic phases were separated. The aqueous phase was extracted with EtOAc, dried via Na$_2$SO$_4$, and concentrated to afford 2-fluoro-5-methyl-4-((1-methyl-1H-benzo[d]imidazol-5-yl)oxy)aniline (1.9 g, 100%). m/z (APCI-pos) M$^+$1=272.2.

Step C: A solution of 2-fluoro-5-methyl-4-((1-methyl-1H-benzo[d]imidazol-5-yl)oxy)aniline (0.160 g, 0.590 mmol) in DMF (6 mL) was added to 8-chloro-2-(methylthio)pyrimido[5,4-d]pyrimidine (0.125 g, 0.590 mmol) and heated to 80° C. After 2 hours, the reaction mixture was concentrated. This crude solid was purified via reverse phase chromatography (120 g) using a gradient of 5 to 95% ACN/water over 10 column volumes (0.1% TFA buffer). Product containing fractions were combined and treated with saturated NaHCO$_3$ (aqueous). After 10 minutes, the aqueous solution was extracted with 25% IPA/DCM (2×), dried via Na$_2$SO$_4$, and concentrated to afford N-(2-fluoro-5-methyl-4-((1-methyl-1H-benzo[d]imidazol-5-yl)oxy)phenyl)-6-(methylthio)pyrimido[5,4-d]pyrimidin-4-amine (52 mg, 20%). m/z (APCI-pos) M$^+$1=448.2.

Step D: 3-Chlorobenzoperoxoic acid (0.056 g, 0.23 mmol) was added to a solution of N-(2-fluoro-5-methyl-4-((1-methyl-1H-benzo[d]imidazol-5-yl)oxy)phenyl)-6-(methylthio)pyrimido[5,4-d]pyrimidin-4-amine (0.051 g, 0.11 mmol) in DCM (2 mL). After 19 hours, the reaction mixture was concentrated. The crude solid was taken up in EtOAc, washed with saturated NaHCO$_3$ (aqueous), followed by saturated Na$_2$S$_2$O$_3$ (aqueous), brine, dried via Na$_2$SO$_4$, and concentrated to afford N-(2-fluoro-5-methyl-4-((1-methyl-1H-benzo[d]imidazol-5-yl)oxy)phenyl)-6-(methylsulfonyl)pyrimido[5,4-d]pyrimidin-4-amine (0.031 g, 57%). m/z (APCI-pos) M$^+$1=480.2.

Step E: A solution of N-(2-fluoro-5-methyl-4-((1-methyl-1H-benzo[d]imidazol-5-yl)oxy)phenyl)-6-(methylsulfonyl)pyrimido[5,4-d]pyrimidin-4-amine (0.65 mL, 0.065 mmol) in DMF (1 mL) was added to morpholine (0.057 mL, 0.65 mmol). The reaction mixture was heated to 80° C. After 1 hour 15 minutes, the reaction mixture was concentrated. This crude material was purified via a Gilson reverse phase preparatory HPLC using a gradient of 5 to 95% ACN/water over 20 minutes (0.1% TFA buffer). Product containing fractions were combined and lyophilized overnight to afford N-(2-fluoro-5-methyl-4-((1-methyl-1H-benzo[d]imidazol-5-yl)oxy)phenyl)-6-morpholinopyrimido[5,4-d]pyrimidin-4-amine 2,2,2-trifluoroacetate (0.019 g, 60%). m/z (APCI-pos) M$^+$1=487.2; $^1$H NMR (400 MHz, CDCl$_3$) δ 9.25 (s, 1H), 9.03 (br s, 1H), 9.01 (s, 1H), 8.67 (s, 1H), 8.65 (d, J=8.9 Hz, 1H), 7.57 (d, J=9.0 Hz, 1H), 7.33 (dd, J=2.3, 9.0 Hz, 1H), 7.28 (d, J=2.2, 1H), 6.82 (d, J=11.2 Hz, 1H), 4.06 (s, 3H), 3.99 (t, J=4.9 Hz, 4H), 3.85 (t, J=4.9 Hz, 4H), 2.28 (s, 3H).

Example 79

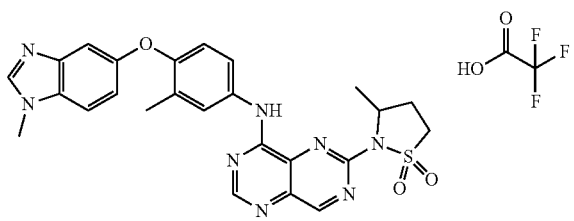 [SMILES: Cc1cc(Nc2ncnc3cnc(N4C(C)CCS4(=O)=O)nc23)ccc1Oc1ccc2c(c1)ncn2C ; O=C(O)C(F)(F)F]

3-methyl-2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide 2,2,2-trifluoroacetate A solution of N-(3-methyl-4-((1-methyl-1H-benzo[d]imidazol-5-yl)oxy)phenyl)-6-(methylsulfonyl)pyrimido[5,4-d]pyrimidin-4-amine (0.02 g, 0.043 mmol) and 3-methylisothiazolidine 1,1-dioxide (0.012 g, 0.087 mmol) in DMF (1 mL) was added to sodium hydride (0.0045 g, 0.13 mmol). The reaction mixture was heated to 80° C. After 3 hours, the reaction vessel was diluted with water and extracted with EtOAc (3×). The combined organic phases were washed with brine (3×), dried via Na$_2$SO$_4$, and concentrated. This crude material was purified via a Gilson reverse phase preparatory HPLC using a gradient of 5 to 95% ACN/water over 20 minutes (0.1% TFA in each solvent). Product containing fractions were combined and lyophilized overnight to afford 3-methyl-2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide 2,2,2-trifluoroacetate (0.0049 g, 22%). m/z (APCI-pos) M$^+$1=517.2; $^1$H NMR (400 MHz, CDCl$_3$) δ 9.29 (s, 1H), 8.70 (s, 1H), 8.64 (s, 1H), 7.71 (d, J=2.7 Hz, 1H), 7.65 (dd, J=2.8, 8.7 Hz, 1H), 7.33 (m, 2H) 7.05 (dd, J=2.3, 8.6 Hz, 1H), 6.92 (d, J=8.7 Hz, 1H), 4.84 (m, 1H), 3.85 (s, 3H), 3.61 (m, 1H), 3.47 (m, 1H), 2.78 (m, 1H), 2.36 (s, 3H), 2.25 (m, 1H), 1.61 (d, J=6.3 Hz, 3H).

Example 80

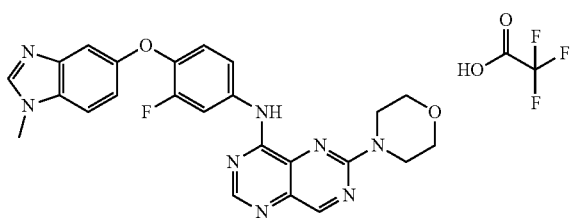 [SMILES: Cn1cnc2cc(Oc3ccc(Nc4ncnc5cnc(N6CCOCC6)nc45)cc3F)ccc21 ; O=C(O)C(F)(F)F]

N-(3-fluoro-4-((1-methyl-1H-benzo[d]imidazol-5-yl)oxy)phenyl)-6-morpholinopyrimido[5,4-d]pyrimidin-4-amine 2,2,2-trifluoroacetate Step A: A solution of 3-fluoro-4-((1-methyl-1H-benzo[d]imidazol-5-yl)oxy)aniline (0.106 g, 0.412 mmol) in DMF (4 mL) was added to 8-chloro-2-(methylthio)pyrimido[5,4-d]pyrimidine (0.0876 g, 0.412 mmol) and heated to 80° C. After 2 hours, the reaction mixture was concentrated. The crude solid was purified via reverse phase chromatography (120 g, C18) using a gradient of 5 to 95% ACN/water over 8 column volumes. Product containing fractions were combined and treated with saturated NaHCO$_3$ (aqueous). After 10 minutes, the aqueous solution was extracted with 25% IPA/DCM (2×), dried via Na$_2$SO$_4$, and concentrated to afford N-(3-fluoro-4-((1-methyl-1H-benzo[d]imidazol-5-yl)oxy)phenyl)-6-(methylthio)pyrimido[5,4-d]pyrimidin-4-amine (103 mg, 58%). m/z (APCI-pos) M$^+$1=434.1.

Step B: A solution of N-(3-fluoro-4-((1-methyl-1H-benzo[d]imidazol-5-yl)oxy)phenyl)-6-(methylthio)pyrimido[5,4-d]pyrimidin-4-amine (0.045 g, 0.10 mmol) in DCM (2 mL) was added to 3-chlorobenzoperoxoic acid (0.051 g, 0.21 mmol). After 19 hours, the reaction mixture was concentrated. The crude solid was taken up in EtOAc, washed with saturated NaHCO$_3$ (aqueous), followed by saturated Na$_2$S$_2$O$_3$ (aqueous), then brine, dried via Na$_2$SO$_4$, and concentrated to afford N-(3-fluoro-4-((1-methyl-1H-benzo[d]imidazol-5-yl)oxy)phenyl)-6-(methylsulfonyl)pyrimido[5,4-d]pyrimidin-4-amine (0.028 g, 58%). m/z (APCI-pos) M$^+$1=466.1.

Step C: A solution of N-(3-fluoro-4-((1-methyl-1H-benzo[d]imidazol-5-yl)oxy)phenyl)-6-(methylsulfonyl)pyrimido[5,4-d]pyrimidin-4-amine (0.028 g, 0.060 mmol) in DMF (1 mL) was added to morpholine (0.053 mL, 0.60 mmol). The reaction mixture was heated to 80° C. After 1 hour 15 minutes, the reaction mixture was concentrated. This crude material was purified via a Gilson reverse phase preparatory HPLC using a gradient of 5 to 95% ACN/water over 20 minutes (0.1% TFA buffer). Product containing fractions were combined and lyophilized overnight to afford N-(3-fluoro-4-((1-methyl-1H-benzo[d]imidazol-5-yl)oxy)phenyl)-6-morpholinopyrimido[5,4-d]pyrimidin-4-amine 2,2,2-trifluoroacetate (0.012 g, 42%). m/z (APCI-pos) M$^+$1=473.2; $^1$H NMR (400 MHz, CDCl$_3$) δ 9.20 (s, 1H), 8.97 (s, 1H), 8.74 (br s, 1H), 8.64 (s, 1H), 8.13 (dd, J=2.6, 12.3 Hz, 1H), 7.55 (d, J=9.1 Hz, 1H), 7.39 (dd, J=2.3, 9.0 Hz, 1H), 7.30 (d, J=2.3 Hz, 1H), 7.21 (m, 2H), 4.06 (s, 3H), 4.01 (t, J=4.8, 4H), 3.86 (t, J=4.8, 4H).

Example 81

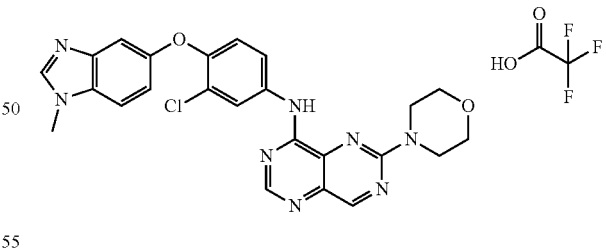

N-(3-chloro-4-((1-methyl-1H-benzo[d]imidazol-5-yl)oxy)phenyl)-6-morpholinopyrimido[5,4-d]pyrimidin-4-amine 2,2,2-trifluoroacetate Step A: A solution of 3-chloro-4-((1-methyl-1H-benzo[d]imidazol-5-yl)oxy)aniline (0.100 g, 0.365 mmol) in IPA (4 mL) was added to 8-chloro-2-(methylthio)pyrimido[5,4-d]pyrimidine (0.0855 g, 0.402 mmol) at ambient temperatures. The reaction vessel was heated to 50° C. After 17 hours, the reaction mixture was cooled to ambient and was concentrated to afford N-(3-chloro-4-((1-methyl-1H-benzo[d]imidazol-5-yl)oxy)phenyl)-6-(methylthio)pyrimido[5,4-d]pyrimidin-4-amine (0.183, 111%). m/z (APCI-pos) M+1=450.1.

Step B: 3-Chlorobenzoperoxoic acid (0.022 g, 0.089 mmol) was added to a solution of N-(3-chloro-4-(O-methyl-1H-benzo[d]imidazol-5-yl)oxy)phenyl)-6-(methylthio)pyrimido[5,4-d]pyrimidin-4-amine (0.02 g, 0.044 mmol) in DCM (2 mL). After 1 hour 30 minutes, the reaction mixture was concentrated. The crude solid was taken up in EtOAc, washed with saturated NaHCO$_3$ (aqueous), followed by saturated Na$_2$S$_2$O$_3$ (aqueous), then brine, dried via Na$_2$SO$_4$, and concentrated to give N-(3-chloro-4-((1-methyl-1H-benzo[d]imidazol-5-yl)oxy)phenyl)-6-(methylsulfonyl)pyrimido[5,4-d]pyrimidin-4-amine (0.0053 g, 25%). m/z (APCI-pos) M+1=482.1.

Step C: A solution of N-(3-chloro-4-((1-methyl-1H-benzo[d]imidazol-5-yl)oxy)phenyl)-6-(methylsulfonyl)pyrimido[5,4-d]pyrimidin-4-amine (0.0053 g, 0.011 mmol) in DMF (0.5 mL) was added morpholine (0.0097 mL, 0.11 mmol). The reaction mixture was heated to 80° C. After 1 hour 30 minutes, the reaction mixture was concentrated. This crude material was purified via a Gilson reverse phase preparatory HPLC using a gradient of 5 to 95% ACN/water over 20 minutes (0.1% TFA buffer). Product containing fractions were combined and lyophilized overnight to provide N-(3-chloro-4-((1-methyl-1H-benzo[d]imidazol-5-yl)oxy)phenyl)-6-morpholinopyrimido[5,4-d]pyrimidin-4-amine 2,2,2-trifluoroacetate (0.0021 g, 39%). m/z (APCI-pos) M+1=450.1; $^1$H NMR (400 MHz, CDCl$_3$) δ 9.23 (s, 1H), 9.00 (s, 1H), 8.65 (s, 1H), 8.19 (d, J=2.6 Hz, 1H), 7.83 (dd, J=2.6, 8.8 Hz, 1H), 7.57 (d, J=9.0 Hz, 1H), 7.39 (dd, J=2.3, 9.0 Hz, 1H), 7.21 (m, 2H), 4.06 (s, 3H), 4.01 (t, J=4.8, 4H), 3.86 (t, J=4.8, 4H).

Example 82

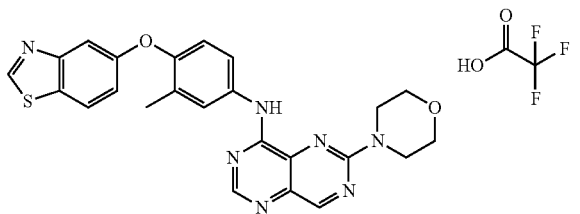 [SMILES: Cc1cc(Nc2ncnc3cnc(N4CCOCC4)nc23)ccc1Oc1ccc2scnc2c1 ; O=C(O)C(F)(F)F]

N-(4-(benzo[d]thiazol-5-yloxy)-3-methylphenyl)-6-morpholinopyrimido[5,4-d]pyrimidin-4-amine 2,2,2-trifluoroacetate Step A: A solution of 4-(benzo[d]thiazol-5-yloxy)-3-methylaniline (0.20 g, 0.78 mmol) in IPA was added to 8-chloro-2-(methylthio)pyrimido[5,4-d]pyrimidine (0.17 g, 0.78 mmol). The reaction mixture was heated to 50° C. After 20 hours, the reaction mixture was cooled to ambient temperature and was concentrated to afford N-(4-(benzo[d]thiazol-5-yloxy)-3-methylphenyl)-6-(methylthio)pyrimido[5,4-d]pyrimidin-4-amine (0.31 g, 92%). m/z (APCI-pos) M+1=433.1.

Step B: A solution of N-(4-(benzo[d]thiazol-5-yloxy)-3-methylphenyl)-6-(methylthio)pyrimido[5,4-d]pyrimidin-4-amine (0.112 g, 0.259 mmol) in DCM (5 mL) was added to 3-chlorobenzoperoxoic acid (0.128 g, 0.518 mmol). After 18 hours, the reaction mixture was concentrated, taken up in EtOAc, washed with saturated Na$_2$S$_2$O$_3$, followed by saturated NaHCO$_3$ (2×), brine, dried via Na$_2$SO$_4$, and concentrated to afford N-(4-(benzo[d]thiazol-5-yloxy)-3-methylphenyl)-6-(methylsulfonyl)pyrimido[5,4-d]pyrimidin-4-amine, which was used as crude in the next step. m/z (APCI-pos) M+1=465.1.

Step C: A solution of N-(4-(benzo[d]thiazol-5-yloxy)-3-methylphenyl)-6-(methylsulfonyl)pyrimido[5,4-d]pyrimidin-4-amine (0.015 g, 0.032 mmol) in IPA (1 mL) was added to morpholine (0.085 mL, 0.97 mmol). The reaction vessel was heated to 50° C. After 21 hours, the reaction was cooled to ambient temperature and was concentrated. This crude material was purified via a Gilson reverse phase preparatory HPLC using a gradient of 5 to 95% ACN/water over 20 minutes (0.1% TFA buffer). Product containing fractions were lyophilized overnight to afford N-(4-(benzo[d]thiazol-5-yloxy)-3-methylphenyl)-6-morpholinopyrimido[5,4-d]pyrimidin-4-amine 2,2,2-trifluoroacetate (0.0032 g, 21%). m/z (APCI-pos) M+1=472.2; $^1$H NMR (400 MHz, CDCl$_3$) δ 9.38 (s, 1H), 9.06 (s, 1H), 8.99 (s, 1H), 8.66 (s, 1H), 7.92 (d, J=8.8 Hz, 1H), 7.77 (d, J=2.7 Hz, 1H), 7.71 (dd, J=2.7, 8.7 Hz, 1H), 7.59 (d, J=2.4, Hz, 1H), 7.22 (m, 1H), 7.06 (d, J=8.7 Hz, 1H), 4.01 (t, J=4.8 Hz, 4H), 3.86 (t, J=4.8 Hz, 4H), 2.36 (s, 3H).

Example 83

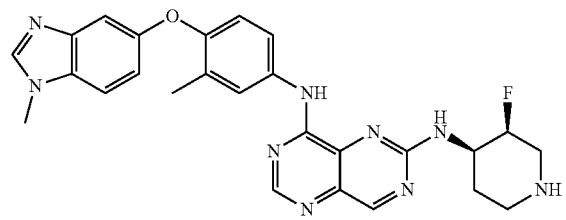 [SMILES: Cc1cc(Nc2ncnc3cnc(N[C@@H]4CCNC[C@@H]4F)nc23)ccc1Oc1ccc2c(c1)ncn2C]

N2-((3S,4R)-3-fluoropiperidin-4-yl)-N8-(3-methyl-4-((1-methyl-1H-benzo[d]imidazol-5-yl)oxy)phenyl)pyrimido[5,4-d]pyrimidine-2,8-diamine Step A: A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.075 g, 0.16 mmol), tert-butyl (3S,4R)-4-amino-3-fluoropiperidine-1-carboxylate (0.053 g, 0.24 mmol), DMA (2 mL), and DIEA (0.042 g, 0.33 mmol) was warmed to 70° C. overnight, then allowed to cool to room temperature. The mixture was diluted with EtOAc, washed with water/brine, dried over sodium sulfate and concentrated under reduced pressure. Flash chromatography (DCM:methanol, 0-35%) afforded tert-butyl (3S,4R)-3-fluoro-4-((8-((3-methyl-4-((1-methyl-1H-benzo[d]imidazol-5-yl)oxy)phenyl)amino)pyrimido[5,4-d]pyrimidin-2-yl)amino)piperidine-1-carboxylate (37 mg, 38%). m/z (APCI-pos) M+1=600.3.

Step B: A mixture of tert-butyl (3S,4R)-3-fluoro-4-((8-((3-methyl-4-((1-methyl-1H-benzo[d]imidazol-5-yl)oxy)phenyl)amino)pyrimido[5,4-d]pyrimidin-2-yl)amino)piperidine-1-carbon/late (0.038 g, 0.0634 mmol), DCM (1 mL) and TFA (50 equivalents) was stirred at room temperature for 1 hour. The mixture was diluted with EtOAc, washed with 10% aqueous potassium carbonate, dried over sodium sulfate and concentrated under reduced pressure to give N2-((3S,4R)-3-fluoropiperidin-4-yl)-N8-(3-methyl-4-((1- methyl-1H-benzo[d]imidazol-5-yl)oxy)phenyl)pyrimido[5,4-d]pyrimidine-2,8-diamine (25.8 mg, 82%). m/z (APCI-pos) M+1=500.2; ¹H NMR (400 MHz, (CD₃)₂SO) δ 9.35 (s, 1H), 9.00 (s, 1H), 8.36 (s, 1H), 8.14 (s, 1H), 7.97-7.75 (m, 2H), 7.72-7.65 (m, 1H), 7.54 (d, J=8.6 Hz, 1H), 7.09-7.04 (m, 1H), 7.00-6.94 (m, 1H), 6.89 (d, J=8.6 Hz, 1H), 4.91-4.66 (m, 1H), 4.53-4.35 (m, 1H), 3.81 (s, 3H), 3.17-3.07 (m, 1H), 3.05-2.81 (m, 2H), 2.73-2.57 (m, 1H), 2.23 (s, 3H), 1.87-1.54 (m, 2H).

Example 84

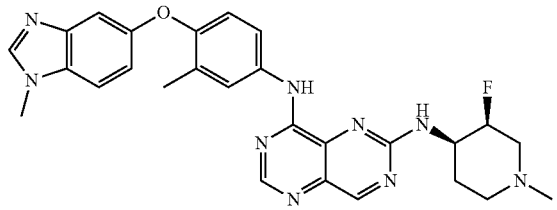 [SMILES: Cc1cc(Nc2ncnc3cnc(N[C@@H]4CCN(C)C[C@@H]4F)nc23)ccc1Oc1ccc2c(c1)ncn2C]

N2-((3S,4R)-3-fluoro-1-methylpiperidin-4-yl)-N8-(3-methyl-4-((1-methyl-1H-benzo[d]imidazol-5-yl)oxy)phenyl)pyrimido[5,4-d]pyrimidine-2,8-diamine In a pressure tube, a mixture of N2-((3S,4R)-3-fluoropiperidin-4-yl)-N8-(3-methyl-4-((1-methyl-1H-benzo[d]imidazol-5-yl)oxy)phenyl)pyrimido[5,4-d]pyrimidine-2,8-diamine (0.015 g, 0.030 mmol), formaldehyde (0.0171 g, 0.210 mmol), and formic acid (0.0138 g, 0.30 mmol) in methanol (0.5 mL) was warmed to 70° C. for 4 hours, then concentrated under reduced pressure. Reverse phase purification (5 to 95% ACN:water) and neutralization of the product fractions (10% aqueous potassium carbonate, extract with DCM) afforded N2-((3S,4R)-3-fluoro-1-methylpiperidin-4-yl)-N8-(3-methyl-4-((1-methyl-1H-benzo[d]imidazol-5-yl)oxy)phenyl)pyrimido[5,4-d]pyrimidine-2,8-diamine (4 mg, 26%). m/z (APCI-pos) M+1=514.2; ¹H NMR (400 MHz, CDCl₃) δ 9.04 (s, 1H), 8.65-8.30 (m, 3H), 7.86 (s, 1H), 7.75 (s, 1H), 7.60 (s, 1H), 7.37-7.28 (m, 4H), 7.15-7.01 (m, 1H), 6.96-6.89 (m, 1H), 5.79 (s, 1H), 4.89 (d, J=49.2 Hz, 1H), 4.33-4.06 (m, 1H), 3.85 (s, 3H), 3.29-3.22 (m, 1H), 3.03-2.95 (m, 1H), 2.55-1.80 (m, 9H), 1.28-1.23 (m, 2H).

Example 85

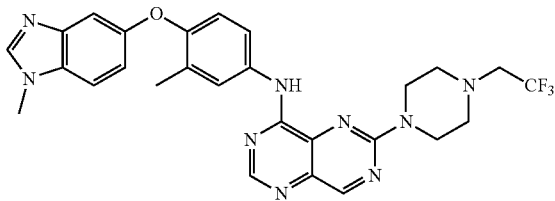 [SMILES: Cc1cc(Nc2ncnc3cnc(N4CCN(CC(F)(F)F)CC4)nc23)ccc1Oc1ccc2c(c1)ncn2C]

N-(3-methyl-4-((1-methyl-1H-benzo[d]imidazol-5-yl)oxy)phenyl)-6-(4-(2,2,2-trifluoroethyl)piperazin-1-yl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.108 mmol), 1-(2,2,2-trifluoroethyl)piperazine hydrochloride (0.0665 g, 0.325 mmol), DIEA (0.070 g, 0.542 mmol) in DMA (1 mL) was warmed to 80° C. for 20 hours, then allowed to cool to room temperature. The mixture was diluted with EtOAc, washed with water/brine, 10% aqueous potassium carbonate, dried over sodium sulfate and concentrated under reduced pressure. Flash chromatography (DCM to 20% MeOH/DCM) afforded N-(3-methyl-4-((1-methyl-1H-benzo[d]imidazol-5-yl)oxy)phenyl)-6-(4-(2,2,2-trifluoroethyl)piperazin-1-yl)pyrimido[5,4-d]pyrimidin-4-amine (51 mg, 86%). m/z (APCI-pos) M+1=550.2; ¹H NMR (400 MHz, (CD₃)₂SO) δ 9.58 (s, 1H), 8.40 (s, 1H), 8.17 (s, 1H), 7.84 (d, J=2.5 Hz, 1H), 7.77 (dd, J=8.7, 2.6 Hz, 1H), 7.57 (d, J=8.7 Hz, 1H), 7.09 (d, J=2.2 Hz, 1H), 6.89 (d, J=8.7 Hz, 1H), 4.06-3.97 (m, 4H), 3.84 (s, 3H), 3.32-3.13 (m, 2H), 2.81-2.72 (m, 4H), 2.26 (s, 3H).

Example 86

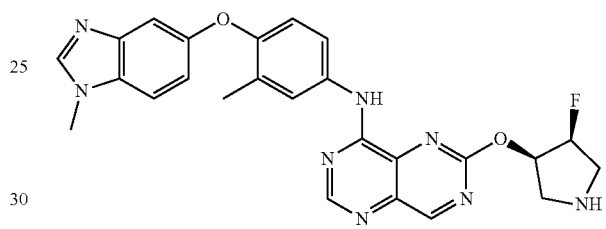

6-(((3R,4S)-4-fluoropyrrolidin-3-yl)oxy)-N-(3-methyl-4-((1-methyl-1H-benzo[d]imidazol-5-yl)oxy)phenyl)pyrimido[5,4-d]pyrimidin-4-amine Step A: NaH (0.013 g, 0.33 mmol, 60% dispersion in mineral oil) was added to a mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol) and tert-butyl (3S,4R)-3-fluoro-4-hydroxypyrrolidine-1-carboxylate (0.044 g, 0.22 mmol) in DMF (1 mL). The mixture was stirred at room temperature for 10 minutes and then warmed to 50° C. After about 45 minutes, LCMS indicated complete consumption of starting material. The mixture was allowed to cool to room temperature, then carefully quenched with water. This mixture was extracted with EtOAc, extracts washed with water/brine, dried over sodium sulfate and concentrated under reduced pressure to give tert-butyl (3S,4R)-3-fluoro-4-((8-((3-methyl-4-((1-methyl-1H-benzo[d]imidazol-5-yl)oxy)phenyl)amino)pyrimido[5,4-d]pyrimidin-2-yl)oxy)pyrrolidine-1-carboxylate (70 mg, 100%) that was used as is for the next reaction. m/z (APCI-pos) M+1=587.25.

Step B: A mixture of tert-butyl (3S,4R)-3-fluoro-4-((8-((3-methyl-4-((1-methyl-1H-benzo[d]imidazol-5-yl)oxy)phenyl)amino)pyrimido[5,4-d]pyrimidin-2-yl)oxy)pyrrolidine-1-carbon/late (0.070 g, 0.119 mmol), DCM (1 mL) and TFA (1 mL) was stirred at room temperature for 1 hour, then concentrated under reduced pressure. Reverse phase purification (5 to 95% ACN:water) and neutralization of the product fractions (10% aqueous potassium carbonate, extract with DCM) afforded 6-(((3R,4S)-4-fluoropyrrolidin-3-yl)oxy)-N-(3-methyl-4-((1-methyl-1H-benzo[d]imidazol-5-yl)oxy)phenyl)pyrimido[5,4-d]pyrimidin-4-amine (16.7 mg, 29%). m/z (APCI-pos) M+1=487.2; ¹H NMR (400

MHz, (CD$_3$)$_2$SO) δ 9.91 (s, 1H), 9.33 (s, 1H), 8.58 (s, 1H), 8.15 (s, 1H), 7.78 (s, 1H), 7.68 (d, J=8.9 Hz, 1H), 7.55 (d, J=8.5 Hz, 1H), 7.09 (s, 1H), 6.98 (d, J=7.4 Hz, 1H), 6.88 (d, J=9.0 Hz, 1H), 5.65-5.27 (m, 2H), 3.82 (s, 3H), 3.43-3.34 (m, 2H), 3.16-2.88 (m, 2H), 2.25 (s, 3H).

Example 87

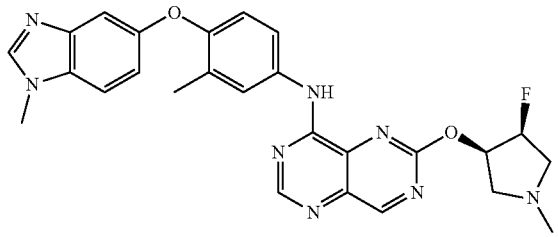 [SMILES: Cc1cc(Nc2ncnc3cnc(O[C@@H]4CN(C)C[C@@H]4F)nc23)ccc1Oc1ccc2c(c1)ncn2C]

6-(((3R,4S)-4-fluoro-1-methylpyrrolidin-3-yl)oxy)-N-(3-methyl-4-((1-methyl-1H-benzo[d]imidazol-5-yl)oxy)phenyl)pyrimido[5,4-d]pyrimidin-4-amine A mixture of 6-(((3R,4S)-4-fluoropyrrolidin-3-yl)oxy)-N-(3-methyl-4-((1-methyl-1H-benzo[d]imidazol-5-yl)oxy)phenyl)pyrimido[5,4-d]pyrimidin-4-amine (0.015 g, 0.0308 mmol), methanol (0.5 mL), formaldehyde (0.0175 g, 0.216 mmol, 37% aqueous solution), and formic acid (0.0142 g, 0.308 mmol) in a pressure tube was warmed to 70° C. for 5 hours, then concentrated under reduced pressure. Reverse phase purification (5 to 95% ACN:water) and neutralization of the product fractions (10% aqueous potassium carbonate, extract with DCM) afforded 6-(((3R,4S)-4-fluoro-1-methylpyrrolidin-3-yl)oxy)-N-(3-methyl-4-((1-methyl-1H-benzo[d]imidazol-5-yl)oxy)phenyl)pyrimido[5,4-d]pyrimidin-4-amine (10.8 mg, 70%). m/z (APCI-pos) M$^+$1=501.3; $^1$H NMR (400 MHz, (CD$_3$)$_2$SO) δ 9.95 (s, 1H), 9.34 (s, 1H), 8.60 (s, 1H), 7.80 (s, 1H), 7.70 (d, J=8.5 Hz, 1H), 7.57 (d, J=8.7 Hz, 1H), 7.11 (s, 1H), 7.01 (d, J=8.7 Hz, 1H), 6.90 (d, J=8.7 Hz, 1H), 5.96-5.37 (m, 2H), 3.84 (s, 3H), 3.12-2.68 (m, 4H), 2.36 (s, 3H), 2.27 (s, 3H).

Example 88

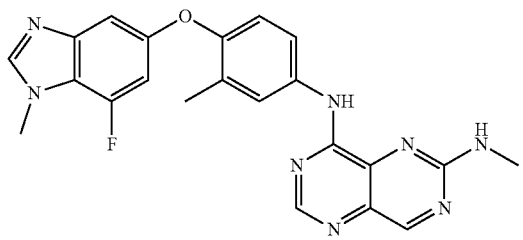 [SMILES: CNc1ncc2ncnc(Nc3ccc(Oc4cc(F)c5c(c4)ncn5C)c(C)c3)c2n1]

N8-(4-((7-fluoro-1-methyl-1H-benzo[d]imidazol-5-yl)oxy)-3-methylphenyl)-N2-methylpyrimido[5,4-d]pyrimidine-2,8-diamine Step A: A 20-mL vial was charged with N-(4-((7-fluoro-1-methyl-1H-benzo[d]imidazol-5-yl)oxy)-3-methylphenyl)-6-(methylthio)pyrimido[5,4-d]pyrimidin-4-amine (0.609 g, 1.36 mmol), acetonitrile (9.07 mL, 1.36 mmol) and water (4.54 mL, 1.36 mmol). Potassium peroxymonosulfate (0.795 g, 1.29 mmol) was added, and the vial was capped and stirred at ambient temperature for 30 minutes. The mixture was diluted with water and saturated aqueous Na$_2$S$_2$O$_3$, and then extracted with 20% IPA/CHCl$_3$ (3×). The combined organic extracts were washed with brine, dried over Na$_2$SO$_4$, filtered and concentrated. The crude product was then purified via column chromatography (24 G Isco RediSep Gold, particle size: 20 to 40 microns, 30 mL/min, 1-6% MeOH/CHCl$_3$) to afford N-(4-((7-fluoro-1-methyl-1H-benzo[d]imidazol-5-yl)oxy)-3-methylphenyl)-6-(methylsulfinyl)pyrimido[5,4-d]pyrimidin-4-amine (452 mg, 72%). m/z (APCI-pos) M$^+$1=464.2.

Step B: A mixture of N-(4-((7-fluoro-1-methyl-1H-benzo[d]imidazol-5-yl)oxy)-3-methylphenyl)-6-(methylsulfinyl)pyrimido[5,4-d]pyrimidin-4-amine (0.050 g, 0.11 mmol), N,O-dimethylhydroxylamine hydrochloride (0.053 g, 0.54 mmol), DIEA (0.084 g, 0.65 mmol) in DMA (1 ML) was warmed to 80° C. for 16 hours, then allowed to cool to room temperature. LCMS indicated a clean reaction to give a product with a mass corresponding to the mono methyl amine and no desired product observed. The mixture was diluted with EtOAc, washed with water/brine, 10% aqueous potassium carbonate, dried over sodium sulfate and concentrated under reduced pressure. Reverse phase purification (5 to 95% ACN:water) and neutralization of the product fractions (10% aqueous potassium carbonate, extract with DCM) afforded N8-(4-((7-fluoro-1-methyl-1H-benzo[d]imidazol-5-yl)oxy)-3-methylphenyl)-N2-methylpyrimido[5,4-d]pyrimidine-2,8-diamine (35 mg, 75%). m/z (APCI-pos) M$^+$1=431.2; $^1$H NMR (400 MHz, (CD$_3$)$_2$SO) δ 9.39 (s, 1H), 8.99 (s, 1H), 8.40 (s, 1H), 8.17 (s, 1H), 7.97-7.67 (m, 3H), 6.98 (d, J=8.7 Hz, 1H), 6.90-6.82 (m, 2H), 3.96 (s, 3H), 3.04 (d, J=4.6 Hz, 3H), 2.23 (s, 3H).

Example 89

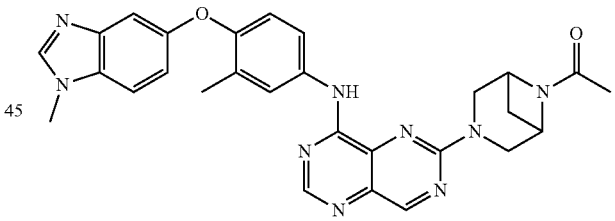

1-(3-(8-((3-methyl-4-((1-methyl-1H-benzo[d]imidazol-5-yl)oxy)phenyl)amino)pyrimido[5,4-d]pyrimidin-2-yl)-3,6-diazabicyclo[3.1.1]heptan-6-yl)ethan-1-one Step A: A mixture of tert-butyl 3,6-diazabicyclo[3.1.1]heptane-3-carboxylate (0.21 g, 1.06 mmol), dry DCM (10 mL), DIEA (0.274 g, 2.12 mmol), and a crystal of DMAP was chilled to 0° C. Aacetic anhydride (0.130 g, 1.27 mmol) was added to this mixture. The mixture stirred at 0° C. for 10 minutes, then allowed to warm to room temperature and stirred for 16 hours. The mixture was then diluted with DCM, washed with 10% aqueous potassium carbonate, dried over sodium sulfate and concentrated under reduced pressure to give tert-butyl 6-acetyl-3,6-diazabicyclo[3.1.1]heptane-3-carboxylate (223 mg, 88%). $^1$H NMR (400 MHz, CDCl$_3$) δ 4.57-4.21 (m, 2H), 4.00-3.86 (m, 1H), 3.78-3.34 (m, 3H), 2.71-2.61 (m, 1H), 1.92 (s, 3H), 1.60-1.52 (m, 1H), 1.48 (s, 9H).

Step B: A round bottom flask containing tert-butyl 6-acetyl-3,6-diazabicyclo[3.1.1]heptane-3-carboxylate (0.223 g, 0.928 mmol) was stirred with 20 equivalents of 4M HCl/dioxane for 2 hours, then concentrated under reduced pressure to give a quantitative yield of 1-(3,6-diazabicyclo[3.1.1]heptan-6-yl)ethan-1-one hydrochloride. This material was used as is in the next step.

Step C: A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol), diazabicyclo[3.1.1]heptan-6-yl)ethan-1-one hydrochloride (0.096 g, 0.54 mmol), and DIEA (0.098 g, 0.76 mmol) in DMA (1 mL) was warmed to 100° C. for 16 hours, then allowed to cool to room temperature. The mixture was diluted with EtOAc, washed with brine, water, dried over sodium sulfate and concentrated under reduced pressure. Reverse phase purification (5 to 95% ACN:water) and neutralization of the product fractions (10% aqueous potassium carbonate, extract with DCM) afforded 1-(3-(8-((3-methyl-4-((1-methyl-1H-benzo[d]imidazol-5-yl)oxy)phenyl)amino)pyrimido[5,4-d]pyrimidin-2-yl)-3,6-diazabicyclo[3.1.1]heptan-6-yl)ethan-1-one (1.5 mg, 2.7%). m/z (APCI-pos) M$^+$1=522.2.

Example 90

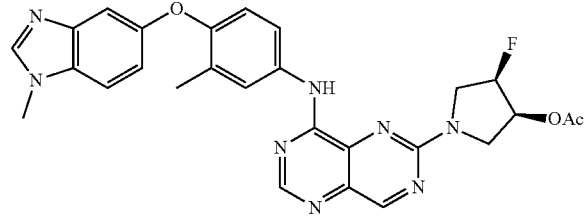 [SMILES: CC(=O)O[C@H]1CN(c2ncc3ncnc(Nc4ccc(Oc5ccc6c(c5)ncn6C)c(C)c4)c3n2)C[C@H]1F]

(3S,4R)-4-fluoro-1-(8-((3-methyl-4-((1-methyl-1H-benzo[d]imidazol-5-yl)oxy)phenyl)amino)pyrimido[5,4-d]pyrimidin-2-yl) pyrrolidin-3-yl acetate Step A: A mixture of tert-butyl (3R,4S)-3-fluoro-4-hydroxypyrrolidine-1-carboxylate (0.258 g, 1.26 mmol) in DCM (12 mL), a spatula tip of DMAP, and DIEA (0.325 g, 2.51 mmol) was chilled to 0° C. Ac$_2$O (0.154 g, 1.51 mmol) was add to the mixture. The mixture was stirred at 0° C. for 10 minutes, then allowed to warm to room temperature and stirred at room temperature overnight. The mixture was diluted with DCM, washed with 10% aqueous potassium carbonate, dried over sodium sulfate and concentrated under reduced pressure to give tert-butyl (3S,4R)-3-acetoxy-4-fluoropyrrolidine-1-carboxylate (287 mg, 92%). $^1$H NMR (400 MHz, CDCl$_3$) δ 5.30-4.95 (m, 2H), 3.89-3.49 (m, 3H), 3.39 (dt, J=19.8, 9.6 Hz, 1H), 2.14 (s, 3H), 1.47 (s, 9H).

Step B: TFA (2.63 g, 1.78 mL, 20 equivalents, 23.1 mmol) was added to a stirred solution of tert-butyl (3S,4R)-3-acetoxy-4-fluoropyrrolidine-1-carboxylate (0.285 g, 11.5 mL, 0.1 molar, 1 Eq, 1.15 mmol) in DCM (11 mL) and stirred at room temperature. After two hours, the mixture was concentrated under reduced pressure to give (3S,4R)-4-fluoropyrrolidin-3-yl acetate 2,2,2-trifluoroacetate (301 mg, quantitative yield). $^1$H NMR (400 MHz, CDCl$_3$) δ 5.52-5.17 (m, 2H), 3.89-3.55 (m, 3H), 3.56-3.39 (m, 1H), 2.16 (s, 3H).

Step C: (3S,4R)-4-Fluoropyrrolidin-3-yl acetate 2,2,2-trifluoroacetate (85 mg, 3 equivalents, 0.33 mmol) was added to a stirred solution of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 1.1 mL, 0.1 molar, 1 equivalents, 0.11 mmol) and DIEA (75 µL, 4 equivalents, 0.43 mmol) in DMSO. The reaction was partitioned between saturated NaCl and EtOAc. The organic layer was dried over sodium sulfate, filtered, and concentrated in vacuo. Reverse phase purification (5 to 95% ACN:water) and neutralization of the product fractions (10% aqueous potassium carbonate, extract with DCM) afforded (3S,4R)-4-fluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-yl acetate (0.040 g, 70%). m/z (APCI-pos) M$^+$1=529.3; $^1$H NMR (400 MHz, DMSO) δ 9.53 (s, 1H), 9.13 (s, 1H), 8.44 (s, 1H), 8.18 (s, 1H), 7.86 (d, J=2.6 Hz, 1H), 7.81 (dd, J=8.7, 2.7 Hz, 1H), 7.57 (d, J=8.7 Hz, 1H), 7.10 (d, J=2.3 Hz, 1H), 7.00 (dd, J=8.7, 2.3 Hz, 1H), 6.89 (d, J=8.7 Hz, 1H), 5.63-5.28 (m, 2H), 4.47-4.11 (m, 1H), 4.11-3.88 (m, 1H), 3.84 (s, 3H), 3.66 (m, 2H), 2.26 (s, 3H), 2.14 (s, 3H).

Example 91

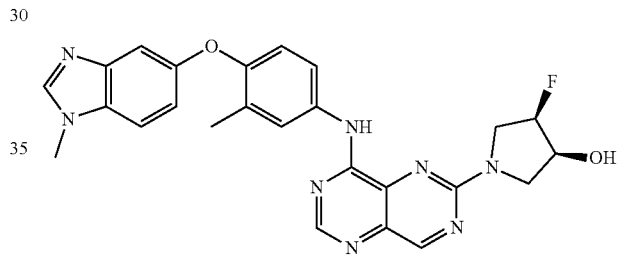

(3S,4R)-4-fluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol LiOH (6.3 mg, 0.13 mL, 2.0 molar, 0.26 mmol) was added to a stirred solution of (3S,4R)-4-fluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-yl acetate (35 mg, 0.66 mL, 0.1 molar, 66 µmol) in 1:1 MeOH/THF (1 mL), and the mixture was stirred at room temperature for 16 hours. The reaction was partitioned between water and EtOAc. The organic layer was dried over sodium sulfate, filtered, and concentrated under reduced pressure. Reverse phase purification (5 to 95% ACN:water) and neutralization of the product fractions (10% aqueous potassium carbonate, extract with DCM) afforded (3S,4R)-4-fluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (18.1 mg, 56%). m/z (APCI-pos) M$^+$1=487.2; $^1$H NMR (400 MHz, (CD$_3$)$_2$SO) δ 9.48 (s, 1H), 9.11 (s, 1H), 8.42 (s, 1H), 8.17 (s, 1H), 7.88 (d, J=2.7 Hz, 1H), 7.82 (dd, J=8.7, 2.7 Hz, 1H), 7.57 (d, J=8.6 Hz, 1H), 7.10 (d, J=2.3 Hz, 1H), 7.00 (dd, J=8.7, 2.3 Hz, 1H), 6.90 (d, J=8.7 Hz, 1H), 5.60 (d, J=6.3 Hz, 1H), 5.18 (d, J=54.5 Hz, 1H), 4.49-4.37 (m, 1H), 4.32-4.09 (m, 1H), 3.97-3.87 (m, 1H), 3.41 (d, J=17.2 Hz, 1H), 2.26 (s, 3H).

Example 92

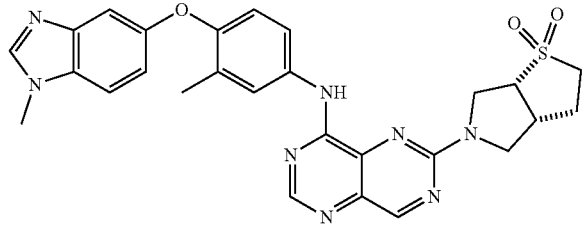

rac-(3aR,6aR)-5-(8-((3-methyl-4-((1-methyl-1H-benzo[d]imidazol-5-yl)oxy)phenyl)amino)pyrimido[5,4-d]pyrimidin-2-yl)hexahydro-2H-thieno[2,3-c]pyrrole 1,1-dioxide (3aR,6aR)-Hexahydro-2H-thieno[2,3-c]pyrrole 1,1-dioxide (35 mg, 0.22 mmol) was added to a stirred solution of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 1.1 mL, 0.1 molar, 0.11 mmol) and DIEA (42 mg, 57 µL, 0.33 mmol) in DMSO (1 mL). This mixture was warmed to 80° C. for 16 hours, then allowed to cool to room temperature. The reaction was partitioned between water and EtOAc. The organic layer was washed with water/brine, dried over sodium sulfate, filtered, and concentrated in vacuo. Reverse phase purification (5 to 95% ACN:water) and neutralization of the product fractions (10% aqueous potassium carbonate, extract with DCM) afforded rac-(3aR,6aR)-5-(8-((3-methyl-4-((1-methyl-1H-benzo[d]imidazol-5-yl)oxy)phenyl)amino)pyrimido[5,4-d]pyrimidin-2-yl)hexahydro-2H-thieno[2,3-c]pyrrole 1,1-dioxide (20 mg, 34%). m/z (APCI-pos) M$^+$1=543.2; $^1$H NMR (400 MHz, (CD$_3$)$_2$SO) δ 9.52 (s, 1H), 9.12 (s, 1H), 8.43 (s, 1H), 8.17 (s, 1H), 7.86 (d, J=2.4 Hz, 1H), 7.80 (dd, J=8.7, 2.6 Hz, 1H), 7.57 (d, J=8.7 Hz, 1H), 7.10 (d, J=2.2 Hz, 1H), 7.00 (dd, J=8.7, 2.3 Hz, 1H), 6.89 (d, J=8.7 Hz, 1H), 4.04-3.72 (m, 4H), 3.83 (s, 3H), 3.58-3.42 (m, 1H), 3.31-3.13 (m, 3H), 2.40-2.28 (m, 1H), 2.26 (s, 3H), 2.11-1.97 (1H, m).

Example 93

Example 93a

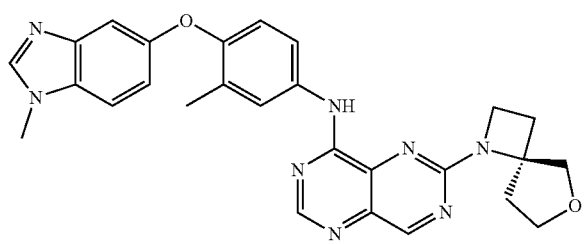

Example 93b

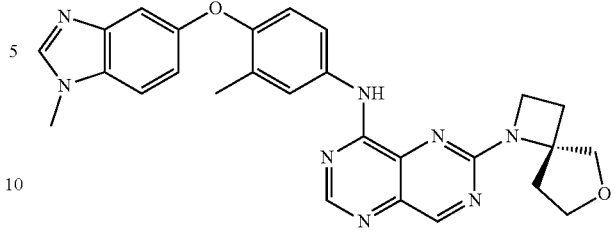

(S)—N-(3-methyl-4-((1-methyl-1H-benzo[d]imidazol-5-yl)oxy)phenyl)-6-(6-oxa-1-azaspiro[3.4]octan-1-yl)pyrimido[5,4-d]pyrimidin-4-amine and (R)—N-(3-methyl-4-((1-methyl-1H-benzo[d]imidazol-5-yl)oxy)phenyl)-6-(6-oxa-1-azaspiro[3.4]octan-1-yl)pyrimido[5,4-d]pyrimidin-4-amine N-(3-Methyl-4-((1-methyl-1H-benzo[d]imidazol-5-yl)oxy)phenyl)-6-(methylsulfonyl)pyrimido[5,4-d]pyrimidin-4-amine (0.300 g, 650 µmol) was added to a stirred solution of 6-oxa-1-azaspiro[3.4]octane HCl salt (292 mg, 1.95 mmol) and N-ethyl-N-isopropylpropan-2-amine (420 mg, 566 µL, 3.25 mmol) in DMA (6.50 mL). The mixture was heated at 120° C. for 30 minutes. The reaction was diluted with EtOAc. The organic layer was washed with brine (10×), dried over Na$_2$SO$_4$, and concentrated in vacuo. The crude residue was purified over 40 g silica cartridge, eluting with DCM/20% MeOH in DCM to afford rac-(R)—N-(3-methyl-4-((1-methyl-1H-benzo[d]imidazol-5-yl)oxy)phenyl)-6-(6-oxa-1-azaspiro[3.4]octan-1-yl)pyrimido[5,4-d]pyrimidin-4-amine (0.186 g, 376 µmol, 57.9%). Chiral chromatography (OJ-H (2×25 cm) 35% isopropanol (0.1% DEA)/CO$_2$, 100 bar) afforded Peak 1 (95 mg) and Peak 2 (96 mg) (>98% enantiomeric excess for both). Peak 1: m/z (APCI-pos) M$^+$1=495.25; $^1$H NMR (400 MHz, (CD$_3$)$_2$SO) δ 9.51-8.97 (m, 2H), 8.44 (s, 1H), 8.16 (s, 1H), 7.84 (d, J=2.4 Hz, 1H), 7.73 (s, 1H), 7.56 (d, J=8.7 Hz, 1H), 7.08 (d, J=2.2 Hz, 1H), 6.98 (dd, J=8.7, 2.3 Hz, 1H), 6.95-6.91 (m, 1H), 4.65-3.98 (m, 4H), 3.98-3.57 (m, 5H), 2.88-2.63 (m, 1H), 2.60-2.51 (m, 2H), 2.25 (s, 3H), 2.22-1.99 (m, 1H). Peak 2: m/z (APCI-pos) M$^+$1=495.30; $^1$H NMR (400 MHz, (CD$_3$)$_2$SO) δ 9.47-8.95 (m, 2H), 8.44 (s, 1H), 8.17 (s, 1H), 7.84 (d, J=2.4 Hz, 1H), 7.73 (s, 1H), 7.56 (d, J=8.7 Hz, 1H), 7.09 (d, J=2.1 Hz, 1H), 6.99 (dd, J=8.7, 2.2 Hz, 1H), 6.95-6.90 (m, 1H), 4.61-3.98 (m, 4H), 3.98-3.57 (m, 5H), 2.77-2.72 (m, 1H), 2.61-2.51 (m, 2H), 2.26 (s, 3H), 2.17-2.13 (m, 1H). Structures of enantiomers are arbitrarily assigned.

Example 94

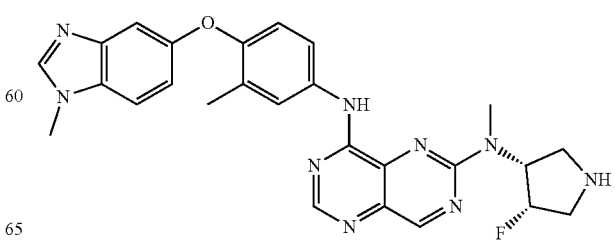

N2-((3R,4S)-4-fluoropyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine Step A: tert-Butyl (3S,4R)-3-fluoro-4-(methylamino)pyrrolidine-1-carboxylate (0.047 g, 0.22 mmol) was added to a stirred solution of N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol) and DIEA (38 μL, 0.22 mmol) in DMSO (1 mL), and the mixture was warmed to 100° C. overnight, then allowed to cool to room temperature. The reaction was partitioned between water and EtOAc. The organic layer was washed with water/brine, dried over sodium sulfate, filtered, and concentrated in vacuo. Flash chromatography (DCM and 20% DCM/MeOH/2% NH$_4$OH as the eluants) afforded tert-butyl (3S,4R)-3-fluoro-4-(methyl(8-((3-methyl-4-((1-methyl-1H-benzo[d]imidazol-5-yl)oxy)phenyl)amino)pyrimido[5,4-d]pyrimidin-2-yl)amino)pyrrolidine-1-carboxylate (14 mg, 22%). m/z (APCI-pos) M$^+$1=600.3.

Step B: TFA (53 mg, 36 μL, 0.47 mmol) was added to a stirred solution of tert-butyl (3S,4R)-3-fluoro-4-(methyl(8-((3-methyl-4-((1-methyl-1H-benzo[d]imidazol-5-yl)oxy)phenyl)amino)pyrimido[5,4-d]pyrimidin-2-yl)amino)pyrrolidine-1-carboxylate (14 mg, 0.23 mL, 0.1 molar, 23 μmol) and DCM (0.5 mL). This mixture was stirred at room temperature for 2 hours, then concentrated under reduced pressure. Reverse phase purification (5% ACN/95% water (TFA modifier, 0.1%) to 60% ACN/40% water) and neutralization of the product fractions (pool fractions in 10% aqueous potassium carbonate, extract with DCM) afforded N2-((3R,4S)-4-fluoropyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine (6.5 mg, 56%). m/z (APCI-pos) M$^+$1=500.2; $^1$H NMR (400 MHz, CD$_3$OD) δ 9.02 (s, 1H), 8.38 (s, 1H), 8.09 (s, 1H), 7.79 (s, 1H), 7.69 (d, J=7.7 Hz, 1H), 7.53 (d, J=8.2 Hz, 1H), 7.14-7.04 (m, 2H), 6.90 (d, J=7.6 Hz, 1H), 5.61-5.19 (m, 2H), 3.90 (s, 3H), 3.38 (s, 3H), 2.30 (s, 3H).

Example 95

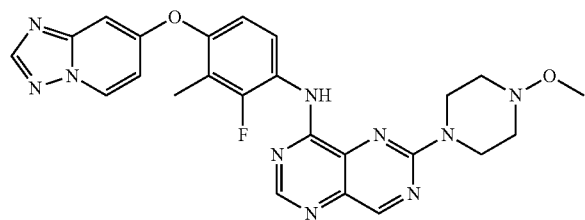 [SMILES: CON1CCN(c2ncc3ncnc(Nc4ccc(Oc5ccn6ncnc6c5)c(C)c4F)c3n2)CC1]

N-(4-([1,2,4]triazolo[1,5-a]pyridin-7-yloxy)-2-fluoro-3-methylphenyl)-6-(4-methoxypiperazin-1-yl)pyrimido[5,4-d]pyrimidin-4-amine Step A: [1,2,4]Triazolo[1,5-a]pyridin-7-ol (1.58 g, 11.7 mmol) was added to a stirred solution of 1,3-difluoro-2-methyl-4-nitrobenzene (2.03 g, 11.7 mmol) and Cs$_2$CO$_3$ (7.64 g, 23.5 mmol) in DMSO. The mixture was warmed to 80° C. for 16 hours, then allowed to cool to room temperature. The reaction was partitioned between water and EtOAc. The organic layer was washed with water/brine, dried over sodium sulfate, filtered, and concentrated in vacuo. Careful flash chromatography (DCM to 50% ethyl acetate/DCM) afforded 7-(3-fluoro-2-methyl-4-nitrophenoxy)-[1,2,4]triazolo[1,5-a]pyridine (415 mg, the more polar isomer). This material was confirmed by NMR studies to be the correct regioisomer. m/z (APCI-pos) M$^+$1=289.15.

Step B: A round bottom flask containing 7-(3-fluoro-2-methyl-4-nitrophenoxy)-[1,2,4]triazolo[1,5-a]pyridine (435 mg, 1.51 mmol) was charged with methanol (15 mL), followed by Pd(OH)$_2$/C (500 mg). The mixture was subjected to a balloon of hydrogen for 2 hours. Celite® was then added to the mixture, followed by methanol. The mixture was filtered through GF/F filter paper, filter cake rinsed, and the filtrate concentrated under reduced pressure to give 4-([1,2,4]triazolo[1,5-a]pyridin-7-yloxy)-2-fluoro-3-methylaniline (342 mg). m/z (APCI-pos) M$^+$1=259.10.

Step C: 4-([1,2,4]triazolo[1,5-a]pyridin-7-yloxy)-2-fluoro-3-methylaniline (342 mg, 1.32 mmol) was added to a stirred solution of 8-chloro-2-(methylthio)pyrimido[5,4-d]pyrimidine (282 mg, 1.32 mmol) in 2-propanol (13 mL). The mixture was warmed to 80° C. for 16 hours, then allowed to cool to room temperature. The mixture was concentrated under reduced pressure to give N-(4-([1,2,4]triazolo[1,5-a]pyridin-7-yloxy)-2-fluoro-3-methylphenyl)-6-(methylthio)pyrimido[5,4-d]pyrimidin-4-amine as a solid that was used as is in the next step. m/z (APCI-pos) M$^+$1=435.15.

Step D: An aqueous solution of oxone (1.22 g, 1.99 mmol) was added to a mixture of N-(4-([1,2,4]triazolo[1,5-a]pyridin-7-yloxy)-2-fluoro-3-methylphenyl)-6-(methylthio)pyrimido[5,4-d]pyrimidin-4-amine (575 mg, 1.32 mmol) in acetonitrile (13 mL, not fully soluble), and the mixture was stirred at room temperature. The mixture was stirred at room temperature for 24 hours. The mixture was diluted with water, extracted (2×) with 25% IPA/DCM, extracts dried over sodium sulfate and concentrated under reduced pressure. Flash chromatography (DCM to 70% MeOH/DCM) afforded N-(4-([1,2,4]triazolo[1,5-a]pyridin-7-yloxy)-2-fluoro-3-methylphenyl)-6-(methylsulfonyl)pyrimido[5,4-d]pyrimidin-4-amine (70 mg, 11%) and N-(4-([1,2,4]triazolo[1,5-a]pyridin-7-yloxy)-2-fluoro-3-methylphenyl)-6-(methylsulfinyl)pyrimido[5,4-d]pyrimidin-4-amine (100 mg, 17%). m/z (APCI-pos) M$^+$1=437.10 for sulfoxide and 467.10 for sulfone.

Step E: 1-Methoxypiperazine (25 mg, 0.21 mmol) was added to a stirred solution of N-(4-([1,2,4]triazolo[1,5-a]pyridin-7-yloxy)-2-fluoro-3-methylphenyl)-6-(methylsulfonyl)pyrimido[5,4-d]pyrimidin-4-amine (20 mg, 43 μmol) in DMSO (0.5 mL). The mixture was warmed to 70° C. for about 1.5 hours, then allowed to cool to room temperature. The reaction was partitioned between water and EtOAc. The organic layer was washed with brine/water, dried over sodium sulfate, filtered, and concentrated in vacuo. Flash chromatography (100% DCM to 50% DCM:50% of a 20% MeOH/DCM/2% NH$_4$OH solution) afforded N-(4-([1,2,4]triazolo[1,5-a]pyridin-7-yloxy)-2-fluoro-3-methylphenyl)-6-(4-methoxypiperazin-1-yl)pyrimido[5,4-d]pyrimidin-4-amine (17 mg, 79%). m/z (APCI-pos) M$^+$1=503.20; $^1$H NMR (400 MHz, (CD$_3$)$_2$SO) δ 9.62 (s, 1H), 9.13 (s, 1H), 8.98 (d, J=7.4 Hz, 1H), 8.41 (d, J=6.6 Hz, 2H), 7.84 (t, J=8.8 Hz, 1H), 7.14 (d, J=8.6 Hz, 1H), 7.07 (dd, J=7.4, 2.6 Hz, 1H), 6.94 (d, J=2.5 Hz, 1H), 4.80-4.75 (m, 2H), 3.51 (s, 3H), 3.42-3.27 (m, 4H), 2.58-2.48 (m, 2H), 2.17 (s, 3H).

Example 96

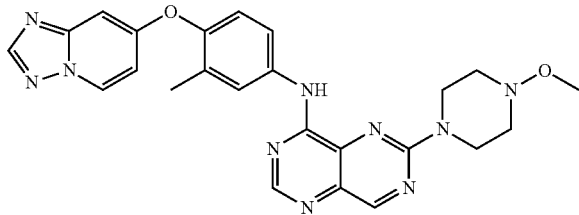 [SMILES: CON1CCN(c2ncc3ncnc(Nc4ccc(Oc5ccn6ncnc6c5)c(C)c4)c3n2)CC1]

N-(4-([1,2,4]triazolo[1,5-a]pyridin-7-yloxy)-3-methylphenyl)-6-(4-methoxypiperazin-1-yl)pyrimido[5,4-d]pyrimidin-4-amine Step A: 1-Fluoro-2-methyl-4-nitrobenzene (0.51 g, 3.3 mmol), [1,2,4]triazolo[1,5-a]pyridin-7-ol (0.40 g, 3.0 mmol), cesium carbonate (1.4 g, 4.4 mmol) and DMF (9.9 mL) were stirred at 50° C. for 45 minutes. The reaction was partitioned between water and EtOAc. The organic layer was dried over sodium sulfate, filtered, and concentrated in vacuo. The crude residue was purified over 40 g silica cartridge, eluting with a gradient of 100% DCM to 75% DCM:25% of a 20% MeOH/DCM solution to furnish 7-(2-methyl-4-nitrophenoxy)-[1,2,4]triazolo[1,5-a]pyridine (0.657 g, 2.43 mmol, 82%). m/z (APCI-pos) $M^+1$=271.15.

Step B: 7-(2-Methyl-4-nitrophenoxy)-[1,2,4]triazolo[1,5-a]pyridine (0.657 g, 2.43 mmol) was added to a mixture of THF/saturated aqueous $NH_4Cl$ (1:1) (24.3 mL, 0.1 molar, 2.43 mmol) and zinc (1.59 g, 24.3 mmol). The mixture was stirred at 25° C. for 3 hours. The reaction was partitioned between water and EtOAc. The aqueous layer was extracted three times with EtOAc, and then the combined organics were dried over sodium sulfate, filtered, and concentrated in vacuo to afford 4-([1,2,4]triazolo[1,5-a]pyridin-7-yloxy)-3-methylaniline (514 mg, 2.14 mmol, 88%). m/z (APCI-pos) $M^+1$=241.2.

Step C: 8-Chloro-2-(methylthio)pyrimido[5,4-d]pyrimidine (482 mg, 2.27 mmol) was added to a stirred solution of 4-([1,2,4]triazolo[1,5-a]pyridin-7-yloxy)-3-methylaniline (0.545 g, 2.27 mmol) and propan-2-ol (9.07 mL, 0.25 molar, 2.27 mmol). The mixture was heated at 50° C. for 2.5 hours and then dry loaded onto silica gel and purified over 40 g silica cartridge, eluting with a gradient of 100% DCM to 75% DCM:25% of a 20% MeOH/DCM solution) to afford N-(4-([1,2,4]triazolo[1,5-a]pyridin-7-yloxy)-3-methylphenyl)-6-(methylthio)pyrimido[5,4-d]pyrimidin-4-amine (0.7 g, 2 mmol, 70%). m/z (APCI-pos) $M^+1$=417.2.

Step D: Oxone (1.5 g, 2.5 mmol) was added to a stirred solution of acetonitrile (69 mg, 11 mL), water (5.6 mL) and N-(4-([1,2,4]triazolo[1,5-a]pyridin-7-yloxy)-3-methylphenyl)-6-(methylthio)pyrimido[5,4-d]pyrimidin-4-amine (0.70 g, 1.7 mmol). The mixture was diluted with water and extracted 3 times with 25% $IPA/CHCl_3$. Organics were combined, dried over sodium sulfate, and concentrated in vacuo to furnish N-(4-([1,2,4]triazolo[1,5-a]pyridin-7-yloxy)-3-methylphenyl)-6-(methylsulfinyl)pyrimido[5,4-d]pyrimidin-4-amine and N-(4-([1,2,4]triazolo[1,5-a]pyridin-7-yloxy)-3-methylphenyl)-6-(methylsulfonyl)pyrimido[5,4-d]pyrimidin-4-amine (0.440 g, 1.02 mmol and 61%). This material was carried on crude. m/z (APCI-pos) $M^+1$=433.15 for sulfoxide and 449.10 for sulfone.

Step E: 1-Methoxypiperazine (82 mg, 0.70 mmol) was added to a stirred solution of N-(4-([1,2,4]triazolo[1,5-a]pyridin-7-yloxy)-3-methylphenyl)-6-(methylsulfonyl)pyrimido[5,4-d]pyrimidin-4-amine (63 mg, 0.14 mmol) in DMSO (2 mL). The mixture was warmed to 80° C. for 2 hours, then allowed to cool to room temperature. The reaction mixture was partitioned between water and EtOAc. The organic layer was washed with water/brine, dried over sodium sulfate, filtered, and concentrated in vacuo. Flash chromatography (100% DCM to 50% DCM: 50% of a 20% MeOH/DCM/2% $NH_4OH$ solution) afforded N-(4-([1,2,4]triazolo[1,5-a]pyridin-7-yloxy)-3-methylphenyl)-6-(4-methoxypiperazin-1-yl)pyrimido[5,4-d]pyrimidin-4-amine (50 mg, 73%). m/z (APCI-pos) $M^+1$=485.2; $^1$H NMR (400 MHz, $CDCl_3$) δ 9.07 (s, 1H), 8.58 (d, J=7.4 Hz, 2H), 8.50 (d, J=7.4 Hz, 1H), 8.22 (s, 1H), 7.89-7.80 (m, 2H), 7.13 (d, J=8.6 Hz, 1H), 6.93-6.82 (m, 3H), 4.88-4.62 (m, 2H), 3.62 (s, 3H), 3.43-3.38 (m, 4H), 2.71-2.66 (m, 2H), 2.27 (s, 3H).

Example 97

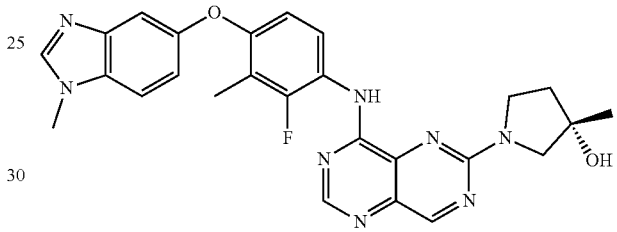

(S)-1-(8-((2-fluoro-3-methyl-4-((1-methyl-1H-benzo[d]imidazol-5-yl)oxy)phenyl)amino)pyrimido[5,4-d]pyrimidin-2-yl)-3-methylpyrrolidin-3-ol Step A: Oxone (582 mg, 946 μmol) (as a solution in 5 mL water) was added to a stirred solution of N-(2-fluoro-3-methyl-4-((1-methyl-1H-benzo[d]imidazol-5-yl)oxy)phenyl)-6-(methylthio)pyrimido[5,4-d]pyrimidin-4-amine (0.605 g, 13.5 mL, 0.1 molar, 1 Eq, 1.35 mmol) in acetonitrile (9 mL) at ambient temperature under air. After 1 hour, an additional 0.2 equivalents of oxone (0.7 equivalent total) was added to the reaction mixture in a solution of water (2 mL). After 2 hours, the reaction mixture was diluted with water and extracted with $CHCl_3$ (3×). The combined organic layers were washed with brine, dried via $Na_2SO_4$, and concentrated to afford N-(2-fluoro-3-methyl-4-((1-methyl-1H-benzo[d]imidazol-5-yl)oxy)phenyl)-6-(methylsulfinyl)pyrimido[5,4-d]pyrimidin-4-amine (0.665 g, 1.43 mmol, 106%). m/z (APCI-pos) $M^+1$=464.2.

Step B: (S)-3-Methylpyrrolidin-3-ol hydrochloride (30 mg, 0.22 mmol) was added to a stirred solution of N-(2-fluoro-3-methyl-4-((1-methyl-1H-benzo[d]imidazol-5-yl)oxy)phenyl)-6-(methylsulfinyl)pyrimido[5,4-d]pyrimidin-4-amine (20 mg, 0.43 mL, 0.1 molar, 43 μmol) and DIEA (38 μL, 0.22 mmol) in DMSO (0.5 mL). The mixture was warmed to 80° C. for 4 hours, then allowed to cool to room temperature. The reaction was partitioned between water and EtOAc. The organic layer was washed with water/brine, dried over sodium sulfate, filtered, and concentrated in vacuo. Flash chromatography (100% DCM to 50% DCM: 50% of a 20% MeOH/DCM/2% $NH_4OH$ solution) afforded (S)-1-(8-((2-fluoro-3-methyl-4-((1-methyl-1H-benzo[d]imidazol-5-yl)oxy)phenyl)amino)pyrimido[5,4-d]pyrimidin-2- yl)-3-methylpyrrolidin-3-ol (13.1 mg, 61%). m/z (APCI-pos) M$^+$1=501.3; $^1$H NMR (400 MHz, CDCl$_3$) δ 9.18-8.77 (m, 2H), 8.54-8.44 (m, 2H), 7.86 (s, 1H), 7.34 (s, 2H), 7.09-7.02 (m, 2H), 6.77-6.70 (m, 1H), 4.03-3.47 (m, 7H), 2.43-1.86 (m, 5H), 1.58 (s, 3H).

Example 98

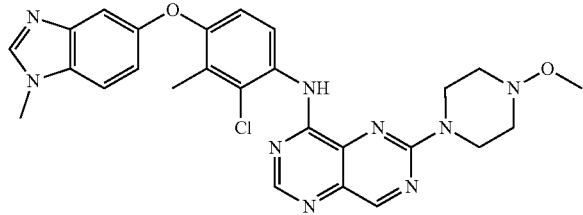 [SMILES: CON1CCN(c2ncc3ncnc(Nc4ccc(Oc5ccc6c(c5)ncn6C)c(C)c4Cl)c3n2)CC1]

N-(2-chloro-3-methyl-4-((1-methyl-1H-benzo[d]imidazol-5-yl)oxy)phenyl)-6-(4-methoxypiperazin-1-yl)pyrimido[5,4-d]pyrimidin-4-amine Step A: Cs$_2$CO$_3$ (4.16 g, 12.8 mmol) was added to a stirred solution of 2-chloro-4-fluoro-3-methyl-1-nitrobenzene (1.21 g, 6.38 mmol) and 1-methyl-1H-benzo[d]imidazol-5-ol (946 mg, 6.38 mmol) in DMA (65 mL). The mixture was warmed to 80° C. for 2 hours, then allowed to cool to room temperature. The reaction was partitioned between water and EtOAc. The organic layer was washed with water/brine (2×), dried over sodium sulfate, filtered, and concentrated in vacuo. Flash chromatography (80 g RediSep column, DCM to 10% MeOH/DCM/1% NH$_4$OH) afforded 5-(3-chloro-2-methyl-4-nitrophenoxy)-1-methyl-1H-benzo[d]imidazole (1.76 g, 87%). m/z (APCI-pos) M$^+$1=318.1.

Step B: Zinc (514 mg, 7.87 mmol) was added to a stirred solution of 5-(3-chloro-2-methyl-4-nitrophenoxy)-1-methyl-1H-benzo[d]imidazole (250 mg, 787 μmol) in THF (8 mL) and saturated ammonium chloride solution (8 mL). This mixture was stirred at room temperature for about 2.5 hours. The mixture was diluted with water/EtOAc, and this mixture was filtered through GF/F filter paper. The filtrate was extracted with EtOAc, extracts dried over sodium sulfate and concentrated under reduced pressure to give 2-chloro-3-methyl-4-((1-methyl-1H-benzo[d]imidazol-5-yl)oxy)aniline (53 mg, 23%). m/z (APCI-pos) M$^+$1=288.15.

Step C: 2-Chloro-3-methyl-4-((1-methyl-1H-benzo[d]imidazol-5-yl)oxy)aniline (54 mg, 0.19 mmol) was added to a stirred solution of 8-chloro-2-(methylthio)pyrimido[5,4-d]pyrimidine (40 mg, 0.19 mmol) in IPA (2 mL). The mixture was warmed to 80° C. for about 4 hours, then concentrated under reduced pressure. Reverse phase purification (5 to 95% ACN:water) and neutralization of the product fractions (10% aqueous potassium carbonate, extract with DCM) afforded N-(2-chloro-3-methyl-4-((1-methyl-1H-benzo[d]imidazol-5-yl)oxy)phenyl)-6-(methylthio)pyrimido[5,4-d]pyrimidin-4-amine (27 mg, 31%). m/z (APCI-pos) M$^+$1=464.10. Step D: Oxone (54 mg, 87 μmol) in water (1 mL) was added to a stirred slurry of N-(2-chloro-3-methyl-4-((1-methyl-1H-benzo[d]imidazol-5-yl)oxy)phenyl)-6-(methylthio)pyrimido[5,4-d]pyrimidin-4-amine (27 mg, 58 μmol) in acetonitrile (1 mL) at room temperature for 16 hours. The reaction was partitioned between water and 25% IPA/DCM. The organic layer was dried over sodium sulfate, filtered, and concentrated in vacuo to give 24 mg of product that is a mixture of N-(2-chloro-3-methyl-4-((1-methyl-1H-benzo[d]imidazol-5-yl)oxy)phenyl)-6-(methylsulfinyl)pyrimido[5,4-d]pyrimidin-4-amine and N-(2-chloro-3-methyl-4-((1-methyl-1H-benzo[d]imidazol-5-yl)oxy)phenyl)-6-(methylsulfonyl)pyrimido[5,4-d]pyrimidin-4-amine. This material was carried on as is. m/z (APCI-pos) M$^+$1=480.0 (sulfoxide) and 496.1 (sulfone).

Step E: 1-Methoxypiperazine (28 mg, 0.24 mmol) was added to a stirred solution of N-(2-chloro-3-methyl-4-((1-methyl-1H-benzo[d]imidazol-5-yl)oxy)phenyl)-6-(methylsulfonyl)pyrimido[5,4-d]pyrimidin-4-amine/N-(2-chloro-3-methyl-4-((1-methyl-1H-benzo[d]imidazol-5-yl)oxy)phenyl)-6-(methylsulfinyl)pyrimido[5,4-d]pyrimidin-4-amine (24 mg, 48 μmol) in DMSO (0.5 mL). The mixture was warmed to 80° C. for 2 hours, then allowed to cool to room temperature. The reaction was partitioned between water and EtOAc. The organic layer was washed with water/brine, dried over sodium sulfate, filtered, and concentrated in vacuo.

Flash chromatography (100% DCM to 50% DCM: 50% of a 20% MeOH/DCM/2% NH$_4$OH solution) afforded N-(2-chloro-3-methyl-4-((1-methyl-1H-benzo[d]imidazol-5-yl)oxy)phenyl)-6-(4-methoxypiperazin-1-yl)pyrimido[5,4-d]pyrimidin-4-amine (10.6 mg, 41%). m/z (APCI-pos) M$^+$1=532.2; $^1$H NMR (400 MHz, CDCl$_3$) δ 9.39 (s, 1H), 9.06 (s, 1H), 8.69 (d, J=9.1 Hz, 1H), 8.55 (s, 1H), 7.86 (s, 1H), 7.38-7.28 (m, 2H), 7.13-6.84 (m, 2H), 4.92-4.62 (m, 2H), 3.85 (s, 3H), 3.62 (s, 3H), 3.53-3.25 (m, 4H), 2.85-2.55 (m, 2H), 2.42 (s, 3H).

Example 99

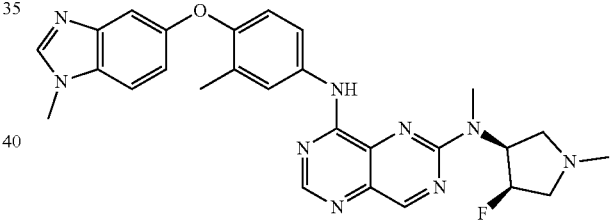

N2-((3S,4R)-4-fluoro-1-methylpyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine Step A: Benzyl chloroformate (708 mg, 592 μL, 3.94 mmol) was added to a stirred solution of tert-butyl (3S,4R)-3-amino-4-fluoropyrrolidine-1-carboxylate (671 mg, 0.1 molar, 3.29 mmol) and DIEA (1.14 mL, 6.57 mmol) in dry DCM (33 mL) at 0° C. The mixture was allowed to warm to room temperature overnight. The mixture was diluted with DCM, washed with 10% aqueous potassium carbonate, dried over sodium sulfate and concentrated under reduced pressure to give tert-butyl (3S,4R)-3-(((benzyloxy)carbonyl)amino)-4-fluoropyrrolidine-1-carboxylate (1.1 g, 99%). $^1$H NMR (400 MHz, CDCl$_3$) δ 7.38-7.34 (m, 5H), 5.26-4.89 (m, 3H), 4.44-4.29 (m, 1H), 3.98-3.42 (m, 3H), 3.19-3.04 (m, 1H), 1.46 (s, 9H).

Step B: MeI (0.61 mL, 9.8 mmol) was added to a stirred solution of tert-butyl (3S,4R)-3-(((benzyloxy)carbonyl)amino)-4-fluoropyrrolidine-1-carboxylate (1.1 g, 3.3 mmol) and Cs$_2$CO$_3$ (3.2 g, 9.8 mmol) in DMF (33 mL). The mixture was stirred at room temperature over the weekend. The reaction was partitioned between water and EtOAc. The organic layer was washed with brine/water, dried over sodium sulfate, filtered, and concentrated in vacuo. Flash chromatography (10% ethyl acetate/heptane to 80% ethyl acetate/heptane) afforded tert-butyl (3S,4R)-3-(((benzyloxy) carbonyl)(methyl)amino)-4-fluoropyrrolidine-1-carboxylate (548 mg, 48%). $^1$H NMR (400 MHz, CDCl$_3$) δ 7.42-7.27 (m, 5H), 5.27-4.98 (m, 3H), 4.83-4.54 (m, 1H), 3.82-3.33 (m, 4H), 3.01 (s, 2H), 1.47 (s, 9H).

Step C: A round bottom flask equipped with a stir bar and containing tert-butyl (3S,4R)-3-(((benzyloxy)carbonyl) (methyl)amino)-4-fluoropyrrolidine-1-carboxylate (545 mg, 1.55 mmol) was charged with methanol (15 mL) and Pd(OH)$_2$/C (600 mg). The mixture was subjected to a balloon of hydrogen for 2 hours, and then the mixture was purged with nitrogen. Celite® (about 2 g) was then added along with methanol. The mixture was stirred for 5 minutes, and then filtered through GF/F filter paper. The filter cake was rinsed with methanol, and the filtrate concentrated under reduced pressure to give tert-butyl (3R,4S)-3-fluoro-4-(methylamino)pyrrolidine-1-carboxylate (271 mg, 80%).

Step D: A pressure tube equipped with a stir bar and containing tert-butyl (3R,4S)-3-fluoro-4-(methylamino)pyrrolidine-1-carboxylate (284 mg, 1.30 mmol) was charged with N-(3-methyl-4-((1-methyl-1H-benzo[d]imidazol-5-yl) oxy)phenyl)-6-(methylsulfonyl)pyrimido[5,4-d]pyrimidin-4-amine (200 mg, 0.433 mmol) and DMSO (4 mL). This mixture was warmed to 100° C. for 16 hours, then allowed to cool to room temperature. The mixture was diluted with water, extracted with EtOAc, extracts washed with water/brine, dried over sodium sulfate and concentrated under reduced pressure. Flash chromatography (100% DCM to 50% DCM: 50% of a 20% MeOH/DCM/2% NH$_4$OH solution) afforded material that contained product and other impurities. This material was subjected to DCM and 10 equivalents of TFA, stirred at room temperature for 2 hours, then concentrated under reduced pressure. Reverse phase purification (5 to 95% ACN:water) and neutralization of the product fractions (pool product fractions in 10% aqueous potassium carbonate, extracted with DCM) afforded N2-((3S,4R)-4-fluoropyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine (13.5 mg). m/z (APCI-pos) M$^+$1=500.3.

Step E: Formic acid (12 μL, 0.33 mmol) was added to a stirred solution of N2-((3S,4R)-4-fluoropyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine (11 mg, 22 μmol) and formaldehyde (16 μL, 37% weight, 0.22 mmol) in MeOH (0.5 mL) at 70° C. for 3 hours. The mixture was then diluted with EtOAc, washed with 10% aqueous potassium carbonate, dried over sodium sulfate and concentrated under reduced pressure. Flash chromatography (100% DCM to 50% DCM: 50% of a 20% MeOH/DCM/2% NH$_4$OH solution) afforded N2-((3S,4R)-4-fluoro-1-methylpyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine (7.8 mg, 69%). m/z (APCI-pos) M$^+$1=514.25; $^1$H NMR (400 MHz, (CD$_3$)$_2$SO) δ 9.55 (s, 1H), 9.11 (s, 1H), 8.55-8.01 (m, 2H), 7.92-7.41 (m, 3H), 7.26-6.72 (m, 3H), 5.97-4.93 (m, 3H), 3.84 (s, 3H), 2.33 (s, 3H).

Example 100

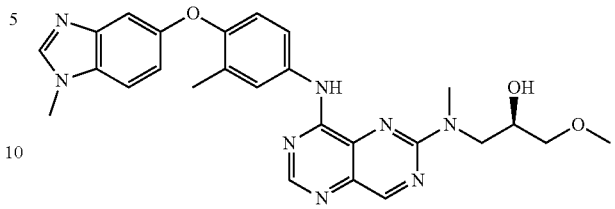

rac-(R)-1-methoxy-3-(methyl(8-((3-methyl-4-((1-methyl-1H-benzo[d]imidazol-5-yl)oxy)phenyl) amino)pyrimido[5,4-d]pyrimidin-2-yl)amino)propan-2-ol 1-Methoxy-3-(methylamino)propan-2-ol (32 mg, 0.27 mmol) was added to a stirred solution of N-(3-methyl-4-((1-methyl-1H-benzo[d]imidazol-5-yl)oxy)phenyl)-6-(methylsulfonyl)pyrimido[5,4-d]pyrimidin-4-amine (25 mg, 54 μmol) in DMSO (0.5 mL). The mixture was warmed to 80° C. for 16 hours, then allowed to cool to room temperature. The reaction was partitioned between water and EtOAc. The organic layer was dried over sodium sulfate, filtered, and concentrated in vacuo. Flash chromatography (100% DCM to 50% DCM: 50% of a 20% MeOH/DCM/2% NH$_4$OH solution) afforded rac-(R)-1-methoxy-3-(methyl(8-((3-methyl-4-((1-methyl-1H-benzo[d]imidazol-5-yl)oxy) phenyl)amino)pyrimido[5,4-d]pyrimidin-2-yl)amino)propan-2-ol (16.7 mg, 62%). m/z (APCI-pos) M$^+$1=501.3; $^1$H NMR (400 MHz, (CD$_3$)$_2$SO) δ 9.52-9.15 (m, 1H), 9.07 (s, 1H), 8.40 (s, 1H), 8.17 (s, 1H), 7.92-7.69 (m, 2H), 7.56 (d, J=8.7 Hz, 1H), 7.09 (d, J=2.2 Hz, 1H), 6.99 (dd, J=8.7, 2.3 Hz, 1H), 6.90 (d, J=8.7 Hz, 1H), 4.96 (d, J=5.4 Hz, 1H), 4.16-3.90 (m, 1H), 3.84 (s, 3H), 3.65 (dd, J=13.8, 7.6 Hz, 1H), 3.47-3.17 (m, 9H), 2.26 (s, 3H).

Example 101

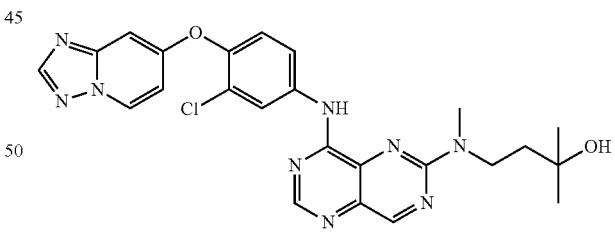

4-((8-((4-([1,2,4]triazolo[1,5-a]pyridin-7-yloxy)-3-chlorophenyl)amino)pyrimido[5,4-d]pyrimidin-2-yl) (methyl)amino)-2-methylbutan-2-ol 2-Methyl-4-(methylamino)butan-2-ol (26 mg, 0.22 mmol) was added to a stirred solution of N-(4-([1,2,4] triazolo[1,5-a]pyridin-7-yloxy)-3-chlorophenyl)-6-(methylsulfinyl)pyrimido[5,4-d]pyrimidin-4-amine (20 mg, 44 μmol) in DMSO (0.5 mL) at 100° C. for 16 hours, then allowed to cool to room temperature. The reaction was partitioned between water and EtOAc. The organic layer was dried over sodium sulfate, filtered, and concentrated in vacuo. Flash chromatography (100% DCM to 50% DCM: 50% of a 20% MeOH/DCM/2% NH₄OH solution) afforded 4-((8-((4-([1,2,4]triazolo[1,5-a]pyridin-7-yloxy)-3-chlorophenyl)amino)pyrimido[5,4-d]pyrimidin-2-yl)(methyl)amino)-2-methylbutan-2-ol (9.6 mg, 43%). m/z (APCI-pos) M⁺1=506.30; ¹H NMR (400 MHz, (CD₃)₂SO) δ 9.60 (s, 1H), 9.12 (s, 1H), 8.96 (d, J=7.5 Hz, 1H), 8.50 (s, 2H), 8.41 (s, 1H), 8.10 (s, 1H), 7.50 (d, J=8.9 Hz, 1H), 7.07 (dd, J=7.5, 2.6 Hz, 1H), 6.94 (d, J=2.4 Hz, 1H), 4.83-4.22 (m, 1H), 3.97-3.74 (m, 2H), 1.86-1.61 (m, 2H), 1.20 (s, 6H).

Example 102

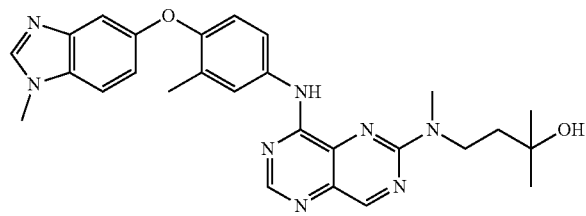 [SMILES: Cc1cc(Nc2ncnc3cnc(N(C)CCC(C)(C)O)nc23)ccc1Oc1ccc2c(c1)ncn2C]

2-methyl-4-(methyl(8-((3-methyl-4-((1-methyl-1H-benzo[d]imidazol-5-yl)oxy)phenyl)amino)pyrimido[5,4-d]pyrimidin-2-yl)amino)butan-2-ol 2-Methyl-4-(methylamino)butan-2-ol (25 mg, 0.22 mmol) was added to a stirred solution of N-(3-methyl-4-((1-methyl-3a,7a-dihydro-1H-benzo[d]imidazol-5-yl)oxy)phenyl)-6-(methylsulfonyl)pyrimido[5,4-d]pyrimidin-4-amine (20 mg, 43 μmol) in DMSO (0.5 mL) at 100° C. for 16 hours then allowed to cool to room temperature. The reaction was partitioned between water and EtOAc. The organic layer was dried over sodium sulfate, filtered, and concentrated in vacuo. Flash chromatography (100% DCM to 50% DCM: 50% of a 20% MeOH/DCM/2% NH₄OH solution) afforded 2-methyl-4-(methyl(8-((3-methyl-4-((1-methyl-1H-benzo[d]imidazol-5-yl)oxy)phenyl)amino)pyrimido[5,4-d]pyrimidin-2-yl)amino)butan-2-ol (16.2 mg, 75%). m/z (APCI-pos) M⁺1=499.35; ¹H NMR (400 MHz, (CD₃)₂SO) δ 9.33 (s, 1H), 9.07 (s, 1H), 8.40 (s, 1H), 8.16 (s, 1H), 7.89 (s, 1H), 7.78 (d, J=8.7 Hz, 1H), 7.56 (d, J=8.7 Hz, 1H), 7.09 (d, J=2.2 Hz, 1H), 6.99 (dd, J=8.7, 2.3 Hz, 1H), 6.89 (d, J=8.7 Hz, 1H), 4.74-4.11 (m, 1H), 3.94-3.73 (m, 5H), 2.26 (s, 3H), 1.80-1.61 (m, 2H), 1.20 (s, 6H).

Example 103

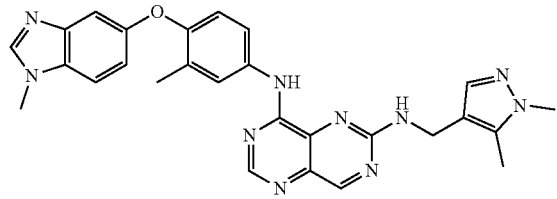 [SMILES: Cc1cc(Nc2ncnc3cnc(NCc4cnn(C)c4C)nc23)ccc1Oc1ccc2c(c1)ncn2C]

N2-((1,5-dimethyl-1H-pyrazol-4-yl)methyl)-N8-(3-methyl-4-((1-methyl-1H-benzo[d]imidazol-5-yl)oxy)phenyl)pyrimido[5,4-d]pyrimidine-2,8-diamine (1,5-Dimethyl-1H-pyrazol-4-yl)methanamine (20 mg, 0.16 mmol) was added to a stirred solution of N-(3-methyl-4-((1-methyl-3a,7a-dihydro-1H-benzo[d]imidazol-5-yl)oxy)phenyl)-6-(methylsulfonyl)pyrimido[5,4-d]pyrimidin-4-amine (25 mg, 54 μmol) in DMSO (0.5 mL) at 100° C. for 16 hours, then allowed to cool to room temperature. The reaction was partitioned between water and EtOAc. The organic layer was dried over sodium sulfate, filtered, and concentrated in vacuo. Flash chromatography (100% DCM to 50% DCM: 50% of a 20% MeOH/DCM/2% NH₄OH solution) afforded N2-((1,5-dimethyl-1H-pyrazol-4-yl)methyl)-N8-(3-methyl-4-((1-methyl-1H-benzo[d]imidazol-5-yl)oxy)phenyl)pyrimido[5,4-d]pyrimidine-2,8-diamine (17.7 mg, 65%). m/z (APCI-pos) M⁺1=507.30; ¹H NMR (400 MHz, (CD₃)₂SO) δ 9.43 (s, 1H), 8.98 (s, 1H), 8.40 (s, 1H), 8.17 (s, 1H), 8.09 (s, 1H), 7.80 (d, J=7.8 Hz, 1H), 7.56 (d, J=8.7 Hz, 1H), 7.40 (s, 1H), 7.10 (d, J=2.2 Hz, 1H), 6.99 (s, 1H), 6.90 (d, J=8.8 Hz, 1H), 4.54 (d, J=4.5 Hz, 2H), 3.84 (s, 3H), 3.67 (s, 3H), 2.30 (s, 3H), 2.26 (s, 3H).

Example 104

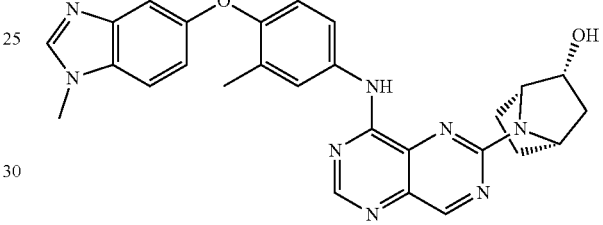

±(1R,2R,4S)-7-(8-((3-methyl-4-((1-methyl-1H-benzo[d]imidazol-5-yl)oxy)phenyl)amino)pyrimido[5,4-d]pyrimidin-2-yl)-7-azabicyclo[2.2.1]heptan-2-ol DIEA (0.14 mL, 0.80 mmol) was added neat by syringe to a stirred solution of N-(3-methyl-4-((1-methyl-1H-benzo[d]imidazol-5-yl)oxy)phenyl)-6-(methylsulfonyl)pyrimido[5,4-d]pyrimidin-4-amine (46 mg, 0.10 mmol) and ±(1S,2S,4R)-7-azabicyclo[2.2.1]heptan-2-ol (45 mg, 0.40 mmol) in DMSO (1 mL) at room temperature in a capped reaction vial. The reaction was capped and heated to 80° C. for 16 hours. At that time, LC/MS showed a large peak with desired product mass. The reaction was cooled to room temperature and partitioned between water (15 mL) and ethyl acetate (15 mL). The organic layer was isolated and washed again with brine (15 mL). The organics were re-isolated, dried over magnesium sulfate, filtered, and concentrated in vacuo. The crude residue was loaded in a minimum of dichloromethane onto a 4 gram Redisep gold silica gel column prewet with dichloromethane and eluted with a dichloromethane/methanol/0.1% NH₄OH gradient (0% to 10% methanol with 0.1% NH₄OH). After some very early eluting material, a couple of small peaks eluted followed by a main peak. TLC in 9/1 dichloromethane/methanol showed two clean fractions of the main peak that were pooled and concentrated to afford ±(1R,2R,4S)-7-(8-((3-methyl-4-((1-methyl-1H-benzo[d]imidazol-5-yl)oxy)phenyl)amino)pyrimido[5,4-d]pyrimidin-2-yl)-7-azabicyclo[2.2.1]heptan-2-ol (27 mg, 55 μmol, 55%) as a solid. m/z (esi) M⁺1=495.3; ¹H NMR (400 MHz, CDCl₃) δ 9.05 (s, 1H), 8.55 (s, 1H), 8.52 (br s, 1H), 7.85 (s, 1H), 7.74 (d, J=2.7 Hz, 1H), 7.65 (dd, J=8.7, 2.7 Hz, 1H), 7.38-7.28 (m, 2H), 7.06 (dd, J=8.7, 2.3 Hz, 1H), 6.93 (d, J=8.7 Hz, 1H), 4.82 (dt, J=10.2, 4.9 Hz, 2H), 4.58-4.38 (m, 1H), 3.85 (s, 3H), 2.46-2.25 (m, 2H), 2.44 (s, 3H), 1.80-1.66 (m, 2H), 1.36-1.16 (m, 2H).

Example 105

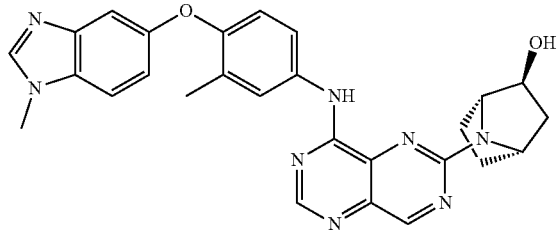 [SMILES: CC[C@@H]1[C@@H](O)C[C@H](C)N1c1ncc2ncnc(Nc3ccc(Oc4ccc5c(c4)ncn5C)c(C)c3)c2n1]

±(1R,2S,4S)-7-(8-((3-methyl-4-((1-methyl-1H-benzo [d]imidazol-5-yl)oxy)phenyl)amino)pyrimido[5,4-d] pyrimidin-2-yl)-7-azabicyclo[2.2.1]heptan-2-ol DIEA (0.14 mL, 0.80 mmol) was added neat by syringe to a stirred solution of N-(3-methyl-4-((1-methyl-1H-benzo [d]imidazol-5-yl)oxy)phenyl)-6-(methylsulfonyl)pyrimido [5,4-d]pyrimidin-4-amine (46 mg, 0.10 mmol) and ±(1S,2R, 4R)-7-azabicyclo[2.2.1]heptan-2-ol (45 mg, 0.40 mmol) in DMSO (1 mL) at room temperature in a capped reaction vial. The reaction was capped and heated to 80° C. for 16 hours. At that time, LC/MS showed a large peak with desired product mass. The reaction was cooled to room temperature and partitioned between water (15 mL) and ethyl acetate (15 mL). The organic layer was isolated and washed again with brine (15 mL). The organics were re-isolated, dried over magnesium sulfate, filtered, and concentrated in vacuo. The crude foam residue was loaded in a minimum of dichloromethane onto a 4 gram Redisep gold silica gel column prewet with dichloromethane and eluted with a dichloromethane/methanol/0.1% NH$_4$OH gradient (0% to 10% methanol with 0.1% NH$_4$OH). After some very early eluting material, a couple of small peaks eluted followed by a main peak. TLC of all fractions in 9/1 dichloromethane/methanol showed two clean fractions of the main peak that were pooled and concentrated to afford ±(1R,2S,4S)-7-(8-((3-methyl-4-((1-methyl-1H-benzo[d]imidazol-5-yl)oxy)phenyl)amino)pyrimido[5,4-d]pyrimidin-2-yl)-7-azabicyclo [2.2.1]heptan-2-ol (31 mg, 56 µmol, 57%, 90% purity) as a solid. m/z (esi) M$^+$1=495.3; $^1$H NMR (400 MHz, CDCl$_3$) δ 9.04 (s, 1H), 8.55 (s, 1H), 8.54 (s, 1H), 7.85 (s, 1H), 7.72 (dd, J=2.7, 0.8 Hz, 1H), 7.67-7.58 (m, 1H), 7.36-7.29 (m, 2H), 7.06 (dd, J=8.6, 2.3 Hz, 1H), 6.92 (d, J=8.7 Hz, 1H), 4.90 (td, J=5.1, 1.0 Hz, 1H), 4.80 (d, J=5.3 Hz, 1H), 4.07 (dd, J=7.0, 2.0 Hz, 1H), 3.84 (s, 3H), 2.34 (s, 3H), 2.05 (dd, J=13.3, 6.9 Hz, 1H), 1.82 (tdd, J=10.2, 6.5, 3.4 Hz, 2H), 1.52-1.33 (m, 2H).

Example 106

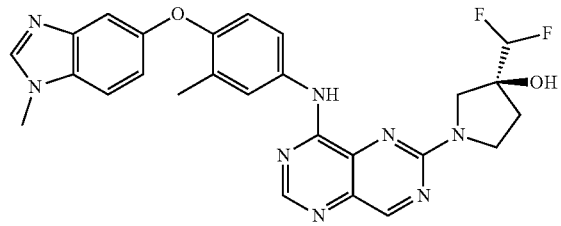 [SMILES: Cc1cc(Nc2ncnc3cnc(N4CC[C@@](O)(C(F)F)C4)nc23)ccc1Oc1ccc2c(c1)ncn2C]

rac-(R)-3-(difluoromethyl)-1-(8-((3-methyl-4-((1-methyl-1H-benzo[d]imidazol-5-yl)oxy)phenyl) amino)pyrimido[5,4-d]pyrimidin-2-yl)pyrrolidin-3-ol DIEA (0.14 mL, 0.80 mmol) was added neat by syringe to a stirred solution of N-(3-methyl-4-((1-methyl-1H-benzo [d]imidazol-5-yl)oxy)phenyl)-6-(methylsulfonyl)pyrimido [5,4-d]pyrimidin-4-amine (46 mg, 0.10 mmol) and ±3-(difluoromethyl)pyrrolidin-3-ol hydrochloride (69 mg, 0.40 mmol) in DMSO (1 mL) at room temperature in a reaction vial. The reaction was capped and heated to 80° C. for 16 hours. At that time, LC/MS showed a large peak with desired product mass. The reaction was cooled to room temperature and partitioned between water (15 mL) and ethyl acetate (15 mL). The organic layer was isolated and washed again with brine (15 mL). The organics were re-isolated, dried over magnesium sulfate, filtered, and concentrated in vacuo. The crude foam residue was loaded in a minimum of dichloromethane onto a 4 gram Redisep gold silica gel column prewet with dichloromethane and eluted with a dichloromethane/methanol/0.1% NH$_4$OH gradient (0% to 10% methanol with 0.1% NH$_4$OH). After some very early eluting material, a couple of small peaks eluted followed by a main peak. TLC of all fractions in 9/1 dichloromethane/methanol showed two clean fractions of the main peak that were pooled and concentrated to afford rac-(R)-3-(difluoromethyl)-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (45 mg, 87 µmol, 87%) as a solid. m/z (esi) M$^+$1=519.2; $^1$H NMR (400 MHz, CDCl$_3$) δ 9.00 (s, 1H), 8.52 (s, 1H), 8.47 (br s, 1H), 7.84 (s, 1H), 7.69 (d, J=2.7 Hz, 1H), 7.61 (dd, J=8.6, 2.7 Hz, 1H), 7.34-7.28 (m, 2H), 7.05 (dd, J=8.7, 2.3 Hz, 1H), 6.90 (d, J=8.7 Hz, 1H), 5.93 (t, J=55.8 Hz, 1H), 4.01 (s, 1H), 3.95 (m, 4H), 2.32 (s, 3H), 2.36-2.07 (m, 2H).

Example 107

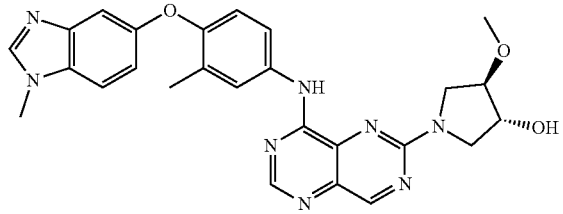 [SMILES: CO[C@@H]1CN(c2ncc3ncnc(Nc4ccc(Oc5ccc6c(c5)ncn6C)c(C)c4)c3n2)C[C@H]1O]

±(3R,4R)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol DIEA (0.14 mL, 0.81 mmol) was added to a stirred solution of ±(3R,4R)-4-methoxypyrrolidin-3-ol (47 mg, 0.40 mmol) and N-(3-methyl-4-((1-methyl-1H-benzo[d]imidazol-5-yl)oxy)phenyl)-6-(methylsulfinyl)pyrimido[5,4-d]pyrimidin-4-amine (45 mg, 0.10 mmol) in DMSO (1 mL) at room temperature in a capped reaction vial. The reaction was heated to 80° C. After 3 hours, LC/MS showed a clean LC peak with desired product mass. The reaction was cooled to room temperature and partitioned between water (15 mL) and ethyl acetate (15 mL). The organic layer was isolated and washed again with brine (15 mL). The organics were re-isolated, dried over magnesium sulfate, filtered, and concentrated in vacuo. The crude residue was purified over a 4 gram Redisep gold silica cartridge, eluting with a gradient of 0% to 10% methanol in dichloromethane to afford ±(3R,4R)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (3.4 mg, 6.5 µmol, 6.4%, 95% purity) as a solid. m/z (esi) M$^+$1=499.2; $^1$H NMR (400 MHz, CDCl$_3$) δ 9.03 (s, 1H), 8.54 (s, 1H), 8.52 (s, 1H), 7.84 (s, 1H), 7.72 (d, J=2.6 Hz, 1H), 7.63 (dd, J=8.7, 2.7 Hz, 1H), 7.35-7.29 (m, 2H), 7.06 (dd, J=8.7, 2.3 Hz, 1H), 6.92 (d, J=8.7 Hz, 1H), 4.56-4.44 (m, 1H), 4.00-3.73 (m, 5H), 3.84 (s, 3H), 3.46 (s, 3H), 2.34 (s, 3H).

Example 108

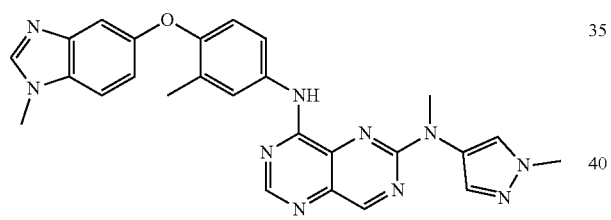

N2-methyl-N2-(1-methyl-1H-pyrazol-4-yl)-N8-(3-methyl-4-((1-methyl-1H-benzo[d]imidazol-5-yl)oxy)phenyl)pyrimido[5,4-d]pyrimidine-2,8-diamine N,1-dimethyl-1H-pyrazol-4-amine (8.13 mg, 73.2 µmol) was added to a stirred solution of N-(3-methyl-4-((1-methyl-1H-benzo[d]imidazol-5-yl)oxy)phenyl)-6-(methylsulfinyl)pyrimido[5,4-d]pyrimidin-4-amine (16.3 mg, 36.6 µmol) in IPA (180 µL) at room temperature in a capped reaction vial. The mixture was heated to 80° C. for 6 hours. LC/MS showed mostly starting sulfoxide but a small LC peak with desired product mass is apparent. After heating for 16 more hours, LC/MS showed further progress but still about a 1:1 ratio of desired and starting material. The reaction was cooled to room temperature, and the mixture was partitioned between dichloromethane (15 mL) and water (15 mL). The aqueous phase was isolated and extracted again with dichloromethane (15 mL). The combined organics were dried over magnesium sulfate, filtered, and concentrated in vacuo. The crude residue was dissolved in a minimum of dichloromethane and loaded onto a 4 gram Redisep gold silica gel column prewet with dichloromethane and eluted with a dichloromethane/methanol/0.01% NH$_4$OH gradient (0% to 10% methanol/0.01% NH$_4$OH). Fractions were thin layer chromatographed in 9/1 dichloromethane/methanol, and fractions of the main TLC band were pooled and concentrated to material corresponding to which appeared by LC/MS to be mostly desired product but with a small amount of starting material impurity present. This crude product was loaded in methanol (1 mL) onto a reverse phase HPLC and eluted with an acetonitrile/water/0.01% TFA gradient (5% to 95% acetonitrile). LC/MS identified fractions that contain what appears to be pure product. The fractions were pooled and partially concentrated to remove acetonitrile. The remaining aqueous solution was stirred and treated with saturated sodium carbonate until pH >10. The aqueous phase was then extracted with 9/1 dichloromethane/methanol (3×15 mL). TLC of the organic and aqueous phase confirmed all the UV active material was in the organics. The combined organics were dried over MgSO$_4$, filtered and concentrated to afford N2-methyl-N2-(1-methyl-1H-pyrazol-4-yl)-N8-(3-methyl-4-((1-methyl-1H-benzo[d]imidazol-5-yl)oxy)phenyl)pyrimido[5,4-d]pyrimidine-2,8-diamine (2.3 mg, 4.4 µmol, 12%, 95% purity) as an oil. m/z (esi) M$^+$1=493.3; $^1$H NMR (500 MHz, CDCl$_3$) δ 9.12 (s, 1H), 8.58 (s, 1H), 8.55 (s, 1H), 7.87 (s, 1H), 7.78-7.66 (m, 2H), 7.63 (d, J=8.1 Hz, 1H), 7.34 (d, J=14.0 Hz, 2H), 7.06 (d, J=8.8 Hz, 1H), 6.94 (d, J=8.7 Hz, 1H), 3.97 (s, 3H), 3.86 (s, 3H), 3.67 (s, 3H), 2.35 (s, 3H).

Example 109

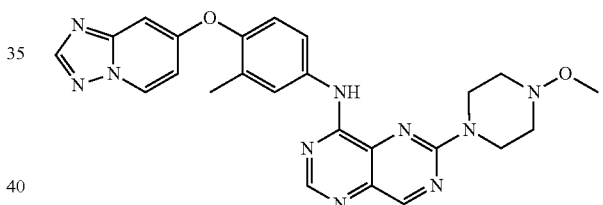

N-(4-([1,2,4]triazolo[1,5-a]pyridin-7-yloxy)-3-methylphenyl)-6-(4-methoxypiperazin-1-yl)pyrimido[5,4-d]pyrimidin-4-amine N-(4-([1,2,4]Triazolo[1,5-a]pyridin-7-yloxy)-3-methylphenyl)-6-(methylsulfinyl)pyrimido[5,4-d]pyrimidin-4-amine (5.7 g, 13.2 mmol) was added to a stirred solution of 1-methoxypiperazine (2.3 g, 20 mmol) and N-ethyl-N-isopropylpropan-2-amine (3.44 mL, 20 mmol) in DMA (132 mL). The mixture was stirred at 100° C. for 80 minutes. The reaction was diluted with EtOAc (850 mL). The organic layer was dried, washed with brine (10×150 mL) and concentrated in vacuo. The crude residue was purified over 330 g silica cartridge, eluting with a gradient of 0% to 5% MeOH in CH$_2$Cl$_2$ to afford N-(4-([1,2,4]triazolo[1,5-a]pyridin-7-yloxy)-3-methylphenyl)-6-(4-methoxypiperazin-1-yl)pyrimido[5,4-d]pyrimidin-4-amine (4.0 g, 64%). m/z (APCI-pos) M$^+$1=485.2; $^1$H NMR (400 MHz, CDCl$_3$) δ 9.07 (s, 1H), 8.58 (s, 1H), 8.57 (s, 1H), 8.50 (dd, J=7.4, 0.7 Hz, 1H), 8.22 (s, 1H), 7.86 (d, J=2.7 Hz, 1H), 7.83 (dd, J=8.6, 2.7 Hz, 1H), 7.13 (d, J=8.6 Hz, 1H), 6.89 (d, J=7.4, 2.6 Hz, 1H), 6.85 (dd, J=2.6, 0.7 Hz, 1H), 4.76 (d, J=12.9 Hz, 2H), 3.62 (s, 3H), 3.41 (s, 4H), 2.68 (s, 2H), 2.27 (s, 3H).

Example 110

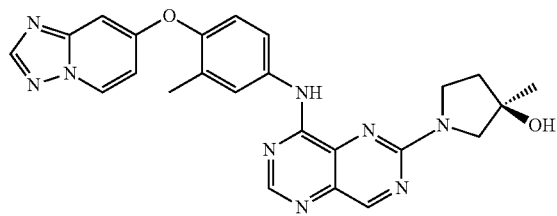

(R)-1-(8-((4-([1,2,4]triazolo[1,5-a]pyridin-7-yloxy)-3-methylphenyl)amino)pyrimido[5,4-d]pyrimidin-2-yl)-3-methylpyrrolidin-3-ol N-(4-([1,2,4]Triazolo[1,5-a]pyridin-7-yloxy)-3-methylphenyl)-6-(methylsulfonyl)pyrimido[5,4-d]pyrimidin-4-amine (15 mg, 33 μmol) was added to a stirred solution of (R)-3-methylpyrrolidin-3-ol (14 mg, 0.13 mmol) and N-ethyl-N-isopropylpropan-2-amine (12 μL, 67 μmol) in (methylsulfinyl)methane (0.17 mL). The mixture was stirred at 100° C. for 16 hours. The reaction was diluted with EtOAc (3 mL). The organic layer was dried washed with brine (10×) and concentrated in vacuo. The crude residue was purified over 12 g silica cartridge, eluting with a gradient of 100% DCM to 95% DCM:5% of a 5% MeOH/DCM mixture to afford (R)-1-(8-((4-([1,2,4]triazolo[1,5-a]pyridin-7-yloxy)-3-methylphenyl)amino)pyrimido[5,4-d]pyrimidin-2-yl)-3-methylpyrrolidin-3-ol (4.4 mg, 28%). m/z (APCI-pos) M+1=470.2; $^1$H NMR (400 MHz, CDCl$_3$) δ 9.06 (s, 1H), 8.64 (s, 1H), 8.56 (s, 1H), 8.49 (dd, J=7.4, 0.8 Hz, 1H), 8.22 (s, 1H), 7.86 (d, J=2.7 Hz, 1H), 7.82 (dd, J=8.5, 2.7 Hz, 1H), 7.12 (d, J=8.6 Hz, 1H), 6.89 (dd, J=7.5, 2.6 Hz, 1H), 6.85 (dd, J=2.6, 0.8 Hz, 1H), 3.94-3.83 (m, 3H), 3.61 (d, J=12.0 Hz, 1H), 2.26 (s, 3H), 2.21-2.03 (m, 2H), 2.02 (s, 1H), 1.58 (s, 3H).

Example 111

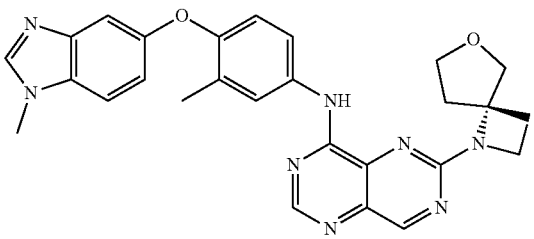 [SMILES: CCN(c1ncc2ncnc(Nc3ccc(Oc4ccc5c(c4)ncn5C)c(C)c3)c2n1)[C@]1(C)CCOC1]

rac-(R)—N-(3-methyl-4-((1-methyl-1H-benzo[c]imidazol-5-yl)oxy)phenyl)-6-(6-oxa-1-azaspiro[3.4]octan-1-yl)pyrimido[5,4-d]pyrimidin-4-amine N-(3-Methyl-4-((1-methyl-1H-benzo[d]imidazol-5-yl)oxy)phenyl)-6-(methylsulfonyl)pyrimido[5,4-d]pyrimidin-4-amine (0.30 g, 650 μmol) was added to a stirred solution of 6-oxa-1-azaspiro[3.4]octane HCl salt (292 mg, 2.0 mmol) and N-ethyl-N-isopropylpropan-2-amine (566 μL, 3.3 mmol) in DMA (6.5 mL). The mixture was heated at 120° C. for 30 minutes. The reaction was diluted with EtOAc. The organic layer was washed with brine (10×), dried over Na$_2$SO$_4$, and concentrated in vacuo. The crude residue was purified over 40 g silica cartridge, eluting with a gradient of 0% to 5% MeOH in CH$_2$Cl$_2$ to afford rac-(R)—N-(3-methyl-4-((1-methyl-1H-benzo[d]imidazol-5-yl)oxy)phenyl)-6-(6-oxa-1-azaspiro[3.4]octan-1-yl)pyrimido[5,4-d]pyrimidin-4-amine (0.19 g, 58%). m/z (APCI-pos) M+1=495.2; $^1$H NMR (400 MHz, CDCl$_3$) δ 9.04 (s, 1H), 8.54 (s, 1H), 7.89-7.80 (m, 2H), 7.67 (d, J=8.7 Hz, 1H), 7.35-7.27 (m, 2H), 7.04 (dd, J=8.7, 2.3 Hz, 1H), 6.93 (d, J=8.7 Hz, 1H), 4.65-4.60 (m, 1H), 4.37-4.33 (m, 1H), 4.24-4.06 (m, 2H), 4.01 (q, J=7.8 Hz, 1H), 3.84 (s, 3H), 3.80-3.75 (m, 1H), 2.89-2.78 (m, 1H), 2.67-2.49 (m, 2H), 2.34 (s, 3H), 2.27-2.06 (m, 1H).

Example 112

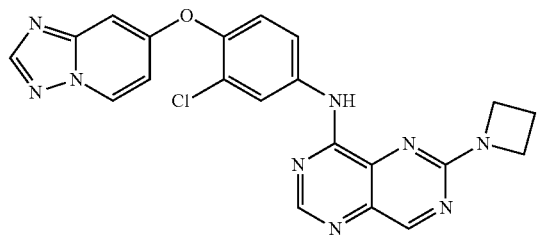 [SMILES: Clc1cc(Nc2ncnc3cnc(N4CCC4)nc23)ccc1Oc1ccn2ncnc2c1]

N-(4-([1,2,4]triazolo[1,5-a]pyridin-7-yloxy)-3-chlorophenyl)-6-(azetidin-1-yl)pyrimido[5,4-d]pyrimidin-4-amine Azetidine (5.7 mg, 99.4 μmol), N-(4-([1,2,4]triazolo[1,5-a]pyridin-7-yloxy)-3-chlorophenyl)-6-(methylsulfinyl)pyrimido[5,4-d]pyrimidin-4-amine (0.015 g, 33 μmol), Hunig's base (12 μL, 66.2 μmol), and DMA (331 μL) were charged to a dram vial equipped with a stir bar. The mixture was heated to 100° C. for 4 hours. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$ to afford N-(4-([1,2,4]triazolo[1,5-a]pyridin-7-yloxy)-3-chlorophenyl)-6-(azetidin-1-yl)pyrimido[5,4-d]pyrimidin-4-amine (0.005 g, 35%). m/z (APCI-pos) M+1=446.2; $^1$H NMR (400 MHz, CDCl$_3$) δ 9.07 (s, 1H), 8.68 (s, 1H), 8.60 (s, 1H), 8.52 (d, J=7.4 Hz, 1H), 8.28 (d, J=2.6 Hz, 1H), 8.24 (s, 1H), 7.86 (dd, J=8.8, 2.6 Hz, 1H), 7.26 (d, J=8.7 Hz, 1H), 6.91 (dd, J=7.4, 2.6 Hz, 1H), 6.88 (dd, J=2.6, 0.7 Hz, 1H), 4.33 (t, J=8.6 Hz, 4H), 2.49 (p, J=6.5 Hz, 2H).

Example 113

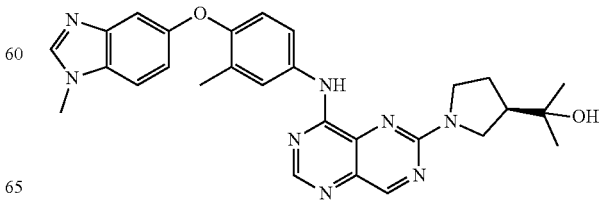

(R)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)propan-2-ol N-Ethyl-N-isopropylpropan-2-amine (0.038 mL, 0.22 mmol), (R)-2-(pyrrolidin-3-yl)propan-2-ol (0.0046 g, 0.036 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 mL) were charged to a dram vial equipped with a stir bar. The mixture was heated to 120° C. overnight with stirring. The mixture was diluted with ethyl acetate and washed with brine (10×). Organics were dried over Na₂SO₄, concentrated in vacuo, and purified by column chromatography (Redisep 4 g, 0 to 6% MeOH/DCM with 2% NH₄OH) to furnish (R)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)propan-2-ol (0.013 g, 73%) as a solid. m/z (APCI-pos) M$^+$1=511.3; $^1$H NMR (400 MHz, CDCl₃) δ 9.02 (d, J=1.5 Hz, 1H), 8.55 (s, 1H), 8.49 (s, 1H), 7.83 (s, 1H), 7.71 (s, 1H), 7.64 (dd, J=8.6, 2.6 Hz, 1H), 7.34-7.28 (m, 2H), 7.07-7.00 (m, 1H), 6.91 (d, J=8.7, 1.5 Hz, 1H), 4.06-3.84 (m, 2H), 3.82 (s, 3H), 3.63-3.49 (m, 2H), 2.52-2.41 (m, 1H), 2.32 (s, 3H), 2.07 (d, J=39.1 Hz, 2H), 1.34 (s, 6H).

Example 114

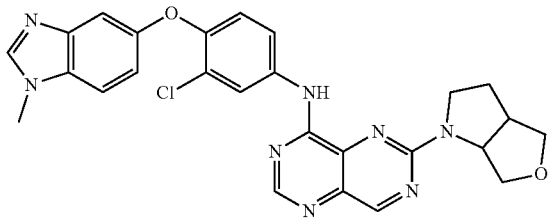

N-(3-chloro-4-((1-methyl-1H-benzo[d]imidazol-5-yl)oxy)phenyl)-6-(hexahydro-1H-furo[3,4-b]pyrrol-1-yl)pyrimido[5,4-d]pyrimidin-4-amine Hexahydro-1H-furo[3,4-b]pyrrole (11 mg, 97 μmol), N-(3-chloro-4-((1-methyl-1H-benzo[d]imidazol-5-yl)oxy)phenyl)-6-(methylsulfinyl)pyrimido[5,4-d]pyrimidin-4-amine (0.015 g, 32 μmol), Hunig's base (11.2 μL, 64 μmol), and DMSO (322 μL) were charged to a dram vial equipped with a stir bar. The mixture was heated to 100° C. for 1 hour. The resultant solid was filtered and washed with water to yield N-(3-chloro-4-((1-methyl-1H-benzo[d]imidazol-5-yl)oxy)phenyl)-6-(hexahydro-1H-furo[3,4-b]pyrrol-1-yl)pyrimido[5,4-d]pyrimidin-4-amine (12.7 mg, 75%). m/z (APCI-pos) M$^+$1=515.3; $^1$H NMR (400 MHz, CDCl₃) δ 9.03 (s, 1H), 8.56 (s, 1H), 8.51 (s, 1H), 8.15 (d, J=2.6 Hz, 1H), 7.86 (s, 1H), 7.63 (dd, J=8.9, 2.6 Hz, 1H), 7.41-7.32 (m, 2H), 7.09 (dd, J=8.7, 2.3 Hz, 1H), 7.00 (d, J=8.8 Hz, 1H), 4.48 (t, J=6.5 Hz, 1H), 4.34-4.20 (m, 2H), 4.03 (t, J=6.9 Hz, 1H), 3.98-3.90 (m, 1H), 3.85 (s, 3H), 3.78-3.73 (m, 1H), 3.68 (dd, J=11.4, 7.2 Hz, 1H), 2.85-2.72 (m, 1H), 2.28-2.17 (m, 1H), 2.04-1.89 (m, 1H).

Example 115

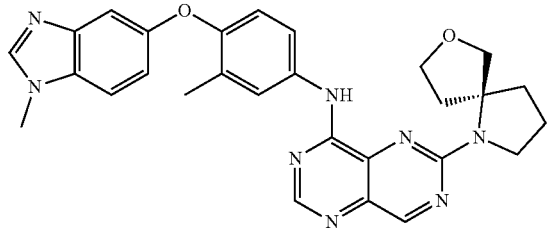 [SMILES: Cc1cc(Nc2ncnc3cnc(N4CCC[C@@]45CCOC5)nc23)ccc1Oc1ccc2c(c1)ncn2C]

rac-(R)—N-(3-methyl-4-((1-methyl-1H-benzo[d]imidazol-5-yl)oxy)phenyl)-6-(7-oxa-1-azaspiro[4.4]nonan-1-yl)pyrimido[5,4-d]pyrimidin-4-amine N-Ethyl-N-isopropylpropan-2-amine (0.013 mL, 0.072 mmol), 7-oxa-1-azaspiro[4.4]nonane (0.014 g, 0.11 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 mL) were charged to a dram vial equipped with a stir bar. The temperature was elevated to 75° C. for 4 hours with stirring. The mixture was diluted with ethyl acetate and washed with brine (10×). Organics were dried over Na₂SO₄, concentrated in vacuo, and purified by column chromatography (Redisep 4 g, 0 to 6% MeOH/DCM with 2% NH₄OH) to furnish rac-(R)—N-(3-methyl-4-((1-methyl-1H-benzo[d]imidazol-5-yl)oxy)phenyl)-6-(7-oxa-1-azaspiro[4.4]nonan-1-yl)pyrimido[5,4-d]pyrimidin-4-amine (0.007 g, 36% yield) as a solid. m/z (APCI-pos) M$^+$1=509.3; $^1$H NMR (400 MHz, CDCl₃) δ 9.78 (s, 1H), 9.07 (s, 1H), 8.55 (s, 1H), 7.99 (s, 1H), 7.83 (s, 1H), 7.78 (d, J=8.9 Hz, 1H), 7.36-7.27 (m, 2H), 7.04 (dd, J=8.7, 2.4 Hz, 1H), 6.94 (d, J=8.7 Hz, 1H), 4.67 (d, J=9.6 Hz, 1H), 4.43 (t, J=8.7 Hz, 1H), 3.99 (s, 1H), 3.86-3.82 (m, 4H), 3.63 (d, J=8.8 Hz, 1H), 3.57 (d, J=9.5 Hz, 1H), 2.65 (t, J=11.0 Hz, 1H), 2.33 (s, 3H), 2.22-2.17 (m, 2H), 2.07 (td, J=19.2, 14.9, 8.1 Hz, 2H), 1.73 (dd, J=12.2, 5.8 Hz, 1H).

Example 116

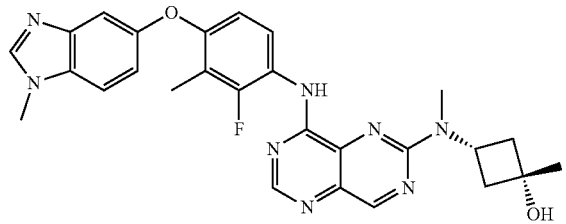 [SMILES: Cc1c(Oc2ccc3c(c2)ncn3C)ccc(Nc2ncnc3cnc(N(C)[C@H]4C[C@@](C)(O)C4)nc23)c1F]

(1s,3s)-3-((8-((2-fluoro-3-methyl-4-((1-methyl-1H-benzo[d]imidazol-5-yl)oxy)phenyl)amino)pyrimido[5,4-d]pyrimidin-2-yl)(methyl)amino)-1-methylcyclobutan-1-ol (1s,3s)-1-Methyl-3-(methylamino)cyclobutan-1-ol (11 mg, 97 μmol), N-(2-fluoro-3-methyl-4-((1-methyl-1H-benzo[d]imidazol-5-yl)oxy)phenyl)-6-(methylsulfinyl)pyrimido[5,4-d]pyrimidin-4-amine (0.015 g, 32 μmol), Hunig's base (11 μL, 65 μmol), and DMSO (324 μL) were charged to a dram vial equipped with a stir bar. The mixture was heated to 100° C. for 16 hours. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$ to afford ((1s,3s)-3-((8-((2-fluoro-3-methyl-4-((1-methyl-1H-benzo[d]imidazol-5-yl)oxy)phenyl)amino)pyrimido[5,4-d]pyrimidin-2-yl)(methyl)amino)-1-methylcyclobutan-1-ol (4.6 mg, 27%). m/z (APCI-pos) M$^+$1=515.3; $^1$H NMR (400 MHz, CDCl$_3$) δ 9.06 (s, 1H), 8.98 (s, 1H), 8.53 (s, 1H), 8.52 (t, J=9.1 Hz, 1H), 7.86 (s, 1H), 7.38-7.31 (m, 2H), 7.06 (dd, J=8.6, 2.3 Hz, 1H), 6.76 (dd, J=9.0, 1.8 Hz, 1H), 4.75-4.71 (m, 1H), 3.86 (s, 3H), 3.29 (s, 3H), 2.61-2.52 (m, 2H), 2.47-2.37 (m, 2H), 2.29 (d, J=2.2 Hz, 3H), 1.56 (s, 3H).

Example 117

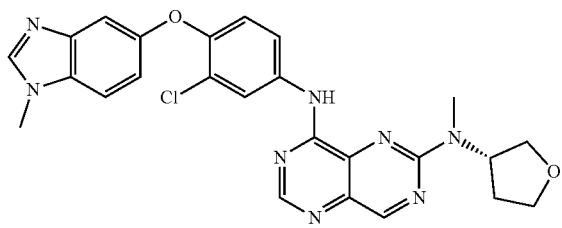 [SMILES: CN(c1ncc2ncnc(Nc3ccc(Oc4ccc5c(c4)ncn5C)c(Cl)c3)c2n1)[C@H]1CCOC1]

(S)—N8-(3-chloro-4-((1-methyl-1H-benzo[d]imidazol-5-yl)oxy)phenyl)-N2-methyl-N2-(tetrahydrofuran-3-yl)pyrimido[5,4-d]pyrimidine-2,8-diamine (S)—N-Methyltetrahydrofuran-3-amine (9.8 mg, 97 μmol), N-(3-chloro-4-((1-methyl-1H-benzo[d]imidazol-5-yl)oxy)phenyl)-6-(methylsulfinyl)pyrimido[5,4-d]pyrimidin-4-amine (0.015 g, 32 μmol), Hunig's base (11.2 μL), and DMSO (322 μL) were charged to a dram vial equipped with a stir bar. The mixture was heated to 100° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$. The material was subjected to column conditions once more with a 0 to 4% methanol in dichloromethane gradient to afford (S)—N8-(3-chloro-4-((1-methyl-1H-benzo[d]imidazol-5-yl)oxy)phenyl)-N2-methyl-N2-(tetrahydrofuran-3-yl)pyrimido[5,4-d]pyrimidine-2,8-diamine (3.2 mg, 18%). m/z (APCI-pos) M$^+$1=503.2; $^1$H NMR (400 MHz, CDCl$_3$) δ 9.07 (s, 1H), 8.87 (s, 1H), 8.57 (s, 1H), 8.20 (d, J=2.6 Hz, 1H), 7.87 (s, 1H), 7.70 (dd, J=8.9, 2.7 Hz, 1H), 7.41-7.32 (m, 2H), 7.14-7.06 (m, 1H), 7.01 (dd, J=8.9, 1.6 Hz, 1H), 4.21 (td, J=8.6, 4.0 Hz, 1H), 4.10-4.03 (m, 1H), 3.92 (dd, J=9.7, 7.6 Hz, 1H), 3.92-3.80 (m, 4H), 3.80 (td, J=8.8, 7.5 Hz, 1H), 3.28 (s, 3H), 2.48-2.29 (m, 1H), 2.08 (s, 1H).

Example 118


2-(1-(8-((3-methyl-4-((1-methyl-1H-benzo[d]imidazol-5-yl)oxy)phenyl)amino)pyrimido[5,4-d]pyrimidin-2-yl)azetidin-3-yl)propan-2-ol N-Ethyl-N-isopropylpropan-2-amine (0.019 mL), 2-(azetidin-3-yl)propan-2-ol hydrochloride (0.008 g, 0.053 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 mL) were charged to a dram vial equipped with a stir bar. The temperature was elevated to 75° C. for 1 hour with stirring. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH2Cl$_2$. The material was subjected to column conditions with a 0 to 4% methanol in dichloromethane gradient to afford 2-(1-(8-((3-methyl-4-((1-methyl-1H-benzo[d]imidazol-5-yl)oxy)phenyl)amino)pyrimido[5,4-d]pyrimidin-2-yl)azetidin-3-yl)propan-2-ol (0.012 g, 0.024 mmol, 66%). m/z (APCI-pos) M$^+$1=497.3; $^1$H NMR (400 MHz, CDCl$_3$) δ 9.00 (s, 1H), 8.53 (s, 1H), 8.51 (s, 1H), 7.83 (s, 1H), 7.71 (d, J=2.7 Hz, 1H), 7.63 (dd, J=8.7, 2.7 Hz, 1H), 7.35-7.27 (m, 2H), 7.04 (dd, J=8.8, 2.2 Hz, 1H), 6.90 (d, J=8.7 Hz, 1H), 4.27-4.14 (m, 4H), 3.83 (s, 3H), 2.87-2.75 (m, 1H), 2.32 (s, 3H), 1.99 (s, 1H), 1.27 (s, 6H).

Example 119

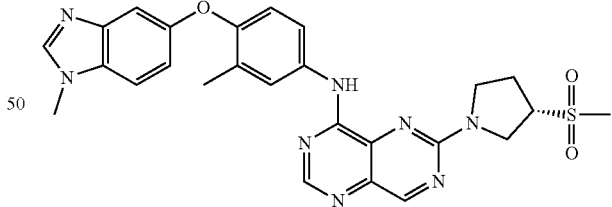

(S)—N-(3-methyl-4-((1-methyl-1H-benzo[d]imidazol-5-yl)oxy)phenyl)-6-(3-(methylsulfonyl)pyrrolidin-1-yl)pyrimido[5,4-d]pyrimidin-4-amine N-Ethyl-N-isopropylpropan-2-amine (0.013 mL, 0.072 mmol), (S)-3-(methylsulfonyl)pyrrolidine (0.027 g, 0.18 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 mL) were charged to a dram vial equipped with a stir bar. The temperature was elevated to 45° C. for 16 hours with stirring. The mixture was diluted with ethyl acetate and washed with brine (5×). Organics were dried over Na$_2$SO$_4$, concentrated in vacuo, and purified by column chromatography (Redisep 4 g, 0 to 6% MeOH/DCM with 2% NH$_4$OH). The material was further purified by reverse-phase preparatory HPLC (5-95% ACN/water with 0.1% TFA over 20 minutes). Product containing fractions were diluted with 2M aqueous K$_2$CO$_3$ and ethyl acetate. The aqueous layer was washed with ethyl acetate (3×) and organics were combined, dried over Na$_2$SO$_4$, and concentrated in vacuo to furnish (S)—N-(3-methyl-4-((1-methyl-1H-benzo[d]imidazol-5-yl)oxy)phenyl)-6-(3-(methylsulfonyl)pyrrolidin-1-yl)pyrimido[5,4-d]pyrimidin-4-amine (0.003 g, 18%). m/z (APCI-pos) M$^+$1=531.2; $^1$H NMR (400 MHz, CDCl$_3$) δ 9.07 (d, J=0.8 Hz, 1H), 8.54 (d, J=10.8 Hz, 1H), 7.84 (s, 1H), 7.72 (d, J=2.7 Hz, 1H), 7.69-7.58 (m, 1H), 7.35-7.25 (m, 2H), 7.26 (s, 1H), 7.12-7.01 (m, 1H), 6.92 (d, J=8.7 Hz, 1H), 4.30-4.14 (m, 1H), 4.07-4.03 (m, 1H), 3.93-3.79 (m, 4H), 3.02-2.97 (m, 6H), 2.93 (s, 3H), 2.61-2.48 (m, 1H), 2.34 (s, 3H).

Example 120

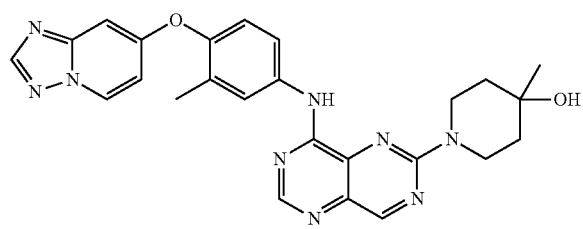 [SMILES: Cc1cc(Nc2ncnc3cnc(N4CCC(C)(O)CC4)nc23)ccc1Oc1ccn2ncnc2c1]

1-(8-((4-([1,2,4]triazolo[1,5-a]pyridin-7-yloxy)-3-methylphenyl)amino)pyrimido[5,4-d]pyrimidin-2-yl)-4-methylpiperidin-4-ol N-(4-([1,2,4]Triazolo[1,5-a]pyridin-7-yloxy)-3-methylphenyl)-6-(methylsulfonyl)pyrimido[5,4-d]pyrimidin-4-amine (0.015 g, 33 μmol) was added to a stirred solution of 4-methylpiperidin-4-ol (15 mg, 0.13 mmol) and N-ethyl-N-isopropylpropan-2-amine (12 μL, 67 μmol) in (methylsulfinyl)methane (0.17 mL) at 100° C. for 16 hours. The reaction was diluted with EtOAc (3 mL). The organic layer was dried washed with brine (10×) and concentrated in vacuo. The crude residue was purified over 12 g silica cartridge, eluting with a gradient of 0% to 5% MeOH in CH$_2$Cl$_2$ to afford 1-(8-((4-([1,2,4]triazolo[1,5-a]pyridin-7-yloxy)-3-methylphenyl)amino)pyrimido[5,4-d]pyrimidin-2-yl)-4-methylpiperidin-4-ol (6.8 mg, 42%). m/z (APCI-pos) M$^+$1=484.3; $^1$H NMR (400 MHz, CDCl$_3$) δ 9.04 (s, 1H), 8.58 (s, 1H), 8.55 (s, 1H), 8.50 (dd, J=7.4, 0.8 Hz, 1H), 8.22 (s, 1H), 7.87 (d, J=2.7 Hz, 1H), 7.83 (dd, J=8.6, 2.7 Hz, 1H), 7.12 (d, J=8.6 Hz, 1H), 6.89 (dd, J=7.5, 2.6 Hz, 1H), 6.85 (dd, J=2.6, 0.7 Hz, 1H), 4.56-4.46 (m, 2H), 3.69-3.57 (m, 2H), 2.27 (s, 3H), 1.81-1.65 (m, 4H), 1.35 (s, 3H).

Example 121

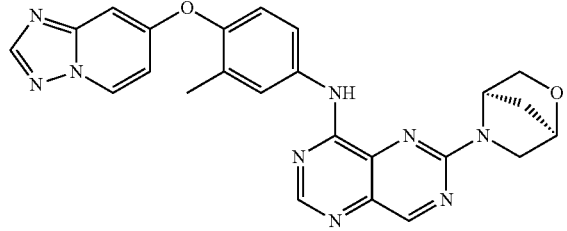 [SMILES: Cc1cc(Nc2ncnc3cnc(N4C[C@H]5C[C@@H]4CO5)nc23)ccc1Oc1ccn2ncnc2c1]

N-(4-([1,2,4]triazolo[1,5-a]pyridin-7-yloxy)-3-methylphenyl)-6-((1R,4R)-2-oxa-5-azabicyclo[2.2.1]heptan-5-yl)pyrimido[5,4-d]pyrimidin-4-amine N-Ethyl-N-isopropylpropan-2-amine (0.040 mL), (1R,4R)-2-oxa-5-azabicyclo[2.2.1]heptane (14 mg, 0.14 mmol), N-(4-([1,2,4]triazolo[1,5-a]pyridin-7-yloxy)-3-methylphenyl)-6-(methylsulfinyl)pyrimido[5,4-d]pyrimidin-4-amine (0.020 g, 0.046 mmol), and DMA (0.23 mL) were charged to a dram vial equipped with a stir bar. The mixture was heated to 100° C. for 1 hour. The mixture was diluted with ethyl acetate and washed with brine (5×). Organics were dried over Na$_2$SO$_4$, concentrated in vacuo, and purified by column chromatography (Redisep 4 g, 0 to 6% MeOH/DCM with 2% NH$_4$OH) to furnish N-(4-([1,2,4]triazolo[1,5-a]pyridin-7-yloxy)-3-methylphenyl)-6-((1R,4R)-2-oxa-5-azabicyclo[2.2.1]heptan-5-yl)pyrimido[5,4-d]pyrimidin-4-amine (0.006 g, 30% yield). m/z (APCI-pos) M$^+$1=468.3; $^1$H NMR (400 MHz, CDCl$_3$) δ 9.07 (s, 1H), 8.61 (s, 1H), 8.58 (s, 1H), 8.50 (d, J=7.3 Hz, 1H), 8.22 (s, 1H), 7.86 (d, J=2.6 Hz, 1H), 7.82 (dd, J=8.7, 2.7 Hz, 1H), 7.13 (d, J=8.6 Hz, 1H), 6.89 (dd, J=7.4, 2.6 Hz, 1H), 6.85 (d, J=2.5 Hz, 1H), 5.25 (s, 1H), 4.80 (s, 1H), 3.99 (s, 1H), 3.92 (s, 1H), 3.72 (d, J=33.4 Hz, 2H), 2.26 (s, 3H), 2.12-2.01 (m, 2H).

Example 122

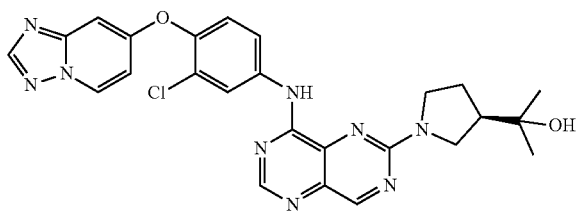 [SMILES: CC(C)(O)[C@@H]1CCN(c2ncc3ncnc(Nc4ccc(Oc5ccn6ncnc6c5)c(Cl)c4)c3n2)C1]

(R)-2-(1-(8-((4-([1,2,4]triazolo[1,5-a]pyridin-7-yloxy)-3-chlorophenyl)amino)pyrimido[5,4-d]pyrimidin-2-yl)pyrrolidin-3-yl)propan-2-ol (R)-2-(Pyrrolidin-3-yl)propan-2-ol (13 mg, 99 μmol), N-(4-([1,2,4]triazolo[1,5-a]pyridin-7-yloxy)-3-chlorophenyl)-6-(methylsulfinyl)pyrimido[5,4-d]pyrimidin-4-amine (0.015 g, 33 μmol), Hunig's base (12 μL), and DMSO (331 μL) were charged to a dram vial equipped with a stir bar. The mixture was heated to 100° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% in CH₂Cl₂ to afford (R)-2-(1-(8-((4-([1,2,4]triazolo[1,5-a]pyridin-7-yloxy)-3-chlorophenyl)amino)pyrimido[5,4-d]pyrimidin-2-yl)pyrrolidin-3-yl)propan-2-ol (11 mg, 63%). m/z (APCI-pos) M⁺1=518.2; ¹H NMR (400 MHz, CDCl₃) δ 9.08 (s, 1H), 8.68 (s, 1H), 8.58 (s, 1H), 8.52 (dd, J=7.4, 0.8 Hz, 1H), 8.28 (d, J=2.6 Hz, 1H), 8.24 (s, 1H), 7.86 (dd, J=8.8, 2.6 Hz, 1H), 6.95-6.90 (m, 1H), 6.89 (dd, J=2.6, 0.9 Hz, 1H), 4.34-3.64 (m, 2H), 3.64-3.43 (m, 2H), 2.57-2.38 (m, 1H), 2.22-1.91 (m, 2H), 1.35 (s, 6H).

Example 123

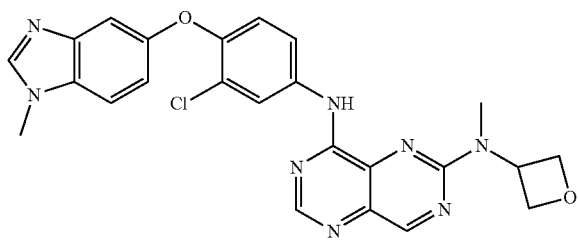 [SMILES: CN(c1ncc2ncnc(Nc3ccc(Oc4ccc5c(c4)ncn5C)c(Cl)c3)c2n1)C1COC1]

N8-(3-chloro-4-((1-methyl-1H-benzo[d]imidazol-5-yl)oxy)phenyl)-N2-methyl-N2-(oxetan-3-yl)pyrimido[5,4-d]pyrimidine-2,8-diamine N-Methyloxetan-3-amine (8.4 mg, 97 μmol), N-(3-chloro-4-((1-methyl-1H-benzo[d]imidazol-5-yl)oxy)phenyl)-6-(methylsulfinyl)pyrimido[5,4-d]pyrimidin-4-amine (0.015 g, 32 μmol), Hunig's base (11.2 μL), and DMSO (322 μL) were charged to a dram vial equipped with a stir bar. The mixture was heated to 100° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH₂Cl₂ to afford N8-(3-chloro-4-((1-methyl-1H-benzo[d]imidazol-5-yl)oxy)phenyl)-N2-methyl-N2-(oxetan-3-yl)pyrimido[5,4-d]pyrimidine-2,8-diamine (7.0 mg, 41%). m/z (APCI-pos) M⁺1=489.2; ¹H NMR (400 MHz, CDCl₃) δ 9.08 (s, 1H), 8.64 (s, 1H), 8.59 (s, 1H), 8.17 (d, J=2.6 Hz, 1H), 7.87 (s, 1H), 7.66 (dd, J=8.9, 2.7 Hz, 1H), 7.40-7.31 (m, 2H), 7.10 (dd, J=8.7, 2.3 Hz, 1H), 7.01 (d, J=8.8 Hz, 1H), 5.04-4.93 (m, 4H), 4.87-4.34 (m, 1H), 3.86 (s, 3H), 3.40 (s, 3H).

Example 124

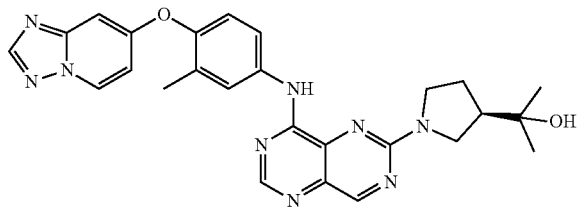 [SMILES: Cc1cc(Nc2ncnc3cnc(N4CC[C@@H](C(C)(C)O)C4)nc23)ccc1Oc1ccn2ncnc2c1]

(R)-2-(1-(8-((4-([1,2,4]triazolo[1,5-a]pyridin-7-yloxy)-3-methylphenyl)amino)pyrimido[5,4-d]pyrimidin-2-yl)pyrrolidin-3-yl)propan-2-ol N-(4-([1,2,4]Triazolo[1,5-a]pyridin-7-yloxy)-3-methylphenyl)-6-(methylsulfonyl)pyrimido[5,4-d]pyrimidin-4-amine (0.010 g, 22 μmol) was added to a stirred solution of (R)-2-(pyrrolidin-3-yl)propan-2-ol (8.6 mg, 67 μmol) and N-ethyl-N-isopropylpropan-2-amine (7.8 μL) in DMSO (0.22 mL). The mixture was stirred at 100° C. for 1 hour. The reaction was diluted with EtOAc (3 mL). The organic layer was dried washed with brine (10×) and concentrated in vacuo. The crude residue was purified over 12 g silica cartridge, eluting with a gradient of 0% to 5% in CH₂Cl₂ to afford (R)-2-(1-(8-((4-([1,2,4]triazolo[1,5-a]pyridin-7-yloxy)-3-methylphenyl)amino)pyrimido[5,4-d]pyrimidin-2-yl)pyrrolidin-3-yl)propan-2-ol (6.8 mg, 61%). m/z (APCI-pos) M⁺1=498.3; ¹H NMR (400 MHz, CDCl₃) δ 9.08 (s, 1H), 8.66 (s, 1H), 8.56 (s, 1H), 8.49 (dd, J=7.4, 0.8 Hz, 1H), 8.22 (s, 1H), 7.89-7.80 (m, 2H), 7.12 (d, J=8.5 Hz, 1H), 6.89 (dd, J=7.4, 2.5 Hz, 1H), 6.86 (dd, J=2.6, 0.8 Hz, 1H), 4.00 (s, 1H), 3.68-3.52 (m, 2H), 2.53-2.41 (m, 1H), 2.26 (s, 3H), 2.18-1.94 (m, 2H), 1.53-1.45 (m, 1H), 1.39-1.33 (m, 6H).

Example 125

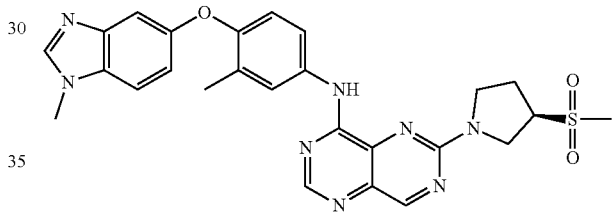

(R)—N-(3-methyl-4-((1-methyl-1H-benzo[d]imidazol-5-yl)oxy)phenyl)-6-(3-(methylsulfonyl)pyrrolidin-1-yl)pyrimido[5,4-d]pyrimidin-4-amine N-Ethyl-N-isopropylpropan-2-amine (0.013 mL, 0.072 mmol), (R)-3-(methylsulfonyl)pyrrolidine (0.016 g, 0.11 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 mL) were charged to a dram vial equipped with a stir bar. The temperature was elevated to 45° C. for 16 hours with stirring. The temperature was further raised to 60° C. where the mixture was stirred for 2 hours. The mixture was diluted with ethyl acetate and washed with brine (10×). Organics were dried over Na₂SO₄, concentrated in vacuo, and purified by column chromatography (Redisep 4 g, 0 to 8% MeOH/DCM with 2% NH₄OH). The material was further purified by reverse-phase preparatory HPLC (5-95% ACN/water with 0.1% TFA over 20 minutes). Product containing fractions were diluted with 2M aqueous K₂CO₃ and ethyl acetate. The organic layer was washed with ethyl acetate (3×), and organics were combined, dried over Na₂SO₄, and concentrated in vacuo to furnish (R)—N-(3-methyl-4-((1-methyl-1H-benzo[d]imidazol-5-yl)oxy)phenyl)-6-(3-(methylsulfonyl)pyrrolidin-1-yl)pyrimido[5,4-d]pyrimidin-4-amine (0.008 g, 44% yield). m/z (APCI-pos) M⁺1=531.2; ¹H NMR (400 MHz, CDCl₃) δ 9.08 (s, 1H), 8.56 (s, 1H), 8.53 (s, 1H), 7.85 (s, 1H), 7.73 (dd, J=2.7, 0.8 Hz, 1H), 7.67 (dd, J=8.8, 2.7 Hz, 1H), 7.36-7.29 (m, 2H), 7.06 (dd, J=8.6, 2.4 Hz, 1H), 6.93 (d, J=8.7 Hz, 1H), 4.31-4.15 (m, 2H), 4.09-4.00 (m, 1H), 4.00-3.82 (m, 2H), 3.85 (s, 3H), 3.00 (s, 3H), 2.73-2.63 (m, 1H), 2.62-2.50 (m, 1H), 2.35 (s, 3H).

Example 126

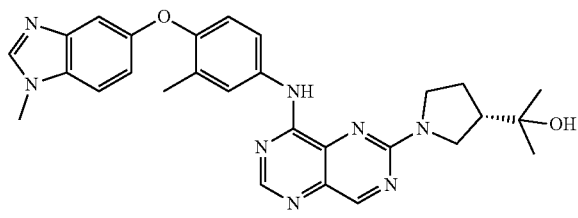 [SMILES: Cc1cc(Nc2ncnc3cnc(N4CC[C@H](C(C)(C)O)C4)nc23)ccc1Oc1ccc2c(c1)ncn2C]

(S)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)propan-2-ol N-Ethyl-N-isopropylpropan-2-amine (0.038 mL), (S)-2-(pyrrolidin-3-yl)propan-2-ol (0.0046 g, 0.036 mmol), 6-chloro-N-(3-methyl-4-((1-methyl-1H-benzo[d]imidazol-5-yl)oxy)phenyl)pyrimido[5,4-d]pyrimidin-4-amine (0.015 g, 0.036 mmol), and DMA (0.18 ml) were charged to a dram vial equipped with a stir bar. The mixture was heated to 120° C. overnight with stirring. The mixture was diluted with ethyl acetate and washed with brine (10×). Organics were dried over Na$_2$SO$_4$, concentrated in vacuo, and purified by column chromatography (Redisep 4 g, 0 to 6% MeOH/DCM with 2% NH$_4$OH) to furnish (S)-2-(1-(8-((3-methyl-4-(O-methyl-1H-benzo[d]imidazol-5-yl)oxy)phenyl)amino)pyrimido[5,4-d]pyrimidin-2-yl)pyrrolidin-3-yl)propan-2-ol (9.3 mg, 51%). m/z (APCI-pos) M$^+$1=511.2; $^1$H NMR (400 MHz, CDCl$_3$) δ 9.04 (s, 1H), 8.57 (s, 1H), 8.51 (s, 1H), 7.84 (s, 1H), 7.73 (d, J=2.7 Hz, 1H), 7.65 (dd, J=8.7, 2.7 Hz, 1H), 7.36-7.29 (m, 2H), 7.05 (dd, J=8.8, 2.2 Hz, 1H), 6.92 (d, J=8.6 Hz, 1H), 3.98 (s, 1H), 3.84 (s, 3H), 3.65-3.50 (m, 2H), 2.52-2.40 (m, 1H), 2.34 (s, 3H), 2.17-1.90 (m, 2H), 1.78-1.61 (m, 2H), 1.50 (s, 2H), 1.38-1.32 (m, 6H).

Example 127

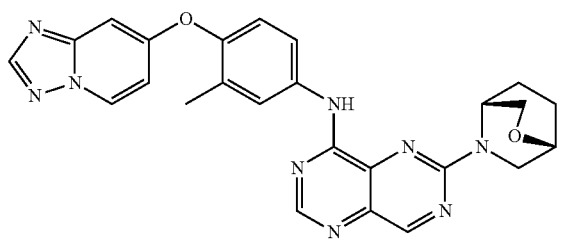 [SMILES: Cc1cc(Nc2ncnc3cnc(N4C[C@H]5CC[C@@H]4CO5)nc23)ccc1Oc1ccn2ncnc2c1]

N-(4-([1,2,4]triazolo[1,5-a]pyridin-7-yloxy)-3-methylphenyl)-6-((1R,4R)-2-oxa-5-azabicyclo[2.2.2]octan-5-yl)pyrimido[5,4-d]pyrimidin-4-amine N-Ethyl-N-isopropylpropan-2-amine (0.040 mL), (1R,4R)-2-oxa-5-azabicyclo[2.2.2]octane (0.016 g, 0.14 mmol), N-(4-([1,2,4]triazolo[1,5-a]pyridin-7-yloxy)-3-methylphenyl)-6-(methylsulfinyl)pyrimido[5,4-d]pyrimidin-4-amine (0.020 g, 0.046 mmol), and DMA (0.23 mL) were charged to a dram vial equipped with a stir bar. The mixture was heated to 100° C. for 1 hour. The mixture was diluted with ethyl acetate and washed with brine (5×). Organics were dried over Na$_2$SO$_4$, concentrated in vacuo, and purified by column chromatography (Redisep 4 g, 0 to 6% MeOH/DCM with 2% NH$_4$OH) to furnish N-(4-([1,2,4]triazolo[1,5-a]pyridin-7-yloxy)-3-methylphenyl)-6-((1R,4R)-2-oxa-5-azabicyclo[2.2.2]octan-5-yl)pyrimido[5,4-d]pyrimidin-4-amine (0.006 g, 24%). m/z (APCI-pos) M$^+$1=511.2; $^1$H NMR (400 MHz, CDCl$_3$) δ 9.05 (s, 1H), 8.66 (s, 1H), 8.58 (s, 1H), 8.50 (dd, J=7.4, 0.7 Hz, 1H), 8.22 (s, 1H), 7.87 (d, J=2.7 Hz, 1H), 7.83 (dd, J=8.5, 2.7 Hz, 1H), 7.13 (d, J=8.6 Hz, 1H), 6.89 (dd, J=7.4, 2.6 Hz, 1H), 6.85 (d, J=2.5 Hz, 1H), 5.01-4.96 (m, 1H), 4.33-4.07 (m, 4H), 3.87-3.79 (m, 1H), 2.48-2.28 (m, 1H), 2.27 (s, 4H), 2.08 (s, 2H), 1.89-1.77 (m, 1H).

Example 128

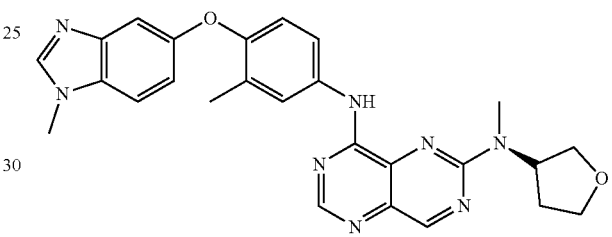

(R)—N2-methyl-N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine N-(3-Methyl-4-((1-methyl-1H-benzo[d]imidazol-5-yl)oxy)phenyl)-6-(methylsulfonyl)pyrimido[5,4-d]pyrimidin-4-amine (0.015 g, 33 μmol) was added to a stirred solution of (R)—N-methyltetrahydrofuran-3-amine HCl salt (22 mg, 0.16 mmol) and N-ethyl-N-isopropylpropan-2-amine (45 μL) in (methylsulfinyl)methane (0.16 mL). The mixture was stirred at 100° C. for 3 hours. The reaction was diluted with EtOAc (3 mL). The organic layer was dried washed with brine (10×) and concentrated in vacuo. The crude residue was purified over 12 g silica cartridge, eluting with a gradient of 0% to 5% MeOH in CH$_2$Cl$_2$ to afford (R)—N2-methyl-N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine (0.003 g, 19%). m/z (APCI-pos) M$^+$1=483.3; $^1$H NMR (400 MHz, CDCl$_3$) δ 9.06 (s, 1H), 8.75 (s, 1H), 8.54 (s, 1H), 7.84 (s, 1H), 7.78 (d, J=2.7 Hz, 1H), 7.67 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 5.50 (s, 1H), 4.19 (td, J=8.6, 4.3 Hz, 1H), 4.02 (s, 1H), 3.93 (dd, J=9.8, 7.4 Hz, 1H), 3.85 (s, 3H), 3.86-3.75 (m, 1H), 3.27 (s, 3H), 2.47-2.24 (m, 5H), 2.09 (dt, J=13.2, 6.8 Hz, 1H).

Example 129

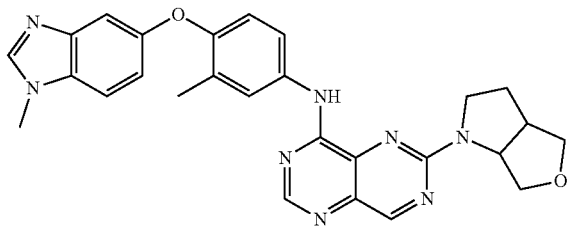 [SMILES: Cc1cc(Nc2ncnc3cnc(N4CCC5COCC54)nc23)ccc1Oc1ccc2c(c1)ncn2C]

6-(hexahydro-1H-furo[3,4-b]pyrrol-1-yl)-N-(3-methyl-4-((1-methyl-1H-benzo[d]imidazol-5-yl)oxy)phenyl)pyrimido[5,4-d]pyrimidin-4-amine N-(3-Methyl-4-((1-methyl-1H-benzo[d]imidazol-5-yl)oxy)phenyl)-6-(methylsulfinyl)pyrimido[5,4-d]pyrimidin-4-amine (0.015 g, 34 μmol) was added to a stirred solution of hexahydro-1H-furo[3,4-b]pyrrole (11 mg, 101 μmol) and N-ethyl-N-isopropylpropan-2-amine (29 μL) in DMSO (168 μL). The mixture was stirred at 100° C. for 16 hours. The reaction was diluted with EtOAc (3 mL). The organic layer was dried washed with brine (10×) and concentrated in vacuo. The crude residue was purified over 12 g silica cartridge, eluting with a gradient of 0% to 5% MeOH in CH$_2$Cl$_2$ to afford 6-(hexahydro-1H-furo[3,4-b]pyrrol-1-yl)-N-(3-methyl-4-((1-methyl-1H-benzo[d]imidazol-5-yl)oxy)phenyl)pyrimido[5,4-d]pyrimidin-4-amine (11 mg, 67%). m/z (APCI-pos) M$^+$1=495.3; $^1$H NMR (400 MHz, CDCl$_3$) δ 9.02 (s, 1H), 8.54 (s, 1H), 8.50 (s, 1H), 7.84 (s, 1H), 7.71 (d, J=2.7 Hz, 1H), 7.67 (dd, J=8.8, 2.7 Hz, 1H), 7.36-7.29 (m, 2H), 7.05 (dd, J=8.6, 2.3 Hz, 1H), 6.93 (d, J=8.7 Hz, 1H), 4.49 (t, J=6.5 Hz, 1H), 4.35-4.20 (m, 2H), 4.03 (t, J=6.9 Hz, 1H), 4.00-3.90 (m, 1H), 3.84 (s, 3H), 3.78-3.74 (m, 1H), 3.73-3.64 (m, 1H), 2.87-2.72 (m, 1H), 2.34 (s, 3H), 2.27-2.17 (m, 1H), 2.04-1.89 (m, 1H).

Example 130

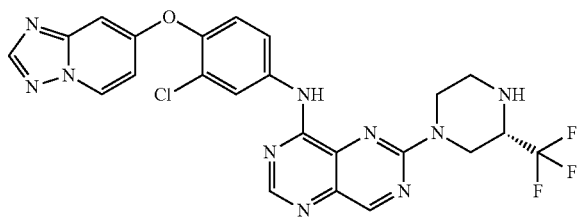 [SMILES: FC(F)(F)[C@@H]1CN(c2ncc3ncnc(Nc4ccc(Oc5ccn6ncnc6c5)c(Cl)c4)c3n2)CCN1]

(S)—N-(4-([1,2,4]triazolo[1,5-a]pyridin-7-yloxy)-3-chlorophenyl)-6-(3-(trifluoromethyl)piperazin-1-yl)pyrimido[5,4-d]pyrimidin-4-amine (S)-2-(Trifluoromethyl)piperazine di-HCl salt (23 mg, 99 μmol), N-(4-([1,2,4]triazolo[1,5-a]pyridin-7-yloxy)-3-chlorophenyl)-6-(methylsulfinyl)pyrimido[5,4-d]pyrimidin-4-amine (0.015 g, 33 μmol), Hunig's base (46 μL), and DMSO (331 μL) were charged to a dram vial equipped with a stir bar. The mixture was heated to 100° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$ to afford (S)—N-(4-([1,2,4]triazolo[1,5-a]pyridin-7-yloxy)-3-chlorophenyl)-6-(3-(trifluoromethyl)piperazin-1-yl)pyrimido[5,4-d]pyrimidin-4-amine (11.2 mg, 60%). m/z (APCI-pos) M$^+$1=543.2; $^1$H NMR (400 MHz, CDCl$_3$) δ 9.12 (s, 1H), 8.64 (s, 1H), 8.60 (s, 1H), 8.52 (d, J=7.4 Hz, 1H), 8.29 (d, J=2.6 Hz, 1H), 8.24 (s, 1H), 7.83 (dd, J=8.8, 2.7 Hz, 1H), 7.27 (d, J=8.8 Hz, 1H), 6.92 (dd, J=7.4, 2.7 Hz, 1H), 6.87 (d, J=2.6 Hz, 1H), 4.93-4.84 (m, 1H), 4.70-4.60 (m, 1H), 3.51-3.27 (m, 3H), 3.00-2.87 (m, 1H), 2.89-2.70 (m, 1H).

Example 131

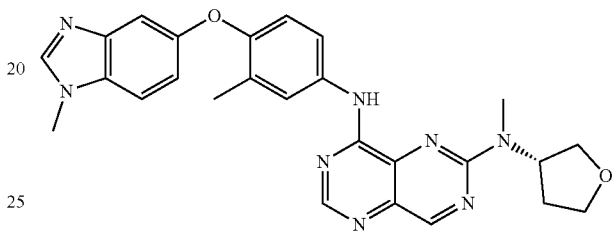

(S)—N2-methyl-N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine N-(3-Methyl-4-((1-methyl-1H-benzo[d]imidazol-5-yl)oxy)phenyl)-6-(methylsulfonyl)pyrimido[5,4-d]pyrimidin-4-amine (0.040 g, 87 μmol) was added to a stirred solution of (S)—N-methyltetrahydrofuran-3-amine (26 mg, 0.26 mmol) and N-ethyl-N-isopropylpropan-2-amine (45 μL, 0.26 mmol) in N,N-dimethylformamide (0.35 mL) at 70° C. for 3 hours. The reaction was diluted with EtOAc (3 mL). The organic layer was dried washed with brine (10×) and concentrated in vacuo. The crude residue was purified over 12 g silica cartridge, eluting with a gradient of 0% to 5% MeOH in CH$_2$Cl$_2$ to afford (S)—N2-methyl-N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine (10 mg, 25%). m/z (APCI-pos) M$^+$1=483.3; $^1$H NMR (400 MHz, CDCl$_3$) δ 9.05 (s, 1H), 8.75 (s, 1H), 8.54 (s, 1H), 7.84 (s, 1H), 7.78 (d, J=2.7 Hz, 1H), 7.67 (dd, J=8.6, 2.7 Hz, 1H), 7.39-7.28 (m, 2H), 7.05 (dd, J=8.7, 2.3 Hz, 1H), 6.93 (d, J=8.7 Hz, 1H), 4.24-4.14 (m, 1H), 4.06-3.98 (m, 1H), 3.97-3.88 (m, 1H), 3.88-3.72 (m, 5H), 3.27 (s, 3H), 2.43-2.30 (m, 1H), 2.35 (s, 4H), 2.14-2.02 (m, 1H).

Example 132

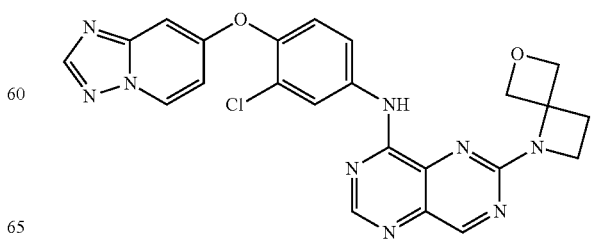

N-(4-([1,2,4]triazolo[1,5-a]pyridin-7-yloxy)-3-chlorophenyl)-6-(6-oxa-1-azaspiro[3.3]heptan-1-yl)pyrimido[5,4-d]pyrimidin-4-amine 6-Oxa-1-azaspiro[3.3]heptane hemioxalate (14 mg, 99 μmol), N-(4-([1,2,4]triazolo[1,5-a]pyridin-7-yloxy)-3-chlorophenyl)-6-(methylsulfinyl)pyrimido[5,4-d]pyrimidin-4-amine (0.015 g, 33 μmol), Hunig's base (28.8 μL), and DMSO (331 μL) were charged to a dram vial equipped with a stir bar. The mixture was heated to 100° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$ to afford N-(4-([1,2,4]triazolo[1,5-a]pyridin-7-yloxy)-3-chlorophenyl)-6-(6-oxa-1-azaspiro[3.3]heptan-1-yl)pyrimido[5,4-d]pyrimidin-4-amine (7.9 mg, 47%). m/z (APCI-pos) M$^+$1=488.2; $^1$H NMR (400 MHz, CDCl$_3$) δ 9.16 (s, 1H), 8.65 (s, 1H), 8.51 (dd, J=7.4, 0.7 Hz, 1H), 8.36 (s, 1H), 8.24 (s, 1H), 7.79 (d, J=8.7 Hz, 1H), 7.24 (d, J=8.8 Hz, 1H), 6.90 (dd, J=7.4, 2.6 Hz, 1H), 6.88-6.84 (m, 1H), 5.60 (d, J=7.1 Hz, 2H), 4.89-4.84 (m, 2H), 4.14 (t, J=7.2 Hz, 2H), 2.70 (t, J=7.3 Hz, 2H).

Example 133

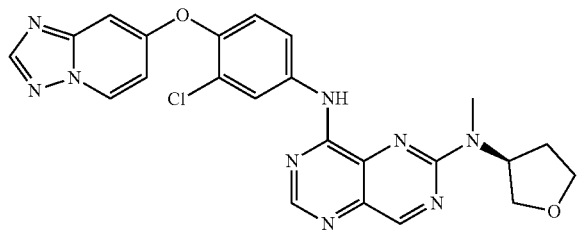 [SMILES: CN(c1ncc2ncnc(Nc3ccc(Oc4ccn5ncnc5c4)c(Cl)c3)c2n1)[C@H]1CCOC1]

(S)—N8-(4-([1,2,4]triazolo[1,5-a]pyridin-7-yloxy)-3-chlorophenyl)-N2-methyl-N2-(tetrahydrofuran-3-yl)pyrimido[5,4-d]pyrimidine-2,8-diamine (S)—N-Methyltetrahydrofuran-3-amine (10 mg, 99 μmol), N-(4-([1,2,4]triazolo[1,5-a]pyridin-7-yloxy)-3-chlorophenyl)-6-(methylsulfinyl)pyrimido[5,4-d]pyrimidin-4-amine (0.015 g, 33 μmol), Hunig's base (12 μL, 66 μmol), and DMA (331 μL) were charged to a dram vial equipped with a stir bar. The mixture was heated to 100° C. for 16 hours. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% MeOH in CH$_2$Cl$_2$ to afford (S)—N8-(4-([1,2,4]triazolo[1,5-a]pyridin-7-yloxy)-3-chlorophenyl)-N2-methyl-N2-(tetrahydrofuran-3-yl)pyrimido[5,4-d]pyrimidine-2,8-diamine (2.7 mg, 15%). m/z (APCI-pos) M$^+$1=490.2; $^1$H NMR (400 MHz, CDCl$_3$) δ 9.11 (s, 1H), 8.61 (s, 1H), 8.52 (d, J=7.5 Hz, 1H), 8.35 (d, J=2.6 Hz, 1H), 8.24 (s, 1H), 7.90 (dd, J=8.8, 2.6 Hz, 1H), 7.26 (d, J=8.8 Hz, 1H), 6.92 (dd, J=7.4, 2.7 Hz, 1H), 6.88 (dd, J=2.6, 0.8 Hz, 1H), 4.27-4.18 (m, 1H), 4.16-4.05 (m, 1H), 4.05-3.87 (m, 2H), 3.81 (d, J=8.9 Hz, 1H), 3.31 (s, 3H), 2.43-2.19 (m, 1H), 2.19-1.98 (m, 1H), 1.60 (s, 3H).

Example 134

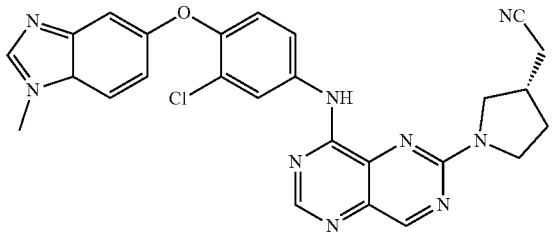

(S)-2-(1-(8-((3-chloro-4-((1-methyl-1H-benzo[d]imidazol-5-yl)oxy)phenyl)amino)pyrimido[5,4-d]pyrimidin-2-yl)pyrrolidin-3-yl)acetonitrile Step A: HCl (4M in dioxane) (0.24 mL, 0.95 mmol) was added to tert-butyl (S)-3-(cyanomethyl)pyrrolidine-1-carboxylate (0.040 g, 0.19 mmol). The mixture was stirred at room temperature for 8 hours and then concentrated in vacuo to furnish (S)-2-(pyrrolidin-3-yl)acetonitrile HCl salt (0.028 g, 100%).

Step B: (S)-2-(Pyrrolidin-3-yl)acetonitrile HCl salt (14 mg, 97 μmol), N-(3-chloro-4-((1-methyl-1H-benzo[d]imidazol-5-yl)oxy)phenyl)-6-(methylsulfinyl)pyrimido[5,4-d]pyrimidin-4-amine (0.015 g, 32 μmol), Hunig's base (28 μL), and DMSO (322 μL) were charged to a dram vial equipped with a stir bar. The mixture was heated to 80° C. for 1 hour. The mixture was diluted with ethyl acetate and washed with brine (10×). The organic layer was dried over sodium sulfate, filtered, and concentrated in vacuo. The crude residue was purified over 12 g silica cartridge, eluting with a gradient of 0% to 5% methanol in CH$_2$Cl$_2$ to afford (S)-2-(1-(8-((3-chloro-4-((1-methyl-1H-benzo[d]imidazol-5-yl)oxy)phenyl)amino)pyrimido[5,4-d]pyrimidin-2-yl)pyrrolidin-3-yl)acetonitrile (10 mg, 60%). m/z (APCI-pos) M$^+$1=512.3; $^1$H NMR (400 MHz, CDCl$_3$) δ 9.07 (s, 1H), 8.56 (s, 1H), 8.56 (s, 1H), 8.15 (d, J=2.6 Hz, 1H), 7.86 (s, 1H), 7.67 (dd, J=8.9, 2.6 Hz, 1H), 7.41-7.32 (m, 2H), 7.10 (dd, J=8.7, 2.3 Hz, 1H), 7.00 (d, J=8.8 Hz, 1H), 4.05 (d, J=10.9 Hz, 1H), 3.99-3.88 (m, 1H), 3.85 (s, 3H), 3.80-3.69 (m, 1H), 3.51 (dd, J=11.6, 7.3 Hz, 1H), 2.79 (p, J=7.1 Hz, 1H), 2.68-2.52 (m, 2H), 2.42-2.33 (m, 1H), 2.03-1.92 (m, 1H).

Example 135

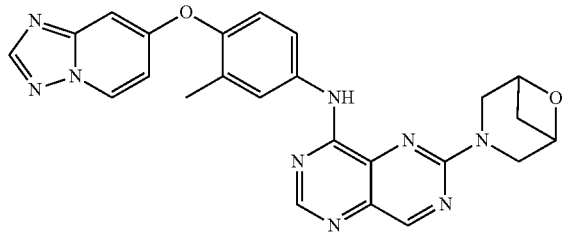 [SMILES: Cc1cc(Nc2ncnc3cnc(N4CC5CC(C4)O5)nc23)ccc1Oc1ccn2ncnc2c1]

N-(4-([1,2,4]triazolo[1,5-a]pyridin-7-yloxy)-3-methylphenyl)-6-(6-oxa-3-azabicyclo[3.1.1]heptan-3-yl)pyrimido[5,4-d]pyrimidin-4-amine N-(4-([1,2,4]Triazolo[1,5-a]pyridin-7-yloxy)-3-methylphenyl)-6-(methylsulfinyl)pyrimido[5,4-d]pyrimidin-4- amine (0.015 g, 35 μmol) was added to a stirred solution of 6-oxa-3-azabicyclo[3.1.1]heptane HCl salt (14 mg, 104 μmol) and N-ethyl-N-isopropylpropan-2-amine (30 μL) in DMSO (173 μL). The mixture was stirred at 100° C. for 1 hour. The reaction was diluted with EtOAc (3 mL). The organic layer was dried washed with brine (10×) and concentrated in vacuo. The crude residue was purified over 12 g silica cartridge, eluting with a gradient of 0% to 5% MeOH in $CH_2Cl_2$ to afford N-(4-([1,2,4]triazolo[1,5-a]pyridin-7-yloxy)-3-methylphenyl)-6-(6-oxa-3-azabicyclo[3.1.1]heptan-3-yl)pyrimido[5,4-d]pyrimidin-4-amine (0.014 g, 80%). m/z (APCI-pos) M$^+$1=468.3; $^1$H NMR (400 MHz, CDCl$_3$) δ 9.15 (s, 1H), 8.69 (s, 1H), 8.61 (s, 1H), 8.50 (dd, J=7.4, 0.7 Hz, 1H), 8.22 (s, 1H), 7.87 (d, J=2.7 Hz, 1H), 7.84 (dd, J=8.4, 2.6 Hz, 1H), 7.13 (d, J=8.6 Hz, 1H), 6.89 (dd, J=7.4, 2.6 Hz, 1H), 6.85 (dd, J=2.6, 0.7 Hz, 1H), 4.84 (s, 2H), 4.21-4.04 (m, 2H), 3.99 (dd, J=13.3, 2.3 Hz, 2H), 3.42-3.32 (m, 1H), 2.27 (s, 3H), 2.03 (d, J=9.0 Hz, 1H).

Example 136

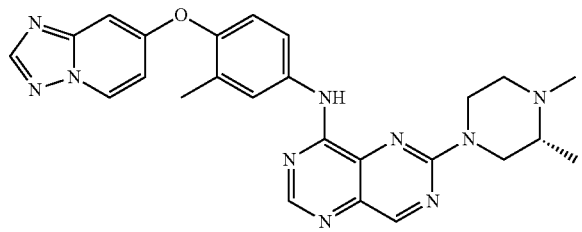 [SMILES: Cc1cc(Nc2ncnc3cnc(N4CCN(C)[C@H](C)C4)nc23)ccc1Oc1ccn2ncnc2c1]

(R)—N-(4-([1,2,4]triazolo[1,5-a]pyridin-7-yloxy)-3-methylphenyl)-6-(3,4-dimethylpiperazin-1-yl)pyrimido[5,4-d]pyrimidin-4-amine Step A: tert-Butyl (R)-4-(8-((4-([1,2,4]triazolo[1,5-a]pyridin-7-yloxy)-3-methylphenyl)amino)pyrimido[5,4-d]pyrimidin-2-yl)-2-methylpiperazine-1-carboxylate (19 mg, 63%) was prepared according to the general method described in Example 109, substituting tert-butyl (R)-2-methylpiperazine-1-carboxylate for 1-methoxypiperazine.

Step B: Trifluoroacetic acid (0.43 mL, 5.5 mmol) was added to a stirred solution of tert-butyl (R)-4-(8-((4-([1,2,4]triazolo[1,5-a]pyridin-7-yloxy)-3-methylphenyl)amino)pyrimido[5,4-d]pyrimidin-2-yl)-2-methylpiperazine-1-carboxylate (0.021 g, 37 μmol) and dichloromethane (0.36 mL). The mixture was stirred at 25° C. for 30 minutes. The reaction was partitioned between 2M $K_2CO_3$ and EtOAc. The organic layer was dried over sodium sulfate, filtered, and concentrated in vacuo. The crude residue was purified over 12 g silica cartridge, eluting with a gradient of 0% to 5% MeOH in $CH_2Cl_2$ to afford (R)—N-(4-([1,2,4]triazolo[1,5-a]pyridin-7-yloxy)-3-methylphenyl)-6-(3-methylpiperazin-1-yl)pyrimido[5,4-d]pyrimidin-4-amine (12 mg, 71%). m/z (APCI-pos) M$^+$1=469.2.

Step C: (R)—N-(4-([1,2,4]Triazolo[1,5-a]pyridin-7-yloxy)-3-methylphenyl)-6-(3-methylpiperazin-1-yl)pyrimido[5,4-d]pyrimidin-4-amine (0.012 g, 26 μmol) was added to a stirred solution of formic acid (9.7 μL, 0.26 mmol) and formaldehyde (37% aqueous solution; 15 mg, 0.18 mmol) in methanol (0.26 mL). The vessel was sealed and heated at 70° C. for 4 hours. The mixture was dry loaded onto silica gel and purified by column chromatography (Redisep 12 g, 0 to 25% MeOH/DCM with 2% NH$_4$OH) to furnish (R)—N-(4-([1,2,4]triazolo[1,5-a]pyridin-7-yloxy)-3-methylphenyl)-6-(3,4-dimethylpiperazin-1-yl)pyrimido[5,4-d]pyrimidin-4-amine (9.84 mg, 20.4 μmol, 80%). m/z (APCI-pos) M$^+$1=483.3; $^1$H NMR (400 MHz, CDCl$_3$) δ 9.06 (s, 1H), 8.57 (s, 2H), 8.50 (dd, J=7.4, 0.7 Hz, 1H), 8.22 (s, 1H), 7.86 (d, J=2.7 Hz, 1H), 7.86-7.79 (m, 1H), 7.13 (d, J=8.6 Hz, 1H), 6.89 (dd, J=7.4, 2.6 Hz, 1H), 6.85 (dd, J=2.6, 0.8 Hz, 1H), 4.76-4.56 (m, 2H), 3.41-3.30 (m, 1H), 3.01-2.91 (m, 2H), 2.39 (s, 4H), 2.27 (s, 3H), 2.25-2.18 (m, 1H), 1.22 (d, J=6.2 Hz, 3H).

Example 137

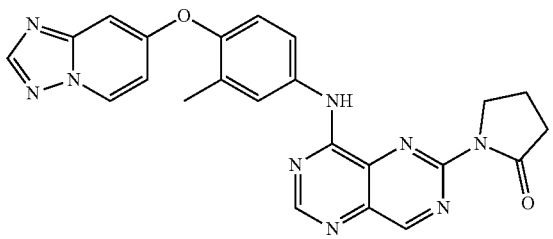 [SMILES: Cc1cc(Nc2ncnc3cnc(N4CCCC4=O)nc23)ccc1Oc1ccn2ncnc2c1]

1-(8-((4-([1,2,4]triazolo[1,5-a]pyridin-7-yloxy)-3-methylphenyl)amino)pyrimido[5,4-d]pyrimidin-2-yl)pyrrolidin-2-one Sodium hydride (60% weight dispersion in mineral oil) (2.0 mg, 52 μmol) was added to a stirred solution of N-(4-([1,2,4]triazolo[1,5-a]pyridin-7-yloxy)-3-methylphenyl)-6-(methylsulfinyl)pyrimido[5,4-d]pyrimidin-4-amine (0.015 g, 35 μmol) and pyrrolidin-2-one (10.2 μL, 104 μmol) in THF (347 μL). The mixture was stirred at 25° C. for 4 hours and then dry loaded onto silica gel and purified over 12 g silica cartridge, eluting with a gradient of 0% to 5% MeOH in $CH_2Cl_2$. The material was further purified by preparatory reverse-phase HPLC (5-95% ACN/water with 0.1% TFA over 20 minutes). Product containing fraction were diluted with ethyl acetate and 2M $K_2CO_3$. Organics were dried washed once with brine, dried over Na$_2$SO$_4$, and concentrated in vacuo to furnish 1-(8-((4-([1,2,4]triazolo[1,5-a]pyridin-7-yloxy)-3-methylphenyl)amino)pyrimido[5,4-d]pyrimidin-2-yl)pyrrolidin-2-one (1.4 mg, 9%). m/z (APCI-pos) M$^+$1=454.2; $^1$H NMR (400 MHz, CDCl$_3$) δ 9.39 (s, 1H), 8.96 (s, 1H), 8.79 (s, 1H), 8.50 (dd, J=7.4, 0.8 Hz, 1H), 8.23 (s, 1H), 7.90 (dd, J=8.5, 2.7 Hz, 1H), 7.87 (d, J=2.7 Hz, 1H), 7.14 (d, J=8.6 Hz, 1H), 6.89 (dd, J=7.4, 2.6 Hz, 1H), 6.86 (dd, J=2.6, 0.8 Hz, 1H), 4.30-4.22 (m, 2H), 2.78 (t, J=7.8 Hz, 2H), 2.31-2.18 (m, 5H).

Example 138

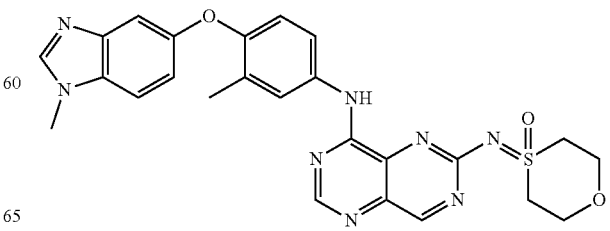

4-((8-((3-methyl-4-((1-methyl-1H-benzo[d]imidazol-5-yl)oxy)phenyl)amino)pyrimido[5,4-d]pyrimidin-2-yl)imino)-1,4λ⁶-oxathiane 4-oxide In a 10 mL glass microwave vessel equipped with a stir bar, 4-imino-1,4λ⁶-oxathiane 4-oxide HCl salt (25 mg, 0.14 mmol), 6-chloro-N-(3-methyl-4-((1-methyl-1H-benzo[d]imidazol-5-yl)oxy)phenyl)pyrimido[5,4-d]pyrimidin-4-amine (0.020 g, 48 µmol), cesium carbonate (94 mg, 0.29 mmol), Pd₂(dba)₃ (6.6 mg, 7.2 µmol), (9,9-dimethyl-9H-xanthene-4,5-diyl)bis(diphenylphosphane) (4.2 mg, 7.2 µmol), and 1,4-dioxane (0.48 mL) were combined. The mixture was sparged with argon for 5 minutes and sealed and heated to 100° C. for 16 hours. Additional portions of Pd₂(dba)₃ (6.6 mg, 7.2 µmol) and (9,9-dimethyl-9H-xanthene-4,5-diyl)bis(diphenylphosphane) (4.2 mg, 7.2 µmol) were added, and the mixture was sparged with argon for 5 minutes and sealed for 48 hours. The mixture was pressed through a syringe filter, concentrated in vacuo, and purified over 12 g silica cartridge, eluting with a gradient of 0% to 5% MeOH in CH₂Cl₂ to afford 4-((8-((3-methyl-4-((1-methyl-1H-benzo[d]imidazol-5-yl)oxy)phenyl)amino)pyrimido[5,4-d]pyrimidin-2-yl)imino)-1,4λ⁶-oxathiane 4-oxide (0.0060 g, 24%). m/z (APCI-pos) M⁺1=517.3; ¹H NMR (400 MHz, CDCl₃) δ 9.16 (s, 1H), 8.76 (s, 1H), 8.65 (s, 1H), 7.85 (s, 1H), 7.77 (d, J=2.7 Hz, 1H), 7.61 (dd, J=8.7, 2.7 Hz, 1H), 7.37-7.30 (m, 2H), 7.06 (dd, J=8.6, 2.4 Hz, 1H), 6.90 (d, J=8.7 Hz, 1H), 4.35-4.16 (m, 4H), 3.94-3.82 (m, 1H), 3.85 (s, 3H), 3.68-3.58 (m, 2H), 2.35 (s, 3H).

Example 139

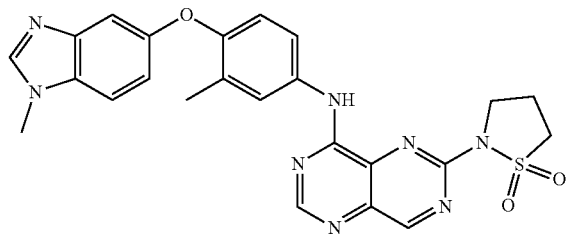 [SMILES: Cc1cc(Nc2ncnc3cnc(N4CCCS4(=O)=O)nc23)ccc1Oc1ccc2c(c1)ncn2C]

2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide A solution of N-(3-methyl-4-((1-methyl-1H-benzo[d]imidazol-5-yl)oxy)phenyl)-6-(methylsulfonyl)pyrimido[5,4-d]pyrimidin-4-amine (0.04 g, 0.08 mmol) in DMF (1.5 mL) was added to isothiazolidine 1,1-dioxide (0.018 g, 0.15 mmol), followed by sodium hydride (0.01 g, 0.23 mmol). After 10 minutes of stirring at room temperature, the reaction vessel was sealed and heated to 80° C. The reaction vessel was sealed and heated to 80° C. After 1 hour, the reaction mixture was concentrated and purified via a Gilson reverse phase preparatory HPLC using a gradient of 5 to 95% water/ACN over 20 minutes (0.1% TFA buffer). Product containing fractions were combined and treated with saturated NaHCO₃. After 10 minutes of stirring, the aqueous solution was extracted with 25% IPA/CHCl₃ (3×), dried over Na₂SO₄, and concentrated to afford 2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide (0.0117 g, 0.0233 mmol, 30.7% yield). m/z (APCI-pos) M⁺1=503.2; ¹H NMR (400 MHz, CDCl₃) δ 9.29 (s, 1H), 8.70 (s, 1H), 8.61 (m, 1H), 7.85 (s, 1H), 7.72 (m, 1H), 7.65 (dd, J=8.7, 2.8 Hz, 1H), 7.33 (m, 2H), 7.06 (dd, J=8.8, 2.2 Hz, 1H), 6.92 (d, J=8.7 Hz, 1H), 4.21 (t, J=6.6 Hz, 2H), 3.85 (s, 3H), 3.53 (t, J=7.24 Hz, 2H), 2.60 (p, J=6.9 Hz, 2H), 2.36 (s, 3H).

Example 140

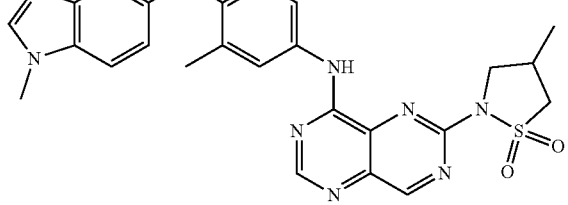

4-methyl-2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide A solution of N-(3-methyl-4-((1-methyl-1H-benzo[d]imidazol-5-yl)oxy)phenyl)-6-(methylsulfonyl)pyrimido[5,4-d]pyrimidin-4-amine (0.05 g, 0.108 mmol) in DMF (2 mL) was added to 4-methylisothiazolidine 1,1-dioxide (0.029 g, 0.22 mmol), followed by sodium hydride (0.013 g, 0.33 mmol). After these additions, the reaction mixture was stirred at ambient temperature for 5 minutes. The reaction vessel was sealed and heated to 80° C. After 1 hour, the reaction mixture was concentrated and purified via a Gilson reverse phase preparatory HPLC using a gradient of 5 to 95% water/ACN over 20 minutes (0.1% TFA buffer). Product containing fractions were combined and treated with saturated NaHCO₃. After 10 minutes, the aqueous solution was extracted with 25% IPA/CHCl₃ (3×), dried over Na₂SO₄, and concentrated to afford 4-methyl-2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide (0.014 g, 0.026 mmol, 24% yield). m/z (APCI-pos) M⁺1=517.2; ¹H NMR (400 MHz, CDCl₃) δ 9.26 (s, 1H), 8.70 (s, 1H), 8.60 (m, 1H), 7.85 (s, 1H), 7.72 (m, 1H), 7.65 (dd, J=8.7, 2.8 Hz, 1H), 7.34 (m, 2H), 7.06 (dd, J=8.7, 2.2 Hz, 1H), 6.92 (d, J=8.7 Hz, 1H), 4.38 (m, 1H), 3.85 (s, 3H), 3.67 (m, 2H), 3.21 (m, 1H), 2.97 (m, 1H), 2.83 (s, 3H), 1.40 (d, J=6.6 Hz, 3H).

Example 141

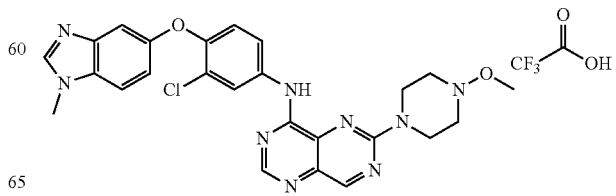

N-(3-chloro-4-((1-methyl-1H-benzo[d]imidazol-5-yl)oxy)phenyl)-6-(4-methoxypiperazin-1-yl)pyrimido[5,4-d]pyrimidin-4-amine 2,2,2-trifluoroacetate 1-Methoxypiperazine (0.06 g, 0.5 mmol) was added to a stirred solution of N-(3-chloro-4-((1-methyl-1H-benzo[d]imidazol-5-yl)oxy)phenyl)-6-(methylsulfinyl)pyrimido[5,4-d]pyrimidin-4-amine (0.05 g, 0.1 mmol) in DMSO (1 mL). Following this, the reaction mixture was heated to 100° C. under sealed tube. After 24 hours, the reaction mixture was concentrated, and the resulting material was purified via reverse phase chromatography using a gradient of 5 to 95% ACN/water over 50 minutes (0.1% TFA buffer). Product containing fractions were lyophilized overnight to afford N-(3-chloro-4-((1-methyl-1H-benzo[d]imidazol-5-yl)oxy)phenyl)-6-(4-methoxypiperazin-1-yl)pyrimido[5,4-d]pyrimidin-4-amine 2,2,2-trifluoroacetate (0.035 g, 0.068 mmol, 60%). m/z (APCI-pos) M$^+$1=518.2; $^1$H NMR (400 MHz, CDCl$_3$) δ 9.16 (s, 1H), 8.89 (s, 1H), 8.67 (m, 1H), 8.62 (s, 1H), 8.19 (d, J=2.6 Hz, 1H), 7.82 (dd, J=8.9, 2.6 Hz, 1H), 7.55 (d, J=9.3 Hz, 1H), 7.36 (dd, J=9.0, 2.3 Hz, 1H), 7.24 (d, J=1.8 Hz, 1H), 7.17 (d, J=8.8 Hz, 1H), 4.73 (m, 2H), 4.04 (s, 3H), 3.63 (s, 3H), 3.43 (m, 4H), 2.70 (m, 2H).

Example 142

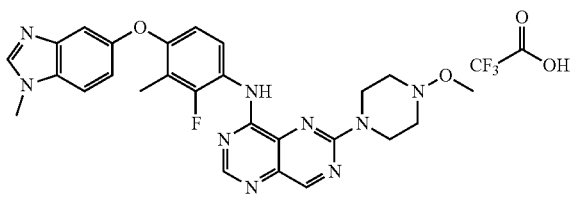

N-(2-fluoro-3-methyl-4-((1-methyl-1H-benzo[d]imidazol-5-yl)oxy)phenyl)-6-(4-methoxypiperazin-1-yl)pyrimido[5,4-d]pyrimidin-4-amine 2,2,2-trifluoroacetate 1-Methoxypiperazine (0.06 g, 0.5 mmol) was added to a stirred solution of N-(2-fluoro-3-methyl-4-((1-methyl-1H-benzo[d]imidazol-5-yl)oxy)phenyl)-6-(methylsulfinyl)pyrimido[5,4-d]pyrimidin-4-amine (0.05 g, 0.1 mmol) in DMSO (1 mL) at 100° C. under sealed tube. After 24 hours, the reaction mixture was cooled to ambient temperature then was concentrated. The crude material was purified via a Gilson reverse phase HPLC using a gradient of 5 to 70% water/ACN over 45 minutes (0.1% TFA buffer). Product containing fractions were combined and lyophilized overnight to afford N-(2-fluoro-3-methyl-4-((1-methyl-1H-benzo[d]imidazol-5-yl)oxy)phenyl)-6-(4-methoxypiperazin-1-yl)pyrimido[5,4-d]pyrimidin-4-amine 2,2,2-trifluoroacetate (0.025 g, 0.049 mmol, 50%). m/z (APCI-pos) M$^+$1=516.3; $^1$H NMR (400 MHz, CDCl$_3$) δ 9.27 (s, 1H), 9.17 (m, 1H), 9.07 (m, 1H), 8.64 (s, 1H), 8.55 (t, J=8.9 Hz, 1H), 7.57 (d, J=9.0 Hz, 1H), 7.35 (dd, J=9.0, 2.1 Hz, 1H), 7.28 (m, 1H), 7.17 (d, J=8.8 Hz, 1H), 4.72 (m, 2H), 4.07 (s, 3H), 3.64 (s, 3H), 3.47 (m, 4H), 2.74 (m, 2H), 2.23 (d, J=2.1 Hz, 3H).

Example 143

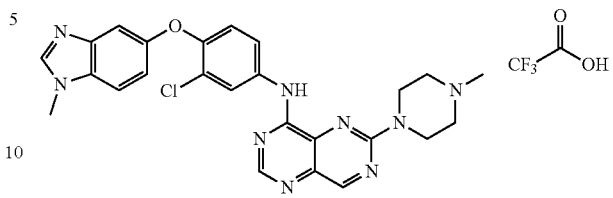

N-(3-chloro-4-((1-methyl-1H-benzo[d]imidazol-5-yl)oxy)phenyl)-6-(4-methylpiperazin-1-yl)pyrimido[5,4-d]pyrimidin-4-amine 2,2,2-trifluoroacetate 1-Methoxypiperazine (0.05 g, 0.5 mmol) was added to a stirred solution of N-(3-chloro-4-((1-methyl-1H-benzo[d]imidazol-5-yl)oxy)phenyl)-6-(methylsulfonyl)pyrimido[5,4-d]pyrimidin-4-amine (0.05 g, 0.1 mmol) in DMSO (1 mL) at 100° C. under sealed tube. After 24 hours, the reaction mixture was concentrated, and the crude material was purified via reverse phase chromatography using a gradient of 5 to 50% ACN/water (0.1% TFA buffer) over 65 minutes. Product containing fraction were combined and lyophilized overnight to afford N-(3-chloro-4-((1-methyl-1H-benzo[d]imidazol-5-yl)oxy)phenyl)-6-(4-methylpiperazin-1-yl)pyrimido[5,4-d]pyrimidin-4-amine 2,2,2-trifluoroacetate (0.0368 g, 0.073 mmol, 70%). m/z (APCI-pos) M$^+$1=502.2; $^1$H NMR (400 MHz, CDCl$_3$) δ 9.20 (s, 1H), 8.97 (s, 1H), 8.68 (s, 1H), 8.55 (m, 1H), 8.25 (d, J=2.6 Hz, 1H), 7.78 (dd, J=8.8, 2.6 Hz, 1H), 7.56 (d, J=9.0 Hz, 1H), 7.40 (dd, J=9.0, 2.3 Hz, 1H), 7.19 (m, 2H), 4.04 (s, 3H), 3.70 (m, 4H), 3.51 (s, 3H), 2.23 (m, 2H), 1.97 (m, 2H).

Example 144

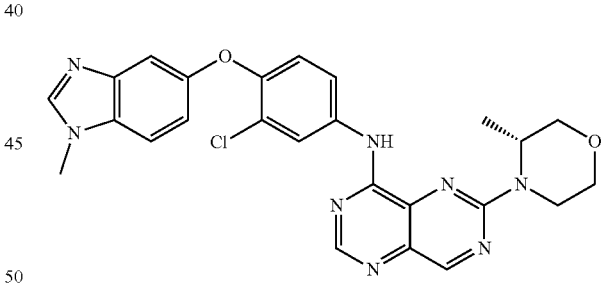

(R)—N-(3-chloro-4-((1-methyl-1H-benzo[d]imidazol-5-yl)oxy)phenyl)-6-(3-methylmorpholino)pyrimido[5,4-d]pyrimidin-4-amine N-(3-Chloro-4-((1-methyl-1H-benzo[d]imidazol-5-yl)oxy)phenyl)-6-(methylsulfonyl)pyrimido[5,4-d]pyrimidin-4-amine (0.05 g, 0.1 mmol) was added to a stirred solution of (R)-3-methylmorpholine hydrochloride (0.04 g, 0.3 mmol) and N-ethyl-N-isopropylpropan-2-amine (0.1 g, 0.8 mmol) in DMSO (1 mL) at 100° C. under sealed tube. After 24 hours, the reaction mixture was concentrated, and the crude material was purified via reverse phase chromatography using a gradient of 5 to 50% ACN/water (0.1% TFA buffer) over 65 minutes. Product containing fractions were combined and treated to saturated NaHCO$_3$. After 10 minutes, the aqueous solution was extracted with CHCl₃ (3×), dried over Na₂SO₄ and concentrated to afford (R)—N-(3-chloro-4-((1-methyl-1H-benzo[d]imidazol-5-yl)oxy)phenyl)-6-(3-methylmorpholino)pyrimido[5,4-d]pyrimidin-4-amine (0.006 g, 0.011 mmol, 10%). m/z (APCI-pos) M$^+$1=503.2; ¹H NMR (400 MHz, CDCl₃) δ 9.07 (s, 1H), 8.57 (s, 1H), 8.50 (s, 1H), 8.12 (d, J=2.6 Hz, 1H), 7.88 (s, 1H), 7.67 (dd, J=8.9, 2.6 Hz, 1H), 7.37 (m, 2H), 7.11 (dd, J=8.7, 2.3 Hz, 1H), 7.01 (d, J=8.7 Hz, 1H), 4.68 (m, 2H), 4.08 (dd, J=11.5, 3.7 Hz, 1H), 3.86 (s, 3H), 3.68 (m, 2H), 3.21 (m, 1H), 2.85 (m, 1H), 1.39 (d, J=6.8 Hz, 3H).

Example 145

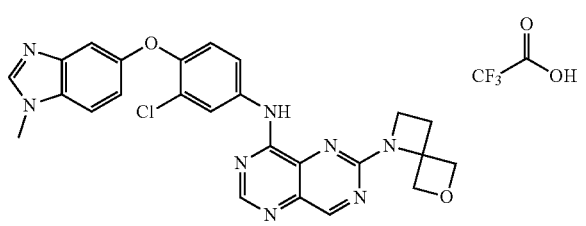 [SMILES: Cn1cnc2cc(Oc3ccc(Nc4ncnc5cnc(N6CCC67COC7)nc45)cc3Cl)ccc21 ; O=C(O)C(F)(F)F]

N-(3-chloro-4-((1-methyl-1H-benzo[d]imidazol-5-yl)oxy)phenyl)-6-(6-oxa-1-azaspiro[3.3]heptan-1-yl)pyrimido[5,4-d]pyrimidin-4-amine N-(3-Chloro-4-((1-methyl-1H-benzo[d]imidazol-5-yl)oxy)phenyl)-6-(methylsulfonyl)pyrimido[5,4-d]pyrimidin-4-amine (0.05 g, 0.1 mmol) was added to a stirred solution of 6-oxa-1-azaspiro[3.3]heptane hemioxalate (0.09 g, 0.3 mmol) and N-ethyl-N-isopropylpropan-2-amine (0.1 g, 1 mmol) in DMSO (1 mL) at 100° C. under sealed tube. After 24 hours, the reaction mixture was concentrated, and the crude material was purified via reverse phase chromatography using a gradient of 5 to 50% ACN/water (0.1% TFA buffer) over 65 minutes. Product containing fraction were combined and lyophilized overnight to afford N-(3-chloro-4-((1-methyl-1H-benzo[d]imidazol-5-yl)oxy)phenyl)-6-(6-oxa-1-azaspiro[3.3]heptan-1-yl)pyrimido[5,4-d]pyrimidin-4-amine 2,2,2-trifluoroacetate (33.6 mg, 0.067 mmol, 60%). m/z (APCI-pos) M$^+$1=501.3; ¹H NMR (400 MHz, CDCl₃) δ 9.14 (s, 1H), 8.61 (s, 1H), 8.21 (m, 1H), 7.87 (s, 1H), 7.64 (dd, J=8.9, 2.7 Hz, 1H), 7.36 (m, 2H), 7.09 (dd, J=8.8, 2.3 Hz, 1H), 7.00 (d, J=8.9 Hz, 1H), 5.59 (d, J=7.1 Hz, 2H), 4.83 (m, 2H), 4.12 (t, J=7.2 Hz, 2H), 3.86 (s, 3H), 2.69 (m, 2H).

Example 146

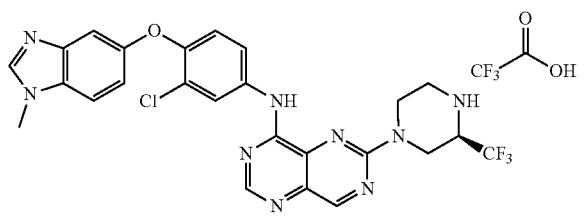

(R)—N-(3-chloro-4-((1-methyl-1H-benzo[d]imidazol-5-yl)oxy)phenyl)-6-(3-(trifluoromethyl)piperazin-1-yl)pyrimido[5,4-d]pyrimidin-4-amine 2,2,2-trifluoroacetate N-(3-Chloro-4-((1-methyl-1H-benzo[d]imidazol-5-yl)oxy)phenyl)-6-(methylsulfonyl)pyrimido[5,4-d]pyrimidin-4-amine (0.05 g, 0.1 mmol) was added to a stirred solution of (R)-2-(trifluoromethyl)piperazine dihydrochloride (0.07 g, 0.3 mmol) and N-ethyl-N-isopropylpropan-2-amine (0.01 g, 0.1 mmol) in DMSO (1 mL) at 100° C. under sealed tube. After 24 hours, the reaction mixture was concentrated, and the crude material was purified via reverse phase chromatography using a gradient of 5 to 50% ACN/water (0.1% TFA buffer) over 65 minutes. Product containing fraction were combined and lyophilized overnight to afford (R)—N-(3-chloro-4-((1-methyl-1H-benzo[d]imidazol-5-yl)oxy)phenyl)-6-(3-(trifluoromethyl)piperazin-1-yl)pyrimido[5,4-d]pyrimidin-4-amine 2,2,2-trifluoroacetate (0.011 g, 0.021 mmol, 20%). m/z (APCI-pos) M$^+$1=556.2; ¹H NMR (400 MHz, CDCl₃) δ 9.23 (s, 1H), 9.06 (s, 1H), 8.71 (m, 1H), 8.66 (s, 1H), 8.22 (d, J=2.6 Hz, 1H), 7.79 (dd, J=8.8, 2.6 Hz, 1H), 7.57 (d, J=9.0, 1H), 7.39 (dd, J=9.0, 2.3 Hz, 1H), 7.21 (m, 2H), 4.89 (m, 1H), 4.66 (m, 1H), 4.07 (s, 3H), 3.48 (m, 4H), 3.33 (m, 1H), 2.99 (m, 1H).

Example 147

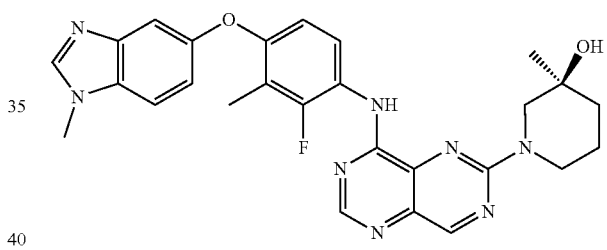

(S)-1-(8-((2-fluoro-3-methyl-4-((1-methyl-1H-benzo[d]imidazol-5-yl)oxy)phenyl)amino)pyrimido[5,4-d]pyrimidin-2-yl)-3-methylpiperidin-3-ol N-(2-Fluoro-3-methyl-4-((1-methyl-1H-benzo[d]imidazol-5-yl)oxy)phenyl)-6-(methylsulfonyl)pyrimido[5,4-d]pyrimidin-4-amine (0.03 g, 0.06 mmol) was added to a stirred solution of (S)-3-methylpiperidin-3-ol (0.02 g, 0.2 mmol) in DMSO at 100° C. under sealed tube. After 24 hours, the reaction mixture was concentrated, and the crude residue was purified via reverse phase chromatography using a gradient of 5 to 50% ACN/water over 65 minutes (0.1% TFA buffer). Product containing fractions were combined and treated to saturated NaHCO₃. After 10 minutes, the aqueous solution was extracted with CHCl₃ (3×), dried over sodium sulfate, and concentrated to afford (S)-1-(8-((2-fluoro-3-methyl-4-((1-methyl-1H-benzo[d]imidazol-5-yl)oxy)phenyl)amino)pyrimido[5,4-d]pyrimidin-2-yl)-3-methylpiperidin-3-ol (0.023 g, 0.045 mmol, 70%). m/z (APCI-pos) M$^+$1=515.3; ¹H NMR (400 MHz, CDCl₃) δ 9.04 (s, 1H), 8.83 (d, J=3.1 Hz, 1H), 8.52 (s, 1H), 8.47 (t, J=9.1 Hz, 1H), 7.87 (s, 1H), 7.35 (m, 2H), 7.06 (dd, J=8.8, 2.0 Hz, 1H), 6.75 (m, 1H), 4.57 (m, 1H), 4.47 (m, 1H), 3.86 (s, 3H), 3.34 (m, 2H) 2.30 (d, J=2.2, 3H), 1.95 (m, 1H), 1.85 (m, 1H), 1.74 (m, 2H), 1.66 (m, 1H), 1.35 (s, 3H).

Example 148

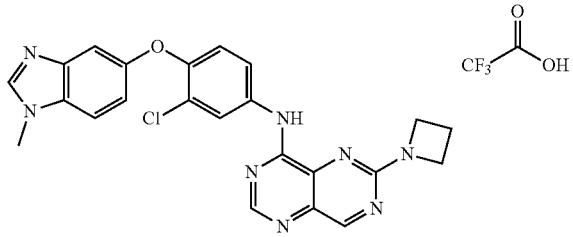 [SMILES: Cn1cnc2cc(Oc3ccc(Nc4ncnc5cnc(N6CCC6)nc45)cc3Cl)ccc21 ; O=C(O)C(F)(F)F]

6-(azetidin-1-yl)-N-(3-chloro-4-((1-methyl-1H-benzo[d]imidazol-5-yl)oxy)phenyl)pyrimido[5,4-d]pyrimidin-4-amine 2,2,2-trifluoroacetate Azetidine (0.021 g, 0.38 mmol) was added to a stirred solution of N-(3-chloro-4-((1-methyl-1H-benzo[d]imidazol-5-yl)oxy)phenyl)-6-(methylsulfinyl)pyrimido[5,4-d]pyrimidin-4-amine (0.035 g, 0.075 mmol) in DMSO (1 mL) at 100° C. under sealed tube. After 24 hours, the reaction mixture was diluted with water, and the aqueous solution was extracted with CHCl₃ (3×). The combined organic layers were washed with brine (3×), dried over sodium sulfate, and concentrated. The resulting crude oil was purified via reverse phase chromatography using a gradient of 5 to 50% ACN/water over 65 minutes (0.1% TFA buffer). Product containing fractions were combined and lyophilized to afford 6-(azetidin-1-yl)-N-(3-chloro-4-((1-methyl-1H-benzo[d]imidazol-5-yl)oxy)phenyl)pyrimido[5,4-d]pyrimidin-4-amine 2,2,2-trifluoroacetate (0.014 g, 0.031 mmol, 41%). m/z (APCI-pos) M⁺1=459.2; ¹H NMR (400 MHz, CDCl₃) δ 9.20 (s, 1H), 9.01 (s, 1H), 8.86 (m, 1H), 8.63 (s, 1H), 8.19 (d, J=2.6, 1H), 7.82 (dd, J=8.8, 2.6 Hz, 1H), 7.57 (d, J=9.0 Hz, 1H), 7.37 (dd, J=9.0, 2.3 Hz, 1H), 7.24 (m, 1H), 7.18 (d, J=8.8 Hz, 1H), 4.34 (m, 4H), 4.06 (s, 3H), 2.52 (m, 2H).

Example 149

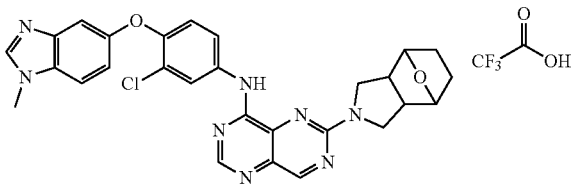 [SMILES: Cn1cnc2cc(Oc3ccc(Nc4ncnc5cnc(N6CC7C8CCC(O8)C7C6)nc45)cc3Cl)ccc21 ; O=C(O)C(F)(F)F]

N-(3-chloro-4-((1-methyl-1H-benzo[d]imidazol-5-yl)oxy)phenyl)-6-(octahydro-2H-4,7-epoxyisoindol-2-yl)pyrimido[5,4-d]pyrimidin-4-amine Octahydro-1H-4,7-epoxyisoindole (0.01 g, 0.075 mmol) was added to a stirred solution of N-(3-chloro-4-((1-methyl-1H-benzo[d]imidazol-5-yl)oxy)phenyl)-6-(methylsulfinyl)pyrimido[5,4-d]pyrimidin-4-amine (0.035 g, 0.075 mmol) in DMSO (1 mL) at 100° C. under sealed tube. The reaction was diluted with water, and the aqueous solution was extracted with CHCl₃ (3×). The combined organic layers were washed with brine (3×), dried over sodium sulfate, and concentrated in vacuo. The crude residue was purified using reverse phase chromatography eluting with a gradient of 5 to 50% ACN/water over 65 minutes (0.1% TFA buffer). Product containing fractions were combined and lyophilized overnight to afford N-(3-chloro-4-((1-methyl-1H-benzo[d]imidazol-5-yl)oxy)phenyl)-6-(octahydro-2H-4,7-epoxyisoindol-2-yl)pyrimido[5,4-d]pyrimidin-4-amine 2,2,2-trifluoroacetate (0.025 g, 0.047 mmol, 62%). m/z (APCI-pos) M⁺1=541.2; ¹H NMR (400 MHz, CDCl₃) δ 9.17 (s, 1H), 8.99 (s, 1H), 8.83 (m, 1H), 8.60 (s, 1H), 8.18 (d, J=2.6 Hz, 1H), 7.84 (dd, J=8.8, 2.6 Hz, 1H), 7.54 (d, J=9.0 Hz, 1H), 7.35 (dd, J=9.0, 2.3 Hz, 1H), 7.17 (d, J=8.8 Hz, 1H), 4.50 (s, 2H), 4.09 (m, 2H), 4.04 (s, 3H), 3.60 (m, 2H), 2.72 (m, 2H), 1.77 (m, 2H), 1.55 (m, 2H).

Example 150

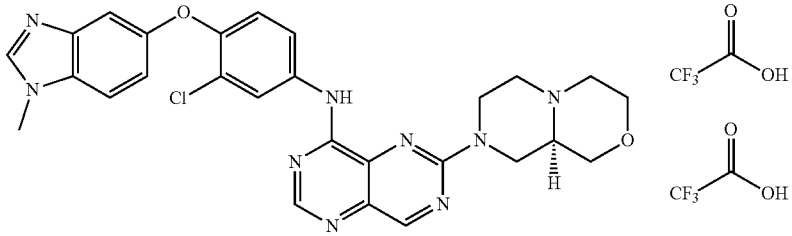 [SMILES: Cn1cnc2cc(Oc3ccc(Nc4ncnc5cnc(N6CCN7CCOC[C@H]7C6)nc45)cc3Cl)ccc21 ; O=C(O)C(F)(F)F ; O=C(O)C(F)(F)F]

(R)—N-(3-chloro-4-((1-methyl-1H-benzo[d]imidazol-5-yl)oxy)phenyl)-6-(hexahydropyrazino[2,1-c][1,4]oxazin-8(1H)-yl)pyrimido[5,4-d]pyrimidin-4-amine bis(2,2,2-trifluoroacetate)

(R)-Octahydropyrazino[2,1-c][1,4]oxazine dihydrochloride (0.065 g, 0.30 mmol) was added to a stirred solution of N-(3-chloro-4-((1-methyl-1H-benzo[d]imidazol-5-yl)oxy)phenyl)-6-(methylsulfinyl)pyrimido[5,4-d]pyrimidin-4-amine (0.035 g, 0.075 mmol) and N-ethyl-N-isopropylpropan-2-amine (0.097 g, 0.75 mmol) in DMSO (1 mL) at 100° C. under sealed tube. The reaction mixture was diluted with water, and the aqueous solution was extracted with CHCl₃ (3×). The combined organic layers were washed with brine (3×), dried over Na₂SO₄, and concentrated. This crude material was purified via reverse phase chromatography using a gradient of 5 to 50% ACN/water over 65 minutes (0.1% TFA buffer). Product containing fractions were combined and lyophilized overnight to afford (R)—N-(3-chloro-4-((1-methyl-1H-benzo[d]imidazol-5-yl)oxy)phenyl)-6-(hexahydropyrazino[2,1-c][1,4]oxazin-8(1H)-yl)pyrimido[5,4-d]pyrimidin-4-amine bis(2,2,2 trifluoroacetate) (0.02 g, 0.038 mmol, 50%). m/z (APCI-pos) M⁺1=544.2; ¹H NMR (400 MHz, CDCl₃) δ 9.19 (s, 1H), 8.99 (s, 1H), 8.67 (s, 1H), 8.22 (d, J=2.6 Hz, 1H), 7.78 (dd, J=8.8, 2.6 Hz, 1H), 7.57 (d, J=9.0 Hz, 1H), 7.39 (dd, J=9.0 Hz, 2.3 Hz, 1H), 7.21 (d, J=2.2 Hz, 1H), 7.18 (d, J=8.8 Hz, 1H), 5.04 (m, 2H), 4.06 (m, 7H), 3.73 (m, 2H), 3.58 (d, J=11.8 Hz, 1H), 3.49 (m, 1H), 3.21 (m, 1H), 2.93 (m, 2H).

Example 151

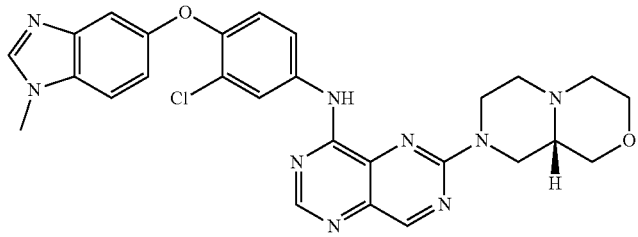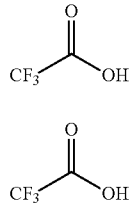

(S)—N-(3-chloro-4-((1-methyl-1H-benzo[d]imidazol-5-yl)oxy)phenyl)-6-(hexahydropyrazino[2,1-c][1,4]oxazin-8(1H)-yl)pyrimido[5,4-d]pyrimidin-4-amine bis(2,2,2-trifluoroacetate)

(S)-Octahydropyrazino[2,1-c][1,4]oxazine dihydrochloride (0.065 g, 0.30 mmol) was added to a stirred solution of N-(3-chloro-4-((1-methyl-1H-benzo[d]imidazol-5-yl)oxy)phenyl)-6-(methylsulfinyl)pyrimido[5,4-d]pyrimidin-4-amine (0.035 g, 0.075 mmol) and N-ethyl-N-isopropylpropan-2-amine (0.097 g, 0.75 mmol) in DMSO (1 mL) at 100° C. under sealed tube. After 24 hours, the reaction mixture was diluted with water, and the aqueous solution was extracted with CHCl₃ (3×). The combined organic layers were washed with brine (3×), dried over Na₂SO₄, and concentrated. This crude material was purified via reverse phase chromatography using a gradient of 5 to 50% ACN/water over 65 minutes (0.1% TFA buffer). Product containing fractions were combined and lyophilized overnight to afford (S)—N-(3-chloro-4-((1-methyl-1H-benzo[d]imidazol-5-yl)oxy)phenyl)-6-(hexahydropyrazino[2,1-c][1,4]oxazin-8(1H)-yl)pyrimido[5,4-d]pyrimidin-4-amine bis-2,2,2-trifluoroacetate (0.024 g, 0.043 mmol, 58%). m/z (APCI-pos) M⁺1=544.2; ¹H NMR (400 MHz, CDCl₃) δ 9.20 (s, 1H), 8.98 (s, 1H), 8.67 (s, 1H), 8.63 (m, 1H), 8.23 (d, J=2.6 Hz, 1H), 7.78 (dd, J=8.8, 2.6 Hz, 1H), 7.57 (d, J=9.0 Hz, 1H), 7.39 (dd, J=9.0, 2.3 Hz, 1H), 7.19 (m, 2H), 5.03 (m, 2H), 4.06 (m, 7H), 3.73 (m, 2H), 3.58 (d, J=11.8 Hz, 1H), 3.50 (m, 1H), 3.21 (m, 1H), 2.93 (m, 2H).

Example 152

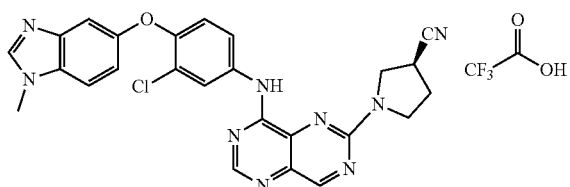

(S)-1-(8-((3-chloro-4-((1-methyl-1H-benzo[d]imidazol-5-yl)oxy)phenyl)amino)pyrimido[5,4-d]pyrimidin-2-yl)pyrrolidine-3-carbonitrile 2,2,2-trifluoroacetate (S)-Pyrrolidine-3-carbonitrile hydrochloride (0.029 g, 0.22 mmol) was added to a stirred solution of N-(3-chloro-4-((1-methyl-1H-benzo[d]imidazol-5-yl)oxy)phenyl)-6-(methylsulfonyl)pyrimido[5,4-d]pyrimidin-4-amine (0.035 g, 0.073 mmol) and N-ethyl-N-isopropylpropan-2-amine (0.047 g, 0.36 mmol) in DMSO (1 mL) at 100° C. under sealed tube. The reaction mixture was diluted with water, and the aqueous solution was extracted with CHCl₃ (3×). The combined organic layers were washed with brine (3×), dried over Na₂SO₄, and concentrated. This crude material was purified via reverse phase chromatography using a gradient of 5 to 50% ACN/water over 65 minutes (0.1% TFA buffer). Product containing fractions were combined and lyophilized overnight to afford (S)-1-(8-((3-chloro-4-((1-methyl-1H-benzo[d]imidazol-5-yl)oxy)phenyl)amino)pyrimido[5,4-d]pyrimidin-2-yl)pyrrolidine-3-carbonitrile 2,2,2-trifluoroacetate (0.014 g, 0.029 mmol, 40%). m/z (APCI-pos) M⁺1=498.2; ¹H NMR (400 MHz, CDCl₃) δ 9.22 (s, 1H), 8.95 (s, 1H), 8.73 (m, 1H), 8.66 (s, 1H), 8.22 (d, J=2.6 Hz, 1H), 7.82 (dd, J=8.8, 2.6 Hz, 1H), 7.56 (J=9.0 Hz, 1H), 7.38 (dd, J=9.0, 2.3 Hz, 1H), 7.23 (d, J=2.3 Hz, 1H), 7.19 (d, J=8.8 Hz, 1H), 4.11 (m, 2H), 4.05 (s, 3H), 3.89 (m, 1H), 3.37 (m, 2H), 2.51 (m, 2H).

Example 153

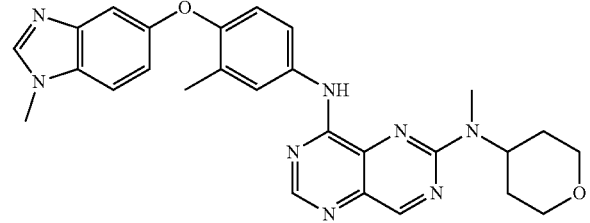 [SMILES: Cc1cc(Nc2ncnc3cnc(N(C)C4CCOCC4)nc23)ccc1Oc1ccc2c(c1)ncn2C]

N2-methyl-N8-(3-methyl-4-((1-methyl-1H-benzo[d]imidazol-5-yl)oxy)phenyl)-N2-(tetrahydro-2H-pyran-4-yl)pyrimido[5,4-d]pyrimidine-2,8-diamine A mixture of N-methyltetrahydropyran-4-amine (37 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was heated to 80° C. where it stirred for 4 hours. The mixture was then cooled to ambient temperature and was

Example 154

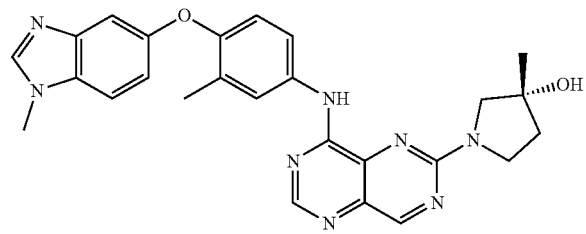 [SMILES: Cc1cc(Nc2ncnc3cnc(N4CC[C@@](C)(O)C4)nc23)ccc1Oc1ccc2c(c1)ncn2C]

(R)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (R)-3-methylpyrrolidin-3-ol (33 mg, 0.33 mmol) and N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol) in DMSO (0.72 mL) was heated to 80° C. for 4 hours. The mixture was then cooled to ambient temperature, and the mixture was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford (R)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (45 mg, 84%) as a solid. m/z (APCI-pos) M$^+$1=483.2; $^1$H NMR (400 MHz, CDCl$_3$) δ 9.05 (s, 1H), 8.57 (s, 1H), 8.53 (s, 1H), 7.84 (s, 1H), 7.74 (d, J=2.7 Hz, 1H), 7.65 (dd, J=8.8, 2.8 Hz, 1H), 7.36-7.30 (m, 2H), 7.05 (dd, J=8.8, 2.2 Hz, 1H), 6.93 (d, J=8.7 Hz, 1H), 3.89 (m, 3H), 3.85 (s, 3H), 3.61 (d, J=12.0 Hz, 1H), 2.34 (s, 3H), 2.12 (m, 2H), 1.58 (m, 4H).

Example 155

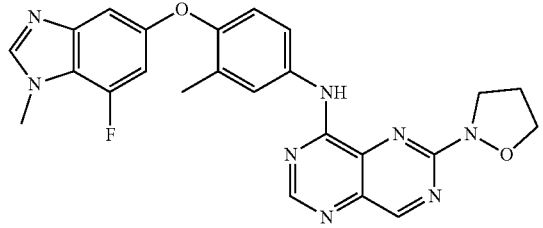 [SMILES: Cc1cc(Nc2ncnc3cnc(N4CCCO4)nc23)ccc1Oc1cc(F)c2c(c1)ncn2C]

N-(4-((7-fluoro-1-methyl-1H-benzo[d]imidazol-5-yl)oxy)-3-methylphenyl)-6-(isoxazolidin-2-yl)pyrimido[5,4-d]pyrimidin-4-amine A mixture of 1,2-oxazolidine hydrochloride (30 mg, 0.27 mmol), N-(4-((7-fluoro-1-methyl-1H-benzo[d]imidazol-5-yl)oxy)-3-methylphenyl)-6-(methylsulfinyl)pyrimido[5,4-d]pyrimidin-4-amine (0.025 g, 54 μmol) and DMSO (0.54 mL) was treated with N,N-diisopropylethylamine (49 mg, 0.38 mmol). The vial was capped and heated to 80° C. for 4 hours. The mixture was then cooled to ambient temperature. The mixture was diluted with water, and the resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford N-(4-((7-fluoro-1-methyl-1H-benzo[d]imidazol-5-yl)oxy)-3-methylphenyl)-6-(isoxazolidin-2-yl)pyrimido[5,4-d]pyrimidin-4-amine as a solid. m/z (APCI-pos) M$^+$1=473.1; $^1$H NMR (400 MHz, CDCl$_3$) δ 9.19 (s, 1H), 8.69 (s, 1H), 8.65 (s, 1H), 7.82-7.73 (m, 2H), 7.70 (dd, J=8.7, 2.8 Hz, 1H), 7.05 (d, J=2.0 Hz, 1H), 6.98 (d, J=8.7 Hz, 1H), 6.76 (dd, J=12.2, 2.0 Hz, 1H), 4.18 (t, J=7.1 Hz, 2H), 4.08 (t, J=7.2 Hz, 2H), 4.00 (s, 3H), 2.43 (p, J=7.2 Hz, 2H), 2.32 (s, 3H).

Example 156

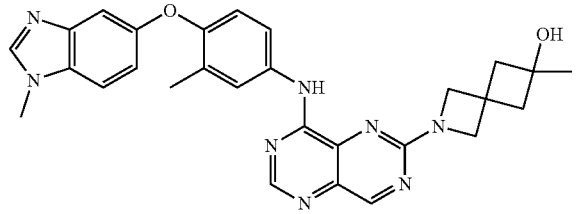 [SMILES: Cc1cc(Nc2ncnc3cnc(N4CC5(C4)CC(C)(O)C5)nc23)ccc1Oc1ccc2c(c1)ncn2C]

6-methyl-2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol A mixture of 6-methyl-2-azaspiro[3.3]heptan-6-ol hydrochloride (53 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (67 mg, 0.52 mmol). The vial was capped and heated to 80° C. for 2 hours. The mixture was then cooled to ambient temperature, and the mixture was diluted with water. The resulting mixture was extracted with CHCl₃ (3×). The combined organic extracts were dried over Na₂SO₄, filtered and concentrated. The crude product was then purified via column chromatography (silica, 12 g, 1-8% MeOH/CHCl₃) to afford 6-methyl-2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol (27 mg, 80%) as a solid. m/z (APCI-pos) M⁺1=509.2; ¹H NMR (400 MHz, CDCl₃) δ 9.02 (s, 1H), 8.54-8.53 (m, 2H), 7.85 (s, 1H), 7.74 (d, J=2.6, 1H), 7.65 (dd, J=8.7, 2.7 Hz, 1H), 7.36-7.28 (m, 2H), 7.06 (dd, J=8.7, 2.2 Hz, 1H), 6.93 (d, J=8.7 Hz, 1H), 4.28 (d, J=9.8 Hz, 4H), 3.85 (s, 3H), 2.41 (s, 4H), 2.34 (s, 3H), 1.42 (s, 3H).

Example 157

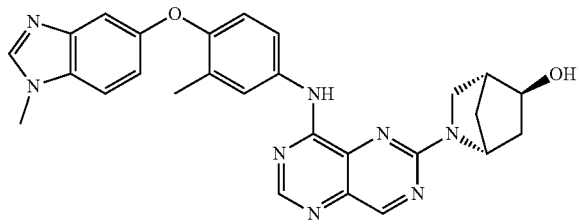 [SMILES: Cc1cc(Nc2ncnc3cnc(N4C[C@H]5C[C@@H]4C[C@@H]5O)nc23)ccc1Oc1ccc2c(c1)ncn2C]

(1R,4R,5S)-2-(8-((3-methyl-4-((1-methyl-1H-benzo[d]imidazol-5-yl)oxy)phenyl)amino)pyrimido[5,4-d]pyrimidin-2-yl)-2-azabicyclo[2.2.1]heptan-5-ol A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol), (1R,4R,5S)-2-azabicyclo[2.2.1]heptan-5-ol hydrochloride (39 mg, 0.26 mmol) and DMSO (0.50 mL) was treated with diisopropylethylamine (50 mg, 0.39 mmol). The vial was capped and heated to 80° C. for 1.5 hours. The mixture was then cooled to ambient temperature, and the mixture was diluted with water. The resulting solid was isolated by vacuum filtration. The solid was then dissolved in CH₂Cl₂. The filtrate was dried over Na₂SO₄, filtered and concentrated. The crude product was then purified via column chromatography (silica, 12 g, 1-8% MeOH/CHCl₃) to afford (1R,4R,5S)-2-(8-((3-methyl-4-((1-methyl-1H-benzo[d]imidazol-5-yl)oxy)phenyl)amino)pyrimido[5,4-d]pyrimidin-2-yl)-2-azabicyclo[2.2.1]heptan-5-ol (27 mg, 80%) as a solid. m/z (APCI-pos) M⁺1=495.2; ¹H NMR (400 MHz, CDCl₃) δ 9.01 (s, 1H), 8.53 (s, 1H), 8.50 (s, 1H), 7.85 (s, 1H), 7.76-7.71 (m, 1H), 7.64 (d, J=8.5 Hz, 1H), 7.35-7.30 (m, 2H), 7.06 (dd, J=8.7, 2.3 Hz, 1H), 6.93 (d, J=8.7 Hz, 1H), 4.94-4.84 (m, 1H), 4.15 (d, J=6.7 Hz, 1H), 3.85 (s, 3H), 3.59 (dd, J=10.9, 4.0 Hz, 1H), 3.21 (d, J=10.9 Hz, 1H), 2.69 (s, 1H), 2.34 (s, 3H), 2.26-2.12 (m, 1H), 2.05 (d, J=10.1 Hz, 1H), 1.79 (d, J=10.0 Hz, 2H), 1.67 (d, J=13.6 Hz, 1H).

Example 158

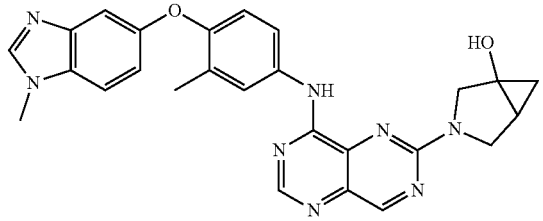 [SMILES: Cc1cc(Nc2ncnc3cnc(N4CC5CC5(O)C4)nc23)ccc1Oc1ccc2c(c1)ncn2C]

3-(8-((3-methyl-4-((1-methyl-1H-benzo[d]imidazol-5-yl)oxy)phenyl)amino)pyrimido[5,4-d]pyrimidin-2-yl)-3-azabicyclo[3.1.0]hexan-1-ol A mixture of 3-azabicyclo[3.1.0]hexan-ol hydrochloride (0.0441 g, 0.325 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.0650 mmol) and DMSO (0.46 mL, 0.0650 mmol) was treated with N,N-diisopropylethylamine (0.0906 mL, 0.520 mmol). The vial was capped and heated to 80° C. for 2.5 hours. The mixture was then cooled to ambient temperature, and the mixture was diluted with water. The resulting solid was isolated by vacuum filtration. The solid was then dissolved in CH₂Cl₂. The filtrate was dried over Na₂SO₄, filtered and concentrated. The crude product was then purified via column chromatography (silica, 12 g, 1-6% MeOH/CHCl₃) to afford 3-(8-((3-methyl-4-((1-methyl-1H-benzo[d]imidazol-5-yl)oxy)phenyl)amino)pyrimido[5,4-d]pyrimidin-2-yl)-3-azabicyclo[3.1.0]hexan-1-ol (23 mg, 70%) as a solid. m/z (APCI-pos) M⁺1=481.2; ¹H NMR (400 MHz, CDCl₃) δ 9.04 (s, 1H), 8.52 (s, 1H), 7.85 (s, 1H), 7.72 (s, 1H), 7.64 (dd, J=8.7, 2.7 Hz, 1H), 7.37-7.28 (m, 2H), 7.07 (dd, J=8.7, 2.3 Hz, 1H), 6.93 (d, J=8.7 Hz, 1H), 5.30 (s, 1H), 4.34 (d, J=10.9 Hz, 1H), 3.87-3.75 (m, 6H), 2.98 (s, 1H), 2.34 (s, 3H), 2.04 (s, 1H), 1.37-1.22 (m, 2H).

Example 159

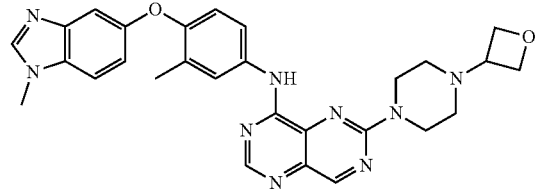 [SMILES: Cc1cc(Nc2ncnc3cnc(N4CCN(C5COC5)CC4)nc23)ccc1Oc1ccc2c(c1)ncn2C]

N-(3-methyl-4-((1-methyl-1H-benzo[d]imidazol-5-yl)oxy)phenyl)-6-(4-(oxetan-3-yl)piperazin-1-yl)pyrimido[5,4-d]pyrimidin-4-amine A mixture of 1-(oxetan-3-yl)piperazine (54 mg, 0.38 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.035 g, 76 µmol) and DMSO (0.51 mL) was heated to 80° C. where it stirred for 4 hours. The mixture was then cooled to ambient temperature and was poured into a stirring solution of 1:1 water:saturated aqueous NaHCO₃. The mixture was stirred for 15 minutes. The resulting solid was isolated by vacuum filtration through qualitative paper. The solid was then dissolved in CH₂Cl₂, and the filtrate was dried over Na₂SO₄, filtered and concentrated. The crude product was then purified via column chromatography (silica, 12 g, 1-6% MeOH/CHCl₃) to afford N-(3-methyl-4-((1-methyl-1H-benzo[d]imidazol-5-yl)oxy)phenyl)-6-(4-(oxetan-3-yl)piperazin-1-yl)pyrimido[5,4-d]pyrimidin-4-amine (32 mg, 79%) as a solid. m/z (APCI-pos) M$^+$1=524.2; $^1$H NMR (400 MHz, CDCl₃) δ 9.05 (s, 1H), 8.54 (s, 1H), 8.48 (s, 1H), 7.85 (s, 1H), 7.73 (d, J=2.7 Hz, 1H), 7.64 (dd, J=8.6, 2.7 Hz, 1H), 7.36-7.28 (m, 2H), 7.06 (dd, J=8.7, 2.3 Hz, 1H), 6.93 (d, J=8.7 Hz, 1H), 4.71 (p, J=6.4 Hz, 4H), 4.04 (t, J=5.1 Hz, 4H), 3.85 (s, 3H), 3.56 (p, J=6.3 Hz, 1H), 2.48 (t, J=5.1 Hz, 4H), 2.34 (s, 3H).

Example 160

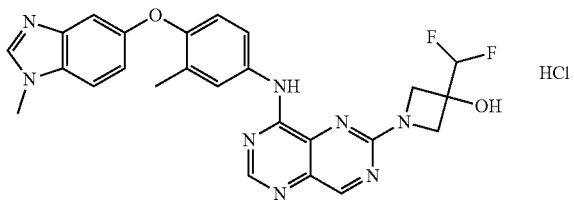 [SMILES: Cc1cc(Nc2ncnc3cnc(N4CC(O)(C(F)F)C4)nc23)ccc1Oc1ccc2c(c1)ncn2C ; Cl]

3-(difluoromethyl)-1-(8-((3-methyl-4-((1-methyl-1H-benzo[d]imidazol-5-yl)oxy)phenyl)amino)pyrimido[5,4-d]pyrimidin-2-yl)azetidin-3-ol hydrochloride A mixture of 3-(difluoromethyl)azetidin-3-ol hydrochloride (41 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (50 mg, 0.39 mmol). The vial was capped and heated to 80° C. for 2 hours. The mixture was then cooled to ambient temperature and was diluted with water. The resulting solid was isolated by vacuum filtration. The solid was then dissolved in IPA/CH₂Cl₂. The filtrate was dried over Na₂SO₄, filtered and concentrated. Due to poor solubility in MeOH/CH2Cl₂ after concentration, the crude product was sonicated in EtOAc. The solid was isolated by vacuum filtration. The crude product was then treated with 5N HCl/IPA (1 mL) until a homogenous mixture formed. The mixture was then concentrated to afford 3-(difluoromethyl)-1-(8-((3-methyl-4-((1-methyl-1H-benzo[d]imidazol-5-yl)oxy)phenyl)amino)pyrimido[5,4-d]pyrimidin-2-yl)azetidin-3-ol (26 mg, 94%) as an HCl salt. m/z (APCI-pos) M$^+$1=505.1; $^1$H NMR (400 MHz, CDCl₃) δ 9.49 (s, 1H), 9.12 (s, 1H), 8.45 (s, 1H), 8.17 (s, 1H), 7.88 (d, J=2.8 Hz, 1H), 7.80 (dd, J=8.8, 2.7 Hz, 1H), 7.56 (d, J=8.7 Hz, 1H), 7.09 (d, J=2.2 Hz, 1H), 7.00 (dd, J=8.7, 2.3 Hz, 1H), 6.89 (d, J=8.8 Hz, 1H), 6.79 (s, 1H), 6.22 (t, J=55.5 Hz, 1H), 4.41 (d, J=10.2 Hz, 2H), 4.12 (d, J=10.2 Hz, 2H), 3.84 (s, 3H), 2.26 (s, 3H).

Example 161

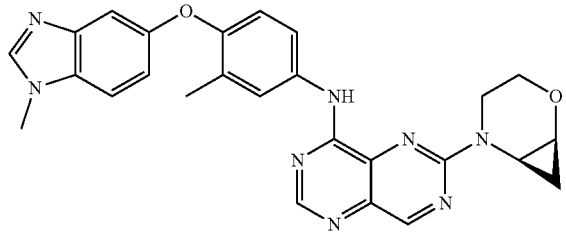 [SMILES: Cc1cc(Nc2ncnc3cnc(N4CCO[C@H]5C[C@H]54)nc23)ccc1Oc1ccc2c(c1)ncn2C]

6-((1S,6R)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine A vial was charged with N-(3-methyl-4-((1-methyl-1H-benzo[d]imidazol-5-yl)oxy)phenyl)-6-(methylsulfonyl)pyrimido[5,4-d]pyrimidin-4-amine (0.400 g, 0.867 mmol), 2-oxa-5-azabicyclo[4.1.0]heptane hydrochloride (0.470 g, 3.47 mmol) and DMSO (5.78 mL). N,N-Diisopropylethylamine (1.21 mL, 6.93 mmol) was added. The vial was capped, and the slurry was heated to 80° C. and stirred for 16 hours. Upon cooling to ambient temperature, the solution was poured into H₂O (40 mL). The resulting solid was isolated by vacuum filtration and then dissolved in CH₂Cl₂. The filtrate was then dried over anhydrous sodium sulfate, filtered, and concentrated. The crude product was then purified via column chromatography (silica, 24 g, 1-5% MeOH/CH₂Cl₂) to afford 6-((1S,6R)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine (95 mg, 45%) as a solid. m/z (APCI-pos) M$^+$1=481.2; $^1$H NMR (400 MHz, CDCl₃) δ 9.16 (s, 1H), 8.58 (s, 1H), 7.85 (s, 1H), 7.73 (d, J=2.7 Hz, 1H), 7.64 (dd, J=8.7, 2.7 Hz, 1H), 7.36-7.29 (m, 2H), 7.06 (dd, J=8.7, 2.2 Hz, 1H), 6.93 (d, J=8.7 Hz, 1H), 3.97-3.84 (m, 1H), 3.85 (s, 3H), 3.66 (d, J=10.3 Hz, 2H), 3.35 (s, 1H), 3.17 (d, J=6.0 Hz, 1H), 2.35 (s, 3H), 1.26 (s, 1H), 1.13 (q, J=6.9 Hz, 1H), 0.73 (dt, J=7.8, 4.2 Hz, 1H).

Example 162

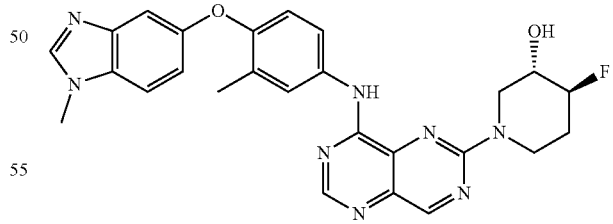

(3S,4S)-4-fluoro-1-(8-((3-methyl-4-((1-methyl-1H-benzo[d]imidazol-5-yl)oxy)phenyl)amino)pyrimido[5,4-d]pyrimidin-2-yl)piperidin-3-ol A mixture of (3S,4S)-4-fluoropiperidin-3-ol hydrochloride (46 mg, 0.29 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (59 mg, 0.46 mmol). The vial was capped and heated to 80° C. for 2 hours. The mixture was then cooled to ambient temperature and was diluted with water. The resulting solid was isolated by vacuum filtration. The solid was then dissolved in $CH_2Cl_2$. The filtrate was dried over $Na_2SO_4$, filtered and concentrated. The crude product was then purified via column chromatography (silica, 12 g, 1-8% MeOH/ $CHCl_3$) to afford (3S,4S)-4-fluoro-1-(8-((3-methyl-4-((1-methyl-1H-benzo[d]imidazol-5-yl)oxy)phenyl)amino) pyrimido[5,4-d]pyrimidin-2-yl)piperidin-3-ol (31 mg, 92%) as a solid. m/z (APCI-pos) M+1=501.2; $^1$H NMR (400 MHz, $CDCl_3$) δ 9.04 (s, 1H), 8.55 (s, 1H), 8.45 (s, 1H), 7.85 (s, 1H), 7.71-7.68 (m, 1H), 7.63 (dd, J=8.6, 2.7 Hz, 1H), 7.35-7.30 (m, 2H), 7.06 (dd, J=8.7, 2.3 Hz, 1H), 6.92 (d, J=8.6 Hz, 1H), 4.77-4.57 (m, 2H), 4.46 (d, J=13.9 Hz, 1H), 3.94 (ddt, J=12.5, 7.3, 4.1 Hz, 1H), 3.85 (s, 3H), 3.66-3.55 (m, 2H), 2.79 (br s, 1H), 2.33 (s, 3H), 2.32-2.19 (m, 1H), 1.87 (dqd, J=13.5, 9.4, 4.2 Hz, 1H).

Example 163

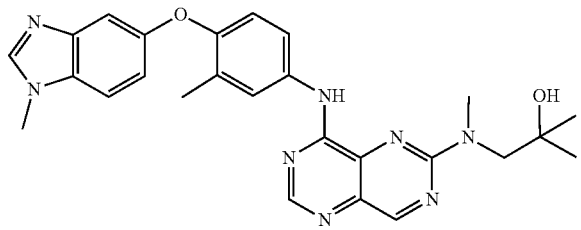 [SMILES: Cc1cc(Nc2ncnc3cnc(N(C)CC(C)(C)O)nc23)ccc1Oc1ccc2c(c1)ncn2C]

2-methyl-1-(methyl(8-((3-methyl-4-((1-methyl-1H-benzo[d]imidazol-5-yl)oxy)phenyl)amino)pyrimido [5,4-d]pyrimidin-2-yl)amino)propan-2-ol A 1-dram vial was charged with 2-methyl-1-(methylamino)propan-2-ol (0.034 g, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.50 mL, 0.065 mmol). The vial was capped and heated to 100° C. for 3 hours. The mixture was then cooled to ambient temperature and was diluted with water and saturated aqueous $NH_4Cl$. The resulting mixture was extracted with $CHCl_3$ (3×). The combined organic extracts were dried over $Na_2SO_4$ filtered and concentrated. The crude product was then purified via column chromatography (silica, g, 1-6% MeOH/$CHCl_3$) to afford 2-methyl-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol (17 mg, 50%) as a solid. m/z (APCI-pos) M+1=485.2; $^1$H NMR (400 MHz, $CDCl_3$) δ 9.01 (s, 1H), 8.55 (s, 1H), 7.85 (s, 1H), 7.74 (d, J=2.7 Hz, 1H), 7.63 (d, J=8.7, 2.6 Hz, 1H), 7.33 (d, J=6.6 Hz, 1H), 7.32 (s, 1H), 7.05 (dd, J=8.6, 2.3 Hz, 1H), 6.93 (d, J=8.6 Hz, 1H), 3.95 (s, 1H), 3.83 (d, J=13.1 Hz, 5H), 3.41 (s, 3H), 2.35 (s, 3H), 1.33 (s, 6H), 1.30-1.22 (m, 1H).

Example 164

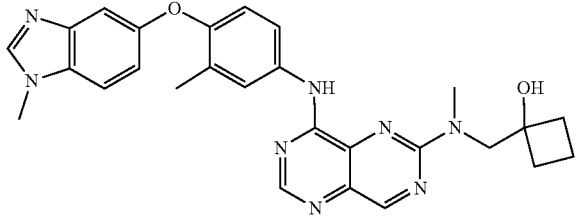 [SMILES: Cc1cc(Nc2ncnc3cnc(N(C)CC4(O)CCC4)nc23)ccc1Oc1ccc2c(c1)ncn2C]

1-((methyl(8-((3-methyl-4-((1-methyl-1H-benzo[d] imidazol-5-yl)oxy)phenyl)amino)pyrimido[5,4-d] pyrimidin-2-yl)amino)methyl)cyclobutan-1-ol A mixture of 1-[(methylamino)methyl]cyclobutan-1-ol (0.030 g, 0.26 mmol), N-(3-methyl-4-((1-methyl-1H-benzo [d]imidazol-5-yl)oxy)phenyl)-6-(methylsulfonyl)pyrimido [5,4-d]pyrimidin-4-amine (0.030 g, 0.065 mmol) and DMSO (0.50 mL) was heated to 80° C. and stirred for 6 hours. The mixture was then cooled to ambient temperature. The mixture was diluted with water and a saturated aqueous $NH_4Cl$ solution (1:1) and then extracted with $CHCl_3$ (3×). The combined organic layers were dried over $Na_2SO_4$, filtered and concentrated. The crude product was then purified via column chromatography (silica, 12 g, 1-6% MeOH/ $CHCl_3$) to afford 1-((methyl(8-((3-methyl-4-((1-methyl-1H-benzo[d]imidazol-5-yl)oxy)phenyl)amino)pyrimido[5,4-d] pyrimidin-2-yl)amino)methyl)cyclobutan-1-ol (18 mg, 53%) as a solid. m/z (APCI-pos) M+1=497.2; $^1$H NMR (400 MHz, $CDCl_3$) δ 9.01 (s, 1H), 8.54 (s, 1H), 8.51 (s, 1H), 7.85 (s, 1H), 7.73 (d, J=2.6 Hz, 1H), 7.63 (dd, J=8.8, 2.7 Hz, 1H), 7.36-7.29 (m, 2H), 7.05 (dd, J=8.7, 2.4 Hz, 1H), 6.93 (d, J=8.7 Hz, 1H), 4.66 (s, 1H), 3.98 (s, 2H), 3.85 (s, 3H), 3.45 (s, 3H), 2.35 (s, 3H), 2.23-2.07 (m, 4H), 1.82 (d, J=10.8 Hz, 1H), 1.60 (dd, J=19.5, 9.8 Hz, 1H).

Example 165

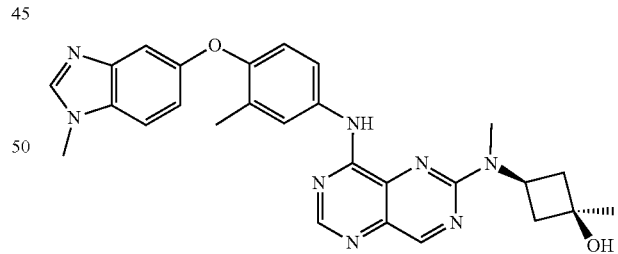

(1s, 3s)-1-methyl-3-(methyl(8-((3-methyl-4-((1-methyl-1H-benzo[d]imidazol-5-yl)oxy)phenyl) amino)pyrimido[5,4-d]pyrimidin-2-yl)amino)cyclobutan-1-ol A mixture of (1s,3s)-1-methyl-3-(methylamino)cyclobutan-1-ol (30 mg, 0.26 mmol), N-(3-methyl-4-((1-methyl-1H-benzo[d]imidazol-5-yl)oxy)phenyl)-6-(methylsulfonyl) pyrimido[5,4-d]pyrimidin-4-amine (0.030 g, 65 µmol) and DMSO (0.50 mL) was heated to 80° C. for 2 hours. The mixture was then cooled to ambient temperature and was diluted with water. The resulting mixture was extracted with CHCl₃ (3×10 mL). The combined extracts were dried over Na₂SO₄, filtered and concentrated. The crude product was then purified via column chromatography (silica, 12 g, 1-8% MeOH/CHCl₃) to afford (1s,3s)-1-methyl-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol (22 mg, 63%) as a solid. m/z (APCI-pos) M⁺1=497.2; ¹H NMR (400 MHz, CDCl₃) δ 9.05 (s, 1H), 8.71 (s, 1H), 8.53 (s, 1H), 7.85 (s, 1H), 7.76 (d, J=2.7 Hz, 1H), 7.62 (dd, J=8.6, 2.7 Hz, 1H), 7.35-7.29 (m, 2H), 7.06 (dd, J=8.6, 2.3 Hz, 1H), 6.93 (d, J=8.7 Hz, 1H), 4.69 (br s, 1H), 3.85 (s, 3H), 3.29 (s, 3H), 2.62-2.55 (m, 2H), 2.54-2.45 (m, 2H), 2.34 (s, 3H), 1.92 (s, 1H), 1.53 (s, 3H).

Example 166

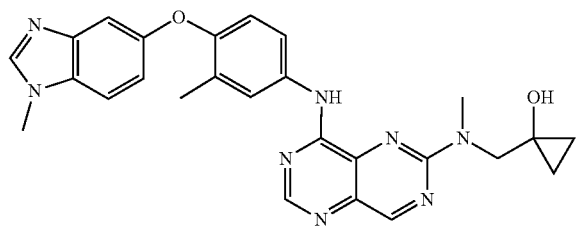 [SMILES: Cc1cc(Nc2ncnc3cnc(N(C)CC4(O)CC4)nc23)ccc1Oc1ccc2c(c1)ncn2C]

1-((methyl(8-((3-methyl-4-((1-methyl-1H-benzo[d]imidazol-5-yl)oxy)phenyl)amino)pyrimido[5,4-d]pyrimidin-2-yl)amino)methyl)cyclopropan-1-ol A mixture of 1-[(methylamino)methyl]cyclopropan-1-ol hydrochloride (0.0406 g, 0.295 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.034 g, 0.0737 mmol) and DMSO (0.49 mL) was treated with N,N-diisopropylethylamine (0.103 mL, 0.589 mmol). The vial was capped and heated to 80° C. for 6 hours. The mixture was then cooled to ambient temperature and was diluted with water. The resulting solid was isolated by vacuum filtration. The solid was then dissolved in CH₂Cl₂. The filtrate was dried over Na₂SO₄, filtered and concentrated. The crude product was then purified via column chromatography (silica, 12 g, 1-6% MeOH/CHCl₃) to afford 1-((methyl(8-((3-methyl-4-((1-methyl-1H-benzo[d]imidazol-5-yl)oxy)phenyl)amino)pyrimido[5,4-d]pyrimidin-2-yl)amino)methyl)cyclopropan-1-ol (25 mg, 67%) as a solid. m/z (APCI-pos) M⁺1=483.2; ¹H NMR (400 MHz, CDCl₃) δ 9.01 (s, 1H), 8.53 (s, 1H), 8.52 (s, 1H), 7.84 (s, 1H), 7.72 (d, J=2.7 Hz, 1H), 7.63 (dd, J=8.6, 2.7 Hz, 1H), 7.33 (d, J=6.1 Hz, 1H), 7.31 (s, 1H), 7.05 (dd, J=8.8, 2.3 Hz, 1H), 6.92 (d, J=8.6 Hz, 1H), 4.00 (s, 2H), 3.85 (s, 3H), 3.47 (s, 1H), 3.42 (s, 3H), 2.34 (s, 3H), 2.04 (s, 1H), 1.26 (t, J=7.1 Hz, 1H), 0.93-0.81 (m, 2H).

Example 167

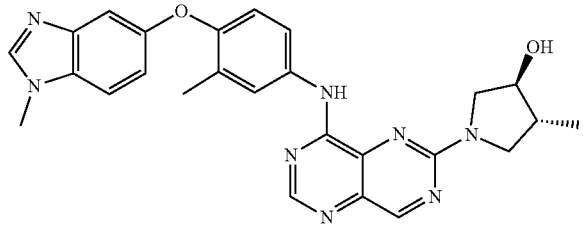 [SMILES: Cc1cc(Nc2ncnc3cnc(N4C[C@@H](C)[C@H](O)C4)nc23)ccc1Oc1ccc2c(c1)ncn2C]

(3S,4R)-4-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (3S,4R)-4-methylpyrrolidin-3-ol hydrochloride (45 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (0.50 mL) was treated with diisopropylethylamine (67 mg, 0.52 mmol). The vial was capped and heated to 80° C. for 2 hours. The mixture was then cooled to ambient temperature and was diluted with water. The resulting solid was isolated by vacuum filtration. The solid was then dissolved in CH₂Cl₂, and the filtrate was dried over Na₂SO₄, filtered and concentrated. The crude product was then purified via column chromatography (silica, 12 g, 1-8% MeOH/CHCl₃) to afford (3S,4R)-4-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (27 mg, 83%) as a solid. m/z (APCI-pos) M⁺1=483.2; ¹H NMR (400 MHz, CDCl₃) δ 9.06 (s, 1H), 8.58 (s, 1H), 8.53 (s, 1H), 7.85 (s, 1H), 7.74 (d, J=2.5 Hz, 1H), 7.66 (dd, J=8.6, 2.7 Hz, 1H), 7.36-7.30 (m, 2H), 7.06 (dd, J=8.7, 2.3 Hz, 1H), 6.93 (d, J=8.7 Hz, 1H), 4.21 (q, J=4.6 Hz, 1H), 4.05-3.98 (m, 2H), 3.85 (s, 3H), 3.71-3.61 (m, 1H), 3.46 (dd, J=11.2, 5.1 Hz, 1H), 2.44-2.36 (m, 1H), 2.34 (s, 3H), 1.97 (br s, 1H), 1.16 (d, J=7.0 Hz, 3H).

Example 168

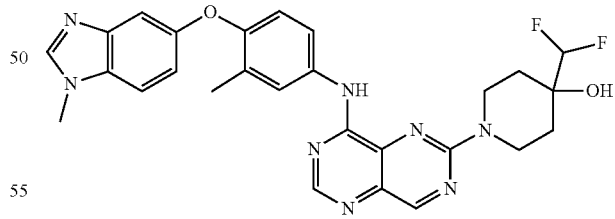

4-(difluoromethyl)-1-(8-((3-methyl-4-((1-methyl-1H-benzo[d]imidazol-5-yl)oxy)phenyl)amino)pyrimido[5,4-d]pyrimidin-2-yl)piperidin-4-ol A mixture of 4-(difluoromethyl)piperidin-4-ol hydrochloride (49 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (0.50 mL) was treated with diisopropylethylamine (50 mg, 0.39 mmol). The vial was capped and heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford 4-(difluoromethyl)-1-(8-((3-methyl-4-((1-methyl-1H-benzo[d]imidazol-5-yl)oxy)phenyl)amino)pyrimido[5,4-d]pyrimidin-2-yl)piperidin-4-ol (24 mg, 66%) as a solid. m/z (APCI-pos) M$^+$1=533.2; $^1$H NMR (400 MHz, CDCl$_3$) δ 9.04 (s, 1H), 8.53 (s, 1H), 8.47 (s, 1H), 7.85 (s, 1H), 7.73 (d, J=2.5 Hz, 1H), 7.64 (dd, J=8.6, 2.7 Hz, 1H), 7.33 (d, J=8.8 Hz, 1H), 7.30 (d, J=2.3 Hz, 1H), 7.07 (dd, J=8.7, 2.3 Hz, 1H), 6.94 (d, J=8.7 Hz, 1H), 5.56 (t, J=56.3 Hz, 1H), 4.86 (d, J=13.4 Hz, 2H), 3.85 (s, 3H), 3.42 (ddd, J=13.4, 11.9, 3.5 Hz, 2H), 2.35 (s, 3H), 1.90-1.72 (m, 4H).

Example 169

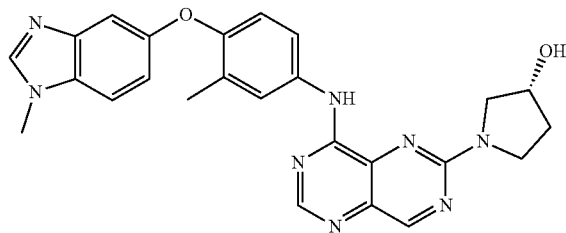 [SMILES: Cc1cc(Nc2ncnc3cnc(N4CC[C@@H](O)C4)nc23)ccc1Oc1ccc2c(c1)ncn2C]

(R)-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (R)-3-hydroxypyrrolidine (23 µL, 0.27 mmol) and N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 54 µmol) in DMSO (0.54 mL, 54 µmol) was heated to 80° C. for 2 hours. The mixture was then cooled to ambient temperature and was diluted with water. The resulting solid was isolated by vacuum filtration. The solid was then dissolved in IPA/CH$_2$Cl$_2$. The filtrate was dried over Na$_2$SO$_4$, filtered and concentrated. The crude product was then purified via column chromatography (silica, 12 g, 1-8% MeOH/CHCl$_3$) to afford (R)-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (21 mg, 81%) as a solid. m/z (APCI-pos) M$^+$1=469.2; $^1$H NMR (400 MHz, CDCl$_3$) δ 9.05 (s, 1H), 8.57 (s, 1H), 8.53 (s, 1H), 7.85 (s, 1H), 7.74 (d, J=4 Hz, 1H), 7.65 (dd, J=8.7, 2.7 Hz, 1H), 7.36-7.28 (m, 2H), 7.06 (dd, J=8.6, 2.3 Hz, 1H), 6.93 (d, J=8.7 Hz, 1H), 4.70 (s, 1H), 3.96-3.79 (m, 4H), 3.84 (s, 3H), 2.34 (s, 3H), 2.30-2.11 (m, 2H).

Example 170

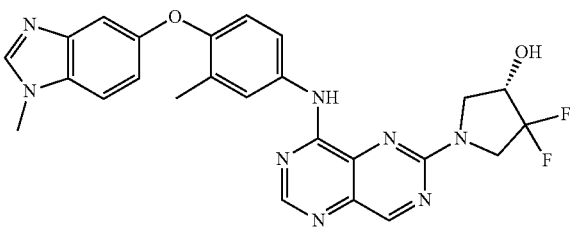 [SMILES: Cc1cc(Nc2ncnc3cnc(N4C[C@H](O)C(F)(F)C4)nc23)ccc1Oc1ccc2c(c1)ncn2C]

(S)-4,4-difluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (S)-4,4-difluoropyrrolidin-3-ol hydrochloride (52 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (5.1 mg, 65 µmol) was treated with diisopropylethylamine (91 µL, 0.52 mmol). The vial was capped and heated to 80° C. for 2 hours. The mixture was then cooled to ambient temperature and was diluted with water. The resulting solid was isolated by vacuum filtration. The solid was then dissolved in IPA/CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (S)-4,4-difluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol 24 mg, 72%) as a solid. m/z (APCI-pos) M$^+$1=505.2; $^1$H NMR (400 MHz, CDCl$_3$) δ 9.55 (s, 1H), 9.15 (s, 1H), 8.45 (s, 1H), 8.17 (s, 1H), 7.87 (d, J=2.7 Hz, 1H), 7.81 (dd, J=8.7, 2.7 Hz, 1H), 7.57 (d, J=8.7 Hz, 1H), 7.10 (d, J=2.2 Hz, 1H), 7.00 (dd, J=8.7, 2.3 Hz, 1H), 6.90 (d, J=8.7 Hz, 1H), 6.23 (d, J=5.0 Hz, 1H), 4.44 (s, 1H), 4.31-3.97 (m, 4H), 3.84 (s, 3H), 2.26 (s, 3H).

Example 171

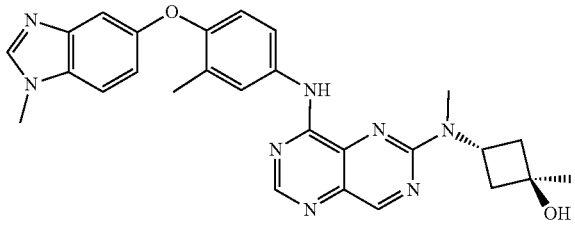 [SMILES: Cc1cc(Nc2ncnc3cnc(N(C)[C@H]4C[C@](C)(O)C4)nc23)ccc1Oc1ccc2c(c1)ncn2C]

(1r,3r)-1-methyl-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 54 µmol), (1r,3r)-1-methyl-3-(methylamino)cyclobutan-1-ol (22 mg, 0.19 mmol) and DMSO (0.54 mL) was heated to 80° C. for 2 hours. The mixture was then cooled to ambient temperature and was diluted with water. The resulting mixture was extracted with CHCl$_3$ (3×10 mL). The combined extracts were dried over Na$_2$SO$_4$, filtered and concentrated. The crude product was then purified via column chromatography (silica, 12 g, 1-8% MeOH/CHCl$_3$) to afford (1r,3r)-methyl-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol (20 mg, 70%) as a solid. m/z (APCI-pos) M$^+$1=497.2; $^1$H NMR (400 MHz, CDCl$_3$) δ 9.05 (s, 1H), 8.71 (s, 1H), 8.53 (s, 1H), 7.85 (s, 1H), 7.76 (d, J=2.7 Hz, 1H), 7.62 (dd, J=8.6, 2.7 Hz, 1H), 7.36-7.28 (m, 2H), 7.06 (dd, J=8.7, 2.4 Hz, 1H), 6.93 (d, J=8.6 Hz, 1H), 4.69 (s, 1H), 3.85 (s, 3H), 3.29 (s, 3H), 2.62-2.54 (m, 2H), 2.54-2.45 (m, 2H), 2.34 (s, 3H), 1.91 (s, 1H), 1.53 (s, 3H).

Example 172

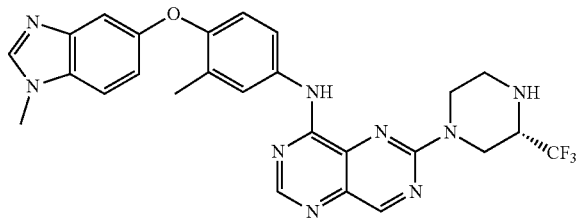 [SMILES: Cc1cc(Nc2ncnc3cnc(N4CCN[C@H](C(F)(F)F)C4)nc23)ccc1Oc1ccc2c(c1)ncn2C]

(S)—N-(3-methyl-4-((1-methyl-1H-benzo[d]imidazol-5-yl)oxy)phenyl)-6-(3-(trifluoromethyl)piperazin-1-yl)pyrimido[5,4-d]pyrimidin-4-amine A mixture of (2S)-2-(trifluoromethyl)piperazine dihydrochloride (59 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (84 mg, 0.65 mmol). The vial was capped and heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-7% MeOH/CHCl$_3$) to afford (S)—N-(3-methyl-4-((1-methyl-1H-benzo[d]imidazol-5-yl)oxy)phenyl)-6-(3-(trifluoromethyl)piperazin-1-yl)pyrimido[5,4-d]pyrimidin-4-amine (25 mg, 70%) as a solid. m/z (APCI-pos) M$^+$1=536.2; $^1$H NMR (400 MHz, CDCl$_3$) δ 9.08 (s, 1H), 8.57 (s, 1H), 8.46 (s, 1H), 7.85 (s, 1H), 7.73 (d, J=2.7 Hz, 1H), 7.63 (dd, J=8.7, 2.7 Hz, 1H), 7.36-7.28 (m, 2H), 7.06 (dd, J=8.7, 2.3 Hz, 1H), 6.93 (d, J=8.7 Hz, 1H), 4.89 (d, J=12.1 Hz, 1H), 4.66 (d, J=13.1 Hz, 1H), 3.85 (s, 3H), 3.47-3.32 (m, 3H), 3.27 (dt, J=12.0, 3.0 Hz, 1H), 2.95 (td, J=11.3, 3.4 Hz, 1H), 2.35 (s, 3H), 2.10 (s, 1H).

Example 173

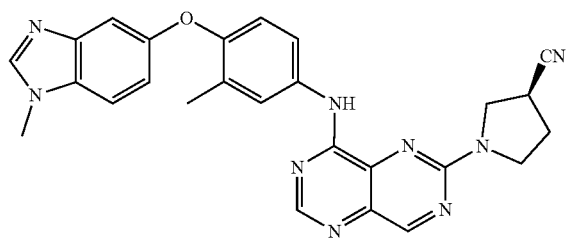 [SMILES: Cc1cc(Nc2ncnc3cnc(N4CC[C@H](O)C4)nc23)ccc1Oc1ccc2c(c1)ncn2C]

(S)-1-(8-((3-methyl-4-((1-methyl-1H-benzo[d]imidazol-5-yl)oxy)phenyl)amino)pyrimido[5,4-d]pyrimidin-2-yl)pyrrolidine-3-carbonitrile A mixture of (3S)-pyrrolidine-3-carbonitrile hydrochloride (34 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with N,N-diisopropylethylamine (50 mg, 0.39 mmol). The vial was capped and heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford (S)-1-(8-((3-methyl-4-((1-methyl-1H-benzo[d]imidazol-5-yl)oxy)phenyl)amino)pyrimido[5,4-d]pyrimidin-2-yl)pyrrolidine-3-carbonitrile (24 mg, 73%) as a solid. m/z (APCI-pos) M$^+$1=478.2; $^1$H NMR (400 MHz, CDCl$_3$) δ 9.09 (s, 1H), 8.57 (s, 1H), 8.53 (s, 1H), 7.85 (s, 1H), 7.74 (d, J=2.7 Hz, 1H), 7.65 (dd, J=8.7, 2.7 Hz, 1H), 7.37-7.30 (m, 2H), 7.06 (dd, J=8.7, 2.3 Hz, 1H), 6.93 (d, J=8.7 Hz, 1H), 4.15-3.94 (m, 3H), 3.89-3.83 (m, 1H), 3.85 (s, 3H), 3.40-3.27 (m, 1H), 2.49 (ddt, J=15.3, 12.9, 6.3 Hz, 2H), 2.35 (s, 3H).

Example 174

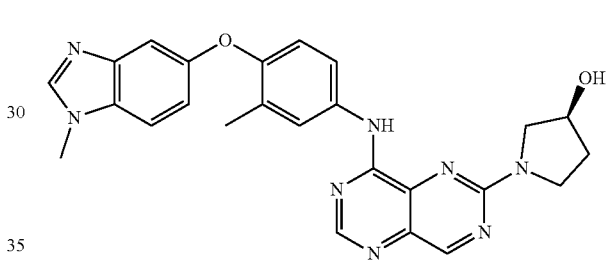

(S)-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (S)-pyrrolidin-3-ol (24 mg, 0.27 mmol) and N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 54 μmol) in DMSO (0.36 mL) was heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford (S)-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (23 mg, 89%) as a solid. m/z (APCI-pos) M$^+$1=469.2; $^1$H NMR (400 MHz, CDCl$_3$) δ 9.05 (s, 1H), 8.57 (s, 1H), 8.53 (s, 1H), 7.85 (s, 1H), 7.74 (d, J=4 Hz, 1H), 7.65 (dd, J=8.7, 2.7 Hz, 1H), 7.36-7.28 (m, 2H), 7.06 (dd, J=8.6, 2.3 Hz, 1H), 6.93 (d, J=8.7 Hz, 1H), 4.70 (s, 1H), 3.96-3.79 (m, 4H), 3.84 (s, 3H), 2.34 (s, 3H), 2.30-2.11 (m, 2H).

Example 175

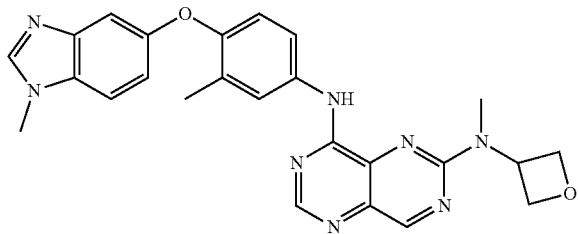 [SMILES: Cc1cc(Nc2ncnc3cnc(N(C)C4COC4)nc23)ccc1Oc1ccc2c(c1)ncn2C]

N2-methyl-N8-(3-methyl-4-((1-methyl-1H-benzo[d]imidazol-5-yl)oxy)phenyl)-N2-(oxetan-3-yl)pyrimido[5,4-d]pyrimidine-2,8-diamine A mixture of N-methyl-3-aminooxetane (28 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.43 mL, 65 μmol) was heated to 80° C. where it stirred for 4 hours. The mixture was then cooled to ambient temperature and was poured into a stirring solution of 1:1 water:saturated aqueous NaHCO$_3$. The mixture was stirred for 15 minutes. The resulting solid was isolated by vacuum filtration through qualitative paper. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford N2-methyl-N8-(3-methyl-4-((1-methyl-1H-benzo[d]imidazol-5-yl)oxy)phenyl)-N2-(oxetan-3-yl)pyrimidine-2,8-diamine (17 mg, 51%) as a solid foam. m/z (APCI-pos) M$^+$1=469.1; $^1$H NMR (400 MHz, CDCl$_3$) δ 9.06 (s, 1H), 8.59 (s, 1H), 8.57 (s, 1H), 7.85 (s, 1H), 7.74 (d, J=2.4 Hz, 1H), 7.67 (dd, J=8.7, 2.7 Hz, 1H), 7.36-7.30 (m, 2H), 7.06 (dd, J=8.7, 2.3 Hz, 1H), 6.94 (d, J=8.7 Hz, 1H), 5.64 (br s, 1H), 5.02-4.94 (m, 4H), 3.85 (s, 3H), 3.40 (s, 3H), 2.35 (s, 3H).

Example 176

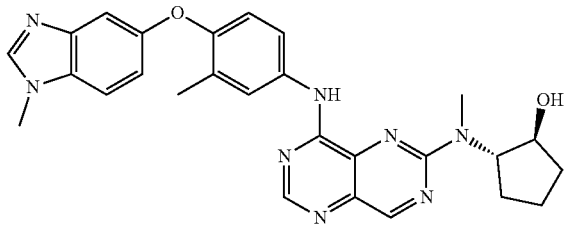 [SMILES: Cc1cc(Nc2ncnc3cnc(N(C)[C@H]4CCC[C@@H]4O)nc23)ccc1Oc1ccc2c(c1)ncn2C]

(1S,2S)-2-(methyl(8-((3-methyl-4-((1-methyl-1H-benzo[d]imidazol-5-yl)oxy)phenyl)amino)pyrimido[5,4-d]pyrimidin-2-yl)amino)cyclopentan-1-ol A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was heated to 80° C. for 2 hours. The mixture was then cooled to ambient temperature and diluted with 1:1 water:saturated aqueous NaHCO$_3$. The resulting solid was isolated by vacuum filtration. The solid was then dissolved in CH$_2$Cl$_2$. The filtrate was dried over Na$_2$SO$_4$, filtered and concentrated. The crude product was then purified via column chromatography (silica, 12 g, 1-7% MeOH/CHCl$_3$) to afford (1S,2S)-2-(methyl(8-((3-methyl-4-((1-methyl-1H-benzo[d]imidazol-5-yl)oxy)phenyl)amino)pyrimido[5,4-d]pyrimidin-2-yl)amino)cyclopentan-1-ol (11 mg, 32%) as a solid. m/z (APCI-pos) M$^+$1=497.2; $^1$H NMR (400 MHz, CDCl$_3$) δ 9.02 (s, 1H), 8.54 (s, 1H), 8.52 (s, 1H), 7.85 (s, 1H), 7.72 (d, J=2.7 Hz, 1H), 7.62 (dd, J=8.7, 2.7 Hz, 1H), 7.33 (d, J=6.0 Hz, 1H), 7.31 (s, 1H), 7.05 (dd, J=8.8, 2.2 Hz, 1H), 6.92 (d, J=8.7 Hz, 1H), 5.03 (q, J=8.2 Hz, 1H), 4.31 (q, J=7.0 Hz, 1H), 3.85 (s, 3H), 3.22 (s, 3H), 2.34 (s, 3H), 2.15-2.02 (m, 2H), 1.97-1.71 (m, 4H).

Example 177

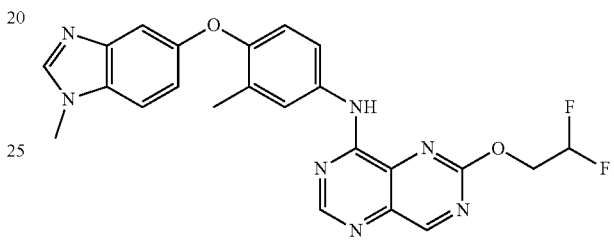

6-(2,2-difluoroethoxy)-N-(3-methyl-4-((1-methyl-1H-benzo[d]imidazol-5-yl)oxy)phenyl)pyrimido[5,4-d]pyrimidin-4-amine 2,2-Difluoroethanol (0.041 mL, 0.65 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMF (0.65 mL, 0.065 mmol) were added to a vial. The mixture was then treated with sodium tert-butoxide (0.031 g, 0.32 mmol), and the mixture was heated to 60° C. where it stirred for 2 hours. Upon cooling to ambient temperature, the solution was diluted with H$_2$O (2 mL). The mixture was then cooled to ambient temperature and diluted with water and saturated aqueous NH$_4$Cl. The resulting mixture was extracted with CHCl$_3$ (3×). The combined organic extracts were dried over Na$_2$SO$_4$, filtered and concentrated. The crude product was then purified via column chromatography (silica, 12 g, 1-4% MeOH/CH$_2$Cl$_2$) to afford 6-(2,2-difluoroethoxy)-N-(3-methyl-4-((1-methyl-1H-benzo[d]imidazol-5-yl)oxy)phenyl)pyrimido[5,4-d]pyrimidin-4-amine (22 mg, 70%) as a solid. m/z (APCI-pos) M$^+$1=464.2; $^1$H NMR (400 MHz, CDCl$_3$) δ 9.30 (s, 1H), 8.74 (s, 1H), 8.57 (s, 1H), 7.86 (s, 1H), 7.75 (d, J=2.7 Hz, 1H), 7.64 (dd, J=8.7, 2.7 Hz, 1H), 7.38-7.30 (m, 2H), 7.07 (dd, J=8.7, 2.3 Hz, 1H), 6.92 (d, J=8.7 Hz, 1H), 4.77 (td, J=13.1, 4.1 Hz, 2H), 3.86 (s, 3H), 2.37 (s, 3H).

Example 178

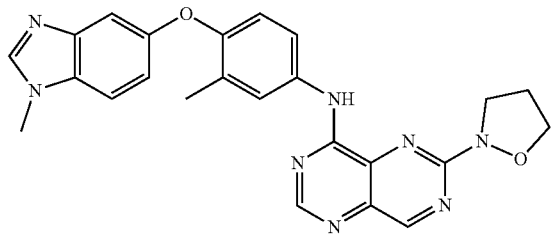 [SMILES: Cc1cc(Nc2ncnc3cnc(N4CCCO4)nc23)ccc1Oc1ccc2c(c1)ncn2C]

6-(isoxazolidin-2-yl)-N-(3-methyl-4-((1-methyl-1H-benzo[d]imidazol-5-yl)oxy)phenyl)pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.025 g, 0.054 mmol), isoxazolidine hydrochloride (0.030 g, 0.27 mmol) and DMSO (0.542 mL) was treated with N,N-diisopropylethylamine (0.094 mL, 0.54 mmol), and the vial was capped and heated to 70° C. for 4 hours. The mixture was cooled to ambient temperature and diluted with water and saturated aqueous NH$_4$Cl. The resulting mixture was extracted with CHCl$_3$ (3×), and the combined organic extracts were dried over Na$_2$SO$_4$, filtered and concentrated. The crude product was then purified via column chromatography (silica, 12 g, 1-6% MeOH/CHCl$_3$) to afford 6-(isoxazolidin-2-yl)-N-(3-methyl-4-((1-methyl-1H-benzo[d]imidazol-5-yl)oxy)phenyl)pyrimido[5,4-d]pyrimidin-4-amine (4 mg, 10%) as a solid. m/z (APCI-pos) M$^+$1=497.2; $^1$H NMR (400 MHz, CDCl$_3$) δ 9.19 (s, 1H), 8.65 (d, J=13.6 Hz, 2H), 7.85 (s, 1H), 7.76 (d, J=2.6 Hz, 1H), 7.65 (dd, J=8.7, 2.7 Hz, 1H), 7.34 (d, J=6.4 Hz, 1H), 7.32 (s, 1H), 7.06 (dd, J=8.7, 2.3 Hz, 1H), 6.92 (d, J=8.7 Hz, 1H), 4.18 (t, J=7.1 Hz, 2H), 4.12-4.04 (m, 2H), 3.85 (s, 3H), 2.48-2.37 (m, 2H), 2.35 (s, 3H).

Example 179

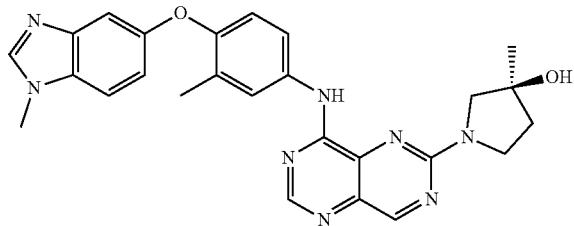 [SMILES: Cc1cc(Nc2ncnc3cnc(N4CC[C@](C)(O)C4)nc23)ccc1Oc1ccc2c(c1)ncn2C]

(S)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (S)-3-methylpyrrolidin-3-ol hydrochloride (60 mg, 0.43 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.050 g, 0.11 mmol) and DMSO (0.72 mL) was treated with diisopropylethylamine (70 mg, 0.54 mmol). The vial was capped and heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (S)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (52 mg, 86%) as a solid. m/z (APCI-pos) M$^+$1=483.3; $^1$H NMR (400 MHz, CDCl$_3$) δ 9.05 (s, 1H), 8.57 (s, 1H), 8.53 (s, 1H), 7.84 (s, 1H), 7.74 (d, J=2.7 Hz, 1H), 7.65 (dd, J=8.7, 2.7 Hz, 1H), 7.35-7.29 (m, 2H), 7.05 (dd, J=8.8, 2.2 Hz, 1H), 6.93 (d, J=8.7 Hz, 1H), 3.89 (m, 3H), 3.85 (s, 3H), 3.61 (d, J=12.0 Hz, 1H), 2.34 (s, 3H), 2.21-2.03 (m, 2H), 1.58 (s, 4H).

Example 180

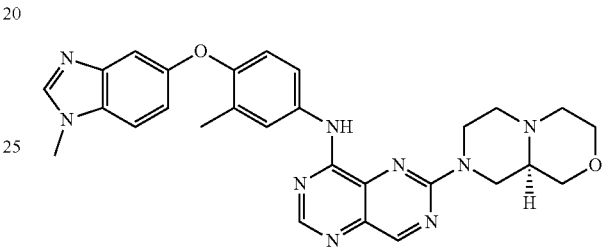

(R)-6-(hexahydropyrazino[2,1-c][1,4]oxazin-8(1H)-yl)-N-(3-methyl-4-((1-methyl-1H-benzo[d]imidazol-5-yl)oxy)phenyl)pyrimido[5,4-d]pyrimidin-4-amine A mixture of (R)-octahydropyrazino[2,1-c][1,4]oxazine dihydrochloride (56 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (0.50 mL) was treated with diisopropylethylamine (84 mg, 0.65 mmol). The vial was capped and heated to 80° C. for 2 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-7% MeOH/CHCl$_3$) to afford (R)-6-(hexahydropyrazino[2,1-c][1,4]oxazin-8(1H)-yl)-N-(3-methyl-4-((1-methyl-1H-benzo[d]imidazol-5-yl)oxy)phenyl)pyrimido[5,4-d]pyrimidin-4-amine (24 mg, 68%) as a solid. m/z (APCI-pos) M$^+$1=524.2; $^1$H NMR (400 MHz, CDCl$_3$) δ 9.05 (s, 1H), 8.54 (s, 1H), 8.46 (s, 1H), 7.85 (s, 1H), 7.73 (d, J=2.7 Hz, 1H), 7.63 (dd, J=8.6, 2.7 Hz, 1H), 7.36-7.29 (m, 2H), 7.06 (dd, J=8.7, 2.3 Hz, 1H), 6.93 (d, J=8.7 Hz, 1H), 4.85 (d, J=13.1 Hz, 1H), 4.68 (d, J=12.7 Hz, 1H), 3.93-3.86 (m, 2H), 3.85 (s, 3H), 3.77 (td, J=11.5, 1.9 Hz, 1H), 3.39 (t, J=10.6 Hz, 1H), 3.27 (td, J=12.0, 2.5 Hz, 1H), 2.93 (d, J=11.4 Hz, 1H), 2.75 (t, J=10.3 Hz, 2H), 2.51-2.39 (m, 2H), 2.38-2.30 (m, 1H), 2.35 (s, 3H).

Example 181

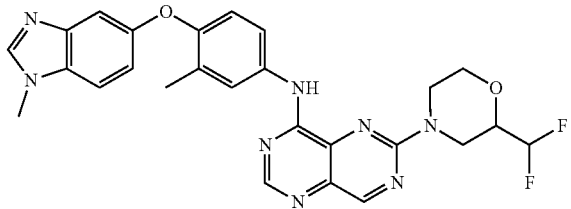 [SMILES: Cc1cc(Nc2ncnc3cnc(N4CCOC(C(F)F)C4)nc23)ccc1Oc1ccc2c(c1)ncn2C]

6-(2-(difluoromethyl)morpholino)-N-(3-methyl-4-
((1-methyl-1H-benzo[d]imidazol-5-yl)oxy)phenyl)
pyrimido[5,4-d]pyrimidin-4-amine A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.040 g, 0.0867 mmol) and 2-(difluoromethyl)morpholine hydrochloride (0.0527 g, 0.303 mmol) in DMSO (0.578 mL, 0.0867 mmol) was treated with N,N-diisopropylethylamine (0.106 mL, 0.607 mmol). The mixture was then heated to 80° C. where it stirred for 1.5 hours. Upon cooling to ambient temperature, the solution was diluted with H$_2$O. The resulting solid was isolated by vacuum filtration and then dissolved in CH$_2$Cl$_2$. The filtrate was then dried over anhydrous sodium sulfate, filtered, and concentrated. The crude product was then purified via column chromatography (silica, 12 g, 1-6% MeOH/CH$_2$Cl$_2$) to afford 6-(2-(difluoromethyl)morpholino)-N-(3-methyl-4-((1-methyl-1H-benzo[d]imidazol-5-yl)oxy)phenyl)pyrimido[5,4-d]pyrimidin-4-amine (32 mg, 67%) as a solid. m/z (APCI-pos) M$^+$1=519.2; $^1$H NMR (400 MHz, CDCl$_3$) 9.09 (s, 1H), 8.58 (s, 1H), 8.46 (s, 1H), 7.85 (s, 1H), 7.73 (d, J=2.7 Hz, 1H), 7.63 (dd, J=8.7, 2.7 Hz, 1H), 7.37-7.29 (m, 2H), 7.06 (dd, J=8.7, 2.2 Hz, 1H), 6.93 (d, J=8.7 Hz, 1H), 4.86 (d, J=13.3 Hz, 1H), 4.70 (d, J=13.5 Hz, 1H), 4.17 (dd, J=11.1, 3.3 Hz, 1H), 3.85 (s, 3H), 3.84-3.70 (m, 2H), 3.30 (ddd, J=13.5, 11.6, 3.6 Hz, 1H), 3.20 (dd, J=13.3, 10.7 Hz, 1H), 2.35 (s, 3H).

Example 182

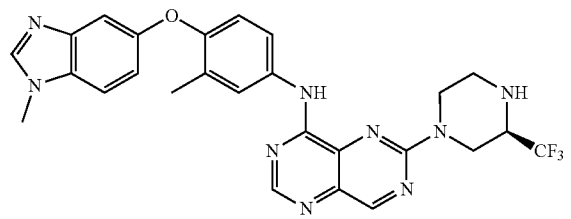 [SMILES: Cc1cc(Nc2ncnc3cnc(N4CCN[C@@H](C(F)(F)F)C4)nc23)ccc1Oc1ccc2c(c1)ncn2C]

(R)—N-(3-methyl-4-((1-methyl-1H-benzo[d]imidazol-5-yl)oxy)phenyl)-6-(3-(trifluoromethyl)piperazin-1-yl)pyrimido[5,4-d]pyrimidin-4-amine A mixture of (2R)-2-(trifluoromethyl)piperazine dihydrochloride (59 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (0.11 mL, 0.65 mmol). The vial was capped and heated to 80° C. for 1.5 hours. The mixture was then cooled to ambient temperature and was diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (R)—N-(3-methyl-4-((1-methyl-1H-benzo[d]imidazol-5-yl)oxy)phenyl)-6-(3-(trifluoromethyl)piperazin-1-yl)pyrimido[5,4-d]pyrimidin-4-amine (22 mg, 61%) as a solid. m/z (APCI-pos) M$^+$1=536.2; $^1$H NMR (400 MHz, CDCl$_3$) δ 9.08 (s, 1H), 8.57 (s, 1H), 8.46 (s, 1H), 7.85 (s, 1H), 7.73 (d, J=2.7 Hz, 1H), 7.63 (dd, J=8.7, 2.7 Hz, 1H), 7.36-7.28 (m, 2H), 7.06 (dd, J=8.7, 2.3 Hz, 1H), 6.93 (d, J=8.7 Hz, 1H), 4.89 (d, J=12.1 Hz, 1H), 4.66 (d, J=13.1 Hz, 1H), 3.85 (s, 3H), 3.47-3.32 (m, 3H), 3.27 (dt, J=12.0, 3.0 Hz, 1H), 2.95 (td, J=11.3, 3.4 Hz, 1H), 2.35 (s, 3H), 2.10 (s, 1H).

Example 183

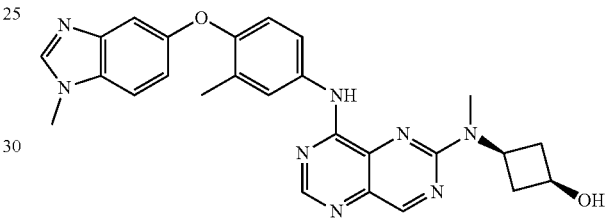

1s,3s)-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol A mixture of (1s,3s)-3-(methylamino)cyclobutan-1-ol hydrochloride (45 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (91 μL, 0.52 mmol). The vial was capped and heated to 80° C. for 2 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (1s,3s)-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol (19 mg, 58%) as a solid. m/z (APCI-pos) M$^+$1=483.2; $^1$H NMR (400 MHz, CDCl$_3$) δ 9.04 (s, 1H), 8.65 (s, 1H), 8.53 (s, 1H), 7.85 (s, 1H), 7.74 (d, J=2.7 Hz, 1H), 7.65 (dd, J=8.6, 2.7 Hz, 1H), 7.33 (d, J=8.7 Hz, 1H), 7.30 (d, J=2.2 Hz, 1H), 7.06 (dd, J=8.7, 2.3 Hz, 1H), 6.93 (d, J=8.7 Hz, 1H), 4.67 (br s, 1H), 4.22 (p, J=7.1 Hz, 1H), 3.85 (s, 3H), 3.29 (s, 3H), 2.84-2.72 (m, 2H), 2.39-2.29 (m, 2H), 2.34 (s, 3H).

Example 184

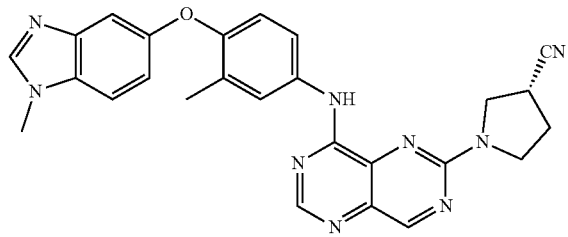 [SMILES: Cc1cc(Nc2ncnc3cnc(N4CC[C@@H](C#N)C4)nc23)ccc1Oc1ccc2c(c1)ncn2C]

(R)-1-(8-((3-methyl-4-((1-methyl-1H-benzo[d]imidazol-5-yl)oxy)phenyl)amino)pyrimido[5,4-d]pyrimidin-2-yl)pyrrolidine-3-carbonitrile A mixture of (R)-pyrrolidine-3-carbonitrile hydrochloride (0.0345 g, 0.260 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.0650 mmol) and DMSO (0.500 mL, 0.0650 mmol) was treated with N,N-diisopropylethylamine (0.0679 mL, 0.390 mmol). The vial was capped and heated to 80° C. for 5 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford (R)-1-(8-((3-methyl-4-((1-methyl-1H-benzo[d]imidazol-5-yl)oxy)phenyl)amino)pyrimido[5,4-d]pyrimidin-2-yl)pyrrolidine-3-carbonitrile (84%) as a solid. m/z (APCI-pos) M$^+$1=478.2; $^1$H NMR (400 MHz, CDCl$_3$) δ 9.09 (s, 1H), 8.55 (d, J=16.8 Hz, 2H), 7.85 (s, 1H), 7.74 (d, J=2.9 Hz, 1H), 7.65 (dd, J=8.7, 2.7 Hz, 1H), 7.37-7.29 (m, 2H), 7.06 (dd, J=8.7, 2.3 Hz, 1H), 6.93 (d, J=8.7 Hz, 1H), 4.17-3.94 (m, 3H), 3.92-3.81 (m, 1H), 3.85 (s, 3H), 3.34 (p, J=6.8 Hz, 1H), 2.49 (ddt, J=15.2, 12.8, 6.3 Hz, 2H), 2.35 (s, 3H).

Example 185

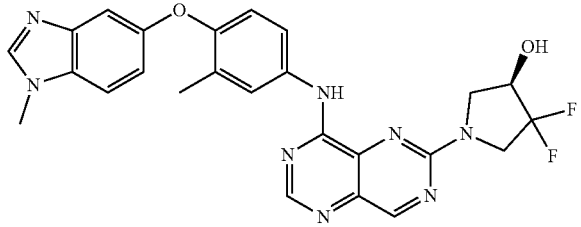 [SMILES: Cc1cc(Nc2ncnc3cnc(N4C[C@@H](O)C(F)(F)C4)nc23)ccc1Oc1ccc2c(c1)ncn2C]

(R)-4,4-difluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (R)-4,4-difluoropyrrolidin-3-ol hydrochloride (52 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisoproylethylamine (91 μL, 0.52 mmol). The vial was capped and heated to 80° C. for 2 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (R)-4,4-difluoro-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (26 mg, 78) as a solid. m/z (APCI-pos) M$^+$1=505.1; $^1$H NMR (400 MHz, CDCl$_3$) δ 9.55 (s, 1H), 9.15 (s, 1H), 8.45 (s, 1H), 8.17 (s, 1H), 7.87 (d, J=2.7 Hz, 1H), 7.81 (dd, J=8.7, 2.7 Hz, 1H), 7.57 (d, J=8.7 Hz, 1H), 7.10 (d, J=2.2 Hz, 1H), 7.00 (dd, J=8.7, 2.3 Hz, 1H), 6.90 (d, J=8.7 Hz, 1H), 6.23 (d, J=5.0 Hz, 1H), 4.44 (s, 1H), 4.31-3.97 (m, 4H), 3.84 (s, 3H), 2.26 (s, 3H).

Example 186

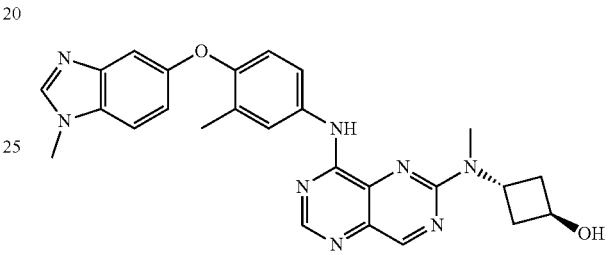

(1r,3r)-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol A mixture of (1r,3r)-3-(methylamino)cyclobutan-1-ol hydrochloride (45 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (67 mg, 0.52 mmol). The vial was capped and heated to 80° C. for 2 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (1r,3r)-3-(methyl(8-((3-methyl-4-((1-methyl-1H-benzo[d]imidazol-5-yl)oxy)phenyl)amino)pyrimido[5,4-d]pyrimidin-2-yl)amino)cyclobutan-1-ol (20 mg, 62%) as a solid. m/z (APCI-pos) M$^+$1=483.2; $^1$H NMR (400 MHz, CDCl$_3$) δ 9.05 (s, 1H), 8.55 (s, 1H), 8.53 (s, 1H), 7.85 (s, 1H), 7.74 (d, J=2.7 Hz, 1H), 7.64 (dd, J=8.6, 2.7 Hz, 1H), 7.36-7.30 (m, 2H), 7.06 (dd, J=8.6, 2.3 Hz, 1H), 6.93 (d, J=8.7 Hz, 1H), 5.58 (p, J=8.2 Hz, 1H), 4.61-4.51 (m, 1H), 3.85 (s, 3H), 3.28 (s, 3H), 2.65-2.54 (m, 2H), 2.43 (ddt, J=11.0, 8.4, 2.6 Hz, 2H), 2.35 (s, 3H).

Example 187

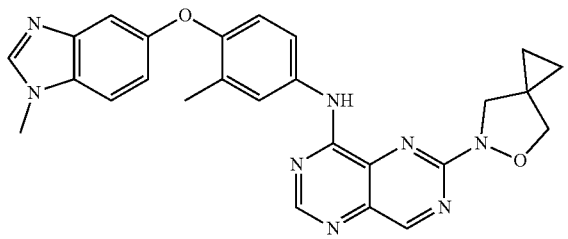 [SMILES: Cc1cc(Nc2ncnc3cnc(N4CC5(CC5)CO4)nc23)ccc1Oc1ccc2c(c1)ncn2C]

N-(3-methyl-4-((1-methyl-1H-benzo[d]imidazol-5-yl)oxy)phenyl)-6-(5-oxa-6-azaspiro[2.4]heptan-6-yl)pyrimido[5,4-d]pyrimidin-4-amine A mixture of 5-oxa-6-azaspiro[2.4]heptane hydrochloride (0.044 g, 0.32 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.50 mL) was treated with N,N-diisopropylethylamine (0.084 g, 0.65 mmol). The vial was capped and heated to 60° C. for 7 hours. The mixture was cooled to ambient temperature and diluted with water and saturated aqueous NH$_4$Cl. The resulting mixture was extracted with CHCl$_3$ (3×). The combined organic extracts were dried over Na$_2$SO$_4$, filtered and concentrated. The crude product was then purified via column chromatography (silica, 12 g, 1-6% MeOH/CHCl$_3$) to afford N-(3-methyl-4-((1-methyl-1H-benzo[d]imidazol-5-yl)oxy)phenyl)-6-(5-oxa-6-azaspiro[2.4]heptan-6-yl)pyrimido[5,4-d]pyrimidin-4-amine as solid that was contaminated with starting material. The material was then purified via RP column chromatography (5 to 75% ACN/H$_2$O with 1% TFA buffer). The fractions containing product were combined, concentrated, and treated with saturated aqueous NaHCO$_3$. The mixture was extracted with CHCl$_3$ (3×). The combined organic extracts were dried over Na$_2$SO$_4$, filtered and concentrated to afford clean N-(3-methyl-4-((1-methyl-1H-benzo[d]imidazol-5-yl)oxy)phenyl)-6-(5-oxa-6-azaspiro[2.4]heptan-6-yl)pyrimido[5,4-d]pyrimidin-4-amine (9 mg, 27%) as a solid. m/z (APCI-pos) M$^+$1=481.2; $^1$H NMR (400 MHz, CDCl$_3$) δ 9.19 (s, 1H), 8.65 (d, J=6.8 Hz, 2H), 7.85 (s, 1H), 7.75 (d, J=2.7 Hz, 1H), 7.65 (dd, J=8.6, 2.7 Hz, 1H), 7.34 (d, J=6.8 Hz, 1H), 7.32 (s, 1H), 7.06 (dd, J=8.6, 2.4 Hz, 1H), 6.92 (d, J=8.7 Hz, 1H), 4.09 (s, 2H), 4.04 (s, 2H), 3.85 (s, 3H), 2.35 (s, 3H), 1.25 (s, 1H), 0.92-0.78 (m, 4H).

Example 188

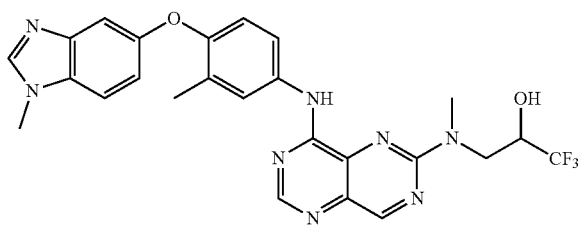 [SMILES: Cc1cc(Nc2ncnc3cnc(N(C)CC(O)C(F)(F)F)nc23)ccc1Oc1ccc2c(c1)ncn2C]

1,1,1-trifluoro-3-(methyl(8-((3-methyl-4-((1-methyl-1H-benzo[d]imidazol-5-yl)oxy)phenyl)amino)pyrimido[5,4-d]pyrimidin-2-yl)amino)propan-2-ol A mixture of 1,1,1-trifluoro-3-(methylamino)propan-2-ol (47 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was heated to 80° C. for 2 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford 1,1,1-trifluoro-3-(methyl(8-((3-methyl-4-((1-methyl-1H-benzo[d]imidazol-5-yl)oxy)phenyl)amino)pyrimido[5,4-d]pyrimidin-2-yl)amino)propan-2-ol (32 mg, 92%) as a solid. m/z (APCI-pos) M$^+$1=525.2; $^1$H NMR (400 MHz, CDCl$_3$) δ 9.02 (s, 1H), 8.55 (s, 1H), 8.49 (s, 1H), 7.84 (s, 1H), 7.71 (d, J=2.7 Hz, 1H), 7.60 (dd, J=8.7, 2.7 Hz, 1H), 7.32 (d, J=8.7 Hz, 1H), 7.29 (d, J=2.3 Hz, 1H), 7.05 (dd, J=8.7, 2.3 Hz, 1H), 6.90 (d, J=8.7 Hz, 1H), 4.44 (br s, 1H), 4.24-3.90 (m, 2H), 3.84 (s, 3H), 3.42 (s, 3H), 2.33 (s, 3H).

Example 189

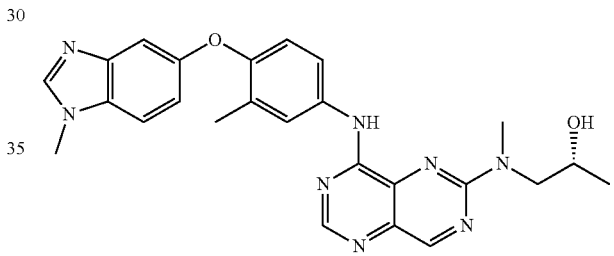

(R)-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol A mixture of (2R)-1-(methylamino)propan-2-ol hydrochloride (0.0327 g, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.650 mL) was treated with N,N-diisopropylethylamine (0.090 mL, 0.520 mmol). The vial was capped and heated to 80° C. for 15 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered, and concentrated. The crude product was then purified via column chromatography (silica, 12 g, 1-6% MeOH/CHCl$_3$) to afford (R)-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol (24 mg, 74%) as a solid. m/z (APCI-pos) M$^+$1=498.2; $^1$H NMR (400 MHz, CDCl$_3$) δ 9.02 (s, 1H), 8.54 (s, 1H), 8.51 (s, 1H), 7.85 (s, 1H), 7.73 (d, J=3.3 Hz, 1H), 7.63 (dd, J=8.6, 2.7 Hz, 1H), 7.36-7.29 (m, 2H), 7.05 (dd, J=8.6, 2.4 Hz, 1H), 6.93 (d, J=8.7 Hz, 1H), 4.26 (s, 1H), 3.91-3.81 (m, 1H), 3.85 (s, 3H), 3.73 (dd, J=14.5, 3.3 Hz, 1H), 3.39 (s, 3H), 2.91 (s, 1H), 2.35 (s, 3H), 1.31 (d, J=6.3 Hz, 3H).

Example 190

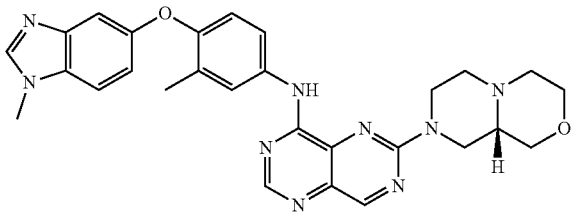 [SMILES: Cc1cc(Nc2ncnc3cnc(N4CCN5CCOC[C@@H]5C4)nc23)ccc1Oc1ccc2c(c1)ncn2C]

(S)-6-(hexahydropyrazino[2,1-c][1,4]oxazin-8(1H)-yl)-N-(3-methyl-4-((1-methyl-1H-benzo[d]imidazol-5-yl)oxy)phenyl)pyrimido[5,4-d]pyrimidin-4-amine A mixture of (S)-octahydro-pyrazino[2,1-c][1,4]oxazine dihydrochloride (56 mg, 0.26 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL, 65 μmol) was treated with diisopropylethylamine (84 mg, 0.65 mmol). The vial was capped and heated to 80° C. for 2 hours. The mixture was then cooled to ambient temperature and diluted with water. The resulting solid was isolated by vacuum filtration. The solid was then dissolved in $CH_2Cl_2$, and the filtrate was dried over $Na_2SO_4$, filtered and concentrated. The crude product was then purified via column chromatography (silica, 12 g, 1-7% MeOH/CHCl$_3$) to afford (S)-6-(hexahydropyrazino[2,1-c][1,4]oxazin-8(1H)-yl)-N-(3-methyl-4-((1-methyl-1H-benzo[d]imidazol-5-yl)oxy)phenyl)pyrimido[5,4-d]pyrimidin-4-amine (27 mg, 77%) as a solid. m/z (APCI-pos) M$^+$1=524.2; $^1$H NMR (400 MHz, CDCl$_3$) δ 9.05 (s, 1H), 8.54 (s, 1H), 8.46 (s, 1H), 7.85 (s, 1H), 7.73 (d, J=2.7 Hz, 1H), 7.63 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 4.85 (d, J=13.1 Hz, 1H), 4.68 (d, J=12.7 Hz, 1H), 3.94-3.86 (m, 2H), 3.85 (s, 3H), 3.77 (td, J=11.5, 2.4 Hz, 1H), 3.39 (t, J=10.6 Hz, 1H), 3.26 (td, J=12.6, 3.2 Hz, 1H), 2.93 (d, J=11.4 Hz, 1H), 2.81-2.69 (m, 2H), 2.50-2.39 (m, 2H), 2.38-2.30 (m, 1H), 2.35 (s, 3H).

Example 191

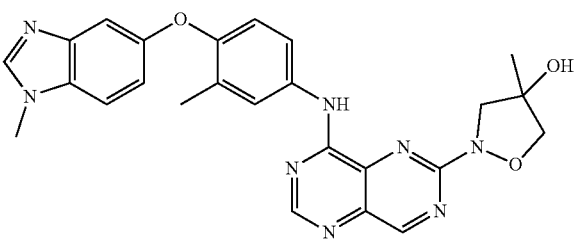 [SMILES: Cc1cc(Nc2ncnc3cnc(N4CC(C)(O)CO4)nc23)ccc1Oc1ccc2c(c1)ncn2C]

4-methyl-2-(8-((3-methyl-4-((1-methyl-1H-benzo[d]imidazol-5-yl)oxy)phenyl)amino)pyrimido[5,4-d]pyrimidin-2-yl)isoxazolidin-4-ol A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol), 4-methyl-1,2-oxazolidin-4-ol hydrochloride (0.045 g, 0.33 mmol) and DMSO (0.46 mL) was treated with N,N-diisopropylethylamine (0.11 mL, 0.65 mmol). The vial was capped and heated to 80° C. for 4 hours. The mixture was cooled to ambient temperature and diluted with water and saturated aqueous NH$_4$Cl. The resulting mixture was extracted with CHCl$_3$ (3×), and the combined organic extracts were dried over Na$_2$SO$_4$, filtered and concentrated. The crude product was then purified via column chromatography (silica, 12 g, 1-8% MeOH/CHCl$_3$) to afford 4-methyl-2-(8-((3-methyl-4-((1-methyl-1H-benzo[d]imidazol-5-yl)oxy)phenyl)amino)pyrimido[5,4-d]pyrimidin-2-yl)isoxazolidin-4-ol as a solid (0.018 g). The product contained a significant impurity (>10%) that was identified as aniline. The solid was then heated and sonicated in EtOAc and then cooled to 0° C. The resulting solid was isolated by vacuum filtration to provide 4-methyl-2-(8-((3-methyl-4-((1-methyl-1H-benzo[d]imidazol-5-yl)oxy)phenyl)amino)pyrimido[5,4-d]pyrimidin-2-yl)isoxazolidin-4-ol (8 mg, 25%) with 2% of the impurity. m/z (APCI-pos) M$^+$1=524.2; $^1$H NMR (400 MHz, CDCl$_3$) δ 9.16 (s, 1H), 8.65 (d, J=9.8 Hz, 2H), 7.85 (s, 1H), 7.75 (d, J=2.7 Hz, 1H), 7.64 (dd, J=8.7, 2.7 Hz, 1H), 7.37-7.30 (m, 2H), 7.06 (dd, J=8.6, 2.4 Hz, 1H), 6.92 (d, J=8.7 Hz, 1H), 5.30 (s, 2H), 4.27-4.07 (m, 2H), 3.97 (d, J=8.7 Hz, 1H), 3.91 (d, J=11.1 Hz, 1H), 3.85 (s, 3H), 2.50 (s, 1H), 2.35 (s, 3H), 1.26 (t, J=7.2 Hz, 1H).

Example 192

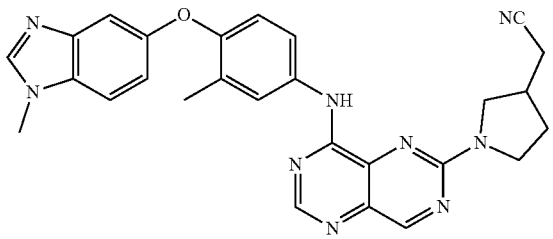

2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)acetonitrile A mixture of 2-(pyrrolidin-3-yl)acetonitrile hydrochloride (0.0381 g, 0.260 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.50 mL) was treated with N,N-diisopropylethylamine (0.068 mL). The vial was capped and heated to 80° C. for 3 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford 2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)acetonitrile (29 mg, 86%) as a solid. m/z (APCI-pos) M$^+$1=492.2; $^1$H NMR (400 MHz, CDCl$_3$) δ 9.07 (s, 1H), 8.55 (s, 2H), 7.85 (s, 1H), 7.75 (d, J=2.7 Hz, 1H), 7.66 (dd, J=8.7, 2.7 Hz, 1H), 7.36-7.29 (m, 2H), 7.06 (dd, J=8.6, 2.3 Hz, 1H), 6.93 (d, J=8.7 Hz, 1H), 4.05 (dd, J=11.5, 7.1 Hz, 1H), 3.85 (s, 3H), 3.76 (dt, J=11.5, 7.7 Hz, 1H), 3.52

(dd, J=11.5, 7.2 Hz, 1H), 2.79 (hept, J=7.1 Hz, 1H), 2.68-2.52 (m, 2H), 2.40 (dd, J=12.4, 6.6 Hz, 1H), 2.35 (s, 3H), 2.07-1.93 (m, 1H).

Example 193

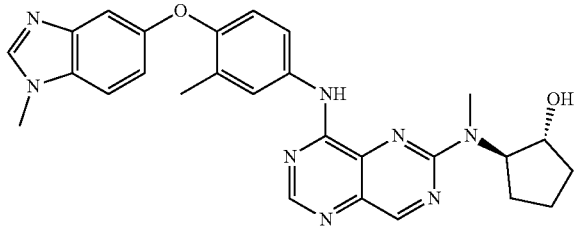 [SMILES: Cc1cc(Nc2ncnc3cnc(N(C)[C@@H]4CCC[C@H]4O)nc23)ccc1Oc1ccc2c(c1)ncn2C]

(1R,2R)-2-(methyl(8-((3-methyl-4-((1-methyl-1H-benzo[d]imidazol-5-yl)oxy)phenyl)amino)pyrimido[5,4-d]pyrimidin-2-yl)amino)cyclopentan-1-ol A mixture of (1R,2R)-2-(methylamino)cyclopentan-1-ol (37 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (0.50 mL) was heated to 80° C. for 3 hours. The mixture was then cooled to ambient temperature and diluted with water. The resulting mixture was extracted with CHCl$_3$ (3×10 mL). The combined extracts were dried over Na$_2$SO$_4$, filtered and concentrated. The crude product was then purified via column chromatography (silica, 12 g, 1-8% MeOH/CHCl$_3$) to afford (1R,2R)-2-(methyl(8-((3-methyl-4-((1-methyl-1H-benzo[d]imidazol-5-yl)oxy)phenyl)amino)pyrimido[5,4-d]pyrimidin-2-yl)amino)cyclopentan-1-ol (12 mg, 34%) as a solid. m/z (APCI-pos) M$^+$1=497.2; $^1$H NMR (400 MHz, CDCl$_3$) δ 9.01 (s, 1H), 8.53 (s, 1H), 8.52 (s, 1H), 7.85 (s, 1H), 7.72 (d, J=2.7 Hz, 1H), 7.62 (dd, J=8.6, 2.7 Hz, 1H), 7.35-7.29 (m, 2H), 7.05 (dd, J=8.9, 2.2 Hz, 1H), 6.92 (d, J=8.7 Hz, 1H), 5.03 (q, J=8.3 Hz, 1H), 4.31 (q, J=7.0 Hz, 1H), 3.85 (s, 3H), 3.22 (s, 3H), 2.34 (s, 3H), 2.15-2.03 (m, 2H), 1.95-1.72 (m, 4H).

Example 194

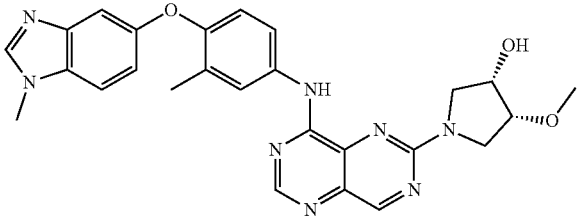 [SMILES: CO[C@@H]1CN(c2ncc3ncnc(Nc4ccc(Oc5ccc6c(c5)ncn6C)c(C)c4)c3n2)C[C@@H]1O]

(3S,4R)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (3S,4R)-4-methoxypyrrolidin-3-ol hydrochloride (50 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 µmol) and DMSO (0.50 mL) was treated with diisopropylethylamine (67 mg, 0.52 mmol). The vial was capped and heated to 80° C. for 2 hours. The mixture was then cooled to ambient temperature and diluted with water. The resulting mixture was extracted with CHCl3 (3×), and the combined extracts were dried over Na$_2$SO$_4$, filtered and concentrated. The crude product was then purified via column chromatography (silica, 12 g, 1-8% MeOH/CHCl$_3$) to afford (3S,4R)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (28 mg, 85%) as a solid. m/z (APCI-pos) M$^+$1=499.1; $^1$H NMR (400 MHz, CDCl$_3$) δ 9.07 (s, 1H), 8.57 (s, 1H), 8.54 (s, 1H), 7.85 (s, 1H), 7.74 (d, J=2.7 Hz, 1H), 7.66 (dd, J=8.6, 2.7 Hz, 1H), 7.35-7.30 (m, 2H), 7.06 (dd, J=8.7, 2.3 Hz, 1H), 6.93 (d, J=8.7 Hz, 1H), 4.56-4.47 (m, 1H), 4.07-4.02 (m, 1H), 3.95 (ddd, J=17.5, 12.0, 5.7 Hz, 2H), 3.85 (s, 3H), 3.78 (br s, 2H), 3.54 (s, 3H), 2.35 (s, 3H).

Example 195

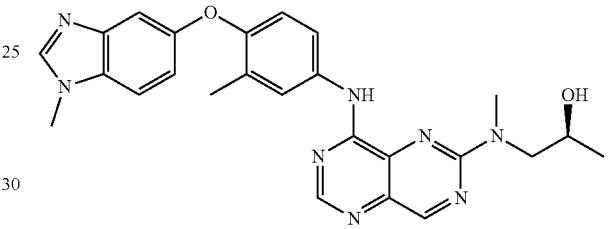

(S)-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol A mixture of (2S)-1-(methylamino)propan-2-ol hydrochloride (0.0327 g, 0.260 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.0650 mmol) and DMSO (0.650 mL, 0.0650 mmol) was treated with N,N-diisopropylethylamine (0.0906 mL, 0.520 mmol). The vial was capped and heated to 80° C. for 5 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (S)-1-(methyl(8-((3-methyl-4-((1-methyl-1H-benzo[d]imidazol-5-yl)oxy)phenyl)amino)pyrimido[5,4-d]pyrimidin-2-yl)amino)propan-2-ol (25 mg, 77%) as a solid. m/z (APCI-pos) M$^+$1=499.1; $^1$H NMR (400 MHz, CDCl$_3$) 9.02 (s, 1H), 8.54 (s, 1H), 8.51 (s, 1H), 7.85 (s, 1H), 7.73 (d, J=2.7 Hz, 1H), 7.63 (dd, J=8.7, 2.7 Hz, 1H), 7.33 (d, J=6.8 Hz, 1H), 7.31 (s, 1H), 7.05 (dd, J=8.6, 2.4 Hz, 1H), 6.93 (d, J=8.7 Hz, 1H), 4.26 (s, 1H), 4.12 (q, J=7.1 Hz, 1H), 3.91-3.81 (m, 1H), 3.85 (s, 3H), 3.73 (dd, J=14.5, 3.4 Hz, 1H), 3.39 (s, 3H), 2.35 (s, 3H), 2.04 (s, 1H), 1.31 (d, J=6.3 Hz, 2H), 1.26 (t, J=7.1 Hz, 1H).

Example 196

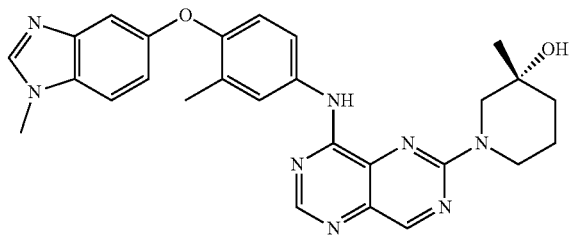 [SMILES: Cc1cc(Nc2ncnc3cnc(N4CCC[C@@](C)(O)C4)nc23)ccc1Oc1ccc2c(c1)ncn2C]

(R)-3-methyl-1-(8-((3-methyl-4-((1-methyl-1H-benzo[d]imidazol-5-yl)oxy)phenyl)amino)pyrimido[5,4-d]pyrimidin-2-yl)piperidin-3-ol A mixture of (R)-3-methylpiperidin-3-ol hydrochloride (43 mg, 0.28 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.026 g, 56 μmol) and DMSO (0.43 mL, 56 μmol) was treated with diisopropylethylamine (58 mg, 0.45 mmol). The vial was capped and heated to 80° C. for 2 hours. The mixture was then cooled to ambient temperature and diluted with water. The resulting solid was isolated by vacuum filtration. The solid was then dissolved in $CH_2Cl_2$, and the filtrate was dried over $Na_2SO_4$, filtered and concentrated. The crude product was then purified via column chromatography (silica, 12 g, 1-8% MeOH/$CHCl_3$) to afford (R)-3-methyl-1-(8-((3-methyl-4-((1-methyl-1H-benzo[d]imidazol-5-yl)oxy)phenyl)amino)pyrimido[5,4-d]pyrimidin-2-yl)piperidin-3-ol (25 mg, 88%) as a solid. m/z (APCI-pos) $M^+1$=497.2; $^1$H NMR (400 MHz, $CDCl_3$) δ 9.03 (s, 1H), 8.52 (s, 1H), 8.48 (s, 1H), 7.85 (s, 1H), 7.73 (d, J=2.6 Hz, 1H), 7.64 (dd, J=8.7, 2.7 Hz, 1H), 7.37-7.30 (m, 2H), 7.06 (dd, J=8.8, 2.2 Hz, 1H), 6.93 (d, J=8.6 Hz, 1H), 4.58-4.51 (m, 1H), 4.44 (d, J=13.4 Hz, 1H), 3.85 (s, 3H), 3.38-3.28 (m, 2H), 2.35 (s, 3H), 2.00-1.90 (m, 1H), 1.87-1.81 (m, 2H), 1.78-1.63 (m, 2H), 1.35 (s, 3H).

Example 197

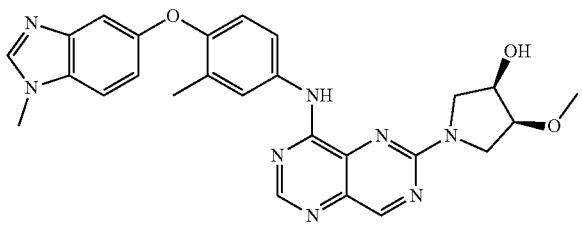 [SMILES: CO[C@H]1CN(c2ncc3ncnc(Nc4ccc(Oc5ccc6c(c5)ncn6C)c(C)c4)c3n2)C[C@H]1O]

(3R,4S)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol A mixture of (3R,4S)-4-methoxypyrrolidin-3-ol hydrochloride (50 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.65 mL) was treated with diisopropylethylamine (67 mg, 0.52 mmol). The vial was capped and heated to 80° C. for 2 hours. The mixture was then cooled to ambient temperature and diluted with water. The resulting mixture was extracted with $CHCl_3$ (3×), and the combined extracts were dried over $Na_2SO_4$, filtered and concentrated. The crude product was then purified via column chromatography (silica, 12 g, 1-8% MeOH/$CHCl_3$) to afford (3R,4S)-4-methoxy-1-(8-((3-methyl-4-((1-methyl-1H-benzo[d]imidazol-5-yl)oxy)phenyl)amino)pyrimido[5,4-d]pyrimidin-2-yl)pyrrolidin-3-ol (30 mg, 90%) as a solid. m/z (APCI-pos) $M^+1$=499.2; $^1$H NMR (400 MHz, $CDCl_3$) δ 9.07 (s, 1H), 8.57 (s, 1H), 8.54 (s, 1H), 7.85 (s, 1H), 7.74 (d, J=2.6 Hz, 1H), 7.66 (dd, J=8.5, 2.7 Hz, 1H), 7.35-7.30 (m, 2H), 7.06 (dd, J=8.7, 2.3 Hz, 1H), 6.93 (d, J=8.7 Hz, 1H), 4.55-4.47 (m, 1H), 4.07-4.03 (m, 1H), 3.95 (ddd, J=17.5, 12.0, 5.7 Hz, 2H), 3.85 (s, 3H), 3.79 (br s, 2H), 3.54 (s, 3H), 2.35 (s, 3H).

Example 198

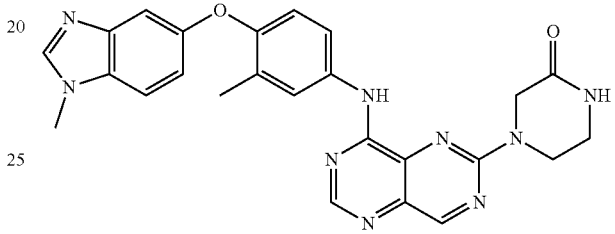

4-(8-((3-methyl-4-((1-methyl-1H-benzo[d]imidazol-5-yl)oxy)phenyl)amino)pyrimido[5,4-d]pyrimidin-2-yl)piperazin-2-one A mixture of piperazin-2-one (33 mg, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol) and DMSO (0.50 mL) was treated with diisopropylethylamine (17 mg, 0.13 mmol). The vial was capped and heated to 80° C. for 2 hours. The mixture was then cooled to ambient temperature and diluted with water. The resulting solid was isolated by vacuum filtration. The solid was then dissolved in $CH_2Cl_2$, and the filtrate was dried over $Na_2SO_4$, filtered and concentrated. The crude product was then purified via column chromatography (silica, 12 g, 1-7% MeOH/$CHCl_3$) to afford 4-(8-((3-methyl-4-((1-methyl-1H-benzo[d]imidazol-5-yl)oxy)phenyl)amino)pyrimido[5,4-d]pyrimidin-2-yl)piperazin-2-one (23 mg, 69%) as a solid. m/z (APCI-pos) $M^+1$=482.1; $^1$H NMR (400 MHz, $CDCl_3$) δ 9.10 (s, 1H), 8.59 (s, 1H), 8.51 (s, 1H), 7.86 (s, 1H), 7.75-7.65 (m, 2H), 7.37-7.31 (m, 2H), 7.07 (dd, J=8.7, 2.4 Hz, 1H), 6.93 (d, J=8.6 Hz, 1H), 6.22 (s, 1H), 4.60 (s, 2H), 4.25 (t, J=5.4 Hz, 2H), 3.85 (s, 3H), 3.58 (td, J=5.4, 2.7 Hz, 2H), 2.36 (s, 3H).

Example 199

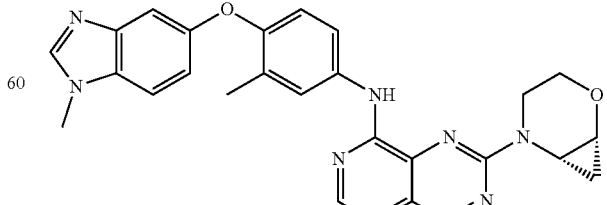

6-((1R,6S)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine A vial was charged with N-(3-methyl-4-((1-methyl-1H-benzo[d]imidazol-5-yl)oxy)phenyl)-6-(methylsulfonyl)pyrimido[5,4-d]pyrimidin-4-amine (0.400 g, 0.86 mmol), 2-oxa-5-azabicyclo[4.1.0]heptane hydrochloride (0.470 g, 3.47 mmol) and DMSO (5.78 mL). N,N-diisopropylethylamine (1.21 mL, 6.93 mmol) was added. The vial was capped, and the slurry was heated to 80° C. and stirred for 16 hours. Upon cooling to ambient temperature, the solution was poured into H$_2$O (40 mL). The resulting solid was isolated by vacuum filtration and then dissolved in CH$_2$Cl$_2$. The filtrate was then dried over anhydrous sodium sulfate, filtered, and concentrated. The crude product was then purified via column chromatography (silica, 24 g, 1-5% MeOH/CH$_2$Cl$_2$) to afford 6-((1R,6S)-2-oxa-5-azabicyclo[4.1.0]heptan-5-yl)-N-(3-methyl-4-((1-methyl-1H-benzo[d]imidazol-5-yl)oxy)phenyl)pyrimido[5,4-d]pyrimidin-4-amine as a solid. m/z (APCI-pos) M$^+$1=491.2; $^1$H NMR (400 MHz, CDCl$_3$) δ 9.16 (s, 1H), 8.58 (s, 2H), 7.85 (s, 1H), 7.73 (d, J=2.7 Hz, 1H), 7.64 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 3.97-3.84 (m, 2H), 3.85 (s, 3H), 3.67 (s, 2H), 3.17 (d, J=6.5 Hz, 1H), 2.35 (s, 3H), 1.13 (q, J=6.9 Hz, 1H), 0.73 (dt, J=7.8, 4.3 Hz, 1H).

Example 200

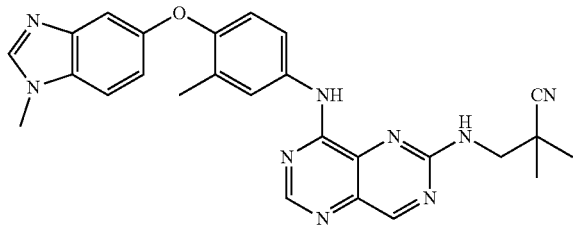 [SMILES: Cc1cc(Nc2ncnc3cnc(NCC(C)(C)C#N)nc23)ccc1Oc1ccc2c(c1)ncn2C]

2,2-dimethyl-3-((8-((3-methyl-4-((1-methyl-1H-benzo[d]imidazol-5-yl)oxy)phenyl)amino)pyrimido[5,4-d]pyrimidin-2-yl)amino)propanenitrile A mixture of 3-amino-2,2-dimethylpropanenitrile (0.032 g, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.43 mL) was heated to 70° C. for 7 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered, and concentrated. The crude product was then purified via column chromatography (silica, 12 g, 1-6% MeOH/CHCl$_3$) to afford 2,2-dimethyl-3-((8-((3-methyl-4-((1-methyl-1H-benzo[d]imidazol-5-yl)oxy)phenyl)amino)pyrimido[5,4-d]pyrimidin-2-yl)amino)propanenitrile (27 mg, 81%) as a solid. m/z (APCI-pos) M$^+$1=480.2; $^1$H NMR (400 MHz, CDCl$_3$) δ 9.05 (s, 1H), 8.59 (d, J=6.3 Hz, 2H), 7.85 (s, 1H), 7.76 (d, J=2.6 Hz, 1H), 7.64 (dd, J=8.8, 2.7 Hz, 1H), 7.36-7.29 (m, 2H), 7.06 (dd, J=8.7, 2.3 Hz, 1H), 6.93 (d, J=8.7 Hz, 1H), 5.77 (t, J=6.8 Hz, 1H), 5.30 (s, 1H), 3.85 (s, 3H), 3.80 (d, J=6.9 Hz, 2H), 3.75-3.65 (m, 1H), 3.69-3.63 (m, 1H), 3.68-3.58 (m, 1H), 2.35 (s, 3H), 1.25 (s, 1H).

Example 201

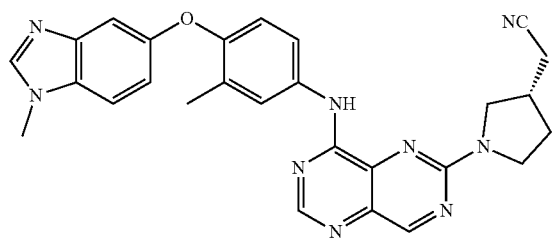 [SMILES: Cc1cc(Nc2ncnc3cnc(N4CC[C@@H](CC#N)C4)nc23)ccc1Oc1ccc2c(c1)ncn2C]

(S)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)acetonitrile A mixture of N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 65 μmol), (S)-2-(pyrrolidin-3-yl)acetonitrile (50 mg, 0.46 mmol) and DMSO (0.50 mL) was treated with diisopropylethylamine (0.12 g, 0.91 mmol). The vial was capped and heated to 80° C. for 2 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-8% MeOH/CHCl$_3$) to afford (S)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)acetonitrile (26 mg, 78%) as a glass when concentrated from CH$_3$CN. m/z (APCI-pos) M$^+$1=492.2; $^1$H NMR (400 MHz, CDCl$_3$) δ 9.07 (s, 1H), 8.55 (s, 2H), 7.85 (s, 1H), 7.75 (d, J=2.7, 1H), 7.66 (dd, J=8.7, 2.7 Hz, 1H), 7.37-7.29 (m, 2H), 7.06 (dd, J=8.7, 2.3 Hz, 1H), 6.93 (d, J=8.7 Hz, 1H), 4.05 (dd, J=11.6, 7.2 Hz, 1H), 3.94 (ddd, J=11.7, 7.9, 4.1 Hz, 1H), 3.85 (s, 3H), 3.76 (dt, J=11.5, 7.5 Hz, 1H), 3.52 (dd, J=11.5, 7.2 Hz, 1H), 2.79 (dt, J=14.3, 7.1 Hz, 1H), 2.64-2.56 (m, 2H), 2.42-2.35 (m, 1H), 2.35 (s, 3H), 2.04-1.97 (m, 1H).

Example 202

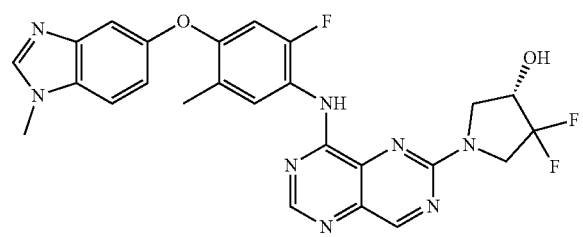 [SMILES: Cc1cc(Nc2ncnc3cnc(N4C[C@H](O)C(F)(F)C4)nc23)c(F)cc1Oc1ccc2c(c1)ncn2C]

(S)-4,4-difluoro-1-(8-((2-fluoro-5-methyl-4-((1-methyl-1H-benzo[d]imidazol-5-yl)oxy)phenyl)amino)pyrimido[5,4-d]pyrimidin-2-yl)pyrrolidin-3-ol Step A: A 16-mL scintillation vial was charged with 8-chloro-2-(methylthio)pyrimido[5,4-d]pyrimidine (67 mg, 0.31 mmol), 2-fluoro-5-methyl-4-((1-methyl-1H-benzo[d]imidazol-5-yl)oxy)aniline (85 mg, 0.31 mmol), and 2-propanol (3.0 mL). The vial was capped and heated to 60° C. for 2 hours, upon which the slurry was diluted with CHCl$_3$ (60 mL) and washed with Na$_2$CO$_3$ (30 mL). The organic phase was dried over anhydrous sodium sulfate, filtered, and concentrated to a wax. Purification by column chromatography (Biotage Selekt, RediSep Gold 12 G, 1-7% MeOH/CHCl$_3$) provided N-(2-fluoro-5-methyl-4-((1-methyl-1H-benzo[d]imidazol-5-yl)oxy)phenyl)-6-(methylthio)pyrimido[5,4-d]pyrimidin-4-amine (0.14 g, 0.31 mmol, 100%). m/z (APCI-pos) M$^+$1=448.1

Step B: A 16-mL scintillation vial was charged with N-(2-fluoro-5-methyl-4-((1-methyl-1H-benzo[d]imidazol-5-yl)oxy)phenyl)-6-(methylthio)pyrimido[5,4-d]pyrimidin-4-amine (0.14 g, 0.31 mmol), water (1 mL), and acetonitrile (2 mL). The slurry was stirred vigorously, and oxone (0.19 g, 0.31 mmol) was added in one aliquot. After stirring for 30 minutes, the mixture was diluted with water and extracted with 10% i-PrOH/CHCl$_3$ (3×). The combined organic extracts were washed with sodium thiosulfate (saturated aqueous) and brine, dried over anhydrous sodium sulfate, filtered, and concentrated in vacuo. Purification by column chromatography (Biotage Selekt, RediSep Gold, 12 G, 1-7% MeOH/CHCl$_3$) provided N-(2-fluoro-5-methyl-4-((1-methyl-1H-benzo[d]imidazol-5-yl)oxy)phenyl)-6-(methylsulfinyl)pyrimido[5,4-d]pyrimidin-4-amine (0.093 g, 0.20 mmol, 64%). m/z (APCI-pos) M$^+$1=448.1.

Step C: A mixture of (S)-4,4-difluoropyrrolidin-3-ol hydrochloride (28 mg, 0.17 mmol), N-(2-fluoro-5-methyl-4-((1-methyl-1H-benzo[d]imidazol-5-yl)oxy)phenyl)-6-(methylsulfinyl)pyrimido[5,4-d]pyrimidin-4-amine (0.020 g, 43 µmol) and DMSO (0.39 mL) was treated with diisopropylethylamine (33 mg, 0.26 mmol). The vial was capped and heated to 60° C. for 2 hours, then at 80° C. for 1 hour. The mixture was then cooled to ambient temperature and diluted with water. The resulting solid was isolated by vacuum filtration. The solid was then dissolved in IPA/CH$_2$Cl$_2$, and the filtrate was dried over Na$_2$SO$_4$, filtered and concentrated. The crude product was then purified via column chromatography (silica, 12 g, 1-7% MeOH/CHCl$_3$) to afford (S)-4,4-difluoro-1-(8-((2-fluoro-5-methyl-4-((1-methyl-1H-benzo[d]imidazol-5-yl)oxy)phenyl)amino)pyrimido[5,4-d]pyrimidin-2-yl)pyrrolidin-3-ol (11 mg, 46%) as a solid. m/z (APCI-pos) M$^+$1=523.1; $^1$H NMR (400 MHz, CDCl$_3$) δ 9.11 (s, 1H), 8.74 (s, 1H), 8.62 (s, 1H), 8.58 (d, J=9.1 Hz, 1H), 7.88 (s, 1H), 7.39-7.34 (m, 2H), 7.07 (dd, J=8.7, 2.3 Hz, 1H), 6.69 (d, J=11.9 Hz, 1H), 4.47 (s, 1H), 4.23-3.93 (m, 4H), 3.87 (s, 3H), 2.36 (s, 3H).

Example 203

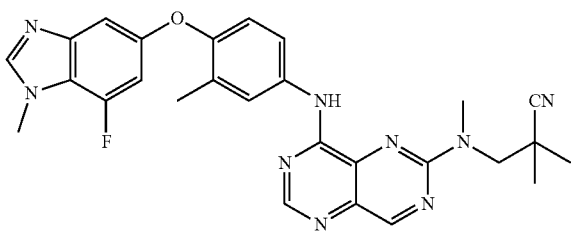 [SMILES: Cc1cc(Nc2ncnc3cnc(N(C)CC(C)(C)C#N)nc23)ccc1Oc1cc(F)c2c(c1)ncn2C]

1-((8-((4-((7-fluoro-1-methyl-1H-benzo[d]imidazol-5-yl)oxy)-3-methylphenyl)amino)pyrimido[5,4-d]pyrimidin-2-yl)(methyl)amino)-2-methylpropan-2-ol A mixture of 2-methyl-1-(methylamino)propan-2-ol (28 mg, 0.27 mmol), N-(4-((7-fluoro-1-methyl-1H-benzo[d]imidazol-5-yl)oxy)-3-methylphenyl)-6-(methylsulfinyl)pyrimido[5,4-d]pyrimidin-4-amine (0.025 g, 54 µmol) and DMSO (0.54 mL) was heated to 80° C. for 2 hours. The mixture was then cooled to ambient temperature and diluted with water and saturated aqueous NH$_4$Cl. The resulting mixture was extracted with CHCl$_3$ (3×), and the combined organic extracts were dried over Na$_2$SO$_4$ filtered and concentrated. The crude product was then purified via column chromatography (silica, 12 g, 1-6% MeOH/CHCl$_3$) to afford 1-((8-((4-((7-fluoro-1-methyl-1H-benzo[d]imidazol-5-yl)oxy)-3-methylphenyl)amino)pyrimido[5,4-d]pyrimidin-2-yl)(methyl)amino)-2-methylpropan-2-ol (27 mg, 70%) as a solid. m/z (APCI-pos) M$^+$1=503.2; $^1$H NMR (400 MHz, CDCl$_3$) δ 9.02 (s, 1H), 8.56 (s, 2H), 7.76-7.73 (m, 2H), 7.68 (m, 1H), 7.04 (d, J=2.0 Hz, 1H), 6.99 (d, J=8.6 Hz, 1H), 6.75 (dd, J=12.2, 2.0 Hz, 1H), 4.00 (s, 3H), 3.92 (br s, 1H), 3.82 (s, 2H), 3.41 (s, 3H), 2.31 (s, 3H), 1.33 (s, 6H).

Example 204

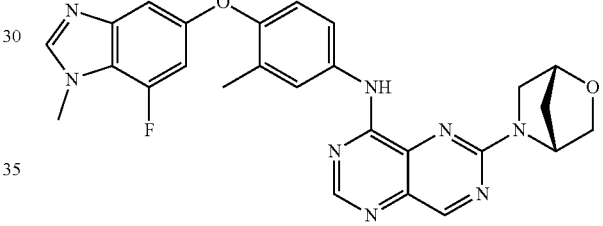

6-((1R,4R)-2-oxa-5-azabicyclo[2.2.1]heptan-5-yl)-N-(4-((7-fluoro-1-methyl-1H-benzo[d]imidazol-5-yl)oxy)-3-methylphenyl)pyrimido[5,4-d]pyrimidin-4-amine A suspension of N-(4-((7-fluoro-1-methyl-1H-benzo[d]imidazol-5-yl)oxy)-3-methylphenyl)-6-(methylsulfinyl)pyrimido[5,4-d]pyrimidin-4-amine (0.030 g, 0.0647 mmol), (1R,4R)-2-oxa-5-azabicyclo[2.2.1]heptane hydrochloride (0.0351 g, 0.259 mmol) and DMSO (0.50 mL) was treated with N,N-diisopropylethylamine (0.0902 mL, 0.518 mmol). The vial was capped and heated to 80° C. for 1.5 hours. Upon cooling to ambient temperature, the solution was diluted with H$_2$O (2 mL). The resulting solid was isolated by vacuum filtration and then dissolved in CH$_2$Cl$_2$. The filtrate was then dried over anhydrous sodium sulfate, filtered, and concentrated. The crude product was then purified via column chromatography (silica, 12 g, 1-6% MeOH/CH$_2$Cl$_2$) to afford 6-((1R,4R)-2-oxa-5-azabicyclo[2.2.1]heptan-5-yl)-N-(4-((7-fluoro-1-methyl-1H-benzo[d]imidazol-5-yl)oxy)-3-methylphenyl)pyrimido[5,4-d]pyrimidin-4-amine (30 mg, 90%) as a solid. m/z (APCI-pos) M$^+$1=499.2; $^1$H NMR (400 MHz, CDCl$_3$) δ 9.05 (s, 1H), 8.55 (s, 1H), 8.54 (s, 1H), 7.75 (d, J=2.3 Hz, 2H), 7.69 (dd, J=8.7, 2.7 Hz, 1H), 7.04 (d, J=2.0 Hz, 1H), 6.99 (d, J=8.7 Hz, 1H), 6.75 (dd, J=12.2, 2.0 Hz, 1H), 5.23 (s, 1H), 4.80 (s, 1H), 4.00 (d, J=1.2 Hz, 3H), 3.93 (s, 1H), 3.75 (d, J=11.1 Hz, 1H), 3.69 (dd, J=11.0, 1.5 Hz, 1H), 2.31 (s, 3H), 1.56 (s, 1H).

Example 205

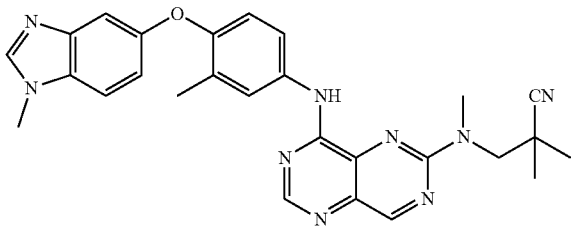 [SMILES: Cc1cc(Nc2ncnc3cnc(N(C)CC(C)(C)C#N)nc23)ccc1Oc1ccc2c(c1)ncn2C]

2,2-dimethyl-3-(methyl(8-((3-methyl-4-((1-methyl-1H-benzo[d]imidazol-5-yl)oxy)phenyl)amino)pyrimido[5,4-d]pyrimidin-2-yl)amino)propanenitrile A mixture of 2,2-dimethyl-3-(methylamino)propanenitrile hydrochloride (0.0417 g, 0.281 mmol), N-(3-methyl-4-((1-methyl-1H-benzo[d]imidazol-5-yl)oxy)phenyl)-6-(methylsulfinyl)pyrimido[5,4-d]pyrimidin-4-amine (0.025 g, 0.056 mmol) and DMSO (0.561 mL) was treated with N,N-diisopropylethylamine (0.078 mL, 0.449 mmol). The vial was capped and heated to 80° C. for 23 hours. The mixture was then cooled to ambient temperature and diluted with water. The resulting solid was isolated by vacuum filtration. The solid was then dissolved in CH$_2$Cl$_2$, and the filtrate was dried over Na$_2$SO$_4$, filtered and concentrated. The crude product was then purified via column chromatography (silica, 12 g, 1-6% MeOH/CHCl$_3$) to afford impure 2,2-dimethyl-3-(methyl(8-((3-methyl-4-((1-methyl-1H-benzo[d]imidazol-5-yl)oxy)phenyl)amino)pyrimido[5,4-d]pyrimidin-2-yl)amino)propanenitrile as a solid (6 mg). The product was further purified via Reverse Phase LC (Isco ACCQ Prep LC, 5 to 75% ACN/H$_2$O with 1% TFA modifier), the fractions containing product were combined and concentrated then treated with saturated aqueous NaHCO$_3$. The mixture was extracted with CHCl$_3$. The combined organic extracts were dried over Na$_2$SO$_4$, filtered, and concentrated to afford 2,2-dimethyl-3-(methyl(8-((3-methyl-4-((1-methyl-1H-benzo[d]imidazol-5-yl)oxy)phenyl)amino)pyrimido[5,4-d]pyrimidin-2-yl)amino)propanenitrile (2.6 mg, 9%) as a solid. m/z (APCI-pos) M$^+$1=494.2; $^1$H NMR (400 MHz, CDCl$_3$) δ1H NMR (400 MHz, CDCl3) δ 9.05 (s, 1H), 8.63 (br s, 1H), 8.57 (s, 1H), 7.85 (s, 1H), 7.75 (d, J=2.7 Hz, 1H), 7.64 (dd, J=8.7, 2.7 Hz, 1H), 7.36-7.29 (m, 2H), 7.06 (dd, J=8.7, 2.3 Hz, 1H), 6.93 (d, J=8.7 Hz, 1H), 4.05 (s, 2H), 3.85 (s, 3H), 3.49 (s, 3H), 2.35 (s, 3H), 1.46 (s, 6H).

Example 206

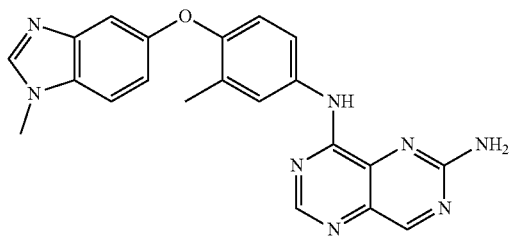 [SMILES: Cc1cc(Nc2ncnc3cnc(N)nc23)ccc1Oc1ccc2c(c1)ncn2C]

N8-(3-methyl-4-((1-methyl-1H-benzo[d]imidazol-5-yl)oxy)phenyl)pyrimido[5,4-d]pyrimidine-2,8-diamine bis(2,2,2-trifluoroacetate)

N-(3-Methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and ammonia (1.30 mL) (0.5M dioxane) were added to a vial. The vial was capped and heated to 60° C., where it stirred for 1 hour, and then at 80° C. for 6 hours. Upon cooling to ambient temperature, the solution was diluted with H$_2$O (2 mL). The resulting solid was isolated by vacuum filtration and dissolved in 1:1 ACN/H$_2$O with 2% TFA. The crude product was purified via Isco Accu Prep LC RP chromatography (20 to 80% ACN/H$_2$O with 0.1% TFA buffer) to afford N8-(3-methyl-4-((1-methyl-1H-benzo[d]imidazol-5-yl)oxy)phenyl)pyrimido[5,4-d]pyrimidine-2,8-diamine bis(2,2,2-trifluoroacetate) (0.037 g, 88%) as a solid. m/z (APCI-pos) M$^+$1=399.2; $^1$H NMR (400 MHz, CDCl$_3$) δ 9.29-9.25 (m, 1H), 8.99 (s, 1H), 8.52 (s, 1H), 7.94-7.86 (m, 2H), 7.85-7.73 (m, 1H), 7.37 (ddd, J=9.1, 4.8, 2.3 Hz, 1H), 7.26-7.15 (m, 1H), 7.08 (d, J=8.7 Hz, 1H), 5.49 (s, 1H), 4.13 (dd, J=2.4, 0.7 Hz, 3H), 2.29 (s, 3H), 2.25 (d, J=17.4 Hz, 1H).

Example 207

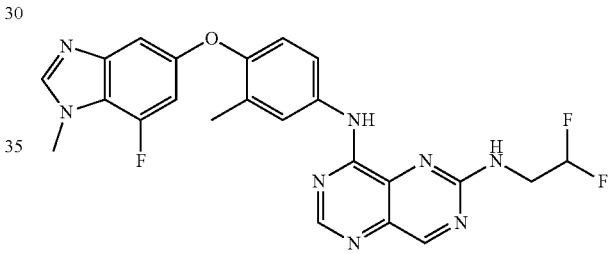

N2-(2,2-difluoroethyl)-N8-(4-((7-fluoro-1-methyl-1H-benzo[d]imidazol-5-yl)oxy)-3-methylphenyl)pyrimido[5,4-d]pyrimidine-2,8-diamine A suspension of N-(4-((7-fluoro-1-methyl-1H-benzo[d]imidazol-5-yl)oxy)-3-methylphenyl)-6-(methylsulfinyl)pyrimido[5,4-d]pyrimidin-4-amine (0.030 g, 0.065 mmol), 2,2-difluoroethylamine (0.053 g, 0.65 mmol) and DMA (0.65 mL) was heated to 70° C. where it stirred for 6 hours. The mixture was cooled to ambient temperature and diluted with water and saturated aqueous NH$_4$Cl. The resulting mixture was extracted with CHCl$_3$ (3×), and the combined organic extracts were dried over Na$_2$SO$_4$, filtered and concentrated. The crude product was then purified via column chromatography (silica, 12 g, 1-6% MeOH/CH$_2$Cl$_2$) to afford N2-(2,2-difluoroethyl)-N8-(4-((7-fluoro-1-methyl-1H-benzo[d]imidazol-5-yl)oxy)-3-methylphenyl)pyrimido[5,4-d]pyrimidine-2,8-diamine (28 mg, 86%) as a solid. m/z (APCI-pos) M$^+$1=481.2; $^1$H NMR (400 MHz, CDCl$_3$) δ 9.08 (s, 1H), 8.61 (s, 1H), 8.51 (s, 1H), 7.75 (d, J=2.3 Hz, 2H), 7.69 (dd, J=8.6, 2.7 Hz, 1H), 7.04 (d, J=2.1 Hz, 1H), 6.99 (d, J=8.6 Hz, 1H), 6.75 (dd, J=12.2, 2.0 Hz, 1H), 6.05 (t, J=4.1 Hz, 1H), 5.72 (s, 1H), 4.08-3.94 (m, 5H), 2.32 (s, 3H), 1.58 (s, 1H), 1.32-1.22 (m, 1H).

Example 208

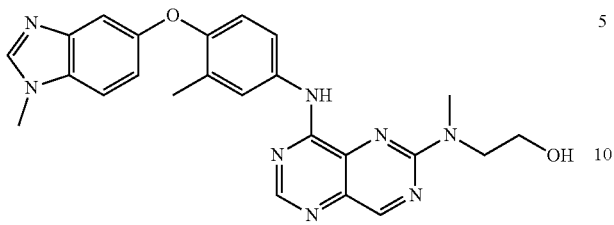

2-(methyl(8-((3-methyl-4-((1-methyl-1H-benzo[d]imidazol-5-yl)oxy)phenyl)amino)pyrimido[5,4-d]pyrimidin-2-yl)amino)ethan-1-ol A mixture of 2-(methylamino)ethanol (0.024 g, 0.33 mmol), N-(3-methyl-4-((1-methyl-1H-benzo[d]imidazol-5-yl)oxy)phenyl)-6-(methylsulfonyl)pyrimido[5,4-d]pyrimidin-4-amine (0.030 g, 0.065 mmol) and DMSO (0.43 mL) was heated to 70° C. for 1.5 hours. The mixture was then cooled to ambient temperature and diluted with water and saturated aqueous NH$_4$Cl. The resulting mixture was extracted with CHCl$_3$ (3×), and the combined organic extracts were dried over Na$_2$SO$_4$, filtered and concentrated. The crude product was then purified via column chromatography (silica, 12 g, 1-6% MeOH/CHCl$_3$) to afford 2-(methyl(8-((3-methyl-4-((1-methyl-1H-benzo[d]imidazol-5-yl)oxy)phenyl)amino)pyrimido[5,4-d]pyrimidin-2-yl)amino)ethan-1-ol (18 mg, 58%) as a solid. m/z (APCI-pos) M$^+$1=481.2; $^1$H NMR (400 MHz, CDCl$_3$) δ 9.02 (s, 1H), 8.53 (s, 1H), 8.51 (s, 1H), 7.84 (s, 1H), 7.72 (d, J=2.7 Hz, 1H), 7.63 (dd, J=8.7, 2.7 Hz, 1H), 7.36-7.30 (m, 1H), 7.31 (s, 1H), 7.05 (dd, J=8.6, 2.4 Hz, 1H), 6.92 (d, J=8.7 Hz, 1H), 3.97 (s, 4H), 3.85 (s, 3H), 3.38 (s, 3H), 2.34 (s, 3H), 1.28-1.23 (m, 1H).

Example 209

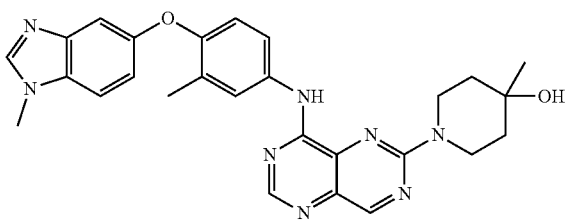 [SMILES: Cc1cc(Nc2ncnc3cnc(N4CCC(C)(O)CC4)nc23)ccc1Oc1ccc2c(c1)ncn2C]

4-methyl-1-(8-((3-methyl-4-((1-methyl-1H-benzo[d]imidazol-5-yl)oxy)phenyl)amino)pyrimido[5,4-d]pyrimidin-2-yl)piperidin-4-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (35 mg, 0.0758 mmol), 4-methylpiperidin-4-ol (44 mg, 0.379 mmol) and DMSO (0.75 mL). The vial was capped and heated to 80° C. for 2.5 hours. Upon cooling to ambient temperature, the solution was concentrated in vacuo. Purification by Biotage Selekt column chromatography (silica, 12 g, 1-8% MeOH/CHCl$_3$) provided 4-methyl-1-(8-((3-methyl-4-((1-methyl-1H-benzo[d]imidazol-5-yl)oxy)phenyl)amino)pyrimido[5,4-d]pyrimidin-2-yl)piperidin-4-ol (39 mg, 0.0750 mmol, 99% yield) as a foam. m/z (APCI-pos) M$^+$1=497.3; $^1$H NMR (400 MHz, CDCl$_3$) δ 9.03 (s, 1H), 8.52 (s, 1H), 8.50 (s, 1H), 7.85 (s, 1H), 7.74 (dd, J=2.7, 0.8 Hz, 1H), 7.65 (dd, J=8.6, 2.7 Hz, 1H), 7.37-7.27 (m, 2H), 7.06 (dd, J=8.7, 2.3 Hz, 1H), 6.93 (d, J=8.7 Hz, 1H), 4.50 (dt, J=13.6, 4.2 Hz, 2H), 3.85 (s, 3H), 3.63 (ddd, J=14.1, 9.7, 4.8 Hz, 2H), 2.35 (s, 3H), 1.80-1.65 (m, 4H), 1.35 (s, 3H).

Example 210

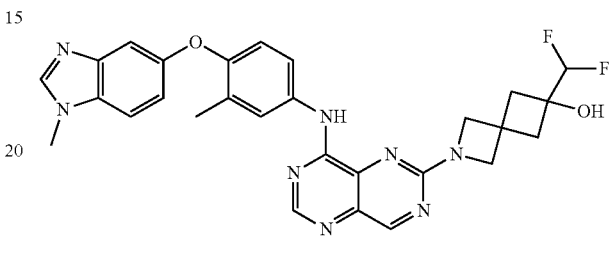

6-(difluoromethyl)-2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (30 mg, 65 μmol), 6-(difluoromethyl)-2-azaspiro[3.3]heptan-6-ol hydrochloride (39 mg, 0.20 mmol), N-ethyl-N-isopropylpropan-2-amine (68 μL, 0.39 mmol), and DMSO (0.60 mL). The vial was capped and heated to 80° C. for 1 hour. The solution was concentrated in vacuo and purified using column chromatography (Silica, 12 g, 1-7% MeOH/CHCl$_3$), providing 6-(difluoromethyl)-2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol (28 mg, 49 μmol, 75%, 95% purity) as a foam. m/z (APCI-pos) M$^+$1=545.3; $^1$H NMR (400 MHz, CDCl$_3$) δ 8.98 (s, 1H), 8.53 (s, 1H), 7.85 (s, 1H), 7.79-7.74 (m, 1H), 7.70 (dd, J=8.5, 2.7 Hz, 1H), 7.34 (dd, J=8.8, 0.6 Hz, 1H), 7.30-7.24 (m, 1H), 7.09 (dd, J=8.7, 2.3 Hz, 1H), 6.95 (d, J=8.7 Hz, 1H), 4.27 (d, J=16.7 Hz, 4H), 3.86 (s, 3H), 3.06 (s, 1H), 2.71 (d, J=14.5 Hz, 2H), 2.34 (s, 3H), 1.58 (s, 4H).

Example 211

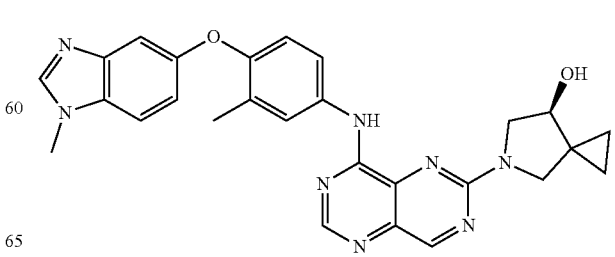

(S)-5-(8-((3-methyl-4-((1-methyl-1H-benzo[d]imidazol-5-yl)oxy)phenyl)amino)pyrimido[5,4-d]pyrimidin-2-yl)-5-azaspiro[2.4]heptan-7-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (33 mg, 72 μmol), (S)-5-azaspiro[2.4]heptan-7-ol (40 mg, 0.36 mmol), and DMSO (0.65 mL). The vial was capped and heated to 80° C. for 3 hours, upon which the mixture was concentrated in vacuo. Purification by column chromatography (silica, 12 g, 1-7% MeOH/DCM) provided (S)-5-(8-((3-methyl-4-((1-methyl-1H-benzo[d]imidazol-5-yl)oxy)phenyl)amino)pyrimido[5,4-d]pyrimidin-2-yl)-5-azaspiro[2.4]heptan-7-ol (39 mg, 75 μmol, 100%, 95% purity) as a powder. m/z (APCI-pos) M$^+$1=495.3; $^1$H NMR (400 MHz, CDCl$_3$) δ 9.05 (s, 1H), 8.52 (s, 2H), 7.85 (s, 1H), 7.76-7.71 (m, 1H), 7.64 (dd, J=8.6, 2.7 Hz, 1H), 7.32 (d, J=8.8 Hz, 2H), 7.05 (dd, J=8.7, 2.2 Hz, 1H), 6.92 (d, J=8.7 Hz, 1H), 4.08-3.99 (m, 2H), 3.98 (dd, J=12.2, 4.0 Hz, 1H), 3.90 (s, 1H), 3.84 (s, 3H), 3.48 (d, J=11.0 Hz, 1H), 2.34 (s, 3H), 2.06 (s, 1H), 0.97 (dt, J=11.7, 5.7 Hz, 1H), 0.85-0.78 (m, 1H), 0.80-0.70 (m, 1H).

Example 212

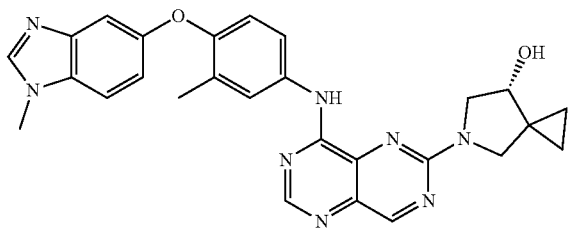 [SMILES: Cc1cc(Nc2ncnc3cnc(N4C[C@H](O)C5(CC5)C4)nc23)ccc1Oc1ccc2c(c1)ncn2C]

(R)-5-(8-((3-methyl-4-((1-methyl-1H-benzo[d]imidazol-5-yl)oxy)phenyl)amino)pyrimido[5,4-d]pyrimidin-2-yl)-5-azaspiro[2.4]heptan-7-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (30 mg, 65 μmol), (R)-5-azaspiro[2.4]heptan-7-ol (37 mg, 0.33 mmol), and DMSO (0.65 mL). The vial was capped and heated to 80° C. for 3 hours, upon which the mixture was concentrated in vacuo. Purification by column chromatography (silica, 12 g, 1-7% MeOH/DCM) provided (R)-5-(8-((3-methyl-4-((1-methyl-1H-benzo[d]imidazol-5-yl)oxy)phenyl)amino)pyrimido[5,4-d]pyrimidin-2-yl)-5-azaspiro[2.4]heptan-7-ol (24 mg, 49 μmol, 75%). m/z (APCI-pos) M$^+$1=495.3; $^1$H NMR (400 MHz, CDCl$_3$) δ 9.05 (s, 1H), 8.52 (s, 2H), 7.84 (s, 1H), 7.76-7.71 (m, 1H), 7.64 (dd, J=8.6, 2.7 Hz, 1H), 7.32 (d, J=9.0 Hz, 2H), 7.05 (dd, J=8.6, 2.3 Hz, 1H), 6.92 (d, J=8.7 Hz, 1H), 4.08-3.99 (m, 2H), 3.98 (dd, J=12.2, 4.0 Hz, 1H), 3.90 (s, 1H), 3.84 (s, 3H), 3.48 (d, J=11.1 Hz, 1H), 2.34 (s, 3H), 1.25 (s, 1H), 0.97 (dt, J=11.8, 5.9 Hz, 1H), 0.82 (d, J=5.7 Hz, 1H), 0.80-0.70 (m, 1H).

Example 213

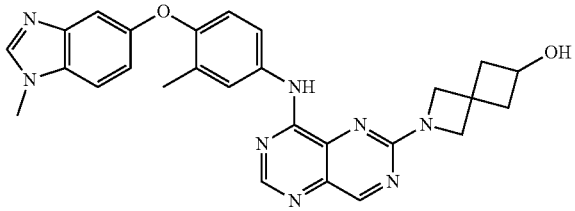 [SMILES: Cc1cc(Nc2ncnc3cnc(N4CC5(CC(O)C5)C4)nc23)ccc1Oc1ccc2c(c1)ncn2C]

2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (25 mg, 56 μmol), 2-azaspiro[3.3]heptan-6-ol hydrochloride (25 mg, 0.17 mmol), diisopropylethylamine (59 μL, 0.34 mmol), and DMSO (0.56 mL). The vial was capped and heated to 80° C. for 2.5 hours, upon which the volatiles were removed in vacuo. Purification by column chromatography (Biotage Selekt, RediSep Gold 12 G, 1-8% MeOH/CHCl$_3$) provided 2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-6-ol (24 mg, 45 μmol, 80%, 93% purity) as a foam. m/z (APCI-pos) M$^+$1=495.3; $^1$H NMR (400 MHz, CDCl$_3$) δ 9.00 (s, 1H), 8.53 (d, J=3.7 Hz, 2H), 7.84 (s, 1H), 7.74 (dd, J=2.8, 0.8 Hz, 1H), 7.66 (dd, J=8.6, 2.7 Hz, 1H), 7.33 (dd, J=8.7, 0.5 Hz, 1H), 7.29 (dd, J=2.3, 0.6 Hz, 1H), 7.07 (dd, J=8.7, 2.3 Hz, 1H), 6.94 (d, J=8.6 Hz, 1H), 4.34 (q, J=7.1 Hz, 1H), 4.24 (d, J=5.0 Hz, 4H), 3.85 (s, 3H), 2.67 (ddd, J=10.0, 6.9, 3.1 Hz, 2H), 2.23 (ddd, J=10.1, 7.3, 3.1 Hz, 2H), 2.17 (s, 1H), 1.60 (s, 2H).

Example 214

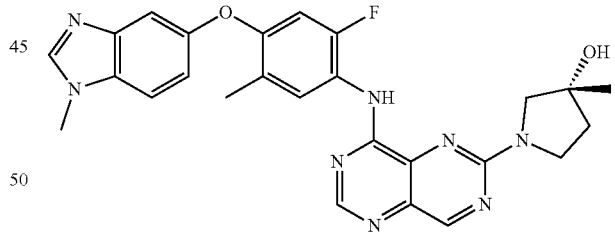

(R)-1-(8-((2-fluoro-5-methyl-4-((1-methyl-1H-benzo[d]imidazol-5-yl)oxy)phenyl)amino)pyrimido[5,4-d]pyrimidin-2-yl)-3-methylpyrrolidin-3-ol A 1-dram vial was charged with (R)-3-methylpyrrolidin-3-ol (29 mg, 0.29 mmol), N-(2-fluoro-5-methyl-4-((1-methyl-1H-benzo[d]imidazol-5-yl)oxy)phenyl)-6-(methylsulfonyl)pyrimido[5,4-d]pyrimidin-4-amine (27 mg, 58 μmol), and DMSO (0.70 mL). The vial was capped and heated to 80° C. for 3 hours. The solution was concentrated in vacuo and purified using column chromatography (Silica, 12 g, 1-7% MeOH/CHCl$_3$), providing (R)-1-(8-((2-fluoro-5-methyl-4-((1-methyl-1H-benzo[d]imidazol-5-yl)oxy)phenyl)amino)pyrimido[5,4-d]pyrimidin-2-yl)-3-methylpyrrolidin-3-ol (20.1 mg, 65%, 95% purity) as a foam. m/z (APCI-pos) M+1=501.2; $^1$H NMR (400 MHz, CDCl$_3$) δ 9.06 (s, 1H), 8.79 (s, 1H), 8.59 (d, J=9.0 Hz, 1H), 8.57 (s, 1H), 7.87 (s, 1H), 7.39-7.32 (m, 2H), 7.06 (dd, J=8.7, 2.2 Hz, 1H), 6.68 (d, J=11.9 Hz, 1H), 3.86 (s, 3H), 3.60 (d, J=12.0 Hz, 1H), 2.36 (d, J=0.9 Hz, 3H), 2.14 (d, J=5.0 Hz, 1H), 2.14-2.02 (m, 1H), 1.74 (s, 1H).

Example 215

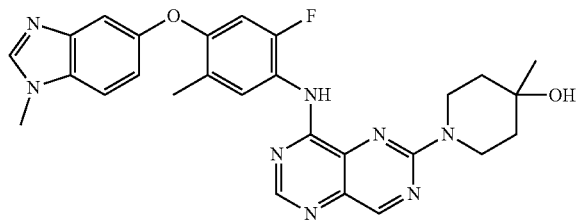 [SMILES: Cc1cc(Nc2ncnc3cnc(N4CCC(C)(O)CC4)nc23)c(F)cc1Oc1ccc2c(c1)ncn2C]

1-(8-((2-fluoro-5-methyl-4-((1-methyl-1H-benzo[d]imidazol-5-yl)oxy)phenyl)amino)pyrimido[5,4-d]pyrimidin-2-yl)-4-methylpiperidin-4-ol A 1-dram vial was charged with 4-methylpiperidin-4-ol (24 mg, 0.21 mmol), N-(2-fluoro-5-methyl-4-((1-methyl-1H-benzo[d]imidazol-5-yl)oxy)phenyl)-6-(methylsulfinyl)pyrimido[5,4-d]pyrimidin-4-amine (32 mg, 69 μmol), and DMSO (700 μL). The vial was capped and heated to 80° C. for 3 hours, upon which the volatiles were removed in vacuo. Purification by column chromatography (silica, 12 g, 1-7% MeOH/DCM) provided 1-(8-((2-fluoro-5-methyl-4-((1-methyl-1H-benzo[d]imidazol-5-yl)oxy)phenyl)amino)pyrimido[5,4-d]pyrimidin-2-yl)-4-methylpiperidin-4-ol (27 mg, 72%). m/z (APCI-pos) M+1=515.2; $^1$H NMR (400 MHz, CDCl$_3$) δ 9.04 (s, 1H), 8.75-8.70 (m, 1H), 8.61-8.54 (m, 2H), 7.87 (s, 1H), 7.39-7.32 (m, 2H), 7.06 (dd, J=8.8, 2.2 Hz, 1H), 6.69 (d, J=11.9 Hz, 1H), 4.47 (d, J=13.4 Hz, 1H), 3.86 (s, 3H), 3.62 (ddd, J=13.9, 9.5, 4.9 Hz, 2H), 2.36 (d, J=0.9 Hz, 3H), 1.71 (t, J=4.7 Hz, 3H), 1.57 (s, 2H), 1.33 (s, 3H), 1.27 (s, 1H).

Example 216

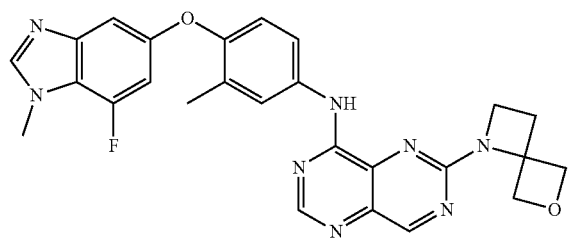 [SMILES: Cc1cc(Nc2ncnc3cnc(N4CCC45COC5)nc23)ccc1Oc1cc(F)c2c(c1)ncn2C]

N-(4-((7-fluoro-1-methyl-1H-benzo[d]imidazol-5-yl)oxy)-3-methylphenyl)-6-(6-oxa-1-azaspiro[3.3]heptan-1-yl)pyrimido[5,4-d]pyrimidin-4-amine A 1-dram vial was charged with N-(4-((7-fluoro-1-methyl-1H-benzo[d]imidazol-5-yl)oxy)-3-methylphenyl)-6-(methylsulfinyl)pyrimido[5,4-d]pyrimidin-4-amine (25 mg, 0.0539 mmol), 6-oxa-1-azaspiro[3.3]heptane oxalate (2:1, 46.7 mg, 0.162 mmol), N,N-diisopropylethylamine (58.1 μL, 0.324 mmol), and DMA (1079 μL, 0.0539 mmol). The vial was capped and heated to 80° C. for 2.5 hours. Upon cooling to ambient temperature, the slurry was diluted with EtOAc (20 mL) and washed with brine (aqueous, half saturated, 3×7 mL). The organic phase was dried over anhydrous sodium sulfate, filtered, and concentrated in vacuo. Purification by column chromatography (silica, 12 g, 1-7% MeOH/CHCl$_3$) provided N-(4-((7-fluoro-1-methyl-1H-benzo[d]imidazol-5-yl)oxy)-3-methylphenyl)-6-(6-oxa-1-azaspiro[3.3]heptan-1-yl)pyrimido[5,4-d]pyrimidin-4-amine (23.9 mg, 84% yield) as a foam. m/z (APCI-pos) M+1=499.2; $^1$H NMR (400 MHz, CDCl$_3$) δ 9.12 (s, 1H), 8.96 (s, 1H), 8.59 (s, 1H), 7.79 (d, J=2.7 Hz, 1H), 7.76 (s, 1H), 7.72 (dd, J=8.6, 2.7 Hz, 1H), 7.04 (s, 1H), 6.98 (d, J=8.7 Hz, 1H), 6.73 (d, J=12.1 Hz, 1H), 5.62 (d, J=7.1 Hz, 2H), 4.82 (s, 2H), 4.12 (t, J=7.2 Hz, 2H), 4.00 (d, J=1.0 Hz, 3H), 2.69 (t, J=7.1 Hz, 2H), 2.30 (s, 3H).

Example 217

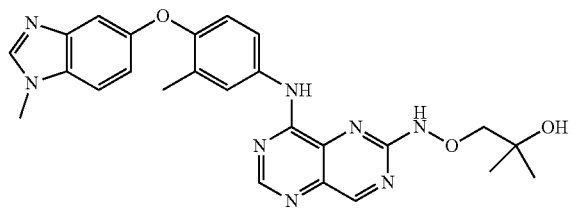 [SMILES: Cc1cc(Nc2ncnc3cnc(NOCC(C)(C)O)nc23)ccc1Oc1ccc2c(c1)ncn2C]

2-methyl-1-(((8-((3-methyl-4-((1-methyl-1H-benzo[d]imidazol-5-yl)oxy)phenyl)amino)pyrimido[5,4-d]pyrimidin-2-yl)amino)oxy)propan-2-ol A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (30 mg, 0.0650 mmol), 1-(aminooxy)-2-methylpropan-2-ol (34.2 mg, 0.325 mmol), and DMSO (650 μL, 0.0650 mmol). The vial was capped and heated to 80° C. for 25 hours. Upon cooling to ambient temperature, the solution was concentrated in vacuo. Purification by column chromatography (12 g, 1-8% MeOH/CHCl$_3$) provided 2-methyl-1-(((8-((3-methyl-4-((1-methyl-1H-benzo[d]imidazol-5-yl)oxy)phenyl)amino)pyrimido[5,4-d]pyrimidin-2-yl)amino)oxy)propan-2-ol (16 mg, 46% yield) as a foam. m/z (APCI-pos) M+1=487.2; $^1$H NMR (400 MHz, CDCl$_3$) δ 9.14 (s, 1H), 8.95 (s, 1H), 8.68 (s, 1H), 8.22 (s, 1H), 7.95-7.89 (m, 1H), 7.85 (s, 1H), 7.73 (dd, J=8.7, 2.7 Hz, 1H), 7.36-7.29 (m, 2H), 7.06 (dd, J=8.6, 2.4 Hz, 1H), 6.92 (d, J=8.7 Hz, 1H), 4.61 (s, 1H), 4.08 (s, 2H), 3.85 (s, 3H), 2.35 (s, 3H), 1.36 (s, 6H).

Example 218

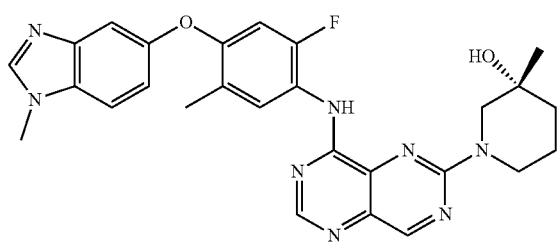 [SMILES: Cc1cc(Nc2ncnc3cnc(N4CCC[C@@](C)(O)C4)nc23)c(F)cc1Oc1ccc2c(c1)ncn2C]

(R)-1-(8-((2-fluoro-5-methyl-4-((1-methyl-1H-benzo
[d]imidazol-5-yl)oxy)phenyl)amino)pyrimido[5,4-d]
pyrimidin-2-yl)-3-methylpiperidin-3-ol A 1-dram vial was charged with N-(2-fluoro-5-methyl-4-((1-methyl-1H-benzo[d]imidazol-5-yl)oxy)phenyl)-6-(methylsulfinyl)pyrimido[5,4-d]pyrimidin-4-amine (20 mg, 43 μmol), (R)-3-methylpiperidin-3-ol hydrochloride (20 mg, 0.13 mmol), diisopropylethylamine (28 mg, 0.22 mmol), and DMSO (0.60 mL). The vial was capped and heated to 80° C. for 17 hours, upon which the volatiles were removed in vacuo. Purification by column chromatography (12 g, 1-7% MeOH/CHCl$_3$) provided (R)-1-(8-((2-fluoro-5-methyl-4-((1-methyl-1H-benzo[d]imidazol-5-yl)oxy)phenyl)amino)pyrimido[5,4-d]pyrimidin-2-yl)-3-methylpiperidin-3-ol (11 mg, 45%). m/z (APCI-pos) M$^+$1=515.3; $^1$H NMR (400 MHz, CDCl$_3$) δ 9.04 (s, 1H), 8.74-8.69 (m, 1H), 8.56 (d, J=8.7 Hz, 2H), 7.87 (s, 1H), 7.39-7.29 (m, 2H), 7.09-7.01 (m, 1H), 6.69 (d, J=11.9 Hz, 1H), 4.55 (d, J=13.2 Hz, 1H), 4.45 (d, J=13.3 Hz, 1H), 3.86 (s, 3H), 3.36-3.24 (m, 2H), 2.36 (d, J=1.0 Hz, 3H), 1.87-1.78 (m, 1H), 1.77-1.59 (m, 3H), 1.33 (s, 3H), 1.25 (s, 1H).

Example 219

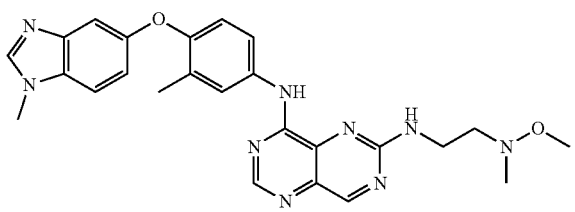 [SMILES: CON(C)CCNc1ncc2ncnc(Nc3ccc(Oc4ccc5c(c4)ncn5C)c(C)c3)c2n1]

N2-(2-(methoxy(methyl)amino)ethyl)-N8-(3-methyl-
4-((1-methyl-1H-benzo[d]imidazol-5-yl)oxy)phenyl)
pyrimido[5,4-d]pyrimidine-2,8-diamine A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (30 mg, 0.0650 mmol), 2-[methoxy(methyl)amino]ethan-1-amine (33.9 mg, 0.325 mmol), and DMSO (650 μL). The vial was capped and heated to 80° C. for 19 hours, upon which the volatiles were removed in vacuo. Purification by column chromatography (12 g, 1-8% MeOH/CHCl$_3$) provided N2-(2-(methoxy(methyl)amino)ethyl)-N8-(3-methyl-4-((1-methyl-1H-benzo[d]imidazol-5-yl)oxy)phenyl)pyrimido[5,4-d]pyrimidine-2,8-diamine (28.4 mg, 86% yield) as a foam. m/z (APCI-pos) M$^+$1=486.3; $^1$H NMR (400 MHz, CDCl$_3$) δ 9.01 (s, 1H), 8.61 (s, 1H), 8.55 (s, 1H), 7.85 (s, 1H), 7.79-7.73 (m, 1H), 7.65 (dd, J=8.6, 2.7 Hz, 1H), 7.36-7.29 (m, 2H), 7.06 (dd, J=8.7, 2.2 Hz, 1H), 6.93 (d, J=8.7 Hz, 1H), 6.02 (s, 1H), 3.85 (s, 3H), 3.74 (q, J=5.5 Hz, 2H), 3.59 (s, 3H), 2.94 (t, J=5.8 Hz, 2H), 2.67 (s, 3H), 1.25 (s, 2H).

Example 220

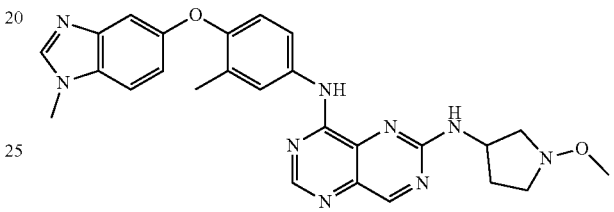

N2-(1-methoxypyrrolidin-3-yl)-N8-(3-methyl-4-((1-
methyl-1H-benzo[d]imidazol-5-yl)oxy)phenyl)py-
rimido[5,4-d]pyrimidine-2,8-diamine A 1-dram vial was charged with N-(3-methyl-4-((1-methyl-1H-benzo[d]imidazol-5-yl)oxy)phenyl)-6-(methylsulfonyl)pyrimido[5,4-d]pyrimidin-4-amine (30 mg, 0.0650 mmol), 1-methoxypyrrolidin-3-amine (37.8 mg, 0.325 mmol), and DMSO (650 μL). The vial was capped and heated to 80° C. for 2.5 hours, upon which the volatiles were removed in vacuo. Purification by column chromatography (12 g, 1-8% MeOH/CHCl$_3$) provided N2-(1-methoxypyrrolidin-3-yl)-N8-(3-methyl-4-((1-methyl-1H-benzo[d]imidazol-5-yl)oxy)phenyl)pyrimido[5,4-d]pyrimidine-2,8-diamine (26.1 mg, 0.0509 mmol, 78.3% yield) as a foam. m/z (APCI-pos) M$^+$1=498.3; $^1$H NMR (400 MHz, CDCl$_3$) δ 9.00 (s, 1H), 8.55 (d, J=2.2 Hz, 2H), 7.85 (s, 1H), 7.76-7.71 (m, 1H), 7.64 (dd, J=8.6, 2.7 Hz, 1H), 7.36-7.29 (m, 2H), 7.06 (dd, J=8.7, 2.2 Hz, 1H), 6.93 (d, J=8.7 Hz, 1H), 5.97 (s, 1H), 4.80 (s, 1H), 3.85 (s, 3H), 3.58 (s, 3H), 3.28 (s, 2H), 3.02 (dt, J=12.5, 8.3 Hz, 1H), 2.35 (s, 3H), 1.59 (s, 2H), 1.25 (s, 1H).

Additional compounds of the invention were prepared by modifications of the methods exemplified above and are shown in Table 1 below. The method in Table 1 refers to the Example number procedure above in which the compound in the table was prepared in a similar procedure as the Example, changing the appropriate intermediate or reactant.

TABLE 1

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 221 (Ex. 6) | N-(3-methyl-4-((1-methyl-1H-benzo[d]imidazol-5-yl)oxy)phenyl)-6-propoxypyrimido[5,4-d]pyrimidin-4-amine | 441.2 | ¹H NMR (400 MHz, CDCl₃) δ 8.67 (s, 1H), 8.57 (s, 1H), 8.04 (d, J = 9.1 Hz, 1H), 7.86 (s, 1H), 7.74 (s, 1H), 7.64 (d, J = 8.6 Hz, 1H), 7.46-7.12 (m, 4H), 7.06 (d, J = 8.7 Hz, 1H), 6.94 (d, J = 8.7 Hz, 1H), 4.44 (t, J = 6.8 Hz, 2H), 3.85 (s, 3H), 2.35 (s, 3H), 1.92 (q, J = 7.4 Hz, 2H), 1.31-1.23 (m, 3H) |
| 222 (Ex. 40) | N-(3-methyl-4-((1-methyl-1H-benzo[d]imidazol-5-yl)oxy)phenyl)-6-(pyrrolidin-1-yl)pyrimido[5,4-d]pyrimidin-4-amine | 453.3 | ¹H NMR (400 MHz, CD₃OD) δ 8.89 (s, 1H), 8.30 (s, 1H), 8.08 (s, 1H), 7.78 (d, J = 2.7 Hz, 1H), 7.68 (dd, J = 8.7, 2.7 Hz, 1H), 7.51 (d, J = 8.8 Hz, 1H), 7.11 (d, J = 2.3 Hz, 1H), 7.05 (dd, J = 8.8, 2.3 Hz, 1H), 6.86 (d, J = 8.8 Hz, 1H), 3.89 (s, 3H), 3.73-3.65 (m, 4H), 2.28 (s, 3H), 2.10-2.03 (m, 4H) |
| 223 (Ex. 42) | N-(3-methyl-4-((1-methyl-1H-benzo[d]imidazol-5-yl)oxy)phenyl)-6-(2-methyloxazol-5-yl)pyrimido[5,4-d]pyrimidin-4-amine | 465.2 | ¹H NMR (400 MHz, CDCl₃) δ 9.39 (d, J = 1.2 Hz, 1H), 8.89 (s, 1H), 8.79 (s, 1H), 7.94 (s, 1H), 7.86 (s, 1H), 7.79 (d, J = 2.6 Hz, 1H), 7.68 (dd, J = 8.7, 2.7 Hz, 1H), 7.38-7.31 (m, 2H), 7.07 (dd, J = 8.7, 2.1 Hz, 1H), 6.93 (d, J = 8.7 Hz, 1H), 3.85 (s, 3H), 2.67 (s, 3H), 2.37 (s, 3H) |
| 224 (Ex. 40) | N-(3-methyl-4-((1-methyl-1H-benzo[d]imidazol-5-yl)oxy)phenyl)-6-(4-(methylsulfonyl)piperidin-1-yl)pyrimido[5,4-d]pyrimidin-4-amine | 545.2 | ¹H NMR (400 MHz, (CD₃)₂SO) δ 9.62 (s, 1H), 9.09 (s, 1H), 8.40 (s, 1H), 8.17 (s, 1H), 7.84 (d, J = 2.9 Hz, 1H), 7.77 (dd, J = 8.8, 2.8 Hz, 1H), 7.56 (dd, J = 8.9, 2.4 Hz, 1H), 7.09 (d, J = 2.2 Hz, 1H), 6.99 (dd, J = 8.4, 2.7 Hz, 1H), 6.89 (d, J = 8.8 Hz, 1H), 3.83 (s, 3H), 3.56-3.27 (m, 2H), 3.14-3.01 (m, 3H), 2.96 (s, 3H), 2.25 (s, 3H), 2.20-2.05 (m, 2H), 1.75-1.52 (m, 2H) |
| 225 (Ex. 39) | N-(3-methyl-4-((1-methyl-1H-benzo[d]imidazol-5-yl)oxy)phenyl)-6-(1-methyl-3-azabicyclo[3.1.0]hexan-3-yl)pyrimido[5,4-d]pyrimidin-4-amine | 479.2 | ¹H NMR (400 MHz, CDCl₃) δ 9.03 (s, 1H), 8.57 (s, 1H), 8.52 (s, 1H), 7.85 (s, 1H), 7.75 (d, J = 2.6 Hz, 1H), 7.66 (dd, J = 8.8, 2.7 Hz, 1H), 7.37-7.29 (m, 2H), 7.06 (dd, J = 8.7, 2.3 Hz, 1H), 6.93 (d, J = 8.7 Hz, 1H), 3.85 (s, 3H), 3.76-3.68 (m, 1H), 3.52-3.42 (m, 2H), 2.35 (s, 3H), 1.46-1.37 (m, 5H), 0.73 (dd, J = 8.0, 4.8 Hz, 1H), 0.46 (t, J = 4.4 Hz, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 226 (Ex. 41) | N-(3-methyl-4-((1-methyl-1H-benzo[d]imidazol-5-yl)oxy)phenyl)-6-(oxazol-2-yl)pyrimido[5,4-d]pyrimidin-4-amine | 451.2 | 1H NMR (400 MHz, CDCl3) δ 9.52 (s, 1H), 9.30 (s, 1H), 8.85 (s, 1H), 7.96 (s, 1H), 7.88 (s, 1H), 7.82 (s, 1H), 7.74-7.67 (m, 1H), 7.49 (s, 1H), 7.39-7.32 (m, 2H), 7.08 (dd, J = 8.7, 2.3 Hz, 1H), 6.92 (d, J = 8.7 Hz, 1H), 3.86 (s, 3H), 2.37 (s, 3H) |
| 227 (Ex. 45) | (R)-6-(3-methoxypiperidin-1-yl)-N-(3-methyl-4-((1-methyl-1H-benzo[d]imidazol-5-yl)oxy)phenyl)pyrimido[5,4-d]pyrimidin-4-amine | 497.3 | 1H NMR (400 MHz, (CD3)2SO) δ 7.85 (d, J = 2.7 Hz, 1H), 7.78 (dd, J = 8.7, 2.7 Hz, 1H), 7.11 (d, J = 2.2 Hz, 1H), 9.58 (s, 1H), 9.06 (s, 1H), 8.41 (d, J = 16.9 Hz, 2H), 7.65 (d, J = 8.7 Hz, 1H), 7.09-7.02 (m, 1H), 6.93 (d, J = 8.7 Hz, 1H), 4.21 (d, J = 13.3 Hz, 1H), 4.08 (d, J = 20.9 Hz, 1H), 3.97-3.77 (m, 3H), 3.52-3.33 (m, 3H), 3.31 (s, 3H), 2.24 (s, 3H), 2.01-1.89 (m, 1H), 1.79 (s, 1H), 1.70-1.57 (m, 1H), 1.56-1.45 (m, 1H) |
| 228 (Ex. 42) | 6-(isothiazol-4-yl)-N-(3-methyl-4-((1-methyl-1H-benzo[d]imidazol-5-yl)oxy)phenyl)pyrimido[5,4-d]pyrimidin-4-amine | 467.1 | 1H NMR (400 MHz, CDCl3) δ 9.59 (s, 1H), 9.42 (d, J = 16.3 Hz, 2H), 8.89 (s, 1H), 8.81 (s, 1H), 7.86 (s, 1H), 7.79 (d, J = 2.7 Hz, 1H), 7.68 (dd, J = 8.7, 2.7 Hz, 1H), 7.39-7.31 (m, 2H), 7.08 (dd, J = 8.7, 2.3 Hz, 1H), 6.94 (d, J = 8.7 Hz, 1H), 3.86 (s, 3H), 2.39 (s, 3H) |
| 229 (Ex. 45) | (R)-N-(3-methyl-4-((1-methyl-1H-benzo[d]imidazol-5-yl)oxy)phenyl)-6-(2-(trifluoromethyl)pyrrolidin-1-yl)pyrimido[5,4-d]pyrimidin-4-amine | 521.2 | 1H NMR (400 MHz, CDCl3) δ 9.12 (s, 1H), 8.59 (s, 2H), 7.91 (s, 1H), 7.73 (d, J = 2.7 Hz, 1H), 7.64 (dd, J = 8.8, 2.7 Hz, 1H), 7.34 (d, J = 8.8 Hz, 1H), 7.31 (d, J = 2.3 Hz, 1H), 7.07 (dd, J = 8.6, 2.2 Hz, 1H), 6.93 (d, J = 8.7 Hz, 1H), 3.92-3.85 (m, 2H), 3.86 (s, 3H), 2.38-2.32 (m, 4H), 2.19-2.15 (m, 1H), 1.27-1.23 (m, 3H) |
| 230 (Ex. 45) | N-(3-methyl-4-((1-methyl-1H-benzo[d]imidazol-5-yl)oxy)phenyl)-6-(2-oxa-5-azaspiro[3.4]octan-5-yl)pyrimido[5,4-d]pyrimidin-4-amine | 495.2 | 1H NMR (400 MHz, CDCl3) δ 9.55 (s, 1H), 9.14 (s, 1H), 8.59 (s, 1H), 7.86-7.80 (m, 2H), 7.76 (d, J = 8.8 Hz, 1H), 7.34-7.27 (m, 2H), 7.03 (dd, J = 8.7, 2.3 Hz, 1H), 6.93 (d, J = 8.7 Hz, 1H), 5.73 (d, J = 6.1 Hz, 2H), 4.72 (s, 2H), 3.84 (s, 3H), 3.79 (t, J = 6.6 Hz, 2H), 2.48 (t, J = 6.8 Hz, 2H), 2.32 (s, 3H), 1.92 (p, J = 6.8 Hz, 2H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 231 (Ex. 41) | N-(3-methyl-4-((1-methyl-1H-benzo[d]imidazol-5-yl)oxy)phenyl)-6-(5-methyloxazol-2-yl)pyrimido[5,4-d]pyrimidin-4-amine | 465.2 | $^1$H NMR (400 MHz, CDCl$_3$) δ 9.48 (s, 1H), 9.48 (s, 1H), 8.81 (s, 1H), 7.85 (s, 1H), 7.81 (d, J = 2.7 Hz, 1H), 7.69 (dd, J = 8.7, 2.7 Hz, 1H), 7.37-7.30 (m, 2H), 7.09 (d, J = 1.2 Hz, 1H), 7.06 (dd, J = 8.8, 2.2 Hz, 1H), 6.88 (d, J = 8.7 Hz, 1H), 3.84 (s, 3H), 2.53 (s, 3H), 2.34 (s, 3H) |
| 232 (Ex. 43) | N-(3-methyl-4-((1-methyl-1H-benzo[d]imidazol-5-yl)oxy)phenyl)-6-(3-((methylsulfonyl)methyl)azetidin-1-yl)pyrimido[5,4-d]pyrimidin-4-amine | 531.2 | $^1$H NMR (400 MHz, CDCl$_3$) δ 9.04 (s, 1H), 8.55 (s, 1H), 8.53 (s, 1H), 7.84 (s, 1H), 7.73 (d, J = 2.6 Hz, 1H), 7.67 (dd, J = 8.7, 2.7 Hz, 1H), 7.36-7.29 (m, 2H), 7.06 (dd, J = 8.7, 2.3 Hz, 1H), 6.92 (d, J = 8.7 Hz, 1H), 4.56 (dd, J = 9.4, 7.6 Hz, 2H), 4.18 (dd, J = 9.4, 5.0 Hz, 2H), 3.84 (s, 3H), 3.47 (d, J = 7.7 Hz, 3H), 2.99 (s, 3H), 2.35 (s, 3H) |
| 233 (Ex. 47) | •TFA •TFA N-(3-methyl-4-((1-methyl-1H-benzo[d]imidazol-5-yl)oxy)phenyl)-6-(pyridin-3-yl)pyrimido[5,4-d]pyrimidin-4-amine bis(2,2,2-trifluoroacetate) | 461.2 | $^1$H NMR (400 MHz, (CD$_3$)$_2$SO) δ 10.52 (s, 1H), 10.04 (s, 1H), 9.60 (s, 1H), 9.15 (d, J = 8.0 Hz, 1H), 8.86 (s, 1H), 8.77 (s, 1H), 8.02-7.96 (m, 2H), 7.93 (dd, J = 8.7, 2.7 Hz, 1H), 7.73 (dd, J = 8.1, 4.3 Hz, 1H), 7.35 (d, J = 9.0 Hz, 1H), 7.22 (s, 1H), 7.12 (d, J = 8.7 Hz, 1H), 4.05 (s, 3H), 2.26 (s, 3H) |
| 234 (Ex. 39) | 6-(6,6-difluoro-3-azabicyclo[3.1.0]hexan-3-yl)-N-(3-methyl-4-((1-methyl-1H-benzo[d]imidazol-5-yl)oxy)phenyl)pyrimido[5,4-d]pyrimidin-4-amine | 501.2 | $^1$H NMR (400 MHz, CDCl$_3$) δ 9.11 (s, 1H), 8.63 (s, 1H), 8.58 (s, 1H), 7.78 (d, J = 2.6 Hz, 1H), 7.73 (dd, J = 8.6, 2.7 Hz, 1H), 7.24 (d, J = 8.9 Hz, 1H), 6.99 (d, J = 8.6 Hz, 1H), 5.30 (s, 3H), 4.21 (d, J = 11.4 Hz, 2H), 3.99 (s, 5H), 2.51 (dd, J = 12.0, 3.8 Hz, 2H), 2.28 (s, 3H) |
| 235 (Ex. 42) | N-(3-methyl-4-((1-methyl-1H-benzo[d]imidazol-5-yl)oxy)phenyl)-6-(thiazol-4-yl)pyrimido[5,4-d]pyrimidin-4-amine | 467.2 | $^1$H NMR (400 MHz, CDCl$_3$) δ 9.48 (s, 1H), 9.44 (s, 1H), 9.02 (dd, J = 2.1, 0.7 Hz, 1H), 8.79 (s, 1H), 8.55 (dd, J = 2.1, 0.7 Hz, 1H), 7.85 (s, 1H), 7.81 (d, J = 2.7 Hz, 1H), 7.70 (dd, J = 8.7, 2.7 Hz, 1H), 7.34 (s, 1H), 7.33 (d, J = 5.2 Hz, 1H), 7.06 (dd, J = 8.8, 2.3 Hz, 1H), 6.90 (d, J = 8.7 Hz, 1H), 3.84 (s, 3H), 2.35 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 236 (Ex. 39) | 6-(4,4-difluoropiperidin-1-yl)-N-(3-methyl-4-((1-methyl-1H-benzo[d]imidazol-5-yl)oxy)phenyl)pyrimido[5,4-d]pyrimidin-4-amine | 503.2 | 1H NMR (400 MHz, CDCl$_3$) δ 9.07 (s, 1H), 8.56 (s, 1H), 8.46 (s, 1H), 7.85 (s, 1H), 7.73 (d, J = 2.7 Hz, 1H), 7.64 (dd, J = 8.7, 2.8 Hz, 1H), 7.37-7.29 (m, 2H), 7.06 (dd, J = 8.7, 2.3 Hz, 1H), 6.93 (d, J = 8.7 Hz, 1H), 4.16-4.12 (m, 4H), 3.85 (s, 3H), 2.35 (s, 3H), 2.16-2.05 (m, 4H) |
| 237 (Ex. 43) | 6-(6-methoxy-2-azaspiro[3.3]heptan-2-yl)-N-(3-methyl-4-((1-methyl-1H-benzo[d]imidazol-5-yl)oxy)phenyl)pyrimido[5,4-d]pyrimidin-4-amine | 509.2 | 1H NMR (400 MHz, CD$_3$OD) δ 8.82 (d, J = 1.6 Hz, 1H), 8.30 (d, J = 1.7 Hz, 1H), 8.07 (s, 1H), 7.72 (d, 1H), 7.65 (dd, J = 8.6, 2.7 Hz, 1H), 7.49 (d, J = 8.8 Hz, 1H), 7.12 (d, J = 2.3 Hz, 1H), 7.04 (dd, J = 8.8, 2.3 Hz, 1H), 6.84 (d, J = 8.7 Hz, 1H), 4.18 (d, J = 20.8 Hz, 4H), 3.94-3.72 (m, 4H), 3.32-3.30 (m, 1H), 3.23 (d, J = 1.5 Hz, 3H), 2.62-2.53 (m, 2H), 2.26 (s, 2H), 2.20-2.10 (m, 2H) |
| 238 (Ex. 52) | N-(3-methyl-4-((1-methyl-1H-benzo[d]imidazol-5-yl)oxy)phenyl)-6-(2-(trifluoromethyl)azetidin-1-yl)pyrimido[5,4-d]pyrimidin-4-amine | 507.2 | 1H NMR (400 MHz, CDCl$_3$) δ 9.13 (s, 1H), 8.61 (s, 1H), 8.60 (s, 1H), 7.87 (s, 1H), 7.73 (d, J = 2.7 Hz, 1H), 7.63 (dd, J = 8.7, 2.7 Hz, 1H), 7.36-7.29 (m, 2H), 7.06 (dd, J = 8.7, 2.2 Hz, 1H), 6.93 (d, J = 8.7 Hz, 1H), 4.99-4.89 (m, 1H), 4.41-4.31 (m, 1H), 4.31-4.21 (m, 1H), 3.85 (s, 3H), 2.72-2.60 (m, 2H), 2.34 (s, 3H) |
| 239 (Ex. 41) | N-(3-methyl-4-((1-methyl-1H-benzo[d]imidazol-5-yl)oxy)phenyl)-6-(pyridin-2-yl)pyrimido[5,4-d]pyrimidin-4-amine | 461.2 | 1H NMR (400 MHz, CDCl$_3$) δ 9.79 (s, 1H), 9.53 (s, 1H), 8.89-8.84 (m, 1H), 8.82 (s, 1H), 8.71-8.64 (m, 1H), 7.96 (td, J = 7.8, 1.8 Hz, 1H), 7.89-7.83 (m, 2H), 7.74 (dd, J = 8.7, 2.7 Hz, 1H), 7.53-7.45 (m, 1H), 7.37-7.30 (m, 2H), 7.07 (dd, J = 8.8, 2.2 Hz, 1H), 6.91 (d, J = 8.7 Hz, 1H), 3.85 (s, 3H), 2.35 (s, 3H) |
| 240 (Ex. 43) | 6-(3-(2-methoxyethoxy)azetidin-1-yl)-N-(3-methyl-4-((1-methyl-1H-benzo[d]imidazol-5-yl)oxy)phenyl)pyrimido[5,4-d]pyrimidin-4-amine | 513.2 | 1H NMR (400 MHz, CD$_3$OD) δ 8.82 (s, 1H), 8.30 (s, 1H), 8.06 (s, 1H), 7.71 (d, J = 2.6 Hz, 1H), 7.65 (dd, J = 8.7, 2.7 Hz, 1H), 7.47 (d, J = 8.8 Hz, 1H), 7.11 (d, J = 2.3 Hz, 1H), 7.03 (dd, J = 8.8, 2.2 Hz, 1H), 6.83 (d, J = 8.7 Hz, 1H), 4.53-4.44 (m, 1H), 4.44-4.35 (m, 2H), 4.12-4.04 (m, 2H), 3.86 (s, 3H), 3.67-3.60 (m, 2H), 3.56 (dt, J = 4.6, 3.8 Hz, 2H), 3.37 (s, 3H), 2.25 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 241 (Ex. 49) | N8-(4-(benzo[c]isothiazol-6-yloxy)-3-methylphenyl)-N2-methylpyrimido[5,4-d]pyrimidine-2,8-diamine 2,2,2-trifluoroacetate | 416.1 | 1H NMR (400 MHz, MeOD) δ 9.43 (s, 1H), 8.88 (s, 1H), 8.43 (s, 1H), 7.79 (d, J = 9.2 Hz, 2H), 7.73 (dd, J = 8.7, 2.6 Hz, 1H), 7.11 (dd, J = 9.3, 2.2 Hz, 1H), 7.08 (d, J = 8.7 Hz, 1H), 6.72 (dd, J = 2.0, 0.9 Hz, 1H), 3.20 (s, 3H), 3.05 (s, 3H), 2.19 (s, 3H) |
| 242 (Ex. 39) | N-(3-methyl-4-((1-methyl-1H-benzo[d]imidazol-5-yl)oxy)phenyl)-6-(piperidin-1-yl)pyrimido[5,4-d]pyrimidin-4-amine | 467.3 | 1H NMR (400 MHz, CDCl3) δ 9.02 (s, 1H), 8.53 (s, 1H), 7.74 (dd, J = 2.7, 0.8 Hz, 1H), 8.50 (s, 1H), 7.66 (dd, J = 8.7, 2.7 Hz, 1H), 7.36-7.29 (m, 2H), 7.06 (dd, J = 8.7, 2.3 Hz, 1H), 6.93 (d, J = 8.7 Hz, 1H), 3.98-3.91 (m, 4H), 3.85 (s, 3H), 2.34 (s, 3H), 1.78-1.63 (m, 6H) |
| 243 (Ex. 49) | N-(4-(benzo[c]isothiazol-6-yloxy)-3-methylphenyl)-6-morpholinopyrimido[5,4-d]pyrimidin-4-amine 2,2,2-trifluoroacetate | 472.2 | 1H NMR (400 MHz, (CD3)2SO) δ 10.00 (s, 1H), 9.74 (s, 1H), 9.13 (s, 1H), 8.53 (s, 1H), 7.95 (d, J = 9.3 Hz, 1H), 7.92-7.85 (m, 2H), 7.24-7.16 (m, 2H), 6.77-6.71 (m, 1H), 4.00 (t, J = 4.6 Hz, 4H), 3.75 (t, J = 4.8 Hz, 4H), 2.22 (s, 3H) |
| 244 (Ex. 43) | 6-(3-(difluoromethoxy)azetidin-1-yl)-N-(3-methyl-4-((1-methyl-1H-benzo[d]imidazol-5-yl)oxy)phenyl)pyrimido[5,4-d]pyrimidin-4-amine | 505.2 | 1H NMR (400 MHz, CDCl3) δ 9.06 (s, 1H), 8.56 (s, 1H), 8.53 (s, 1H), 7.85 (s, 1H), 7.74 (d, J = 2.6 Hz, 1H), 7.65 (dd, J = 8.7, 2.7 Hz, 1H), 7.36-7.29 (m, 2H), 7.06 (dd, J = 8.7, 2.4 Hz, 1H), 6.93 (d, J = 8.7 Hz, 1H), 6.33 (t, J = 72.9 Hz, 1H), 5.23-5.13 (m, 1H), 4.64-4.55 (m, 2H), 4.37-4.29 (m, 2H), 3.85 (s, 3H), 2.35 (s, 3H) |
| 245 (Ex. 43) | 6-(3-((difluoromethoxy)methyl)azetidin-1-yl)-N-(3-methyl-4-((1-methyl-1H-benzo[d]imidazol-5-yl)oxy)phenyl)pyrimido[5,4-d]pyrimidin-4-amine | 519.2 | 1H NMR (400 MHz, (CD3)2SO) δ 9.40 (s, 1H), 9.08 (s, 1H), 8.43 (s, 1H), 8.17 (s, 1H), 7.87 (d, J = 2.6 Hz, 1H), 7.80 (dd, J = 8.8, 2.7 Hz, 1H), 7.56 (d, J = 8.7 Hz, 1H), 7.09 (d, J = 2.3 Hz, 1H), 6.99 (dd, J = 8.7, 2.3 Hz, 1H), 6.88 (d, J = 8.7 Hz, 1H), 6.85 (t, J = 75.9 Hz, 1H), 4.32 (t, J = 8.8 Hz, 2H), 4.10 (dd, J = 10.6, 5.9 Hz, 2H), 4.01 (dd, J = 9.3, 5.5 Hz, 2H), 3.84 (s, 3H), 3.13-3.03 (m, 1H), 2.25 (s, 3H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 246 (Ex. 43) | 3-methyl-1-(8-((3-methyl-4-((1-methyl-1H-benzo[d]imidazol-5-yl)oxy)phenyl)amino)pyrimido[5,4-d]pyrimidin-2-yl)azetidin-3-ol | 469.2 | $^1$H NMR (400 MHz, CD$_3$OD) δ 8.90 (d, J = 0.6 Hz, 1H), 8.34 (s, 1H), 8.08 (s, 1H), 7.76 (d, J = 2.7 Hz, 1H), 7.68 (dd, J = 8.8, 2.7 Hz, 1H), 7.50 (d, J = 8.8 Hz, 1H), 7.11 (d, J = 2.3 Hz, 1H), 7.05 (dd, J = 8.8, 2.2 Hz, 1H), 6.86 (d, J = 8.7 Hz, 1H), 4.21-4.10 (m, 4H), 3.88 (s, 3H), 2.27 (s, 3H), 1.57 (s, 3H) |
| 247 (Ex. 41) | N-(3-methyl-4-((1-methyl-1H-benzo[d]imidazol-5-yl)oxy)phenyl)-6-(2-methylthiazol-4-yl)pyrimido[5,4-d]pyrimidin-4-amine | 481.2 | $^1$H NMR (400 MHz, CDCl$_3$) δ 9.54 (s, 1H), 9.43 (s, 1H), 8.79 (s, 1H), 8.35 (s, 1H), 7.85 (s, 1H), 7.84 (s, 1H), 7.72 (dd, J = 8.7, 2.7 Hz, 1H), 7.37-7.31 (m, 2H), 7.07 (dd, J = 8.7, 2.3 Hz, 1H), 6.91 (d, J = 8.7 Hz, 1H), 3.85 (s, 3H), 2.88 (s, 3H), 2.36 (s, 3H) |
| 248 (Ex. 39) | (S)-6-(3-methoxypiperidin-1-yl)-N-(3-methyl-4-((1-methyl-1H-benzo[d]imidazol-5-yl)oxy)phenyl)pyrimido[5,4-d]pyrimidin-4-amine | 497.3 | $^1$H NMR (400 MHz, (CD$_3$)$_2$SO) δ 9.59 (s, 1H), 9.06 (s, 1H), 8.47 (s, 1H), 8.39 (s, 1H), 7.86 (d, J = 2.6 Hz, 1H), 7.79 (dd, J = 8.8, 2.7 Hz, 1H), 7.66 (d, J = 8.7 Hz, 1H), 7.11 (d, J = 2.2 Hz, 1H), 7.08 (dd, J = 8.8, 2.3 Hz, 1H), 6.93 (d, J = 8.7 Hz, 1H), 4.20 (d, J = 13.1 Hz, 1H), 4.10-4.00 (m, 1H), 3.95-3.83 (m, 4H), 3.40-3.33 (m, 2H), 3.31 (s, 3H), 2.24 (s, 3H), 2.01-1.83 (m, 1H), 1.86-1.68 (m, 1H), 1.76-1.57 (m, 1H), 1.56-1.45 (m, 1H) |
| 249 (Ex. 52) | (S)-N-(3-methyl-4-((1-methyl-1H-benzo[d]imidazol-5-yl)oxy)phenyl)-6-(2-(trifluoromethyl)pyrrolidin-1-yl)pyrimido[5,4-d]pyrimidin-4-amine | 521.2 | $^1$H NMR (400 MHz, CDCl$_3$) δ 9.05 (s, 1H), 8.65 (s, 1H), 8.59 (s, 1H), 7.91 (s, 1H), 7.74 (d, J = 3.5 Hz, 1H), 7.69-7.60 (m, 1H), 7.37-7.28 (m, 2H), 7.07 (dd, J = 8.7, 2.2 Hz, 1H), 6.93 (d, J = 8.7 Hz, 1H), 5.01-4.79 (m, 1H), 3.86 (s, 3H), 2.59-2.38 (m, 2H), 2.34 (s, 3H), 1.85-1.75 (m, 1H), 1.27-1.23 (m, 2H), 0.90-0.85 (m, 1H) |
| 250 (Ex. 51) | (S)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-2-one | 481.2 | $^1$H NMR (400 MHz, CDCl$_3$) δ 9.34 (s, 1H), 8.91 (s, 1H), 8.73 (s, 1H), 7.85 (s, 1H), 7.75 (d, J = 2.7 Hz, 1H), 7.70 (dd, J = 8.6, 2.7 Hz, 1H), 7.37-7.28 (m, 2H), 7.06 (dd, J = 8.8, 2.2 Hz, 1H), 6.91 (d, J = 8.7 Hz, 1H), 4.32-4.22 (m, 1H), 4.10-3.99 (m, 1H), 3.85 (s, 3H), 2.89-2.75 (m, 1H), 2.50-2.38 (m, 1H), 2.35 (s, 3H), 1.92-1.78 (m, 1H), 1.38 (d, J = 7.1 Hz, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 251 (Ex. 61) | N2-(2,2-difluoroethyl)-N8-(3-methyl-4-((1-methyl-1H-benzo[d]imidazol-5-yl)oxy)phenyl)pyrimido[5,4-d]pyrimidine-2,8-diamine | 463.2 | 1H NMR (400 MHz, CDCl3) δ 9.07 (s, 1H), 8.59 (s, 1H), 8.48 (s, 1H), 7.85 (s, 1H), 7.75-7.69 (m, 1H), 7.63 (dd, J = 8.7, 2.7 Hz, 1H), 7.38-7.29 (m, 2H), 7.06 (dd, J = 8.7, 2.4 Hz, 1H), 6.92 (d, J = 8.7 Hz, 1H), 6.04 (tt, J = 56.4, 4.7 Hz, 1H), 5.73 (m, 1H), 4.00 (tdd, J = 14.5, 6.5, 4.1 Hz, 2H), 3.85 (s, 3H), 2.35 (s, 3H) |
| 252 (Ex. 63) | (S)-6-(3-(difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine | 503.2 | 1H NMR (400 MHz, CDCl3) δ 9.07 (s, 1H), 8.56 (s, 1H), 8.55 (s, 1H), 7.85 (s, 1H), 7.75 (d, J = 2.7 Hz, 1H), 7.66 (dd, J = 8.7, 2.7 Hz, 1H), 7.36-7.30 (m, 2H), 7.06 (dd, J = 8.6, 2.4 Hz, 1H), 6.93 (d, J = 8.7 Hz, 1H), 5.90 (td, J = 56.3, 4.9 Hz, 1H), 3.98-3.89 (m, 2H), 3.85 (s, 3H), 3.82-3.71 (m, 2H), 2.90 (dh, J = 13.6, 6.7 Hz, 1H), 2.35 (s, 3H), 2.33-2.23 (m, 1H), 2.21-2.13 (m, 1H) |
| 253 (Ex. 63) | (R)-6-(3-(difluoromethyl)pyrrolidin-1-yl)-N-(3-methyl-4-((1-methyl-1H-benzo[d]imidazol-5-yl)oxy)phenyl)pyrimido[5,4-d]pyrimidin-4-amine | 503.2 | 1H NMR (400 MHz, CDCl3) δ 9.07 (s, 1H), 8.56 (s, 1H), 8.55 (s, 1H), 7.85 (s, 1H), 7.75 (d, J = 2.7 Hz, 1H), 7.66 (dd, J = 8.7, 2.7 Hz, 1H), 7.36-7.30 (m, 2H), 7.06 (dd, J = 8.6, 2.4 Hz, 1H), 6.93 (d, J = 8.7 Hz, 1H), 5.90 (td, J = 56.3, 4.9 Hz, 1H), 3.98-3.89 (m, 2H), 3.85 (s, 3H), 3.82-3.71 (m, 2H), 2.90 (dh, J = 13.6, 6.7 Hz, 1H), 2.35 (s, 3H), 2.33-2.23 (m, 1H), 2.21-2.13 (m, 1H) |
| 254 (Ex. 66) | (S)-2-(8-((3-methyl-4-((1-methyl-1H-benzo[d]imidazol-5-yl)oxy)phenyl)amino)pyrimido[5,4-d]pyrimidin-2-yl)hexahydro-3H-pyrrolo[1,2-c]imidazol-3-one | 508.2 | 1H NMR (400 MHz, CDCl3) δ 9.30 (s, 1H), 8.87 (s, 1H), 8.69 (s, 1H), 7.85 (s, 1H), 7.75 (d, J = 2.7 Hz, 1H), 7.71 (dd, J = 8.7, 2.7 Hz, 1H), 7.33 (dd, J = 5.5, 3.0 Hz, 2H), 7.05 (dd, J = 8.9, 2.1 Hz, 1H), 6.90 (d, J = 8.6 Hz, 1H), 4.33 (dd, J = 11.0, 8.6 Hz, 1H), 4.15 (dd, J = 11.1, 3.8 Hz, 1H), 3.97-3.87 (m, 1H), 3.87-3.80 (m, 1H), 3.85 (s, 3H), 3.32-3.23 (m, 1H), 2.34 (s, 3H), 2.27-2.07 (m, 2H), 2.07-1.89 (m, 1H), 1.59-1.44 (m, 1H) |
| 255 (Ex. 77) | 6-(3-oxa-6-azabicyclo[3.1.1]heptan-6-yl)-N-(3-methyl-4-((1-methyl-1H-benzo[d]imidazol-5-yl)oxy)phenyl)pyrimido[5,4-d]pyrimidin-4-amine 2,2,2-trifluoroacetate | 481.2 | 1H NMR (400 MHz, CDCl3) δ 9.29 (s, 1H), 9.01 (s, 1H), 8.65 (s, 1H), 7.73 (m, 2H), 7.54 (m, 1H), 7.35 (dd, J = 2.2, 9.1 Hz, 1H), 7.21 (d, J = 2.2 Hz, 1H) 7.03 (d, J = 8.6 Hz, 1H), 4.65 (d, J = 6.2 Hz, 2H), 4.41 (m, 2H) 4.06 (s, 3H), 3.93 (d, J = 10.7 Hz, 2H) 2.26 (m, 5H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 256 (Ex. 69) | 6-(8-oxa-3-azabicyclo[3.2.1]octan-3-yl)-N-(3-methyl-4-((1-methyl-1H-benzo[d]imidazol-5-yl)oxy)phenyl)pyrimido[5,4-d]pyrimidin-4-amine 2,2,2-trifluoroacetate | 495.2 | 1H NMR (400 MHz CDCl3) δ 9.28 (s, 1H), 8.99 (s, 1H), 8.87 (s, 1H), 8.63 (s, 1H), 7.77 (m, 2H), 7.55 (m, 1H), 7.36 (dd, J = 2.3, 9.0 Hz, 1H), 7.19 (d, J = 2.3 Hz, 1H) 7.04 (d, J = 8.6 Hz, 1H), 4.56 (s, 2H), 4.06 (s, 3H), 3.40 (d, J = 13.0 Hz, 2H), 2.28 (s, 3H) 2.03 (m, 3H), 1.84 (m, 2H) |
| 257 (Ex. 70) | (R)-N-(3-methyl-4-((1-methyl-1H-benzo[d]imidazol-5-yl)oxy)phenyl)-6-(3-methylmorpholino)pyrimido[5,4-d]pyrimidin-4-amine 2,2,2-trifluoroacetate | 483.2 | 1H NMR (400 MHz, CDCl3) δ 9.07 (s, 1H), 8.55 (s, 1H), 8.48 (s, 1H), 7.85 (s, 1H), 7.73 (d, J = 2.7 Hz, 1H), 7.64 (dd, J = 2.8, 8.7 Hz, 1H) 7.31 (m, 2H), 7.06 (dd, J = 2.8, 8.7 Hz, 1H), 6.93 (d, J = 8.7 Hz, 1H), 4.87 (m, 1H), 4.50 (m, 1H), 3.85 (m, 4H), 3.78 (dd, J = 3.3, 11.5 Hz, 1H) 3.63 (td, J = 3.01, 11.7, 11.9 Hz, 1H), 3.42 (m, 1H), 2.35 (s, 3H), 1.39 (d, J = 6.8 Hz, 3H) |
| 258 (Ex. 70) | (S)-N-(3-methyl-4-((1-methyl-1H-benzo[d]imidazol-5-yl)oxy)phenyl)-6-(3-methylmorpholino)pyrimido[5,4-d]pyrimidin-4-amine | 483.2 | 1H NMR (400 MHz, CDCl3) δ 9.07 (s, 1H), 8.55 (s, 1H), 8.48 (s, 1H), 7.85 (s, 1H), 7.73 (d, J = 2.7 Hz, 1H), 7.64 (dd, J = 2.8, 8.7 Hz, 1H) 7.31 (m, 2H), 7.06 (dd, J = 2.8, 8.7 Hz, 1H), 6.93 (d, J = 8.7 Hz, 1H), 4.87 (m, 1H), 4.50 (m, 1H), 3.85 (m, 4H), 3.78 (dd, J = 3.3, 11.5 Hz, 1H) 3.63 (td, J = 3.01, 11.7, 11.9 Hz, 1H), 3.42 (m, 1H), 2.35 (s, 3H), 1.39 (d, J = 6.8 Hz, 3H) |
| 259 (Ex. 40) | N8-(3-methyl-4-((1-methyl-1H-benzo[d]imidazol-5-yl)oxy)phenyl)-N2-(oxetan-3-yl)pyrimido[5,4-d]pyrimidine-2,8-diamine 2,2,2-trifluoroacetate | 445.3 | 1H NMR (400 MHz, CDCl3) δ 9.19 (s, 1H), 8.95 (s, 1H), 8.65 (s, 1H), 7.79 (m, 2H), 7.54 (d, J = 9.0 Hz, 1H), 7.04 (d, J = 8.6 Hz, 1H), 5.11 (m, 2H), 4.78 (m, 2H), 4.04 (s, 3H), 3.24 (m, 1H), 2.27 (s, 3H) |
| 260 (Ex. 69) | N2-((1s,3s)-3-methoxycyclobutyl)-N8-(3-methyl-4-((1-methyl-1H-benzo[d]imidazol-5-yl)oxy)phenyl)pyrimido[5,4-d]pyrimidine-2,8-diamine 2,2,2-trifluoroacetate | 483.2 | 1H NMR (400 MHz, CDCl3) δ 9.23 (s, 1H), 8.98 (s, 1H), 8.63 (s, 1H), 7.78 (m, 2H), 7.55 (d, J = 9.0 Hz, 1H), 7.35 (dd, J = 2.3, 9.0 Hz, 1H), 7.22 (d, J = 2.2 Hz, 1H), 7.03 (d, J = 8.7 Hz, 1H), 5.95 (m, 1H), 4.05 (s, 3H), 3.82 (m, 1H), 3.30 (s, 3H), 2.88 (m, 2H) 2.28 (s, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 261 (Ex. 72) | N2-isopropyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate | 441.2 | ¹H NMR (400 MHz, CDCl₃) δ 9.27 (s, 1H), 9.05 (s, 1H), 8.64 (s, 1H), 7.78 (m, 2H), 7.56 (d, J = 9.2 Hz, 1H), 7.36 (dd, J = 2.3, 9.0 Hz, 1H), 7.21 (d, J = 2.3 Hz, 1H) 7.04 (d, J = 8.6 Hz, 1H), 4.32 (br s, 1H), 4.06 (s, 3H), 2.28 (s, 3H), 1.38 (d, J = 6.5 Hz, 6H) |
| 262 (Ex 69) | 6-((1R,4R)-2-oxa-5-azabicyclo[2.2.1]heptan-5-yl)-N-(3-methyl-4-((1-methyl-1H-benzo[d]imidazol-5-yl)oxy)phenyl)pyrimido[5,4-d]pyrimidin-4-amine 2,2,2-trifluoroacetate | 481.2 | ¹H NMR (400 MHz, CDCl₃) δ 9.05 (s, 1H), 8.54 (s, 1H), 8.52 (br s, 1H), 7.85 (s, 1H), 7.73 (d, J = 2.4 Hz, 1H), 7.64 (dd, J = 2.7, 8.7 Hz, 1H), 7.32 (m, 2H) 7.06 (d, J = 2.3, 8.7 Hz, 1H), 6.93 (d, J = 8.7 Hz, 1H), 5.22 (br s, 1H), 4.79 (s, 1H), 3.98 (m, 2H), 3.85 (s, 3H), 3.70 (m, 2H), 2.35 (s, 3H), 2.05 (m, 2H), 1.57 (s, 3H) |
| 263 (Ex. 142) | N-(2-fluoro-3-methyl-4-((1-methyl-1H-benzo[d]imidazol-5-yl)oxy)phenyl)-6-morpholinopyrimido[5,4-d]pyrimidin-4-amine 2,2,2-trifluoroacetate | 487.2 | ¹H NMR (400 MHz, CDCl₃) δ 9.30 (s, 1H), 9.20 (s, 1H), 9.06 (s, 1H), 8.65 (s, 1H), 8.57 (t, J = 8.9 Hz, 1H), 7.58 (d, J = 9.0 Hz, 1H), 7.36 (dd, J = 2.2, 9.0 Hz, 1H), 6.87 (dd, J = 1.7, 9.0 Hz, 1H), 4.07 (s, 3H), 4.01 (t, J = 4.9 Hz, 4H), 3.86 (t, J = 4.8, 4H), 3.61 (tt, J = 3.7, 7.1 Hz, 1H) 2.23 (d, J = 2.1 Hz, 3H) |
| 264 (Ex. 79) | 6-(8-((3-methyl-4-((1-methyl-1H-benzo[d]imidazol-5-yl)oxy)phenyl)amino)pyrimido[5,4-d]pyrimidin-2-yl)-5-thia-6-azaspiro[2.4]heptane 5,5-dioxide 2,2,2-trifluoroacetate | 529.2 | ¹H NMR (400 MHz, CDCl₃) δ 9.28 (s, 1H), 8.70 (s, 1H), 8.59 (br s, 1H), 7.85 (s, 1H), 7.72 (d, J = 2.7 Hz, 1H), 7.64 (dd, J = 2.7, 8.8 Hz, 1H), 7.34 (dd, J = 3.1, 5.5 Hz, 2H), 7.06 (dd, J = 2.8, 8.8 Hz, 1H), 6.92 (d, J = 8.7 Hz, 1H), 4.03 (s, 2H), 3.85 (s, 3H), 3.47 (s, 2H) 2.36 (s, 3H), 1.04 (m, 2H), 1.01 (m, 2H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 265 (Ex. 72) | (R)-N-(3-methyl-4-((1-methyl-1H-benzo[d]imidazol-5-yl)oxy)phenyl)-6-(2-methylmorpholino)pyrimido[5,4-d]pyrimidin-4-amine 2,2,2-trifluoroacetate | 483.2 | 1H NMR (400 MHz, CDCl3) δ 9.28 (s, 1H), 9.02 (s, 1H), 8.89 (br s, 1H), 8.62 (s, 1H), 7.76 (m, 2H), 7.56 (d, J = 9.1 Hz, 1H), 7.36 (dd, J = 2.3, 9.1 Hz, 1H), 7.20 (d, J = 2.2 Hz, 1H) 7.04 (d, J = 8.6 Hz, 1H), 4.70 (t, J = 12.6 Hz, 2H), 4.09 (m, 1H), 4.06 (s, 3H), 3.70 (m, 2H) 3.25 (td, J = 3.6, 12.4, 1H), 2.90 (dd, J = 10.5, 13.3 Hz, 1H), 2.28 (s, 3H) 1.33 (d, J = 6.2 Hz, 3H) |
| 266 (Ex. 69) | N-(2-fluoro-3-methyl-4-((1-methyl-1H-benzo[d]imidazol-5-yl)oxy)phenyl)-6-(methylthio)pyrimido[5,4-d]pyrimidin-4-amine 2,2,2-trifluoroacetate | 448.1 | 1H NMR (400 MHz, CDCl3) δ 9.25 (s, 1H), 9.11 (s, 1H), 8.77 (s, 1H), 8.03 (s, 1H), 2.70 (s, 3H), 1.53 (s, 3H), 1.21 (s, 3H) |
| 267 (Ex. 79) | 5-methyl-2-(8-((3-methyl-4-((1-methyl-1H-benzo[d]imidazol-5-yl)oxy)phenyl)amino)pyrimido[5,4-d]pyrimidin-2-yl)isothiazolidine 1,1-dioxide 2,2,2-trifluoroacetate | 517.2 | 1H NMR (400 MHz, CDCl3) δ 9.29 (s, 1H), 8.70 (s, 1H), 8.64 (s, 1H), 7.86 (s, 1H), 7.67 (m, 2H), 7.34 (m, 2H), 7.05 (dd, J = 2.2, 8.4 Hz), 6.92 (d, J = 8.7 Hz, 1H), 5.35 (m, 1H), 4.03 (m, 1H), 3.85 (s, 3H), 3.59 (m, 1H), 2.35 (s, 3H), 1.60 (d, 3H) |
| 268 (Ex. 69) | N8-(3-methyl-4-((1-methyl-1H-benzo[d]imidazol-5-yl)oxy)phenyl)-N2-(1-methylcyclopropyl)pyrimido[5,4-d]pyrimidine-2,8-diamine 2,2,2-trifluoroacetate | 453.3 | 1H NMR (400 MHz, CDCl3) δ 9.02 (s, 1H), 8.66 (s, 1H), 7.81 (d, J = 2.7 Hz, 1H), 7.75 (dd, J = 2.7, 8.7 Hz, 1H), 7.56 (d, J = 9.0 Hz, 1H), 7.36 (dd, J = 2.3, 9.0 Hz, 1H), 7.21 (d, J = 2.4 Hz, 1H), 7.05 (d, J = 8.7 Hz, 1H), 4.06 (s, 3H), 2.29 (s, 3H), 1.57 (s, 3H), 0.88 (m, 4H) |
| 269 (Ex. 71) | N2-ethyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate | 427.2 | 1H NMR (400 MHz, CDCl3) δ 9.17 (s, 1H), 8.90 (s, 1H), 8.62 (s, 1H), 7.80 (d, J = 2.6 Hz, 1H), 7.76 (dd, J = 2.7, 9.0 Hz, 1H), 7.52 (m, 1H), 7.32 (m, 1H), 7.22 (d, J = 2.3 Hz, 1H), 7.02 (d, J = 8.6 Hz, 1H), 4.04 (s, 3H), 3.63 (m, 2H), 2.27 (s, 3H), 1.37 (t, J = 7.2 Hz, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 270 (Ex. 35) | N2-cyclopropyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate | 439.2 | ¹H NMR (400 MHz, CDCl₃) δ 9.03 (s, 1H), 8.68 (s, 1H), 8.62 (s, 1H), 8.57 (s, 1H), 7.75 (d, J = 2.7, 1H), 7.65 (dd, J = 2.7, 8.7 Hz, 1H), 7.32 (m, 1H), 7.07 (dd, J = 2.3, 8.7 Hz, 1H), 6.94 (d, J = 8.7 Hz, 1H), 5.68 (s, 1H), 3.86 (s, 3H), 2.91 (m, 1H), 2.35 (s, 3H), 0.93 (m, 2H), 0.67 (m, 2H) |
| 271 (Ex. 71) | N8-(4-(benzo[d]thiazol-5-yloxy)-3-methylphenyl)-N2,N2-dimethylpyrimido[5,4-d]pyrimidine-2,8-diamine 2,2,2-trifluoroacetate | 430.1 | ¹H NMR (400 MHz, CDCl₃) δ 9.35 (s, 1H), 9.05 (s, 1H), 9.03 (s, 1H), 8.63 (s, 1H), 7.91 (d, J = 8.8 Hz, 1H), 7.78 (d, J = 2.7, 1H), 7.72 (dd, J = 2.7, 8.8 Hz, 1H), 7.60 (d, J = 2.4 Hz, 1H), J = 7.22 (m, 1H), 7.06 (d, J = 8.7 Hz, 1H), 3.38 (s, 6H), 2.35 (s, 3H) |
| 272 (Ex. 72) | 6-(2,2-dimethylmorpholino)-N-(3-methyl-4-((1-methyl-1H-benzo[d]imidazol-5-yl)oxy)phenyl)pyrimido[5,4-d]pyrimidin-4-amine 2,2,2-trifluoroacetate | 497.3 | ¹H NMR (400 MHz, CDCl₃) δ 9.34 (s, 1H), 9.10 (s, 1H), 8.99 (br s, 1H), 8.63 (s, 1H), 7.75 (m, 2H), 7.58 (d, J = 9.0 Hz, 1H), 7.38 (dd, J = 2.3, 9.0 Hz, 1H), 7.20 (d, J = 2.2 Hz, 1H), 7.06 (s, 1H), 4.08 (s, 3H), 4.00 (t, J = 5.0, 2H), 3.89 (t, J = 5.0, 2H), 3.84 (s, 2H), 2.29 (s, 3H), 1.31 (s, 6H) |
| 273 (Ex. 70) | N2-cyclopentyl-N8-(3-methyl-4-((1-methyl-1H-benzo[d]imidazol-5-yl)oxy)phenyl)pyrimido[5,4-d]pyrimidine-2,8-diamine 2,2,2-trifluoroacetate | 467.2 | ¹H NMR (400 MHz, CDCl₃) δ 9.21 (br s, 1H), 8.96 (s, 1H), 8.63 (s, 1H), 7.77 (m, 2H), 7.54 (d, J = 9.1 Hz, 1H), 7.34 (dd, J = 2.3, 9.0 Hz, 1H), 7.21 (m, 1H), 7.04 (d, J = 8.6 Hz, 1H), 4.42 (br s, 1H) 4.05 (s, 3H), 2.28 (s, 3H), 2.20 (m, 2H), 1.79 (m, 4H), 1.63 (m, 2H) |
| 274 (Ex. 77) | 6-((1S,4S)-2-oxa-5-azabicyclo[2.2.1]heptan-5-yl)-N-(3-methyl-4-((1-methyl-1H-benzo[d]imidazol-5-yl)oxy)phenyl)pyrimido[5,4-d]pyrimidin-4-amine 2,2,2-trifluoroacetate | 481.2 | ¹H NMR (400 MHz, CDCl₃) δ 9.33 (s, 1H), 9.07 (s, 1H), 8.64 (s, 1H), 7.76 (m, 2H), 7.57 (d, J = 9.0 Hz, 1H), 7.36 (dd, J = 2.2, 9.1 Hz, 1H), 7.21 (s, 1H), 7.04 (d, J = 8.6 Hz, 1H), 4.82 (br s, 1H), 4.07 (s, 3H), 3.96 (m, 2H), 3.71 (m, 2H), 2.28 (s, 3H), 2.08 (q, J = 10.2, 10.3 Hz, 2H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 275 (Ex. 35) | (R)-N8-(3-methyl-4-((1-methyl-1H-benzo[d]imidazol-5-yl)oxy)phenyl)-N2-(tetrahydrofuran-3-yl)pyrimido[5,4-d]pyrimidine-2,8-diamine | 469.2 | ¹H NMR (400 MHz, CDCl₃) δ 9.24 (s, 1H), 9.04 (s, 1H), 8.64 (s, 1H), 7.79 (m, 2H), 7.55 (d, J = 9.1 Hz, 1H), 7.36 (dd, J = 2.3, 9.1 Hz, 1H), 7.20 (d, J = 2.3 Hz, 1H), 7.04 (d, J = 8.6 Hz, 1H), 4.73 (br s, 1H), 4.07 (m, 5H), 3.93 (m, 2H), 2.45 (m, 1H), 2.28 (s, 3H), 2.04 (m, 1H) |
| 276 (Ex. 83) | N2-((3S,4R)-4-fluoropyrrolidin-3-yl)-N8-(3-methyl-4-((1-methyl-1H-benzo[d]imidazol-5-yl)oxy)phenyl)pyrimido[5,4-d]pyrimidine-2,8-diamine | 486.2 | ¹H NMR (400 MHz, (CD₃)₂SO) δ 9.45 (s, 1H), 9.03 (s, 1H), 8.40 (s, 1H), 8.17 (s, 1H), 7.92 (s, 1H), 7.79 (s, 1H), 7.71 (d, J = 8.6 Hz, 1H), 7.56 (d, J = 8.7 Hz, 1H), 7.09 (s, 1H), 6.99 (d, J = 8.7 Hz, 1H), 6.90 (d, J = 8.7 Hz, 1H), 5.32 (d, J = 56.1 Hz, 1H), 4.81-4.55 (m, 1H), 3.84 (s, 3H), 3.25-2.83 (m, 4H), 2.26 (s, 3H) |
| 277 (Ex. 83) | (R)-N-(3-methyl-4-((1-methyl-1H-benzo[d]imidazol-5-yl)oxy)phenyl)-6-(3-methylpiperazin-1-yl)pyrimido[5,4-d]pyrimidin-4-amine | 482.2 | ¹H NMR (400 MHz, (CD₃)₂SO) δ 9.53 (s, 1H), 9.05 (s, 1H), 8.38 (s, 1H), 8.17 (s, 1H), 7.83 (d, J = 2.5 Hz, 1H), 7.76 (dd, J = 8.7, 2.6 Hz, 1H), 7.56 (d, J = 8.7 Hz, 1H), 7.09 (d, J = 2.2 Hz, 1H), 6.99 (dd, J = 8.7, 2.3 Hz, 1H), 6.89 (d, J = 8.7 Hz, 1H), 5.01-4.66 (m, 2H), 3.84 (s, 3H), 3.03-2.88 (m, 2H), 2.75-2.67 (m, 2H), 2.63-2.53 (m, 1H), 2.25 (s, 3H), 1.08 (d, J = 6.1 Hz, 3H) |
| 278 (Ex. 83) | (S)-N-(3-methyl-4-((1-methyl-1H-benzo[d]imidazol-5-yl)oxy)phenyl)-6-(3-methylpiperazin-1-yl)pyrimido[5,4-d]pyrimidin-4-amine | 482.2 | ¹H NMR (400 MHz, (CD₃)₂SO) δ 9.53 (s, 1H), 9.05 (s, 1H), 8.38 (s, 1H), 8.17 (s, 1H), 7.83 (d, J = 2.4 Hz, 1H), 7.76 (dd, J = 8.7, 2.6 Hz, 1H), 7.09 (d, J = 2.2 Hz, 1H), 6.89 (d, J = 8.7 Hz, 1H), 4.86-4.82 (m, 2H), 3.84 (s, 3H), 3.04-2.88 (m, 2H), 2.76-2.64 (m, 2H), 2.63-2.53 (m, 1H), 1.08 (d, J = 6.1 Hz, 3H) |
| 279 (Ex. 84) | N2-((3S,4R)-4-fluoro-1-methylpyrrolidin-3-yl)-N8-(3-methyl-4-((1-methyl-1H-benzo[d]imidazol-5-yl)oxy)phenyl)pyrimido[5,4-d]pyrimidine-2,8-diamine | 500.2 | ¹H NMR (400 MHz, (CD₃)₂SO) δ 9.52 (s, 1H), 9.02 (s, 1H), 8.39 (s, 1H), 8.17 (s, 1H), 8.00-7.95 (m, 1H), 7.79 (s, 1H), 7.72 (d, J = 9.0 Hz, 1H), 7.56 (d, J = 8.7 Hz, 1H), 7.11-7.10 (m, 1H), 7.03-6.96 (m, 1H), 6.90 (d, J = 8.6 Hz, 1H), 5.37 (d, J = 56.3 Hz, 1H), 5.01-4.72 (m, 1H), 3.84 (s, 3H), 3.25-3.11 (m, 1H), 3.01-2.92 (m, 1H), 2.72-2.65 (m, 1H), 2.61-2.53 (m, 1H), 2.34 (s, 3H), 2.26 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 280 (Ex. 84) | (S)-6-(3,4-dimethylpiperazin-1-yl)-N-(3-methyl-4-((1-methyl-1H-benzo[d]imidazol-5-yl)oxy)phenyl)pyrimido[5,4-d]pyrimidin-4-amine | 496.2 | 1H NMR (400 MHz, (CD$_3$)$_2$SO) δ 9.57 (s, 1H), 9.07 (s, 1H), 8.39 (s, 1H), 8.17 (s, 1H), 7.92-7.66 (m, 2H), 7.56 (s, 1H), 7.24-6.67 (m, 3H), 5.09-4.45 (m, 2H), 3.84 (s, 3H), 3.07-2.72 (m, 1H), 2.41-1.87 (m, 6H), 1.40-0.92 (m, 3H) |
| 281 (Ex. 84) | (R)-6-(3,4-dimethylpiperazin-1-yl)-N-(3-methyl-4-((1-methyl-1H-benzo[d]imidazol-5-yl)oxy)phenyl)pyrimido[5,4-d]pyrimidin-4-amine | 496.2 | 1H NMR (400 MHz, (CD$_3$)$_2$SO) δ 9.56 (s, 1H), 9.06 (s, 1H), 8.38 (s, 1H), 8.17 (s, 1H), 7.83 (s, 1H), 7.56 (d, J = 8.7 Hz, 1H), 7.09 (d, J = 2.0 Hz, 1H), 6.99 (dd, J = 8.7, 2.1 Hz, 1H), 6.89 (d, J = 8.7 Hz, 1H), 4.93-4.58 (m, 2H), 3.84 (s, 3H), 3.25-3.14 (m, 1H), 2.90-2.77 (m, 2H), 2.35-1.97 (m, 8H), 1.09 (d, J = 15.1, 6.2 Hz, 3H) |
| 282 (Ex. 85) | N-(3-methyl-4-((1-methyl-1H-benzo[d]imidazol-5-yl)oxy)phenyl)-6-(1-oxa-6-azaspiro[3.3]heptan-6-yl)pyrimido[5,4-d]pyrimidin-4-amine | 481.2 | 1H NMR (400 MHz, (CD$_3$)$_2$SO) δ 9.41 (s, 1H), 9.08 (s, 1H), 8.44 (s, 1H), 8.17 (s, 1H), 7.88 (d, J = 2.4 Hz, 1H), 7.79 (dd, J = 8.7, 2.6 Hz, 1H), 7.57 (d, J = 8.7 Hz, 1H), 7.10 (d, J = 2.2 Hz, 1H), 7.00 (dd, J = 8.7, 2.3 Hz, 1H), 6.89 (d, J = 8.7 Hz, 1H), 4.54-4.44 (m, 3H), 4.38-4.30 (m, 2H), 3.84 (s, 3H), 2.92 (t, J = 7.5 Hz, 2H), 2.26 (s, 3H) |
| 283 (Ex. 83) | 6-(((3R,4S)-4-fluoropyrrolidin-3-yl)oxy)-N-(3-methyl-4-((1-methyl-1H-benzo[d]imidazol-5-yl)oxy)phenyl)pyrimido[5,4-d]pyrimidin-4-amine | 487.2 | 1H NMR (400 MHz, (CD$_3$)$_2$SO) δ 9.91 (s, 1H), 9.33 (s, 1H), 8.58 (s, 1H), 8.15 (s, 1H), 7.78 (s, 1H), 7.68 (d, J = 8.9 Hz, 1H), 7.55 (d, J = 8.5 Hz, 1H), 7.09 (s, 1H), 6.98 (d, J = 7.4 Hz, 1H), 6.88 (d, J = 9.0 Hz, 1H), 5.65-5.27 (m, 2H), 3.82 (s, 3H), 3.43-3.34 (m, 2H), 3.16-2.88 (m, 2H), 2.25 (s, 3H) |
| 284 (Ex. 86) | 6-(((3R,4S)-3-fluoropiperidin-4-yl)oxy)-N-(3-methyl-4-((1-methyl-1H-benzo[d]imidazol-5-yl)oxy)phenyl)pyrimido[5,4-d]pyrimidin-4-amine | 501.25 | 1H NMR (400 MHz, (CD$_3$)$_2$SO) δ 9.90 (s, 1H), 9.34 (s, 1H), 8.60 (s, 1H), 8.17 (s, 1H), 7.71 (dd, J = 8.7, 2.6 Hz, 1H), 7.10 (d, J = 2.2 Hz, 1H), 7.00 (dd, J = 8.7, 2.3 Hz, 1H), 6.90 (d, J = 8.7 Hz, 1H), 5.66 (dt, J = 25.3, 6.8 Hz, 1H), 5.02 (d, J = 50.3 Hz, 1H), 3.84 (s, 3H), 3.32-3.19 (m, 1H), 3.08-2.92 (m, 2H), 2.84-2.75 (m, 1H), 2.27 (s, 3H), 2.00-1.89 (m, 2H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 285 (Ex. 86) | 6-(((3S,4S)-3-fluoropiperidin-4-yl)oxy)-N-(3-methyl-4-((1-methyl-1H-benzo[d]imidazol-5-yl)oxy)phenyl)pyrimido[5,4-d]pyrimidin-4-amine | 501.3 | 1H NMR (400 MHz, (CD3)2SO) δ 9.96 (s, 1H), 9.33 (s, 1H), 8.59 (s, 1H), 8.17 (s, 1H), 7.84 (d, J = 2.4 Hz, 1H), 7.72 (dd, J = 8.7, 2.6 Hz, 1H), 7.57 (d, J = 8.7 Hz, 1H), 7.11 (d, J = 2.2 Hz, 1H), 7.00 (dd, J = 8.7, 2.3 Hz, 1H), 6.90 (d, J = 8.7 Hz, 1H), 5.72-5.58 (m, 1H), 4.65 (dtd, J = 51.3, 9.2, 5.2 Hz, 1H), 3.84 (s, 3H), 3.36-3.21 (m, 2H), 2.95-2.87 (m, 1H), 2.72-2.60 (m, 2H), 2.26 (s, 3H), 1.60-1.46 (m, 1H) |
| 286 (Ex. 86) | 6-(((3R,4S)-3-fluoro-1-methylpiperidin-4-yl)oxy)-N-(3-methyl-4-((1-methyl-1H-benzo[d]imidazol-5-yl)oxy)phenyl)pyrimido[5,4-d]pyrimidin-4-amine | 515.25 | 1H NMR (400 MHz, (CD3)2SO) δ 9.93 (s, 1H), 9.34 (s, 1H), 8.59 (s, 1H), 8.17 (s, 1H), 7.83 (s, 1H), 7.72 (s, 1H), 7.57 (d, J = 8.7 Hz, 1H), 7.10 (s, 1H), 6.90 (d, J = 8.3 Hz, 1H), 5.67-5.58 (m, 1H), 5.02 (d, J = 49.6 Hz, 1H), 3.84 (s, 3H), 2.95-2.91 (m, 1H), 2.78-2.55 (m, 2H), 2.41-2.19 (m, 7H), 2.11-2.04 (m, 1H), 2.00-1.94 (m, 1H) |
| 287 (Ex. 86) | 6-(((3S,4R)-4-fluoro-1-methylpyrrolidin-3-yl)oxy)-N-(3-methyl-4-((1-methyl-1H-benzo[d]imidazol-5-yl)oxy)phenyl)pyrimido[5,4-d]pyrimidin-4-amine | 501.25 | 1H NMR (400 MHz, (CD3)2SO) δ 9.95 (s, 1H), 9.34 (s, 1H), 8.60 (s, 1H), 8.17 (s, 1H), 7.80 (s, 1H), 7.70 (d, J = 8.8 Hz, 1H), 7.57 (d, J = 8.7 Hz, 1H), 7.11 (d, J = 1.9 Hz, 1H), 7.00 (dd, J = 8.7, 2.0 Hz, 1H), 6.90 (d, J = 8.7 Hz, 1H), 5.79-5.66 (m, 1H), 5.54 (d, J = 56.3 Hz, 1H), 3.84 (s, 3H), 3.11-2.69 (m, 4H), 2.35 (s, 3H), 2.27 (s, 3H) |
| 288 (Ex. 86) | 6-(((3S,4S)-3-fluoro-1-methylpiperidin-4-yl)oxy)-N-(3-methyl-4-((1-methyl-1H-benzo[d]imidazol-5-yl)oxy)phenyl)pyrimido[5,4-d]pyrimidin-4-amine | 515.25 | 1H NMR (400 MHz, (CD3)2SO) δ 9.98 (s, 1H), 9.34 (s, 1H), 8.59 (s, 1H), 8.17 (s, 1H), 7.84 (d, J = 2.4 Hz, 1H), 7.71 (dd, J = 8.7, 2.6 Hz, 1H), 7.57 (d, J = 8.7 Hz, 1H), 7.10 (d, J = 2.2 Hz, 1H), 7.00 (dd, J = 8.7, 2.3 Hz, 1H), 6.90 (d, J = 8.7 Hz, 1H), 5.67-5.52 (m, 1H), 4.81 (dtd, J = 50.5, 8.8, 4.8 Hz, 1H), 3.84 (s, 3H), 3.15-3.05 (m, 1H), 2.74-2.67 (m, 1H), 2.37-2.24 (m, 10H), 1.75-1.61 (m, 1H) |
| 289 (Ex. 86) | 6-(((3S,4S)-4-fluoropiperidin-3-yl)oxy)-N-(3-methyl-4-((1-methyl-1H-benzo[d]imidazol-5-yl)oxy)phenyl)pyrimido[5,4-d]pyrimidin-4-amine | 501.2 | 1H NMR (400 MHz, (CD3)2SO) δ 9.93 (s, 1H), 9.33 (s, 1H), 8.59 (s, 1H), 8.32 (s, 1H), 8.17 (s, 1H), 7.84 (d, J = 2.3 Hz, 1H), 7.73 (dd, J = 8.7, 2.5 Hz, 1H), 7.57 (d, J = 8.7 Hz, 1H), 7.11 (d, J = 2.2 Hz, 1H), 7.00 (dd, J = 8.7, 2.3 Hz, 1H), 6.89 (d, J = 8.7 Hz, 1H), 5.49-5.36 (m, 1H), 4.83 (dtd, J = 51.7, 10.4, 5.2 Hz, 1H), 3.84 (s, 3H), 3.45-3.35 (m, 1H), 3.03-2.95 (m, 1H), 2.65-2.38 (m, 2H), 2.26 (s, 3H), 2.22-2.10 (m, 1H), 1.77-1.62 (m, 1H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 290 (Ex. 86) | 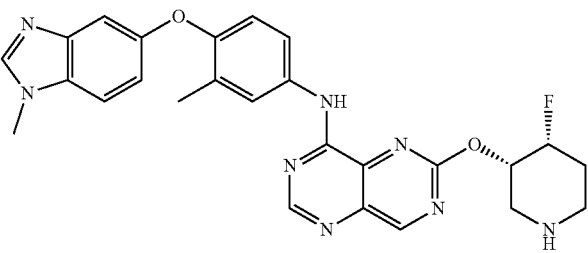<br>6-(((3S,4R)-4-fluoropiperidin-3-yl)oxy)-N-(3-methyl-4-((1-methyl-1H-benzo[d]imidazol-5-yl)oxy)phenyl)pyrimido[5,4-d]pyrimidin-4-amine | 501.3 | $^1$H NMR (400 MHz, (CD$_3$)$_2$SO) δ 9.93 (s, 1H), 9.33 (s, 1H), 8.59 (s, 1H), 8.32 (s, 1H), 8.17 (s, 1H), 7.83 (d, J = 2.4 Hz, 1H), 7.72 (dd, J = 8.7, 2.6 Hz, 1H), 7.57 (d, J = 8.7 Hz, 1H), 7.11 (d, J = 2.2 Hz, 1H), 7.00 (dd, J = 8.7, 2.3 Hz, 1H), 6.89 (d, J = 8.7 Hz, 1H), 5.68-5.47 (m, 1H), 5.26-4.99 (m, 1H), 3.84 (s, 3H), 3.09-2.95 (m, 2H), 2.90-2.77 (m, 1H), 2.75-2.65 (m, 1H), 2.26 (s, 3H), 2.09-1.77 (m, 2H) |
| 291 (Ex. 86) | 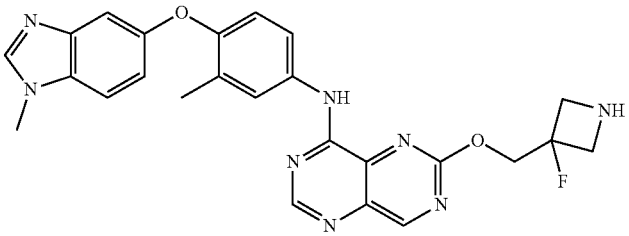<br>6-((3-fluoroazetidin-3-yl)methoxy)-N-(3-methyl-4-((1-methyl-1H-benzo[d]imidazol-5-yl)oxy)phenyl)pyrimido[5,4-d]pyrimidin-4-amine | 487.2 | $^1$H NMR (400 MHz, (CD$_3$)$_2$SO) δ 9.99 (s, 1H), 9.35 (s, 1H), 8.61 (s, 1H), 8.32 (s, 1H), 8.17 (s, 1H), 7.85 (d, J = 2.3 Hz, 1H), 7.75 (dd, J = 8.7, 2.5 Hz, 1H), 7.57 (d, J = 8.7 Hz, 1H), 7.11 (d, J = 2.2 Hz, 1H), 7.00 (dd, J = 8.7, 2.3 Hz, 1H), 6.89 (d, J = 8.7 Hz, 1H), 5.01 (s, 1H), 4.95 (s, 1H), 3.84 (s, 3H), 3.78-3.66 (m, 2H), 3.63-3.53 (m, 2H), 2.27 (s, 3H) |
| 292 (Ex. 84) | 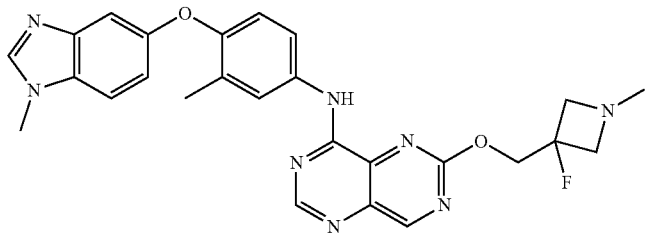<br>6-((3-fluoro-1-methylazetidin-3-yl)methoxy)-N-(3-methyl-4-((1-methyl-1H-benzo[d]imidazol-5-yl)oxy)phenyl)pyrimido[5,4-d]pyrimidin-4-amine | 501.2 | $^1$H NMR (400 MHz, (CD$_3$)$_2$SO) δ 9.98 (s, 1H), 9.35 (s, 1H), 8.61 (s, 1H), 8.17 (s, 1H), 7.85 (s, 1H), 7.75 (d, J = 8.7 Hz, 1H), 7.57 (d, J = 8.7 Hz, 1H), 7.11 (s, 1H), 7.00 (d, J = 8.4 Hz, 1H), 6.89 (d, J = 8.8 Hz, 1H), 4.97 (s, 1H), 4.91 (s, 1H), 3.84 (s, 3H), 3.68-3.58 (m, 2H), 2.37 (s, 3H), 2.27 (s, 3H) |
| 293 (Ex. 84) | 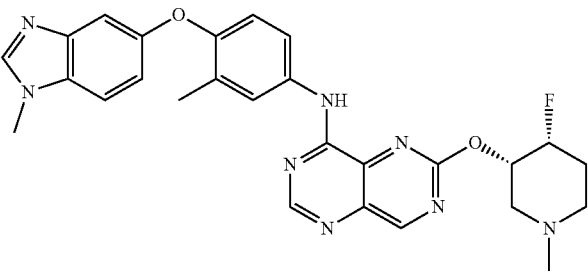<br>6-(((3S,4R)-4-fluoro-1-methylpiperidin-3-yl)oxy)-N-(3-methyl-4-((1-methyl-1H-benzo[d]imidazol-5-yl)oxy)phenyl)pyrimido[5,4-d]pyrimidin-4-amine | 515.2 | $^1$H NMR (400 MHz, (CD$_3$)$_2$SO) δ 10.00 (s, 1H), 9.34 (s, 1H), 8.59 (s, 1H), 8.17 (s, 1H), 7.83 (d, J = 2.4 Hz, 1H), 7.71 (dd, J = 8.7, 2.6 Hz, 1H), 7.57 (d, J = 8.7 Hz, 1H), 7.10 (d, J = 2.2 Hz, 1H), 7.00 (dd, J = 8.7, 2.3 Hz, 1H), 6.89 (d, J = 8.7 Hz, 1H), 5.83-5.61 (m, 1H), 5.08 (d, J = 50.2 Hz, 1H), 3.84 (s, 3H), 2.83-2.79 (m, 1H), 2.62-2.57 (m, 1H), 2.44-2.17 (m, 7H), 2.02-1.95 (m, 2H) |
| 294 (Ex. 85) | 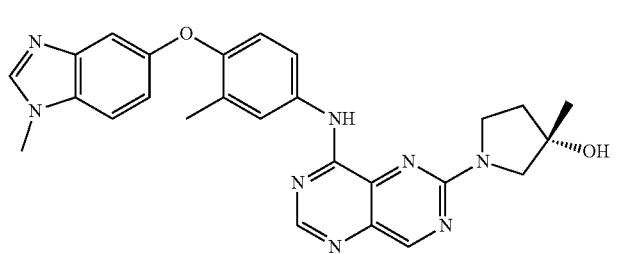<br>rac-(S)-3-methyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol | 483.3 | $^1$H NMR (400 MHz, (CD$_3$)$_2$SO) δ 9.44-9.28 (m, 1H), 9.06 (s, 1H), 8.39 (s, 1H), 8.17 (s, 1H), 7.87 (s, 1H), 7.82 (d, J = 8.7 Hz, 1H), 7.56 (d, J = 8.7 Hz, 1H), 7.09 (d, J = 2.1 Hz, 1H), 6.99 (dd, J = 8.7, 2.3 Hz, 1H), 6.89 (d, J = 8.7 Hz, 1H), 4.89 (s, 1H), 3.98-3.62 (m, 6H), 3.56-3.43 (m, 1H), 2.26 (s, 3H), 2.01-1.92 (m, 2H), 1.43-1.37 (m, 3H) |

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 295 (Ex. 86) | 6-(((3S,5R)-5-fluoropiperidin-3-yl)oxy)-N-(3-methyl-4-((1-methyl-1H-benzo[d]imidazol-5-yl)oxy)phenyl)pyrimido[5,4-d]pyrimidin-4-amine | 501.2 | ¹H NMR (400 MHz, $(CD_3)_2SO$) δ 9.87 (s, 1H), 9.32 (s, 1H), 8.58 (s, 1H), 8.17 (s, 1H), 7.82 (d, J = 2.5 Hz, 1H), 7.70 (dd, J = 8.7, 2.6 Hz, 1H), 7.57 (d, J = 8.6 Hz, 1H), 7.11 (d, J = 2.1 Hz, 1H), 7.00 (dd, J = 8.7, 2.3 Hz, 1H), 6.89 (d, J = 8.7 Hz, 1H), 5.54-5.44 (m, 1H), 5.00-4.77 (m, 1H), 3.84 (s, 3H), 3.23 (dd, J = 12.8, 2.4 Hz, 1H), 2.93-2.78 (m, 2H), 2.75-2.60 (m, 1H), 2.40-1.98 (m, 5H) |
| 296 (Ex. 84) | 6-(((3S,4S)-4-fluoro-1-methylpiperidin-3-yl)oxy)-N-(3-methyl-4-((1-methyl-1H-benzo[d]imidazol-5-yl)oxy)phenyl)pyrimido[5,4-d]pyrimidin-4-amine | 515.25 | ¹H NMR (400 MHz, $(CD_3)_2SO$) δ 10.07 (s, 1H), 9.34 (s, 1H), 8.59 (s, 1H), 8.17 (s, 1H), 7.83 (d, J = 2.4 Hz, 2H), 7.57 (d, J = 8.7 Hz, 1H), 7.11 (d, J = 2.2 Hz, 1H), 7.00 (dd, J = 8.7, 2.3 Hz, 1H), 6.88 (d, J = 8.7 Hz, 1H), 5.79-5.66 (m, 1H), 4.94-4.60 (m, 1H), 3.84 (s, 3H), 3.11-3.04 (m, 1H), 2.79-2.67 (m, 1H), 2.28-2.09 (m, 9H), 1.92-1.87 (m, 1H) |
| 297 (Ex. 83) | rac-(R)-N2-(4,4-difluoropyrrolidin-3-yl)-N8-(3-methyl-4-((1-methyl-1H-benzo[d]imidazol-5-yl)oxy)phenyl)pyrimido[5,4-d]pyrimidine-2,8-diamine | 504.2 | ¹H NMR (400 MHz, $(CD_3)_2SO$) δ 9.42 (s, 1H), 9.09 (s, 1H), 8.45 (s, 1H), 8.19-8.15 (m, 2H), 7.90-7.64 (m, 2H), 7.56 (s, 1H), 7.21-6.77 (m, 3H), 5.38-5.01 (m, 1H), 3.84 (s, 3H), 3.57-3.55 (m, 4H), 2.26 (s, 3H) |
| 298 (Ex. 85) | 6-(3-methoxy-3-methylazetidin-1-yl)-N-(3-methyl-4-((1-methyl-1H-benzo[d]imidazol-5-yl)oxy)phenyl)pyrimido[5,4-d]pyrimidin-4-amine | 483.25 | ¹H NMR (400 MHz, $(CD_3)_2SO$) δ 9.40 (s, 1H), 9.09 (s, 1H), 8.44 (s, 1H), 8.21 (s, 1H), 7.88 (d, J = 2.4 Hz, 1H), 7.80 (dd, J = 8.7, 2.5 Hz, 1H), 7.58 (d, J = 8.7 Hz, 1H), 7.10 (d, J = 2.2 Hz, 1H), 7.01 (d, J = 8.7 Hz, 1H), 6.89 (d, J = 8.7 Hz, 1H), 4.18 (d, J = 9.6 Hz, 2H), 4.06 (d, J = 9.7 Hz, 2H), 3.84 (s, 3H), 3.25 (s, 3H), 2.25 (s, 3H), 1.51 (s, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 299 (Ex. 85) | 6-(3,3-difluoropyrrolidin-1-yl)-N-(3-methyl-4-((1-methyl-1H-benzo[d]imidazol-5-yl)oxy)phenyl)pyrimido[5,4-d]pyrimidin-4-amine | 489.2 | ¹H NMR (400 MHz, (CD₃)₂SO) δ 9.54 (s, 1H), 9.15 (s, 1H), 8.45 (s, 1H), 8.20 (s, 1H), 7.87 (s, 1H), 7.85-7.78 (m, 1H), 7.58 (d, J = 8.7 Hz, 1H), 7.10 (d, J = 2.1 Hz, 1H), 7.00 (dd, J = 8.7, 1.8 Hz, 1H), 6.90 (d, J = 8.7 Hz, 1H), 4.20-4.16 (m, 2H), 3.96-3.92 (m, 2H), 3.84 (s, 3H), 2.70-2.55 (m, 2H), 2.26 (s, 3H) |
| 300 (Ex. 85) | 6-(1,1-difluoro-5-azaspiro[2.3]hexan-5-yl)-N-(3-methyl-4-((1-methyl-1H-benzo[d]imidazol-5-yl)oxy)phenyl)pyrimido[5,4-d]pyrimidin-4-amine | 501.2 | ¹H NMR (400 MHz, (CD₃)₂SO) δ 9.49 (s, 1H), 9.14 (s, 1H), 8.47 (s, 1H), 8.19 (s, 1H), 7.87 (d, J = 2.4 Hz, 1H), 7.80 (dd, J = 8.7, 2.6 Hz, 1H), 7.57 (d, J = 8.7 Hz, 1H), 7.10 (d, J = 2.2 Hz, 1H), 7.00 (dd, J = 8.7, 2.2 Hz, 1H), 6.89 (d, J = 8.7 Hz, 1H), 4.46-4.33 (m, 4H), 3.84 (s, 3H), 2.25 (s, 3H), 1.89-1.80 (m, 2H) |
| 301 (Ex. 86) | (R)-6-((4,4-difluoropyrrolidin-3-yl)oxy)-N-(3-methyl-4-((1-methyl-1H-benzo[d]imidazol-5-yl)oxy)phenyl)pyrimido[5,4-d]pyrimidin-4-amine | 505.2 | ¹H NMR (400 MHz, (CD₃)₂SO) δ 9.95 (s, 1H), 9.37 (s, 1H), 8.63 (s, 1H), 8.17 (s, 1H), 7.83 (d, J = 2.4 Hz, 1H), 7.72 (dd, J = 8.7, 2.6 Hz, 1H), 7.57 (d, J = 8.7 Hz, 1H), 7.11 (d, J = 2.2 Hz, 1H), 7.00 (dd, J = 8.7, 2.3 Hz, 1H), 6.90 (d, J = 8.7 Hz, 1H), 5.91-5.83 (m, 1H), 3.84 (s, 3H), 3.71-3.62 (m, 1H), 3.23-3.07 (m, 1H), 3.02-2.95 (m, 1H), 2.27 (s, 3H) |
| 302 (Ex. 84) | 6-(((3S,5R)-5-fluoro-1-methylpiperidin-3-yl)oxy)-N-(3-methyl-4-((1-methyl-1H-benzo[d]imidazol-5-yl)oxy)phenyl)pyrimido[5,4-d]pyrimidin-4-amine | 515.3 | ¹H NMR (400 MHz, (CD₃)₂SO) δ 9.97 (s, 1H), 9.34 (s, 1H), 8.59 (s, 1H), 8.17 (s, 1H), 7.84 (d, J = 2.4 Hz, 1H), 7.73 (dd, J = 8.7, 2.5 Hz, 1H), 7.57 (d, J = 8.7 Hz, 1H), 7.10 (d, J = 2.2 Hz, 1H), 7.00 (dd, J = 8.7, 2.3 Hz, 1H), 6.88 (d, J = 8.7 Hz, 1H), 5.74-5.62 (m, 1H), 4.97 (d, J = 47.8 Hz, 1H), 3.84 (s, 3H), 2.84-2.76 (m, 1H), 2.67-2.54 (m, 2H), 2.26 (s, 6H), 2.21-2.01 (m, 2H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 303 (Ex. 86) | (S)-6-((4,4-difluoropyrrolidin-3-yl)oxy)-N-(3-methyl-4-((1-methyl-1H-benzo[d]imidazol-5-yl)oxy)phenyl)pyrimido[5,4-d]pyrimidin-4-amine | 505.2 | ¹H NMR (400 MHz, (CD₃)₂SO) δ 9.95 (s, 1H), 9.37 (s, 1H), 8.63 (s, 1H), 8.17 (s, 1H), 7.83 (d, J = 2.6 Hz, 1H), 7.72 (dd, J = 8.6, 2.7 Hz, 1H), 7.57 (d, J = 8.7 Hz, 1H), 7.11 (d, J = 2.3 Hz, 1H), 7.00 (dd, J = 8.7, 2.3 Hz, 1H), 6.90 (d, J = 8.7 Hz, 1H), 5.91-5.83 (m, 1H), 3.84 (s, 3H), 3.67 (dd, J = 12.1, 6.5 Hz, 1H), 3.15 (dt, J = 23.1, 11.9 Hz, 1H), 2.99 (dd, J = 12.7, 5.1 Hz, 1H), 2.27 (s, 3H) |
| 304 (Ex. 95) | 1-(8-((4-([1,2,4]triazolo[1,5-a]pyridin-7-yloxy)-2-fluoro-3-methylphenyl)amino)pyrimido[5,4-d]pyrimidin-2-yl)-4-methylpiperidin-4-ol | 502.2 | ¹H NMR (400 MHz, (CD₃)₂SO) δ 9.51 (s, 1H), 9.09 (s, 1H), 8.97 (dd, J = 7.5, 0.6 Hz, 1H), 8.39 (d, J = 14.7 Hz, 1H), 7.92 (t, J = 8.8 Hz, 1H), 7.17-7.11 (m, 1H), 7.07 (dd, J = 7.4, 2.6 Hz, 1H), 6.96-6.90 (m, 1H), 4.45 (s, 1H), 3.71-3.45 (m, 4H), 2.17 (d, J = 1.8 Hz, 3H), 1.71-1.44 (m, 4H), 1.19 (s, 3H) |
| 305 (Ex. 95) | N2-((3R,4S)-4-fluoro-1-methylpyrrolidin-3-yl)-N2-methyl-N8-(3-methyl-4-((1-methyl-1H-benzo[d]imidazol-5-yl)oxy)phenyl)pyrimido[5,4-d]pyrimidine-2,8-diamine | 514.3 | ¹H NMR (400 MHz, CDCl₃) δ 9.06 (s, 1H), 8.55 (s, 2H), 7.85 (s, 1H), 7.73 (d, J = 2.3 Hz, 1H), 7.64 (dd, J = 8.7, 2.6 Hz, 1H), 7.39-7.29 (m, 3H), 7.06 (dd, J = 8.8, 2.2 Hz, 1H), 6.93 (d, J = 8.7 Hz, 1H), 5.58-5.12 (m, OH), 3.85 (s, 3H), 3.42-3.34 (m, 4H), 3.14 (dd, J = 9.8, 6.1 Hz, 1H), 2.47 (s, 3H), 2.35 (s, 3H) |
| 306 (Ex. 95) | 1-((8-((4-([1,2,4]triazolo[1,5-a]pyridin-7-yloxy)-2-fluoro-3-methylphenyl)amino)pyrimido[5,4-d]pyrimidin-2-yl)(methyl)amino)-2-methylpropan-2-ol | 490.2 | ¹H NMR (400 MHz, (CD₃)₂SO) δ 9.46-9.23 (m, 1H), 9.20-9.01 (m, 1H), 8.97 (d, J = 7.5 Hz, 1H), 8.46-8.38 (m, 2H), 8.27-8.04 (m, 1H), 7.16 (d, J = 9.0 Hz, 1H), 7.07 (dd, J = 7.5, 2.6 Hz, 1H), 6.93 (d, J = 2.3 Hz, 1H), 4.55 (s, 1H), 3.82 (s, 2H), 3.38 (s, 3H), 2.09 (s, 3H), 1.37-1.00 (m, 6H) |
| 307 (Ex. 95) | (S)-1-(8-((4-([1,2,4]triazolo[1,5-a]pyridin-7-yloxy)-2-fluoro-3-methylphenyl)amino)pyrimido[5,4-d]pyrimidin-2-yl)-3-methylpyrrolidin-3-ol | 488.2 | ¹H NMR (400 MHz, (CD₃)₂SO) δ 9.44-9.24 (m, 1H), 9.13 (s, 1H), 8.97 (d, J = 7.4 Hz, 1H), 8.52-8.33 (m, 2H), 8.32-8.04 (m, 1H), 7.16 (d, J = 8.7 Hz, 1H), 7.07 (dd, J = 7.5, 2.6 Hz, 1H), 6.94 (d, J = 2.4 Hz, 1H), 4.91 (s, 1H), 3.89-3.63 (m, 3H), 3.53-3.45 (m, 1H), 2.17 (s, 3H), 1.44-1.36 (m, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 308 (Ex. 95) | (R)-1-(8-((4-([1,2,4]triazolo[1,5-a]pyridin-7-yloxy)-2-fluoro-3-methylphenyl)amino)pyrimido[5,4-d]pyrimidin-2-yl)-3-methylpyrrolidin-3-ol | 488.2 | 1H NMR (400 MHz, (CD3)2SO) δ 9.34 (d, J = 11.0 Hz, 1H), 9.13 (s, 1H), 8.97 (d, J = 7.5 Hz, 1H), 8.48-8.36 (m, 2H), 8.30-8.05 (m, 1H), 7.16 (d, J = 8.9 Hz, 1H), 7.07 (dd, J = 7.5, 2.6 Hz, 1H), 6.94 (d, J = 2.4 Hz, 1H), 4.91 (s, 1H), 3.89-3.63 (m, 2H), 3.58-3.41 (m, 1H), 2.17 (s, 3H), 2.04-1.93 (m, 3H), 1.49-1.30 (m, 3H) |
| 309 (Ex. 95) | (S)-2-(1-(8-((4-([1,2,4]triazolo[1,5-a]pyridin-7-yloxy)-2-fluoro-3-methylphenyl)amino)pyrimido[5,4-d]pyrimidin-2-yl)azetidin-2-yl)propan-2-ol | 502.2 | 1H NMR (400 MHz, CDCl3) δ 9.05 (s, 1H), 9.02-8.81 (m, 1H), 8.74 (t, J = 9.0 Hz, 1H), 8.62 (s, 1H), 8.51 (dd, J = 7.3, 0.8 Hz, 1H), 8.24 (s, 1H), 7.00 (dd, J = 9.0, 1.6 Hz, 1H), 6.95-6.78 (m, 2H), 4.69-4.48 (m, 1H), 4.31-3.97 (m, 2H), 2.45 (ddt, J = 8.9, 6.6,4.1 Hz, 1H), 2.29-2.12 (m, 4H), 1.37 (s, 3H), 1.23 (s, 3H) |
| 310 (Ex. 97) | (S)-1-(8-((2-fluoro-3-methyl-4-((1-methyl-1H-benzo[d]imidazol-5-yl)oxy)phenyl)amino)pyrimido[5,4-d]pyrimidin-2-yl)-3-methylpyrrolidin-3-ol | 501.15 | 1H NMR (400 MHz, (CD3)2SO) δ 9.43-9.22 (m, 1H), 9.10 (s, 1H), 8.36 (s, 1H), 8.20 (s, 1H), 7.99-7.74 (m, 1H), 7.60 (d, J = 8.4 Hz, 1H), 7.21 (s, 1H), 7.04 (d, J = 7.8 Hz, 1H), 6.71 (d, J = 7.4 Hz, 1H), 4.90 (s, 1H), 3.99-3.56 (m, 6H), 3.47 (d, J = 11.3 Hz, 1H), 2.24 (s, 3H), 2.01-1.92 (m, 2H), 1.40 (s, 3H) |
| 311 (Ex. 95) | (S)-1-(8-((4-([1,2,4]triazolo[1,5-a]pyridin-7-yloxy)-2-fluoro-3-methylphenyl)amino)pyrimido[5,4-d]pyrimidin-2-yl)pyrrolidin-3-ol | 474.2 | 1H NMR (400 MHz, (CDCl3) δ 9.11 (s, 1H), 9.05 (s, 1H), 8.79 (t, J = 9.0 Hz, 1H), 8.59 (s, 1H), 8.51 (d, J = 7.2 Hz, 1H), 8.24 (s, 1H), 7.00 (d, J = 7.7 Hz, 1H), 6.90 (d, J = 2.5 Hz, 1H), 6.88 (s, 1H), 4.72 (s, 1H), 3.94-3.83 (m, 4H), 2.32-2.10 (m, 5H), 1.76 (s, 1H) |
| 312 (Ex. 95) | (R)-1-(8-((4-([1,2,4]triazolo[1,5-a]pyridin-7-yloxy)-2-fluoro-3-methylphenyl)amino)pyrimido[5,4-d]pyrimidin-2-yl)pyrrolidin-3-ol | 474.2 | |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 313 (Ex. 95) | N-(4-([1,2,4]triazolo[1,5-a]pyridin-7-yloxy)-2-fluoro-3-methylphenyl)-6-((1S,4S)-2-oxa-5-azabicyclo[2.2.1]heptan-5-yl)pyrimido[5,4-d]pyrimidin-4-amine | 486.2 | 1H NMR (400 MHz, (CD3)2SO) δ 9.68-9.29 (m, 1H), 9.14 (s, 1H), 8.97 (d, J = 7.5 Hz, 1H), 8.49-8.31 (m, 2H), 8.22-7.78 (m, 1H), 7.15 (d, J = 8.8 Hz, 1H), 7.07 (dd, J = 7.5, 2.6 Hz, 1H), 6.94 (d, J = 2.2 Hz, 1H), 5.46-5.07 (m, 1H), 4.77 (s, 1H), 4.01-3.69 (m, 2H), 3.68-3.43 (m, 2H)), 2.17 (s, 3H), 2.05-1.92 (m, 2H) |
| 314 (Ex. 95) | 1-(((8-((4-([1,2,4]triazolo[1,5-a]pyridin-7-yloxy)-2-fluoro-3-methylphenyl)amino)pyrimido[5,4-d]pyrimidin-2-yl)(methyl)amino)methyl)cyclopropan-1-ol | 488.2 | 1H NMR (400 MHz, (CD3)2SO) δ 9.38 (s, 1H), 9.09 (s, 1H), 8.97 (dd, J = 7.5, 0.5 Hz, 1H), 8.41 (s, 2H), 8.10 (t, J = 8.4 Hz, 1H), 7.16 (d, J = 8.9 Hz, 1H), 7.07 (dd, J = 7.5, 2.6 Hz, 1H), 6.94 (d, J = 2.2 Hz, 1H), 5.39 (s, 1H), 3.96 (s 2H), 3.40 (s, 3H), 2.17 (s, 3H), 0.77-0.51 (m, 4H) |
| 315 (Ex. 95) | 1-(((8-((4-([1,2,4]triazolo[1,5-a]pyridin-7-yloxy)-2-fluoro-3-methylphenyl)amino)pyrimido[5,4-d]pyrimidin-2-yl)(methyl)amino)methyl)cyclobutan-1-ol | 502.2 | 1H NMR (400 MHz, (CD3)2SO) δ 9.45-9.19 (m, 1H), 9.18-9.05 (m, 1H), 8.97 (d, 1H), 8.48-8.35 (m, 2H), 8.35-7.99 (m, 1H), 7.16 (d, J = 8.9 Hz, 1H), 7.06 (dd, J = 7.5, 2.6 Hz, 1H), 6.94 (d, J = 2.4 Hz, 1H), 5.23 (s, 1H), 4.13-3.88 (m, 2H), 3.36 (s, 3H), 2.17 (s, 3H), 2.12-1.79 (m, 4H), 1.76-1.49 (m, 2H) |
| 316 (Ex. 95) | (R)-1-(8-((4-([1,2,4]triazolo[1,5-a]pyridin-7-yloxy)-2-fluoro-3-methylphenyl)amino)pyrimido[5,4-d]pyrimidin-2-yl)-4,4-difluoropyrrolidin-3-ol | 510.2 | 1H NMR (400 MHz, (CD3)2SO) δ 9.57 (s, 1H), 9.21 (s, 1H), 8.98 (dd, J = 7.5, 0.6 Hz, 1H), 8.46 (s, 1H), 8.41 (s, 1H), 7.95 (s, 1H), 7.15 (dd, J = 8.8, 1.3 Hz, 1H), 7.07 (dd, J = 7.4, 2.6 Hz, 1H), 6.95 (d, J = 2.1 Hz, 1H), 6.23 (d, J = 5.3 Hz, 1H), 4.48-4.43 (m, 1H), 4.23-3.94 (m, 3H), 3.76-3.72 (m, 1H), 2.18 (d, J = 1.8 Hz, 3H) |
| 317 (Ex. 95) | N8-(4-([1,2,4]triazolo[1,5-a]pyridin-7-yloxy)-2-fluoro-3-methylphenyl)-N2-(2,2-difluoroethyl)-N2-methylpyrimido[5,4-d]pyrimidine-2,8-diamine | 482.2 | 1H NMR (400 MHz, (CD3)2SO) δ 9.58 (s, 1H), 9.19 (s, 1H), 8.98 (d, J = 7.5 Hz, 1H), 8.43 (d, J = 14.4 Hz, 2H), 7.95 (s, 1H), 7.16 (d, J = 8.8 Hz, 1H), 7.07 (dd, J = 7.5, 2.5 Hz, 1H), 6.94 (d, J = 2.4 Hz, 1H), 6.54-6.09 (m, 1H), 4.41-4.13 (m, 2H), 3.37 (s, 3H), 2.18 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 318 (Ex. 94,95) | N8-(4-([1,2,4]triazolo[1,5-a]pyridin-7-yloxy)-2-fluoro-3-methylphenyl)-N2-((3S,4R)-4-fluoropyrrolidin-3-yl)pyrimido[5,4-d]pyrimidine-2,8-diamine | 491.1 | |
| 319 (Ex. 85) | 3-(((8-((3-methyl-4-((1-methyl-1H-benzo[d]imidazol-5-yl)oxy)phenyl)amino)pyrimido[5,4-d]pyrimidin-2-yl)amino)methyl)oxetan-3-ol | 485.3 | 1H NMR (400 MHz, (CD3)2SO) δ 9.44 (s, 1H), 9.01 (s, 1H), 8.39 (s, 1H), 8.17 (s, 1H), 7.91-7.66 (m, 3H), 7.56 (d, J = 8.7 Hz, 1H), 7.12-7.07 (m, 1H), 6.99 (d, J = 8.6 Hz, 1H), 6.90 (d, J = 8.7 Hz, 1H), 5.76 (s, 1H), 4.63-4.49 (m, 2H), 4.44 (d, J = 6.2 Hz, 2H), 3.91 (s, 2H), 3.84 (s, 3H), 2.26 (s, 3H) |
| 320 (Ex. 99) | N8-(4-([1,2,4]triazolo[1,5-a]pyridin-7-yloxy)-2-fluoro-3-methylphenyl)-N2-((3S,4R)-4-fluoro-1-methylpyrrolidin-3-yl)-N2-methylpyrimido[5,4-d]pyrimidine-2,8-diamine | 519.25 | |
| 321 (Ex. 101) | (R)-N-(4-([1,2,4]triazolo[1,5-a]pyridin-7-yloxy)-3-chlorophenyl)-6-(2-(methoxymethyl)azetidin-1-yl)pyrimido[5,4-d]pyrimidin-4-amine | 490.2 | 1H NMR (400 MHz, (CD3)2SO) δ 9.60 (s, 1H), 9.12 (s, 1H), 8.97 (d, J = 7.5 Hz, 1H), 8.52 (s, 1H), 8.44 (d, J = 2.4 Hz, 1H), 8.41 (s, 1H), 8.09 (d, J = 7.1 Hz, 1H), 7.50 (d, J = 8.9 Hz, 1H), 7.07 (dd, J = 7.5, 2.6 Hz, 1H), 6.94 (d, J = 2.4 Hz, 1H), 4.69 (s, 1H), 4.13 (t, J = 7.4 Hz, 2H), 3.94 (s, 1H), 3.73 (dd, J = 10.2, 2.8 Hz, 1H), 3.32 (s, 3H), 2.46-2.27 (m, 2H) |
| 322 (Ex. 101) | N-(4-([1,2,4]triazolo[1,5-a]pyridin-7-yloxy)-3-chlorophenyl)-6-(3-oxa-8-azabicyclo[3.2.1]octan-8-yl)pyrimido[5,4-d]pyrimidin-4-amine | 502.2 | 1H NMR (400 MHz, (CD3)2SO) δ 9.76 (s, 1H), 9.15 (s, 1H), 8.97 (d, J = 7.5 Hz, 1H), 8.52 (s, 1H), 8.44 (d, J = 2.5 Hz, 1H), 8.41 (s, 1H), 8.16 (dd, J = 8.9, 2.6 Hz, 1H), 7.50 (d, J = 8.9 Hz, 1H), 7.07 (dd, J = 7.5, 2.7 Hz, 1H), 6.94 (d, J = 2.3 Hz, 1H), 5.22 (s, 1H), 4.79 (s, 1H), 3.84-3.58 (m, 4H), 2.17-1.90 (m, 4H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 323 (Ex. 101) | (R)-1-(8-((4-([1,2,4]triazolo[1,5-a]pyridin-7-yloxy)-3-chlorophenyl)amino)pyrimido[5,4-d]pyrimidin-2-yl)-4,4-difluoropyrrolidin-3-ol | 512.2 | 1H NMR (400 MHz, (CD3)2SO) δ 9.75 (s, 1H), 9.20 (s, 1H), 8.97 (dd, J = 7.5, 0.5 Hz, 1H), 8.56 (s, 1H), 8.45 (d, J = 2.6 Hz, 1H), 8.41 (s, 1H), 8.17 (dd, J = 8.9, 2.5 Hz, 1H), 7.51 (d, J = 8.9 Hz, 1H), 7.08 (dd, J = 7.5, 2.7 Hz, 1H), 6.95 (d, J = 2.2 Hz, 1H), 6.25 (d, J = 5.3 Hz, 1H), 4.47-4.42 (m, 1H), 4.36-3.52 (m, 5H) |
| 324 (Ex. 101) | 1-(8-((4-([1,2,4]triazolo[1,5-a]pyridin-7-yloxy)-3-chlorophenyl)amino)pyrimido[5,4-d]pyrimidin-2-yl)-3-methylazetidin-3-ol | 476.2 | 1H NMR (400 MHz, (CD3)2SO) δ 9.67 (s, 1H), 9.12 (s, 1H), 9.00-8.93 (m, 1H), 8.53 (s, 1H), 8.47 (d, J = 2.6 Hz, 1H), 8.41 (s, 1H), 8.15 (dd, J = 8.9, 2.6 Hz, 1H), 7.50 (d, J = 8.9 Hz, 1H), 7.07 (dd, J = 7.5, 2.6 Hz, 1H), 6.94 (d, J = 2.3 Hz, 1H), 5.74 (s, 1H), 4.24-3.99 (m, 4H), 1.48 (s, 3H) |
| 325 (Ex. 101) | rac-(R)-1-((8-((4-([1,2,4]triazolo[1,5-a]pyridin-7-yloxy)-3-chlorophenyl)amino)pyrimido[5,4-d]pyrimidin-2-yl)(methyl)amino)-3-methoxypropan-2-ol | 508.2 | 1H NMR (400 MHz, (CD3)2SO) δ 9.77-9.34 (m, 1H), 9.12 (s, 1H), 8.97 (dd, J = 7.5, 0.6 Hz, 1H), 8.61-8.30 (m, 3H), 8.26-7.91 (m, 1H), 7.51 (d, J = 8.7 Hz, 1H), 7.07 (dd, J = 7.5, 2.7 Hz, 1H), 6.94 (d, J = 2.5 Hz, 1H), 4.96 (d, J = 5.4 Hz, 1H), 4.17-3.59 (m, 3H), 3.53-3.09 (m, 8H) |
| 326 (Ex. 101) | 3-(((8-((4-([1,2,4]triazolo[1,5-a]pyridin-7-yloxy)-3-chlorophenyl)amino)pyrimido[5,4-d]pyrimidin-2-yl)amino)methyl)oxetan-3-ol | 492.2 | 1H NMR (400 MHz, (CD3)2SO) δ 9.69 (s, 1H), 9.07 (s, 1H), 8.96 (d, 1H), 8.50 (s, 1H), 8.41 (s, 2H), 8.09 (dd, J = 8.9, 2.6 Hz, 1H), 7.86 (s, 1H), 7.50 (d, J = 8.9 Hz, 1H), 7.07 (dd, J = 7.5, 2.7 Hz, 1H), 6.94 (d, J = 2.4 Hz, 1H), 5.79 (s, 1H), 4.56 (s, 2H), 4.46 (d, J = 6.5 Hz, 2H), 3.95 (s, 2H) |
| 327 (Ex. 101) | (S)-N-(4-([1,2,4]triazolo[1,5-a]pyridin-7-yloxy)-3-chlorophenyl)-6-(2-methylmorpholino)pyrimido[5,4-d]pyrimidin-4-amine | 490.2 | 1H NMR (400 MHz, (CD3)2SO) δ 9.79 (s, 1H), 9.15 (s, 1H), 8.97 (dd, J = 7.5, 0.6 Hz, 1H), 8.52 (s, 1H), 8.44 (d, J = 2.6 Hz, 1H), 8.41 (s, 1H), 8.14 (dd, J = 8.9, 2.6 Hz, 1H), 7.07 (dd, J = 7.5, 2.6 Hz, 1H), 6.93 (d, J = 2.2 Hz, 1H), 4.85 (s, 2H), 3.98 (dd, J = 11.6, 2.3 Hz, 1iH), 3.70-3.49 (m, 2H), 3.17-3.05 (m, 1H), 2.79 (dd, J = 13.3, 10.5 Hz, 1H), 1.22 (d, J = 6.2 Hz, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 328 (Ex. 101) | (S)-N-(4-([1,2,4]triazolo[1,5-a]pyridin-7-yloxy)-3-chlorophenyl)-6-(2-(methoxymethyl)azetidin-1-yl)pyrimido[5,4-d]pyrimidin-4-amine | 490.2 | 1H NMR (400 MHz, (CD$_3$)$_2$SO) δ 9.60 (s, 1H), 9.12 (s, 1H), 8.97 (dd, J = 7.5, 0.6 Hz, 2H), 8.52 (s, 1H), 8.44 (d, J = 2.5 Hz, 1H), 8.41 (s, 1H), 8.09 (d, J = 6.9 Hz, 1H), 7.50 (d, J = 8.9 Hz, 1H), 7.07 (dd, J = 7.5, 2.6 Hz, 1H), 6.94 (d, J = 2.2 Hz, 1H), 4.69 (s, 1H), 4.13 (t, J = 7.3 Hz, 2H), 3.95 (s, 1H), 3.73 (dd, J = 10.2, 2.8 Hz, 1H), 3.32 (s, 3H), 2.50-2.27 (m, 2H) |
| 329 (Ex. 101) | 1-(((8-((4-([1,2,4]triazolo[1,5-a]pyridin-7-yloxy)-3-chlorophenyl)amino)pyrimido[5,4-d]pyrimidin-2-yl)(methyl)amino)methyl)cyclobutan-1-ol | 504.2 | 1H NMR (400 MHz, (CD$_3$)$_2$SO) δ 9.66 (s, 1H), 9.11 (s, 1H), 8.96 (d, J = 7.5 Hz, 1H), 8.49 (s, 1H), 8.51-8.44 (m, 2H), 8.16-8.04 (m, 1H), 7.50 (d, J = 8.8 Hz, 1H), 7.07 (dd, J = 7.5, 2.6 Hz, 1H), 6.94 (d, J = 2.5 Hz, 1H), 5.21 (s, 1H), 4.25-3.83 (m, 2jH), 3.53-3.32 (m, 3H), 2.02 (s, OH), 2.08-1.96 (m, 2H), 1.96-1.85 (m, 2H), 1.66-1.61 (m, 2H) |
| 330 (Ex. 101) | N-(4-([1,2,4]triazolo[1,5-a]pyridin-7-yloxy)-3-chlorophenyl)-6-(2,2-dimethylmorpholino)pyrimido[5,4-d]pyrimidin-4-amine | 504.2 | 1H NMR (400 MHz, (CD$_3$)$_2$SO) δ 9.75 (s, 1H), 9.13 (s, 1H), 8.97 (d, J = 7.5 Hz, 1H), 8.50 (s, 1H), 8.41 (s, 2H), 8.13 (d, J = 6.9 Hz, 1H), 7.51 (d, J = 8.9 Hz, 1H), 7.07 (dd, J = 7.5, 2.4 Hz, 1H), 6.94 (d, J = 2.3 Hz, 1H), 4.07-3.96 (m, 2H), 3.91-3.71 (m, 4H), 1.22 (s, 6H) |
| 331 (Ex. 103) | N2-benzyl-N2-methyl-N8-(3-methyl-4-((1-methyl-1H-benzo[d]imidazol-5-yl)oxy)phenyl)pyrimido[5,4-d]pyrimidine-2,8-diamine | 503.3 | 1H NMR (400 MHz, (CD$_3$)$_2$SO) δ 9.50 (s, 1H), 9.11 (s, 1H), 8.41 (s, 1H), 8.16 (s, 1H), 7.83 (s, 1H), 7.76 (d, J = 7.7 Hz, 1H), 7.56 (d, J = 8.7 Hz, 1H), 7.40-7.20 (m, 5H), 7.09 (d, J = 2.2 Hz, 1H), 6.99 (dd, J = 8.7, 2.3 Hz, 1H), 6.88 (d, J = 8.7 Hz, 1H), 5.10 (s, 2H), 3.83 (s, 3H), 2.25 (s, 3H) |
| 332 (Ex. 101) | (1R,4R,5R)-2-(8-((4-([1,2,4]triazolo[1,5-a]pyridin-7-yloxy)-3-chlorophenyl)amino)pyrimido[5,4-d]pyrimidin-2-yl)-2-azabicyclo[2.2.1]heptan-5-ol | 502.2 | 1H NMR (400 MHz, (CD$_3$)$_2$SO) δ 9.63 (d, J = 24.6 Hz, 1H), 9.08 (d, J = 12.5 Hz, 1H), 8.97 (d, J = 7.5 Hz, 1H), 8.50-8.44 (m, 2H), 8.41 (s, 1H), 8.21-8.13 (m, 1H), 7.49 (d, J = 8.8 Hz, 1H), 7.07 (dd, J = 7.5, 2.7 Hz, 1H), 6.94 (d, J = 2.5 Hz, 1H), 5.22-4.61 (m, 2H), 4.35-4.31 (m, 1H), 4.00 (dd, J = 57.9, 10.7 Hz, 1H), 3.53-3.34 (m, 1H), 2.66-2.62 (m, 1H), 2.19-1.99 (m, 1H), 1.81-1.76 (m, 1H), 1.71-1.64 (m, 1H), 1.29-1.15 (m, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 333 (Ex. 101) | (1S,4S,5R)-2-(8-((4-([1,2,4]triazolo[1,5-a]pyridin-7-yloxy)-3-chlorophenyl)amino)pyrimido[5,4-d]pyrimidin-2-yl)-2-azabicyclo[2.2.1]heptan-5-ol | 502.2 | ¹H NMR (400 MHz, (CD₃)₂SO) δ 9.74-9.47 (m, 1H), 9.07 (s, 1H), 8.96 (d, 1H), 8.48-8.44 (m, 2H), 8.41 (s, 1H), 8.22-8.11 (m, 1H), 7.50 (d, J = 8.9 Hz, 1H), 7.07 (dd, J = 7.5, 2.7 Hz, 1H), 6.94 (d, J = 2.2 Hz, 1H), 5.32-4.68 (m, 2H), 3.92-3.88 (m, 1H), 3.62-3.40 (m, 1H), 3.33-3.01 (m, 1H), 2.58-2.44 (m, 1H), 2.05-1.82 (m, 2H), 1.70-1.60 (m, 1H), 1.55-1.48 (m, 1H) |
| 334 (Ex. 101) | (1S,4S,5S)-2-(8-((4-([1,2,4]triazolo[1,5-a]pyridin-7-yloxy)-3-chlorophenyl)amino)pyrimido[5,4-d]pyrimidin-2-yl)-2-azabicyclo[2.2.1]heptan-5-ol | 502.2 | ¹H NMR (400 MHz, (CD₃)₂SO) δ 9.72-9.56 (m, 1H), 9.08 (d, J = 12.5 Hz, 1H), 8.96 (d, J = 7.5 Hz, 1H), 8.50-8.44 (m, 2H), 8.41 (s, 1H), 8.23-8.11 (m, 1H), 7.49 (d, J = 9.0 Hz, 1H), 7.07 (dd, J = 7.5, 2.7 Hz, 1H), 6.94 (d, J = 2.5 Hz, 1H), 5.17-4.62 (m, 2H), 4.44-4.23 (m, 1H), 4.14-3.84 (m 1H), 3.55-3.34 (m, 1H), 2.67-2.62 (m, 1H), 2.20-2.03 (m, 1H), 1.81-1.76 (m, 1H), 1.71-1.64 (m, 1H), 1.29-1.15 (m, 1H) |
| 335 (Ex. 101) | (1R,4R,5S)-2-(8-((4-([1,2,4]triazolo[1,5-a]pyridin-7-yloxy)-3-chlorophenyl)amino)pyrimido[5,4-d]pyrimidin-2-yl)-2-azabicyclo[2.2.1]heptan-5-ol | 502.2 | ¹H NMR (400 MHz, (CD₃)₂SO) δ 9.75-9.47 (m, 1H), 9.07 (s, 1H), 8.97 (d, J = 7.5 Hz, 1H), 8.51-8.44 (m, 2H), 8.41 (s, 1H), 8.22-8.11 (m, 1H), 7.50 (d, J = 8.9 Hz, 1H), 7.07 (dd, J = 7.5, 2.6 Hz, 1H), 6.94 (d, J = 2.4 Hz, 1H), 5.31-4.72 (m, 2H), 3.92-3.88 (m, 1H), 3.62-3.40 (m, 1H), 3.31-3.06 (m, 1H), 2.58-2.51 (m, 1H), 2.06-1.85 (m, 2H), 1.70-1.62 (m, 1H), 1.55-1.48 (m, 1H) |
| 336 (Ex. 101) | (1R,5S,6r)-3-(8-((4-([1,2,4]triazolo[1,5-a]pyridin-7-yloxy)-3-chlorophenyl)amino)pyrimido[5,4-d]pyrimidin-2-yl)-3-azabicyclo[3.1.1]heptan-6-ol | 502.2 | |
| 337 (Ex. 101) | rac-(S)-1-(8-((4-([1,2,4]triazolo[1,5-a]pyridin-7-yloxy)-3-chlorophenyl)amino)pyrimido[5,4-d]pyrimidin-2-yl)-3,3-dimethylpiperidin-4-ol | 518.2 | ¹H NMR (400 MHz, (CD₃)₂SO) δ 9.71 (s, 1H), 9.08 (s, 1H), 8.97 (d, J = 7.5 Hz, 1H), 8.46 (s, 1H), 8.44-8.40 (m, 2H), 8.14 (d, J = 8.7 Hz, 1H), 7.50 (d, J = 8.9 Hz, 1H), 7.07 (dd, J = 7.5, 2.7 Hz, 1H), 6.93 (d, J = 2.5 Hz, 1H), 4.88-4.06 (m, 3H), 3.55-3.39 (m, 2H), 3.24-3.16 (m, 1H), 1.90-1.70 (m, 1H), 1.70-1.46 (m, 1H), 0.97 (s, 3H), 0.83 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 338 (Ex. 101) | (3S,4S)-1-(8-((4-([1,2,4]triazolo[1,5-a]pyridin-7-yloxy)-3-chlorophenyl)amino)pyrimido[5,4-d]pyrimidin-2-yl)-4-fluoropiperidin-3-ol | 508.2 | 1H NMR (400 MHz, (CD3)2SO) δ 9.81 (s, 1H), 9.13 (s, 1H), 8.97 (dd, J = 7.5, 0.5 Hz, 1H), 8.51 (s, 1H), 8.45-8.39 (m, 2H), 8.14 (dd, J = 8.9, 2.6 Hz, 1H), 7.50 (d, J = 8.9 Hz, 1H), 6.94 (d, J = 2.2 Hz, 1H), 5.53 (d, J = 4.8 Hz, 1H), 4.78-4.45 (m, 3H), 3.63-3.59 (m, 1H), 3.48 (t, J = 10.4 Hz, 1H), 2.54 (s, 3H), 2.19-2.14 (m, 1H), 1.74-1.62 (m, 1H) |
| 339 (Ex. 101) | (S)-1-(8-((4-([1,2,4]triazolo[1,5-a]pyridin-7-yloxy)-3-chlorophenyl)amino)pyrimido[5,4-d]pyrimidin-2-yl)-4,4-dimethylpyrrolidin-3-ol | 504.2 | 1H NMR (400 MHz, (CD3)2SO) δ 9.63 (d, J = 4.8 Hz, 1H), 9.12 (s, 1H), 8.97 (d, J = 7.5 Hz, 1H), 8.51-8.44 (m, 2H), 8.41 (s, 1H), 8.17 (d, J = 8.9 Hz, 1H), 7.49 (d, J = 8.9 Hz, 1H), 7.07 (dd, J = 7.5, 2.6 Hz, 1H), 6.94 (d, J = 2.5 Hz, 1H), 5.19-5.14 (m, 1H), 4.14-3.80 (m, 2H), 3.72-3.41 (m, 3H), 2.54 (s, 1H), 1.20-0.98 (m, 6H) |
| 340 (Ex. 101) | (3R,4S)-1-(8-((4-([1,2,4]triazolo[1,5-a]pyridin-7-yloxy)-3-chlorophenyl)amino)pyrimido[5,4-d]pyrimidin-2-yl)-4-methylpyrrolidin-3-ol | 490.2 | 1H NMR (400 MHz, (CD3)2SO) δ 9.63 (s, 1H), 9.12 (s, 1H), 8.97 (d, J = 7.5 Hz, 1H), 8.52-8.44 (m, 2H), 8.41 (s, 1H), 8.17 (dd, J = 8.9, 2.5 Hz, 1H), 7.49 (d, J = 8.9 Hz, 1H), 7.07 (dd, J = 7.5, 2.6 Hz, 1H), 6.94 (d, J = 2.5 Hz, 121H), 5.21 (s, 1H), 4.12-3.78 (m, 3H), 3.71-3.40 (m, 1H), 2.24-2.20 (m, 1H), 1.08-1.04 (s, 3H) |
| 341 (Ex. 101) | (1R,5S,8s)-3-(8-((4-([1,2,4]triazolo[1,5-a]pyridin-7-yloxy)-3-chlorophenyl)amino)pyrimido[5,4-d]pyrimidin-2-yl)-3-azabicyclo[3.2.1]octan-8-ol | 516.2 | 1H NMR (400 MHz, (CD3)2SO) δ 9.67 (s, 1H), 9.10 (s, 1H), 8.97 (d, J = 7.4 Hz, 1H), 8.48 (s, 1H), 8.45 (d, J = 2.5 Hz, 1H), 8.41 (s, 1H), 8.21-8.13 (m, 1H), 7.49 (d, J = 8.8 Hz, 1H), 7.07 (dd, J = 7.5, 2.5 Hz, 1H), 6.93 (d, J = 2.5 Hz, 1H), 5.18 (s, 1H), 4.74-4.54 (m, 1H), 4.42-4.22 (m, 1H), 3.95 (s, 1H), 3.52-3.44 (m, 1H), 2.10-2.06 (m, 2H), 1.73-1.69 (m, 2H), 1.57-1.39 (m, 2H) |
| 342 (Ex. 101) | (1R,5S,8r)-3-(8-((4-([1,2,4]triazolo[1,5-a]pyridin-7-yloxy)-3-chlorophenyl)amino)pyrimido[5,4-d]pyrimidin-2-yl)-3-azabicyclo[3.2.1]octan-8-ol | 516.2 | 1H NMR (500 MHz, (CD3)2SO) δ 9.68 (s, 1H), 9.10 (s, 1H), 8.97 (d, J = 7.5 Hz, 1H), 8.48 (s, 1H), 8.45 (d, J = 2.4 Hz, 1H), 8.41 (s, 1H), 8.17 (dd, J = 9.0, 2.5 Hz, 1H), 7.49 (d, J = 8.9 Hz, 1H), 7.07 (dd, J = 7.5, 2.6 Hz, 1H), 6.93 (d, J = 2.5 Hz, 1H), 5.18 (s, 1H), 4.70-4.56 (m, 1H), 4.42-4.23 (m, 1H), 3.97-3.93 (m, 1H), 3.51-3.45 (m, 1H), 2.10-2.07 (m, 2H), 1.73-1.69 (m, 2H), 1.55-1.38 (m, 2H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 343 (Ex. 109) | 2-(1-(8-((4-([1,2,4]triazolo[1,5-a]pyridin-7-yloxy)-3-methylphenyl)amino)pyrimido[5,4-d]pyrimidin-2-yl)azetidin-3-yl)propan-2-ol | 484.3 | $^1$H NMR (400 MHz, CDCl$_3$) δ 9.04 (s, 1H), 8.63 (s, 1H), 8.56 (s, 1H), 8.49 (d, J = 7.0 Hz, 1H), 8.22 (s, 1H), 7.87-7.78 (m, 2H), 7.11 (d, J = 8.6 Hz, 1H), 6.92-6.82 (m, 2H), 4.23 (p, J = 8.7 Hz, 4H), 2.89-2.77 (m, 1H), 2.25 (s, 3H), 1.94 (s, 1H), 1.29 (s, 6H) |
| 344 (Ex. 111) | N2,N2-bis(2,2-difluoroethyl)-N8-(3-methyl-4-((1-methyl-1H-benzo[d]imidazol-5-yl)oxy)phenyl)pyrimido[5,4-d]pyrimidine-2,8-diamine | 527.3 | $^1$H NMR (400 MHz, CDCl$_3$) δ 9.14 (s, 1H), 8.63 (s, 1H), 8.42 (s, 1H), 7.85 (s, 1H), 7.71 (d, J = 2.6 Hz, 1H), 7.61 (dd, J = 8.7, 2.8 Hz, 1H), 7.37-7.29 (m, 2H), 7.06 (dd, J = 8.7, 2.3 Hz, 1H), 6.93 (d, J = 8.7 Hz, 1H), 6.14 (t, J = 56.1 Hz, 2H), 4.20 (td, J = 13.5, 4.3 Hz, 4H), 3.85 (s, 3H), 2.36 (s, 3H) |
| 345 (Ex. 114) | N-(3-methyl-4-((1-methyl-1H-benzo[d]imidazol-5-yl)oxy)phenyl)-6-(1-oxa-7-azaspiro[3.5]nonan-7-yl)pyrimido[5,4-d]pyrimidin-4-amine | 509.3 | $^1$H NMR (400 MHz, CDCl$_3$) δ 9.08 (s, 1H), 8.57 (s, 1H), 8.44 (s, 1H), 7.85 (s, 1H), 7.72 (d, J = 2.7 Hz, 1H), 7.63 (dd, J = 8.6, 2.7 Hz, 1H), 7.34 (d, J = 9.0 Hz, 1H), 7.31 (d, J = 2.2 Hz, 1H), 7.07 (dd, J = 8.7, 2.3 Hz, 1H), 6.93 (d, J = 8.7 Hz, 1H), 4.99-4.87 (m, 2H), 4.82-4.73 (m, 1H), 4.24 (d, J = 3.9 Hz, 2H), 4.19-4.07 (m, 1H), 3.85 (s, 3H), 3.77-3.66 (m, 2H), 3.23-3.11 (m, 1H), 3.07-2.95 (m, 1H), 2.95-2.84 (m, 1H), 2.35 (s, 3H) |
| 346 (Ex. 111) | (R)-8-(8-((3-methyl-4-((1-methyl-1H-benzo[d]imidazol-5-yl)oxy)phenyl)amino)pyrimido[5,4-d]pyrimidin-2-yl)hexahydropyrazino[2,1-c][1,4]oxazin-4(3H)-one | 538.3 | $^1$H NMR (400 MHz, CDCl$_3$) δ 9.08 (s, 1H), 8.57 (s, 1H), 8.44 (s, 1H), 7.85 (s, 1H), 7.72 (d, J = 2.7 Hz, 1H), 7.63 (dd, J = 8.6, 2.7 Hz, 1H), 7.34 (d, J = 9.0 Hz, 1H), 7.31 (d, J = 2.2 Hz, 1H), 7.07 (dd, J = 8.7, 2.3 Hz, 1H), 6.93 (d, J = 8.7 Hz, 1H), 4.99-4.87 (m, 2H), 4.82-4.73 (m, 1H), 4.24 (d, J = 3.9 Hz, 2H), 4.19-4.07 (m, 1H), 3.85 (s, 3H), 3.77-3.66 (m, 2H), 3.23-3.11 (m, 1H), 3.07-2.95 (m, 1H), 2.95-2.84 (m, 1H), 2.35 (s, 3H) |
| 347 (Ex. 115) | 3-(8-((2-fluoro-3-methyl-4-((1-methyl-1H-benzo[d]imidazol-5-yl)oxy)phenyl)amino)pyrimido[5,4-d]pyrimidin-2-yl)-3-azabicyclo[3.1.0]hexan-1-ol | 499.3 | $^1$H NMR (400 MHz, CDCl$_3$) δ 9.05 (s, 1H), 8.87 (s, 1H), 8.52 (s, 1H), 8.48 (t, J = 9.0 Hz, 1H), 7.89 (s, 1H), 7.38-7.29 (m, 2H), 7.07 (dd, J = 8.7, 2.3 Hz, 1H), 6.75 (dd, J = 8.9, 1.7 Hz, 1H), 4.35 (d, J = 11.0 Hz, 1H), 3.88-3.76 (m, 5H), 2.29 (d, J = 2.2 Hz, 3H), 1.39-1.27 (m, 2H), 0.96-0.83 (m, 1H), 0.73 (t, J = 5.3 Hz, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 348 (Ex. 111) | rac-6-((1S,5R)-3-oxa-6-azabicyclo[3.2.0]heptan-6-yl)-N-(3-methyl-4-((1-methyl-1H-benzo[d]imidazol-5-yl)oxy)phenyl)pyrimido[5,4-d]pyrimidin-4-amine | 481.2 | 1H NMR (400 MHz, CDCl3) δ 9.13 (s, 1H), 8.68-8.59 (m, 2H), 8.52 (d, J = 7.4 Hz, 1H), 8.29 (d, J = 2.6 Hz, 1H), 8.24 (s, 1H), 7.83 (dd, J = 9.2, 2.6 Hz, 1H), 7.27 (d, J = 8.8 Hz, 1H), 6.92 (dd, J = 7.4, 2.6 Hz, 1H), 6.88 (d, J = 2.7 Hz, 1H), 6.08 (t, J = 56.2 Hz, 1H), 4.14 (td, J = 13.9, 4.3 Hz, 2H), 3.44 (s, 3H) |
| 349 (Ex. 109) | (S)-N8-(4-([1,2,4]triazolo[1,5-a]pyridin-7-yloxy)-3-methylphenyl)-N2-methyl-N2-(tetrahydro-2H-pyran-3-yl)pyrimido[5,4-d]pyrimidine-2,8-diamine | 484.3 | 1H NMR (400 MHz, CDCl3) δ 9.09 (s, 1H), 8.63 (s, 1H), 8.58 (s, 1H), 8.49 (dd, J = 7.4, 0.8 Hz, 1H), 8.22 (s, 1H), 7.87 (d, J = 2.7 Hz, 1H), 7.82 (dd, J = 8.6, 2.7 Hz, 1H), 7.13 (d, J = 8.6 Hz, 1H), 6.89 (dd, J = 7.4, 2.6 Hz, 1H), 6.86 (dd, J = 2.6, 0.7 Hz, 1H), 4.94 (s, 1H), 3.98 (d, J = 10.5 Hz, 2H), 3.54 (t, J = 10.5 Hz, 1H), 3.42 (td, J = 11.1, 3.0 Hz, 1H), 3.24 (s, 3H), 2.27 (s, 3H), 2.07-2.00 (m, 1H), 1.99-1.81 (m, 2H), 1.67 (s, 1H) |
| 350 (Ex. 114) | (R)-N2-methyl-N8-(3-methyl-4-((1-methyl-1H-benzo[d]imidazol-5-yl)oxy)phenyl)-N2-(oxetan-2-ylmethyl)pyrimido[5,4-d]pyrimidine-2,8-diamine | 483.3 | 1H NMR (400 MHz, CDCl3) δ 9.03 (s, 1H), 8.63 (s, 1H), 8.53 (s, 1H), 7.84 (s, 1H), 7.73 (d, J = 3.2 Hz, 1H), 7.63 (dd, J = 8.7, 2.7 Hz, 1H), 7.32 (d, J = 6.9 Hz, 1H), 7.31 (s, 1H), 7.05 (dd, J = 8.6, 2.4 Hz, 1H), 6.93 (d, J = 8.7 Hz, 1H), 5.17 (s, 1H) 4.71 (td, J = 8.0, 5.9 Hz, 1H), 4.59 (dt, J = 9.1, 5.8 Hz, 1H), 4.17-3.97 (m, 2H), 3.84 (s, 3H), 3.43 (s, 3H), 2.72 (s, 1H), 2.53 (s, 1H), 2.34 (s, 3H) |
| 351 (Ex. 132) | N-(4-([1,2,4]triazolo[1,5-a]pyridin-7-yloxy)-3-chlorophenyl)-6-((3aR,4R,7S,7aS)-octahydro-2H-4,7-epoxyisoindol-2-yl)pyrimido[5,4-d]pyrimidin-4-amine | 528.2 | 1H NMR (400 MHz, CDCl3) δ 9.07 (s, 1H), 8.69 (s, 1H), 8.58 (s, 1H), 8.52 (dd, J = 7.4, 0.8 Hz, 1H), 8.26 (d, J = 2.6 Hz, 1H), 8.24 (s, 1H), 7.88 (dd, J = 8.8, 2.6 Hz, 1H), 7.26 (d, J = 8.8 Hz, 1H), 6.91 (dd, J = 7.4, 2.6 Hz, 1H), 6.89 (dd, J = 2.7, 0.8 Hz, 1H), 4.50 (t, J = 2.7 Hz, 2H), 4.17-4.04 (m, 2H), 3.59 (dd, J = 11.8, 3.6 Hz, 2H), 2.77-2.66 (m, 2H), 1.83-1.69 (m, 2H), 1.61-1.48 (m, 2H) |
| 352 (Ex. 136) | (R)-N-(4-([1,2,4]triazolo[1,5-a]pyridin-7-yloxy)-3-methylphenyl)-6-(3-methylpiperazin-1-yl)pyrimido[5,4-d]pyrimidin-4-amine | 469.2 | 1H NMR (400 MHz, CDCl3) δ 9.06 (s, 1H), 8.57 (d, J = 4.6 Hz, 2H), 8.50 (dd, J = 7.4, 0.7 Hz, 1H), 8.22 (s, 1H), 7.86 (d, J = 2.7 Hz, 1H), 7.83 (dd, J = 8.6, 2.7 Hz, 1H), 7.12 (d, J = 8.6 Hz, 1H), 6.89 (dd, J = 7.4, 2.6 Hz, 1H), 6.85 (dd, J = 2.6, 0.7 Hz, 1H), 4.83-4.73 (m, 2H), 3.19 (dt, J = 11.7, 2.5 Hz, 1H), 3.15-3.05 (m, 1H), 2.97 (dd, J = 11.6, 3.1 Hz, 1H), 2.94-2.84 (m, 1H), 2.73 (dd, J = 12.8, 10.4 Hz, 1H), 2.27 (s, 3H), 1.21 (d, J = 6.2 Hz, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 353 (Ex. 114) | (R)-N2-((1,4-dioxan-2-yl)methyl)-N2-methyl-N8-(3-methyl-4-((1-methyl-1H-benzo[d]imidazol-5-yl)oxy)phenyl)pyrimido[5,4-d]pyrimidine-2,8-diamine | 513.3 | 1H NMR (400 MHz, CDCl3) δ 9.05 (s, 1H), 8.58 (s, 1H), 8.54 (s, 1H), 7.84 (s, 1H), 7.74 (dd, J = 2.8, 0.8 Hz, 1H), 7.63 (dd, J = 8.6, 2.7 Hz, 1H), 7.33 (dd, J = 6.2, 0.5 Hz, 1H), 7.31 (s, 1H), 7.05 (dd, J = 8.7, 2.3 Hz, 1H), 6.93 (d, J = 8.7 Hz, 1H), 3.99-3.92 (m, 2H), 3.85 (s, 3H), 3.89-3.80 (m, 2H), 3.78-3.60 (m, 4H), 3.55-3.42 (m, 1H), 3.37 (s, 3H), 2.35 (s, 3H) |
| 354 (Ex. 133) | (R)-N-(4-([1,2,4]triazolo[1,5-a]pyridin-7-yloxy)-3-chlorophenyl)-6-(3-(difluoromethoxy)pyrrolidin-1-yl)pyrimido[5,4-d]pyrimidin-4-amine | 526.2 | 1H NMR (400 MHz, CDCl3) δ 9.12 (s, 1H), 8.69 (s, 1H), 8.61 (s, 1H), 8.52 (dd, J = 7.4, 0.8 Hz, 1H), 8.29 (d, J = 2.6 Hz, 1H), 8.24 (s, 1H), 7.87 (dd, J = 8.8, 2.6 Hz, 1H), 7.27 (d, J = 8.8 Hz, 1H), 6.92 (dd, J = 7.4, 2.6 Hz, 1H), 6.88 (dd, J = 2.6, 0.8 Hz, 1H), 6.32 (t, J = 73.6 Hz, 1H), 5.07 (s, 1H), 4.03-3.77 (m, 3H), 2.38-2.27 (m, 1H), 1.69 (s, 1H) |
| 355 (Ex. 109) | (S)-N-(4-([1,2,4]triazolo[1,5-a]pyridin-7-yloxy)-3-methylphenyl)-6-(3-(trifluoromethyl)piperazin-1-yl)pyrimido[5,4-d]pyrimidin-4-amine | 523.2 | 1H NMR (400 MHz, CDCl3) δ 9.11 (s, 1H), 8.61 (s, 1H), 8.56 (s, 1H), 8.50 (dd, J = 7.4, 0.7 Hz, 1H), 8.23 (s, 1H), 7.86 (d, J = 3.2 Hz, 1H), 7.82 (dd, J = 8.6, 2.7 Hz, 1H), 7.13 (d, J = 8.6 Hz, 1H), 6.89 (dd, J = 7.5, 2.6 Hz, 1H), 6.85 (dd, J = 2.6, 0.7 Hz, 1H), 4.89 (d, J = 11.1 Hz, 1H), 4.71-4.62 (m, 1H), 3.50-3.33 (m, 3H), 3.28 (dt, J = 12.0, 3.3 Hz, 1H), 2.96 (ddd, J = 11.9, 10.6, 3.4 Hz, 1H), 2.27 (s, 3H) |
| 356 (Ex. 133) | rac-(R)-N-(4-([1,2,4]triazolo[1,5-a]pyridin-7-yloxy)-3-chlorophenyl)-6-(2-oxa-7-azaspiro[4.4]nonan-7-yl)pyrimido[5,4-d]pyrimidin-4-amine | 516.2 | 1H NMR (400 MHz, CDCl3) δ 9.10 (s, 1H), 8.69 (s, 1H), 8.60 (s, 1H), 8.52 (dd, J = 7.4, 0.8 Hz, 1H), 8.31-8.26 (m, 1H), 8.24 (s, 1H), 7.91-7.84 (m, 1H), 7.27 (d, J = 8.8 Hz, 1H), 6.92 (dd, J = 7.4, 2.6 Hz, 1H), 6.88 (dd, J = 2.6, 0.8 Hz, 1H), 4.05-3.97 (m, 2H), 3.82-3.70 (m, 6H), 2.22-1.95 (m, 4H) |
| 357 (Ex. 114) | rac-(R)-N-(3-methyl-4-((1-methyl-1H-benzo[d]imidazol-5-yl)oxy)phenyl)-6-(2,6-dioxa-9-azaspiro[4.5]decan-9-yl)pyrimido[5,4-d]pyrimidin-4-amine | 525.3 | 1H NMR (400 MHz, CDCl3) δ 9.34 (s, 1H), 9.17 (s, 1H), 9.13 (s, 1H), 8.63 (s, 1H), 7.79-7.70 (m, 2H), 7.58 (d, J = 9.1 Hz, 1H), 7.37 (dd, J = 9.0, 2.3 Hz, 1H), 7.21 (d, J = 2.3 Hz, 1H), 7.04 (d, J = 8.6 Hz, 1H), 4.09 (s, 3H), 4.05-3.94 (m, 7H), 3.92-3.77 (m, 3H), 2.28 (s, 3H), 2.22-2.06 (m, 2H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 358 (Ex. 133) | (R)-2-(1-(8-((3-chloro-4-((1-methyl-1H-benzo[d]imidazol-5-yl)oxy)phenyl)amino)pyrimido[5,4-d]pyrimidin-2-yl)pyrrolidin-3-yl)acetonitrile | 512.3 | $^1$H NMR (400 MHz, CDCl$_3$) δ 9.07 (s, 1H), 8.56 (s, 1H), 8.55 (s, 1H), 8.15 (d, J = 2.6 Hz, 1H), 7.86 (s, 1H), 7.66 (dd, J = 8.9, 2.6 Hz, 1H), 7.40-7.32 (m, 2H), 7.10 (dd, J = 8.7, 2.3 Hz, 1H), 7.00 (d, J = 8.8 Hz, 1H), 4.06-4.02 (m, 1H), 3.95-3.91 (m, 1H), 3.85 (s, 3H), 3.80-3.68 (m, 1H), 3.51 (dd, J = 11.5, 7.3 Hz, 1H), 2.84-2.72 (m, 1H), 2.68-2.56 (m, 2H), 2.44-2.33 (m, 1H), 2.06-1.92 (m, 1H) |
| 359 (Ex. 134) | (S)-N-(4-([1,2,4]triazolo[1,5-a]pyridin-7-yloxy)-3-methylphenyl)-6-(3-(difluoromethyl)pyrrolidin-1-yl)pyrimido[5,4-d]pyrimidin-4-amine | 490.2 | $^1$H NMR (400 MHz, CDCl$_3$) δ 9.10 (s, 1H), 8.65 (s, 1H), 8.59 (s, 1H), 8.50 (dd, J = 7.5, 0.8 Hz, 1H), 8.22 (s, 1H), 7.90-7.81 (m, 2H), 7.13 (d, J = 8.5 Hz, 1H), 6.89 (dd, J = 7.4, 2.6 Hz, 1H), 6.85 (dd, J = 2.6, 0.8 Hz, 1H), 5.91 (td, J = 56.6, 4.8 Hz, 1H), 4.01-3.89 (m, 2H), 3.84-3.73 (m, 2H), 3.01-2.83 (m, 1H), 2.38-2.26 (m, 1H), 2.27 (s, 3H), 2.24-2.11 (m, 1H) |
| 360 (Ex. 131) | (S)-N8-(4-([1,2,4]triazolo[1,5-a]pyridin-7-yloxy)-3-chlorophenyl)-N2-methyl-N2-(tetrahydro-2H-pyran-3-yl)pyrimido[5,4-d]pyrimidine-2,8-diamine | 504.2 | $^1$H NMR (400 MHz, CDCl$_3$) δ 9.11 (s, 1H), 8.67 (s, 1H), 8.61 (s, 1H), 8.52 (dd, J = 7.4, 0.8 Hz, 1H), 8.30 (d, J = 2.6 Hz, 1H), 8.24 (s, 1H), 7.84 (dd, J = 8.7, 2.7 Hz, 1H), 7.27 (d, J = 8.8 Hz, 1H), 6.92 (dd, J = 7.4, 2.7 Hz, 1H), 6.89 (dd, J = 2.6, 0.8 Hz, 1H), 4.93 (s, 1H), 4.03-3.95 (m, 2H), 3.53 (t, J = 10.5 Hz, 1H), 3.47-3.34 (m, 1H), 3.24 (s, 3H), 2.10-1.79 (m, 4H) |
| 361 (Ex. 109) | (S)-N-(4-([1,2,4]triazolo[1,5-a]pyridin-7-yloxy)-3-methylphenyl)-6-(3-(difluoromethoxy)pyrrolidin-1-yl)pyrimido[5,4-d]pyrimidin-4-amine | 506.2 | $^1$H NMR (400 MHz, CDCl$_3$) δ 9.10 (s, 1H), 8.65 (s, 1H), 8.58 (s, 1H), 8.50 (dd, J = 7.4, 0.7 Hz, 1H), 8.22 (s, 1H), 7.89-7.80 (m, 2H), 7.13 (d, J = 8.5 Hz, 1H), 6.89 (dd, J = 7.4, 2.6 Hz, 1H), 6.85 (dd, J = 2.6, 0.7 Hz, 1H), 6.32 (t, J = 73.6 Hz, 1H), 5.10-5.05 (m, 1H), 4.09-3.80 (m, 4H), 2.33 (tq, J = 13.4, 4.8, 4.1 Hz, 2H), 2.27 (s, 3H) |
| 362 (Ex. 109) | N8-(4-([1,2,4]triazolo[1,5-a]pyridin-7-yloxy)-3-methylphenyl)-N2-(4,4-dimethyl-4,5-dihydrooxazol-2-yl)pyrimido[5,4-d]pyrimidine-2,8-diamine | 483.3 | $^1$H NMR (400 MHz, CDCl$_3$) δ 9.22 (s, 1H), 9.12 (s, 1H), 8.70 (s, 1H), 8.51-8.47 (m, 1H), 8.22 (s, 1H), 7.94 (d, J = 2.6 Hz, 1H), 7.85 (dd, J = 8.8, 2.7 Hz, 1H), 7.11 (d, J = 8.7 Hz, 1H), 6.91-6.83 (m, 2H), 4.25 (s, 2H), 2.62 (s, 6H), 2.26 (s, 3H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 363 (Ex. 111) | N-(3-methyl-4-((1-methyl-1H-benzo[d]imidazol-5-yl)oxy)phenyl)-6-((3aR,4S,7R,7aS)-octahydro-2H-4,7-epoxyisoindol-2-yl)pyrimido[5,4-d]pyrimidin-4-amine | 521.3 | $^1$H NMR (400 MHz, CDCl$_3$) δ 9.03 (s, 1H), 8.57 (s, 1H), 8.51 (s, 1H), 7.84 (s, 1H), 7.74 (dd, J = 2.7, 0.8 Hz, 1H), 7.65 (dd, J = 8.6, 2.7 Hz, 1H), 7.32 (dd, J = 5.5, 3.1 Hz, 2H), 7.05 (dd, J = 8.8, 2.3 Hz, 1H), 6.93 (d, J = 8.7 Hz, 1H), 4.51-4.46 (m, 2H), 4.17-4.01 (m, 2H), 3.84 (s, 3H), 3.56 (dd, J = 11.5, 3.7 Hz, 2H), 2.75-2.64 (m, 2H), 2.34 (s, 3H), 1.80-1.70 (m, 2H), 1.57-1.48 (m, 2H) |
| 364 (Ex. 111) | 2,2-dimethyl-3-(methyl(8-((3-methyl-4-((1-methyl-1H-benzo[d]imidazol-5-yl)oxy)phenyl)amino)pyrimido[5,4-d]pyrimidin-2-yl)amino)propan-1-ol | 499.3 | $^1$H NMR (400 MHz, CDCl$_3$) δ 9.03 (s, 1H), 8.55 (s, 1H), 7.84 (s, 1H), 7.75 (d, J = 2.6 Hz, 1H), 7.63 (dd, J = 8.7, 2.7 Hz, 1H), 7.36-7.28 (m, 2H), 7.06 (dd, J = 8.7, 2.4 Hz, 1H), 6.92 (d, J = 8.7 Hz, 1H), 4.69 (s, 1H), 3.85 (s, 3H), 3.59 (s, 2H), 3.34 (s, 3H), 3.20 (s, 2H), 2.34 (s, 3H), 1.03 (s, 6H) |
| 365 (Ex. 134) | (S)-1-(8-((4-([1,2,4]triazolo[1,5-a]pyridin-7-yloxy)-3-methylphenyl)amino)pyrimido[5,4-d]pyrimidin-2-yl)-3-methylpyrrolidin-3-ol | 470.2 | $^1$H NMR (400 MHz, CDCl$_3$) δ 9.04 (s, 1H), 8.62 (s, 1H), 8.55 (s, 1H), 8.49 (dd, J = 7.5, 0.8 Hz, 1H), 8.22 (s, 1H), 7.88-7.78 (m, 2H), 7.11 (d, J = 8.6 Hz, 1H), 6.88 (dd, J = 7.4, 2.6 Hz, 1H), 6.85 (dd, J = 2.6, 0.8 Hz, 1H), 3.93-3.81 (m, 3H), 2.26 (s, 3H), 2.17-2.05 (m, 3H), 1.58 (s, 3H) |
| 366 (Ex. 134) | (1r,3r)-3-((8-((4-([1,2,4]triazolo[1,5-a]pyridin-7-yloxy)-3-methylphenyl)amino)pyrimido[5,4-d]pyrimidin-2-yl)(methyl)amino)cyclobutan-1-ol | 470.3 | $^1$H NMR (400 MHz, CDCl$_3$) δ 9.07 (s, 1H), 8.64 (s, 1H), 8.56 (s, 1H), 8.50 (dd, J = 7.5, 0.7 Hz, 1H), 8.23 (s, 1H), 7.85 (d, J = 2.6 Hz, 1H), 7.85-7.78 (m, 1H), 7.12 (d, J = 8.6 Hz, 1H), 6.89 (dd, J = 7.4, 2.6 Hz, 1H), 6.85 (dd, J = 2.6, 0.7 Hz, 1H), 5.66-5.53 (m, 1H), 4.62-4.53 (m, 1H), 3.28 (s, 3H), 2.66-2.53 (m, 2H), 2.50-2.38 (m, 2H), 2.33 (s, 1H), 2.26 (s, 3H) |
| 367 (Ex. 131) | (S)-1-(8-((4-([1,2,4]triazolo[1,5-a]pyridin-7-yloxy)-3-chlorophenyl)amino)pyrimido[5,4-d]pyrimidin-2-yl)pyrrolidine-3-carbonitrile | 485.2 | $^1$H NMR (400 MHz, CDCl$_3$) δ 9.14 (s, 1H), 8.66 (s, 1H), 8.65 (s, 1H), 8.52 (dd, J = 7.5, 0.7 Hz, 1H), 8.29 (d, J = 2.6 Hz, 1H), 8.24 (s, 1H), 7.86 (dd, J = 8.8, 2.6 Hz, 1H), 7.28 (d, J = 8.7 Hz, 1H), 6.92 (dd, J = 7.4, 2.6 Hz, 1H), 6.88 (dd, J = 2.6, 0.7 Hz, 1H), 4.17-4.04 (m, 2H), 4.07-3.96 (m, 1H), 3.94-3.83 (m, 1H), 3.36 (p, J = 6.7 Hz, 1H), 2.59-2.41 (m, 2H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 368 (Ex. 131) | (R)-N8-(4-([1,2,4]triazolo[1,5-a]pyridin-7-yloxy)-3-chlorophenyl)-N2-methyl-N2-(tetrahydro-2H-pyran-3-yl)pyrimido[5,4-d]pyrimidine-2,8-diamine | 504.2 | ¹H NMR (400 MHz, CDCl₃) δ 9.11 (s, 1H), 8.68 (s, 1H), 8.61 (s, 1H), 8.52 (dd, J = 7.3, 0.8 Hz, 1H), 8.30 (d, J = 2.6 Hz, 1H), 8.25 (s, 1H), 7.84 (dd, J = 8.8, 2.6 Hz, 1H), 7.27 (d, J = 8.8 Hz, 1H), 6.92 (dd, J = 7.4, 2.6 Hz, 1H), 6.89 (dd, J = 2.6, 0.8 Hz, 1H), 4.93 (s, 1H), 4.03-3.95 (m, 2H), 3.53 (t, J = 10.6 Hz, 1H), 3.42 (td, J = 11.1, 3.0 Hz, 1H), 3.24 (s, 3H), 2.24-2.00 (m, 2H), 2.00-1.83 (m, 2H) |
| 369 (Ex. 134) | N-(4-([1,2,4]triazolo[1,5-a]pyridin-7-yloxy)-3-methylphenyl)-6-(6-oxa-1-azaspiro[3.3]heptan-1-yl)pyrimido[5,4-d]pyrimidin-4-amine | 468.2 | ¹H NMR (400 MHz, CDCl₃) δ 9.14 (s, 1H), 8.62 (s, 1H), 8.49 (d, J = 7.5 Hz, 1H), 8.22 (s, 1H), 7.89 (d, J = 2.7 Hz, 1H), 7.84 (dd, J = 8.7, 2.7 Hz, 1H), 7.11 (d, J = 8.6 Hz, 1H), 6.88 (dd, J = 7.4, 2.6 Hz, 1H), 6.83 (d, J = 2.6 Hz, 1H), 5.63 (d, J = 7.1 Hz, 2H), 4.84 (s, 2H), 3.49 (s, 1H), 2.70 (t, J = 7.2 Hz, 2H), 2.26 (s, 3H), 2.17 (s, 1H) |
| 370 (Ex. 134) | (S)-2-(1-(8-((4-([1,2,4]triazolo[1,5-a]pyridin-7-yloxy)-3-methylphenyl)amino)pyrimido[5,4-d]pyrimidin-2-yl)azetidin-2-yl)propan-2-ol | 484.3 | ¹H NMR (400 MHz, CDCl₃) δ 9.04 (s, 1H), 8.60 (s, 1H), 8.53-8.46 (m, 1H), 8.22 (s, 1H), 7.86 (d, J = 2.7 Hz, 1H), 7.80 (dd, J = 8.7, 2.7 Hz, 1H), 7.12 (d, J = 8.6 Hz, 1H), 6.89 (dd, J = 7.4, 2.6 Hz, 1H), 6.84 (d, J = 2.5 Hz, 1H), 5.72 (s, 1H), 4.58 (d, J = 3.0 Hz, 1H), 4.27-4.17 (m, 1H), 4.17-4.07 (m, 1H), 2.52-2.39 (m, 1H), 2.26 (s, 3H), 2.26-2.13 (m, 1H), 1.37 (s, 3H), 1.22 (s, 3H) |
| 371 (Ex. 114) | (R)-2-(1-(8-((3-methyl-4-((1-methyl-1H-benzo[d]imidazol-5-yl)oxy)phenyl)amino)pyrimido[5,4-d]pyrimidin-2-yl)pyrrolidin-2-yl)propan-2-ol | 511.3 | ¹H NMR (400 MHz, CDCl₃) δ 9.01 (s, 1H), 8.54 (s, 1H), 7.84 (s, 1H), 7.74 (d, J = 2.9 Hz, 1H), 7.64 (dd, J = 8.7, 2.7 Hz, 1H), 7.36-7.29 (m, 2H), 7.05 (dd, J = 8.8, 2.3 Hz, 1H), 6.92 (d, J = 8.7 Hz, 1H), 5.96 (s, 1H), 4.44-4.37 (m, 1H), 4.22-4.14 (m, 1H), 3.84 (s, 3H), 3.70-3.59 (m, 1H), 2.35 (s, 3H), 2.29-2.04 (m, 2H), 2.00-1.85 (m, 2H), 1.34 (s, 3H), 1.19 (s, 3H) |
| 372 (Ex. 134) | N8-(4-([1,2,4]triazolo[1,5-a]pyridin-7-yloxy)-3-methylphenyl)-N2-(2,2-difluoroethyl)-N2-methylpyrimido[5,4-d]pyrimidine-2,8-diamine | 464.3 | ¹H NMR (400 MHz, CDCl₃) δ 9.11 (s, 1H), 8.61 (s, 1H), 8.49 (dd, J = 7.5, 0.8 Hz, 1H), 8.22 (s, 1H), 7.91-7.78 (m, 2H), 7.26 (s, 1H), 7.13 (d, J = 8.6 Hz, 1H), 6.89 (dd, J = 7.4, 2.6 Hz, 1H), 6.84 (d, J = 2.3 Hz, 1H), 6.08 (d, J = 57.1 Hz, 1H), 4.13 (td, J = 13.8, 4.3 Hz, 2H), 3.43 (s, 3H), 2.26 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 373 (Ex. 109) | N-(4-([1,2,4]triazolo[1,5-a]pyridin-7-yloxy)-3-methylphenyl)-6-(6-oxa-2-azaspiro[3.4]octan-2-yl)pyrimido[5,4-d]pyrimidin-4-amine | 482.2 | 1H NMR (400 MHz, CDCl3) δ 9.08 (s, 1H), 8.63 (s, 1H), 8.59 (s, 1H), 8.50 (dd, J = 7.5, 0.7 Hz, 1H), 8.22 (s, 1H), 7.88-7.79 (m, 2H), 7.12 (d, J = 8.6 Hz, 1H), 6.89 (dd, J = 7.4, 2.6 Hz, 1H), 6.85 (dd, J = 2.6, 0.8 Hz, 1H), 4.28 (s, 4H), 4.00 (s, 2H), 3.94 (t, J = 7.0 Hz, 2H), 2.34-2.18 (m, 5H) |
| 374 (Ex. 134) | rac-(R)-N-(4-([1,2,4]triazolo[1,5-a]pyridin-7-yloxy)-3-methylphenyl)-6-(6-oxa-1-azaspiro[3.4]octan-1-yl)pyrimido[5,4-d]pyrimidin-4-amine | 482.3 | 1H NMR (400 MHz, CDCl3) δ 9.17 (s, 1H), 9.06 (s, 1H), 8.58 (s, 1H), 8.48 (d, J = 7.5 Hz, 1H), 8.22 (s, 1H), 7.96 (s, 1H), 7.82 (dd, J = 8.7, 2.7 Hz, 1H), 7.11 (d, J = 8.7 Hz, 1H), 6.88 (dd, J = 7.4, 2.6 Hz, 1H), 6.84 (dd, J = 2.6, 0.8 Hz, 1H), 4.66 (s, 1H), 4.39 (d, J = 9.3 Hz, 1H), 4.24-3.93 (m, 3H), 3.77 (s, 1H), 2.84 (ddd, J = 13.1, 8.0, 6.9 Hz, 1H), 2.69-2.50 (m, 1H), 2.57 (s, 1H), 2.26 (s, 4H) |
| 375 (Ex. 111) | rac-(S)-N-(3-methyl-4-((1-methyl-1H-benzo[d]imidazol-5-yl)oxy)phenyl)-6-(1-oxa-6-azaspiro[3.4]octan-6-yl)pyrimido[5,4-d]pyrimidin-4-amine | 495.3 | 1H NMR (400 MHz, CDCl3) δ 9.05 (s, 1H), 8.58 (s, 1H), 8.53 (s, 1H), 7.84 (s, 1H), 7.75 (s, 1H), 7.66 (dd, J = 9.0, 2.6 Hz, 1H), 7.36-7.29 (m, 2H), 7.05 (dd, J = 8.8, 2.2 Hz, 1H), 6.93 (d, J = 8.7 Hz, 1H), 4.61 (t, J = 7.7 Hz, 2H), 4.19 (s, 1H), 3.93-3.86 (m, 1H), 3.84 (s, 3H), 3.83-3.71 (m, 3H), 2.88-2.84 (m, 1H), 2.82-2.72 (m, 1H), 2.63-2.46 (m, 1H), 2.35 (s, 3H), 2.26-2.14 (m, 1H), 1.75 (s, 1H) |
| 376 (Ex. 132) | rac-N-(4-([1,2,4]triazolo[1,5-a]pyridin-7-yloxy)-3-chlorophenyl)-6-((3aS,6aS)-hexahydro-1H-furo[3,4-b]pyrrol-1-yl)pyrimido[5,4-d]pyrimidin-4-amine | 502.2 | 1H NMR (400 MHz, CDCl3) δ 9.07 (s, 1H), 8.71-8.59 (m, 2H), 8.52 (dd, J = 7.4, 0.7 Hz, 1H), 8.29 (d, J = 2.6 Hz, 1H), 8.24 (s, 1H), 7.83 (d, J = 8.8 Hz, 1H), 7.27 (d, J = 8.8 Hz, 1H), 6.92 (dd, J = 7.5, 2.6 Hz, 1H), 6.88 (dd, J = 2.6, 0.7 Hz, 1H), 4.77 (s, 1H), 4.50 (t, J = 6.5 Hz, 1H), 4.36-4.22 (m, 2H), 4.05 (t, J = 6.9 Hz, 1H), 4.00-3.95 (m, 1H), 3.80-3.75 (m, 1H), 3.74-3.65 (m, 1H), 2.30-2.19 (m, 1H), 2.06-1.91 (m, 1H) |
| 377 (Ex. 132) | N-(4-([1,2,4]triazolo[1,5-a]pyridin-7-yloxy)-3-chlorophenyl)-6-(hexahydro-1H-furo[3,4-b]pyrrol-1-yl)pyrimido[5,4-d]pyrimidin-4-amine | 502.2 | 1H NMR (400 MHz, CDCl3) δ 9.07 (s, 1H), 8.65-8.59 (m, 2H), 8.52 (dd, J = 7.4, 0.8 Hz, 1H), 8.29 (d, J = 2.6 Hz, 1H), 8.24 (s, 1H), 7.83 (d, J = 8.5 Hz, 1H), 7.26 (d, J = 8.7 Hz, 1H), 6.92 (dd, J = 7.5, 2.6 Hz, 1H), 6.88 (dd, J = 2.6, 0.7 Hz, 1H), 4.50 (t, J = 6.5 Hz, 1H), 4.36-4.21 (m, 2H), 4.05 (t, J = 6.9 Hz, 1H), 4.00-3.91 (m, 1H), 3.77 (s, 1H), 3.74-3.65 (m, 1H), 2.83-2.78 (m, 1H), 2.30-2.13 (m, 1H), 2.06-1.91 (m, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 378 (Ex. 111) | rac-6-((1S,5R)-3-oxa-6-azabicyclo[3.2.0]heptan-6-yl)-N-(3-methyl-4-((1-methyl-1H-benzo[d]imidazol-5-yl)oxy)phenyl)pyrimido[5,4-d]pyrimidin-4-amine | 481.2 | ¹H NMR (400 MHz, CDCl₃) δ 9.02 (s, 1H), 8.53 (s, 1H), 8.52-8.46 (m, 1H), 7.84 (s, 1H), 7.72 (d, J = 2.7 Hz, 1H), 7.62 (dd, J = 8.7, 2.8 Hz, 1H), 7.33 (dd, J = 6.1, 0.6 Hz, 1H), 7.31 (s, 1H), 7.05 (dd, J = 8.8, 2.2 Hz, 1H), 6.92 (d, J = 8.7 Hz, 1H), 5.12 (dd, J = 6.4, 3.2 Hz, 1H), 4.50-4.43 (m, 1H), 4.33 (t, J = 8.4 Hz, 1H), 4.14 (d, J = 9.8 Hz, 1H), 3.98 (dd, J = 9.2, 4.2 Hz, 1H), 3.84 (s, 3H), 3.62 (dd, J = 9.9, 5.0 Hz, 1H), 3.50 (dd, J = 10.6, 3.3 Hz, 1H), 3.38-3.27 (m, 1H), 2.34 (s, 3H) |
| 379 (Ex. 109) | N-(4-([1,2,4]triazolo[1,5-a]pyridin-7-yloxy)-3-methylphenyl)-6-(azetidin-1-yl)pyrimido[5,4-d]pyrimidin-4-amine | 426.2 | ¹H NMR (400 MHz, CDCl₃) δ 9.06 (s, 1H), 8.65 (s, 1H), 8.57 (s, 1H), 8.49 (dd, J = 7.5, 0.7 Hz, 1H), 8.22 (s, 1H), 7.87 (d, J = 2.7 Hz, 1H), 7.83 (dd, J = 8.6, 2.7 Hz, 1H), 7.12 (d, J = 8.6 Hz, 1H), 6.89 (dd, J = 7.4, 2.6 Hz, 1H), 6.85 (dd, J = 2.6, 0.7 Hz, 1H), 4.33 (t, J = 7.4 Hz, 4H), 2.55-2.43 (m, 2H), 2.26 (s, 3H) |
| 380 (Ex. 114) | N-(3-methyl-4-((1-methyl-1H-benzo[d]imidazol-5-yl)oxy)phenyl)-6-((3aR,4R,7S,7aS)-octahydro-2H-4,7-epoxyisoindol-2-yl)pyrimido[5,4-d]pyrimidin-4-amine | 521.3 | ¹H NMR (400 MHz, CDCl₃) δ 9.02 (s, 1H), 8.57 (s, 1H), 8.51 (s, 1H), 7.84 (s, 1H), 7.74 (dd, J = 2.7, 0.8 Hz, 1H), 7.65 (dd, J = 8.6, 2.7 Hz, 1H), 7.35-7.29 (m, 2H), 7.05 (dd, J = 8.8, 2.2 Hz, 1H), 6.93 (d, J = 8.7 Hz, 1H), 4.51-4.45 (m, 2H), 4.17-4.01 (m, 2H), 3.84 (s, 3H), 3.56 (dd, J = 11.6, 3.7 Hz, 2H), 2.75-2.64 (m, 2H), 2.34 (s, 3H), 1.81-1.70 (m, 2H), 1.58-1.48 (m, 2H) |
| 381 (Ex. 114) | (S)-N8-(4-([1,2,4]triazolo[1,5-a]pyridin-7-yloxy)-3-methylphenyl)-N2-methyl-N2-(tetrahydrofuran-3-yl)pyrimido[5,4-d]pyrimidine-2,8-diamine | 470.2 | ¹H NMR (400 MHz, CDCl₃) δ 9.08 (s, 1H), 8.91 (s, 1H), 8.58 (s, 1H), 8.50 (dd, J = 7.4, 0.7 Hz, 1H), 8.22 (s, 1H), 7.92 (d, J = 2.6 Hz, 1H), 7.91-7.79 (m, 1H), 7.13 (dd, J = 8.6, 3.1 Hz, 1H), 6.92-6.85 (m, 1H), 6.85 (dd, J = 2.6, 0.7 Hz, 1H), 4.27-4.17 (m, 1H), 4.10-4.04 (m, 1H), 3.99-3.90 (m, 1H), 3.90-3.76 (m, 1H), 3.36 (s, 1H), 3.29 (s, 2H), 2.51-2.31 (m, 1H), 2.27 (s, 3H), 2.10 (s, 1H), 2.21-2.00 (m, 1H) |
| 382 (Ex. 134) | N-(4-([1,2,4]triazolo[1,5-a]pyridin-7-yloxy)-3-methylphenyl)-6-(2-oxa-5-azabicyclo[4.1.0]heptan-5-yl)pyrimido[5,4-d]pyrimidin-4-amine | 468.2 | ¹H NMR (400 MHz, CDCl₃) δ 9.18 (s, 1H), 8.69 (s, 1H), 8.62 (s, 1H), 8.50 (dd, J = 7.4, 0.7 Hz, 1H), 8.22 (s, 1H), 7.86 (d, J = 2.7 Hz, 1H), 7.82 (dd, J = 8.6, 2.7 Hz, 1H), 7.13 (d, J = 8.5 Hz, 1H), 6.89 (dd, J = 7.4, 2.6 Hz, 1H), 6.85 (dd, J = 2.7, 0.7 Hz, 1H), 4.03-3.85 (m, 3H), 3.71-3.63 (m, 1H), 3.21-3.15 (m, 1H), 2.27 (s, 3H), 1.14 (q, J = 6.8 Hz, 1H), 0.78-0.70 (m, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 383 (Ex. 132) | N-(4-([1,2,4]triazolo[1,5-a]pyridin-7-yloxy)-3-chlorophenyl)-6-(8-oxa-3-azabicyclo[3.2.1]octan-3-yl)pyrimido[5,4-d]pyrimidin-4-amine | 502.2 | ¹H NMR (400 MHz, CDCl$_3$) δ 9.09 (s, 1H), 8.62 (s, 1H), 8.61 (s, 1H), 8.52 (dd, J = 7.5, 0.7 Hz, 1H), 8.27 (d, J = 2.6 Hz, 1H), 8.24 (s, 1H), 7.88 (dd, J = 8.8, 2.6 Hz, 1H), 7.27 (d, J = 8.8 Hz, 1H), 6.92 (dd, J = 7.4, 2.6 Hz, 1H), 6.87 (dd, J = 2.6, 0.7 Hz, 1H), 4.56 (dd, J = 4.8, 2.4 Hz, 2H), 4.46-4.39 (m, 2H), 3.38 (dd, J = 13.1, 2.6 Hz, 2H), 2.12-1.87 (m, 2H), 1.90-1.80 (m, 2H) |
| 384 (Ex. 131) | rac-N-(4-([1,2,4]triazolo[1,5-a]pyridin-7-yloxy)-3-chlorophenyl)-6-((1S,6R)-2-oxa-5-azabicyclo[4.1.0]heptan-5-yl)pyrimido[5,4-d]pyrimidin-4-amine | 488.2 | ¹H NMR (400 MHz, CDCl$_3$) δ 9.20 (s, 1H), 8.72 (s, 1H), 8.65 (s, 1H), 8.52 (dd, J = 7.5, 0.7 Hz, 1H), 8.27 (d, J = 2.6 Hz, 1H), 8.24 (s, 1H), 7.86 (dd, J = 8.8, 2.6 Hz, 1H), 7.27 (d, J = 8.8 Hz, 1H), 6.92 (dd, J = 7.4, 2.6 Hz, 1H), 6.88 (dd, J = 2.7, 0.7 Hz, 1H), 3.99-3.88 (m, 3H), 3.71-3.63 (m, 2H), 3.18 (s, 1H), 1.18-1.10 (m, 1H), 0.74 (s, 1H) |
| 385 (Ex. 134) | 1-(((8-((4-([1,2,4]triazolo[1,5-a]pyridin-7-yloxy)-3-methylphenyl)amino)pyrimido[5,4-d]pyrimidin-2-yl)(methyl)amino)methyl)cyclopropan-1-ol | 470.2 | ¹H NMR (400 MHz, CDCl$_3$) δ 9.00 (s, 1H), 8.61-8.57 (m, 1H), 8.56 (s, 1H), 8.49 (dd, J = 7.4, 0.7 Hz, 1H), 8.22 (s, 1H), 7.83 (d, J = 2.7 Hz, 1H), 7.79 (dd, J = 8.5, 2.7 Hz, 1H), 7.11 (d, J = 8.6 Hz, 1H), 6.88 (dd, J = 7.4, 2.6 Hz, 1H), 6.84 (dd, J = 2.7, 0.8 Hz, 1H), 4.01 (s, 2H), 3.71 (s, 1H), 3.42 (s, 3H), 2.25 (s, 3H), 0.95-0.81 (m, 2H), 0.85-0.71 (m, 2H) |
| 386 (Ex. 111) | rac-(R)-N-(3-methyl-4-((1-methyl-1H-benzo[d]imidazol-5-yl)oxy)phenyl)-6-(1-oxa-6-azaspiro[3.5]nonan-6-yl)pyrimido[5,4-d]pyrimidin-4-amine | 509.3 | ¹H NMR (400 MHz, CDCl$_3$) δ 9.04 (s, 1H), 8.52 (s, 1H), 8.51 (s, 1H), 7.84 (s, 1H), 7.77-7.71 (m, 1H), 7.64 (dd, J = 8.6, 2.7 Hz, 1H), 7.36-7.30 (m, 1H), 7.31 (s, 1H), 7.06 (dd, J = 8.7, 2.3 Hz, 1H), 6.93 (d, J = 8.7 Hz, 1H), 4.71-4.61 (m, 1H), 4.61-4.51 (m, 1H), 4.34 (d, J = 13.1 Hz, 1H), 4.08-3.99 (m, 1H), 3.93 (d, J = 13.1 Hz, 1H), 3.84 (s, 3H), 3.77-3.66 (m, 1H), 2.54-2.32 (m, 2H), 2.35 (s, 3H), 2.05-2.00 (m, 1H), 2.04-1.92 (m, 1H), 1.96-1.83 (m, 1H), 1.71-1.57 (m, 1H) |
| 387 (Ex. 131) | (R)-1-(8-((4-([1,2,4]triazolo[1,5-a]pyridin-7-yloxy)-3-chlorophenyl)amino)pyrimido[5,4-d]pyrimidin-2-yl)pyrrolidine-3-carbonitrile | 485.2 | ¹H NMR (400 MHz, CDCl$_3$) δ 9.14 (s, 1H), 8.66 (s, 1H), 8.65 (s, 1H), 8.52 (dd, J = 7.5, 0.7 Hz, 1H), 8.29 (d, J = 2.6 Hz, 1H), 8.24 (s, 1H), 7.87 (dd, J = 8.8, 2.6 Hz, 1H), 7.28 (d, J = 8.8 Hz, 1H), 6.92 (ddd, J = 7.4, 2.6, 0.5 Hz, 1H), 6.88 (dd, J = 2.6, 0.8 Hz, 1H), 4.17-4.04 (m, 2H), 4.07-3.96 (m, 1H), 3.94-3.83 (m, 1H), 3.36 (p, J = 6.7 Hz, 1H), 2.59-2.41 (m, 2H), 1.59 (s, 2H) |

TABLE 1-continued

| Example No. (Method) | Structure; IUPAC name | LCMS M+1 | $^1$H NMR (ppm); $^{19}$F NMR (ppm); optical rotation; Chiral HPLC/SFC conditions |
|---|---|---|---|
| 388 (Ex. 111) | rac-(S)-6-(2-(difluoromethyl)azetidin-1-yl)-N-(3-methyl-4-((1-methyl-1H-benzo[d]imidazol-5-yl)oxy)phenyl)pyrimido[5,4-d]pyrimidin-4-amine | 489.2 | $^1$H NMR (400 MHz, CDCl$_3$) δ 9.04 (s, 1H), 8.56 (s, 1H), 8.52 (s, 1H), 7.83 (s, 1H), 7.71 (d, J = 2.7 Hz, 1H), 7.62 (dd, J = 8.7, 2.7 Hz, 1H), 7.35-7.22 (m, 2H), 7.04 (dd, J = 8.6, 2.3 Hz, 1H), 6.91 (d, J = 8.7 Hz, 1H), 6.35 (t, J = 56.5, 2.5 Hz, 1H), 4.85-4.61 (m, 1H), 4.34-4.16 (m, 2H), 3.83 (s, 3H), 2.73-2.60 (m, 1H), 2.58-2.45 (m, 1H), 2.34 (s, 3H) |
| 389 (Ex. 131) | N-(4-([1,2,4]triazolo[1,5-a]pyridin-7-yloxy)-3-chlorophenyl)-6-((1R,4R)-2-oxa-5-azabicyclo[2.2.2]octan-5-yl)pyrimido[5,4-d]pyrimidin-4-amine | 502.2 | $^1$H NMR (400 MHz, CDCl$_3$) δ 9.07 (s, 1H), 8.71 (s, 1H), 8.60 (s, 1H), 8.52 (dd, J = 7.4, 0.7 Hz, 1H), 8.28 (s, 1H), 8.24 (s, 1H), 7.86 (d, J = 9.3 Hz, 1H), 7.26 (d, J = 6.6 Hz, 1H), 6.92 (dd, J = 7.4, 2.6 Hz, 1H), 6.89 (s, 1H), 4.22-4.18 (m, 2H), 3.87-3.77 (m, 1H), 2.33-2.03 (m, 6H), 1.84-1.80 (m, 1H) |
| 390 (Ex. 134) | rac-(S)-N-(4-([1,2,4]triazolo[1,5-a]pyridin-7-yloxy)-3-methylphenyl)-6-(2-(difluoromethyl)azetidin-1-yl)pyrimido[5,4-d]pyrimidin-4-amine | 476.2 | $^1$H NMR (400 MHz, CDCl$_3$) δ 9.09 (s, 1H), 8.63 (d, J = 1.9 Hz, 2H), 8.51 (d, J = 7.4 Hz, 1H), 8.24 (s, 1H), 7.85 (d, J = 2.7 Hz, 1H), 7.81 (dd, J = 8.6, 2.7 Hz, 1H), 7.13 (d, J = 8.6 Hz, 1H), 6.89 (dd, J = 7.4, 1.8 Hz, 1H), 6.85 (s, 1H), 6.56-6.16 (m, 1H), 4.86-4.72 (m, 1H), 4.34-4.19 (m, 2H), 2.76-2.62 (m, 1H), 2.61-2.48 (m, 1H), 2.27 (s, 3H) |
| 391 (Ex. 136) | rac-(S)-7-(8-((3-methyl-4-((1-methyl-1H-benzo[d]imidazol-5-yl)oxy)phenyl)amino)pyrimido[5,4-d]pyrimidin-2-yl)-2-oxa-7-azaspiro[4.4]nonan-8-one | 523.3 | $^1$H NMR (400 MHz, CDCl$_3$) δ 9.05 (s, 1H), 8.55 (s, 1H), 8.55 (s, 1H), 7.84 (s, 1H), 7.72 (dd, J = 2.8, 0.8 Hz, 1H), 7.62 (dd, J = 8.7, 2.8 Hz, 1H), 7.32 (dd, J = 5.5, 3.1 Hz, 2H), 7.05 (dd, J = 8.8, 2.2 Hz, 1H), 6.92 (d, J = 8.7 Hz, 1H), 4.57 (d, J = 8.9 Hz, 2H), 4.13 (d, J = 8.8 Hz, 2H), 3.85 (s, 3H), 3.41 (d, J = 7.3 Hz, 2H), 2.93 (s, 3H), 2.50 (t, J = 6.9 Hz, 2H) |
| 392 (Ex. 115) | (R)-1-(8-((2-fluoro-3-methyl-4-((1-methyl-1H-benzo[d]imidazol-5-yl)oxy)phenyl)amino)pyrimido[5,4-d]pyrimidin-2-yl)pyrrolidin-3-ol | 487.3 | $^1$H NMR (400 MHz, (CD$_3$)$_2$SO) δ 9.45 (s, 1H), 9.19 (d, J = 3.0 Hz, 1H), 8.67 (s, 1H), 8.01 (d, J = 8.9 Hz, 1H), 7.62 (t, J = 8.7 Hz, 1H), 7.47-7.37 (m, 2H), 6.92 (dd, J = 8.9, 1.4 Hz, 1H), 4.55-4.51 (m, 1H), 4.10 (s, 3H), 3.94-3.69 (m, 4H), 2.25 (d, J = 1.9 Hz, 3H), 2.21-2.08 (m, 1H), 2.08-1.99 (m, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 393 (Ex. 133) | (1R,5S,6r)-3-(8-((3-chloro-4-((1-methyl-1H-benzo[d]imidazol-5-yl)oxy)phenyl)amino)pyrimido[5,4-d]pyrimidin-2-yl)-3-azabicyclo[3.1.0]hexane-6-carbonitrile | 510.2 | 1H NMR (400 MHz, CDCl3) δ 9.06 (s, 1H), 8.58 (s, 1H), 8.50 (s, 1H), 8.14 (d, J = 2.6 Hz, 1H), 7.87 (s, 1H), 7.63 (dd, J = 8.8, 2.7 Hz, 1H), 7.44-7.33 (m, 2H), 7.11 (dd, J = 8.7, 2.3 Hz, 1H), 7.00 (d, J = 8.8 Hz, 1H), 4.22 (d, J = 12.0 Hz, 2H), 3.86 (s, 3H), 3.74 (dt, J = 12.0, 1.7 Hz, 2H), 3.13-2.88 (m, 1H), 2.46-2.40 (m, 2H) |
| 394 (Ex. 114) | N-(3-methyl-4-((1-methyl-1H-benzo[d]imidazol-5-yl)oxy)phenyl)-6-(1-oxa-7-azaspiro[3.5]nonan-7-yl)pyrimido[5,4-d]pyrimidin-4-amine | 509.3 | 1H NMR (400 MHz, CDCl3) δ 9.02 (s, 1H), 8.52 (s, 1H), 8.49 (s, 1H), 7.84 (s, 1H), 7.74 (dd, J = 2.7, 0.8 Hz, 1H), 7.65 (dd, J = 8.6, 2.7 Hz, 1H), 7.37-7.29 (m, 2H), 7.06 (dd, J = 8.6, 2.4 Hz, 1H), 6.93 (d, J = 8.7 Hz, 1H), 4.61 (t, J = 7.8 Hz, 2H), 4.18-4.07 (m, 2H), 3.94-3.83 (m, 2H), 3.85 (s, 3H), 2.48 (t, J = 7.8 Hz, 2H), 2.35 (s, 3H), 2.15-2.02 (m, 2H), 1.96-1.85 (m, 2H) |
| 395 (Ex. 134) | (R)-N-(4-([1,2,4]triazolo[1,5-a]pyridin-7-yloxy)-3-methylphenyl)-6-(3-methoxypyrrolidin-1-yl)pyrimido[5,4-d]pyrimidin-4-amine | 470.3 | 1H NMR (400 MHz, CDCl3) δ 9.09 (s, 1H), 8.68 (s, 1H), 8.57 (s, 1H), 8.49 (dd, J = 7.4, 0.8 Hz, 1H), 8.22 (s, 1H), 7.89-7.80 (m, 2H), 7.12 (d, J = 8.6 Hz, 1H), 6.89 (dd, J = 7.4, 2.6 Hz, 1H), 6.86 (dd, J = 2.6, 0.8 Hz, 1H), 4.17 (s, 1H), 3.97-3.87 (m, 3H), 3.85-3.74 (m, 2H), 3.42 (s, 3H), 2.27 (s, 3H), 2.23-2.11 (m, 1H) |
| 396 (Ex. 132) | N8-(4-([1,2,4]triazolo[1,5-a]pyridin-7-yloxy)-3-chlorophenyl)-N2,N2-dimethylpyrimido[5,4-d]pyrimidine-2,8-diamine | 534.2 | 1H NMR (400 MHz, CDCl3) δ 9.09 (s, 1H), 8.70 (s, 1H), 8.59 (s, 1H), 8.52 (dd, J = 7.4, 0.8 Hz, 1H), 8.28 (d, J = 2.6 Hz, 1H), 8.24 (s, 1H), 7.86 (dd, J = 8.8, 2.6 Hz, 1H), 7.26 (d, J = 8.8 Hz, 1H), 6.92 (dd, J = 7.4, 2.6 Hz, 1H), 6.88 (dd, J = 2.6, 0.8 Hz, 1H), 3.36 (s, 6H) |
| 397 (Ex. 40) | (R)-2-(1-(8-((3-methyl-4-((1-methyl-1H-benzo[d]imidazol-5-yl)oxy)phenyl)amino)pyrimido[5,4-d]pyrimidin-2-yl)azetidin-2-yl)propan-2-ol | 497.2 | 1H NMR (400 MHz, CD3OD) δ 8.33 (s, 1H), 8.08 (s, 1H), 7.81-7.75 (m, 1H), 7.70 (d, J = 9.2 Hz, 1H), 7.65 (dd, J = 8.7, 2.7 Hz, 1H), 7.51 (d, J = 8.8 Hz, 1H), 7.13-7.07 (m, 2H), 7.05 (dd, J = 8.8, 2.3 Hz, 1H), 6.89 (d, J = 8.7 Hz, 1H), 4.80 (t, J = 7.6 Hz, 1H), 4.04-3.90 (m, 2H), 3.89 (s, 3H), 2.58-2.45 (m, 1H), 2.28 (s, 3H), 2.08-1.94 (m, 1H), 1.48 (s, 3H), 1.17 (s, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 398 (Ex. 131) | N-(4-([1,2,4]triazolo[1,5-a]pyridin-7-yloxy)-3-chlorophenyl)-6-(4-oxa-7-azaspiro[2.5]octan-7-yl)pyrimido[5,4-d]pyrimidin-4-amine | 502.2 | ¹H NMR (400 MHz, CDCl₃) δ 9.08 (s, 1H), 8.61 (s, 1H), 8.58 (s, 1H), 8.52 (dd, J = 7.5, 0.7 Hz, 1H), 8.28-8.22 (m, 2H), 7.86 (dd, J = 8.8, 2.6 Hz, 1H), 7.27 (d, J = 8.8 Hz, 1H), 6.92 (dd, J = 7.4, 2.6 Hz, 1H), 6.87 (dd, J = 2.6, 0.7 Hz, 1H), 4.10-4.03 (m, 2H), 3.98-3.89 (m, 4H), 0.94-0.82 (m, 2H), 0.79-0.67 (m, 2H) |
| 399 (Ex. 131) | N-(4-([1,2,4]triazolo[1,5-a]pyridin-7-yloxy)-3-chlorophenyl)-6-((3aR,4S,7R,7aS)-octahydro-2H-4,7-epoxyisoindol-2-yl)pyrimido[5,4-d]pyrimidin-4-amine | 528.2 | ¹H NMR (400 MHz, CDCl₃) δ 9.07 (s, 1H), 8.70 (s, 1H), 8.58 (s, 1H), 8.52 (dd, J = 7.4, 0.8 Hz, 1H), 8.26 (d, J = 2.6 Hz, 1H), 8.24 (s, 1H), 7.88 (dd, J = 8.8, 2.6 Hz, 1H), 7.26 (d, J = 8.7 Hz, 1H), 6.92 (dd, J = 7.4, 2.6 Hz, 1H), 6.89 (dd, J = 2.6, 0.8 Hz, 1H), 4.53-4.47 (m, 2H), 4.14-4.04 (m, 2H), 3.59 (dd, J = 11.8, 3.6 Hz, 2H), 2.77-2.66 (m, 2H), 1.82-1.72 (m, 2H), 1.62-1.49 (m, 2H) |
| 400 (Ex. 134) | (R)-N-(4-([1,2,4]triazolo[1,5-a]pyridin-7-yloxy)-3-methylphenyl)-6-(3-(difluoromethyl)pyrrolidin-1-yl)pyrimido[5,4-d]pyrimidin-4-amine | 490.2 | ¹H NMR (400 MHz, CDCl₃) δ 9.10 (s, 1H), 8.65 (s, 1H), 8.59 (s, 1H), 8.50 (dd, J = 7.5, 0.7 Hz, 1H), 8.22 (s, 1H), 7.90-7.81 (m, 2H), 7.13 (d, J = 8.4 Hz, 1H), 6.89 (dd, J = 7.5, 2.6 Hz, 1H), 6.85 (dd, J = 2.6, 0.7 Hz, 1H), 6.12-5.69 (m, 1H), 4.01-3.89 (m, 2H), 3.83-3.72 (m, 2H), 2.97-2.83 (m, 1H), 2.38-2.26 (m, 1H), 2.27 (s, 3H), 2.24-2.13 (m, 1H) |
| 401 (Ex. 111) | (1R,5S,6r-3-(8-((3-methyl-4-((1-methyl-1H-benzo[d]imidazol-5-yl)oxy)phenyl)amino)pyrimido[5,4-d]pyrimidin-2-yl)-3-azabicyclo[3.1.0]hexane-6-carbonitrile | 490.3 | ¹H NMR (400 MHz, CDCl₃) δ 9.05 (s, 1H), 8.56 (s, 1H), 8.49 (s, 1H), 7.85 (s, 1H), 7.73 (d, J = 2.9 Hz, 1H), 7.63 (dd, J = 8.7, 2.7 Hz, 1H), 7.37-7.28 (m, 2H), 7.07 (dd, J = 8.7, 2.3 Hz, 1H), 6.93 (d, J = 8.7 Hz, 1H), 4.22 (d, J = 11.9 Hz, 2H), 3.85 (s, 3H), 3.80-3.68 (m, 2H), 2.47-2.37 (m, 2H), 2.35 (s, 3H), 1.39 (t, J = 3.4 Hz, 1H) |
| 402 (Ex. 114) | N2-methyl-N8-(3-methyl-4-((1-methyl-1H-benzo[d]imidazol-5-yl)oxy)phenyl)-N2-(oxetan-3-ylmethyl)pyrimido[5,4-d]pyrimidine-2,8-diamine | 483.3 | ¹H NMR (400 MHz, CDCl₃) δ 9.04 (s, 1H), 8.53 (d, J = 3.4 Hz, 2H), 7.84 (s, 1H), 7.73 (dd, J = 2.7, 0.8 Hz, 1H), 7.62 (dd, J = 8.7, 2.7 Hz, 1H), 7.36-7.29 (m, 2H), 7.05 (dd, J = 8.7, 2.3 Hz, 1H), 6.93 (d, J = 8.7 Hz, 1H), 4.85 (dd, J = 7.7, 6.1 Hz, 2H), 4.60 (t, J = 6.1 Hz, 2H), 4.18-4.12 (m, 2H), 3.84 (s, 3H), 3.51-3.40 (m, 1H), 3.31 (s, 3H), 2.34 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 403 (Ex. 109) | N8-(4-([1,2,4]triazolo[1,5-a]pyridin-7-yloxy)-3-methylphenyl)-N2-methyl-N2-(oxetan-3-yl)pyrimido[5,4-d]pyrimidine-2,8-diamine | 456.2 | 1H NMR (400 MHz, CDCl3) δ 9.09 (s, 1H), 8.72 (s, 1H), 8.61 (s, 1H), 8.50 (dd, J = 7.5, 0.7 Hz, 1H), 8.22 (s, 1H), 7.85 (d, J = 8.3 Hz, 2H), 7.13 (d, J = 8.3 Hz, 1H), 6.89 (dd, J = 7.4, 2.6 Hz, 1H), 6.85 (dd, J = 2.6, 0.7 Hz, 1H), 5.65-5.60 (m, 1H), 5.06-4.95 (m, 4H), 3.41 (s, 3H), 2.27 (s, 3H) |
| 404 (Ex. 134) | (R)-1-(8-((4-([1,2,4]triazolo[1,5-a]pyridin-7-yloxy)-3-methylphenyl)amino)pyrimido[5,4-d]pyrimidin-2-yl)pyrrolidine-3-carbonitrile | 465.3 | 1H NMR (400 MHz, CDCl3) δ 9.11 (s, 1H), 8.62 (d, J = 2.0 Hz, 2H), 8.50 (d, J = 7.4 Hz, 1H), 8.23 (s, 1H), 7.85 (d, J = 8.1 Hz, 2H), 7.17-7.10 (m, 1H), 6.90 (dd, J = 7.4, 2.5 Hz, 1H), 6.85 (d, J = 2.5 Hz, 1H), 4.16-4.07 (m, 1H), 4.10-3.95 (m, 2H), 3.93-3.82 (m, 1H), 3.41-3.30 (m, 1H), 2.59-2.42 (m, 2H), 2.27 (s, 3H) |
| 405 (Ex. 132) | 1-((8-((4-([1,2,4]triazolo[1,5-a]pyridin-7-yloxy)-3-chlorophenyl)amino)pyrimido[5,4-d]pyrimidin-2-yl)(methyl)amino)-2-methylpropan-2-ol | 492.2 | 1H NMR (400 MHz, CDCl3) δ 9.07 (s, 1H), 8.68 (s, 1H), 8.62 (s, 1H), 8.52 (dd, J = 7.4, 0.8 Hz, 1H), 8.29 (d, J = 2.6 Hz, 1H), 8.25 (s, 1H), 7.88-7.80 (m, 1H), 7.27 (d, J = 8.7 Hz, 1H), 6.92 (dd, J = 7.4, 2.6 Hz, 1H), 6.90-6.86 (m, 1H), 3.84 (s, 2H), 3.43 (s, 3H), 1.34 (s, 6H) |
| 406 (Ex. 131) | (R)-2-(1-(8-((4-([1,2,4]triazolo[1,5-a]pyridin-7-yloxy)-3-chlorophenyl)amino)pyrimido[5,4-d]pyrimidin-2-yl)pyrrolidin-3-yl)acetonitrile | 499.2 | 1H NMR (400 MHz, CDCl3) δ 9.11 (s, 1H), 8.67 (s, 1H), 8.62 (s, 1H), 8.52 (d, J = 7.4 Hz, 1H), 8.29 (d, J = 2.6 Hz, 1H), 8.24 (s, 1H), 7.87 (dd, J = 8.8, 2.6 Hz, 1H), 7.27 (d, J = 8.8 Hz, 1H), 6.92 (dd, J = 7.4, 2.6 Hz, 1H), 6.88 (d, J = 2.5 Hz, 1H), 4.09-4.04 (m, 1H), 3.98-3.94 (m, 1H), 3.82-3.71 (m, 1H), 3.58-3.49 (m, 1H), 2.80 (p, J = 7.2 Hz, 1H), 2.62 (d, J = 6.4 Hz, 2H), 2.43-2.36 (m, 1H), 2.01 (s, 1H) |
| 407 (Ex. 114) | (S)-2-(1-(8-((3-methyl-4-((1-methyl-1H-benzo[d]imidazol-5-yl)oxy)phenyl)amino)pyrimido[5,4-d]pyrimidin-2-yl)azetidin-2-yl)propan-2-ol | 497.2 | 1H NMR (400 MHz, CDCl3) δ 8.99 (s, 1H), 8.55 (s, 1H), 8.45 (s, 1H), 7.83 (s, 1H), 7.72 (d, J = 2.7 Hz, 1H), 7.61 (dd, J = 8.7, 2.7 Hz, 1H), 7.35-7.28 (m, 2H), 7.04 (dd, J = 8.6, 2.3 Hz, 1H), 6.91 (d, J = 8.7 Hz, 1H), 4.55 (t, J = 7.9 Hz, 1H), 4.23-4.13 (m, 1H), 4.09 (td, J = 9.1, 4.6 Hz, 1H), 3.84 (s, 3H), 2.49-2.36 (m, 1H), 2.33 (s, 3H), 2.18 (ddd, J = 11.7, 9.5, 5.8 Hz, 1H), 1.35 (s, 3H), 1.19 (s, 3H), 0.06 (s, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 408 (Ex. 116) | (S)-2-(1-(8-((3-methyl-4-((1-methyl-1H-benzo[d]imidazol-5-yl)oxy)phenyl)amino)pyrimido[5,4-d]pyrimidin-2-yl)pyrrolidin-2-yl)propan-2-ol | 511.2 | 1H NMR (400 MHz, CDCl3) δ 9.00 (s, 1H), 8.54 (s, 1H), 8.53 (s, 1H), 7.83 (s, 1H), 7.72 (d, J = 2.7 Hz, 1H), 7.63 (dd, J = 8.7, 2.7 Hz, 1H), 7.35-7.28 (m, 2H), 7.04 (dd, J = 8.8, 2.3 Hz, 1H), 6.91 (d, J = 8.7 Hz, 1H), 5.95 (s, 1H), 4.43-4.36 (m, 1H), 4.19-4.14 (m, 1H), 3.83 (s, 3H), 3.69-3.58 (m, 1H), 2.33 (s, 3H), 2.27-2.15 (m, 1H), 2.14-2.03 (m, 1H), 1.99-1.83 (m, 2H), 1.32 (s, 3H), 1.18 (s, 3H) |
| 409 (Ex. 132) | N-(4-([1,2,4]triazolo[1,5-a]pyridin-7-yloxy)-3-chlorophenyl)-6-morpholinopyrimido[5,4-d]pyrimidin-4-amine | 476.2 | 1H NMR (400 MHz, CDCl3) δ 9.11 (s, 1H), 8.63 (s, 1H), 8.61 (s, 1H), 8.52 (dd, J = 7.4, 0.7 Hz, 1H), 8.27 (d, J = 2.6 Hz, 1H), 8.24 (s, 1H), 7.87 (dd, J = 8.8, 2.6 Hz, 1H), 7.27 (d, J = 8.8 Hz, 1H), 6.92 (dd, J = 7.4, 2.6 Hz, 1H), 6.87 (dd, J = 2.6, 0.7 Hz, 1H), 4.03-3.96 (m, 4H), 3.90-3.83 (m, 4H) |
| 410 (Ex. 131) | rac-(R)-N-(4-([1,2,4]triazolo[1,5-a]pyridin-7-yloxy)-3-chlorophenyl)-6-(2-(difluoromethyl)azetidin-1-yl)pyrimido[5,4-d]pyrimidin-4-amine | 496.2 | 1H NMR (400 MHz, CDCl3) δ 9.11 (s, 1H), 8.67 (s, 1H), 8.65 (s, 1H), 8.52 (d, J = 7.4 Hz, 1H), 8.29 (d, J = 2.6 Hz, 1H), 8.24 (s, 1H), 7.82 (dd, J = 8.9, 2.6 Hz, 1H), 7.26 (d, J = 8.9 Hz, 1H), 6.92 (dd, J = 7.5, 2.7 Hz, 1H), 6.88 (d, J = 2.6 Hz, 1H), 6.36 (t, J = 58.7 Hz, 1H), 4.87-4.72 (m, 1H), 4.34-4.19 (m, 2H), 2.76-2.62 (m, 1H), 2.62-2.49 (m, 1H) |
| 411 (Ex. 109) | N-(4-([1,2,4]triazolo[1,5-a]pyridin-7-yloxy)-3-methylphenyl)-6-(4-methoxypiperidin-1-yl)pyrimido[5,4-d]pyrimidin-4-amine | 484.3 | 1H NMR (400 MHz, CDCl3) δ 9.05 (s, 1H), 8.59 (s, 1H), 8.56 (s, 1H), 8.49 (dd, J = 7.4, 0.8 Hz, 1H), 8.22 (s, 1H), 7.87 (d, J = 2.7 Hz, 1H), 7.83 (dd, J = 8.5, 2.7 Hz, 1H), 7.12 (d, J = 8.6 Hz, 1H), 6.89 (dd, J = 7.4, 2.6 Hz, 1H), 6.85 (dd, J = 2.6, 0.8 Hz, 1H), 4.41-4.30 (m, 2H), 3.75-3.64 (m, 2H), 3.61-3.51 (m, 1H), 3.43 (s, 3H), 2.26 (s, 3H), 2.07-1.96 (m, 2H), 1.78-1.64 (m, 2H) |
| 412 (Ex. 109) | N-(4-([1,2,4]triazolo[1,5-a]pyridin-7-yloxy)-3-methylphenyl)-6-morpholinopyrimido[5,4-d]pyrimidin-4-amine | 456.2 | 1H NMR (400 MHz, CDCl3) δ 9.09 (s, 1H), 8.59 (s, 1H), 8.57 (s, 1H), 8.50 (dd, J = 7.5, 0.7 Hz, 1H), 8.22 (s, 1H), 7.88-7.80 (m, 2H), 7.13 (d, J = 8.5 Hz, 1H), 6.89 (dd, J = 7.5, 2.6 Hz, 1H), 6.84 (dd, J = 2.6, 0.7 Hz, 1H), 4.02-3.95 (m, 4H), 3.90-3.83 (m, 4H), 2.26 (s, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 413 (Ex. 111) | (S)-N2-((1,4-dioxan-2-yl)methyl)-N2-methyl-N8-(3-methyl-4-((1-methyl-1H-benzo[d]imidazol-5-yl)oxy)phenyl)pyrimido[5,4-d]pyrimidine-2,8-diamine | 513.3 | ¹H NMR (400 MHz, CDCl₃) δ 9.12 (s, 1H), 8.77 (s, 1H), 8.73 (s, 1H), 8.60-8.54 (m, 1H), 7.79 (s, 1H), 7.72 (d, J = 9.0 Hz, 1H), 7.48 (d, J = 9.0 Hz, 1H), 7.24 (s, 2H), 7.00 (d, J = 8.7 Hz, 1H), 4.03-3.98 (m, 3H), 3.97 (s, 2H), 3.89-3.81 (m, 2H), 3.74-3.70 (m, 4H), 3.48-3.43 (m, 1H), 3.42-3.36 (m, 3H), 2.28 (s, 3H) |
| 414 (Ex. 134) | (R)-1-(8-((4-([1,2,4]triazolo[1,5-a]pyridin-7-yloxy)-3-methylphenyl)amino)pyrimido[5,4-d]pyrimidin-2-yl)-3-methylpiperidin-3-ol | 484.3 | ¹H NMR (400 MHz, CDCl₃) δ 9.03 (s, 1H), 8.55 (s, 1H), 8.55 (s, 1H), 8.49 (dd, J = 7.4, 0.8 Hz, 1H), 8.22 (s, 1H), 7.86-7.77 (m, 2H), 7.11 (d, J = 8.5 Hz, 1H), 6.89 (dd, J = 7.4, 2.5 Hz, 1H), 6.85 (dd, J = 2.6, 0.7 Hz, 1H), 4.60-4.50 (m, 1H), 4.49-4.41 (m, 1H), 3.39-3.28 (m, 2H), 2.26 (s, 3H), 2.04-1.89 (m, 1H), 1.89-1.81 (m, 1H), 1.79-1.62 (m, 2H), 1.36 (s, 3H) |
| 415 (Ex. 109) | (R)-N8-(4-([1,2,4]triazolo[1,5-a]pyridin-7-yloxy)-3-methylphenyl)-N2-methyl-N2-(tetrahydro-2H-pyran-3-yl)pyrimido[5,4-d]pyrimidine-2,8-diamine | 484.3 | ¹H NMR (400 MHz, CDCl₃) δ 9.09 (s, 1H), 8.63 (s, 1H), 8.57 (s, 1H), 8.50 (dd, J = 7.4, 0.8 Hz, 1H), 8.22 (s, 1H), 7.89-7.85 (m, 1H), 7.85-7.78 (m, 1H), 7.13 (d, J = 8.6 Hz, 1H), 6.89 (ddd, J = 7.4, 2.6, 0.5 Hz, 1H), 6.86 (dd, J = 2.6, 0.7 Hz, 1H), 3.99 (d, J = 11.0 Hz, 2H), 3.58-3.36 (m, 3H), 3.24 (s, 3H), 2.27 (s, 3H), 2.08-1.81 (m, 4H) |
| 416 (Ex. 131) | (S)-2-(1-(8-((4-([1,2,4]triazolo[1,5-a]pyridin-7-yloxy)-3-chlorophenyl)amino)pyrimido[5,4-d]pyrimidin-2-yl)pyrrolidin-3-yl)acetonitrile | 499.2 | ¹H NMR (400 MHz, CDCl₃) δ 9.11 (s, 1H), 8.67 (s, 1H), 8.62 (s, 1H), 8.52 (dd, J = 7.5, 0.8 Hz, 1H), 8.29 (d, J = 2.7 Hz, 1H), 8.24 (s, 1H), 7.87 (dd, J = 8.8, 2.7 Hz, 1H), 7.27 (d, J = 8.8 Hz, 1H), 6.95-6.86 (m, 2H), 4.09-4.04 (m, 1H), 3.98-3.93 (m, 1H), 3.82-3.71 (m, 1H), 3.58-3.49 (m, 1H), 2.86-2.75 (m, 1H), 2.65-2.59 (m, 2H), 2.43-2.36 (m, 1H), 2.07-1.96 (m, 1H) |
| 417 (Ex. 134) | (R)-N-(4-([1,2,4]triazolo[1,5-a]pyridin-7-yloxy)-3-methylphenyl)-6-(hexahydropyrazino[2,1-c][1,4]oxazin-8(1H)-yl)pyrimido[5,4-d]pyrimidin-4-amine | 511.3 | ¹H NMR (400 MHz, CDCl₃) δ 9.07 (d, J = 1.5 Hz, 1H), 8.58 (s, 1H), 8.56 (s, 1H), 8.50 (d, J = 7.4 Hz, 1H), 8.22 (s, 1H), 7.82 (dd, J = 13.4, 4.8 Hz, 2H), 7.12 (d, J = 8.5 Hz, 1H), 6.89 (dd, J = 7.6, 1.9 Hz, 1H), 6.85 (s, 1H), 4.87 (d, J = 13.1 Hz, 1H), 4.69 (d, J = 12.8 Hz, 1H), 3.95-3.85 (m, 2H), 3.83-3.72 (m, 1H), 3.39 (t, J = 10.6 Hz, 1H), 3.33-3.22 (m, 1H), 2.94 (d, J = 11.4 Hz, 1H), 2.82-2.71 (m, 2H), 2.51-2.30 (m, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 418 (Ex. 131) | N-(4-([1,2,4]triazolo[1,5-a]pyridin-7-yloxy)-3-chlorophenyl)-6-((1R,4R)-2-oxa-5-azabicyclo[2.2.1]heptan-5-yl)pyrimido[5,4-d]pyrimidin-4-amine | 488.2 | ¹H NMR (400 MHz, CDCl₃) δ 9.09 (s, 1H), 8.61 (s, 2H), 8.52 (dd, J = 7.5, 0.8 Hz, 1H), 8.30-8.22 (m, 2H), 7.89-7.82 (m, 1H), 7.27 (d, J = 8.8 Hz, 1H), 6.92 (dd, J = 7.4, 2.6 Hz, 1H), 6.88 (dd, J = 2.6, 0.8 Hz, 1H), 5.26 (s, 1H), 4.81 (s, 1H), 4.02-3.84 (m, 2H), 3.79-3.66 (m, 2H), 2.12-2.01 (m, 2H) |
| 419 (Ex. 109) | N-(4-([1,2,4]triazolo[1,5-a]pyridin-7-yloxy)-3-methylphenyl)-6-(3-oxa-8-azabicyclo[3.2.1]octan-8-yl)pyrimido[5,4-d]pyrimidin-4-amine | 482.3 | ¹H NMR (400 MHz, CDCl₃) δ 9.08 (s, 1H), 8.58 (s, 1H), 8.57 (s, 1H), 8.50 (dd, J = 7.4, 0.8 Hz, 1H), 8.22 (s, 1H), 7.87-7.79 (m, 2H), 7.12 (d, J = 8.4 Hz, 1H), 6.89 (dd, J = 7.5, 2.6 Hz, 1H), 6.84 (dd, J = 2.6, 0.7 Hz, 1H), 4.90-4.84 (m, 2H), 3.89-3.82 (m, 2H), 3.79-3.71 (m, 2H), 2.25-2.04 (m, 4H) |
| 420 (Ex. 109) | N-(4-([1,2,4]triazolo[1,5-a]pyridin-7-yloxy)-3-methylphenyl)-6-(hexahydro-1H-furo[3,4-b]pyrrol-1-yl)pyrimido[5,4-d]pyrimidin-4-amine | 482.3 | ¹H NMR (400 MHz, CDCl₃) δ 9.06 (s, 1H), 8.59 (s, 2H), 8.50 (dd, J = 7.5, 0.7 Hz, 1H), 8.22 (s, 1H), 7.88-7.81 (m, 2H), 7.13 (d, J = 9.0 Hz, 1H), 6.89 (dd, J = 7.4, 2.6 Hz, 1H), 6.85 (dd, J = 2.6, 0.7 Hz, 1H), 4.55-4.47 (m, 1H), 4.37-4.23 (m, 2H), 4.09-4.00 (m, 1H), 4.00-3.92 (m, 1H), 3.80-3.76 (m, 1H), 3.74-3.65 (m, 1H), 2.85-2.75 (m, 1H), 2.27 (s, 3H), 2.28-2.19 (m, 1H), 2.06-1.90 (m, 1H) |
| 421 (Ex. 134) | (R)-N-(4-([1,2,4]triazolo[1,5-a]pyridin-7-yloxy)-3-methylphenyl)-6-(3-(trifluoromethyl)piperazin-1-yl)pyrimido[5,4-d]pyrimidin-4-amine | 523.3 | ¹H NMR (400 MHz, CDCl₃) δ 9.10 (s, 1H), 8.61 (s, 1H), 8.56 (s, 1H), 8.50 (dd, J = 7.4, 0.7 Hz, 1H), 8.22 (s, 1H), 7.85 (d, J = 2.7 Hz, 1H), 7.81 (dd, J = 8.6, 2.7 Hz, 1H), 7.13 (d, J = 8.6 Hz, 1H), 6.89 (dd, J = 7.4, 2.6 Hz, 1H), 6.84 (dd, J = 2.6, 0.7 Hz, 1H), 4.93-4.85 (m, 1H), 4.71-4.62 (m, 1H), 3.48-3.33 (m, 3H), 3.33-3.24 (m, 1H), 3.01-2.90 (m, 1H), 2.27 (s, 3H) |
| 422 (Ex. 114) | N-(3-methyl-4-((1-methyl-1H-benzo[d]imidazol-5-yl)oxy)phenyl)-6-(2-oxa-6-azaspiro[3.4]octan-6-yl)pyrimido[5,4-d]pyrimidin-4-amine | 495.5 | ¹H NMR (400 MHz, CDCl₃) δ 9.07 (d, J = 1.0 Hz, 1H), 8.59 (s, 1H), 8.54 (s, 1H), 8.21 (s, 1H), 7.76 (s, 1H), 7.68 (d, J = 8.8 Hz, 1H), 7.37 (d, J = 8.8 Hz, 1H), 7.30 (d, J = 2.2 Hz, 1H), 7.11 (dd, J = 8.7, 2.3 Hz, 1H), 6.95 (d, J = 8.7 Hz, 1H), 4.78 (d, J = 6.2 Hz, 2H), 4.70 (d, J = 6.2 Hz, 2H), 3.98 (s, 2H), 3.91 (s, 3H), 3.76 (t, J = 7.0 Hz, 2H), 2.39 (t, J = 7.0 Hz, 2H), 2.33 (s, 3H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 423 (Ex. 134) | (R)-2-(1-(8-((4-([1,2,4]triazolo[1,5-a]pyridin-7-yloxy)-3-methylphenyl)amino)pyrimido[5,4-d]pyrimidin-2-yl)azetidin-2-yl)propan-2-ol | 484.3 | 1H NMR (400 MHz, CDCl3) δ 9.04 (s, 1H), 8.60 (s, 1H), 8.50 (d, J = 7.5 Hz, 1H), 8.22 (s, 1H), 7.86 (d, J = 2.7 Hz, 1H), 7.80 (dd, J = 8.7, 2.7 Hz, 1H), 7.12 (d, J = 8.7 Hz, 1H), 6.89 (dd, J = 7.5, 2.6 Hz, 1H), 6.84 (d, J = 2.6 Hz, 1H), 5.72 (s, 1H), 4.63-4.54 (m, 1H), 4.27-4.17 (m, 1H), 4.17-4.07 (m, 1H), 2.52-2.39 (m, 1H), 2.26 (s, 3H), 2.26-2.13 (m, 1H), 1.37 (s, 3H), 1.22 (s, 3H) |
| 424 (Ex. 132) | N8-(4-([1,2,4]triazolo[1,5-a]pyridin-7-yloxy)-3-chlorophenyl)-N2-methyl-N2-(oxetan-3-yl)pyrimido[5,4-d]pyrimidine-2,8-diamine | 476.2 | 1H NMR (400 MHz, CDCl3) δ 9.12 (s, 1H), 8.81 (s, 1H), 8.64 (s, 1H), 8.52 (d, J = 7.4 Hz, 1H), 8.31 (d, J = 2.6 Hz, 1H), 8.24 (s, 1H), 7.85 (dd, J = 8.8, 2.6 Hz, 1H), 7.27 (d, J = 8.8 Hz, 1H), 6.92 (dd, J = 7.5, 2.6 Hz, 1H), 6.87 (d, J = 2.6 Hz, 1H), 5.60 (s, 1H), 5.07-4.99 (m, 4H), 3.42 (s, 3H) |
| 425 (Ex. 114) | 6-methyl-2-(8-((3-methyl-4-((1-methyl-1H-benzo[d]imidazol-5-yl)oxy)phenyl)amino)pyrimido[5,4-d]pyrimidin-2-yl)-2,6-diazaspiro[3.4]octan-5-one | 522.3 | 1H NMR (400 MHz, CDCl3) δ 9.05 (s, 1H), 8.55 (d, J = 2.2 Hz, 2H), 7.84 (s, 1H), 7.72 (dd, J = 2.8, 0.8 Hz, 1H), 7.62 (dd, J = 8.7, 2.8 Hz, 1H), 7.32 (dd, J = 5.5, 3.1 Hz, 2H), 7.05 (dd, J = 8.8, 2.2 Hz, 1H), 6.92 (d J = 8.7 Hz, 1H), 4.57 (d J = 8.9 Hz, 2H), 4.13 (d, J = 8.8 Hz, 2H), 3.85 (s, 3H), 3.41 (t, J = 7.3 Hz, 2H), 2.93 (s, 3H), 2.50 (t, J = 6.9 Hz, 2H), 2.34 (s, 3H) |
| 426 (Ex. 109) | N-(4-([1,2,4]triazolo[1,5-a]pyridin-7-yloxy)-3-chlorophenyl)-6-((1S,4S)-2-oxa-5-azabicyclo[2.2.1]heptan-5-yl)pyrimido[5,4-d]pyrimidin-4-amine | 488.2 | 1H NMR (400 MHz, CDCl3) δ 9.09 (s, 1H), 8.65 (s, 1H), 8.61 (s, 1H), 8.52 (dd, J = 7.5, 0.8 Hz, 1H), 8.30-8.22 (m, 2H), 7.88-7.84 (m, 1H), 7.27 (d, J = 8.8 Hz, 1H), 6.92 (dd, J = 7.4, 2.6 Hz, 1H), 6.88 (dd, J = 2.6, 0.8 Hz, 1H), 5.28-5.09 (m, 1H), 4.81 (s, 1H), 3.96 (d, J = 31.6 Hz, 2H), 3.79-3.66 (m, 2H), 2.12-2.01 (m, 2H) |
| 427 (Ex. 134) | (R)-N8-(4-([1,2,4]triazolo[1,5-a]pyridin-7-yloxy)-3-methylphenyl)-N2-methyl-N2-(tetrahydrofuran-3-yl)pyrimido[5,4-d]pyrimidine-2,8-diamine | 470.2 | 1H NMR (400 MHz, CDCl3) δ 9.08 (s, 1H), 8.91 (s, 1H), 8.58 (s, 1H), 8.49 (dd, J = 7.4, 0.7 Hz, 1H), 8.22 (s, 1H), 7.91 (d, J = 2.7 Hz, 1H), 7.86 (dd, J = 8.6, 2.7 Hz, 1H), 7.12 (d, J = 8.6 Hz, 1H), 6.89 (dd, J = 7.4, 2.6 Hz, 1H), 6.85 (dd, J = 2.6, 0.7 Hz, 1H), 5.44 (s, 1H), 4.27-4.17 (m, 1H), 4.10-4.03 (m, 1H), 3.98-3.89 (m, 1H), 3.87-3.76 (m, 1H), 3.29 (s, 3H), 2.44-2.31 (m, 1H), 2.27 (s, 3H), 2.17-2.04 (m, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 428 (Ex. 109) | N-(4-([1,2,4]triazolo[1,5-a]pyridin-7-yloxy)-3-methylphenyl)-6-(isoxazolidin-2-yl)pyrimido[5,4-d]pyrimidin-4-amine | 442.2 | ¹H NMR (400 MHz, CDCl₃) δ 9.21 (d, J = 1.8 Hz, 1H), 8.77 (s, 1H), 8.67 (s, 1H), 8.53-8.46 (m, 1H), 8.22 (s, 1H), 7.88 (s, 1H), 7.85 (d, J = 9.1 Hz, 1H), 7.13 (d, J = 8.6 Hz, 1H), 6.89 (dd, J = 7.5, 2.2 Hz, 1H), 6.85 (s, 1H), 4.19 (t, J = 7.1 Hz, 2H), 4.09 (t, J = 7.4 Hz, 2H), 2.44 (p, J = 7.3 Hz, 2H), 2.26 (s, 3H) |
| 429 (Ex. 131) | (R)-N-(4-([1,2,4]triazolo[1,5-a]pyridin-7-yloxy)-3-chlorophenyl)-6-(3-(trifluoromethyl)piperazin-1-yl)pyrimido[5,4-d]pyrimidin-4-amine | 543.2 | ¹H NMR (400 MHz, CDCl₃) δ 9.12 (s, 1H), 8.62 (d, J = 17.3 Hz, 2H), 8.52 (dd, J = 7.5, 0.7 Hz, 1H), 8.29 (d, J = 2.6 Hz, 1H), 8.24 (s, 1H), 7.83 (dd, J = 8.8, 2.6 Hz, 1H), 7.27 (d, J = 8.8 Hz, 1H), 6.92 (dd, J = 7.4, 2.6 Hz, 1H), 6.87 (dd, J = 2.6, 0.8 Hz, 1H), 4.91-4.84 (m, 1H), 4.70-4.60 (m, 1H), 3.51-3.35 (m, 3H), 3.35-3.24 (m, 1H), 3.01-2.90 (m, 1H), 1.71 (s, 1H) |
| 430 (Ex. 131) | (R)-N-(4-([1,2,4]triazolo[1,5-a]pyridin-7-yloxy)-3-chlorophenyl)-6-(hexahydropyrazino(2,1-c][1,4]oxazin-8(1H)-yl)pyrimido[5,4-d]pyrimidin-4-amine | 531.2 | ¹H NMR (400 MHz, CDCl₃) δ 9.09 (s, 1H), 8.60 (d, J = 6.2 Hz, 2H), 8.52 (dd, J = 7.4, 0.7 Hz, 1H), 8.26 (d, J = 2.6 Hz, 1H), 8.24 (s, 1H), 7.86 (dd, J = 8.8, 2.6 Hz, 1H), 7.26 (d, J = 8.8 Hz, 1H), 6.92 (dd, J = 7.5, 2.6 Hz, 1H), 6.87 (dd, J = 2.7, 0.7 Hz, 1H), 4.87 (d, J = 13.2 Hz, 1H), 4.69 (d, J = 12.8 Hz, 1H), 3.95-3.85 (m, 2H), 3.85-3.72 (m, 1H), 3.44-3.34 (m, 1H), 3.34-3.22 (m, 1H), 2.98-2.90 (m, 1H), 2.82-2.72 (m, 2H), 2.51-2.29 (m, 3H) |
| 431 (Ex. 131) | (S)-N-(4-([1,2,4]triazolo[1,5-a]pyridin-7-yloxy)-3-chlorophenyl)-6-(hexahydropyrazino(2,1-c][1,4]oxazin-8(1H)-yl)pyrimido[5,4-d]pyrimidin-4-amine | 531.3 | ¹H NMR (400 MHz, CDCl₃) δ 9.09 (s, 1H), 8.61 (s, 1H), 8.59 (s, 1H), 8.52 (dd, J = 7.5, 0.7 Hz, 1H), 8.26 (d, J = 2.6 Hz, 1H), 8.24 (s, 1H), 7.86 (dd, J = 8.8, 2.6 Hz, 1H), 7.26 (d, J = 8.8 Hz, 1H), 6.92 (dd, J = 7.4, 2.6 Hz, 1H), 6.87 (dd, J = 2.7, 0.8 Hz, 1H), 4.87 (d, J = 13.1 Hz, 1H), 4.69 (d, J = 12.8 Hz, 1H), 3.95-3.85 (m, 2H), 3.83-3.72 (m, 1H), 3.44-3.34 (m, 1H), 3.34-3.22 (m, 1H), 2.98-2.90 (m, 1H), 2.82-2.72 (m, 2H), 2.51-2.29 (m, 3H) |
| 432 (Ex. 114) | rac-6-((4aS,7aR)-hexahydrofuro[3,4-b]pyridin-1(2H)-yl)-N-(3-methyl-4-((1-methyl-1H-benzo[d]imidazol-5-yl)oxy)phenyl)pyrimido[5,4-d]pyrimidin-4-amine | 509.2 | ¹H NMR (400 MHz, CDCl₃) δ 9.20 (s, 1H), 8.92 (s, 1H), 8.76 (s, 1H), 8.59 (s, 1H), 7.80-7.71 (m, 2H), 7.52 (d, J = 8.9 Hz, 1H), 7.31 (dd, J = 8.9, 2.2 Hz, 1H), 7.22 (d, J = 2.3 Hz, 1H), 7.02 (d, J = 8.6 Hz, 1H), 5.42 (q, J = 8.2 Hz, 1H), 4.73 (d, J = 13.1 Hz, 1H), 4.19 (t, J = 8.4 Hz, 1H), 4.17-4.00 (m, 1H), 4.03 (s, 3H), 3.81 (d, J = 8.8, 1.4 Hz, 1H), 3.69 (t, J = 8.6 Hz, 1H), 3.16-3.05 (m, 1H), 2.42-2.33 (m, 1H), 2.27 (s, 3H), 2.00-1.82 (m, 2H), 1.82-1.53 (m, 2H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 433 (Ex. 132) | rac-(3aR,6aR)-5-(8-((4-([1,2,4]triazolo[1,5-a]pyridin-7-yloxy)-3-chlorophenyl)amino)pyrimido[5,4-d]pyrimidin-2-yl)hexahydro-2H-thieno[2,3-c]pyrrole 1,1-dioxide | 550.2 | ¹H NMR (400 MHz, CDCl₃) δ 9.20 (s, 1H), 8.76 (s, 1H), 8.67 (s, 1H), 8.55 (d, J = 6.9 Hz, 1H), 8.34-8.28 (m, 2H), 7.94-7.85 (m, 1H), 7.33-7.24 (m, 2H), 7.02-6.93 (m, 2H), 4.62 (d, J = 13.3 Hz, 1H), 4.12 (q, J = 7.3 Hz, 1H), 4.10-4.00 (m, 2H), 3.90-3.76 (m, 2H), 3.56-3.50 (m, 1H), 3.31-3.12 (m, 1H), 2.60-2.46 (m, 1H), 2.26-2.16 (m, 1H) |
| 434 (Ex. 134) | rac-(S)-N-(4-([1,2,4]triazolo[1,5-a]pyridin-7-yloxy)-3-chlorophenyl)-6-(6-oxa-1-azaspiro[3.4]octan-1-yl)pyrimido[5,4-d]pyrimidin-4-amine | 502.2 | ¹H NMR (400 MHz, CDCl₃) δ 9.42 (s, 1H), 9.14 (s, 1H), 8.62 (s, 1H), 8.53 (d, J = 7.4 Hz, 1H), 8.42 (s, 1H), 8.28 (s, 1H), 7.84 (dd, J = 8.8, 2.6 Hz, 1H), 7.26 (d, J = 9.4 Hz, 1H), 6.95 (dd, J = 7.4, 2.6 Hz, 1H), 6.91 (d, J = 2.6 Hz, 1H), 4.68 (d, J = 10.1 Hz, 1H), 4.39 (s, 1H), 4.25-4.20 (m, 1H), 4.18-4.08 (m, 1H), 4.03 (q, J = 8.0 Hz, 1H), 3.76-3.65 (m, 3H), 2.81 (dt, J = 14.7, 7.7 Hz, 1H), 2.70-2.55 (m, 1H) |
| 435 (Ex. 132) | 1-(8-((4-([1,2,4]triazolo[1,5-a]pyridin-7-yloxy)-3-chlorophenyl)amino)pyrimido[5,4-d]pyrimidin-2-yl)-4-methylpiperidin-4-ol | 504.2 | ¹H NMR (400 MHz, CDCl₃) δ 9.06 (s, 1H), 8.60 (d, J = 17.2 Hz, 2H), 8.52 (d, J = 7.4 Hz, 1H), 8.31-8.22 (m, 2H), 7.87 (dd, J = 8.8, 2.6 Hz, 1H), 7.27 (d, J = 8.8 Hz, 1H), 6.92 (dd, J = 7.4, 2.6 Hz, 1H), 6.88 (d, J = 2.6 Hz, 1H), 4.52 (dt, J = 14.0, 4.2 Hz, 2H), 4.17-4.01 (m, 1H), 3.63 (ddd, J = 13.9, 10.3, 4.1 Hz, 2H), 1.81-1.65 (m, 4H), 1.36 (s, 3H) |
| 436 (Ex. 132) | N-(4-([1,2,4]triazolo[1,5-a]pyridin-7-yloxy)-3-chlorophenyl)-6-(4-methoxypiperazin-1-yl)pyrimido[5,4-d]pyrimidin-4-amine | 505.3 | ¹H NMR (400 MHz, CDCl₃) δ 9.09 (s, 1H), 8.61 (s, 2H), 8.55-8.49 (m, 1H), 8.30-8.22 (m, 2H), 7.87 (dd, J = 8.8, 2.6 Hz, 1H), 7.26 (d, J = 8.8 Hz, 1H), 6.92 (dd, J = 7.5, 2.6 Hz, 1H), 6.88 (d, J = 2.5 Hz, 1H), 4.79-4.71 (m, 2H), 3.62 (s, 3H), 3.46-3.38 (m, 4H), 2.71-2.66 (m, 2H) |
| 437 (Ex. 40) | 2-(8-((3-methyl-4-((1-methyl-1H-benzo[d]imidazol-5-yl)oxy)phenyl)amino)pyrimido[5,4-d]pyrimidin-2-yl)-1,2-thiazinane 1,1-dioxide | 517.2 | ¹H NMR (400 MHz, CDCl₃) δ 9.30 (s, 1H), 8.79 (s, 1H), 8.74 (s, 1H), 7.85 (s, 1H), 7.73 (m, 1H), 7.67 (dd, J = 8.7, 2.7 Hz, 1H), 7.34 (m, 2H), 7.06 (dd, J = 8.8, 2.2 Hz, 1H), 6.92 (d, J = 8.7 Hz, 1H), 4.44 (m, 2H), 3.85 (s, 3H), 3.35 (m, 2H), 2.36 (m, 2H), 2.36 (s, 3H), 1.93 (m, 2H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 438 (Ex. 142) | 1-((8-((2-fluoro-3-methyl-4-((1-methyl-1H-benzo[d]imidazol-5-yl)oxy)phenyl)amino)pyrimido[5,4-d]pyrimidin-2-yl)(methyl)amino)-2-methylpropan-2-ol | 503.3 | ¹H NMR (400 MHz, CDCl₃) δ 9.18 (s, 1H), 8.94 (s, 1H), 8.61 (m, 2H), 7.54 (d, J = 9.0 Hz, 1H), 7.32 (dd, J = 9.0, 2.3 Hz, 1H), 6.86 (dd, J = 9.1, 1.7 Hz, 2H), 4.05 (s, 3H), 3.86 (s, 2H), 3.44 (s, 3H), 2.22 (d, J = 2.2 Hz, 3H) 1.25 (m, 6H) |
| 439 (Ex. 101) | (R)-N-(3-chloro-4-((1-methyl-1H-benzo[d]imidazol-5-yl)oxy)phenyl)-6-(3,4-dimethylpiperazin-1-yl)pyrimido[5,4-d]pyrimidin-4-amine 2,2,2-trifluoroacetate | 516.3 | ¹H NMR (400 MHz, CDCl₃) δ 9.16 (s, 1H), 8.88 (s, 1H), 8.68 (s, 1H), 8.64 (bs, 1H), 8.25 (d, J = 2.6 Hz, 1H), 7.79 (dd, J = 8.8, 2.6 Hz, 1H), 7.57 (d, J = 9.0 Hz, 1H), 7.40 (dd, J = 9.0, 2.3 Hz, 1H), 7.19 (m, 2H), 4.06 (s, 3H), 3.82 (m, 3H), 3.57 (m 2H), 2.94 (m, 4H), 2.86 (m, 1H), 1.63 (d, J = 6.5 Hz, 3H) |
| 440 (Ex. 101) | 6-((1S,4S)-2-oxa-5-azabicyclo[2.2.1]heptan-5-yl)-N-(3-chloro-4-((1-methyl-1H-benzo[d]imidazol-5-yl)oxy)phenyl)pyrimido[5,4-d]pyrimidin-4-amine 2,2,2-trifluoroacetate | 500.2 | ¹H NMR (400 MHz, CDCl₃) δ 9.19 (s, 1H), 8.80 (s, 1H), 8.71 (s, 1H), 8.43 (d, J = 9.3 Hz, 1H), 8.08 (d, J = 2.6 Hz, 1H), 7.80 (dd, J = 8.8, 2.6 Hz, 1H), 7.56 (m, 1H), 7.37 (dd, J = 8.9, 2.3 Hz, 1H), 7.17 (d, J = 8.8 Hz, 1H), 4.82 (s, 1H), 4.05 (s, 3H), 4.00 (m, 1H), 3.91 (m, 1H), 3.72 (m, 2H) 2.06 (m, 3H) |
| 441 (Ex. 101) | 6-(3-oxa-8-azabicyclo[3.2.1]octan-8-yl)-N-(3-chloro-4-((1-methyl-1H-benzo[d]imidazol-5-yl)oxy)phenyl)pyrimido[5,4-d]pyrimidin-4-amine 2,2,2-trifluoroacetate | 515.2 | ¹H NMR (400 MHz, CDCl₃) δ 9.24 (s, 1H), 9.01 (s, 1H), 8.77 (m, 1H), 8.64 (s, 1H), 8.17 (d, J = 2.6 Hz, 1H), 7.83 (dd, J = 8.8, 2.6 Hz, 1H), 7.57 (m, 1H), 7.37 (dd, J = 9.0, 2.3 Hz, 1H), 7.22 (d, J = 2.3 Hz, 1H), 7.18 (m, 1H), 4.88 (s, 2H), 4.05 (s, 2H), 3.81 (m, 4H), 2.24 (m, 4H), 2.10 (m, 2H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 442 (Ex. 101) | N-(3-chloro-4-((1-methyl-1H-benzo[d]imidazol-5-yl)oxy)phenyl)-6-(6-oxa-2-azaspiro[3.4]octan-2-yl)pyrimido[5,4-d]pyrimidin-4-amine 2,2,2-trifluoroacetate | 515.2 | 1H NMR (400 MHz, CDCl3) δ 9.21 (s, 1H), 9.04 (m, 1H), 8.82 (m, 1H), 8.64 (s, 1H), 8.20 (d, J = 2.6, 1H), 7.81 (dd, J = 8.8, 2.6 Hz, 1H), 7.57 (d, J = 9.1 Hz, 1H), 7.38 (d, J = 9.0, 2.3 Hz, 1H), 7.23 (d, J = 2.3, Hz, 1H), 7.19 (d, J = 8.8 Hz, 1H), 4.30 (s, 4H), 4.06 (s, 3H), 4.00 (s, 2H), 3.95 (t, J = 7.0 Hz, 2H), 2.29 (t, J = 7.0 Hz, 2H) |
| 443 (Ex. 101) | N-(3-chloro-4-((1-methyl-1H-benzo[d]imidazol-5-yl)oxy)phenyl)-6-(2-oxa-7-azaspiro[4.4]nonan-7-yl)pyrimido[5,4-d]pyrimidin-4-amine 2,2,2-trifluoroacetate | 529.3 | 1H NMR (400 MHz, CDCl3) δ 9.22 (s, 1H), 8.96 (s, 1H), 8.83 (m, 1H), 8.62 (s, 1H), 8.20 (s, 1H), 7.84 (d, J = 8.7 Hz, 1H), 7.55 (m, 1H), 7.37 (dd, J = 9.0, 2.3 Hz, 1H), 7.24 (d, J = 2.3 Hz, 1H), 7.18 (d, J = 8.8 Hz, 1H), 4.05 (s, 3H), 4.01 (m, 2H), 3.77 (m, 5H), 2.10 (m, 5H) |
| 444 (Ex. 101) | (R)-1-(8-((3-chloro-4-((1-methyl-1H-benzo[d]imidazol-5-yl)oxy)phenyl)amino)pyrimido[5,4-d]pyrimidin-2-yl)pyrrolidine-3-carbonitrile | 498.2 | 1H NMR (400 MHz, CDCl3) δ 9.20 (s, 1H), 8.93 (s, 1H), 8.71 (m, 1H), 8.65 (s, 1H), 8.22 (d, J = 2.6 Hz, 1H), 7.82 (dd, J = 8.8, 2.6 Hz, 1H), 7.56 (J = 9.0 Hz, 1H), 7.38 (dd, J = 9.0, 2.3 Hz, 1H), 7.23 (d, J = 2.3 Hz, 1H), 7.19 (d, J = 8.8 Hz, 1H), 4.11 (m, 2H), 4.04 (s, 3H), 3.89 (m, 1H), 3.37 (m, 2H), 2.51 (m, 2H) |
| 445 (Ex. 101) | (S)-N-(3-chloro-4-((1-methyl-1H-benzo[d]imidazol-5-yl)oxy)phenyl)-6-(3-(trifluoromethyl)piperazin-1-yl)pyrimido[5,4-d]pyrimidin-4-amine | 556.2 | 1H NMR (400 MHz, CDCl3) δ 9.23 (s, 1H), 9.05 (s, 1H), 8.71 (m, 1H), 8.66 (s, 1H), 8.22 (d, J = 2.6 Hz, 1H), 7.79 (dd, J = 8.8, 2.7 Hz, 1H), 7.57 (d, J = 9.0, 1H), 7.39 (dd, J = 9.1, 2.3 Hz, 1H), 7.20 (m, 2H), 4.87 (m, 1H), 4.65 (m, 1H), 4.07 (s, 3H), 3.48 (m, 4H), 3.32 (m, 1H), 2.99 (m, 1H) |
| 446 (Ex. 101) | 6-((1S,4S)-2-oxa-5-azabicyclo[2.2.2]octan-5-yl)-N-(3-chloro-4-((1-methyl-1H-benzo[d]imidazol-5-yl)oxy)phenyl)pyrimido[5,4-d]pyrimidin-4-amine | 515.3 | 1H NMR (400 MHz, CDCl3) δ 9.04 (s, 1H), 8.58 (s, 1H), 8.56 (s, 1H), 8.14 (m, 1H) 7.87 (s, 1H), 7.67 (m, 1H), 7.37 (m, 2H), 7.11 (dd, J = 8.7, 2.3 Hz, 1H), 7.01 (d, J = 8.9 Hz, 1H), 4.14 (m, 4H), 3.83 (m, 4H), 2.27 (m, 1H), 2.08 (m, 2H), 1.83 (m, 2H) |

TABLE 1-continued

| Example No. (Method) | Structure; IUPAC name | LCMS M⁺1 | ¹H NMR (ppm); ¹⁹F NMR (ppm); optical rotation; Chiral HPLC/SFC conditions |
|---|---|---|---|
| 447 (Ex. 101) | 6-(8-oxa-3-azabicyclo[3.2.1]octan-3-yl)-N-(3-chloro-4-((1-methyl-1H-benzo[d]imidazol-5-yl)oxy)phenyl)pyrimido[5,4-d]pyrimidin-4-amine 2,2,2-trifluoroacetate | 495.3 | ¹H NMR (400 MHz, CDCl₃) δ 9.06 (s, 1H), 8.57 (s, 1H), 8.50 (s, 1H), 8.13 (d, J = 2.6 Hz, 1H), 7.87 (s, 1H), 7.69 (dd, J = 8.9, 2.7 Hz, 1H), 7.37 (m, 2H), 7.11 (dd, J = 8.8, 2.3 Hz, 1H), 7.01 (d, J = 8.8 Hz, 1H), 4.55 (m, 2H), 4.42 (d, J = 13.3 Hz, 2H), 3.86 (s, 3H), 3.36 (dd, J = 13.0, 2.5 Hz, 2H), 2.02 (m, 2H), 1.84 (m, 2H) |
| 448 (Ex. 101) | N-(3-chloro-4-((1-methyl-1H-benzo[d]imidazol-5-yl)oxy)phenyl)-6-(2,2-dimethylmorpholino)pyrimido[5,4-d]pyrimidin-4-amine | 517.2 | ¹H NMR (400 MHz, CDCl₃) δ 9.06 (s, 1H), 8.56 (s, 1H), 8.47 (m, 1H), 8.12 (d, J = 2.63 Hz, 1H), 7.87 (s, 1H), 7.67 (dd, J = 8.9, 2.6 Hz, 1H), 7.37 (m, 2H), 7.11 (dd, J = 8.8, 2.3 Hz, 1H), 7.01 (d, J = 8.9 Hz, 1H), 3.96 (m, 2H), 3.89 (m, 2H), 3.86 (s, 3H), 3.80 (s, 2H), 1.31 (s, 6H) |
| 449 (Ex. 101) | N-(3-chloro-4-((1-methyl-1H-benzo[d]imidazol-5-yl)oxy)phenyl)-6-(4-oxa-7-azaspiro[2.5]octan-7-yl)pyrimido[5,4-d]pyrimidin-4-amine | 515.2 | ¹H NMR (400 MHz, CDCl₃) δ 9.06 (s, 1H), 8.57 (s, 1H), 8.45 (m, 1H), 8.12 (d, J = 2.63 Hz, 1H), 7.87 (s, 1H), 7.67 (dd, J = 8.9, 2.7 Hz, 1H), 7.37 (m, 2H), 7.11 (dd, J = 8.71, 2.3 Hz, 1H), 7.01 (d, J = 8.8 Hz, 1H), 4.05 (m, 2H), 3.92 (m, 4H), 3.86 (s, 3H), 0.89 (m, 2H), 0.71 (m, 2H) |
| 450 (Ex. 101) | (S)-N-(3-chloro-4-((1-methyl-1H-benzo[d]imidazol-5-yl)oxy)phenyl)-6-(2-methylmorpholino)pyrimido[5,4-d]pyrimidin-4-amine | 503.2 | ¹H NMR (400 MHz, CDCl₃) δ 9.07 (s, 1H), 8.57 (s, 1H), 8.48 (m, 1H), 8.13 (d, J = 2.6 Hz, 1H), 7.87 (s, 1H), 7.67 (dd, J = 8.9, 2.7 Hz, 1H), 7.37 (m, 2H), 7.11 (dd, J = 8.7, 2.3 Hz, 1H), 7.01 (m, 1H), 4.68 (m, 2H), 4.08 (m, 1H), 3.86 (s, 3H), 3.69 (m, 2H), 3.21 (m, 1H), 2.86 (m, 1H), 1.32 (d, J = 6.3 Hz, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 451 (Ex. 101) | 6-((1R,4R)-2-oxa-5-azabicyclo[2.2.2]octan-5-yl)-N-(3-chloro-4-((1-methyl-1H-benzo[d]imidazol-5-yl)oxy)phenyl)pyrimido[5,4-d]pyrimidin-4-amine 2,2,2-trifluoroacetate | 515.2 | ¹H NMR (400 MHz, CDCl₃) δ 9.04 (s, 1H), 8.58 (m, 1H), 8.56 (s, 1H) 8.14 (m, 1H), 7.89 (m, 1H), 7.67 (m, 1H), 7.39 (m, 2H), 7.10 (d, J = 8.7 Hz, 1H), 7.01 (d, J = 8.9 Hz, 1H), 4.14 (m, 4H), 3.83 (m, 4H), 2.27 (m, 1H), 2.08 (m, 2H), 1.83 (m, 2H) |
| 452 (Ex. 101) | (R)-N-(3-chloro-4-((1-methyl-1H-benzo[d]imidazol-5-yl)oxy)phenyl)-6-(2-methylmorpholino)pyrimido[5,4-d]pyrimidin-4-amine | 503.2 | ¹H NMR (400 MHz, CDCl₃) δ 9.07 (s, 1H), 8.57 (s, 1H), 8.48 (m, 1H), 8.13 (d, J = 2.6 Hz, 1H), 7.88 (s, 1H), 7.67 (dd, J = 8.9, 2.6 Hz, 1H), 7.37 (m, 2H), 7.11 (dd, J = 8.7, 2.3 Hz, 1H), 7.01 (d, J = 8.9 Hz, 1H), 4.68 (m, 2H), 4.08 (m, 1H), 3.86 (s, 3H), 3.69 (m, 2H), 3.21 (m, 1H), 2.86 (m, 1H), 1.32 (d, J = 6.2 Hz, 3H) |
| 453 (Ex. 142) | (S)-2-(1-(8-((2-fluoro-3-methyl-4-((1-methyl-1H-benzo[d]imidazol-5-yl)oxy)phenyl)amino)pyrimido[5,4-d]pyrimidin-2-yl)azetidin-2-yl)propan-2-ol | 515.3 | ¹H NMR (400 MHz, (CD₃)₂SO) δ 9.13 (s, 1H), 8.42 (s, 1H), 8.20 (s, 1H), 8.00 (m, 1H), 7.60 (d, J = 8.7 Hz, 1H), 7.20 (d, J = 2.3 Hz, 1H), 7.04 (dd, J = 8.7, 2.3 Hz, 1H), 6.37 (d, J = 8.9 Hz, 1H), 4.44 (m, 1H), 4.09 (m, 2H), 3.85 (s, 3H), 3.31 (m, 4H), 2.74 (m, 2H), 2.33 (m, 2H), 2.23 (d, J = 2.1 Hz, 3H) |
| 454 (Ex. 142) | 6-(2-oxa-5-azabicyclo[2.2.1]heptan-5-yl)-N-(2-fluoro-3-methyl-4-((1-methyl-1H-benzo[d]imidazol-5-yl)oxy)phenyl)pyrimido[5,4-[d]imidazol-5-d]pyrimidin-4-amine | 499.3 | ¹H NMR (400 MHz, CDCl₃) δ 9.06 (m, 1H), 8.87 (m, 1H), 8.54 (s, 1H), 8.48 (t, J = 9.1 Hz, 1H), 7.86 (s, 1H), 7.34 (m, 2H), 7.06 (dd, J = 8.8, 2.3 Hz, 1H), 6.75 (d, J = 9.0 Hz, 1H), 3.95 (m, 3H), 3.86 (s, 3H), 3.72 (m, 2H), 2.29 (d, J = 2.1 Hz, 3H), 2.07 (m, 3H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 455 (Ex. 101) | 6-((1R,4R)-2-oxa-5-azabicyclo[2.2.1]heptan-5-yl)-N-(3-chloro-4-((1-methyl-1H-benzo[d]imidazol-5-yl)oxy)phenyl)pyrimido[5,4-d]pyrimidin-4-amine | 501.2 | ¹H NMR (400 MHz, CDCl₃) δ 9.07 (m, 1H), 8.55 (m, 2H), 8.13 (d, J = 2.6 Hz, 1H), 7.66 (m, 1H), 7.37 (m, 2H), 7.11 (dd, J = 8.7, 2.2 Hz, 1H), 7.01 (d, J = 8.9 Hz, 1H), 3.95 (m, 3H), 3.86 (s, 3H), 3.72 (m, 2H), 2.07 (m, 3H) |
| 456 (Ex. 101) | 1-((8-((3-chloro-4-((1-methyl-1H-benzo[d]imidazol-5-yl)oxy)phenyl)amino)pyrimido[5,4-d]pyrimidin-2-yl)(methyl)amino)-2-methylpropan-2-ol | 518.2 | ¹H NMR (400 MHz, CDCl₃) δ 9.07 (bs, 1H), 8.55 (m, 2H), 8.13 (d, J = 2.6 Hz, 1H), 7.66 (s, 1H), 7.37 (m, 2H), 7.11 (dd, J = 8.7, 2.2 Hz, 1H), 7.01 (d, J = 8.9 Hz, 1H), 3.92 (m, 3H), 3.83 (s, 3H), 3.72 (m, 2H), 1.31 (s, 6H) |
| 457 (Ex. 142) | 6-((1R,4R)-2-oxa-5-azabicyclo[2.2.1]heptan-5-yl)-N-(2-fluoro-3-methyl-4-((1-methyl-1H-benzo[d]imidazol-5-yl)oxy)phenyl)pyrimido[5,4-d]pyrimidin-4-amine | 499.2 | ¹H NMR (400 MHz, CDCl₃) δ 9.06 (m, 1H), 8.87 (m, 1H), 8.54 (s, 1H), 8.48 (t, J = 9.1 Hz, 1H), 7.86 (s, 1H), 7.34 (m, 2H), 7.06 (dd, J = 8.8, 2.3 Hz, 1H), 6.75 (d, J = 9.0 Hz, 1H), 3.95 (m, 3H), 3.86 (s, 3H), 3.72 (m, 2H), 2.29 (d, J = 2.1 Hz, 3H), 2.07 (m, 3H) |
| 458 (Ex. 142) | (S)-1-(8-((2-fluoro-3-methyl-4-((1-methyl-1H-benzo[d]imidazol-5-yl)oxy)phenyl)amino)pyrimido[5,4-d]pyrimidin-2-yl)pyrrolidin-3-ol | 487.3 | ¹H NMR (400 MHz, CDCl₃) δ 9.12 (s, 1H), 9.00 (m, 1H), 8.73 (s, 1H), 8.59 (m, 2H), 7.51 (m, 1H), 7.27 (m, 2H), 6.83 (dd, J = 9.0, 1.7 Hz, 1H), 4.52 (m, 2H), 4.01 (s, 3H), 3.65 (m, 2H), 2.23 (d, J = 2.1 Hz, 3H) 1.35 (s, 3H) |
| 459 (Ex. 40) | (1R,4R,5R)-2-(8-((3-methyl-4-((1-methyl-1H-benzo[d]imidazol-5-yl)oxy)phenyl)amino)pyrimido[5,4-d]pyrimidin-2-yl)-2-azabicyclo[2.2.1]heptan-5-ol | 495.2 | ¹H NMR (400 MHz, CD₃OD) δ 9.05-8.98 (m, 1H), 8.61-8.53 (m, 1H), 8.50 (s, 1H), 7.84 (s, 1H), 7.74 (d, J = 2.7 Hz, 1H), 7.64 (dd, J = 8.8, 2.6 Hz, 1H), 7.35-7.29 (m, 2H), 7.05 (dd, J = 8.7, 2.3 Hz, 1H), 6.92 (d, J = 8.7 Hz, 1H), 4.85-4.76 (m, 1H), 4.60-4.52 (m, 1H), 4.07 (d, J = 10.8 Hz, 1H), 3.84 (s, 3H), 3.53 (d, J = 10.7 Hz, 1H), 2.83 (s, 1H), 2.34 (s, 3H), 2.28-2.22 (m, 1H), 1.95-1.70 (m, 3H), 1.45 (d, J = 13.6 Hz, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 460 (Ex. 40) | (S)-4,4-difluoro-1-(8-((3-methyl-4-((1-methyl-1H-benzo[d]imidazol-5-yl)oxy)phenyl)amino)pyrimido[5,4-d]pyrimidin-2-yl)piperidin-3-ol | 519.2 | 1H NMR (400 MHz, CDCl3) δ 9.06 (s, 1H), 8.56 (s, 1H), 8.44 (s, 1H), 7.85 (s, 1H), 7.71 (d, J = 2.7 Hz, 1H), 7.63 (dd, J = 8.6, 2.7 Hz, 1H), 7.35-7.29 (m, 2H), 7.06 (dd, J = 8.7, 2.3 Hz, 1H), 6.92 (d, J = 8.7 Hz, 1H), 4.51-4.33 (m, 2H), 4.08-3.98 (m, 2H), 3.93-3.86 (m, 1H), 3.85 (s, 3H), 2.46-2.31 (m, 1H), 2.34 (s, 3H), 2.13-2.02 (m, 1H), 2.01 (s, 1H) |
| 461 (Ex. 40) | (S)-3-methyl-1-(8-((3-methyl-4-((1-methyl-1H-benzo[d]imidazol-5-yl)oxy)phenyl)amino)pyrimido[5,4-d]pyrimidin-2-yl)piperidin-3-ol | 497.2 | 1H NMR (400 MHz, CDCl3) δ 9.03 (s, 1H), 8.52 (s, 1H), 8.48 (s, 1H), 7.85 (s, 1H), 7.73 (d, J = 2.6 Hz, 1H), 7.64 (dd, J = 8.7, 2.7 Hz, 1H), 7.37-7.30 (m, 2H), 7.06 (dd, J = 8.8, 2.2 Hz, 1H), 6.93 (d, J = 8.6 Hz, 1H), 4.58-4.51 (m, 1H), 4.44 (d, J = 13.4 Hz, 1H), 3.85 (s, 3H), 3.38-3.28 (m, 2H), 2.35 (s, 3H), 2.00-1.90 (m, 1H), 1.87-1.81 (m, 2H), 1.78-1.63 (m, 2H), 1.35 (s, 3H) |
| 462 (Ex. 40) | 6-(hexahydro-5H-furo[2,3-c]pyrrol-5-yl)-N-(3-methyl-4-((1-methyl-1H-benzo[d]imidazol-5-yl)oxy)phenyl)pyrimido[5,4-d]pyrimidin-4-amine | 495.2 | 1H NMR (400 MHz, CDCl3) δ 9.06 (s, 1H), 8.58 (s, 1H), 8.53 (s, 1H), 7.85 (s, 1H), 7.75 (d, J = 2.6 Hz, 1H), 7.66 (dd, J = 8.7, 2.7 Hz, 1H), 7.35-7.30 (m, 2H), 7.06 (dd, J = 8.7, 2.3 Hz, 1H), 6.93 (d, J = 8.7 Hz, 1H), 4.70 (t, J = 5.2 Hz, 1H), 4.14-3.90 (m, 4H), 3.85 (s, 3H), 3.80 (dd, J = 13.1, 5.0 Hz, 1H), 3.61 (dd, J = 11.7, 6.2 Hz, 1H), 3.17-3.05 (m, 1H), 2.35 (s, 3H), 2.29-2.19 (m, 1H), 2.01-1.94 (m, 1H) |
| 463 (Ex. 40) | 4-methyl-1-(8-((3-methyl-4-((1-methyl-1H-benzo[d]imidazol-5-yl)oxy)phenyl)amino)pyrimido[5,4-d]pyrimidin-2-yl)-1,4-azaphosphinane 4-oxide | 515.2 | 1H NMR (400 MHz, CDCl3) δ 9.09 (s, 1H), 8.58 (s, 1H), 8.43 (s, 1H), 7.85 (s, 1H), 7.72 (d, J = 2.7 Hz, 1H), 7.62 (dd, J = 8.7, 2.7 Hz, 1H), 7.37-7.28 (m, 2H), 7.07 (dd, J = 8.7, 2.3 Hz, 1H), 6.93 (d, J = 8.6 Hz, 1H), 4.55-4.39 (m, 2H), 4.30 (tdd, J = 14.1, 9.3, 3.3 Hz, 2H), 3.85 (s, 3H), 2.35 (s, 3H), 2.20-2.07 (m, 2H), 1.94 (ddt, J = 14.7, 10.0, 5.1 Hz, 2H), 1.61 (d, J = 12.9 Hz, 3H) |
| 464 (Ex. 40) | 3-(8-((3-methyl-4-((1-methyl-1H-benzo[d]imidazol-5-yl)oxy)phenyl)amino)pyrimido[5,4-d]pyrimidin-2-yl)-3-azabicyclo[3.1.1]heptan-6-ol hydrochloride | 495.2 | 1H NMR (400 MHz, (CD3)2SO) δ 9.97 (s, 1H), 9.45 (s, 1H), 9.17 (s, 1H), 8.55 (s, 1H), 7.98 (d, J = 9.0 Hz, 1H), 7.91-7.87 (m, 2H), 7.36 (dd, J = 9.0, 2.4 Hz, 1H), 7.18 (d, J = 2.3 Hz, 1H), 7.10 (d, J = 8.4 Hz, 1H), 4.10 (t, J = 5.8 Hz, 1H), 4.06 (s, 3H), 4.03 (d, J = 2.8 Hz, 1H), 3.93 (dd, J = 12.0, 2.8 Hz, 1H), 3.84-3.74 (m, 2H), 2.61 (s, 2H), 2.23 (s, 3H), 1.67 (dt, J = 11.1, 5.9 Hz, 1H), 1.38 (d, J = 9.7 Hz, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 465 (Ex. 40) | 2-(8-((3-methyl-4-((1-methyl-1H-benzo[d]imidazol-5-yl)oxy)phenyl)amino)pyrimido[5,4-d]pyrimidin-2-yl)-2-azaspiro[3.3]heptan-5-ol | 495.2 | 1H NMR (400 MHz, CDCl3) δ 8.99 (s, 1H), 8.54-8.50 (m, 2H), 7.84 (s, 1H), 7.75-7.69 (m, 1H), 7.63 (dd, J = 8.8, 2.7 Hz, 1H), 7.35-7.29 (m, 2H), 7.05 (dd, J = 8.8, 2.3 Hz, 1H), 6.91 (d, J = 8.7 Hz, 1H), 4.75 (d, J = 9.0 Hz, 1H), 4.27 (t, J = 7.4 Hz, 1H), 4.12 (s, 2H), 4.05 (d, J = 9.1 Hz, 1H), 3.84 (s, 3H), 2.34 (s, 3H), 2.31-2.21 (m, 1H), 2.07-2.00 (m, 1H), 1.88-1.72 (m, 2H) |
| 466 (Ex. 40) | N-(3-methyl-4-((1-methyl-1H-benzo[d]imidazol-5-yl)oxy)phenyl)-6-((3aR,6aS)-tetrahydro-1H-furo[3,4-c]pyrrol-5(3H)-yl)pyrimido[5,4-d]pyrimidin-4-amine | 495.2 | 1H NMR (400 MHz, CDCl3) δ 9.06 (s, 1H), 8.57 (s, 1H), 8.54 (s, 1H), 7.86 (s, 1H), 7.74 (d, J = 2.7 Hz, 1H), 7.65 (dd, J = 8.7, 2.7 Hz, 1H), 7.35-7.30 (m, 2H), 7.06 (dd, J = 8.7, 2.3 Hz, 1H), 6.93 (d, J = 8.7 Hz, 1H), 4.08-3.93 (m, 4H), 3.85 (s, 3H), 3.79-3.72 (m, 4H), 3.16 (tq, J = 7.2, 3.9 Hz, 2H), 2.34 (s, 3H) |
| 467 (Ex. 40) | 2-((1s,3s)-3-(methyl(8-((3-methyl-4-((1-methyl-1H-benzo[d]imidazol-5-yl)oxy)phenyl)amino)pyrimido[5,4-d]pyrimidin-2-yl)amino)cyclobutyl)propan-2-ol | 525.3 | 1H NMR (400 MHz, CDCl3) δ 9.04 (s, 1H), 8.59 (s, 1H), 8.52 (s, 1H), 7.85 (s, 1H), 7.75 (d, J = 2.7 Hz, 1H), 7.64 (dd, J = 8.6, 2.7 Hz, 1H), 7.36-7.30 (m, 2H), 7.06 (dd, J = 8.6, 2.3 Hz, 1H), 6.93 (d, J = 8.7 Hz, 1H), 5.08-4.97 (m, 1H), 3.85 (s, 3H), 3.26 (s, 3H), 2.35 (s, 3H), 2.31-2.25 (m, 4H), 2.14-2.02 (m, 1H), 1.20 (s, 6H) |
| 468 (Ex. 40) | (S)-4,4-dimethyl-1-(8-((3-methyl-4-((1-methyl-1H-benzo[d]imidazol-5-yl)oxy)phenyl)amino)pyrimido[5,4-d]pyrimidin-2-yl)pyrrolidin-3-ol | 497.2 | 1H NMR (400 MHz, CDCl3) δ 9.05 (s, 1H), 8.57 (s, 1H), 8.52 (s, 1H), 7.85 (s, 1H), 7.75 (d, J = 2.7 Hz, 1H), 7.66 (d, J = 8.6 Hz, 1H), 7.36-7.29 (m, 2H), 7.06 (dd, J = 8.7, 2.3 Hz, 1H), 6.93 (d, J = 8.7 Hz, 1H), 4.11-4.00 (m, 2H), 3.85 (s, 3H), 3.75-3.68 (m, 1H), 3.61 (br s, 2H), 2.35 (s, 3H), 1.89 (br s, 1H), 1.22 (br s, 3H), 1.15 (s, 3H) |
| 469 (Ex. 40) | (R)-2-(1-(8-((3-methyl-4-((1-methyl-1H-benzo[d]imidazol-5-yl)oxy)phenyl)amino)pyrimido[5,4-d]pyrimidin-2-yl)pyrrolidin-3-yl)acetonitrile | 492.2 | 1H NMR (400 MHz, CDCl3) δ 9.07 (s, 1H), 8.55 (s, 2H), 7.85 (s, 1H), 7.75 (d, J = 2.7 Hz, 1H), 7.66 (dd, J = 8.7, 2.7 Hz, 1H), 7.37-7.29 (m, 2H), 7.06 (dd, J = 8.7, 2.3 Hz, 1H), 6.93 (d, J = 8.7 Hz, 1H), 4.05 (dd, J = 11.6, 7.2 Hz, 1H), 3.99-3.90 (m, 1H), 3.85 (s, 3H), 3.76 (dt, J = 11.5, 7.5 Hz, 1H), 3.52 (dd, J = 11.5, 7.2 Hz, 1H), 2.79 (dt, J = 14.3, 7.1 Hz, 1H), 2.64-2.56 (m, 2H), 2.42-2.35 (obs m, 1H), 2.35 (s, 3H), 2.04-1.97 (m, 1H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 470 (Ex. 40) | (1S,4S,5S)-2-(8-((3-methyl-4-((1-methyl-1H-benzo[d]imidazol-5-yl)oxy)phenyl)amino)pyrimido[5,4-d]pyrimidin-2-yl)-2-azabicyclo[2.2.1]heptan-5-ol | 495.2 | 1H NMR (400 MHz, CDCl3) δ 9.01 (br s, 1H), 8.56 (br s, 1H), 8.50 (s, 1H), 7.84 (s, 1H), 7.73 (d, J = 2.7 Hz, 1H), 7.64 (d, J = 8.7, 2.7 Hz, 1H), 7.35-7.29 (m, 2H), 7.05 (dd, J = 8.7, 2.2 Hz, 1H), 6.92 (d, J = 8.7 Hz, 1H), 4.86-4.76 (m, 1H), 4.61-4.49 (m, 1H), 4.07 (d, J = 10.7 Hz, 1H), 3.84 (s, 3H), 3.53 (dd, J = 10.6, 3.3 Hz, 1H), 2.83 (s, 1H), 2.34 (s, 3H), 2.25 (t, J = 11.6 Hz, 1H), 1.93 (d, J = 10.5 Hz, 1H), 1.73 (d, J = 10.3 Hz, 1H), 1.48-1.41 (m, 1H) |
| 471 (Ex. 40) | (1S,4S,5R)-2-(8-((3-methyl-4-((1-methyl-1H-benzo[d]imidazol-5-yl)oxy)phenyl)amino)pyrimido[5,4-d]pyrimidin-2-yl)-2-azabicyclo[2.2.1]heptan-5-ol | 495.2 | 1H NMR (400 MHz, CDCl3) δ 9.01 (s, 1H), 8.53 (s, 1H), 8.50 (s, 1H), 7.85 (s, 1H), 7.73 (s, 1H), 7.64 (d, J = 8.6 Hz, 1H), 7.35-7.29 (m, 2H), 7.06 (dd, J = 8.7, 2.3 Hz, 1H), 6.93 (d, J = 8.7 Hz, 1H), 4.95-4.83 (m, 1H), 4.15 (d, J = 6.6 Hz, 1H), 3.85 (s, 3H), 3.59 (dd, J = 10.9, 4.0 Hz, 1H), 3.21 (d, J = 10.9 Hz, 1H), 2.69 (s, 1H), 2.34 (s, 3H), 2.25-2.13 (m, 1H), 2.05 (d, J = 10.1 Hz, 1H), 1.79 (d, J = 9.8 Hz, 2H), 1.67 (d, J = 13.7 Hz, 1H) |
| 472 (Ex. 40) | 6-(hexahydro-1H-furo[3,4-b]pyrrol-1-yl)-N-(3-methyl-4-((1-methyl-1H-benzo[d]imidazol-5-yl)oxy)phenyl)pyrimido[5,4-d]pyrimidin-4-amine | 495.2 | 1H NMR (400 MHz, CDCl3) δ 9.03 (s, 1H), 8.55 (s, 1H), 8.51 (s, 1H), 7.85 (s, 1H), 7.74-7.70 (m, 1H), 7.68-7.64 (m, 1H), 7.35-7.30 (m, 2H), 7.06 (dd, J = 8.7, 2.3 Hz, 1H), 6.93 (d, J = 8.7 Hz, 1H), 4.50 (t, J = 6.5 Hz, 1H), 4.34-4.22 (m, 2H), 4.04 (t, J = 6.9 Hz, 1H), 4.01-3.90 (m, 1H), 3.85 (s, 3H), 3.79-3.73 (m, 1H), 3.69 (dd, J = 11.4, 7.2 Hz, 1H), 2.79 (dt, J = 11.8, 5.9 Hz, 1H), 2.35 (s, 3H), 2.23 (dtd, J = 11.1, 5.4, 2.0 Hz, 1H), 2.04-1.89 (m, 1H) |
| 473 (Ex. 40) | (R)-N2-methyl-N8-(3-methyl-4-((1-methyl-1H-benzo[d]imidazol-5-yl)oxy)phenyl)-N2-(tetrahydro-2H-pyran-3-yl)pyrimido[5,4-d]pyrimidine-2,8-diamine | 497.2 | 1H NMR (400 MHz, CDCl3) δ 9.07 (s, 1H), 8.56 (s, 1H), 8.54 (s, 1H), 8.18 (s, 1H), 7.75 (d, J = 2.7 Hz, 1H), 7.66 (dd, J = 8.7, 2.7 Hz, 1H), 7.37 (d, J = 8.8 Hz, 1H), 7.32 (d, J = 2.3 Hz, 1H), 7.10 (dd, J = 8.8, 2.3 Hz, 1H), 6.95 (d, J = 8.7 Hz, 1H), 4.96-4.88 (m, 1H), 4.04-3.94 (m, 2H), 3.91 (s, 3H), 3.53 (t, J = 10.5 Hz, 1H), 3.41 (td, J = 11.1, 2.9 Hz, 1H), 3.22 (s, 3H), 2.33 (s, 3H), 2.02 (s, 1H), 1.96-1.78 (m, 3H) |
| 474 (Ex. 30) | 6-(4,4-dimethyl-1,4-azasilinan-1-yl)-N-(3-methyl-4-((1-methyl-1H-benzo[d]imidazol-5-yl)oxy)phenyl)pyrimido[5,4-d]pyrimidin-4-amine | 511.2 | 1H NMR (400 MHz, CDCl3) δ 9.04 (s, 1H), 8.53 (d, J = 12.9 Hz, 1H), 7.84 (s, 1H), 7.73 (d, J = 2.7 Hz, 1H), 7.64 (dd, J = 8.7, 2.7 Hz, 1H), 7.33 (d, J = 5.3 Hz, 1H), 7.31 (s, 1H), 7.05 (dd, J = 8.8, 2.2 Hz, 1H), 6.93 (d, J = 8.7 Hz, 1H), 4.17-4.07 (m, 4H), 3.85 (s, 3H), 2.35 (s, 3H), 1.56 (s, 1H), 0.91 (t, J = 6.3 Hz, 4H), 0.14 (s, 6H) |

TABLE 1-continued

| Example No. (Method) | Structure; IUPAC name | LCMS M+1 | 1H NMR (ppm); 19F NMR (ppm); optical rotation; Chiral HPLC/SFC conditions |
|---|---|---|---|
| 475 (Ex. 40) | 3-methyl-1-(8-((3-methyl-4-((1-methyl-1H-benzo[d]imidazol-5-yl)oxy)phenyl)amino)pyrimido[5,4-d]pyrimidin-2-yl)pyrrolidine-3-carbonitrile | 492.2 | 1H NMR (400 MHz, CDCl3) δ 9.09 (s, 1H), 8.57 (s, 1H), 8.53 (s, 1H), 7.85 (s, 1H), 7.74 (d, J = 2.7 Hz, 1H), 7.66 (dd, J = 8.7, 2.7 Hz, 1H), 7.36-7.31 (m, 2H), 7.06 (dd, J = 8.7, 2.4 Hz, 1H), 6.93 (d, J = 8.7 Hz, 1H), 4.29 (d, J = 11.5 Hz, 1H), 3.97 (dd, J = 8.0, 5.9 Hz, 2H), 3.85 (s, 3H), 3.67 (d, J = 11.5 Hz, 1H), 2.60 (dt, J = 12.3, 5.9 Hz, 1H), 2.35 (s, 3H), 2.17 (dt, J = 12.8, 8.0 Hz, 1H), 1.64 (s, 3H) |
| 476 (Ex. 40) | 2-methyl-1-((8-((3-methyl-4-((1-methyl-1H-benzo[d]imidazol-5-yl)oxy)phenyl)amino)pyrimido[5,4-d]pyrimidin-2-yl)oxy)propan-2-ol | 472.2 | 1H NMR (400 MHz, CDCl3) δ 9.27 (s, 1H), 8.72 (s, 1H), 8.58 (s, 1H), 7.85 (s, 1H), 7.76 (d, J = 2.7 Hz, 1H), 7.65 (dd, J = 8.6, 2.7 Hz, 1H), 7.38-7.30 (m, 2H), 7.07 (dd, J = 8.7, 2.3 Hz, 1H), 6.93 (d, J = 8.7 Hz, 1H), 4.40 (s, 2H), 4.12 (q, J = 7.1 Hz, 1H), 3.86 (s, 3H), 2.37 (s, 3H), 2.29 (s, 1H), 2.04 (s, 1H), 1.45 (s, 6H) |
| 477 (Ex. 40) | 6-(4-(2,2-difluoroethyl)piperazin-1-yl)-N-(3-methyl-4-((1-methyl-1H-benzo[d]imidazol-5-yl)oxy)phenyl)pyrimido[5,4-d]pyrimidin-4-amine | 532.2 | 1H NMR (400 MHz, CDCl3) δ 9.04 (s, 1H), 8.54 (s, 1H), 8.48 (s, 1H), 7.85 (s, 1H), 7.74 (d, J = 2.7 Hz, 1H), 7.64 (dd, J = 8.6, 2.7 Hz, 1H), 7.36-7.29 (m, 2H), 7.06 (dd, J = 8.7, 2.3 Hz, 1H), 6.93 (d, J = 8.7 Hz, 1H), 5.96 (tt, J = 55.8, 4.3 Hz, 1H), 4.05-3.97 (m, 4H), 3.85 (s, 3H), 2.84 (td, J = 15.0, 4.3 Hz, 2H), 2.78-2.70 (m, 4H), 2.35 (s, 3H) |
| 478 (Ex. 40) | 1-(ethyl(8-((3-methyl-4-((1-methyl-1H-benzo[d]imidazol-5-yl)oxy)phenyl)amino)pyrimido[5,4-d]pyrimidin-2-yl)amino)-2-methylpropan-2-ol | 499.3 | 1H NMR (400 MHz, CDCl3) δ 9.02 (s, 1H), 8.54 (s, 1H), 8.48 (br s, 1H), 7.85 (s, 1H), 7.74-7.70 (m, 1H), 7.61 (dd, J = 8.7, 2.7 Hz, 1H), 7.36-7.30 (m, 2H), 7.05 (dd, J = 8.7, 2.3 Hz, 1H), 6.93 (d, J = 8.6 Hz, 1H), 3.86 (obs q, J = 6.9 Hz, 2H) 3.85 (s, 3H), 3.74 (s, 2H), 2.35 (s, 3H), 1.31-1.20 (m, 9H) |
| 479 (Ex. 40) | 4-((8-((3-chloro-4-((1-methyl-1H-benzo[d]imidazol-5-yl)oxy)phenyl)amino)pyrimido[5,4-d]pyrimidin-2-yl)(methyl)amino)-2-methylbutan-2-ol | 519.3 | 1H NMR (400 MHz, CD3OD) δ 9.06 (s, 1H), 8.77 (s, 1H), 8.55 (s, 1H), 8.20 (s, 1H), 7.87 (s, 1H), 7.66 (dd, J = 8.9, 2.6 Hz, 1H), 7.40-7.32 (m, 2H), 7.10 (dd, J = 8.7, 2.3 Hz, 1H), 7.00 (d, J = 8.8 Hz, 1H), 3.94-3.85 (m, 2H), 3.86 (s, 3H), 3.32 (s, 3H), 1.88 (t, J = 7.8 Hz, 2H), 1.34 (s, 6H), 1.26 (s, 1H), 1.32-1.22 (m, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 480 (Ex. 101) | 1-(8-((3-chloro-4-((1-methyl-1H-benzo[d]imidazol-5-yl)oxy)phenyl)amino)pyrimido[5,4-d]pyrimidin-2-yl)-4-methylpiperidin-4-ol | 517.1 | ¹H NMR (400 MHz, CDCl₃) δ 9.04 (s, 1H), 8.54 (s, 1H), 8.51 (s, 1H), 8.13 (d, J = 2.6 Hz, 1H), 7.87 (s, 1H), 7.69 (dd, J = 8.9, 2.6 Hz, 1H), 7.41-7.33 (m, 2H), 7.11 (dd, J = 8.7, 2.3 Hz, 1H), 7.01 (d, J = 8.9 Hz, 1H), 4.54-4.46 (m, 2H), 3.86 (s, 3H), 3.62 (ddd, J = 13.6, 10.0, 4.4 Hz, 2H), 1.72 (dd, J = 9.6, 4.1 Hz, 5H), 1.35 (s, 3H), 1.26 (d, J = 6.9 Hz, 2H) |
| 481 (Ex. 202) | 6-((1R,4R)-2-oxa-5-azabicyclo[2.2.1]heptan-5-yl)-N-(2-fluoro-5-methyl-4-((1-methyl-1H-benzo[d]imidazol-5-yl)oxy)phenyl)pyrimido[5,4-d]pyrimidin-4-amine | 499.3 | ¹H NMR (400 MHz, CDCl₃) δ 9.06 (s, 1H), 8.75 (s, 1H), 8.59 (s, 1H), 8.57 (s, 1H), 7.87 (s, 1H), 7.39-7.33 (m, 2H), 7.06 (dd, J = 8.8, 2.3 Hz, 1H), 6.68 (d, J = 11.9 Hz, 1H), 5.23 (s, 1H), 4.78 (s, 1H), 3.97 (s, 1H), 3.90 (s, 1H), 3.86 (s, 3H), 3.70 (q, J = 11.1 Hz, 2H), 2.36 (d, J = 0.9 Hz, 3H) |
| 482 (Ex. 202) | 1-(8-((2-chloro-5-methyl-4-((1-methyl-1H-benzo[d]imidazol-5-yl)oxy)phenyl)amino)pyrimido[5,4-d]pyrimidin-2-yl)-4-methylpiperidin-4-ol | 531.2 | ¹H NMR (400 MHz, CDCl₃) δ 9.26 (s, 1H), 9.04 (s, 1H), 8.79 (d, J = 0.9 Hz, 1H), 8.57 (s, 1H), 7.87 (s, 1H), 7.39-7.33 (m, 1H), 7.35 (s, 1H), 7.06 (dd, J = 8.7, 2.3 Hz, 1H), 6.94 (s, 1H), 4.47 (dd, J = 11.0, 6.7 Hz, 2H), 3.86 (s, 3H), 3.69-3.57 (m, 2H), 2.61 (s, 1H), 2.38 (d, J = 0.9 Hz, 3H), 1.75-1.63 (m, 4H), 1.33 (s, 3H) |
| 483 (Ex. 40) | 6-(4-ethoxypiperazin-1-yl)-N-(3-methyl-4-((1-methyl-1H-benzo[d]imidazol-5-yl)oxy)phenyl)pyrimido[5,4-d]pyrimidin-4-amine | 512.2 | ¹H NMR (400 MHz, CDCl₃) δ 9.04 (s, 1H), 8.54 (s, 1H), 8.48 (s, 1H), 7.85 (s, 1H), 7.78-7.71 (m, 1H), 7.64 (dd, J = 8.6, 2.7 Hz, 1H), 7.36-7.29 (m, 2H), 7.06 (dd, J = 8.7, 2.2 Hz, 1H), 6.93 (d, J = 8.7 Hz, 1H), 4.72 (s, 1H), 3.85 (s, 3H), 3.83 (q, J = 7.0 Hz, 2H), 3.37 (s, 4H), 2.70 (s, 2H), 2.62 (s, 1H), 2.35 (s, 3H), 1.23 (t, J = 7.0 Hz, 3H) |
| 484 (Ex. 101) | N-(3-chloro-4-((1-methyl-1H-benzo[d]imidazol-5-yl)oxy)phenyl)-6-(4-(2,2-difluoroethyl)piperazin-1-yl)pyrimido[5,4-d]pyrimidin-4-amine | 495.2 | ¹H NMR (400 MHz, CDCl₃) δ 9.06 (s, 1H), 8.56 (s, 1H), 8.49 (s, 1H), 8.13 (d, J = 2.6 Hz, 1H), 7.87 (s, 1H), 7.68 (dd, J = 8.9, 2.6 Hz, 1H), 7.41-7.33 (m, 2H), 7.11 (dd, J = 8.7, 2.3 Hz, 1H), 7.01 (d, J = 8.9 Hz, 1H), 5.96 (t, J = 4.3 Hz, 1H), 4.04-3.97 (m, 4H), 3.86 (s, 3H), 2.90-2.70 (m, 7H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 485 (Ex. 101) | N-(3-chloro-4-((1-methyl-1H-benzo[d]imidazol-5-yl)oxy)phenyl)-6-(4-(oxetan-3-yl)piperazin-1-yl)pyrimido[5,4-d]pyrimidin-4-amine | 544.3 | ¹H NMR (400 MHz, CDCl₃) 9.06 (s, 1H), 8.70 (d, J = 2.6 Hz, 1H), 8.61-8.53 (m, 2H), 7.87 (s, 1H), 7.36 (dd, J = 5.5, 3.1 Hz, 2H), 7.06 (dd, J = 8.8, 2.2 Hz, 1H), 6.68 (d, J = 12.0 Hz, 1H), 4.72 (d, J = 13.1 Hz, 2H), 3.87 (s, 3H), 3.60 (s, 3H), 3.38 (s, 4H), 2.66 (s, 2H), 2.36 (d, J = 0.9 Hz, 3H), 1.25 (s, 1H) |
| 486 (Ex. 202) | N-(2-fluoro-5-methyl-4-((1-methyl-1H-benzo[d]imidazol-5-yl)oxy)phenyl)-6-(4-methoxypiperazin-1-yl)pyrimido[5,4-d]pyrimidin-4-amine | 516.2 | ¹H NMR (400 MHz, CDCl₃) δ 9.06 (s, 1H), 8.70 (d, J = 2.6 Hz, 1H), 8.61-8.53 (m, 2H), 7.87 (s, 1H), 7.36 (dd, J = 5.5, 3.1 Hz, 2H), 7.06 (dd, J = 8.8, 2.2 Hz, 1H), 6.68 (d, J = 12.0 Hz, 1H), 4.72 (d, J = 13.1 Hz, 2H), 3.87 (s, 3H), 3.60 (s, 3H), 3.38 (s, 4H), 2.66 (s, 2H), 2.36 (d, J = 0.9 Hz, 3H), 1.25 (s, 1H) |
| 487 (Ex. 40) | 2-(8-((3-methyl-4-((1-methyl-1H-benzo[d]imidazol-5-yl)oxy)phenyl)amino)pyrimido[5,4-d]pyrimidin-2-yl)-6-(trifluoromethyl)-2-azaspiro[3.3]heptan-6-ol | 563.2 | ¹H NMR (400 MHz, CDCl₃) δ 8.92 (s, 1H), 8.52 (d, J = 4.2 Hz, 2H), 7.84 (s, 1H), 7.79 (d, J = 3.1 Hz, 1H), 7.75 (dd, J = 8.6, 2.7 Hz, 1H), 7.36 (dd, J = 8.7, 0.6 Hz, 1H), 7.23-7.18 (m, 1H), 7.12 (dd, J = 8.7, 2.3 Hz, 1H), 6.98 (d, J = 8.7 Hz, 1H), 4.56 (s, 1H), 4.25 (d, J = 4.0 Hz, 4H), 3.86 (s, 3H), 2.75 (d, J = 14.6 Hz, 2H), 2.49 (d, J = 13.7 Hz, 2H), 1.59 (s, 4H) |
| 488 (Ex. 202) | (S)-5-(8-((2-chloro-5-methyl-4-((1-methyl-1H-benzo[d]imidazol-5-yl)oxy)phenyl)amino)pyrimido[5,4-d]pyrimidin-2-yl)-5-azaspiro[2.4]heptan-7-ol | 529.3 | ¹H NMR (400 MHz, CDCl₃) δ 9.34 (s, 1H), 9.25 (s, 1H), 9.08 (s, 1H), 8.82 (s, 1H), 8.59 (s, 1H), 7.87 (s, 1H), 7.39-7.29 (m, 2H), 7.06 (dd, J = 8.8, 2.2 Hz, 1H), 6.93 (s, 1H), 4.05 (s, 1H), 3.99 (s, 2H), 3.90 (s, 1H), 3.86 (s, 3H), 3.51 (s, 1H), 2.38 (s, 3H), 1.87 (s, 1H), 0.95 (dt, J = 12.2, 6.0 Hz, 1H), 0.81 (s, 2H), 0.75 (q, J = 6.8, 6.2 Hz, 1H) |
| 489 (Ex. 101) | N-(3-chloro-4-((1-methyl-1H-benzo[d]imidazol-5-yl)oxy)phenyl)-6-((3aS,6aS)-hexahydro-1H-furo[3,4-b]pyrrol-1-yl)pyrimido[5,4-d]pyrimidin-4-amine | 515.1 | ¹H NMR (400 MHz, CDCl₃) δ 9.07 (s, 1H), 8.57 (d, J = 11.9 Hz, 2H), 8.15 (d, J = 2.6 Hz, 1H), 7.87 (s, 1H), 7.68 (d, J = 8.8 Hz, 1H), 7.41-7.33 (m, 2H), 7.11 (dd, J = 8.7, 2.3 Hz, 1H), 7.01 (d, J = 8.9 Hz, 1H), 4.69 (t, J = 5.4 Hz, 1H), 4.14-3.88 (m, 4H), 3.86 (s, 3H), 3.80 (dd, J = 13.1, 5.0 Hz, 1H), 3.61 (dd, J = 11.9, 6.3 Hz, 1H), 3.12 (t, J = 7.1 Hz, 1H), 2.25 (dq, J = 12.5, 7.7 Hz, 1H) |

TABLE 1-continued

| Example No. (Method) | Structure; IUPAC name | LCMS M+1 | ¹H NMR (ppm); ¹⁹F NMR (ppm); optical rotation; Chiral HPLC/SFC conditions |
|---|---|---|---|
| 490 (Ex. 40) | (R)-6-(3,4-dimethylpiperazin-1-yl)-N-(3-methyl-4-((1-methyl-1H-benzo[d]imidazol-5-yl)oxy)phenyl)pyrimido[5,4-d]pyrimidin-4-amine | 530.3 | ¹H NMR (400 MHz, CDCl₃) δ 9.27 (s, 1H), 9.06 (s, 1H), 8.81 (d, J = 0.9 Hz, 1H), 8.60 (s, 1H), 7.87 (s, 1H), 7.39-7.32 (m, 2H), 7.06 (dd, J = 8.6, 2.3 Hz, 1H), 6.94 (s, 1H), 4.72 (s, 1H), 4.66 (d, J = 15.1 Hz, 1H), 3.86 (s, 3H), 3.35 (s, 1H), 2.95 (s, 2H), 2.38 (d, J = 0.7 Hz, 3H), 1.25 (s, 3H), 1.22-1.16 (m, 4H), 0.83 (s, 1H) |
| 491 (Ex. 202) | 1-((8-((2-fluoro-5-methyl-4-((1-methyl-1H-benzo[d]imidazol-5-yl)oxy)phenyl)amino)pyrimido[5,4-d]pyrimidin-2-yl)(methyl)amino)-2-methylpropan-2-ol | 503.3 | ¹H NMR (400 MHz, CDCl₃) δ 9.03 (s, 1H), 8.78 (d, J = 7.3 Hz, 1H), 8.61 (d, J = 10.1 Hz, 2H), 7.87 (s, 1H), 7.39-7.32 (m, 2H), 7.05 (dd, J = 8.8, 2.2 Hz, 1H), 6.69 (d, J = 11.9 Hz, 1H), 3.96 (s, 1H), 3.86 (s, 3H), 3.81 (s, 2H), 3.40 (s, 3H), 1.32 (s, 6H), 1.25 (s, 1H), 0.07 (s, 1H) |
| 492 (Ex. 101) | (1S,4S,5R)-2-(8-((3-chloro-4-((1-methyl-1H-benzo[d]imidazol-5-yl)oxy)phenyl)amino)pyrimido[5,4-d]pyrimidin-2-yl)-2-azabicyclo[2.2.1]heptan-5-ol | 515.2 | ¹H NMR (400 MHz, CDCl₃) δ 9.02 (s, 1H), 8.53 (d, J = 6.5 Hz, 2H), 8.13 (s, 1H), 7.87 (s, 1H), 7.67 (d, J = 8.7 Hz, 1H), 7.40-7.33 (m, 2H), 7.11 (dd, J = 8.7, 2.3 Hz, 1H), 7.01 (d, J = 8.9 Hz, 1H), 4.93 (s, 1H), 4.15 (d, J = 6.7 Hz, 1H), 3.86 (s, 3H), 3.59 (dd, J = 11.0, 4.0 Hz, 1H), 3.20 (d, J = 10.9 Hz, 1H), 2.69 (s, 1H), 1.79 (d, J = 10.3 Hz, 1H), 1.68 (d, J = 13.7 Hz, 1H), 1.61 (s, 3H), 1.25 (s, 1H) |

BIOCHEMICAL ASSAYS

Construction of His8x-Tb-ErbB2(676-775)YVMA$_{insert}$ (776-1255) Expressing Vector and Protein Expression A DNA fragment optimized for insect cell expression that encodes a recombinant protein having the amino sequence shown in SEQ ID NO: 1 was synthesized with a 5'-flanking NcoI restriction enzyme site and two stop codons followed by a NotI restriction enzyme site at the 3'-end. In the sequence shown below, the ErbB2(676-775)YVMA$_{insert}$ (776-1255) amino sequence is underlined. The YVMA (SEQ ID NO: 2) insertion is marked with double underline.

```
SEQ ID NO: 1: Amino sequence of recombinant
His8x-Tb-ErbB2(676-775)YVMA_insert(776-1255)
protein
  1 MAHHHHHHHH GGGGGLVPRG KRRQQKIRKY TMRRLLQETE
    LVEPLTPSGA MPNQAQMRIL

61 KETELRKVKV LGSGAFGTVY KGIWIPDGEN VKIPVAIKVL
    RENTSPKANK EILDEAYVMA

121 YVMAGVGSPY VSRLLGICLT STVQLVTQLM PYGCLLDHVR
    ENRGRLGSQD LLNWCMQIAK

181 GMSYLEDVRL VHRDLAARNV LVKSPNHVKI TDFGLARLLD
    IDETEYHADG GKVPIKWMAL

241 ESILRRRFTH QSDVWSYGVT VWELMTFGAK PYDGIPAREI
    PDLLEKGERL PQPPICTIDV

301 YMIMVKCWMI DSECRPRFRE LVSEFSRMAR DPQRFVVIQN
    EDLGPASPLD STFYRSLLED

361 DDMGDLVDAE EYLVPQQGFF CPDPAPGAGG MVHHRHRSSS
    TRSGGGDLTL GLEPSEEEAP

421 RSPLAPSEGA GSDVFDGDLG MGAAKGLQSL PTHDPSPLQR
    YSEDPTVPLP SETDGYVAPL

481 TCSPQPEYVN QPDVRPQPPS PREGPLPAAR PAGATLERAK
    TLSPGKNGVV KDVFAFGGAV

541 ENPEYLTPQG GAAPQPHPPP AFSPAFDNLY YWDQDPPERG
    APPSTFKGTP TAENPEYLGL

601 DVPV (SEQ ID NO: 1)
```

This synthesized DNA fragment was subsequently cloned into the baculovirus transfer vector, pAcSG2, between the NcoI and NotI sites. The resulting plasmid was used along with BestBac™ linearized Baculovirus DNA from Expression Systems (Davis, CA, USA) to transfect Sf9 cells for generating recombinant Baculovirus that expresses the His8×-Tb-ErbB2(676-775)YVMA$_{insert}$(776-1255) (referred to as HER2-YVMA (SEQ ID NO: 2)) protein. High-titer Baculovirus stock was obtained by amplifying the virus twice from the initial transfection. For HER2-YVMA (SEQ ID NO: 2) protein expression, 10 L of Sf9 cell culture grown in a Wave cellbag (Cytiva, Marlborough, MA, USA), were infected with the recombinant virus stock at multiplicity of infection ("MOI") equal to 2.5 for 68 hours. At the end of the infection period, cells were harvested by centrifugation.

HER2-YVMA (SEQ ID NO: 2) Protein Purification

Insect cells expressing HER2-YVMA (SEQ ID NO: 2) were disrupted with a fluidizer in cold lysis buffer consisting of 50 mM Tris-HCl, pH8.0, 500 mM NaCl, 5 mM Imidazole, 10% glycerol, 1 mM TCEP [Tris-2-carboxyethyl)phosphine], 0.25% CHAPS {3-[(3-Cholamidopropyl)dimethylammonio]-1-propanesulfonate}, and protease inhibitor cocktail (Complete EDTA-free, Roche Applied Science). Cellular debris were removed from the homogenate by centrifugation at 4° C. HER2-YVMA (SEQ ID NO: 2) protein was enriched from the lysate using Talon metal affinity resin (TaKaRa Bio USA, Mountain View, CA, USA) and eluted from the metal resin in a buffer similar with the lysis buffer except an increased imidazole concentration to 200 mM and the omission of protease inhibitors. HER2-YVMA (SEQ ID NO: 2) pool collected from Talon affinity resin was passed through a Superdex-200 size-exclusion column (Cytiva Life Sciences, Marlborough, MA, USA) in 25 mM Tris-Cl, pH8.5 buffer with 500 mM NaCl, 10% glycerol, 1 mM TCEP, and 0.25% CHAPS. Monomeric HER2-YVMA (SEQ ID NO: 2) protein eluted from the size-exclusion column was further fractionated by a Resource Q anionic exchange column (Cytiva Life Sciences, Marlborough, MA, USA) with a linear salt gradient from 50 to 250 mM NaCl in a buffer containing 25 mM Tris-HCl, pH8.5, 10% glycerol, 1 mM TCEP, and 0.25% CHAPS. HER2-YVMA (SEQ ID NO: 2) fractions with the highest kinase activity were combined and designated as the source for HER2-YVMA (SEQ ID NO: 2) in vitro assays and studies.

ErbB Enzyme Assay

Compound potencies were determined using CisBio's HTRF Kinease-TK assay technology. The kinases were incubated with 250 nM TK-substrate biotin (CisBio, part of cat #62TK0PEC) at 1 mM ATP along with test compounds in a buffer consisting of 25 mM HEPES, pH 7.4, 10 mM MgCl2, 0.01% Triton X-100, and 2% DMSO in a volume of 8 µL. Compounds were prepared as a three-fold serial dilution in DMSO and added to the assay to give the appropriate final concentration. After 30-minute incubation at 22° C., the reaction was quenched by adding 8 µL of quench solution containing 62.5 nM Sa-XL665 and 0.25× TK-Ab-Cryptate in HTRF detection buffer (all from CisBio, part of cat #62TK0PEC). After a 1-hour incubation at 22° C., the extent of reaction was determined using a PerkinElmer EnVision multimode plate reader via HTRF dual wavelength detection, and the percent of control (POC) was calculated using a ratiometric emission factor. One hundred POC was determined using DMSO only samples (no compound present), and 0 POC was determined using pre-quenched control reactions. A 4-parameter logistic curve was fit to the POC values as a function of the concentration of compound, and the $IC_{50}$ value was the point where the best-fit curve crossed 50 POC.

Enzyme lots and concentration used are in Table 2.

TABLE 2

| Assay # | Enzyme Form | Vendor | Lot Number | Enzyme Concentration in assay (nM) |
|---|---|---|---|---|
| Assay 1 | ErbB2 insYVMA (SEQ ID NO: 2) | Pfizer | 190510B-P2 | 0.075 |
| Assay 2 | ErbB2 WT | ProQinase | 015 | 2.5 |
| Assay 3 | EGFR | ProQinase | 018 | 0.25 |

Cellular Phosphorylation Assay

Inhibition of constitutive ErbB2 and EGF-stimulated EGFR phosphorylation was determined by the following in vitro cellular mechanistic assay using the compounds that exhibited a level activity in an enzyme assay.

NIH 3T3 cells were engineered to express ErbB2 with Exon 20 YVMA insertion (HER2-YVMA (SEQ ID NO: 2); Assay 4) or EGFR wild type (EGFR WT; Assay 5, footnote 1) with constructs obtained from GenScript and grown in DMEM supplemented with 10% fetal bovine serum and 15 µg/ml blasticidin. Cells were plated in 96-well plates at 40,000 or 45,000 cells/well for HER2-YVMA (SEQ ID NO: 2) and EGFR WT assays, respectively, and allowed to attach overnight at 37° C./5% $CO_2$. Serially diluted compounds were added to the plates for 1 hour at 37° C./5% $CO_2$. EGFR WT cells were stimulated with 100 ng/ml rEGF for an additional 10 minutes at 37° C./5% $CO_2$. After compound incubation, medium was removed from the cells, which were then fixed in 3.7% formaldehyde in PBS at room temperature for 20 minutes. Following a wash with PBS, cells were permeabilized with 100% methanol at room temperature for 10 minutes. Cells were then washed with PBS/0.05% Tween-20 and blocked with Odyssey blocking buffer (LI-COR Biosciences) for at least 1 hour at room temperature. Antibodies to phosphorylated ErbB2 (Y1196, Cell Signaling #6942) or phosphorylated EGFR (Y1068, Cell Signaling #3777) and GAPDH (Millipore #MAB374) were added to the cells in blocking buffer containing 0.05% azide and incubated overnight at 4° C. After washing with PBS/0.05° i° Tween-20, the cells were incubated with fluorescently labeled secondary anti-rabbit antibody (LiCOR, IRDye 800CW #926-32211) and anti-mouse antibody (Molecular Probes, Alexa Fluor 680 #A21058) for 1 hour at room temperature in the dark. Cells were then washed and analyzed for fluorescence at both wavelengths using the Odyssey Infrared Imaging System (LI-COR Biosciences). Phosphorylated ErbB2 and EGFR signal was normalized to GAPDH signal to generate curves and calculate $IC_{50}$ values.

NIH 3T3 cells were engineered to express EGFR wild type (EGFR WT; Assay 5, no footnote) with constructs obtained from GenScript and grown in DMEM supplemented with 10% fetal bovine serum and 15 µg/ml blasticidin. Cells were plated in 96-well plates at 20,000 cells/well and allowed to attach overnight at 37° C./5% $CO_2$. Serially diluted compounds were added to the plates for 1 hour at 37° C./5% $CO_2$. EGFR WT cells were stimulated with 100 ng/ml rEGF for an additional 10 minutes at 37° C./5% $CO_2$. After compound incubation, medium was removed from the cells, which were then lysed in 100 µL/well lysis buffer according to the manufacturer's protocol (R&D Systems, DYC1095, Human Phospho-EGFR DuoSet IC ELISA). Same protocol was followed to determine the total levels of phospho-EGFR by measuring the optical density of each well using a VersaMax microplate reader. Curves were then generated and $IC_{50}$ values calculated.

MDR1 Transfected LLC-PK1, MDR1 Transfected MDCKII Canine Mdr1 Knockout, BCRP Transfected MDCKII, and BCRP Transfected MDCKII Canine Mdr1 Knockout Cell Culture and Experimental Conditions Both MDR1 transfected LLC-PK1 (Assay 6) and MDR1 transfected MDCKII canine Mdr1 knockout cells (Assay 7) were cultured and plated according to manufacturer's recommendations with the exception that the passage media for the MDR1 transfected LLC-PK1 cell line contained only 2% fetal bovine serum so as to extend passage time out to seven days.

BCRP transfected MDCKII cells (Assay 8) and BCRP transfected MDCKII canine Mdr1 knockout cells (Assay 9) were cultured and plated according to manufacturer's recommendations.

Both positive and negative controls were used to assess functionality of P-gp or BCRP efflux in the assays. Stock solutions for assay controls and the test article were prepared in DMSO for final test concentration of 1 µM. Final organic concentration in the assay was 1%. All dosing solutions contained 10 µM lucifer yellow to monitor MDCKII cell monolayer integrity.

For the apical to basolateral determination (A to B), 75 µL of the test article in transport buffer were added to the apical side of the individual transwells and 250 µL of basolateral media, without compound or lucifer yellow, were added to each well. For the basolateral to apical determination (B to A), 250 µL of test article in transport buffer were added to each well and 75 µL transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, PA) at 50 rpm and 37° C. with 5% $CO_2$. All culture plates were removed from the incubator, 50 µL of media were removed from the apical and basolateral portion of each well, and added to 150 µL of 1 µM labetalol in 2:1 acetonitrile (ACN): $H_2O$, v/v.

The plates were read using a Molecular Devices (Sunnyvale, CA) Gemini Fluorometer to evaluate the lucifer yellow concentrations at excitation/emission wavelengths of 425/535 nm. These values were accepted when found to be below 2% for apical to basolateral and 5% basolateral to apical flux across the MDR1-transfected LLC-PK1 or BCRP-transfected MDCKII cell monolayers. The plates were sealed, and the contents of each well analyzed by LC MS/MS. The compound concentrations were determined from the ratio of the peak areas of the compound to the internal standard (labetalol) in comparison to the dosing solution.

A MDS Sciex API 4000 (Applied Biosystems, Foster City, CA) mass spectrometer was used for detection of the analytes in the ion spray positive mode. Analyte responses were measured by multiple reaction monitoring ("MRM") of transitions unique to each compound (the protonated precursor ion and selected product ions for each test article and m/z 329 to m/z 162 for labetalol, the internal standard.

The LC unit was comprised of one of the following systems: (1) HTS-PAL autosampler (Leap Technologies, Carrboro, NC), and a 1200 HPLC (Agilent, Palo Alto, CA). Chromatographic separation of the analyte and internal standard was achieved at room temperature using a C18 column (Kinetics®, 30×3 mm, 2.6 µm particle size, Phenomenex, Torrance, CA) in conjunction with gradient conditions using mobile phases A (water containing 1% isopropyl alcohol and 0.1% formic acid) and B (0.1% formic acid in ACN). The total run time, including re-equilibration, for a single injection was 1.2 minutes. (2) LS-1 autosampler (Sound Analytics, Niantic, CT) and a 1290 Infinity II HPLC (Agilent, Palo Alto, CA). Chromatographic separation of the analyte and internal standard was achieved at room temperature using a C18 column (HALO, 2.1×20 mm, 2.7 µm particle size) in conjunction with gradient conditions using mobile phases A (water containing 1% isopropyl alcohol and 0.1% formic acid) and B (0.1% formic acid in ACN). The total run time, including re-equilibration, for a single injection was 0.61 minutes.

The permeability coefficient ($P_{app}$) is calculated from the following equation:

$$P_{app} = [((C_d * V * (1 \times 10^6))/(t * 0.12 \text{ cm}^2 * C_0]$$

where $C_d$, V, t and $C_0$ are the detected concentration (µM), the volume on the dosing side (mL), the incubation time(s) and the initial dosing concentration (µM), respectively. The calculations for $P_{app}$ were made for each replicate and then averaged.

An efflux ratio is calculated from the mean apical to basolateral (A-B) Papp data and basolateral to apical (B-A) Papp data:

$$\text{Efflux ratio} = P_{app}(B-A)/P_{app}(A-B)$$

Biological activity data for representative compounds of the invention are provided in Table 3 below.

TABLE 3

| Table Example No. | Assay 1 $IC_{50}$ (nM) | Assay 2 $IC_{50}$ (nM) | Assay 3 $IC_{50}$ (nM) | Assay 4 $IC_{50}$ (nM) | Assay 5 $IC_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 1 | 19.3 | 41.1 | 10000 | 29.2 | 5000[1] | 1.2 | 1.4 | | |
| 2 | 7.9 | 14.9 | 4642.8 | 4745.5 | 5000[1] | | | | |
| 3 | 12.5 | 52.4 | 8250.4 | 42.9 | 5000[1] | 1 | 1 | | |
| 4 | 8.9 | 30 | 4902.1 | 7.2 | 5000[1] | 0.9 | 1.4 | | |
| 5 | 9.8 | 10.9 | 4150.1 | 4447.3 | 5000[1] | | | | |
| 6 | 24.6 | 231.9 | 10000 | 1449.4 | 5000[1] | | | | |
| 7 | 18.5 | 56.8 | 2012.9 | 145.5 | 5000[1] | 1 | 1.3 | | |
| 8 | 22.7 | 69.7 | 10000 | 159.1 | 5000[1] | 0.9 | 1 | | |
| 9 | 13.6 | 64 | 10000 | 4.9 | 5000[1] | 0.8 | 1.2 | | |
| 10 | 49 | 143.7 | 10000 | 671.2 | 5000[1] | | | | |
| 11 | 54.4 | 97.4 | 925.1 | 95.1 | 5000[1] | 0.7 | 0.7 | | |
| 12 | 64.2 | 275.4 | 10000 | 402.6 | 5000[1] | | | | |
| 13 | 35.1 | 120.7 | 10000 | 295.4 | 5000 | | | | |
| 14 | 56.2 | 85.9 | 10000 | 37.0 | 5000 | 1.3 | | 0.9 | |
| 15 | 21.4 | 51.1 | 10000 | 23.4 | 5000 | | | | |
| 16 | 26.0 | 60.6 | 10000 | 15.2 | 5000 | 1.2 | | | 1.8 |
| 17 | 7.0 | 6.0 | 2346.5 | 9.2 | 5000 | 6.6 | | | |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 18 | 122.3 | 166.9 | 10000 | 47.8 | 5000 | 2.6 | | | |
| 19 | 28.2 | 36.8 | 4484.9 | 21.6 | 5000 | 1.8 | | | 2.7 |
| 20 | 66.1 | 130.5 | 10000 | 44.8 | 5000 | 1.9 | | 0.7 | |
| 21 | 33.7 | 98.4 | 1000 | 82.7 | | | | | |
| 22 | 25.5 | 52.4 | 8700.8 | 13.0 | 5000 | 1.7 | | | 1.5 |
| 23 | 313.3 | 1340.0 | 10000 | 717.2 | | | | | |
| 24 | 18.2 | 31.5 | 10000 | 7.1 | 5000 | 30.0 | | | |
| 25 | 172.1 | 328.9 | 10000 | 53.4 | | 1.7 | | | 1.4 |
| 26 | 85.6 | 506.6 | 10000 | 62.2 | 5000 | | | | |
| 27 | 20.0 | 50.8 | 10000 | 9.3 | 5000 | 2.2 | | | 1.9 |
| 28 | 68.7 | 162.9 | 10000 | 24.8 | 5000 | 13.3 | | | |
| 29 | 37.8 | 65.9 | 10000 | 20.6 | 5000 | 11.6 | | | |
| 30 | 103.9 | 196.4 | 10000 | 165.3 | 5000 | | | | |
| 31 | 117.2 | 158.3 | 10000 | 23.3 | 5000 | 1.3 | | | 1.4 |
| 32 | 34.6 | 43.4 | 10000 | 13.4 | 5000 | 34.5 | | | |
| 33 | 100.1 | 370.6 | 10000 | 582.8 | | | | | |
| 34 | 123.5 | 306.7 | 10000 | 30.5 | 5000 | 6.3 | | | |
| 35 | 33.5 | 94.2 | 10000 | 7.8 | 5000 | 1.3 | | | 1.2 |
| 36 | 26.3 | 64.6 | 8998.0 | 41.6 | 5000 | 1.2 | | | 0.9 |
| 37 | 78.8 | 393.4 | 10000 | 173.8 | | | | | |
| 38 | 182.7 | 403.4 | 10000 | 65.1 | 5000 | | | | |
| 39 | 198.7 | 357.7 | 10000 | 292.1 | | | | | |
| 40 | 71.5 | 144.7 | 10000 | 91.5 | | | | | |
| 41 | 196.1 | 233.9 | 10000 | 53.0 | | 1.5 | | | 1.9 |
| 42 | 58.2 | 175.6 | 10000 | 16.8 | 5000 | 1.0 | | | 1.5 |
| 43 | 28.8 | 59.8 | 10000 | 92.1 | | | | | |
| 44 | 103.3 | 315.1 | 3309.7 | 70.6 | 5000 | 1.2 | | 1.8 | |
| 45 | 31.0 | 25.0 | 4740.9 | 56.2 | | 2.2 | | | |
| 46 | 95.2 | 760.3 | 4249.6 | 566.1 | 5000 | | | | |
| 47 | 59.6 | 91.0 | 10000 | 13.4 | 5000 | 1.1 | | | 2.3 |
| 48 | 56.6 | 189.4 | 10000 | 48.5 | 5000 | 1.6 | | | 7.2 |
| 49 | 55.3 | 240.6 | 2252.3 | 132.3 | 5000 | 1.7 | | 5.1 | |
| 50 | 4.8 | 11.4 | 362.7 | 93.6 | 5000 | 1.2 | | | |
| 51 | 41.1 | 79.3 | 10000 | 52.1 | | 4.4 | | | |
| 52 | 100.1 | 316.7 | 10000 | 160.1 | | | | | |
| 53 | 25.0 | 75.2 | 10000 | 42.7 | 5000 | 1.7 | | | 1.6 |
| 54 | 5.6 | 31.3 | 3427.6 | 17.8 | 5000 | 1.4 | | | 1.1 |
| 55 | 110.5 | 260.3 | 10000 | 98.4 | | | | | |
| 56 | 205.4 | 403.3 | 10000 | 105.2 | | | | | |
| 57 | 30.2 | 37.7 | 6628.1 | 9.4 | 5000 | 1.1 | | | 1.4 |
| 58 | 62.5 | 123.2 | 10000 | 10.6 | 5000 | | | | |
| 59 | 29.7 | 44.3 | 10000 | 23.5 | 5000 | 2.0 | | | 7.4 |
| 60 | 19.4 | 27.6 | 8863.9 | 8.5 | 5000 | 2.6 | | | |
| 60a | 18.4 | 28.9 | 8275.5 | 16.0 | 5000 | 1.8 | | | 1.2 |
| 60b | 16.1 | 18.7 | 5680.8 | 17.9 | 5000 | 1.9 | | | 1.4 |
| 61 | 36.9 | 106.8 | 10000 | 49.5 | 5000 | | | | |
| 62 | 39.8 | 111.9 | 10000 | 27.1 | 5000 | 1.7 | | | 1.1 |
| 63 | 195.5 | 862.2 | 10000 | 191.1 | | | | | |
| 64 | 156.9 | 1297.8 | 10000 | 324.4 | | | | | |
| 65 | 8.6 | 23.0 | 3000.1 | 8.8 | 5000 | 1.6 | | | 1.9 |
| 66 | 53.9 | 179.7 | 10000 | 41.4 | 5000 | 11.6 | | | |
| 67 | 15.1 | 34.3 | 10000 | 86.7 | | 2.1 | | | |
| 68 | 10.2 | 16.3 | 8231.1 | 10.7 | 5000 | 1.8 | | | 0.9 |
| 69 | 27.6 | 161.1 | 10000 | 35.8 | | 2.6 | | | |
| 70 | 106.2 | 70.3 | 10000 | 4.9 | 5000 | 1.8 | | | 1.0 |
| 71 | 70.2 | 299.4 | 10000 | 76.6 | 5000 | 1.3 | | 3.2 | |
| 72 | 69.6 | 83.9 | 10000 | 76.6 | | | | | |
| 73 | 78.0 | 162.7 | 10000 | 47.5 | 5000 | | | | |
| 74 | 33.0 | 35.5 | 3720.7 | 14.6 | 5000 | 1.7 | | | 1.3 |
| 75 | 51.8 | 141.4 | 10000 | 23.9 | | 1.0 | | | 1.6 |
| 76 | 336.7 | 2336.7 | 10000 | 1297.5 | | | | | |
| 77 | 26.0 | 48.9 | 10000 | 17.2 | 5000 | 1.7 | | | 1.9 |
| 78 | 60.4 | 422.2 | 10000 | 36.7 | 5000 | 1.3 | | | 1.1 |
| 79 | 26.3 | 33.8 | 3494.6 | 7.7 | 5000 | 7.1 | | | 9.8 |
| 80 | 35.6 | 431.4 | 10000 | 47.1 | 5000 | 2.1 | | | 2.4 |
| 81 | 152.6 | 846.9 | 10000 | 77.1 | | | | | |
| 82 | 47.0 | 204.2 | 1222.8 | 54.7 | 5000 | 1.3 | | 1.0 | |
| 83 | 12.4 | 34.5 | 5653.9 | 20.3 | 5000 | 76 | | | |
| 84 | 14.0 | 47.2 | 5376.8 | 25.5 | 5000 | 10.2 | | | |
| 85 | 203.6 | 726.3 | 10000 | 129.5 | 5000 | | | | |
| 86 | 39.5 | 300.6 | 10000 | 261.2 | | | | | |
| 87 | 69.5 | 346.0 | 10000 | 95.1 | 5000 | | | | |
| 88 | 4.8 | 8.6 | 9484.8 | 5.1 | 5000 | 1.9 | | | 1.0 |
| 89 | 68.1 | 284.9 | 10000 | 187.5 | | | | | |
| 90 | 41.0 | 93.1 | 10000 | 29.0 | 5000 | | | | |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 91 | 12.8 | 20.6 | 6834.5 | 14.1 | 5000 | | 2.5 | | 50.1 |
| 92 | 10.7 | 18.9 | 8783.0 | 23.3 | 5000 | | 3.8 | | |
| 93a | 17.0 | 16.0 | 1455.1 | 20.6 | 5000 | | 1.3 | | 1.9 |
| 93b | 16.2 | 11.6 | 1346.2 | 13.9 | 5000 | | | | |
| 94 | 21.3 | 31.3 | 4364.7 | 20.3 | 5000 | | 12.0 | | |
| 95 | 25.2 | 95.1 | 10000 | 178.8 | 5000 | | | | |
| 96 | 23.1 | 81.2 | 8890.4 | 96.1 | 5000 | 1.4 | | | 0.7 |
| 97 | 14.2 | 31.0 | 10000 | 47.5 | 5000 | | 2.0 | | |
| 98 | 232.0 | 1950.8 | 10000 | 266.1 | 5000 | | | | |
| 99 | 17.1 | 18.0 | 6473.0 | 44.5 | 5000 | | | | |
| 100 | 28.8 | 31.8 | 4151.5 | 21.1 | 5000 | | 1.5 | | 18.2 |
| 101 | 15.4 | 14.7 | 10000 | 8.2 | 5000 | | 1.5 | | |
| 102 | 23.8 | 20.7 | 2726.8 | 9.4 | 5000 | | | | |
| 103 | 20.3 | 56.6 | 10000 | 61.5 | 5000 | | | | |
| 104 | 18.6 | 18.2 | 4675.3 | 31.8 | 5000 | | 1.4 | | 16.0 |
| 105 | 56.7 | 48.5 | 10000 | 39.0 | 5000 | | 2.0 | | 8.6 |
| 106 | 16.8 | 16.6 | 2837.4 | 18.4 | 5000 | | 2.6 | | 24.3 |
| 107 | 30.8 | 15.5 | 10000 | 31.3 | 5000 | | 3.2 | | |
| 108 | 38.4 | 38.9 | 4310.2 | | | | | | |
| 109 | 23.1 | 81.2 | 8890.4 | 96.1 | 5000 | 1.4 | | | 0.7 |
| 110 | 33.5 | 32.8 | 3165.1 | 61.7 | 5000 | | 1.9 | | 32.2 |
| 111 | 28.2 | 24.0 | 3527.0 | 13.0 | 5000 | 1.3 | 1.7 | | 1.6 |
| 112 | 18.7 | 44.1 | 10000 | 190.1 | 5000 | | | | |
| 113 | 13.1 | 23.0 | 8477.5 | 9.5 | 5000 | | 0.9 | | 11.0 |
| 114 | 50.1 | 96.3 | 7886.9 | 20.1 | 5000 | | 1.5 | | 1.2 |
| 115 | 52.4 | 56.7 | 2185.5 | 15.6 | 5000 | | | | |
| 116 | 17.3 | 14.8 | 1166.9 | 27.8 | 5000 | | 1.3 | | 1.8 |
| 117 | 46.7 | 93.3 | 10000 | 8.3 | 5000 | | | | |
| 118 | 54.2 | 88.7 | 10000 | 39.8 | 5000 | 7.4 | | | |
| 119 | 26.8 | 30.7 | 9319.2 | 24.7 | 5000 | 29.6 | | | |
| 120 | 20.6 | 19.0 | 5339.3 | 49.4 | 5000 | | 1.3 | | 7.8 |
| 121 | 32.4 | 121.1 | 10000 | 666.8 | 5000 | | | | |
| 122 | 15.2 | 22.7 | 952.9 | 19.7 | 5000 | | 1.7 | | 7.3 |
| 123 | 26.5 | 118.5 | 10000 | 13.2 | 5000 | | 1.6 | | 2.4 |
| 124 | 16.0 | 14.3 | 2748.7 | 64.8 | 5000 | | 1.4 | | 10.3 |
| 125 | 24.8 | 55.6 | 10000 | 32.4 | 5000 | 36.1 | | | |
| 126 | 15.5 | 18.3 | 10000 | 14.3 | 5000 | 3.8 | | | |
| 127 | 40.7 | 113.5 | 10000 | 151.1 | 5000 | | | | |
| 128 | 21.0 | 20.0 | 3270.5 | 36.3 | 5000 | | 1.6 | | 1.4 |
| 129 | 12.4 | 15.0 | 864.8 | 7.6 | 5000 | | 1.4 | | 1.7 |
| 130 | 41.7 | 36.3 | 2561.4 | 43.3 | 5000 | | 1.3 | | 1.0 |
| 131 | 21.0 | 20.0 | 3270.5 | 36.3 | 5000 | | 1.6 | | 1.4 |
| 132 | 5.8 | 5.6 | 800.7 | 19.9 | 5000 | | 1.1 | | 1.8 |
| 133 | 10.8 | 26.2 | 5715.3 | 55.4 | 5000 | | | | |
| 134 | 55.1 | 53.5 | 10000 | 8.5 | 5000 | | 1.8 | | 6.8 |
| 135 | 26.2 | 45.7 | 10000 | 514.1 | 5000 | | | | |
| 136 | 55.3 | 59.3 | 10000 | 314.6 | 5000 | | | | |
| 137 | 97.7 | 166.1 | 10000 | 1079.4 | 5000 | | | | |
| 138 | 32.2 | 33.6 | 4905.5 | 58.2 | 5000 | | | | |
| 139 | 9.6 | 12.6 | 1573.9 | 6.3 | 5000 | 11.5 | | | |
| 140 | 21.3 | 20.3 | 6359.4 | 8.1 | 5000 | 7.5 | | | |
| 141 | 23.2 | 25.9 | 4444.6 | 17.1 | 5000 | | | | 1.4 |
| 142 | 24.2 | 50.7 | 10000 | 72.7 | 5000 | | | | |
| 143 | 35.1 | 50.7 | 7405.3 | 28.2 | 5000 | | | | |
| 144 | 59.5 | 78.2 | 6908.5 | 38.1 | 5000 | | | | |
| 145 | 19.3 | 19.6 | 896.3 | 20.2 | 5000 | | 0.7 | | 2.1 |
| 146 | 54.1 | 58.2 | 3718.8 | 35.5 | 5000 | | 0.8 | | 5.1 |
| 147 | 74.2 | 45.5 | 2649.2 | 32.6 | 5000 | | 1.0 | | 2.7 |
| 148 | 24.3 | 34.0 | 10000 | 13.0 | 5000 | | 1.3 | | |
| 149 | 99.0 | 102.0 | 10000 | 26.5 | 5000 | | 1.0 | | |
| 150 | 32.0 | 22.3 | 10000 | 9.1 | 5000 | | 2.2 | | |
| 151 | 24.6 | 61.4 | 10000 | 18.8 | 5000 | | 1.2 | | |
| 152 | 36.7 | 78.7 | 10000 | 31.9 | 5000 | | | | |
| 153 | 7.6 | 16.3 | 5552.2 | 25.0 | 5000 | | 1.5 | | 1.4 |
| 154 | 10.3 | 8.0 | 1940.7 | 15.7 | 5000 | | 2.1 | | 34.0 |
| 155 | 22.5 | 52.9 | 4284.5 | 5.5 | 5000 | | | | |
| 156 | 6.4 | 5.2 | 10000 | 12.3 | 5000 | | 2.0 | | 26.0 |
| 157 | 33.5 | 56.8 | 10000 | 27.8 | 5000 | | 2.1 | | 21.0 |
| 158 | 29.4 | 58.2 | 10000 | 9.8 | 5000 | | 1.9 | | 33.8 |
| 159 | 28.7 | 40.7 | 7365.7 | 17.0 | 5000 | | 2.1 | | 9.6 |
| 160 | 20.3 | 67.2 | 6757.8 | 42.8 | 5000 | | | | |
| 161 | 18.4 | 28.9 | 8275.5 | 16.0 | 5000 | 1.8 | | | 1.2 |
| 162 | 19.4 | 31.6 | 7360.9 | 36.4 | 5000 | | 2.8 | | |
| 163 | 28.2 | 36.8 | 4484.9 | 21.6 | 5000 | 1.8 | | | 2.7 |
| 164 | 28.0 | 52.3 | 10000 | 9.0 | 5000 | | | | 2.2 |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 165 | 7.5 | 5.6 | 216.0 | 11.4 | 5000 | | 2.1 | | |
| 166 | 16.1 | 39.7 | 10000 | 3.0 | 5000 | 4.6 | | | |
| 167 | 17.7 | 34.6 | 9048.1 | 24.2 | 5000 | | 2.8 | | |
| 168 | 39.1 | 112.9 | 3682.8 | 6.5 | 5000 | | 2.0 | | 16.7 |
| 169 | 8.5 | 11.2 | 1626.7 | 4.7 | 5000 | | 3.6 | | |
| 170 | 20.1 | 28.6 | 10000 | 3.4 | 5000 | | 2.1 | | 36.0 |
| 171 | 13.5 | 5.9 | 471.5 | 7.1 | 5000 | | 1.9 | | 8.6 |
| 172 | 31.0 | 35.2 | 8920.5 | 26.2 | 5000 | | 1.5 | | 2.0 |
| 173 | 21.8 | 50.5 | 10000 | 22.6 | 5000 | | 1.2 | | 4.3 |
| 174 | 11.5 | 31.4 | 2768.9 | 8.0 | 5000 | | 3.1 | | |
| 175 | 4.2 | 6.3 | 6511.5 | 13.9 | 5000 | | 1.4 | | 1.5 |
| 176 | 32.2 | 30.8 | 1245.6 | 25.4 | 5000 | | 1.4 | | 13.5 |
| 177 | 53.2 | 150.5 | 10000 | 108.6 | | | | | |
| 178 | 20.9 | 67.1 | 10000 | 9.9 | 5000 | 3.7 | | | |
| 179 | 10.1 | 12.9 | 3828.1 | 28.2 | 5000 | | 1.9 | | 15.3 |
| 180 | 13.2 | 20.9 | 4593.7 | 15.4 | 5000 | | 1.3 | | 2.7 |
| 181 | 81.5 | 171.2 | 10000 | 53.4 | 5000 | 0.3 | | | |
| 182 | 29.5 | 34.7 | 3132.4 | 17.7 | 5000 | | 1.3 | | 1.9 |
| 183 | 4.4 | 5.8 | 1053.3 | 5.1 | 5000 | | 1.7 | | 19.5 |
| 184 | 11.7 | 38.1 | 10000 | 20.2 | 5000 | | 1.8 | | 4.2 |
| 185 | 24.3 | 12.1 | 10000 | 25.2 | 5000 | | 2.0 | | 31.7 |
| 186 | 5.7 | 3.7 | 592.3 | 4.1 | 5000 | | 1.4 | | 24.2 |
| 187 | 38.4 | 108.7 | 10000 | 14.3 | 5000 | 2.7 | | | |
| 188 | 27.5 | 27.1 | 10000 | 20.5 | 5000 | | 1.0 | | 10.9 |
| 189 | 12.7 | 32.2 | 6464.5 | 13.9 | 5000 | 4.2 | | | |
| 190 | 21.5 | 35.0 | 8138.5 | 14.1 | 5000 | | 1.3 | | 4.7 |
| 191 | 33.0 | 170.6 | 10000 | 36.4 | 5000 | 36.5 | | | |
| 192 | 19.1 | 44.8 | 10000 | 13.1 | 5000 | | 1.6 | | |
| 193 | 21.2 | 31.0 | 4570.0 | 45.6 | 5000 | | 1.6 | | 7.0 |
| 194 | 17.8 | 23.5 | 8729.1 | 44.5 | 5000 | | 1.9 | | 32.4 |
| 195 | 17.3 | 37.5 | 7293.3 | 10.1 | 5000 | | 4.6 | | |
| 196 | 8.2 | 9.1 | 883.5 | 8.7 | 5000 | | 1.6 | | 13.2 |
| 197 | 14.1 | 21.0 | 8640.4 | 44.9 | 5000 | | 1.8 | | 35.7 |
| 198 | 20.0 | 21.9 | 3303.3 | 37.6 | 5000 | | 10.7 | | |
| 199 | 16.1 | 18.7 | 5680.8 | 17.9 | 5000 | 1.9 | | | 1.4 |
| 200 | 18.6 | 52.6 | 10000 | 14.9 | 4520.7 | 8.1 | | | |
| 201 | 27.7 | 88.8 | 10000 | 9.9 | 5000 | | | | |
| 202 | 25.7 | 31.1 | 10000 | 49.2 | 5000 | | 1.2 | | 6.4 |
| 203 | 20.3 | 65.4 | 4580.2 | 8.3 | 5000 | | | | 1.9 |
| 204 | 31.9 | 108.0 | 8056.7 | 13.1 | 5000 | 1.3 | | | 1.2 |
| 205 | 29.7 | 104.4 | 10000 | 25.6 | 5000 | | | | |
| 206 | 12.6 | 40.8 | 10000 | 24.8 | 5000 | 3.3 | | | |
| 207 | 22.4 | 45.1 | 1724.5 | 16.9 | 5000 | 1.6 | | | 1.7 |
| 208 | 17.3 | 25.6 | 3551.6 | 6.0 | 5000 | 11.2 | | | |
| 209 | 29.2 | 57.9 | 9527.4 | 11.7 | 5000 | 3.3 | | | |
| 210 | 40.5 | 30.2 | 10000 | 27.0 | 5000 | | 1.7 | | 36.8 |
| 211 | 10.9 | 31.0 | 3143.2 | 14.8 | 5000 | | 3.3 | | 25.2 |
| 212 | 12.8 | 22.9 | 2412.3 | 10.3 | 5000 | | 2.8 | | 31.4 |
| 213 | 19.7 | 33.9 | 10000 | 34.1 | 5000 | | 2.4 | | |
| 214 | 15.4 | 46.6 | 10000 | 28.1 | 5000 | | 1.5 | | 8.8 |
| 215 | 28.8 | 119.5 | 10000 | 37.8 | 5000 | | | | |
| 216 | 33.2 | 48.6 | 2355.1 | 15.7 | 5000 | 1.7 | | | 0.9 |
| 217 | 23.2 | 53.3 | | 35.1 | 5000 | 6.0 | | | |
| 218 | 41.6 | 40.3 | 10000 | 43.8 | 5000 | | 1.5 | | 2.4 |
| 219 | 14.8 | 27.6 | 2105.2 | 6.2 | 5000 | | | | |
| 220 | 9.3 | 12.1 | 1522.8 | 8.0 | 5000 | | | | |
| 221 | 122.4 | 333.6 | 10000 | 547.6 | | | | | |
| 222 | 34.4 | 41.2 | 10000 | 38.9 | 5000 | 1.0 | | | 1.6 |
| 223 | 91.6 | 100.7 | 10000 | 12.7 | 5000 | 1.9 | | | 3.7 |
| 224 | 27.4 | 84.9 | 10000 | 39.5 | 5000 | 23.7 | | | |
| 225 | 149.0 | 217.5 | 10000 | 85.4 | | | | | |
| 226 | 92.7 | 128.1 | 10000 | 65.4 | 5000 | 3.2 | | | |
| 227 | 47.4 | 66.9 | 10000 | 53.8 | | | | | |
| 228 | 114.8 | 272.2 | 10000 | 24.2 | 5000 | 1.1 | | | 1.0 |
| 229 | 171.0 | 375.6 | 10000 | 164.5 | | | | | |
| 230 | 25.8 | 29.2 | 8560.5 | 15.7 | 5000 | 2.5 | | | |
| 231 | 115.2 | 274.0 | 10000 | 39.2 | 5000 | 4.2 | | | |
| 232 | 15.3 | 12.4 | 6414.6 | 39.6 | 5000 | 31.3 | | | |
| 233 | 27.5 | 41.5 | 3740.9 | 15.7 | 5000 | 1.5 | | | 1.6 |
| 234 | 103.8 | 165.1 | 10000 | 39.1 | 5000 | 1.8 | | | 5.2 |
| 235 | 74.5 | 54.1 | 10000 | 5.6 | 5000 | 2.9 | | | |
| 236 | 149.0 | 352.5 | 10000 | 89.9 | | 1.3 | | | |
| 237 | 32.0 | 70.2 | 10000 | 71.6 | | | | | |
| 238 | 99.3 | 227.2 | 10000 | 163.3 | | | | | |
| 239 | 126.9 | 107.0 | 10000 | 9.1 | 5000 | 2.1 | | | 3.5 |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 240 | 41.3 | 77.7 | 10000 | 66.5 |  | 2.9 |  |  |  |
| 241 | 28.3 | 122.6 | 1638.5 | 244.1 | 5000 |  |  |  |  |
| 242 | 111.3 | 130.1 | 10000 | 76.3 |  |  |  |  |  |
| 243 | 40.6 | 263.9 | 2491.1 | 173.1 | 3037.0 |  |  |  |  |
| 244 | 41.9 | 106.8 | 10000 | 92.2 |  |  |  |  |  |
| 245 | 50.4 | 141.7 | 10000 | 109.1 |  |  |  |  |  |
| 246 | 28.2 | 70.8 | 10000 | 103.4 |  |  |  |  |  |
| 247 | 81.7 | 96.9 | 10000 | 3.5 | 5000 | 1.6 |  |  | 4.7 |
| 248 | 57.4 | 122.0 | 10000 | 65.7 |  |  |  |  |  |
| 249 | 35.9 | 23.4 | 10000 | 37.4 | 5000 | 0.3 |  |  | 3.0 |
| 250 | 46.3 | 67.6 | 10000 | 54.6 |  |  |  |  |  |
| 251 | 11.7 | 21.2 | 1800.8 | 6.6 | 5000 | 2.3 |  |  |  |
| 252 | 92.9 | 241.9 | 10000 | 25.7 | 5000 | 0.7 |  |  | 2.6 |
| 253 | 93.0 | 170.7 | 10000 | 39.3 | 5000 | 1.2 |  |  | 2.0 |
| 254 | 53.2 | 114.0 | 10000 | 44.0 | 5000 | 9.9 |  |  |  |
| 255 | 113.2 | 433.9 | 10000 | 159.9 |  |  |  |  |  |
| 256 | 49.1 | 71.7 | 10000 | 12.2 | 5000 | 1.7 |  |  | 1.2 |
| 257 | 19.8 | 8.2 | 3273.8 | 9.4 | 5000 |  |  |  |  |
| 258 | 88.3 | 176.8 | 10000 | 51.4 |  |  |  |  |  |
| 259 | 29.7 | 45.3 | 10000 | 19.6 | 5000 | 8.8 |  |  |  |
| 260 | 31.8 | 42.0 | 10000 | 21.5 | 5000 | 1.6 |  |  | 2.9 |
| 261 | 48.8 | 86.1 | 10000 | 21.9 | 5000 | 2.2 |  |  |  |
| 262 | 22.3 | 116.4 | 10000 | 44.0 | 5000 | 1.7 |  |  | 2.7 |
| 263 | 57.6 | 137.3 | 10000 | 16.1 | 5000 | 0.9 |  | 1.5 |  |
| 264 | 35.1 | 42.4 | 10000 | 6.6 | 5000 | 9.7 |  |  |  |
| 265 | 46.5 | 45.6 | 5348.7 | 16.8 | 5000 |  | 1.1 |  | 1.8 |
| 266 | 114.9 | 796.4 | 10000 | 641.8 | 5000 |  |  |  |  |
| 267 | 34.3 | 33.4 | 3951.2 | 4.1 | 5000 | 6.0 |  |  |  |
| 268 | 82.0 | 93.7 | 10000 | 39.0 | 5000 | 1.5 |  | 1.1 |  |
| 269 | 12.1 | 16.7 | 2395.5 | 20.7 | 5000 | 2.4 |  |  |  |
| 270 | 10.9 | 22.2 | 10000 | 3.1 | 5000 | 2.2 |  |  |  |
| 271 | 42.2 | 144.9 | 1263.4 | 30.9 | 3082.2 | 1.8 | 0.9 |  |  |
| 272 | 67.3 | 104.0 | 8998.2 | 40.2 | 5000 | 1.6 |  |  | 0.6 |
| 273 | 95.0 | 201.8 | 10000 | 33.5 | 5000 |  |  |  |  |
| 274 | 30.7 | 38.8 | 3249.1 | 12.1 | 5000 | 2.4 |  |  | 1.7 |
| 275 | 13.1 | 16.5 | 1646.7 | 18.0 | 5000 | 6.0 |  |  |  |
| 276 | 8.0 | 13.5 | 1360.7 | 41.5 | 5000 |  |  |  |  |
| 277 | 16.0 | 42.8 | 10000 | 28.3 | 5000 | 10.9 |  |  |  |
| 278 | 22.0 | 42.9 | 9553.0 | 13.5 | 5000 | 13.6 |  |  |  |
| 279 | 25.0 | 50.6 | 4085.3 | 1.2 | 5000 | 16.6 |  |  |  |
| 280 | 38.2 | 78.2 | 10000 | 14.7 | 5000 | 4.0 |  |  |  |
| 281 | 23.8 | 84.2 | 10000 | 26.6 | 5000 | 2.1 |  |  |  |
| 282 | 40.0 | 83.9 | 10000 | 26.3 | 5000 | 1.9 |  |  | 3.5 |
| 283 | 39.5 | 300.6 | 10000 | 261.3 |  |  |  |  |  |
| 284 | 75.6 | 681.0 | 10000 | 53.4 | 5000 | 95.4 |  |  |  |
| 285 | 83.9 | 787.2 | 10000 | 53.2 | 5000 | 72.1 |  |  |  |
| 286 | 98.1 | 467.8 | 10000 | 81.4 | 5000 |  |  |  |  |
| 287 | 42.9 | 118.5 | 10000 | 60.9 | 5000 |  |  |  |  |
| 288 | 79.8 | 262.4 | 10000 | 94.0 | 5000 |  |  |  |  |
| 289 | 108.8 | 584.5 | 10000 | 73.9 | 5000 |  |  |  |  |
| 290 | 92.5 | 600.7 | 10000 | 83.5 | 5000 |  |  |  |  |
| 291 | 76.2 | 446.3 | 10000 | 84.1 | 5000 |  |  |  |  |
| 292 | 105.3 | 557.9 | 10000 | 132.5 | 5000 |  |  |  |  |
| 293 | 87.7 | 568.4 | 10000 | 81.2 | 5000 |  |  |  |  |
| 294 | 10.1 | 12.9 | 3828.1 | 28.2 | 5000 |  | 1.9 |  | 15.3 |
| 295 | 114.6 | 551.5 | 10000 | 40.4 | 5000 |  |  |  |  |
| 296 | 59.6 | 141.0 | 10000 | 68.2 | 5000 |  |  |  |  |
| 297 | 17.6 | 40.0 | 3323.9 | 29.4 | 5000 |  | 3.2 |  |  |
| 298 | 40.2 | 233.6 | 10000 | 38.6 | 5000 |  |  |  |  |
| 299 | 49.8 | 145.7 | 10000 | 30.5 | 5000 | 0.4 |  |  | 1.2 |
| 300 | 75.5 | 284.1 | 10000 | 30.7 | 5000 |  |  |  |  |
| 301 | 39.1 | 241.1 | 10000 | 60.8 | 5000 |  |  |  |  |
| 302 | 65.9 | 390.6 | 10000 | 141.4 | 5000 |  |  |  |  |
| 303 | 64.2 | 402.6 | 10000 | 256.7 | 5000 |  |  |  |  |
| 304 | 11.7 | 48.6 | 2837.4 | 114.5 | 5000 | 1.2 |  |  | 7.3 |
| 305 | 14.1 | 20.3 | 1855.9 | 10.8 | 5000 |  |  |  |  |
| 306 | 16.7 | 35.1 | 6838.1 | 1000.1 | 5000 |  |  |  |  |
| 307 | 28.3 | 54.3 | 10000 | 1147.9 | 5000 |  |  |  |  |
| 308 | 15.1 | 28.8 | 10000 | 492.0 | 5000 |  |  |  |  |
| 309 | 184.5 | 223.4 | 10000 | 5000 |  |  |  |  |  |
| 310 | 14.2 | 31.0 | 10000 | 47.5 | 5000 | 2.0 |  |  |  |
| 311 | 75.3 | 76.3 | 10000 | 3333.9 | 5000 |  |  |  |  |
| 312 | 38.9 | 54.2 | 10000 | 1592.7 | 5000 |  |  |  |  |
| 313 | 21.3 | 40.4 | 4145.8 | 1758.4 | 5000 |  |  |  |  |
| 314 | 29.8 | 88.1 | 6078.7 | 2020.6 | 5000 |  |  |  |  |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 315 | 39.3 | 64.8 | 3693.4 | 1487.9 | 5000 | | | | |
| 316 | 52.2 | 111.2 | 5038.9 | 1318.3 | 5000 | | | | |
| 317 | 18.1 | 100.8 | 10000 | 401.7 | 5000 | | | | |
| 318 | 125.1 | 88.0 | 4331.1 | 928.3 | 5000 | | | | |
| 319 | 16.7 | 4.5 | 870.1 | 26.3 | 5000 | | 10.6 | | |
| 320 | 12.7 | 36.0 | 2338.0 | 271.2 | 5000 | | | | |
| 321 | 12.9 | 65.7 | 4338.5 | 72.0 | 5000 | | | | |
| 322 | 21.6 | 62.1 | 10000 | 102.1 | 5000 | | | | |
| 323 | 12.2 | 75.4 | 9720.6 | 59.9 | 5000 | | | | |
| 324 | 64.4 | 119.4 | 10000 | 123.8 | 5000 | | | | |
| 325 | 27.5 | 45.3 | 4881.2 | 166.5 | 5000 | | | | |
| 326 | 14.4 | 32.6 | 2344.4 | 32.1 | 5000 | | | | |
| 327 | 20.8 | 32.1 | 3815.4 | 105.5 | 5000 | | | | |
| 328 | 17.9 | 104.8 | 10000 | 306.3 | 5000 | | | | |
| 329 | 19.8 | 37.7 | 5057.6 | 85.2 | 5000 | | | | |
| 330 | 34.3 | 72.6 | 8512.5 | 197.2 | 5000 | | | | |
| 331 | 405.8 | 389.4 | 10000 | | | | | | |
| 332 | 48.6 | 50.5 | 10000 | 185.5 | 5000 | | | | |
| 333 | 11.9 | 23.2 | 2233.0 | 82.1 | 5000 | | | | |
| 334 | 20.4 | 55.7 | 1654.7 | 266.3 | 5000 | | | | |
| 335 | 15.7 | 24.1 | 4113.0 | 143.4 | 5000 | | | | |
| 336 | 54.0 | 129.6 | 10000 | 2261 | 5000 | | | | |
| 337 | 17.0 | 13.3 | 2490.0 | 70.3 | 5000 | | | | |
| 338 | 13.2 | 12.8 | 1991.2 | 65.2 | 5000 | | | | |
| 339 | 47.2 | 71.4 | 5238.5 | 586.9 | 5000 | | | | |
| 340 | 16.8 | 41.2 | 3997.6 | 165.2 | 5000 | | | | |
| 341 | 12.7 | 20.7 | 1740.5 | 43.1 | 5000 | | | | |
| 342 | 10.4 | 25.3 | 1666.0 | 107.6 | 5000 | | | | |
| 343 | 112.5 | 119.9 | | 1486.7 | 5000 | | | | |
| 344 | 160.6 | 675.3 | 10000 | 128.3 | 5000 | | | | |
| 345 | 31.3 | 57.8 | 10000 | 18.5 | 5000 | | | | |
| 346 | 39.5 | 60.4 | 10000 | 20.3 | 5000 | | | | |
| 347 | 79.6 | 109.7 | 10000 | 244.1 | 5000 | | | | |
| 348 | 40.1 | 69.1 | 10000 | 14.5 | 5000 | | 1.4 | | 5.0 |
| 349 | 18.9 | 24.0 | 1288.2 | 115.7 | 5000 | | | | |
| 350 | 40.0 | 83.9 | 10000 | 26.3 | 5000 | 1.9 | | | 3.5 |
| 351 | 30.8 | 58.4 | 10000 | 150 | 5000 | | | | |
| 352 | 37.5 | 131.0 | 10000 | 147.4 | 5000 | | | | |
| 353 | 48.2 | 47.5 | 10000 | 18.1 | 5000 | | | | |
| 354 | 27.6 | 29.0 | 10000 | 72.2 | 5000 | | | | |
| 355 | 19.3 | 24.5 | 5043.0 | 181.7 | 5000 | | | | |
| 356 | 36.1 | 92.8 | 10000 | 270.3 | 5000 | | | | |
| 357 | 93.8 | 88.9 | 10000 | 31.0 | 5000 | | | | |
| 358 | 53.2 | 35.8 | 10000 | 19.2 | 5000 | | 1.6 | | 8.9 |
| 359 | 11.7 | 32.7 | 10000 | 277.7 | 5000 | | | | |
| 360 | 24.9 | 25.5 | 10000 | 29.8 | 5000 | | 1.3 | | |
| 361 | 26.4 | 39.2 | 7477.6 | 311.6 | 5000 | | | | |
| 362 | 26.3 | 32.1 | 3386.6 | 1259.7 | 5000 | | | | |
| 363 | 26.1 | 72.4 | 10000 | 26.2 | 5000 | | | | |
| 364 | 32.8 | 29.5 | 2683.7 | 25.7 | 5000 | | | | |
| 365 | 38.4 | 81.8 | 7566.8 | 131.5 | 5000 | | | | |
| 366 | 8.3 | 6.7 | 302.5 | 76.6 | 5000 | | | | |
| 367 | 16.5 | 64.7 | 10000 | 263.9 | 5000 | | | | |
| 368 | 3.6 | 4.8 | 303.3 | 17.4 | 5000 | | | | |
| 369 | 7.3 | 37.1 | 3870.9 | 151.1 | 5000 | | | | |
| 370 | 57.9 | 129.2 | 10000 | 2504.7 | 5000 | | | | |
| 371 | 67.0 | 492.2 | 10000 | 127.4 | 5000 | | | | |
| 372 | 15.1 | 70.7 | 7306.8 | 152.6 | 5000 | | | | |
| 373 | 81.6 | 306.8 | 10000 | 2479.0 | 5000 | | | | |
| 374 | 14.3 | 14.2 | 1176.6 | 215.6 | 5000 | | | | |
| 375 | 22.8 | 34 | 10000 | 14.9 | 5000 | | | | |
| 376 | 13.3 | 11.7 | 1197.8 | 30.8 | 5000 | | | | |
| 377 | 7.6 | 14.7 | 1414.6 | 58.2 | 5000 | | | | |
| 378 | 40.1 | 69.1 | 10000 | 14.5 | 5000 | | 1.4 | | 5.0 |
| 379 | 25.7 | 82.1 | 10000 | 356.0 | 5000 | | | | |
| 380 | 46.4 | 64.0 | 10000 | 43.2 | 5000 | | | | |
| 381 | 15.4 | 9.4 | 5043.0 | 265.5 | 5000 | | | | |
| 382 | 34.5 | 68.9 | 6010.1 | 396.8 | 5000 | | | | |
| 383 | 56.3 | 75.3 | 10000 | 4140.0 | 5000 | | | | |
| 384 | 13.6 | 43.0 | 4312.5 | 91.5 | 5000 | | | | |
| 385 | 18.5 | 40.0 | 5154.3 | 183.1 | 5000 | | | | |
| 386 | 82.1 | 59.4 | 6993.3 | 16.7 | 5000 | | | | |
| 387 | 70.0 | 131.7 | 10000 | 163.3 | 5000 | | | | |
| 388 | 62.1 | 89.4 | 10000 | 52.2 | | | | | |
| 389 | 16.7 | 12.2 | 10000 | 126.6 | 5000 | | | | |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 390 | 24.8 | 44.6 | 3975.0 | 108.0 | 5000 | | | | |
| 391 | 94.3 | 298.5 | 10000 | 143.1 | 5000 | | | | |
| 392 | 16.6 | 14.6 | 10000 | 79.9 | 5000 | | | | |
| 393 | 63.3 | 236.8 | 10000 | 43.2 | 5000 | | | | |
| 394 | 31.3 | 57.8 | 10000 | 18.5 | 5000 | | | | |
| 395 | 24.6 | 57.6 | 10000 | 897.9 | 5000 | | | | |
| 396 | 4.9 | 9.6 | 10000 | 23.9 | 5000 | | | | |
| 397 | 20.3 | 143.7 | 10000 | 115.1 | | | | | |
| 398 | 22.1 | 36.5 | 7765.5 | 70.5 | 5000 | | | | |
| 399 | 28.2 | 29.0 | 10000 | 191.9 | 5000 | | | | |
| 400 | 8.7 | 40.7 | 8416.6 | 217.6 | 5000 | | | | |
| 401 | 149.3 | 161.0 | 10000 | 24.8 | 5000 | | | | |
| 402 | 39.7 | 14.9 | 10000 | 14.9 | 5000 | | 1.4 | | 2.3 |
| 403 | 16.7 | 12.0 | 6628.5 | 339.5 | 5000 | | | | |
| 404 | 22.8 | 37.0 | 7554.8 | 182.3 | 5000 | | | | |
| 405 | 15.7 | 30.3 | 4691.6 | 106.5 | 5000 | | | | |
| 406 | 16.6 | 32.3 | 8284.6 | 63.6 | 5000 | | | | |
| 407 | 31.5 | 116.6 | 10000 | 84.1 | | | | | |
| 408 | 32.6 | 65.6 | 10000 | 42.1 | 5000 | | | | |
| 409 | 18.3 | 32.1 | 3528.9 | 43.0 | 5000 | | | | |
| 410 | 14.7 | 42.3 | 6304.6 | 208.5 | 5000 | | | | |
| 411 | 26.3 | 56.2 | 10000 | 604.4 | 5000 | | | | |
| 412 | 25.9 | 70.5 | 10000 | 69.7 | 5000 | | | | |
| 413 | 49.7 | 102.5 | 10000 | 30.8 | 5000 | | | | |
| 414 | 25.2 | 23.7 | 1408.4 | 140.3 | 5000 | | | | |
| 415 | 16.9 | 16.8 | 970.1 | 94.6 | 5000 | | | | |
| 416 | 11.3 | 21.5 | 2235.8 | 27.1 | 5000 | | | | |
| 417 | 31.4 | 62.1 | 6859.8 | 62.6 | 5000 | | | | |
| 418 | 42.8 | 103.4 | 10000 | 229.1 | 5000 | | | | |
| 419 | 110.5 | 195.7 | 10000 | 538.3 | 5000 | | | | |
| 420 | 8.2 | 12.9 | 1582.6 | 108.5 | 5000 | | | | |
| 421 | 29.3 | 43.0 | 4944.7 | 69.9 | 5000 | | | | |
| 422 | 58.4 | 93.2 | 10000 | 96.7 | | | | | |
| 423 | 110.2 | 336.6 | 10000 | 1952.0 | 5000 | | | | |
| 424 | 16.0 | 19.4 | 3927.2 | 44.9 | 5000 | | | | |
| 425 | 68.1 | 495.4 | 10000 | 185.4 | 5000 | | | | |
| 426 | 16.2 | 16.2 | 4210.5 | 112.4 | 5000 | | | | |
| 427 | 25.0 | 43.1 | 7941.5 | 121.5 | 5000 | | | | |
| 428 | 55.5 | 202.5 | 10000 | 317.4 | 5000 | | | | |
| 429 | 11.2 | 39.6 | 3945.1 | 46.6 | 5000 | | | | |
| 430 | 8.6 | 25.5 | 4028.6 | 31.9 | 5000 | | | | |
| 431 | 21.8 | 63.1 | 10000 | 231.7 | 5000 | | | | |
| 432 | 28.8 | 71.1 | 10000 | 80.2 | 5000 | | | | |
| 433 | 29.3 | 67.4 | 10000 | 384.6 | 5000 | | | | |
| 434 | 8.4 | 10.2 | 759.9 | 161.4 | 5000 | | | | |
| 435 | 11.8 | 32.8 | 4907.9 | 34.7 | 5000 | | 1.2 | | |
| 436 | 15.4 | 25.0 | 10000 | 61.1 | 5000 | | | | |
| 437 | 40.8 | 145.6 | 10000 | 95.8 | | | | | |
| 438 | 27.4 | 47.0 | 10000 | 134.0 | 5000 | | | | |
| 439 | 38.7 | 70.0 | | 45.3 | 5000 | | | | |
| 440 | 48.7 | 175.7 | 10000 | 58.2 | 5000 | | | | |
| 441 | 105.7 | 67.2 | 9568.1 | 89.1 | 5000 | | | | |
| 442 | 69.5 | 179.9 | 10000 | 104.5 | 5000 | | | | |
| 443 | 60.1 | 103.5 | 10000 | 37.7 | 5000 | | | | |
| 444 | 24.3 | 52.6 | 10000 | 41.7 | 5000 | | | | |
| 445 | 65.0 | 64.5 | 4500.0 | 44.2 | 5000 | | | | |
| 446 | 20.7 | 133.5 | 10000 | 123.3 | 5000 | | | | |
| 447 | 46.8 | 91.0 | 10000 | 12.2 | 5000 | | | | |
| 448 | 75.9 | 143.0 | 10000 | 40.8 | 5000 | | | | |
| 449 | 157.1 | 152.3 | 10000 | 6.2 | 5000 | | | | |
| 450 | 26.1 | 55.0 | 4012.4 | 13.4 | 5000 | | | | |
| 451 | 42.7 | 63.8 | 3501.7 | 24.7 | 5000 | | | | |
| 452 | 47.6 | 115.0 | 10000 | 20.2 | 5000 | | | | |
| 453 | 64.6 | 473.9 | 10000 | 383.4 | 5000 | | | | |
| 454 | 15.3 | 48.1 | 4113.0 | 54.7 | | | | | |
| 455 | 48.7 | 175.7 | 10000 | 58.2 | 5000 | | | | |
| 456 | 25.9 | 69.8 | 4517.9 | 47.6 | 5000 | | | | |
| 457 | 25.1 | 83.9 | 8236.7 | 50.6 | 5000 | | 0.8 | | 1.9 |
| 458 | 13.3 | 28.0 | 1634.4 | 75.2 | 5000 | | | | |
| 459 | 18.7 | 36.6 | 10000 | 45.1 | 5000 | | | | |
| 460 | 59.1 | 89.7 | 10000 | 88.0 | 5000 | | | | |
| 461 | 20.5 | 31.9 | 10000 | 46.5 | 5000 | | | | |
| 462 | 20.3 | 41.5 | 10000 | 18.6 | 5000 | | | | |
| 463 | 71.3 | 275.1 | 10000 | 661.6 | 5000 | | | | |
| 464 | 9.4 | 60.2 | 10000 | 83.1 | 5000 | | | | |

TABLE 3-continued

| Table Example No. | Assay 1 IC$_{50}$ (nM) | Assay 2 IC$_{50}$ (nM) | Assay 3 IC$_{50}$ (nM) | Assay 4 IC$_{50}$ (nM) | Assay 5 IC$_{50}$ (nM) | Assay 6 Pe Ratio | Assay 7 Pe Ratio | Assay 8 Pe Ratio | Assay 9 Pe Ratio |
|---|---|---|---|---|---|---|---|---|---|
| 465 | 44.3 | 47.6 | 10000 | 67.8 | 5000 | | | | |
| 466 | 24.1 | 61.3 | 10000 | 16.2 | 5000 | | | | |
| 467 | 26.4 | 34.5 | 4791.8 | 19.4 | 5000 | | | | |
| 468 | 39.1 | 130.0 | 10000 | 87.2 | 5000 | | | | |
| 469 | 19.1 | 44.8 | 10000 | 13.1 | 5000 | | 1.6 | | |
| 470 | 38.3 | 52.3 | 6845.0 | 24.3 | 5000 | | 2.5 | | |
| 471 | 7.1 | 49.4 | 10000 | 42.5 | 5000 | | | | |
| 472 | 12.4 | 15.0 | 864.8 | 7.6 | 5000 | | 1.4 | | 1.7 |
| 473 | 21.6 | 20.0 | 1526.0 | 5.8 | 5000 | | | | |
| 474 | 253.6 | 726.8 | 10000 | 558.8 | | | | | |
| 475 | 22.4 | 88.6 | 10000 | 82.6 | 5000 | | | | |
| 476 | 39.5 | 232.0 | 10000 | 155.2 | | | | | |
| 477 | 59.6 | 47.1 | 10000 | 53.3 | 5000 | | | | |
| 478 | 27.9 | 41.6 | 10000 | 109.4 | 5000 | | | | |
| 479 | 26.5 | 24.4 | 2208.6 | 12.9 | 5000 | | | | |
| 480 | 18.1 | 23.3 | 5035.7 | 4.4 | 5000 | | | | |
| 481 | 29.4 | 41.2 | 10000 | 74.2 | 5000 | | | | |
| 482 | 76.7 | 446.1 | 10000 | 228.7 | 5000 | | | | |
| 483 | 76.5 | 262.1 | 10000 | 58.6 | 5000 | | | | |
| 484 | 34.4 | 123.8 | 10000 | 22.7 | 5000 | | | | |
| 485 | 21.7 | 77.2 | 10000 | 11.1 | 5000 | | 1.3 | | |
| 486 | 29.6 | 137.5 | 10000 | 132.7 | 5000 | | | | |
| 487 | 62.1 | 45.7 | 10000 | 49.1 | 5000 | | | | |
| 488 | 73.8 | 173.6 | 10000 | 118.1 | 5000 | | | | |
| 489 | 17.7 | 9.7 | 3367.7 | 16.4 | 5000 | | | | |
| 490 | 23.8 | 84.2 | 10000 | 26.6 | 5000 | 2.1 | | | |
| 491 | 27.8 | 36.9 | 10000 | 78.6 | 5000 | | | | |
| 492 | 24.7 | 37.8 | 4733.8 | 37.2 | 5000 | | | | |

All publications and patent applications cited in the specification are herein incorporated by reference in their entirety. It will be apparent to those of ordinary skill in the art that certain changes and modifications may be made thereto without departing from the spirit or scope of the appended claims.

The invention claimed is:

1. A compound selected from the group consisting of:

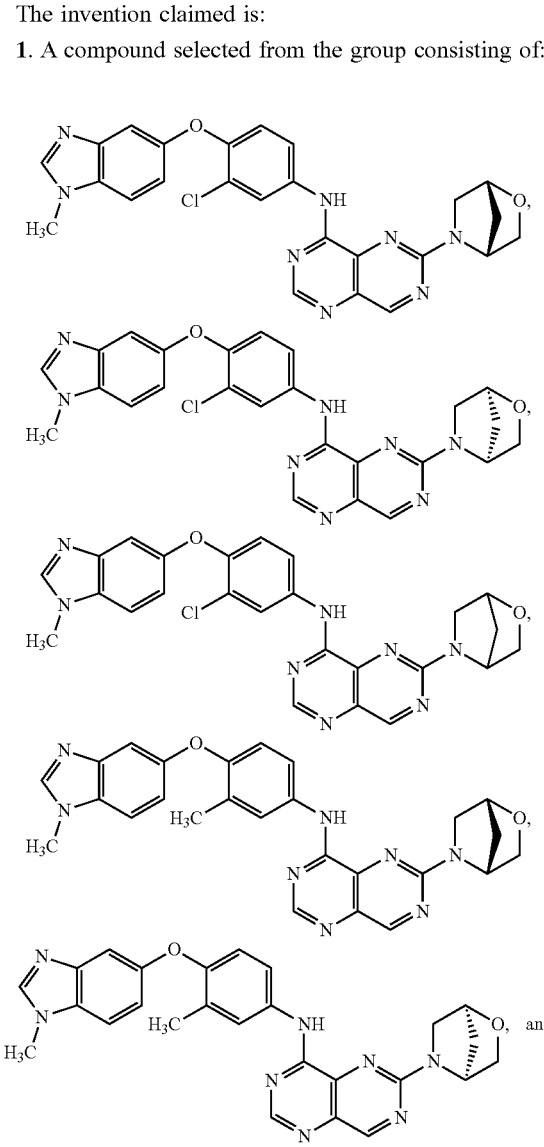

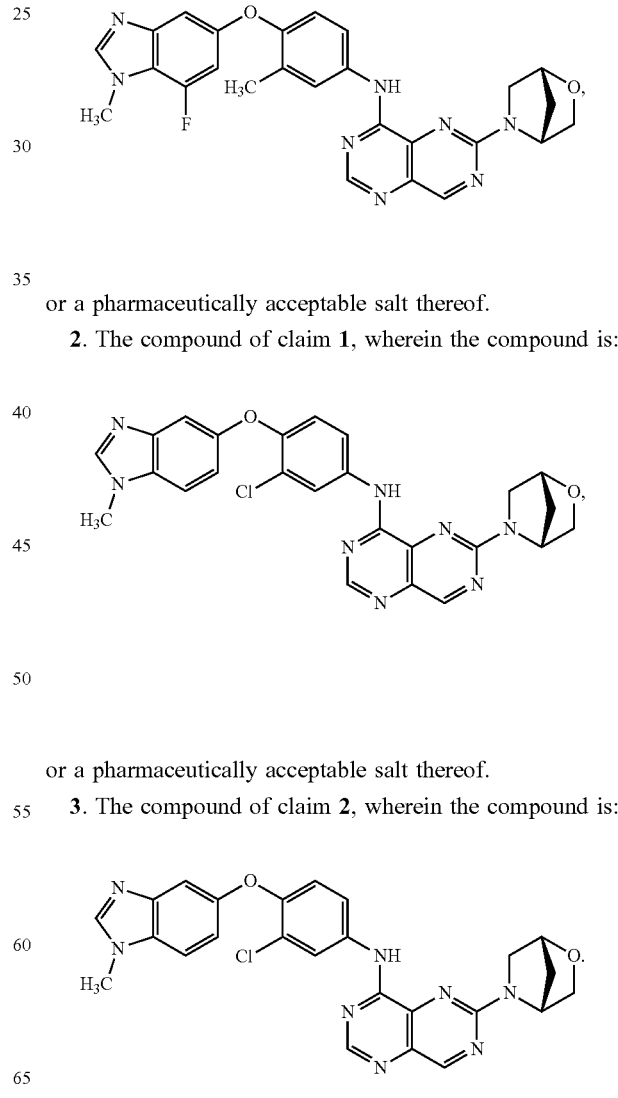

or a pharmaceutically acceptable salt thereof.

2. The compound of claim 1, wherein the compound is:

or a pharmaceutically acceptable salt thereof.

3. The compound of claim 2, wherein the compound is:

4. The compound of claim 1, wherein the compound is:

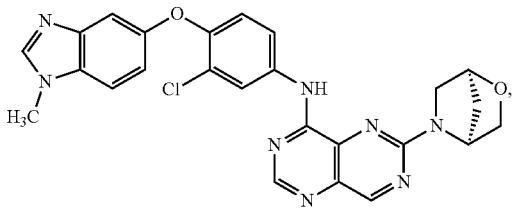 [SMILES: Cn1cnc2cc(Oc3ccc(Nc4ncnc5cnc(N6C[C@@H]7C[C@H]6CO7)nc45)cc3Cl)ccc21]

or a pharmaceutically acceptable salt thereof.

5. The compound of claim 4, wherein the compound is:

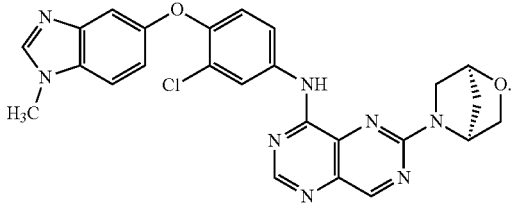

6. The compound of claim 1, wherein the compound is:

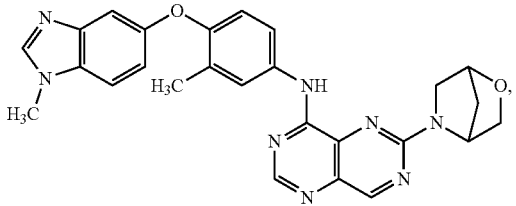 [SMILES: Cc1cc(Nc2ncnc3cnc(N4CC5CC4CO5)nc23)ccc1Oc1ccc2c(c1)ncn2C]

or a pharmaceutically acceptable salt thereof.

7. The compound of claim 6, wherein the compound is:

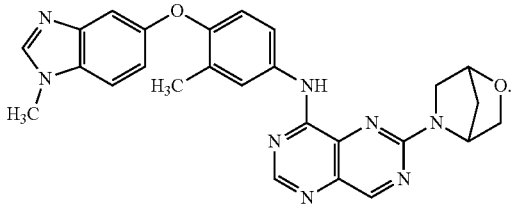

8. The compound of claim 1, wherein the compound is:

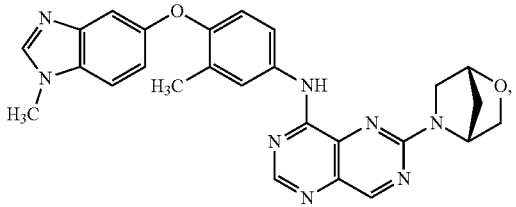 [SMILES: Cc1cc(Nc2ncnc3cnc(N4C[C@H]5C[C@@H]4CO5)nc23)ccc1Oc1ccc2c(c1)ncn2C]

or a pharmaceutically acceptable salt thereof.

9. The compound of claim 8, wherein the compound is:

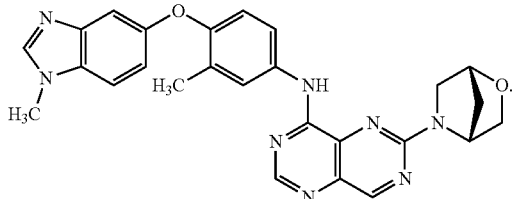

10. The compound of claim 1, wherein the compound is:

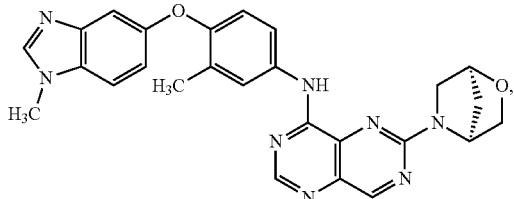

or a pharmaceutically acceptable salt thereof.

11. The compound of claim 10, wherein the compound is:

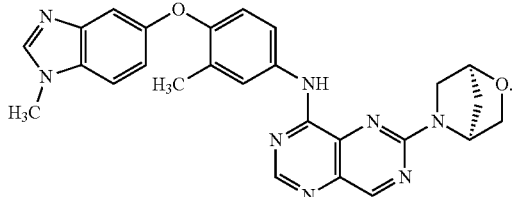

12. The compound of claim 1, wherein the compound is:

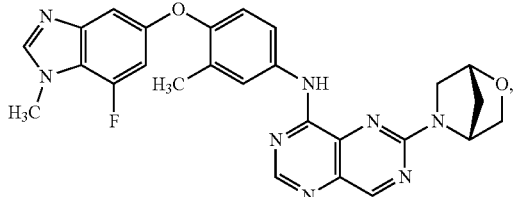

or a pharmaceutically acceptable salt thereof.

13. The compound of claim 12, wherein the compound is:

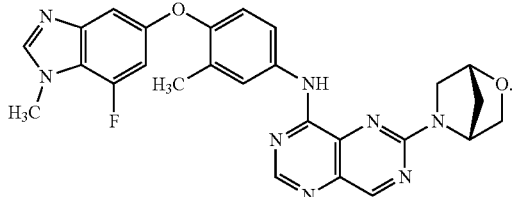

14. A pharmaceutical composition comprising at least one pharmaceutically acceptable carrier, excipient, or diluent and a compound of claim 1, or a pharmaceutically acceptable salt thereof.

15. A method for inhibiting human epidermal growth factor receptor 2 (HER2) mutation activity in a patient in need thereof, wherein the method comprises administering to the patient a therapeutically effective amount of a compound of claim 1, or a pharmaceutically acceptable salt thereof.

16. The method of claim 15, wherein the patient has a disorder mediated by brain metastases from human epidermal growth factor receptor 2 (HER2) amplified or human epidermal growth factor receptor 2 (HER2) positive cancer.

17. The method of claim 16, wherein the patient has a disorder mediated by brain metastases from human epidermal growth factor receptor 2 (HER2) amplified.

18. The method of claim 16, wherein the patient has human epidermal growth factor receptor 2 (HER2) positive cancer.

19. The method of claim 18, wherein the method further comprises administering to the patient a therapeutically effective amount of at least one additional anti-cancer agent.

20. The method of claim 19, wherein the at least one additional anti-cancer agent is selected from the group consisting of a monoclonal antibody, an antibody-drug conjugate, a cyclin dependent kinase 4 (CDK4) inhibitor, a cyclin dependent kinase 6 (CDK6) inhibitor, a human epidermal growth factor receptor 2 (HER2) inhibitor, a mammalian target of rapamycin (mTOR) inhibitor, a phosphoinositide 3-kinase (PI3K) inhibitor, and a poly(adenosine diphosphate-ribose) polymerase (PARP) inhibitor, or a combination thereof.

21. The method of claim 15, wherein the human epidermal growth factor receptor 2 (HER2) mutation is HER2-YVMA (SEQ ID NO: 2).

22. The method of claim 21, wherein the method further comprises administering to the patient a therapeutically effective amount of at least one additional anti-cancer agent.

23. The method of claim 22, wherein the at least one additional anti-cancer agent is selected from the group consisting of a monoclonal antibody, an antibody-drug conjugate, a cyclin dependent kinase 4 (CDK4) inhibitor, a cyclin dependent kinase 6 (CDK6) inhibitor, a human epidermal growth factor receptor 2 (HER2) inhibitor, a mammalian target of rapamycin (mTOR) inhibitor, a phosphoinositide 3-kinase (PI3K) inhibitor, and a poly(adenosine diphosphate-ribose) polymerase (PARP) inhibitor, or a combination thereof.

24. A method for treating abnormal cell growth in a patient in need thereof, wherein the method comprises administering to the patient a therapeutically effective amount of a compound of claim 1, or a pharmaceutically acceptable salt thereof.

25. The method of claim 24, wherein the abnormal cell growth is cancer.

26. The method of claim 25, wherein the cancer is human epidermal growth factor receptor 2 (HER2) positive.

27. The method of claim 25, wherein the method further comprises co-administering to the patient a therapeutically effective amount of at least one additional anti-cancer agent.

28. The method of claim 27, wherein the at least one additional anti-cancer agent is selected from the group consisting of a monoclonal antibody, an antibody-drug conjugate, a cyclin dependent kinase 4 (CDK4) inhibitor, a cyclin dependent kinase 6 (CDK6) inhibitor, a human epidermal growth factor receptor 2 (HER2) inhibitor, a mammalian target of rapamycin (mTOR) inhibitor, a phosphoinositide 3-kinase (PI3K) inhibitor, and a poly(adenosine diphosphate-ribose) polymerase (PARP) inhibitor, or a combination thereof.

* * * * *

```
                        SEQUENCE LISTING

<160> NUMBER OF SEQ ID NOS: 2

<210> SEQ ID NO 1
<211> LENGTH: 604
<212> TYPE: PRT
<213> ORGANISM: Artificial Sequence
<220> FEATURE:
<223> OTHER INFORMATION: Synthetic Construct

<400> SEQUENCE: 1

Met Ala His His His His His His His Gly Gly Gly Gly Gly Leu
1               5                   10                  15

Val Pro Arg Gly Lys Arg Arg Gln Gln Lys Ile Arg Lys Tyr Thr Met
            20                  25                  30

Arg Arg Leu Leu Gln Glu Thr Glu Leu Val Glu Pro Leu Thr Pro Ser
        35                  40                  45

Gly Ala Met Pro Asn Gln Ala Gln Met Arg Ile Leu Lys Glu Thr Glu
    50                  55                  60

Leu Arg Lys Val Lys Val Leu Gly Ser Gly Ala Phe Gly Thr Val Tyr
65                  70                  75                  80

Lys Gly Ile Trp Ile Pro Asp Gly Glu Asn Val Lys Ile Pro Val Ala
                85                  90                  95

Ile Lys Val Leu Arg Glu Asn Thr Ser Pro Lys Ala Asn Lys Glu Ile
            100                 105                 110

Leu Asp Glu Ala Tyr Val Met Ala Tyr Val Met Ala Gly Val Gly Ser
        115                 120                 125
```

-continued

Pro Tyr Val Ser Arg Leu Leu Gly Ile Cys Leu Thr Ser Val Gln
130                 135                 140

Leu Val Thr Gln Leu Met Pro Tyr Gly Cys Leu Leu Asp His Val Arg
145                 150                 155                 160

Glu Asn Arg Gly Arg Leu Gly Ser Gln Asp Leu Leu Asn Trp Cys Met
                165                 170                 175

Gln Ile Ala Lys Gly Met Ser Tyr Leu Glu Asp Val Arg Leu Val His
            180                 185                 190

Arg Asp Leu Ala Ala Arg Asn Val Leu Val Lys Ser Pro Asn His Val
        195                 200                 205

Lys Ile Thr Asp Phe Gly Leu Ala Arg Leu Leu Asp Ile Asp Glu Thr
210                 215                 220

Glu Tyr His Ala Asp Gly Gly Lys Val Pro Ile Lys Trp Met Ala Leu
225                 230                 235                 240

Glu Ser Ile Leu Arg Arg Arg Phe Thr His Gln Ser Asp Val Trp Ser
                245                 250                 255

Tyr Gly Val Thr Val Trp Glu Leu Met Thr Phe Gly Ala Lys Pro Tyr
            260                 265                 270

Asp Gly Ile Pro Ala Arg Glu Ile Pro Asp Leu Leu Glu Lys Gly Glu
        275                 280                 285

Arg Leu Pro Gln Pro Pro Ile Cys Thr Ile Asp Val Tyr Met Ile Met
290                 295                 300

Val Lys Cys Trp Met Ile Asp Ser Glu Cys Arg Pro Arg Phe Arg Glu
305                 310                 315                 320

Leu Val Ser Glu Phe Ser Arg Met Ala Arg Asp Pro Gln Arg Phe Val
                325                 330                 335

Val Ile Gln Asn Glu Asp Leu Gly Pro Ala Ser Pro Leu Asp Ser Thr
            340                 345                 350

Phe Tyr Arg Ser Leu Leu Glu Asp Asp Asp Met Gly Asp Leu Val Asp
        355                 360                 365

Ala Glu Glu Tyr Leu Val Pro Gln Gln Gly Phe Phe Cys Pro Asp Pro
370                 375                 380

Ala Pro Gly Ala Gly Gly Met Val His His Arg His Arg Ser Ser Ser
385                 390                 395                 400

Thr Arg Ser Gly Gly Gly Asp Leu Thr Leu Gly Leu Glu Pro Ser Glu
                405                 410                 415

Glu Glu Ala Pro Arg Ser Pro Leu Ala Pro Ser Glu Gly Ala Gly Ser
            420                 425                 430

Asp Val Phe Asp Gly Asp Leu Gly Met Gly Ala Ala Lys Gly Leu Gln
        435                 440                 445

Ser Leu Pro Thr His Asp Pro Ser Pro Leu Gln Arg Tyr Ser Glu Asp
450                 455                 460

Pro Thr Val Pro Leu Pro Ser Glu Thr Asp Gly Tyr Val Ala Pro Leu
465                 470                 475                 480

Thr Cys Ser Pro Gln Pro Glu Tyr Val Asn Gln Pro Asp Val Arg Pro
                485                 490                 495

Gln Pro Pro Ser Pro Arg Glu Gly Pro Leu Pro Ala Ala Arg Pro Ala
            500                 505                 510

Gly Ala Thr Leu Glu Arg Ala Lys Thr Leu Ser Pro Gly Lys Asn Gly
        515                 520                 525

Val Val Lys Asp Val Phe Ala Phe Gly Gly Ala Val Glu Asn Pro Glu
530                 535                 540

Tyr Leu Thr Pro Gln Gly Gly Ala Ala Pro Gln Pro His Pro Pro Pro

```
545                 550                 555                 560
Ala Phe Ser Pro Ala Phe Asp Asn Leu Tyr Tyr Trp Asp Gln Asp Pro
                565                 570                 575
Pro Glu Arg Gly Ala Pro Pro Ser Thr Phe Lys Gly Thr Pro Thr Ala
            580                 585                 590
Glu Asn Pro Glu Tyr Leu Gly Leu Asp Val Pro Val
        595                 600

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Tyr Val Met Ala
1
```